(12) United States Patent
Masignani et al.

(10) Patent No.: US 8,609,106 B2
(45) Date of Patent: Dec. 17, 2013

(54) COMBINATIONS OF PNEUMOCOCCAL RRGB CLADES

(75) Inventors: Vega Masignani, Siena (IT); Michele Anne Barocchi, Florence (IT); Monica Moschioni, Cose Val D'Elsa (IT); Paolo Ruggiero, Rapolano Terme (IT)

(73) Assignee: Novartis AG, Basel (CH)

( * ) Notice: Subject to any disclaimer, the term of this patent is extended or adjusted under 35 U.S.C. 154(b) by 415 days.

(21) Appl. No.: 12/791,186

(22) Filed: Jun. 1, 2010

(65) Prior Publication Data

US 2011/0020385 A1 Jan. 27, 2011

Related U.S. Application Data

(60) Provisional application No. 61/318,926, filed on Mar. 30, 2010, provisional application No. 61/314,203, filed on Mar. 16, 2010, provisional application No. 61/254,426, filed on Oct. 23, 2009, provisional application No. 61/217,629, filed on Jun. 1, 2009.

(51) Int. Cl.
*A61K 39/02* (2006.01)
*C07K 1/00* (2006.01)

(52) U.S. Cl.
USPC ........................ 424/190.1; 530/350

(58) Field of Classification Search
None
See application file for complete search history.

(56) References Cited

U.S. PATENT DOCUMENTS

2005/0196405 A1 9/2005 Briles et al.

FOREIGN PATENT DOCUMENTS

| WO | 2007/116322 A2 | 10/2007 |
| WO | 2009/016515 A2 | 2/2009 |

OTHER PUBLICATIONS

Tettelin et al. Science vol. 293, Jul. 20, 2001.*
LeMieux, J. et al. "RrgA and RrgB Are Components of a Multisubunit Pilus Encoded by the *Streptococcus pneumoniae* rlrA Pathogenicity Islet," Infection and Immunity, vol. 74, No. 4, 2006, pp. 2453-2456.
Moschioni, M. et al. "*Streptococcus pneumoniae* Contains 3 rlrA Pilus Variants That Are Clonally Related," The Journal of Infectious Diseases, vol. 197, 2008, pp. 888-896.
United States Office Action mailed May 15, 2013, for U.S. Appl. No. 13/375,759, filed Dec. 1, 2011, 15 pages.

* cited by examiner

*Primary Examiner* — N. M. Minnifield
*Assistant Examiner* — Khatol Shahnan-Shah
(74) *Attorney, Agent, or Firm* — Morrison & Foerster LLP

(57) ABSTRACT

Pneumococcal pilus subunit RrgB has at least three clades. Serum raised against a given clade is active against pneumococci which express that RrgB clade, but is not active against strains which express one of the other two clades i.e. there is intra-clade cross-protection, but not inter-clade cross-protection. Thus an immunogenic composition can include at least two different clades of RrgB to improve strain coverage against pilus-containing pneumococci. These multiple clades may be present in the immunogenic composition as separate polypeptides or may be fused as a single polypeptide chain.

7 Claims, 29 Drawing Sheets

FIGURE 7
FIGURE 7A
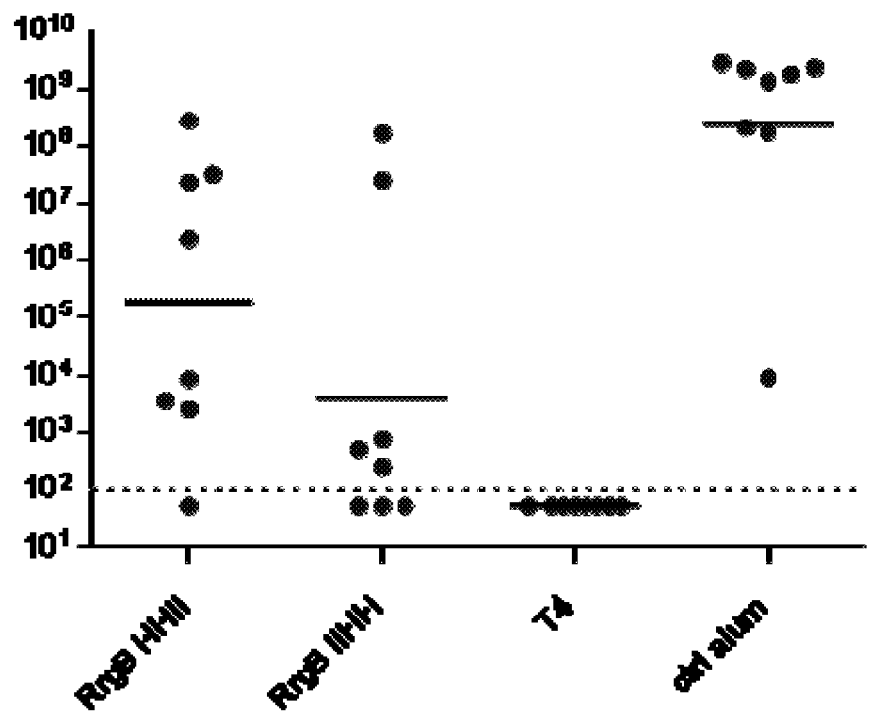
FIGURE 7B
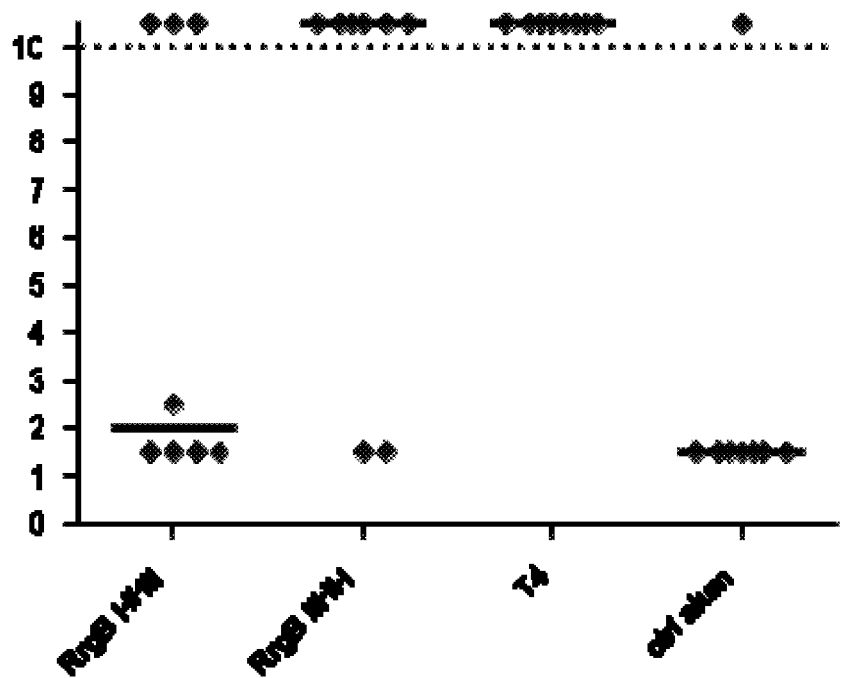

FIGURE 12
FIGURE 12A
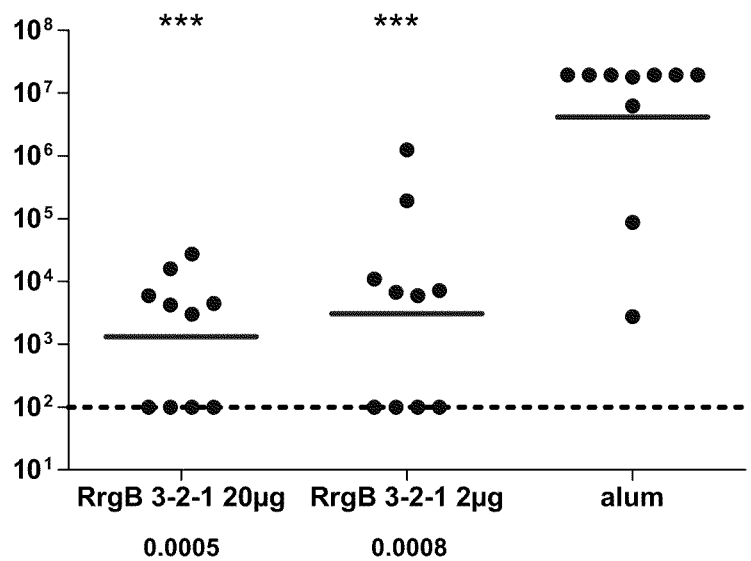
FIGURE 12B
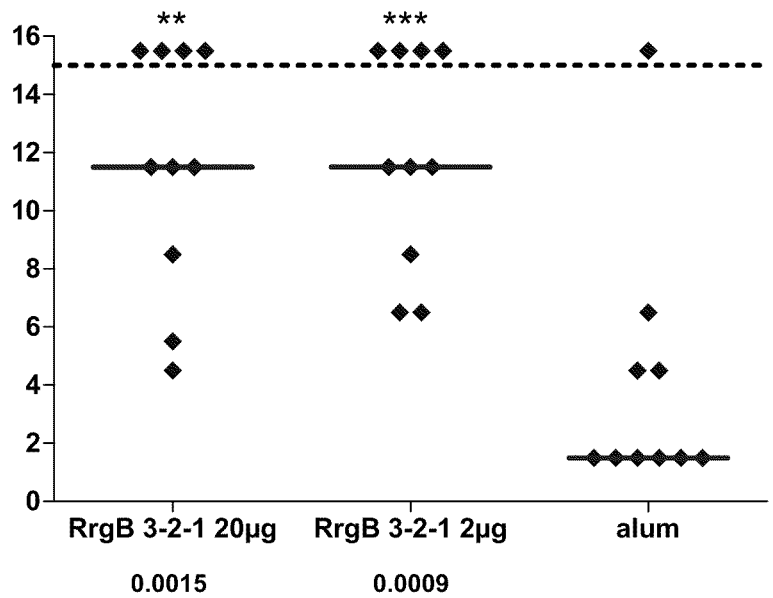

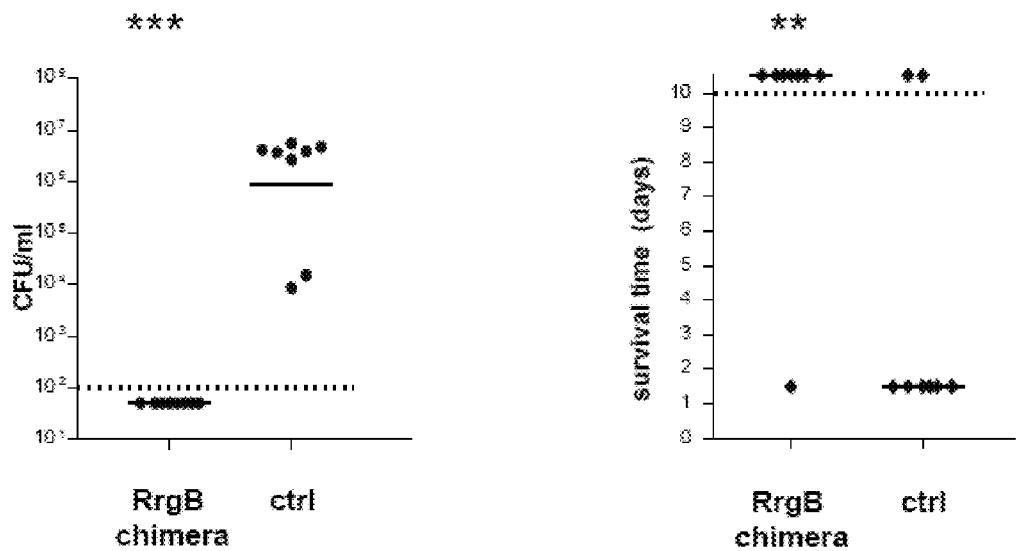
FIGURE 15
FIGURE 15A
FIGURE 15B
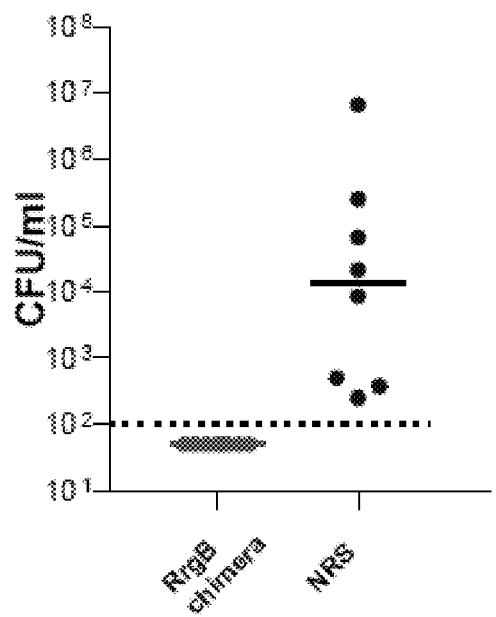
FIGURE 16

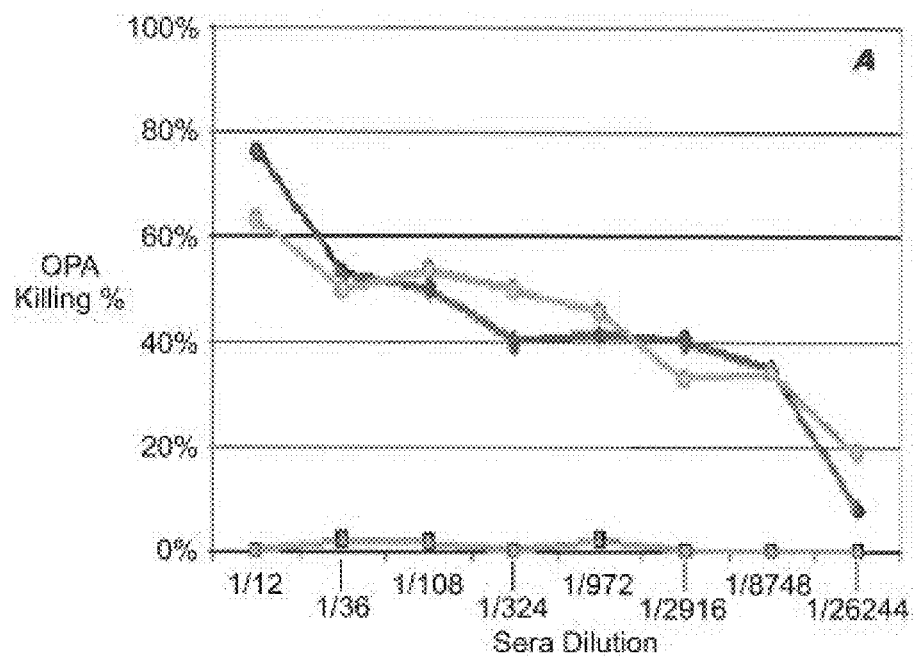
FIGURE 17
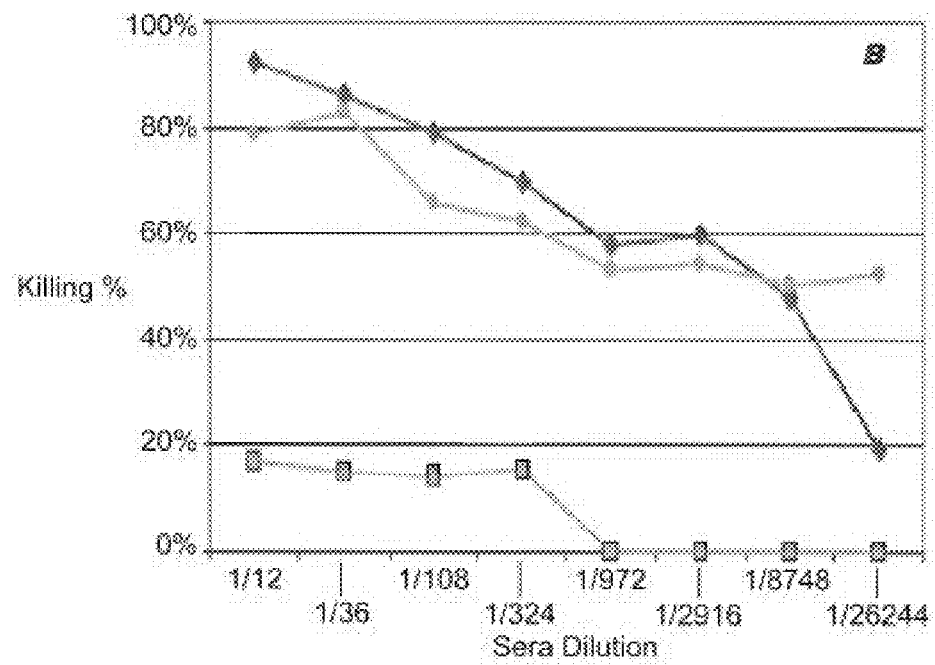

A B C

FIGURE 23
FIGURE 23A
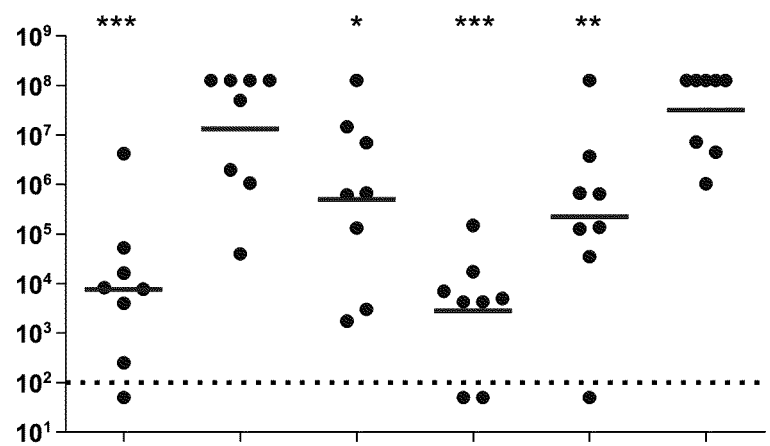
FIGURE 23B
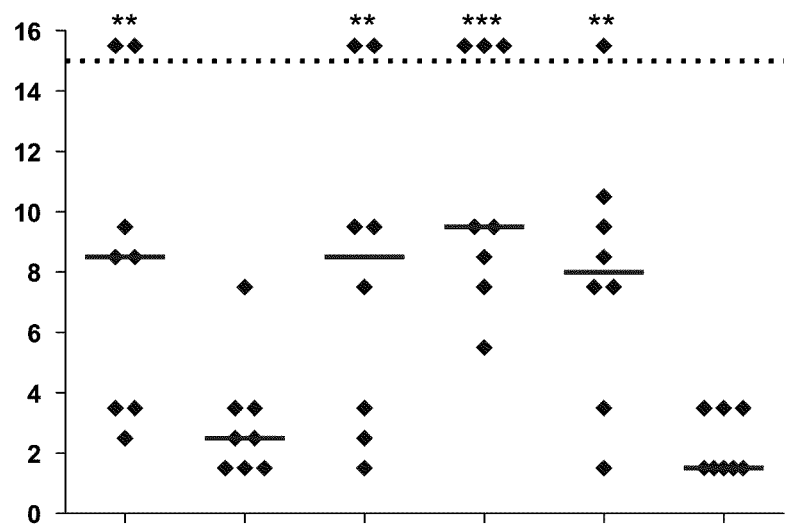

FIGURE 24
FIGURE 24A
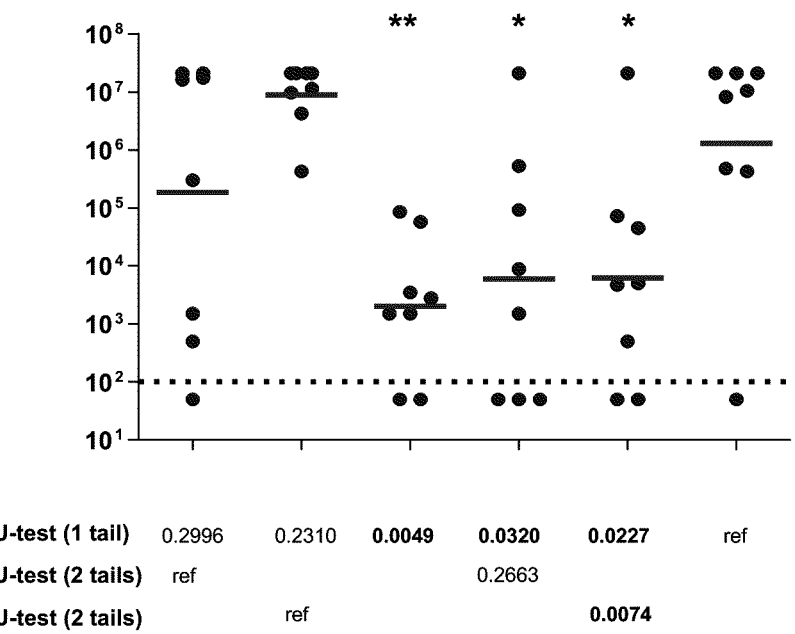
FIGURE 24B
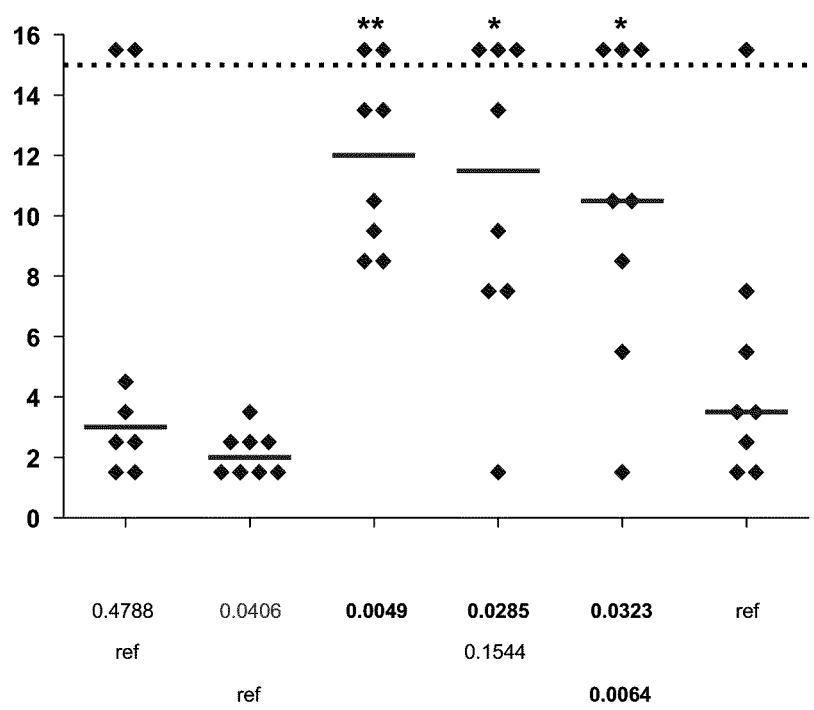

FIGURE 25
FIGURE 25A
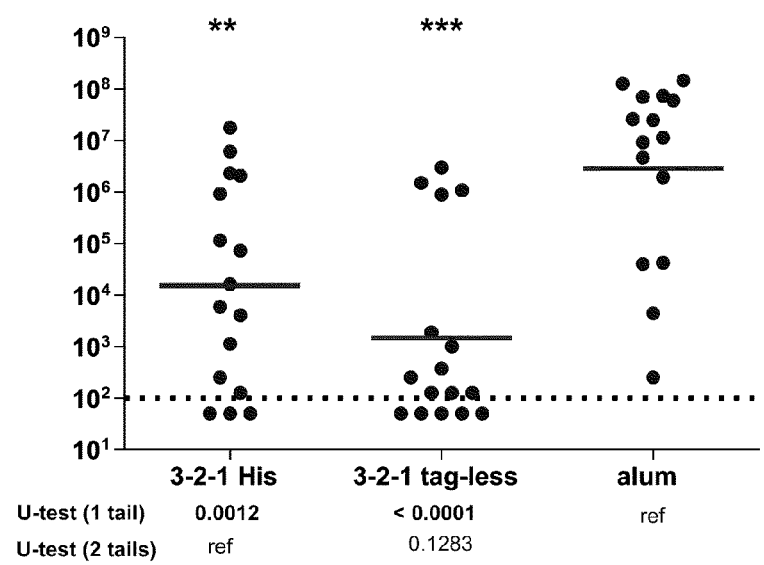
FIGURE 25B
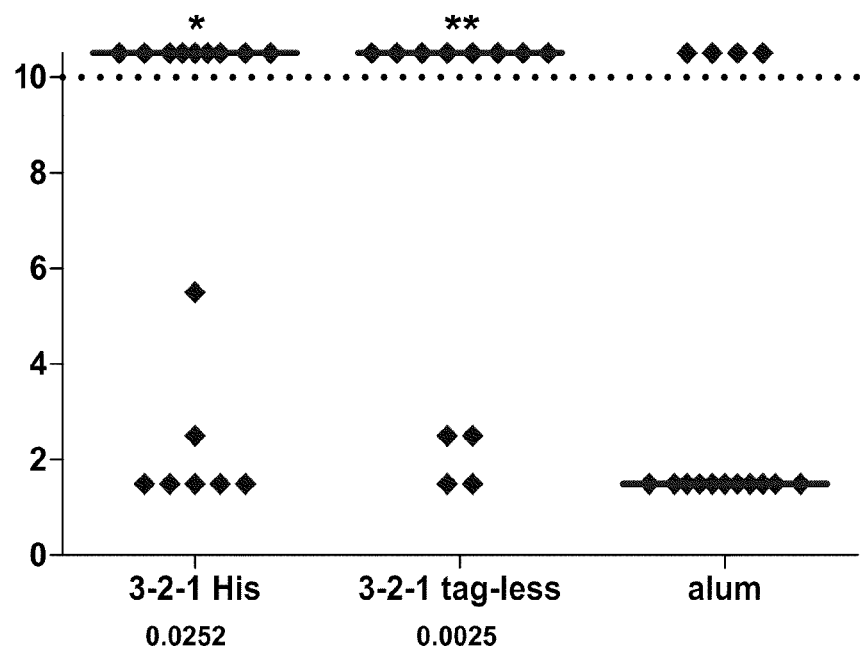

FIGURE 27
FIGURE 27A
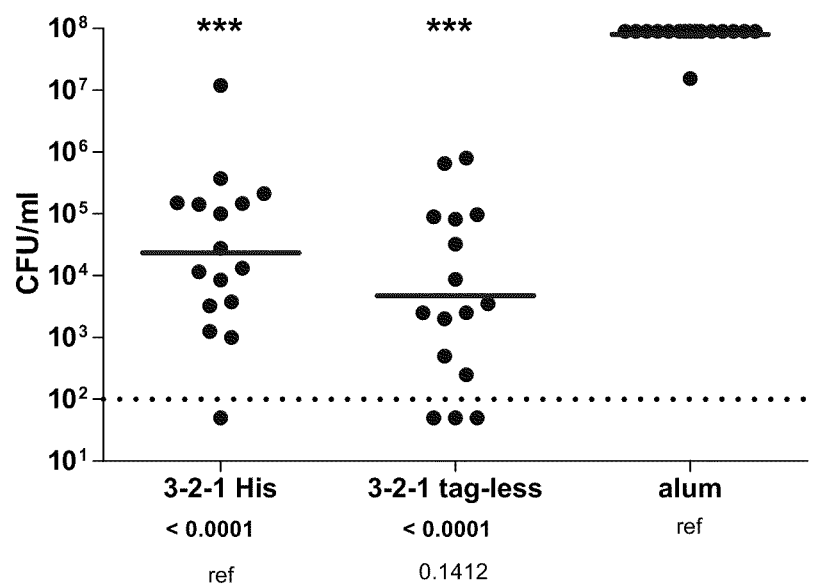
FIGURE 27B
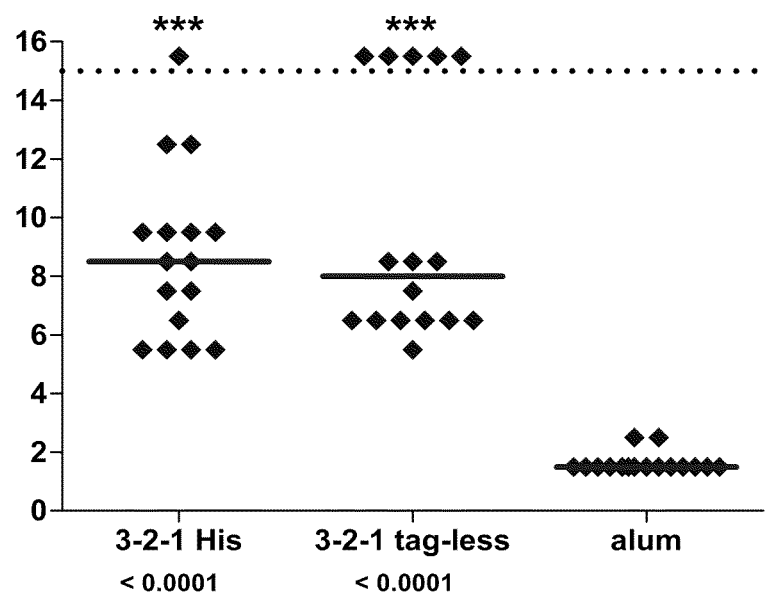

FIGURE 28
FIGURE 28A
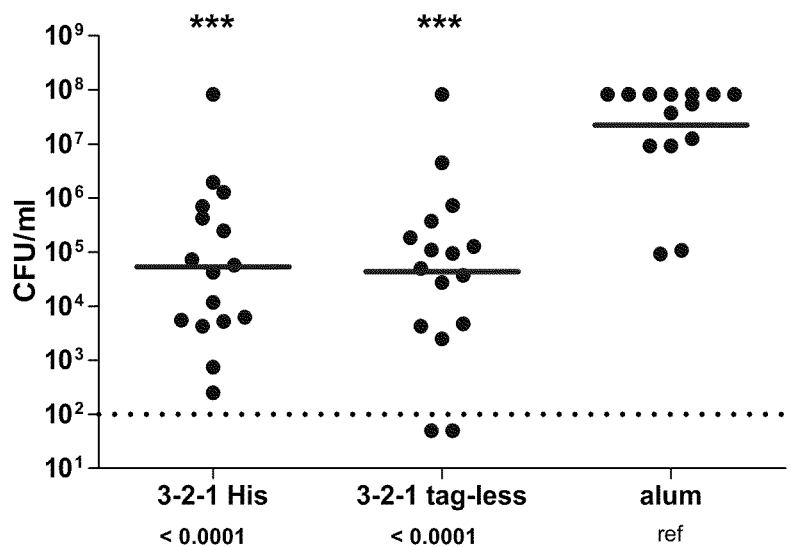
FIGURE 28B
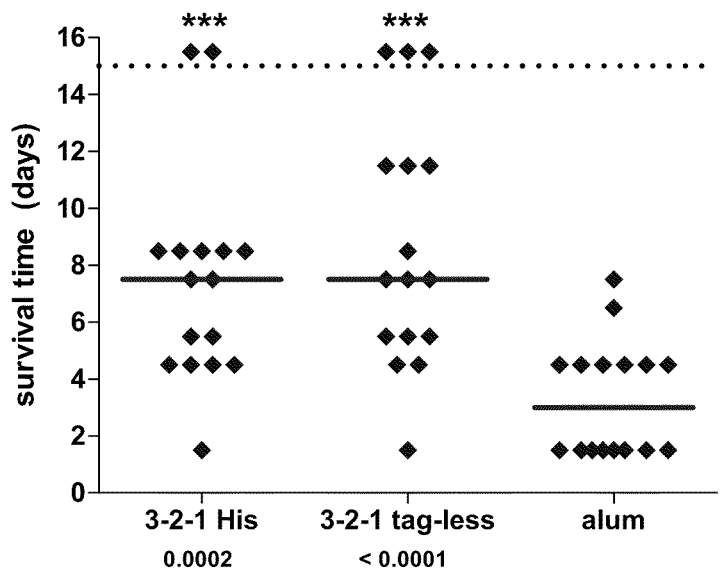

FIGURE 29
FIGURE 29A
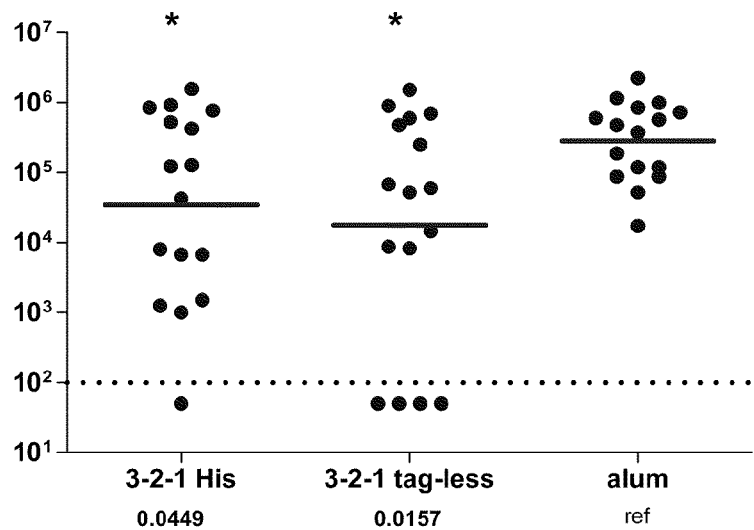
FIGURE 29B
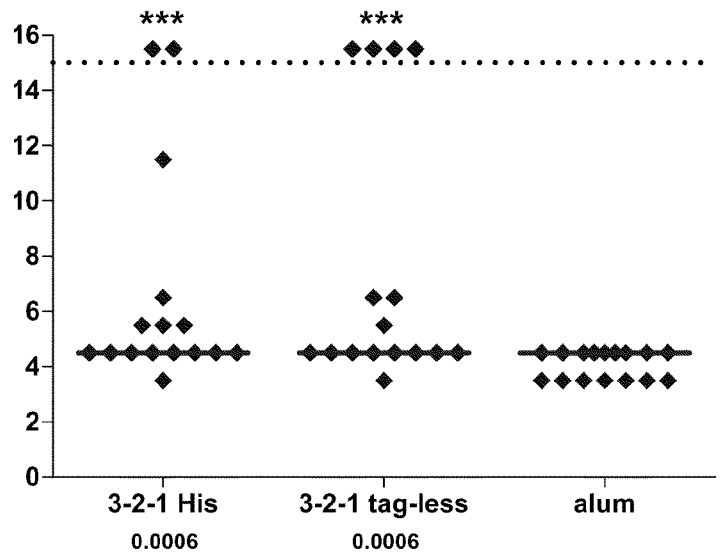

FIGURE 30
FIGURE 30A
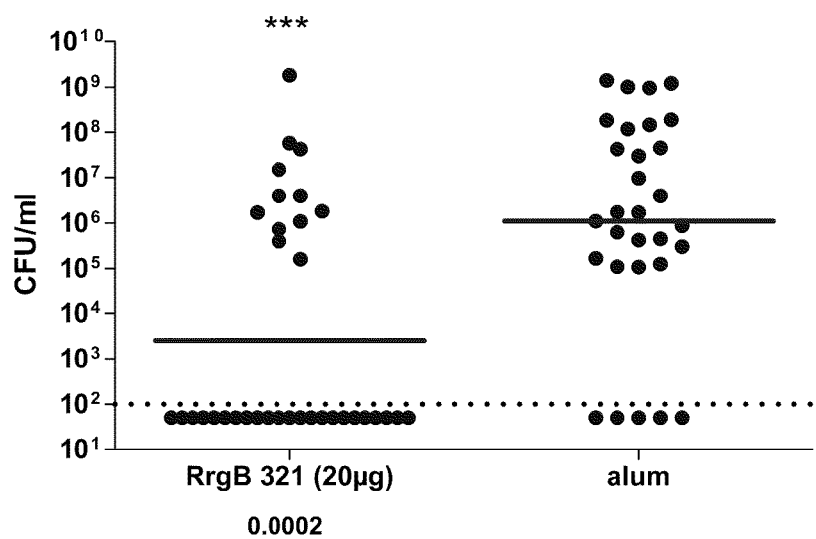
FIGURE 30B
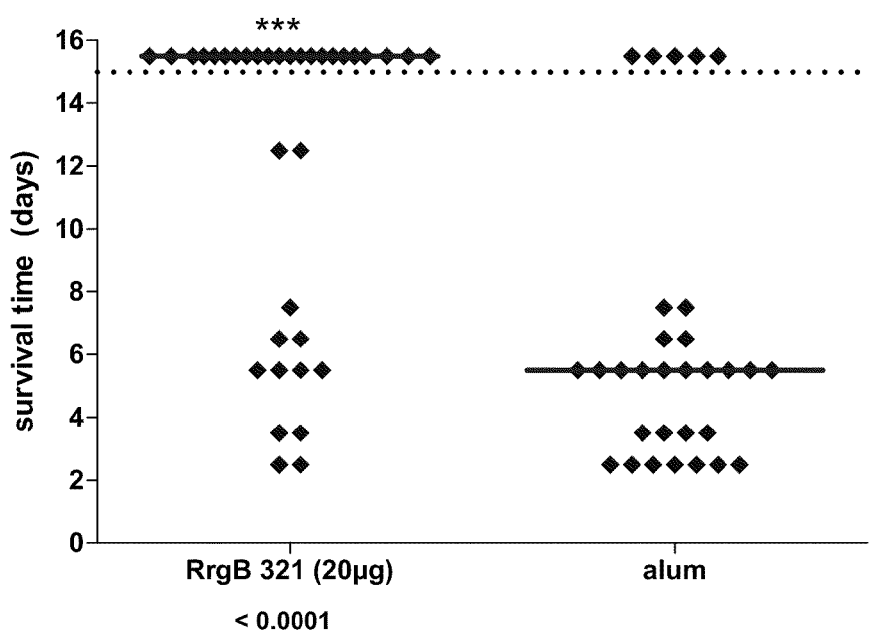

FIGURE 31
FIGURE 31A
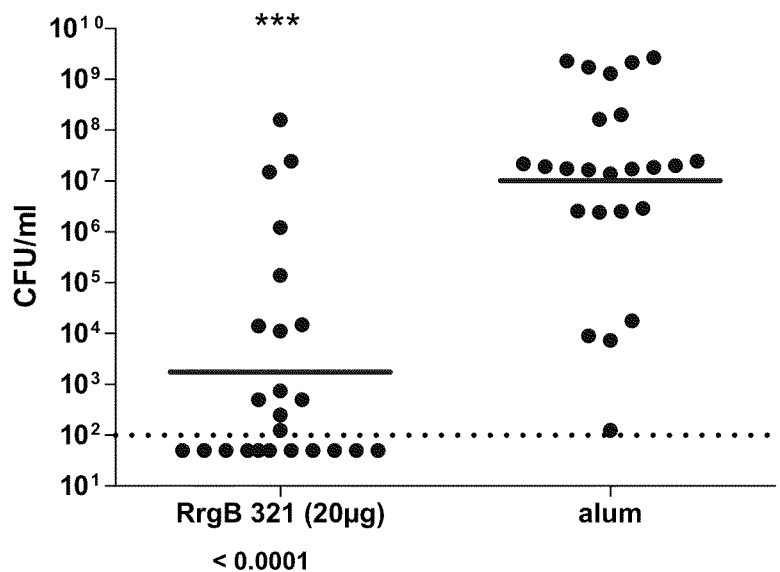
FIGURE 31B
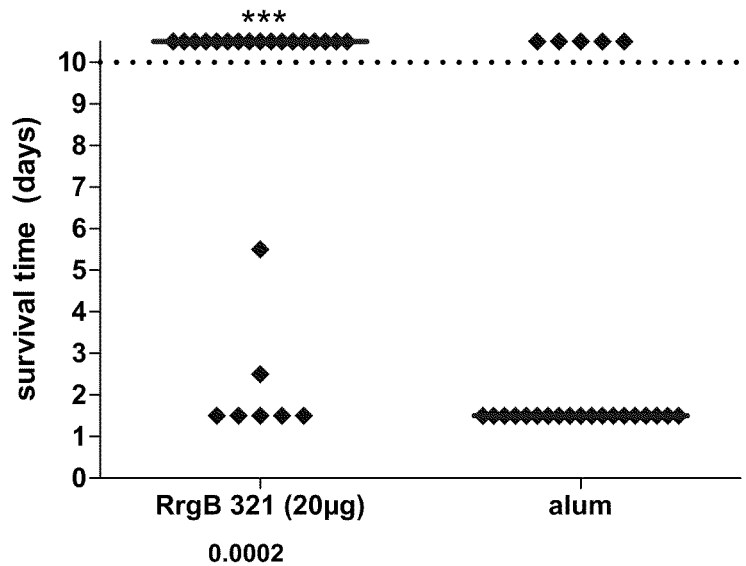

FIGURE 32
FIGURE 32A
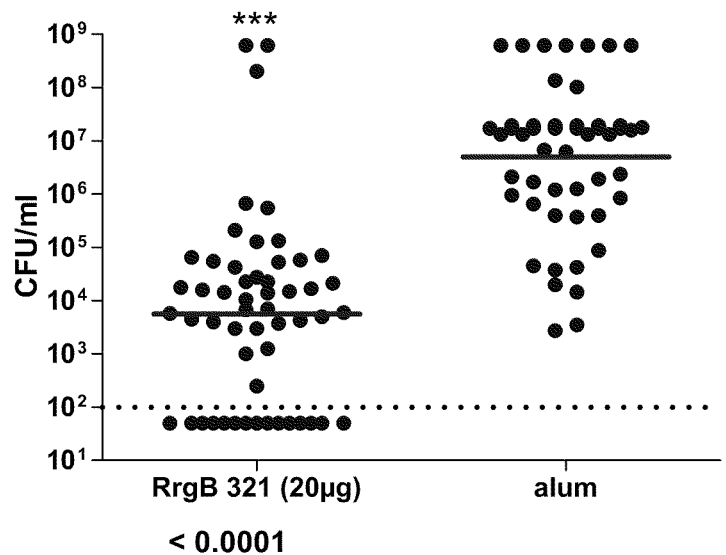
FIGURE 32B
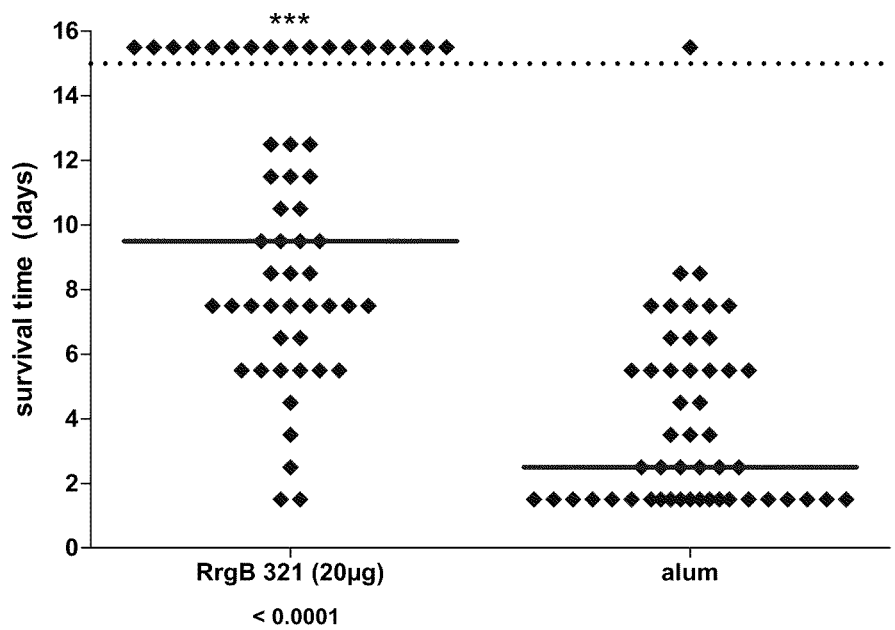

FIGURE 33
FIGURE 33A
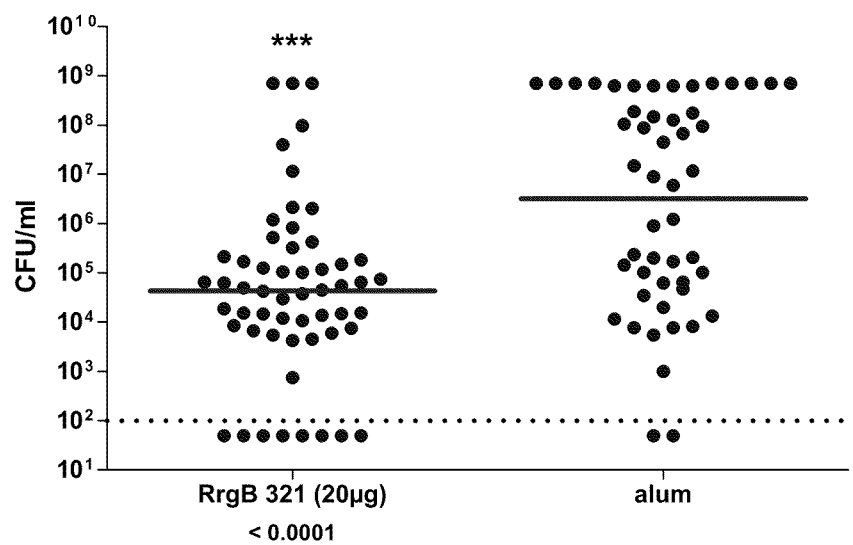
FIGURE 33B
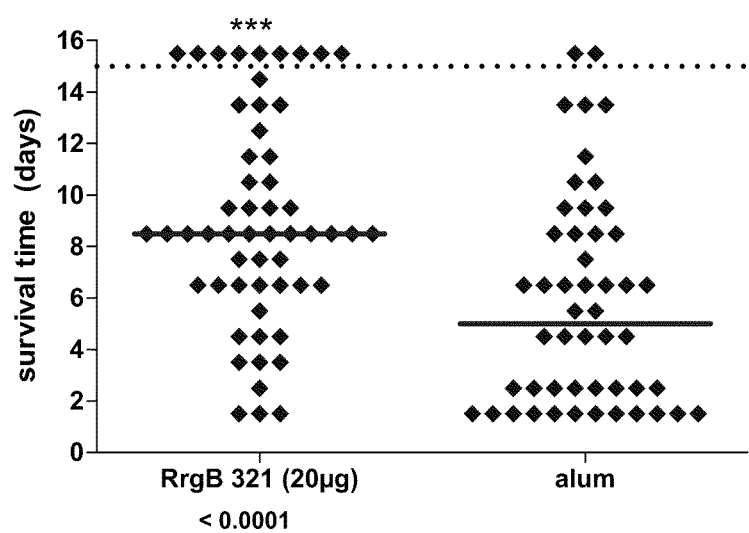

FIGURE 34
FIGURE 34A
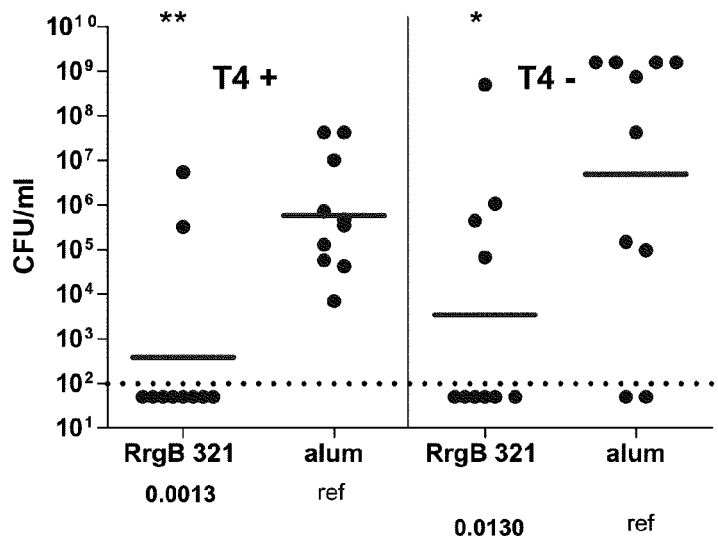
FIGURE 34B
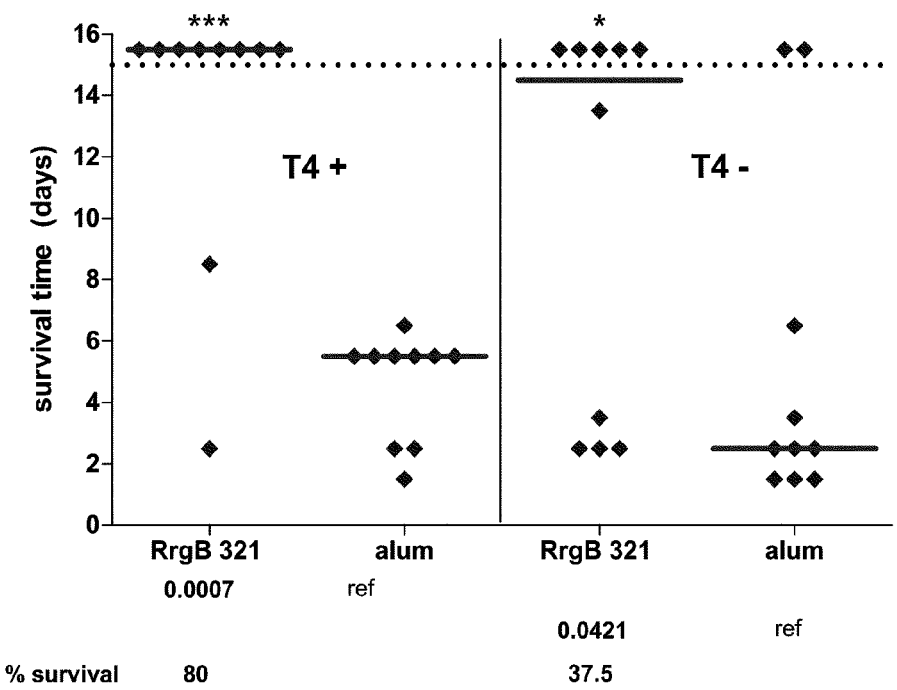

FIGURE 35
FIGURE 35A
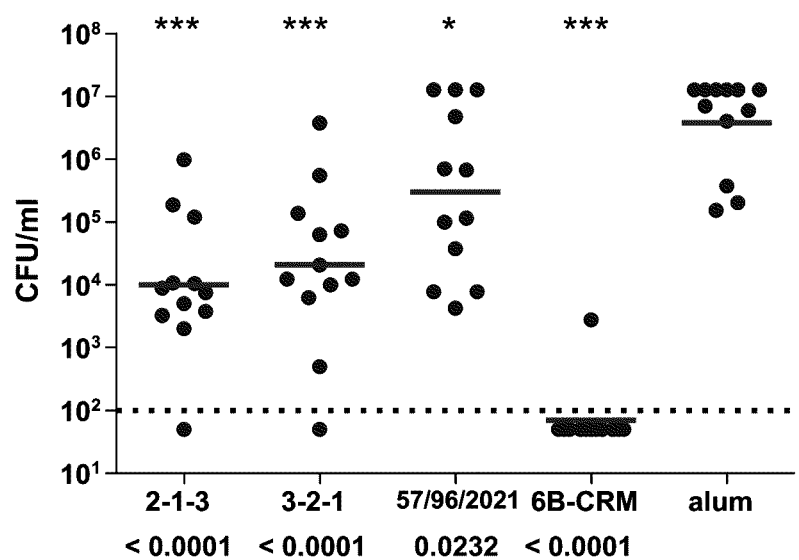
FIGURE 35B
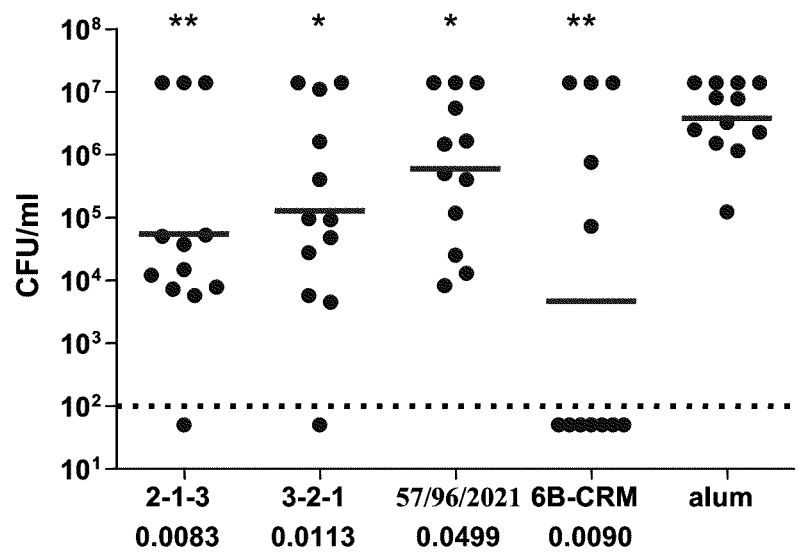

COMBINATIONS OF PNEUMOCOCCAL RRGB CLADES

RELATED APPLICATIONS

This application claims the benefit under 35 U.S.C. 119(e) of U.S. Provisional Application No. 61/217,629, filed Jun. 1, 2009, U.S. Provisional Application No. 61/254,426, filed Oct. 23, 2009, U.S. Provisional Application No. 61/314,203, filed Mar. 16, 2010, and U.S. Provisional Application No. 61/318,926, filed Mar. 30, 2010. The teachings of the above applications are incorporated herein in their entirety by reference.

TECHNICAL FIELD

This invention is in the field of immunising against *Streptococcus pneumoniae* (pneumococcus).

BACKGROUND OF THE INVENTION

*S. pneumoniae* has a pilus known as pilus-1 encoded by a 14-kb islet (PI-1) having seven genes encoding: the RlrA transcriptional regulator, three pilus subunits with LPXTG-type cell wall sorting signals, and three sortase enzymes involved in synthesis of the pilus polymer and in the incorporation of ancillary pilus components. RrgB is the major subunit that forms the backbone of the structure, while the other two pilins (RrgA, RrgC) are ancillary structural proteins [1-4]. RrgA is the major pilus-1 adhesin; bacteria lacking RrgA are less adherent to epithelial cells than wild-type organisms.

SUMMARY OF THE INVENTION

The present invention relates to an immunogenic composition comprising at least two of:

(a) a first polypeptide comprising a first amino acid sequence, where the first amino acid sequence comprises an amino acid sequence (i) having at least 90% sequence identity to SEQ ID NO: 1 and/or (ii) consisting of a fragment of at least 7 contiguous amino acids from SEQ ID NO: 1;

(b) a second polypeptide, comprising a second amino acid sequence, where the second amino acid sequence comprises an amino acid sequence (i) having at least 90% sequence identity to SEQ ID NO: 2 and/or (ii) consisting of a fragment of at least 7 contiguous amino acids from SEQ ID NO: 2; and/or (c) a third polypeptide, comprising a third amino acid sequence, where the third amino acid sequence comprises an amino acid sequence (i) having at least 90% sequence identity to SEQ ID NO: 3 and/or (ii) consisting of a fragment of at least 7 contiguous amino acids from SEQ ID NO: 3.

The present invention also relates to a polypeptide comprising at least two of:

(a) a first amino acid sequence comprising an amino acid sequence (i) having at least 90% sequence identity to SEQ ID NO: 1 and/or (ii) consisting of a fragment of at least 7 contiguous amino acids from SEQ ID NO: 1;

(b) a second amino acid sequence comprising an amino acid sequence (i) having at least 90% sequence identity to SEQ ID NO: 2 and/or (ii) consisting of a fragment of at least 7 contiguous amino acids from SEQ ID NO: 2; and/or (c) a third amino acid sequence comprising an amino acid sequence (i) having at least 90% sequence identity to SEQ ID NO: 3 and/or (ii) consisting of a fragment of at least 7 contiguous amino acids from SEQ ID NO: 3.

The present invention further relates to a polypeptide comprising amino acid sequence:

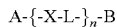

$A\text{-}\{\text{-}X\text{-}L\text{-}\}_n\text{-}B$ wherein: each X is an amino acid sequence of first polypeptide, second polypeptide or third polypeptide as defined in claim 1; L is an optional linker amino acid sequence; A is an optional N terminal amino acid sequence; B is an optional C terminal amino acid sequence; n is an integer of 2 or more. Optionally, the polypeptide comprises at least two of a first, second and third polypeptide as defined in claim 1.

In a particular embodiment, the polypeptides of the invention comprise an amino acid sequence selected from the group consisting of: SEQ ID NOs: 11, 13, 15, 17, 19 and 21.

The present invention also relates to a bacterium which expresses at least two of:

(a) a first polypeptide comprising a first amino acid sequence, where the first amino acid sequence comprises an amino acid sequence (i) having at least 90% sequence identity to SEQ ID NO: 1 and/or (ii) consisting of a fragment of at least 7 contiguous amino acids from SEQ ID NO: 1;

(b) a second polypeptide, comprising a second amino acid sequence, where the second amino acid sequence comprises an amino acid sequence (i) having at least 90% sequence identity to SEQ ID NO: 2 and/or (ii) consisting of a fragment of at least 7 contiguous amino acids from SEQ ID NO: 2; and/or (c) a third polypeptide, comprising a third amino acid sequence, where the third amino acid sequence comprises an amino acid sequence (i) having at least 90% sequence identity to SEQ ID NO: 3 and/or (ii) consisting of a fragment of at least 7 contiguous amino acids from SEQ ID NO: 3.

BRIEF DESCRIPTION OF THE DRAWINGS

FIG. 7 shows (A) bacteremia and (B) mortality data after immunisation with alum-adjuvanted I-II-III chimera, III-II-I chimera, TIGR4 or alum alone. In FIG. 7A the data are CFU/ml and in FIG. 7B the data are survival time in days.

FIG. 12 shows (A) bacteremia and (B) mortality data after immunisation with III-II-I chimera at different doses. In FIG. 12A the data are CFU/ml and in FIG. 12B the data are survival time in days.

In FIG. 13A the data are CFU/ml and in FIG. 13B the data are survival time in days.

FIG. 15 shows (A) bacteremia and (B) mortality data after subcutaneous immunisation with RrgB III-II-I chimera. In FIG. 15A the data are CFU/ml and in FIG. 15B the data are survival time in days.

FIG. 16 shows that RrgB III-II-I chimera elicits production of functional antibodies in a passive protection study, compared to a Normal Rabbit Serum (NRS) control, in a 24 hour bacteremia assay.

FIG. 17 shows OPKA results against (A) TIGR4 and (B) ST35B, showing % killing against serum dilution. Diamonds show Anti-T4, circles show RrgB III-II-I chimera and squares show NSK.

FIG. 23 shows (A) 48 hour bacteremia and (B) mortality data against 6B-Finland strain (i.v. challenge) after i.p. immunisation with RrgB III-II-I chimera when combined with different combinations of further polypeptide antigens (20 µg antigens). In FIG. 23A the data are CFU/ml and in FIG. 23B the data are survival time in days. In both (A) and (B): column 1 shows a combination of spr0057, spr0096 and spr2021; column 2 shows a combination of SP2216-1, SP1732-3 and PsaA; column 3 shows RrgB III-II-I chimera; column 4 shows RrgB III-II-I chimera combined with spr0057, spr0096 and spr2021; column 5 shows RrgB III-II-I chimera combined with SP2216-1, SP1732-3 and PsaA; and column 6 shows an alum control.

FIG. 24 shows (A) 48 hour bacteremia and (B) mortality data against 35B-SME15 strain (i.v. challenge) after i.p. immunisation with RrgB III-II-I chimera when combined with different combinations of further polypeptide antigens (20 µg antigens). In FIG. 24A the data are CFU/ml and in FIG. 24B the data are survival time in days. In both (A) and (B): column 1 shows a combination of spr0057, spr0096 and spr2021; column 2 shows a combination of SP2216-1, SP1732-3 and PsaA; column 3 shows RrgB III-II-I chimera; column 4 shows RrgB III-II-I chimera combined with spr0057, spr0096 and spr2021; column 5 shows RrgB III-II-I chimera combined with SP2216-1, SP1732-3 and PsaA; and column 6 shows an alum control.

FIG. 25 shows (A) a 24 hour bacteremia assay and (B) mortality data using a III-II-I chimera that contains a polyhistidine tag compared to a tag-less III-II-I chimera and an alum control (i.p. immunisation, i.p. challenge with TIGR4 2.1E+02 CFU/mouse). The data in (A) are CFU/ml and in (B) are survival time in days.

FIG. 27 shows (A) a 48 hour bacteremia assay and (B) mortality data using a III-II-I chimera that contains a polyhistidine tag compared to a tag-less III-II-I chimera and an alum control (i.p. immunisation, i.v. challenge with 35B-SME15 4.6E+07 CFU/mouse). The data in (A) are CFU/ml and in (B) are survival time in days.

FIG. 28 shows (A) a 48 hour bacteremia assay and (B) mortality data using a III-II-I chimera that contains a polyhistidine tag compared to a tag-less III-II-I chimera and an alum control (i.p. immunisation, i.v. challenge with 6BFinland12 9.4E+07 CFU/mouse). The data in (A) are CFU/ml and in (B) are survival time in days.

FIG. 29 shows (A) a 48 hour bacteremia assay and (B) mortality data using a III-II-I chimera that contains a polyhistidine tag compared to a tag-less III-II-I chimera and an alum control (i.p. immunisation, i.v. challenge with TIGR4 6.3E+05 CFU/mouse). The data in (A) are CFU/ml and in (B) are survival time in days.

FIG. 30 shows (A) a 48 hour bacteremia assay and (B) mortality data after immunisation with 20 µg III-II-I chimera, compared to an alum control (i.p. immunisation, i.v. challenge with TIGR4). The data in (A) are CFU/ml and in (B) are survival time in days.

FIG. 31 shows (A) a 24 hour bacteremia assay and (B) mortality data after immunisation with 20 µg III-II-I chimera, compared to an alum control (i.p. immunisation, i.p. challenge with TIGR4). The data in (A) are CFU/ml and in (B) are survival time in days.

FIG. 32 shows (A) a 24 hour bacteremia assay and (B) mortality data after immunisation with 20 µg III-II-I chimera, compared to an alum control (i.p. immunisation, i.v. challenge with 35B-SME15). The data in (A) are CFU/ml and in (B) are survival time in days.

FIG. 33 shows (A) a 24 hour bacteremia assay and (B) mortality data after immunisation with 20 µg III-II-I chimera, compared to an alum control (i.p. immunisation, i.v. challenge with 6B Finland12). The data in (A) are CFU/ml and in (B) are survival time in days.

FIG. 34 shows (A) a 48 hour bacteremia assay and (B) mortality data after immunisation with III-II-I chimera, compared to an alum control (i.p. immunisation, i.v. challenge with TIGR4) when challenged with a TIGR4 strain overexpressing pilus (T4+) compared to a TIGR4 train expressing very low amounts of pilus (T4−). The data in (A) are CFU/ml and in (B) are survival time in days.

FIG. 35 shows 48 hour bacteremia assays after immunisation with II-I-III and III-II-I chimeras (A) when challenged with a 6BFinl12 strain overexpressing pilus (i.p. immunisation, i.v. challenge with 6BFinland12 overexpressing pilus 7.0E+09 CFU/mouse) and (B) when challenged with a 6BFinl12 train expressing only very low amounts of pilus (i.p. immunisation, i.v. challenge with 6BFinland12 underexpressing pilus 7.3E+09 CFU/mouse). Both (A) and (B) also show data for: a combination of spr0057, spr0096 and spr2021; a 6BFinland-CRM197 conjugate; and alum. The data in (A) are CFU/ml and in (B) are survival time in days.

DETAILED DESCRIPTION OF THE INVENTION

Figure 1:
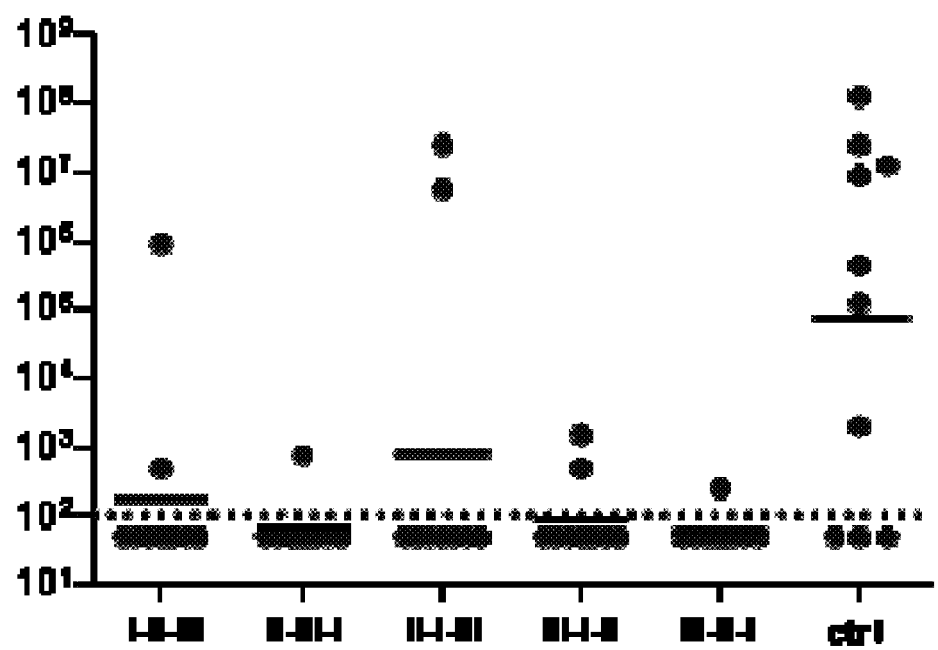
FIG. 1 shows results of a bacteremia study with five RrgB chimeras and a control. The figures are CFU/ml. Each mark shows data for a single mouse.

The RrgB pilus subunit has at least three clades. Reference amino acid sequences for the three clades are SEQ ID NOs: 1, 2 and 3 herein. The clades are well conserved at their N- and C-termini but deviate in between. SEQ ID NOs: 1 and 2 are 46% identical; SEQ ID NOs: 1 and 3 are 51% identical; SEQ ID NOs: 2 and 3 are 65% identical.

It has been found that serum raised against a given RrgB clade is active against pneumococci which express that clade, but is not active against strains which express one of the other two clades i.e. there is intra-clade cross-protection, but not inter-clade cross-protection. According to the invention, therefore, an immunogenic composition includes at least two different clades of RrgB. These may be present in the immunogenic composition as separate polypeptides or may be fused as a single polypeptide chain. The inclusion of multiple RrgB clades as vaccine components improves the strain coverage of the immunogenic composition against pilus-containing pneumococci. Furthermore, it has been observed that there is a significant association between pilus-1 presence and antibiotic resistance; this observation suggests that immunising against pilus-1 using an immunogenic composition including multiple RrgB clades will have the additional advantage of protecting against pneumococci that are resistant to antibiotic treatment.

Thus the invention provides an immunogenic composition comprising at least two of:

(a) a first polypeptide comprising a first amino acid sequence, where the first amino acid sequence comprises an amino acid sequence (i) having at least a % sequence identity to SEQ ID NO: 1 and/or (ii) consisting of a fragment of at least x contiguous amino acids from SEQ ID NO: 1;

(b) a second polypeptide, comprising a second amino acid sequence, where the second amino acid sequence comprises an amino acid sequence (i) having at least b % sequence identity to SEQ ID NO: 2 and/or (ii) consisting of a fragment of at least y contiguous amino acids from SEQ ID NO: 2; and/or (c) a third polypeptide, comprising a third amino acid sequence, where the third amino acid sequence comprises an amino acid sequence (i) having at least c % sequence identity to SEQ ID NO: 3 and/or (ii) consisting of a fragment of at least z contiguous amino acids from SEQ ID NO: 3.

The invention also provides a polypeptide comprising at least two of:

(a) a first amino acid sequence comprising an amino acid sequence (i) having at least a % sequence identity to SEQ ID NO: 1 and/or (ii) consisting of a fragment of at least x contiguous amino acids from SEQ ID NO: 1;

(b) a second amino acid sequence comprising an amino acid sequence (i) having at least b % sequence identity to SEQ ID NO: 2 and/or (ii) consisting of a fragment of at least y contiguous amino acids from SEQ ID NO: 2; and/or (c) a third amino acid sequence comprising an amino acid sequence (i) having at least c % sequence identity to SEQ ID NO: 3 and/or (ii) consisting of a fragment of at least z contiguous amino acids from SEQ ID NO: 3.

The invention also provides a polypeptide comprising amino acid sequence:

$$-A-\{-X-L-\}_n-B-$$

wherein: X is an amino acid sequence of first polypeptide, second polypeptide or third polypeptide as defined above; L is an optional linker amino acid sequence; A is an optional N-terminal amino acid sequence; B is an optional C-terminal amino acid sequence; n is an integer of 2 or more (e.g. 2, 3, 4, 5, 6, etc.). Optionally, the polypeptide comprises at least two of a first, second and third polypeptide as defined in claim 1. Usually n is 2 or 3, and X moieties are selected from the following:

| N | $X_1$ | $X_2$ | $X_3$ |
|---|---|---|---|
| 2 | First amino acid sequence | Second amino acid sequence | — |
| 2 | Second amino acid sequence | First amino acid sequence | — |
| 3 | First amino acid sequence | Second amino acid sequence | Third amino acid sequence |
| 3 | First amino acid sequence | Third amino acid sequence | Second amino acid sequence |
| 3 | Second amino acid sequence | Third amino acid sequence | First amino acid sequence |
| 3 | Second amino acid sequence | First amino acid sequence | Third amino acid sequence |
| 3 | Third amino acid sequence | Second amino acid sequence | First amino acid sequence |
| 3 | Third amino acid sequence | First amino acid sequence | Second amino acid sequence |

The invention also provides a cell (typically a bacterium, such as a pneumococcus) which expresses at least two of:

(a) a first polypeptide comprising a first amino acid sequence, where the first amino acid sequence comprises an amino acid sequence (i) having at least a % sequence identity to SEQ ID NO: 1 and/or (ii) consisting of a fragment of at least x contiguous amino acids from SEQ ID NO: 1;

(b) a second polypeptide, comprising a second amino acid sequence, where the second amino acid sequence comprises an amino acid sequence (i) having at least b % sequence identity to SEQ ID NO: 2 and/or (ii) consisting of a fragment of at least y contiguous amino acids from SEQ ID NO: 2; and/or (c) a third polypeptide, comprising a third amino acid sequence, where the third amino acid sequence comprises an amino acid sequence (i) having at least c % sequence identity to SEQ ID NO: 3 and/or (ii) consisting of a fragment of at least z contiguous amino acids from SEQ ID NO: 3.

The First, Second and Third Amino Acid Sequences

The value of a is at least 75 e.g. 80, 85, 90, 92, 94, 95, 96, 97, 98, 99 or more. The value of b is at least 75 e.g. 80, 85, 90, 92, 94, 95, 96, 97, 98, 99 or more. The value of c is at least 75 e.g. 80, 85, 90, 92, 94, 95, 96, 97, 98, 99 or more. The values of a, b and c may be the same or different. In some embodiments, a b and c are identical. Typically, a, b and c are at least 90 e.g. at least 95.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z may be the same or different. In some embodiments, x y and z are identical.

Fragments preferably comprise an epitope from the respective SEQ ID NO: sequence. Other useful fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of the respective SEQ ID NO: while retaining at least one epitope thereof. Truncation by 20-25 amino acids at the N-terminus is convenient e.g. removal of aa 1-23 of any of SEQ ID NOs: 1 to 3 (or of any one of SEQ ID NOs: 85 to 96).

The RrgB protein can be split into four domains (D1 to D4) between its leader peptide and its LPXTG anchor. These four domains are as follows in SEQ ID NOs: 1 to 3, and the positions in further RrgB sequences which correspond to these residues can readily be identified by alignment:

|   | D1     | D2      | D3      | D4      |
|---|--------|---------|---------|---------|
| 1 | 31-184 | 185-326 | 327-446 | 447-627 |
| 2 | 31-185 | 186-318 | 319-434 | 435-606 |
| 3 | 31-184 | 185-319 | 320-445 | 446-616 |

Figure 20:
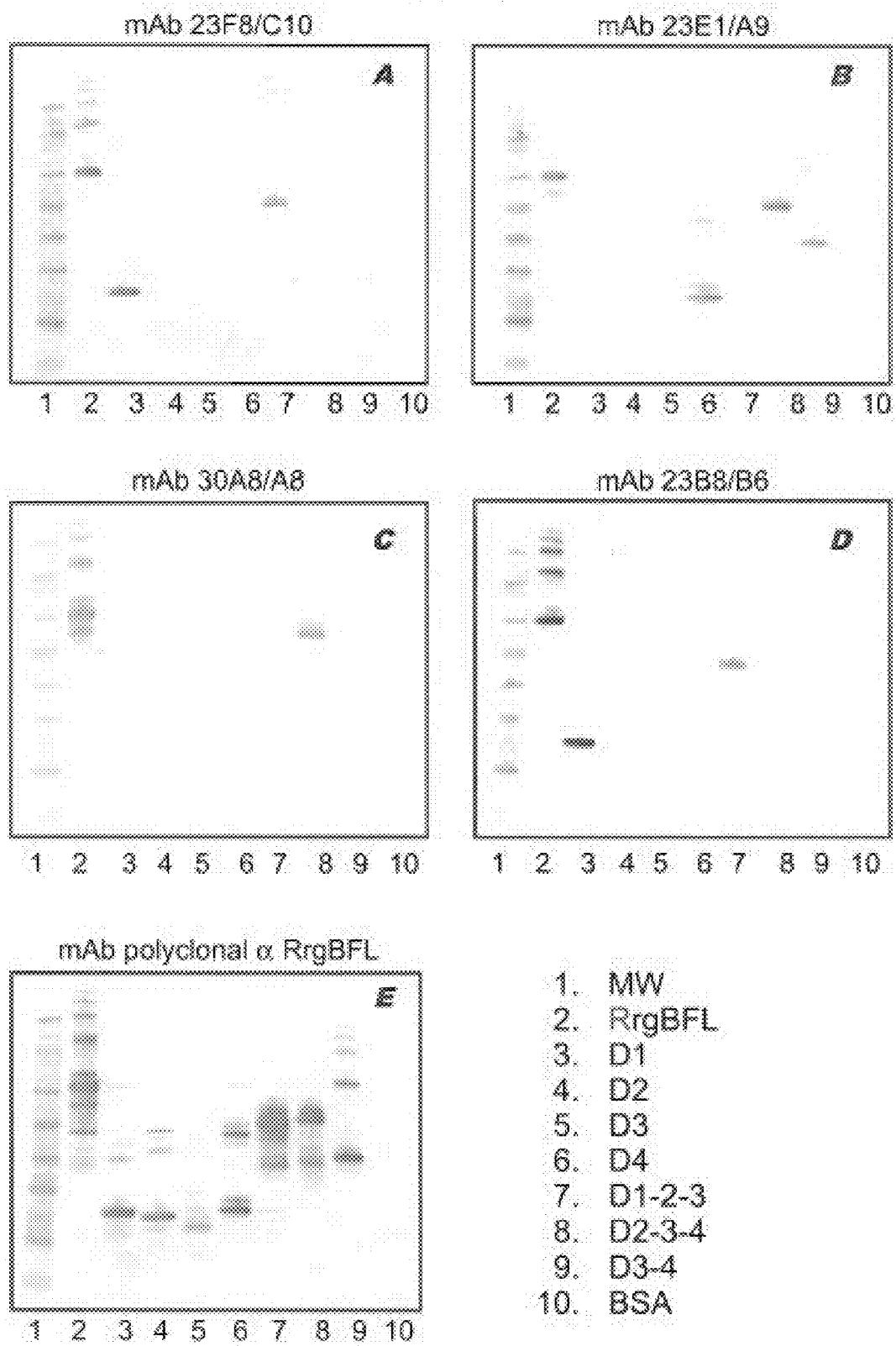
FIG. 20 shows western blot analysis of different RrgB domains (single domains D1, D2, D3 and D4 and multi-domain fragments D1-3, D2-4, D3-4) tested for binding with each of four protective mAbs raised against TIGR4 RrgB.

Based on passive protection studies, useful fragments of RrgB may retain epitopes from at least domains D1 and/or D4. As shown in FIG. 20, antibodies have been raised that bind to domain D1, domain D4 and a fragment containing domains D2 to D4. Accordingly, preferred fragments include domain D1, domain D4 and a fragment containing domains D2 to D4.

A suitable fragment of SEQ ID NO: 1 is SEQ ID NO: 4.
A suitable fragment of SEQ ID NO: 2 is SEQ ID NO: 5.
A suitable fragment of SEQ ID NO: 3 is SEQ ID NO: 6.

The fragment of at least x contiguous amino acids from SEQ ID NO: 1 should not also be present within SEQ ID NO: 2 or within SEQ ID NO: 3. Similarly, the fragment of at least y contiguous amino acids from SEQ ID NO: 2 should not also be present within SEQ ID NO: 1 or within SEQ ID NO: 3. Similarly, the fragment of at least z contiguous amino acids from SEQ ID NO: 3 should not also be present within SEQ ID NO: 1 or within SEQ ID NO: 2. In some embodiments, therefore: a fragment of SEQ ID NO: 1 is preferably from between amino acids 31-614 of SEQ ID NO: 1; a fragment of SEQ ID NO: 2 is preferably from between amino acids 31-593 of SEQ ID NO: 2; and a fragment of SEQ ID NO: 3 is preferably from between amino acids 31-603 of SEQ ID NO: 3. The fragment of at least x contiguous amino acids from SEQ ID NO: 1 may also be present in any one of SEQ ID NOs: 85, 88 and/or 89. Similarly, the fragment of at least y contiguous amino acids from SEQ ID NO: 2 may also be present in any one of SEQ ID NOs: 86, 90, 91, 94 and/or 96. Similarly, the fragment of at least z contiguous amino acids from SEQ ID NO: 3 may also be present in any one of SEQ ID NOs: 87, 92, 93 and/or 95. In some embodiments, when a fragment from one of SEQ ID NOs: 1 to 3 is aligned as a contiguous sequence against the other two SEQ ID NOs, the identity between the fragment and each of the other two SEQ ID NOs is less than 75% e.g. less than 60%, less than 50%, less than 40%, less than 30%.

Based on epitope mapping studies, an epitope of SEQ ID NO:1 has been identified between residues 32 and 141 of SEQ ID NO:1, more specifically between residues 55 and 89 of SEQ ID NO:1. Useful fragments of SEQ ID NO:1 therefore include residues 32 to 141 of SEQ ID NO:1 and residues 55 to 89 of SEQ ID NO:1.

A polypeptide comprising the first amino acid sequence will, when administered to a subject, elicit an antibody response comprising antibodies that bind to the wild-type pneumococcus protein having amino acid sequence SEQ ID NO: 1 (strain TIGR4). In some embodiments these antibodies do not bind to the wild-type pneumococcus protein having amino acid sequence SEQ ID NO: 2 or to the wild-type pneumococcus protein having amino acid sequence SEQ ID NO: 3.

A polypeptide comprising the second amino acid sequence will, when administered to a subject, elicit an antibody response comprising antibodies that bind to the wild-type pneumococcus protein having amino acid sequence SEQ ID NO: 2 (strain Finland[6B]-12). In some embodiments these antibodies do not bind to the wild-type pneumococcus protein having amino acid sequence SEQ ID NO: 1 or to the wild-type pneumococcus protein having amino acid sequence SEQ ID NO: 3.

A polypeptide comprising the third amino acid sequence will, when administered to a subject, elicit an antibody response comprising antibodies that bind to the wild-type pneumococcus protein having amino acid sequence SEQ ID NO: 3 (strain Taiwan[23F]-15). In some embodiments these antibodies do not bind to the wild-type pneumococcus protein having amino acid sequence SEQ ID NO: 1 or to the wild-type pneumococcus protein having amino acid sequence SEQ ID NO: 2.

Although the first, second and third amino acid sequences may share some sequences in common, overall they have different amino acid sequences.

Where the invention uses only two RrgB clades a composition or polypeptide can include both: (a) a first amino acid sequence as defined above; and (b) a second amino acid sequence as defined above. In an alternative embodiment the composition includes both: (a) a first amino acid sequence as defined above; and (b) a third amino acid sequence as defined above. In an alternative embodiment the composition includes both: (a) a second amino acid sequence as defined above; and (b) a third amino acid sequence as defined above.

Amino acid sequences used with the invention, may, compared to SEQ ID NOs: 1, 2 or 3, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may have one or more (e.g. 1, 2, 3, 4, 5, 6, 7, 8, 9, 10, etc.) single amino acid deletions relative to a reference sequence. The polypeptides may also include one or more (e.g. 1, 2, 3, 4, 5, 6, 7, 8, 9, 10, etc.) insertions (e.g. each of 1, 2, 3, 4 or 5 amino acids) relative to a reference sequence.

A polypeptide used with the invention may comprise an amino acid sequence that:

(a) is identical (i.e. 100% identical) to SEQ ID NO: 1, 2 or 3;
(b) shares sequence identity SEQ ID NO: 1, 2 or 3;
(c) has 1, 2, 3, 4, 5, 6, 7, 8, 9 or 10 (or more) single amino acid alterations (deletions, insertions, substitutions), which may be at separate locations or may be contiguous, as compared to the sequences of (a) or (b); and
(d) when aligned SEQ ID 1, 2 or 3 using a pairwise alignment algorithm, each moving window of x amino acids from N-terminus to C-terminus (such that for an alignment that extends to p amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [5], using default parameters (e.g. with Gap opening penalty=10.0, and with Gap extension penalty=0.5, using the EBLOSUM62 scoring matrix). This algorithm is conveniently implemented in the needle tool in the EMBOSS package [6].

Within group (c), deletions or substitutions may be at the N-terminus and/or C-terminus, or may be between the two termini. Thus a truncation is an example of a deletion. Truncations may involve deletion of up to 40 (or more) amino acids at the N-terminus and/or C-terminus.

In general, when a polypeptide of the invention comprises a sequence that is not identical to a complete pneumococcal sequence from SEQ ID NOs: 1 to 3 (e.g. when it comprises a sequence listing with <100% sequence identity thereto, or when it comprises a fragment thereof), it is preferred in each individual instance that the polypeptide can elicit an antibody that recognises the complete pneumococcal sequence.

For reference, SEQ ID NOs: 1 to 3 and 85 to 96 are 15 unique RrgB sequences which have been identified in 45 different strains. Any of these sequences can be used for implementing the invention. Thus, for example: a first polypeptide for use with the invention could comprise any one of SEQ ID NOs listed in group (1) below; a second polypeptide for use with the invention could comprise any one of SEQ ID NOs listed in group (2) below; and a third polypeptide for use with the invention could comprise any one of SEQ ID NOs listed in group (3) below. Groups (1) to (3) are as follows:

(1) SEQ ID NOs: 1, 85, 88, 89
(2) SEQ ID NOs: 2, 86, 90, 91, 94, 96
(3) SEQ ID NOs: 3, 87, 92, 93, 95

Hybrid Polypeptides

Different RrgB clades used in the invention do not have to be present as separate polypeptides but can instead be expressed as a single polypeptide chain (a 'hybrid' polypeptide or 'chimera'). Hybrid polypeptides offer two main advantages: first, a polypeptide that may be unstable or poorly expressed on its own can be assisted by adding a suitable hybrid partner that overcomes the problem; second, commercial manufacture is simplified as only one expression and purification need to be employed in order to produce two polypeptides which are both antigenically useful.

Hybrid polypeptides can include sequences from only RrgB antigens but in other embodiments can include non-RrgB antigens (usually pneumococcal non-RrgB antigens), such as other pilus subunits. If non-RrgB antigens are present these may be to the N-terminus of any two RrgB sequences, to the C-terminus of any two RrgB sequences, or may be between two RrgB sequences.

Different hybrid polypeptides may be mixed together in a single formulation. Hybrids may be combined with non-hybrid RrgB antigens or other non-RrgB antigens.

Hybrid polypeptides may be represented by the formula $NH_2$-A-{-X-L-}$_n$-B—COOH.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {—X-L-}, linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG (SEQ ID NO: 7) or GSGSGGGG (SEQ ID NO: 8), with the Gly-Ser dipeptide being formed from a BamHI restriction site, thus aiding cloning and manipulation, and the (Gly)$_4$ tetrapeptide being a typical poly-glycine linker. Other suitable linkers, particularly for use as the final $L_n$, are a Leu-Glu dipeptide or Gly-Ser. Linkers will usually contain at least one glycine residue to facilitate structural flexibility e.g. a -L- moiety may contain 1, 2, 3, 4, 5, 6, 7, 8, 9, 10 or more glycine residues. Such glycines may be arranged to include at least two consecutive glycines in a Gly-Gly dipeptide sequence, or a longer oligo-Gly sequence i.e. $Gly_n$ where n=2, 3, 4, 5, 6, 7, 8, 9, 10 or more.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue. In a nascent polypeptide the -A- moiety can provide the polypeptide's N-terminal methionine (formyl-methionine, fMet, in bacteria). One or more amino acids may be cleaved from the N-terminus of a nascent -A- moiety, however, such that the -A- moiety in a mature polypeptide of the invention does not necessarily include a N-terminal methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more, such as SEQ ID NO: 9), or sequences which enhance protein stability. Other suitable C-terminal amino acid sequences will be apparent to those skilled in the art, such as a glutathione-S-transferase, thioredoxin, 14 kDa fragment of *S. aureus* protein A, a biotinylated peptide, a maltose-binding protein, an enterokinase flag, etc.

It is preferred that -A-, —B— and -L- sequences do not include a sequence that shares 10 or more contiguous amino acids in common with a human polypeptide sequence.

In some embodiments, a -L- moiety comprises a non-RrgB antigen. In some embodiments, the -A- moiety comprises a non-RrgB antigen, and in some the —B— moiety comprises a non-RrgB antigen.

The invention also provides nucleic acid which encodes a hybrid polypeptide of the invention.

Of the various A, B, X, and L moieties, useful combinations include, but are not limited to:

| SEQ ID | A | X1* | L1* | X2* | L2* | X3* | L3 | B* |
|---|---|---|---|---|---|---|---|---|
| 11 | M-A-S- | 4 | 8 | 5 | 10 | 6 | -L-G- | 9 |
| 13 | M-A-S- | 4 | 8 | 6 | 10 | 5 | -L-G- | 9 |
| 15 | M-A-S- | 6 | 8 | 5 | 10 | 4 | -L-G- | 9 |
| 17 | M-A-S- | 6 | 8 | 4 | 10 | 5 | -L-G- | 9 |
| 19 | M-A-S- | 5 | 8 | 6 | 10 | 4 | -L-G- | 9 |
| 21 | M-A-S- | 5 | 8 | 4 | 10 | 6 | -L-G- | 9 |

*Number indicates SEQ ID NO:

Thus examples of hybrids of the invention include polypeptides comprising an amino acid sequence selected from the group consisting of: SEQ ID NO: 11 (encoded by SEQ ID NO: 12); SEQ ID NO: 13 (encoded by SEQ ID NO: 14); SEQ ID NO: 15 (encoded by SEQ ID NO: 16); SEQ ID NO: 17 (encoded by SEQ ID NO: 18); SEQ ID NO: 19 (encoded by SEQ ID NO: 20); SEQ ID NO: 21 (encoded by SEQ ID NO: 22).

The invention provides a polypeptide comprising an amino acid sequence having at least i % sequence identity to any one of SEQ ID NOs: 11, 13, 15, 17, 19 or 21. The value of i may be selected from 50, 60, 70, 80, 85, 90, 95, 96, 97, 98, 99 or more.

Polypeptides

Polypeptides used with the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis [7,8]. Solid-phase peptide synthesis is particularly preferred, such as methods based on tBoc or Fmoc [9] chemistry. Enzymatic synthesis [10] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [11]. Where D-amino acids are included, however, it is preferred to use chemical synthesis. Polypeptides may have covalent modifications at the C-terminus and/or N-terminus.

Polypeptides can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides are preferably provided in purified or substantially purified form i.e. substantially free from other polypeptides (e.g. free from naturally-occurring polypeptides), particularly from other pneumococcal or host cell polypeptides, and are generally at least about 50% pure (by weight), and usually at least about 90% pure i.e. less than about 50%, and more preferably less than about 10% (e.g. 5% or less) of a composition is made up of other expressed polypeptides.

Polypeptides may be attached to a solid support. Polypeptides may comprise a detectable label (e.g. a radioactive or fluorescent label, or a biotin label).

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains. Polypeptides can be naturally or non-naturally glycosylated (i.e. the polypeptide has a glycosylation pattern that differs from the glycosylation pattern found in the corresponding naturally occurring polypeptide).

The invention provides a process for producing polypeptides of the invention, comprising culturing a host cell of to the invention under conditions which induce polypeptide expression. Although expression of the polypeptide may take place in a *Streptococcus*, the invention will usually use a heterologous host for expression. The heterologous host may be prokaryotic (e.g. a bacterium) or eukaryotic. It will usually be *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

The invention also provides a process for producing a polypeptide of the invention, wherein the polypeptide is synthesised in part or in whole using chemical means.

The invention also provides a composition comprising two or more polypeptides of the invention.

Nucleic Acids

The invention also provides a nucleic acid comprising a nucleotide sequence encoding a hybrid polypeptide of the invention. The invention also provides nucleic acid comprising nucleotide sequences having sequence identity to such nucleotide sequences. Such nucleic acids include those using alternative codons to encode the same amino acid.

The invention also provides nucleic acid which can hybridize to these nucleic acids. Hybridization reactions can be performed under conditions of different "stringency". Conditions that increase stringency of a hybridization reaction of widely known and published in the art. Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1× SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art [e.g. see refs 12 & 239, etc.].

The invention includes nucleic acid comprising sequences complementary to these sequences (e.g. for antisense or probing, or for use as primers).

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably provided in purified or substantially purified form i.e. substantially free from other nucleic acids (e.g. free from naturally-occurring nucleic acids), particularly from other pneumococcal or host cell nucleic acids, generally being at least about 50% pure (by weight), and usually at least about 90% pure. Nucleic acids of the invention are preferably pneumococcal nucleic acids.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acid of the invention may be attached to a solid support (e.g. a bead, plate, filter, film, slide, microarray support, resin, etc.). Nucleic acid of the invention may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T).

Nucleic acids of the invention can be used, for example: to produce polypeptides in vitro or in vivo; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesised in part or in whole using chemical means.

The invention provides vectors comprising nucleotide sequences of the invention (e.g. cloning or expression vectors) and host cells transformed with such vectors.

Immunogenic Compositions

Mixtures and hybrid polypeptides of the invention are useful as active ingredients in immunogenic compositions. Such immunogenic compositions may be useful as vaccines. These vaccines may either be prophylactic (i.e. to prevent infection) or therapeutic (i.e. to treat infection), but will typically be prophylactic.

Compositions may thus be pharmaceutically acceptable. They will usually include components in addition to the antigens e.g. they typically include one or more pharmaceutical carrier(s) and/or excipient(s). A thorough discussion of such components is available in reference 234.

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention may also comprise one or more immunoregulatory agents. Preferably, one or more of the immunoregulatory agents include one or more adjuvants, for example two, three, four or more adjuvants. The adjuvants may include a TH1 adjuvant and/or a TH2 adjuvant, further discussed below.

Adjuvants which may be used in compositions of the invention include, but are not limited to:

A. Mineral-containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref 13], or mixtures of different mineral compounds, with the compounds taking any suitable form (e.g. gel, crystalline, amorphous, etc.), and with adsorption being preferred. The mineral containing compositions may also be formulated as a particle of metal salt.

The adjuvants known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as aluminum hydroxide $Al(OH)_3$, by infrared (IR) spectroscopy, in particular by the presence of an adsorption band at 1070 $cm^{-1}$ and a strong shoulder at 3090-3100 $cm^{-1}$ [chapter 9 of ref. 13]. The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminum hydroxide adjuvants. The pI of aluminum hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminum hydroxide adjuvants.

The adjuvants known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt. Hydroxyphosphates generally have a $PO_4$/Al molar ratio between 0.3 and 1.2. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls [ch. 9 of ref. 13].

The $PO_4/Al^{3+}$ molar ratio of an aluminum phosphate adjuvant will generally be between 0.3 and 1.2, preferably between 0.8 and 1.2, and more preferably 0.95±0.1. The aluminum phosphate will generally be amorphous, particularly for hydroxyphosphate salts. A typical adjuvant is amorphous aluminum hydroxyphosphate with $PO_4$/Al molar ratio between 0.84 and 0.92, included at 0.6 mg $Al^{3+}$/ml. The aluminum phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+-+}$ at pH 7.4 have been reported for aluminum phosphate adjuvants.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5 e.g. about 5.7.

Suspensions of aluminum salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

In one embodiment, an adjuvant component includes a mixture of both an aluminum hydroxide and an aluminum phosphate. In this case there may be more aluminum phosphate than hydroxide e.g. a weight ratio of at least 2:1 e.g. ≥5:1, ≥6:1, ≥7:1, ≥8:1, ≥9:1, etc.

The concentration of Al$^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of <0.85 mg/dose is preferred.

B. Oil Emulsions

Oil emulsion compositions suitable for use as adjuvants in the invention include squalene-water emulsions, such as MF59 [Chapter 10 of ref 13; see also ref. 14] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various suitable oil-in-water emulsions are known, and they typically include at least one oil and at least one surfactant, with the oil(s) and surfactant(s) being biodegradable (metabolisable) and biocompatible. The oil droplets in the emulsion are generally less than 5 μm in diameter, and advantageously the emulsion comprises oil droplets with a submicron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticalc and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene. Other preferred oils are the tocopherols (see below). Oil in water emulsions comprising squalene are particularly preferred. Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Preferred surfactants for including in the emulsion are Tween 80 (polyoxyethylene sorbitan monooleate), Span 85 (sorbitan trioleate), lecithin and Triton X-100. As mentioned above, detergents such as Tween 80 may contribute to the thermal stability seen in the examples below.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [15-17], as described in more detail in Chapter 10 of ref. 18 and chapter 12 of ref 19. The MF59 emulsion advantageously includes citrate ions e.g. 10 mM sodium citrate buffer.

An emulsion comprising squalene, an α-tocopherol, and polysorbate 80. These emulsions may have from 2 to 10% squalene, from 2 to 10% tocopherol and from 0.3 to 3% Tween 80, and the weight ratio of squalene:tocopherol is preferably ≤1 (e.g. 0.90) as this provides a more stable emulsion. Squalene and Tween 80 may be present volume ratio of about 5:2, or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalene, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [20] (0.05-1% Thr-MDP, 5% squalane, 2.5% Pluronic L121 and 0.2% polysorbate 80). It can also be used without the Thr-MDP, as in the "AF" adjuvant [21] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [22]. The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. As described in reference 23, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 24, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [25].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [25].

An emulsion in which a saponin (e.g. QuilA or QS21) and a sterol (e.g. a cholesterol) are associated as helical micelles [26].

Antigens and adjuvants in a composition will typically be in admixture at the time of delivery to a patient. The emulsions may be mixed with antigen during manufacture, or extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1.

C. Saponin Formulations [Chapter 22 of Ref. 13]

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 27. Saponin formulations may also comprise a sterol, such as cholesterol [28].

Combinations of saponins and cholesterols can be used to form unique particles called immunostimulating complexes (ISCOMs) [chapter 23 of ref. 13]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 28-30. Optionally, the ISCOMS may be devoid of additional detergent [31].

A review of the development of saponin based adjuvants can be found in refs. 32 & 33.

D. Virosomes and Virus-like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 34-39. Virosomes are discussed further in, for example, ref. 40

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 41. Such "small particles" of 3dMPL are small enough to be sterile filtered through a 0.22 μm membrane [41]. Other non-toxic LPS derivatives include monophosphoryl lipid A mimics, such as aminoalkyl glucosaminide phosphate derivatives e.g. RC-529 [42,43].

Lipid A derivatives include derivatives of lipid A from *Escherichia coli* such as OM-174. OM-174 is described for example in refs. 44 & 45.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 46, 47 and 48 disclose possible analog substitutions e.g. replacement of guanosine with 2'-deoxy-7-deazaguanosine. The adjuvant effect of CpG oligonucleotides is further discussed in refs. 49-54.

The CpG sequence may be directed to TLR9, such as the motif GTCGTT or TTCGTT [55]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 56-58. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 55 & 59-61.

A particularly useful adjuvant based around immunostimulatory oligonucleotides is known as IC-31™ [62]. Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 80). The polycationic polymer may be a peptide comprising 11-mer amino acid sequence KLKLLLLLKLK (SEQ ID NO: 81).

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 63 and as parenteral adjuvants in ref. 64. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 65-72. A useful CT mutant is or CT-E29H [73]. Numerical reference for amino acid substitutions is preferably based on the alignments of the A and B subunits of ADP-ribosylating toxins set forth in ref. 74, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [75], etc.) [76], interferons (e.g. interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres [77] or mucoadhesives such as cross-linked derivatives of poly(acrylic acid), polyvinyl alcohol, polyvinyl pyrrolidone, polysaccharides and carboxymethylcellulose. Chitosan and derivatives thereof may also be used as adjuvants in the invention [78].

H. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 13)

Examples of liposome formulations suitable for use as adjuvants are described in refs. 79-81.

J. Polyoxyethylene Ether and Polyoxyethylene Ester Formulations

Adjuvants suitable for use in the invention include polyoxyethylene ethers and polyoxyethylene esters [82]. Such formulations further include polyoxyethylene sorbitan ester surfactants in combination with an octoxynol [83] as well as polyoxyethylene alkyl ethers or ester surfactants in combination with at least one additional non-ionic surfactant such as an octoxynol [84]. Preferred polyoxyethylene ethers are selected from the following group: polyoxyethylene-9-lauryl ether (laureth 9), polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 85 and 86.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 87 and 88.

The invention may also comprise combinations of aspects of one or more of the adjuvants identified above. For example, the following adjuvant compositions may be used in the invention: (1) a saponin and an oil-in-water emulsion [89]; (2) a saponin (e.g. QS21)+a non-toxic LPS derivative (e.g. 3dMPL) [90]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [91]; (5) combinations of 3dMPL with, for example, QS21 and/or oil-in-water emulsions [92]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 13.

The use of an aluminum hydroxide and/or aluminum phosphate adjuvant is useful, particularly in children, and antigens are generally adsorbed to these salts. Squalene-in-water emulsions are also preferred, particularly in the elderly. Useful adjuvant combinations include combinations of Th1 and Th2 adjuvants such as CpG & alum or resiquimod & alum. A combination of aluminum phosphate and 3dMPL may be used.

The compositions of the invention may elicit both a cell mediated immune response as well as a humoral immune response.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-62 ), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminum salts are preferred TH2 adjuvants for use in the invention.

A composition may include a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Pneumococcal infections can affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Nucleic Acid Immunisation

The immunogenic compositions described above include polypeptide antigens from S. pneumoniae. In all cases, however, the polypeptide antigens can be replaced by nucleic acids (typically DNA) encoding those polypeptides, to give compositions, methods and uses based on nucleic acid immunisation [93 to 100

The nucleic acid encoding the immunogen is expressed in vivo after delivery to a patient and the expressed immunogen then stimulates the immune system. The active ingredient will typically take the form of a nucleic acid vector comprising: (i) a promoter; (ii) a sequence encoding the immunogen, operably linked to the promoter; and optionally (iii) a selectable marker. Preferred vectors may further comprise (iv) an origin of replication; and (v) a transcription terminator downstream of and operably linked to (ii). In general, (i) & (v) will be eukaryotic and (iii) & (iv) will be prokaryotic.

Preferred promoters are viral promoters e.g. from cytomegalovirus (CMV). The vector may also include transcriptional regulatory sequences (e.g. enhancers) in addition to the promoter and which interact functionally with the promoter. Preferred vectors include the immediate-early CMV enhancer/promoter, and more preferred vectors also include CMV intron A. The promoter is operably linked to a downstream sequence encoding an immunogen, such that expression of the immunogen-encoding sequence is under the promoter's control.

Where a marker is used, it preferably functions in a microbial host (e.g. in a prokaryote, in a bacteria, in a yeast). The marker is preferably a prokaryotic selectable marker (e.g. transcribed under the control of a prokaryotic promoter). For convenience, typical markers are antibiotic resistance genes.

The vector is preferably an autonomously replicating episomal or extrachromosomal vector, such as a plasmid.

The vector preferably comprises an origin of replication. It is preferred that the origin of replication is active in prokaryotes but not in eukaryotes.

Preferred vectors thus include a prokaryotic marker for selection of the vector, a prokaryotic origin of replication, but a eukaryotic promoter for driving transcription of the immunogen-encoding sequence. The vectors will therefore (a) be amplified and selected in prokaryotic hosts without polypeptide expression, but (b) be expressed in eukaryotic hosts without being amplified. This arrangement is ideal for nucleic acid immunization vectors.

The vector may comprise a eukaryotic transcriptional terminator sequence downstream of the coding sequence. This can enhance transcription levels. Where the coding sequence does not have its own, the vector preferably comprises a polyadenylation sequence. A preferred polyadenylation sequence is from bovine growth hormone.

The vector may comprise a multiple cloning site

In addition to sequences encoding the immunogen and a marker, the vector may comprise a second eukaryotic coding sequence. The vector may also comprise an IRES upstream of said second sequence in order to permit translation of a second eukaryotic polypeptide from the same transcript as the immunogen. Alternatively, the immunogen-coding sequence may be downstream of an IRES.

The vector may comprise unmethylated CpG motifs e.g. unmethylated DNA sequences which have in common a cytosine preceding a guanosine, flanked by two 5' purines and two 3' pyrimidines. In their unmethylated form these DNA motifs have been demonstrated to be potent stimulators of several types of immune cell.

Vectors may be delivered in a targeted way. Receptor-mediated DNA delivery techniques are described in, for example, references 101 to 106. Therapeutic compositions containing a nucleic acid are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts of vector or the same amounts re-administered in a successive protocol of administrations, or several administrations to different adjacent or close tissue portions may be required to effect a positive therapeutic outcome. In all cases, routine experimentation in clinical trials will determine specific ranges for optimal therapeutic effect.

Vectors can be delivered using gene delivery vehicles. The gene delivery vehicle can be of viral or non-viral origin (see generally references 107 to 110).

Viral-based vectors for delivery of a desired nucleic acid and expression in a desired cell are well known in the art. Exemplary viral-based vehicles include, but are not limited to, recombinant retroviruses (e.g. references 111 to 121), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532); hybrids or chimeras of these viruses may also be used), poxvirus vectors (e.g. vaccinia, fowlpox, canarypox, modified vaccinia Ankara, etc.), adenovirus vectors, and adeno-associated virus (AAV) vectors (e.g. see refs. 122 to 127). Administration of DNA linked to killed adenovirus [128] can also be employed.

Non-viral delivery vehicles and methods can also be employed, including, but not limited to, polycationic condensed DNA linked or unlinked to killed adenovirus alone [e.g. 128], ligand-linked DNA [129], eukaryotic cell delivery vehicles cells [e.g. refs. 130 to 134] and nucleic charge neutralization or fusion with cell membranes. Naked DNA can also be employed. Exemplary naked DNA introduction methods are described in refs. 135 and 136. Liposomes (e.g. immunoliposomes) that can act as gene delivery vehicles are described in refs. 137 to 141. Additional approaches are described in references 142 & 143.

Further non-viral delivery suitable for use includes mechanical delivery systems such as the approach described in ref. 143. Moreover, the coding sequence and the product of expression of such can be delivered through deposition of photopolymerized hydrogel materials or use of ionizing radiation [e.g. refs. 144 & 145]. Other conventional methods for gene delivery that can be used for delivery of the coding sequence include, for example, use of hand-held gene transfer particle gun [146] or use of ionizing radiation for activating transferred genes [144 & 145].

Delivery of DNA using PLG {poly(lactide-co-glycolide)} microparticles is a particularly preferred method e.g. by adsorption to the microparticles, which are optionally treated to have a negatively-charged surface (e.g. treated with SDS) or a positively-charged surface (e.g. treated with a cationic detergent, such as CTAB).

Methods of Treatment, and Administration of the Vaccine

The invention also provides a method for raising an immune response in a mammal comprising the step of administering an effective amount of an immunogenic composition of the invention. The immune response is preferably protective and preferably involves antibodies and/or cell-mediated immunity. The method may raise a booster response.

The invention also provides at least two different RrgB clades for combined use as a medicament e.g. for use in raising an immune response in a mammal.

The invention also provides the use of at least two different RrgB clades in the manufacture of a medicament for raising an immune response in a mammal.

By raising an immune response in the mammal by these uses and methods, the mammal can be protected against pneumococcal disease and/or infection e.g. against pneumococcal meningitis.

The invention also provides a delivery device pre-filled with an immunogenic composition of the invention.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

One way of checking efficacy of therapeutic treatment involves monitoring pneumococcal infection after administration of the compositions of the invention. One way of checking efficacy of prophylactic treatment involves testing post-immunisation sera in standard tests; for example, sera can be tested in an opsonophagocytic killing assay (OPKA), with the ability to opsonise bacteria indicating protective efficacy. Another way of checking efficacy of prophylactic treatment involves post-immunisation challenge in an animal model of pneumococcal infection, e.g., guinea pigs or mice. One such model is described in reference 147. Another way of assessing the immunogenicity of the compositions of the present invention is to express the polypeptides recombinantly for screening patient sera or mucosal secretions by immunoblot and/or microarrays. A positive reaction between the polypeptide and the patient sample indicates that the patient has mounted an immune response to the polypeptide in question. This method may also be used to identify immunodominant antigens and/or epitopes within antigens.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal or transcutaneous, intranasal, ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, etc.

Combinations

A composition useful for immunisation comprises at least two RrgB clades, either as a hybrid polypeptide or as separate polypeptides. In addition, a composition may include: (i) one or more further polypeptides that elicit antibody responses against pneumococcal proteins, particularly against pneumococcal proteins other than RrgB; (ii) a capsular saccharide from pneumococcus; and/or (iii) one or more further immunogens that elicit antibody responses that recognise epitopes on non-pneumococcal organisms. As detailed above, compositions of the invention comprising combinations such as these can optionally comprise one or more adjuvants, for example two or more adjuvants. Suitable adjuvants include mineral salts such as aluminum salts, and squalene-water emulsions such as MF59.

Combinations with Further Polypeptide Antigens [148]

RrgB polypeptides from one or more clades may be combined with one or more (i.e. 1, 2, 3, 4, 5, 6, 7, 8, 9, 10, 11, 12, or all 13) polypeptide antigens selected from the group consisting of: (1) a spr0057 antigen; (2) a spr0565 antigen; (3) a spr1098 antigen; (4) a spr1416 antigen; (5) a spr1418 antigen; (6) a spr0867 antigen; (7) a spr1431 antigen; (8) a spr1739 antigen; (9) a spr2021 antigen; (10) a spr0096 antigen; (11) a spr1707 antigen; (12) a spr1875 antigen; and/or (13) a spr0884 antigen.

Similarly, RrgB polypeptides from one or more clades may be combined with one or more (i.e. 1, 2, 3, 4, 5, 6, 7, 8, 9, 10, 11, 12, 13, 14, 15, 16, 17, 18, 19, or all 20) polypeptide antigens selected from the group consisting of: (1) ClpP; (2) LytA; (3) PhtA; (4) PhtB; (5) PhtD; (6) PhtE; (7) ZmpB; (8) CbpD; (9) CbpG; (10) PvaA; (11) CPL1; (12) PspC; (13) PspA; (14) PsaA; (15) PrtA; (16) Sp133; (17) PiaA; (18) PiuA; (19) CbiO; and/or (20) 30S ribosomal protein S8.

These further antigens may be added as separate polypeptides. As an alternative, they may be added as hybrids e.g. a spr0057-spr0096 hybrid or a spr0096-spr2021 hybrid, a spr0565-PhtD hybrid, etc. As a further alternative, they may be fused to a RrgB polypeptide sequence to provide a hybrid polypeptide e.g. a RrgB-spr0057 hybrid.

For example, a chimeric RrgB polypeptide including two or three RrgB clades may be combined with: (a) a mixture of spr0057, spr0096 and spr2021; (b) a mixture of spr0057, spr0565 and spr2021; (c) a mixture of spr0057, spr0096 and spr0565; (d) a mixture of spr0057, spr0096, spr0565 and spr2021; (e) a mixture of spr1418, spr0884 and spr0096; (f) a mixture of spr1418, spr0884 and spr2021; (g) a mixture of spr1418, spr0884, spr0096 and spr2021; (h) a mixture of spr0884, spr1416 and spr0057; (h) a mixture of spr0884, spr1416 and spr0096; (h) a mixture of spr0884, spr1416, spr0057 and spr0096; or (i) a mixture of spr1418, spr1431 and spr0565. Where these mixtures include both spr0057 and spr0096, a hybrid protein can be used e.g. comprising SEQ ID NO: 82 (see SEQ ID NO: 200 of ref. 148) or comprising SEQ ID NO: 83. Where these mixtures include both spr0096 and spr2021, a hybrid protein can be used e.g. comprising SEQ ID NO: 84 (see SEQ ID NO: 205 of ref. 148).

In a further example, a chimeric RrgB polypeptide including two or three RrgB clades may be combined with a pneumococcal immunogen comprising an spr2021 (also referred to as SP2216) antigen, an SP1732 antigen and optionally a PsaA antigen. A suitable pneumococcal immunogen of this sort is the immunogen disclosed in reference 159 that comprises the antigens "SP2216-1" (SEQ ID NO: 1 in reference 159; SEQ ID NO: 97 herein), "SP 1732-3" (SEQ ID NO: 2 in reference 159; SEQ ID NO: 98 herein) and, optionally, PsaA (SEQ ID NO: 3 in reference 159; SEQ ID NO: 99 herein). Polypeptides comprising immunogenic fragments of these SEQ ID NOs can be used in place of the actual disclosed SEQ ID NOs e.g. comprising at least one immunogenic fragment from each of SEQ ID NOs 97 & 98. Polypeptides comprising variants of spr2021 (SP2216), SP1732 and optionally PsaA can also be used in place of the actual disclosed SEQ ID NOs e.g. comprising at least one variant from each of SEQ ID NOs 97 and 98. Examples of this combination include the combination of a pneumococcal immunogen as disclosed in reference 159 with a chimeric RrgB polypeptide comprising chimera II-I-III (e.g. SEQ ID NO: 21) or chimera III-II-I (e.g. SEQ ID NO:15) as detailed below. The further antigens may be added as separate polypeptides. As an alternative, they may be added as hybrids e.g. a spr2021-SP1732 hybrid or a spr2021-SP1732-PsaA hybrid. As a further alternative, they may be fused to a RrgB polypeptide sequence, e.g. a chimeric RrgB polypeptide, to provide a hybrid polypeptide e.g. a RrgB-spr2021-SP1732 hybrid. As detailed above, compositions of the invention comprising combinations such as these can optionally comprise one or more adjuvants. Suitable adjuvants include mineral salts such as aluminum salts, and squalene-water emulsions such as MF59.

Any of these combinations may also include one or more pneumococcal capsular saccharide(s), which will typically be conjugated to carrier protein(s). Further information about such saccharides and conjugation is provided below.

The original 'spr0057' sequence was annotated in reference 149 as 'Beta-N-acetyl-hexosaminidase precursor' (see GI:15902101). For reference purposes, the amino acid sequence of full length spr0057 as found in the R6 strain is given as SEQ ID NO: 23 herein. Preferred spr0057 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 23; and/or (b) comprising a fragment of at least 'n' consecutive amino acids of SEQ ID NO: 23, wherein 'n' is 7 or more (e.g. 8, 10, 12, 14, 16, 18, 20, 25, 30, 35, 40, 50, 60, 70, 80, 90, 100, 150, 200, 250 or more). These spr0057 proteins include variants of SEQ ID NO: 23. Preferred fragments of (b) comprise an epitope from SEQ ID NO: 23. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 23 while retaining at least one epitope of SEQ ID NO: 23. Other fragments omit one or more protein domains. One suitable fragment is SEQ ID NO: 38, which omits the natural leader peptide and sortase recognition sequences. Another suitable fragment is SEQ ID NO: 24, which has N-terminal and C-terminal truncations. SEQ ID NO: 27 is a variant of SEQ ID NO: 24 based on a different wild-type strain and is a useful spr0057 sequence for use with the invention.

The original 'spr0565' sequence was annotated in reference 149 as 'beta-galactosidase precursor' (see GI:15902609). For reference purposes, the amino acid sequence of full length spr0565 as found in the R6 strain is given as SEQ ID NO: 25 herein. Preferred spr0565 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 25; and/or (b) comprising a fragment of at least 'n' consecutive amino acids of SEQ ID NO: 25, wherein 'n' is 7 or more (e.g. 8, 10, 12, 14, 16, 18, 20, 25, 30, 35, 40, 50, 60, 70, 80, 90, 100, 150, 200, 250 or more). These spr0565 proteins include variants of SEQ ID NO: 25 (e.g. SEQ ID NO: 45; see below). Preferred fragments of (b) comprise an epitope from SEQ ID NO: 25. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 25 while retaining at least one epitope of SEQ ID NO: 25. Other fragments omit one or more protein domains. One suitable fragment is SEQ ID NO: 42, which omits the natural leader peptide and sortase recognition sequences. Other suitable fragments are SEQ ID NOs: 43 and 44. These shortened versions of spr0565 are particularly useful because the natural polypeptide is very long (>2000 aa).

A variant form of spr0565 is SEQ ID NO: 45 herein. The use of this variant form for immunisation is reported in reference 150 (SEQ ID NO: 178 therein). Useful spr0565 polypeptides may thus comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 45; and/or (b) comprising a fragment of at least 'n' consecutive amino acids of SEQ ID NO: 45, wherein 'n' is 7 or more (e.g. 8, 10, 12, 14, 16, 18, 20, 25, 30, 35, 40, 50, 60, 70, 80, 90, 100, 150, 200, 250 or more). These polypeptides include variants of SEQ ID NO: 45. Preferred fragments of (b) comprise an epitope from SEQ ID NO: 45. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 45 while retaining at least one epitope of SEQ ID NO: 45. Other fragments omit one or more protein domains. Immunogenic fragments of SEQ ID NO: 45 are identified in table 1 of reference 150.

The original 'spr1098' sequence was annotated in reference 149 as 'Sortase' (see GI:15903141). For reference purposes, the amino acid sequence of full length spr1098 as found in the R6 strain is given as SEQ ID NO: 26 herein. Preferred spr1098 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 26; and/or (b) comprising a fragment of at least 'n' consecutive amino acids of SEQ ID NO: 26, wherein 'n' is 7 or more (e.g. 8, 10, 12, 14, 16, 18, 20, 25, 30, 35, 40, 50, 60, 70, 80, 90, 100, 150, 200, 250 or more). These spr1098 proteins include variants of SEQ ID NO: 26. Preferred fragments of (b) comprise an epitope from SEQ ID NO: 26. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 26 while retaining at least one epitope of SEQ ID NO: 26. Other fragments omit one or more protein domains. One suitable fragment is SEQ ID NO: 46, which omits the natural leader peptide sequence.

The original 'spr1416' sequence was annotated in reference 149 as 'hypothetical protein' (see GI:15903459). For reference purposes, the amino acid sequence of full length spr1416 as found in the R6 strain is given as SEQ ID NO: 28 herein. Preferred spr1416 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 28; and/or (b) comprising a fragment of at least 'n' consecutive amino acids of SEQ ID NO: 28, wherein 'n' is 7 or more (e.g. 8, 10, 12, 14, 16, 18, 20, 25, 30, 35, 40, 50, 60, 70, 80, 90, 100, 150, 200, 250 or more). These spr1416 proteins include variants of SEQ ID NO: 28. Preferred fragments of (b) comprise an epitope from SEQ ID NO: 28. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 28 while retaining at least one epitope of SEQ ID NO: 28. Other fragments omit one or more protein domains.

The original 'spr1418' sequence was annotated in reference 149 as 'hypothetical protein' (see GI:15903461). For reference purposes, the amino acid sequence of full length spr1418 as found in the R6 strain is given as SEQ ID NO: 29 herein. Preferred spr1418 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 29; and/or (b) comprising a fragment of at least 'n' consecutive amino acids of SEQ ID NO: 29, wherein 'n' is 7 or more (e.g. 8, 10, 12, 14, 16, 18, 20, 25, 30, 35, 40, 50, 60, 70, 80, 90, 100, 150, 200, 250 or more). These spr1418 proteins include variants of SEQ ID NO: 29. Preferred fragments of (b) comprise an epitope from SEQ ID NO: 29. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 29 while retaining at least one epitope of SEQ ID NO: 29. Other fragments omit one or more protein domains.

The original 'spr0867' sequence was annotated in reference 149 as 'Endo-beta-N-acetylglucosaminidase' (see GI:15902911). For reference purposes, the amino acid sequence of full length spr0867 as found in the R6 strain is given as SEQ ID NO: 30 herein. Preferred spr0867 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 30; and/or (b) comprising a fragment of at least 'n' consecutive amino acids of SEQ ID NO: 30, wherein 'n' is 7 or more (e.g. 8, 10, 12, 14, 16, 18, 20, 25, 30, 35, 40, 50, 60, 70, 80, 90, 100, 150, 200, 250 or more). These spr0867 proteins include variants of SEQ ID NO: 30. Preferred fragments of (b) comprise an epitope from SEQ ID NO: 30. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 30 while retaining at least one epitope of SEQ ID NO: 30. Other fragments omit one or more protein domains. One suitable fragment is SEQ ID NO: 48, which omits the natural leader peptide sequence.

The original 'spr1431' sequence was annotated in reference 149 as '1,4-beta-N-acetylmuramidase' (see GI:15903474). It is also known as 'LytC', and its use for immunisation is reported in reference 171. For reference purposes, the amino acid sequence of full length spr1431 as found in the R6 strain is given as SEQ ID NO: 31 herein. Preferred spr1431 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 31; and/or (b) comprising a fragment of at least 'n' consecutive amino acids of SEQ ID NO: 31, wherein 'n' is 7 or more (e.g. 8, 10, 12, 14, 16, 18, 20, 25, 30, 35, 40, 50, 60, 70, 80, 90, 100, 150, 200, 250 or more). These spr1431 proteins include variants of SEQ ID NO: 31. Preferred fragments of (b) comprise an epitope from SEQ ID NO: 31. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 31 while retaining at least one epitope of SEQ ID NO: 31. Other fragments omit one or more protein domains. One suitable fragment is SEQ ID NO: 49, which omits the natural leader peptide sequence.

The 'spr1739' polypeptide is pneumolysin (e.g. see GI:15903781). For reference purposes, the amino acid sequence of full length spr1739 as found in the R6 strain is given as SEQ ID NO: 32 herein. Preferred spr1739 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 32; and/or (b) comprising a fragment of at least 'n' consecutive amino acids of SEQ ID NO: 32, wherein 'n' is 7 or more (e.g. 8, 10, 12, 14, 16, 18, 20, 25, 30, 35, 40, 50, 60, 70, 80, 90, 100, 150, 200, 250 or more). These spr1739 proteins include variants of SEQ ID NO: 32. Preferred fragments of (b) comprise an epitope from SEQ ID NO: 32. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 32 while retaining at least one epitope of SEQ ID NO: 32. Other fragments omit one or more protein domains. Mutant forms of pneumolysin for vaccination use are known in the art [183, 151-156], and these mutant forms may be used with the invention. Detoxification can be achieved by C-terminal truncation (e.g. see ref. 157) e.g. deleting 34 amino acids, 45 amino acids, 7 amino acids [158], etc. Further mutations, numbered according to SEQ ID NO: 32, include Pro325→Leu (e.g. SEQ ID NO: 50) and/or Trp433→Phe (e.g. SEQ ID NO: 51). These mutations may be combined with C-terminal truncations e.g. to combine a Pro325→Leu mutation with a 7-mer truncation (e.g. SEQ ID NO: 52).

The original 'spr2021' sequence was annotated in reference 149 as 'General stress protein GSP-781' (see GI:15904062). For reference purposes, the amino acid sequence of full length spr2021 as found in the R6 strain is given as SEQ ID NO: 33 herein. Preferred spr2021 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 33; and/or (b) comprising a fragment of at least 'n' consecutive amino acids of SEQ ID NO: 33, wherein 'n' is 7 or more (e.g. 8, 10, 12, 14, 16, 18, 20, 25, 30, 35, 40, 50, 60, 70, 80, 90, 100, 150, 200, 250 or more). These spr2021 proteins include variants of SEQ ID NO: 33. Preferred fragments of (b) comprise an epitope from SEQ ID NO: 33. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 33 while retaining at least one epitope of SEQ ID NO: 33. Other fragments omit one or more protein domains. One suitable fragment is SEQ ID NO: 53, which omits the natural leader peptide sequence. Reference 150 annotates spr2021 as a secreted 45kDa protein with homology to GbpB and discloses its use as an immunogen (SEQ ID NO: 243 therein; SP2216). Immunogenic fragments of spr2021 are identified in table 1 of reference 150 (page 73). Another useful fragment of spr2021 is disclosed as SEQ ID NO: 1 of reference 159 (amino acids 28-278 of SEQ ID NO: 33 herein; this useful fragment of spr2021 is provided as SEQ ID NO:97 herein; SP2216-1).

The original 'spr0096' sequence was annotated in reference 149 as 'hypothetical protein' (see GI:15902140). For reference purposes, the amino acid sequence of full length spr0096 as found in the R6 strain is given as SEQ ID NO: 34 herein. Preferred spr0096 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 34; and/or (b) comprising a fragment of at least 'n' consecutive amino acids of SEQ ID NO: 34, wherein 'n' is 7 or more (e.g. 8, 10, 12, 14, 16, 18, 20, 25, 30, 35, 40, 50, 60, 70, 80, 90, 100, 150, 200, 250 or more). These spr0096 proteins include variants of SEQ ID NO: 34 (e.g. SEQ ID NO: 54; see below). Preferred fragments of (b) comprise an epitope from SEQ ID NO: 34. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 34 while retaining at least one epitope of SEQ ID NO: 34. Other fragments omit one or more protein domains.

A variant form of spr0096, with an insert near its C-terminus relative to SEQ ID NO: 34, is SEQ ID NO: 54 herein. The use of this variant for immunisation is reported in reference 150 (SEQ ID NO: 150 therein), where it is annotated as a LysM domain protein. Thus a spr0096 for use with the invention may comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 54; and/or (b) comprising a fragment of at least 'n' consecutive amino acids of SEQ ID NO: 54, wherein 'n' is 7 or more (e.g. 8, 10, 12, 14, 16, 18, 20, 25, 30, 35, 40, 50, 60, 70, 80, 90, 100, 150, 200, 250 or more). These polypeptides include variants of SEQ ID NO: 54. Preferred fragments of (b) comprise an epitope from SEQ ID NO: 54. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 54 while retaining at least one epitope of SEQ ID NO: 54. Other fragments omit one or more protein domains. Immunogenic fragments of SEQID NO: 54 are identified in table 1 of reference 150.

A spr0096 polypeptide may be used in the form of a dimer e.g. a homodimer.

The original 'spr1707' sequence was annotated in reference 149 as 'ABC transporter substrate-binding protein—oligopeptide transport' (see GI:15903749). For reference purposes, the amino acid sequence of full length spr1707 as found in the R6 strain is given as SEQ ID NO: 36 herein. Preferred spr1707 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 36; and/or (b) comprising a fragment of at least 'n' consecutive amino acids of SEQ ID NO: 36, wherein 'n' is 7 or more (e.g. 8, 10, 12, 14, 16, 18, 20, 25, 30, 35, 40, 50, 60, 70, 80, 90, 100, 150, 200, 250 or more). These spr1707 proteins include variants of SEQ ID NO: 36 (e.g. SEQ ID NO: 55; see below). Preferred fragments of (b) comprise an epitope from SEQ ID NO: 36. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 36 while retaining at least one epitope of SEQ ID NO: 36. Other fragments omit one or more protein domains.

A variant form of spr1707, differing from SEQ ID NO: 14 by 4 amino acids, is SEQ ID NO: 55 herein. The use of SEQ ID NO: 55 for immunisation is reported in reference 150 (SEQ ID NO: 220 therein). Thus a spr1707 polypeptide for use with the invention may comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 55; and/or (b) comprising a fragment of at least 'n' consecutive amino acids of SEQ ID NO: 55, wherein 'n' is 7 or more (e.g. 8, 10, 12, 14, 16, 18, 20, 25, 30, 35, 40, 50, 60, 70, 80, 90, 100, 150, 200, 250 or more). These polypeptides include variants of SEQ ID NO: 55. Preferred fragments of (b) comprise an epitope from SEQ ID NO: 55. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 55 while retaining at least one epitope of SEQ ID NO: 55. Other fragments omit one or more protein domains. Immunogenic fragments of SEQ ID NO: 55 are identified in table 1 of reference 150.

The original 'spr1875' sequence was annotated in reference 149 as 'hypothetical protein' (see GI:15903916). For reference purposes, the amino acid sequence of full length spr1875 as found in the R6 strain is given as SEQ ID NO: 35 herein. Preferred spr1875 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 35; and/or (b) comprising a fragment of at least 'n' consecutive amino acids of SEQ ID NO: 35, wherein 'n' is 7 or more (e.g. 8, 10, 12, 14, 16, 18, 20, 25, 30, 35, 40, 50, 60, 70, 80, 90, 100, 150, 200, 250 or more). These spr1875 proteins include variants of SEQ ID NO: 35. Preferred fragments of (b) comprise an epitope from SEQ ID NO: 35. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 35 while retaining at least one epitope of SEQ ID NO: 35. Other fragments omit one or more protein domains.

The 'spr0884' protein is a peptidylprolyl isomerase, also known as protease maturation protein. For reference purposes, the amino acid sequence of full length spr0884 is SEQ ID NO: 37 herein. Preferred spr0884 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 37; and/or (b) comprising a fragment of at least 'n' consecutive amino acids of SEQ ID NO: 37, wherein 'n' is 7 or more (e.g. 8, 10, 12, 14, 16, 18, 20, 25, 30, 35, 40, 50, 60, 70, 80, 90, 100, 150, 200, 250 or more). These spr0884 proteins include variants of SEQ ID NO: 37. Preferred fragments of (b) comprise an epitope from SEQ ID NO: 37. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 37 while retaining at least one epitope of SEQ ID NO: 37. Other fragments omit one or more protein domains. One suitable fragment is SEQ ID NO: 56, which omits the natural leader peptide sequence. The use of spr0884 for immunisation is reported in reference 160.

ClpP is the ATP-dependent Clp protease proteolytic subunit. For reference purposes, the amino acid sequence of full length ClpP is SEQ ID NO: 58 herein. In the R6 genome ClpP is spr0656 [149]. Preferred ClpP polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 58; and/or (b) comprising a fragment of at least 'n' consecutive amino acids of SEQ ID NO: 58, wherein 'n' is 7 or more (e.g. 8, 10, 12, 14, 16, 18, 20, 25, 30, 35, 40, 50, 60, 70, 80, 90, 100, 150, 200, 250 or more). These ClpP proteins include variants of SEQ ID NO: 58. Preferred fragments of (b) comprise an epitope from SEQ ID NO: 58. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 58 while retaining at least one epitope of SEQ ID NO: 58. Other fragments omit one or more protein domains. The use of ClpP for immunisation is reported in references 161 and 162. It may advantageously be used in combination with PspA and PsaA and/or PspC [161].

LytA is the N-acetylmuramoyl-L-alanine amidase (autolysin). For reference purposes, the amino acid sequence of full length LytA is SEQ ID NO: 59 herein. In the R6 genome LytA is spr1754 [149]. Preferred LytA polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 59; and/or (b) comprising a fragment of at least 'n' consecutive amino acids of SEQ ID NO: 59, wherein 'n' is 7 or more (e.g. 8, 10, 12, 14, 16, 18, 20, 25, 30, 35, 40, 50, 60, 70, 80, 90, 100, 150, 200, 250 or more). These LytA proteins include variants of SEQ ID NO: 59 (e.g. GI:18568354). Preferred fragments of (b) comprise an epitope from SEQ ID NO: 59. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 59 while retaining at least one epitope of SEQ ID NO: 59. Other fragments omit one or more protein domains. The use of LytA for immunisation is reported in reference 163, particularly in a form comprising the LytA choline binding domain fused to a heterologous promiscuous T helper epitope.

PhtA is the Pneumococcal histidine triad protein A. For reference purposes, the amino acid sequence of full length PhtA precursor is SEQ ID NO: 60 herein. In the R6 genome PhtA is spr1061 [149]. Preferred PhtA polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 60; and/or (b) comprising a fragment of at least 'n' consecutive amino acids of SEQ ID NO: 60, wherein 'n' is 7 or more (e.g. 8, 10, 12, 14, 16, 18, 20, 25, 30, 35, 40, 50, 60, 70, 80, 90, 100, 150, 200, 250 or more). These PhtA proteins include variants of SEQ ID NO: 60. Preferred fragments of (b) comprise an epitope from SEQ ID NO: 60. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 60 while retaining at least one epitope of SEQ ID NO: 60. Other fragments omit one or more protein domains. The use of PhtA for immunisation is reported in references 164 and 165.

PhtB is the pneumococcal histidine triad protein B. For reference purposes, the amino acid sequence of full length PhtB precursor is SEQ ID NO: 61 herein. Xaa at residue 578 can be Lysine. Preferred PhtB polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 61; and/or (b) comprising a fragment of at least 'n' consecutive amino acids of SEQ ID NO: 61, wherein 'n' is 7 or more (e.g. 8, 10, 12, 14, 16, 18, 20, 25, 30, 35, 40, 50, 60, 70, 80, 90, 100, 150, 200, 250 or more). These PhtB proteins include variants of SEQ ID NO: 61. Preferred fragments of (b) comprise an epitope from SEQ ID NO: 61. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 61 while retaining at least one epitope of SEQ ID NO: 61. Other fragments omit one or more protein domains. The use of PhtB for immunisation is reported in references 164, 165 and 166.

PhtD is the Pneumococcal histidine triad protein D. For reference purposes, the amino acid sequence of full length PhtD precursor is SEQ ID NO: 62 herein. In the R6 genome PhtD is spr0907 [149]. Preferred PhtD polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 62; and/or (b) comprising a fragment of at least 'n' consecutive amino acids of SEQ ID NO: 62, wherein 'n' is 7 or more (e.g. 8, 10, 12, 14, 16, 18, 20, 25, 30, 35, 40, 50, 60, 70, 80, 90, 100, 150, 200, 250 or more). These PhtD proteins include variants of SEQ ID NO: 62. Preferred fragments of (b) comprise an epitope from SEQ ID NO: 62. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 62 while retaining at least one epitope of SEQ ID NO: 62. Other fragments omit one or more protein domains. The use of PhtD for immunisation is reported in references 164, 165 and 167.

PhtE is the Pneumococcal histidine triad protein E. For reference purposes, the amino acid sequence of full length PhtE precursor is SEQ ID NO: 63 herein. In the R6 genome PhtE is spr0908 [149]. Preferred PhtE polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 63; and/or (b) comprising a fragment of at least 'n' consecutive amino acids of SEQ ID NO: 63, wherein 'n' is 7 or more (e.g. 8, 10, 12, 14, 16, 18, 20, 25, 30, 35, 40, 50, 60, 70, 80, 90, 100, 150, 200, 250 or more). These PhtE proteins include variants of SEQ ID NO: 63. Preferred fragments of (b) comprise an epitope from SEQ ID NO: 63. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 63 while retaining at least one epitope of SEQ ID NO: 63. Other fragments omit one or more protein domains. The use of PhtE for immunisation is reported in references 164 and 165.

ZmpB is the zinc metalloprotease. For reference purposes, the amino acid sequence of full length ZmpB is SEQ ID NO: 64 herein. In the R6 genome ZmpB is spr0581 [149]. Preferred ZmpB polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 64; and/or (b) comprising a fragment of at least 'n' consecutive amino acids of SEQ ID NO: 64, wherein 'n' is 7 or more (e.g. 8, 10, 12, 14, 16, 18, 20, 25, 30, 35, 40, 50, 60, 70, 80, 90, 100, 150, 200, 250 or more). These ZmpB proteins include variants of SEQ ID NO: 64. Preferred fragments of (b) comprise an epitope from SEQ ID NO: 64. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 64 while retaining at least one epitope of SEQ ID NO: 64. Other fragments omit one or more protein domains.

CbpD is the Choline binding protein D. For reference purposes, the amino acid sequence of full length CbpD is SEQ ID NO: 65 herein. In the R6 genome CbpD is spr2006 [149]. Preferred CbpD polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 65; and/or (b) comprising a fragment of at least 'n' consecutive amino acids of SEQ ID NO: 65, wherein 'n' is 7 or more (e.g. 8, 10, 12, 14, 16, 18, 20, 25, 30, 35, 40, 50, 60, 70, 80, 90, 100, 150, 200, 250 or more). These CbpD proteins include variants of SEQ ID NO: 65 (e.g. SEQ ID NO: 66; see below). Preferred fragments of (b) comprise an epitope from SEQ ID NO: 65. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 65 while retaining at least one epitope of SEQ ID NO: 65. Other fragments omit one or more protein domains. The use of CbpD for immunisation is reported in reference 171.

A variant of SEQ ID NO: 65 is SEQ ID NO: 66 herein. The use of SEQ ID NO: 66 for immunisation is reported in reference 150 (SEQ ID NO: 241 therein). Thus a CbpD polypeptide for use with the invention may comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 66; and/or (b) comprising a fragment of at least 'n' consecutive amino acids of SEQ ID NO: 66, wherein 'n' is 7 or more (e.g. 8, 10, 12, 14, 16, 18, 20, 25, 30, 35, 40, 50, 60, 70, 80, 90, 100, 150, 200, 250 or more). These CbpD proteins include variants of SEQ ID NO: 66. Preferred fragments of (b) comprise an epitope from SEQ ID NO: 66. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 66 while retaining at least one epitope of SEQ ID NO: 66. Other fragments omit one or more protein domains. Immunogenic fragments of SEQ ID NO: 66 are identified in table 1 of ref.150.

CbpG is the Choline binding protein G. For reference purposes, the amino acid sequence of full length CbpG is SEQ ID NO: 67 herein. In the R6 genome CbpG is spr0350 [149]. Preferred CbpG polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 67; and/or (b) comprising a fragment of at least 'n' consecutive amino acids of SEQ ID NO: 67, wherein 'n' is 7 or more (e.g. 8, 10, 12, 14, 16, 18, 20, 25, 30, 35, 40, 50, 60, 70, 80, 90, 100, 150, 200, 250 or more). These CbpG proteins include variants of SEQ ID NO: 67. Preferred fragments of (b) comprise an epitope from SEQ ID NO: 67. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 67 while retaining at least one epitope of SEQ ID NO: 67. Other fragments omit one or more protein domains. The use of CbpG for immunisation is reported in reference 171.

PvaA (Streptococcus pneumoniae pneumococcal vaccine antigen A) is also known as sp101. For reference purposes, the amino acid sequence of full length PvaA is SEQ ID NO: 68 herein. In the R6 genome PvaA is spr0930 [149]. Preferred PvaA polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 68; and/or (b) comprising a fragment of at least 'n' consecutive amino acids of SEQ ID NO: 68, wherein 'n' is 7 or more (e.g. 8, 10, 12, 14, 16, 18, 20, 25, 30, 35, 40, 50, 60, 70, 80, 90, 100, 150, 200, 250 or more). These PvaA proteins include variants of SEQ ID NO: 68. Preferred fragments of (b) comprise an epitope from SEQ ID NO: 68. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 68 while retaining at least one epitope of SEQ ID NO: 68. Other fragments omit one or more protein domains. The use of PvaA for immunisation is reported in references 168 and 169.

CPL1 is the pneumococcal phage CP1 lysozyme. For reference purposes, the amino acid sequence of full length CPL1 is SEQ ID NO: 69 herein. Preferred CPL1 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 69; and/or (b) comprising a fragment of at least 'n' consecutive amino acids of SEQ ID NO: 69, wherein 'n' is 7 or more (e.g. 8, 10, 12, 14, 16, 18, 20, 25, 30, 35, 40, 50, 60, 70, 80, 90, 100, 150, 200, 250 or more). These CPL1 proteins include variants of SEQ ID NO: 69. Preferred fragments of (b) comprise an epitope from SEQ ID NO: 69. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 69 while retaining at least one epitope of SEQ ID NO: 69. Other fragments omit one or more protein domains. The use of CPL1 for immunisation is reported in reference 163, particularly in a form comprising the CPL1 choline binding domain fused to a heterologous promiscuous T helper epitope.

PspC is the pneumococcal surface protein C [170] and is also known as choline-binding protein A (CbpA). Its use for immunisation is reported in references 168 and 171. In the R6 strain it is spr1995 and, for reference, the amino acid sequence of full length spr1995 is SEQ ID NO: 57 herein. Preferred PspC polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 57; and/or (b) comprising a fragment of at least 'n' consecutive amino acids of SEQ ID NO: 57, wherein 'n' is 7 or more (e.g. 8, 10, 12, 14, 16, 18, 20, 25, 30, 35, 40, 50, 60, 70, 80, 90, 100, 150, 200, 250 or more). These spr1995 proteins include variants of SEQ ID NO: 57 (e.g. SEQ ID NO: 71; see below). Preferred fragments of (b) comprise an epitope from SEQ ID NO: 57. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 57 while retaining at least one epitope of SEQ ID NO: 57. Other fragments omit one or more protein domains.

A variant of PspC is known as 'Hic'. It is similar to PspC, as shown in FIG. 1 of reference 172, where it is reported to bind to factor H (fH). For reference purposes, the amino acid sequence of full length Hic is SEQ ID NO: 71 herein. A Hic protein may be used with the invention in addition to or in place of a PspC polypeptide. Preferred Hic polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 71; and/or (b) comprising a fragment of at least 'n' consecutive amino acids of SEQ ID NO: 71, wherein 'n' is 7 or more (e.g. 8, 10, 12, 14, 16, 18, 20, 25, 30, 35, 40, 50, 60, 70, 80, 90, 100, 150, 200, 250 or more). These Hic proteins include variants of SEQ ID NO: 71. Preferred fragments of (b) comprise an epitope from SEQ ID NO: 71. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 71 while retaining at least one epitope of SEQ ID NO: 71. Other fragments omit one or more protein domains. PspC and/or Hic can advantageously be used in combination with PspA and/or PsaA.

PspA is the Pneumococcal surface protein A. For reference purposes, the amino acid sequence of full length PspA is SEQ ID NO: 72 herein. In the R6 genome PspA is spr0121 [149]. Preferred PspA polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 72; and/or (b) comprising a fragment of at least 'n' consecutive amino acids of SEQ ID NO: 72, wherein 'n' is 7 or more (e.g. 8, 10, 12, 14, 16, 18, 20, 25, 30, 35, 40, 50, 60, 70, 80, 90, 100, 150, 200, 250 or more). These PspA proteins include variants of SEQ ID NO: 72. Preferred fragments of (b) comprise an epitope from SEQ ID NO: 72. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 72 while retaining at least one epitope of SEQ ID NO: 72. Other fragments omit one or more protein domains. The use of PspA for immunisation is reported inter alia in reference 173. It can advantageously be administered in combination with PspC.

PsaA is the Pneumococcal surface adhesin. For reference purposes, the amino acid sequence of full length PsaA is SEQ ID NO: 73 herein. Preferred PsaA polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 73; and/or (b) comprising a fragment of at least 'n' consecutive amino acids of SEQ ID NO: 73, wherein 'n' is 7 or more (e.g. 8, 10, 12, 14, 16, 18, 20, 25, 30, 35, 40, 50, 60, 70, 80, 90, 100, 150, 200, 250 or more). These PsaA proteins include variants of SEQ ID NO: 73. Preferred fragments of (b) comprise an epitope from SEQ ID NO: 73. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 73 while retaining at least one epitope of SEQ ID NO: 73. Other fragments omit one or more protein domains. A useful fragment of PsaA is disclosed as SEQ ID NO: 3 in reference 159 (corresponding to amino acids 21-309 of SEQ ID NO: 73 herein; this useful fragment of PsaA is provided as SEQ ID No.99 herein). The use of PsaA for immunisation is reported in reference 174. It can be used in combination with PspA and/or PspC.

PrtA is the cell wall-associated serine proteinase. It has also been known as sp128 and sp130, and is in a subtilisin-like serine protease. For reference purposes, the amino acid sequence of full length PrtA precursor is SEQ ID NO: 74 herein. In the R6 genome PrtA is spr0561 [149]. Preferred PrtA polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 74; and/or (b) comprising a fragment of at least 'n' consecutive amino acids of SEQ ID NO: 74, wherein 'n' is 7 or more (e.g. 8, 10, 12, 14, 16, 18, 20, 25, 30, 35, 40, 50, 60, 70, 80, 90, 100, 150, 200, 250 or more). These PrtA proteins include variants of SEQ ID NO: 74. Preferred fragments of (b) comprise an epitope from SEQ ID NO: 74. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 74 while retaining at least one epitope of SEQ ID NO: 74. Other fragments omit one or more protein domains. The use of PrtA for immunisation is reported in references 175 & 176, and also in reference 168.

Sp133 is a conserved pneumococcal antigen. For reference purposes, the amino acid sequence of full length Sp133 is SEQ ID NO: 75 herein. In the R6 genome Sp133 is spr0931 [149]. Preferred Sp133 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 75; and/or (b) comprising a fragment of at least 'n' consecutive amino acids of SEQ ID NO: 75, wherein 'n' is 7 or more (e.g. 8, 10, 12, 14, 16, 18, 20, 25, 30, 35, 40, 50, 60, 70, 80, 90, 100, 150, 200, 250 or more). These Sp133 proteins include variants of SEQ ID NO: 75. Preferred fragments of (b) comprise an epitope from SEQ ID NO: 75. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 75 while retaining at least one epitope of SEQ ID NO: 75. Other fragments omit one or more protein domains. The use of Sp133 for immunisation is reported in reference 177.

PiaA is the membrane permease involved in iron acquisition by pneumococcus. For reference purposes, the amino acid sequence of full length PiaA is SEQ ID NO: 76 herein. In the R6 genome PiaA is spr0935 [149]. Preferred PiaA polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 76; and/or (b) comprising a fragment of at least 'n' consecutive amino acids of SEQ ID NO: 76, wherein 'n' is 7 or more (e.g. 8, 10, 12, 14, 16, 18, 20, 25, 30, 35, 40, 50, 60, 70, 80, 90, 100, 150, 200, 250 or more). These PiaA proteins include variants of SEQ ID NO: 76. Preferred fragments of (b) comprise an epitope from SEQ ID NO: 76. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 76 while retaining at least one epitope of SEQ ID NO: 76. Other fragments omit one or more protein domains. The use of PiaA for immunisation is reported in references 178, 179 and 180, particularly in combination with PiuA.

PiuA is the ABC transporter substrate-binding protein for ferric iron transport. It is also known as FatB. For reference purposes, the amino acid sequence of full length PiuA is SEQ ID NO: 77 herein. In the R6 genome PiuA is spr1687 [149]. Preferred PiuA polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 77; and/or (b) comprising a fragment of at least 'n' consecutive amino acids of SEQ ID NO: 77, wherein 'n' is 7 or more (e.g. 8, 10, 12, 14, 16, 18, 20, 25, 30, 35, 40, 50, 60, 70, 80, 90, 100, 150, 200, 250 or more). These PiuA proteins include variants of SEQ ID NO: 77. Preferred fragments of (b) comprise an epitope from SEQ ID NO: 77. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 77 while retaining at least one epitope of SEQ ID NO: 77. Other fragments omit one or more protein domains. The use of PiuA for immunisation is reported in refs 178 to 180, particularly in combination with PiaA.

CbiO is annotated as a cobalt transporter ATP-binding subunit. For reference purposes, the amino acid sequence of full length CbiO is SEQ ID NO: 78 herein. In the R6 genome CbiO is spr2025 [149]. The use of CbiO for immunisation is reported in reference 181 ('ID2' therein). Preferred CbiO polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 78; and/or (b) comprising a fragment of at least 'n' consecutive amino acids of SEQ ID NO: 78, wherein 'n' is 7 or more (e.g. 8, 10, 12, 14, 16, 18, 20, 25, 30, 35, 40, 50, 60, 70, 80, 90, 100, 150, 200, 250 or more). These CbiO proteins include variants of SEQ ID NO: 78. Preferred fragments of (b) comprise an epitope from SEQ ID NO: 78. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 78 while retaining at least one epitope of SEQ ID NO: 78. Other fragments omit one or more protein domains.

For reference purposes, the amino acid sequence of 30S ribosomal protein S8 is SEQ ID NO: 79 herein. In the R6 genome the S8 subunit is spr0203 [149]. Preferred S8 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 79; and/or (b) comprising a fragment of at least 'n' consecutive amino acids of SEQ ID NO: 79, wherein 'n' is 7 or more (e.g. 8, 10, 12, 14, 16, 18, 20, 25, 30, 35, 40, 50, 60, 70, 80, 90, 100, 150, 200, 250 or more). These S8 proteins include variants of SEQ ID NO: 79. Preferred fragments of (b) comprise an epitope from SEQ ID NO: 79. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 79 while retaining at least one epitope of SEQ ID NO: 79. Other fragments omit one or more protein domains.

SP1732 is a membrane-associated serine/threonine kinase, StkP. The sequence of SP1732, comprising 659 amino acids, is identified in reference 150 as SEQ ID NO: 214. An exemplary fragment of this sequence, referred to as "SP 1732-3", is identified in reference 159 as SEQ ID NO: 2. For reference purposes, the amino acid sequence of SP 1732-3 is provided as SEQ ID NO: 98 herein. Preferred SP1732 polypeptides for use with the invention comprise an amino acid sequence: (a) having 60% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 98; and/or (b) comprising a fragment of at least 'n' consecutive amino acids of SEQ ID NO: 98, wherein 'n' is 7 or more (e.g. 8, 10, 12, 14, 16, 18, 20, 25, 30, 35, 40, 50, 60, 70, 80, 90, 100, 150, 200, 250 or more). These SP1732 proteins include variants of SEQ ID NO: 98. Preferred fragments of (b) comprise an epitope from SEQ ID NO: 98. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 98 while retaining at least one epitope of SEQ ID NO: 98. Other fragments omit one or more protein domains.

Combinations with Pneumococcal Saccharides

RrgB polypeptides from one or more clades may be combined with one or more pneumococcal capsular saccharide(s), which will typically be conjugated to carrier protein(s). Thus the invention provides an immunogenic composition comprising a combination of:

(1) a combination of at least two RrgB clades as discussed above, as a mixture or hybrid; and
(2) one or more pneumococcal capsular saccharides.

A saccharide used in component (2) of this combination is ideally present as a conjugate comprising a saccharide moiety and a carrier protein moiety. The carrier moiety in the conjugate may be a single RrgB polypeptide, a hybrid RrgB polypeptide, a non-RrgB pneumococcal polypeptide, or a non-pneumococcal polypeptide.

The saccharide is from the capsular saccharide of a pneumococcus. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides are presented as intact polysaccharides while one (the 18C serotype) is presented as an oligosaccharide.

A composition may include a capsular saccharide from one or more of the following pneumococcal serotypes: 1, 2, 3, 4, 5, 6A, 6B, 7F, 8, 9N, 9V, 10A, 11A, 12F, 14, 15B, 17F, 18C, 19A, 19F, 20, 22F, 23F and/or 33F. A composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination.

For example, a 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. One useful 13-valent combination includes capsular saccharide from serotypes 1, 3, 4, 5, 6A, 6B, 7F, 9V, 14, 18C, 19, 19F and 23F. If saccharides are enclosed then it is preferred to include 1, 2 or 3 of serotypes 1, 5 and 14.

A carrier protein in a conjugate may or may not be one of the RrgB antigens of (1). If it is not a RrgB antigen it may instead be a different pneumococcal antigen, such as spr0057, spr0096 and spr2021, etc., or pneumolysin [182] or its non-toxic derivatives [183], or pneumococcal surface protein PspA [184], In some embodiments, though, the carrier is not a pneumococcal antigen, and may be e.g. a bacterial toxin or toxoid. Typical carrier proteins are diphtheria or tetanus toxoids or mutants thereof. The $CRM_{197}$ diphtheria toxin mutant [185] is useful, and is the carrier in the PREVNAR™ product. Other suitable carrier proteins include *N. meningitidis* outer membrane protein complex [186], synthetic peptides [187, 188], heat shock proteins [189, 190], pertussis proteins [191, 192], cytokines [193], lymphokines [193], hormones [193], growth factors [193], artificial proteins comprising multiple human CD4+ T cell epitopes from various pathogen-derived antigens [194] such as N19 [195], protein D from *H. influenzae* [196-198], iron-uptake proteins [199], toxin A or B from *C. difficile* [200], recombinant *P. aeruginosa* exoprotein A (rEPA) [201], etc.

Where a composition includes more than one conjugate, each conjugate may use the same carrier protein or a different carrier protein. Reference 202 describes potential advantages when using different carrier proteins in multivalent pneumococcal conjugate vaccines In some embodiments, a single conjugate may carry saccharides from multiple serotypes [203]. Usually, however, each conjugate will include saccharide from a single serotype.

Conjugates may have excess carrier (w/w) or excess saccharide (w/w). In some embodiments, a conjugate may include equal weights of each.

The carrier molecule may be covalently conjugated to the carrier directly or via a linker. Direct linkages to the protein may be achieved by, for instance, reductive amination between the saccharide and the carrier, as described in, for example, references 204 and 205. The saccharide may first need to be activated e.g. by oxidation. Linkages via a linker group may be made using any known procedure, for example, the procedures described in references 206 and 207. A preferred type of linkage is an adipic acid linker, which may be formed by coupling a free —$NH_2$ group (e.g. introduced to a glucan by amination) with adipic acid (using, for example, diimide activation), and then coupling a protein to the resulting saccharide-adipic acid intermediate [208, 209]. Another preferred type of linkage is a carbonyl linker, which may be formed by reaction of a free hydroxyl group of a saccharide CDI [210, 211] followed by reaction with a protein to form a carbamate linkage. Other linkers include β-propionamido [212], nitrophenyl-ethylamine [213], haloacyl halides [214], glycosidic linkages [215], 6-aminocaproic acid [216], ADH [217], $C_4$ to $C_{12}$ moieties [218], etc. Carbodiimide condensation can also be used [219].

Combinations with Non-pneumococcal Antigens

The RrgB clade combinations may be used in combination with non-pneumococcal antigens. Thus the invention provides an immunogenic composition comprising a combination of:

(1) a combination of at least two RrgB clades as discussed above, as a mixture or hybrid; and
(2) one or more antigen(s) selected from the group consisting of: diphtheria toxoid; tetanus toxoid; one or more pertussis antigens; hepatitis B virus surface antigen; an inactivated poliovirus antigen; a conjugate of the capsular saccharide antigen from *Haemophilus influenzae* type B; a conjugate of the capsular saccharide antigen from serogroup C of *Neisseria meningitidis*; a conjugate of the capsular saccharide antigen from serogroup Y of *Neisseria meningitidis*; a conjugate of the capsular saccharide antigen from serogroup W135 of *Neisseria meningitidis*; and a conjugate of the capsular saccharide antigen from serogroup A of *Neisseria meningitidis*.

Diphtheria toxoid can be obtained by treating (e.g. using formaldehyde) diphtheria toxin from *Corynebacterium diphtheriae*. Diphtheria toxoids are disclosed in more detail in, for example, chapter 13 of reference 220.

Tetanus toxoid can be obtained by treating (e.g. using formaldehyde) tetanus toxin from *Clostridium tetani*. Tetanus toxoids are disclosed in more detail in chapter 27 of reference 220.

Pertussis antigens in vaccines are either cellular (whole cell, Pw) or acellular (Pa). The invention can use either sort of pertussis antigen. Preparation of cellular pertussis antigens is well documented (e.g. see chapter 21 of reference 220) e.g. it may be obtained by heat inactivation of phase I culture of *B. pertussis*. Acellular pertussis antigen(s) comprise specific purified *B. pertussis* antigens, either purified from the native bacterium or purified after expression in a recombinant host. It is usual to use more than one acellular antigen, and so a composition may include one, two or three of the following well-known and well-characterized *B. pertussis* antigens: (1) detoxified pertussis toxin (pertussis toxoid, or 'PT'); (2) filamentous hemagglutinin ('FHA'); (3) pertactin (also known as the '69 kiloDalton outer membrane protein'). FHA and pertactin may be treated with formaldehyde prior to use according to the invention. PT may be detoxified by treatment with formaldehyde and/or glutaraldehyde but, as an alternative to this chemical detoxification procedure, it may be a mutant PT in which enzymatic activity has been reduced by mutagenesis [221]. Further acellular pertussis antigens that can be used include fimbriae (e.g. agglutinogens 2 and 3).

Hepatitis B virus surface antigen (HBsAg) is the major component of the capsid of hepatitis B virus. It is conveniently produced by recombinant expression in a yeast, such as a *Saccharomyces cerevisiae*.

Inactivated poliovirus (IPV) antigens are prepared from viruses grown on cell culture and then inactivated (e.g. using formaldehyde). Because poliomyelitis can be caused by one of three types of poliovirus, as explained in chapter 24 of reference 220, a composition may include three poliovirus antigens: poliovirus Type 1 (e.g. Mahoney strain), poliovirus Type 2 (e.g. MEF-1 strain), and poliovirus Type 3 (e.g. Saukett strain).

When a composition includes one of diphtheria toxoid, tetanus toxoid or an acellular pertussis antigen in component (2) then it will usually include all three of them i.e. component (2) will include a D-T-Pa combination.

When a composition includes one of diphtheria toxoid, tetanus toxoid or a cellular pertussis antigen in component (2) then it will usually include all three of them i.e. component (2) will include a D-T-Pw combination.

Immunogenic compositions of particular interest comprise: (i) a combination of at least two RrgB clades as discussed above as a mixture or hybrid, diphtheria toxoid, tetanus toxoid, whole cell pertussis antigens, a conjugate of *Haemophilus influenzae* type B capsular saccharide, and HBsAg; (ii) a combination of at least two RrgB clades as discussed above as a mixture or hybrid, diphtheria toxoid, tetanus toxoid, acellular pertussis antigen(s), a conjugate of *Haemophilus influenzae* type B capsular saccharide, and HBsAg; (iii) a combination of at least two RrgB clades as discussed above as a mixture or hybrid, and conjugate(s) from one or more of meningococcal serogroups A, C, W135 and Y; (iv) a combination of at least two RrgB clades as discussed above as a mixture or hybrid, and conjugates from all of meningococcal serogroups A, C, W135 and Y; and (v) a combination of at least two RrgB clades as discussed above as a mixture or hybrid, and a meningococcal serogroup B antigen, such as an outer membrane vesicle antigen and/or the combination disclosed in ref. 222.

Antibodies

Antibodies against pneumococcal antigens can be used for passive immunisation [223]. Thus the invention provides a combination of antibodies for simultaneous, separate or sequential administration, wherein the combination includes at least two of: (a) an antibody which recognises a first amino acid sequence as defined above; (b) an antibody which recognises a second amino acid sequence as defined above; and/or (c) an antibody which recognises a third amino acid sequence as defined above;

The invention also provides the use of such antibody combinations in therapy. The invention also provides the use of such antibody combinations in the manufacture of a medicament. The invention also provides a method for treating a mammal comprising the step of administering to the mammal an effective amount of such a combination. As described above for immunogenic compositions, these methods and uses allow a mammal to be protected against pneumococcal infection.

The term "antibody" includes intact immunoglobulin molecules, as well as fragments thereof which are capable of binding an antigen. These include hybrid (chimeric) antibody molecules [224, 225]; F(ab')2 and F(ab) fragments and Fv molecules; non-covalent heterodimers [226, 227]; single-chain Fv molecules (sFv) [228]; dimeric and trimeric antibody fragment constructs; minibodies [229, 230]; humanized antibody molecules [231-233]; and any functional fragments obtained from such molecules, as well as antibodies obtained through non-conventional processes such as phage display.

Preferably, the antibodies are monoclonal antibodies. Methods of obtaining monoclonal antibodies are well known in the art. Humanised or fully-human antibodies are preferred.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 234-241, etc.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Where the invention concerns an "epitope", this epitope may be a B-cell epitope and/or a T-cell epitope. Such epitopes can be identified empirically (e.g. using PEPSCAN [242, 243] or similar methods), or they can be predicted (e.g. using the Jameson-Wolf antigenic index [244], matrix-based approaches [245], MAPITOPE [246], TEPITOPE [247, 248], neural networks [249], OptiMer & EpiMer [250, 251], ADEPT [252], Tsites [253], hydrophilicity [254], antigenic index [255] or the methods disclosed in references 256-260, etc.). Epitopes are the parts of an antigen that are recognised by and bind to the antigen binding sites of antibodies or T-cell receptors, and they may also be referred to as "antigenic determinants".

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Antibodies will generally be specific for their target. Thus they will have a higher affinity for the target than for an irrelevant control protein, such as bovine serum albumin.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref 261. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref 262.

MODES FOR CARRYING OUT THE INVENTION

Construction of RrgB Chimeras

Two different pili have been identified in pneumococcus [2]: PI-1 and PI-2. Knockout studies showed that loss of PI-2 had little effect, but loss of PI-1 reduced a strain's ability to colonise, and thus led to lower bacteremia and lung wash titres. Thus blocking of PI-1 has a better prospect of protecting against pneumococcal disease than blocking PI-2.

Figure 9:
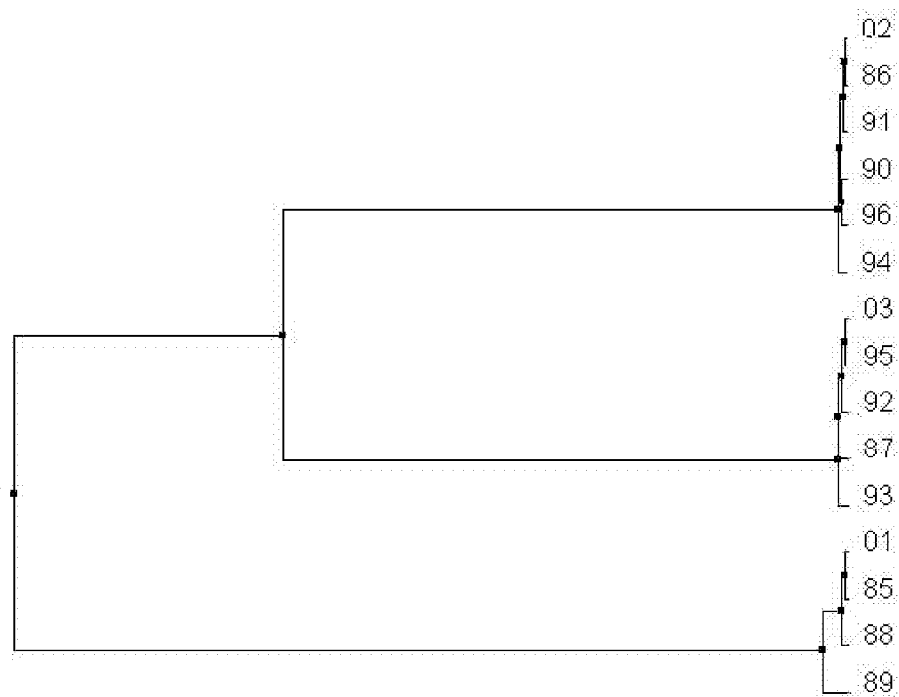
FIG. 9 shows a tree based on % identity for SEQ ID NOs: 1-3 & 85-96. The label is the SEQ ID.

PI-1 RrgB protein has three different clades. Fifteen different RrgB amino acid sequences were found in 45 different strains and FIG. 9 shows their relationship. The wild-type sequences are ≥98% conserved within each clade. RrgB protein was found to elicit immune responses which are protective against homologous strains (intra-clade), but which fail to protect against strains having RrgB from a different clade (inter-clade). Thus it was decided to combine multiple RrgB clades into a single composition, thereby increasing the spectrum of strain coverage.

SEQ ID NOs: 1, 2 and 3 are the full-length encoded sequences for RrgB from strains TIGR4, Finland[6B]-12 and Taiwan[23F]-15. To construct chimeras of these three proteins their N- and C-termini were truncated to give SEQ ID NOs: 4, 5 and 6. Restriction enzymes NheI, BamHI and XhoI were used in this procedure. To join these fragments to make chimeras linkers SEQ ID NOs: 8 and 10 were used, made of either a Gly-Ser or Leu-Gly dipeptide followed by SEQ ID NO: 7. These linkers provide convenient restriction sites for ligation of fragments. The N-terminus of the chimeras was provided as Met-Ala-Ser, and the C-terminus was a Leu-Gly dipeptide followed by a hexa-His tag (SEQ ID NO: 9) to facilitate purification.

Six chimeras were constructed, referred to hereafter as follows:
  RrgB I-II-III=SEQ ID NO: 11
  RrgB I-III-II=SEQ ID NO: 13
  RrgB III-II-I=SEQ ID NO: 15
  RrgB III-I-II=SEQ ID NO: 17
  RrgB II-III-I=SEQ ID NO: 19
  RrgB II-I-III=SEQ ID NO: 21

Figure 3:
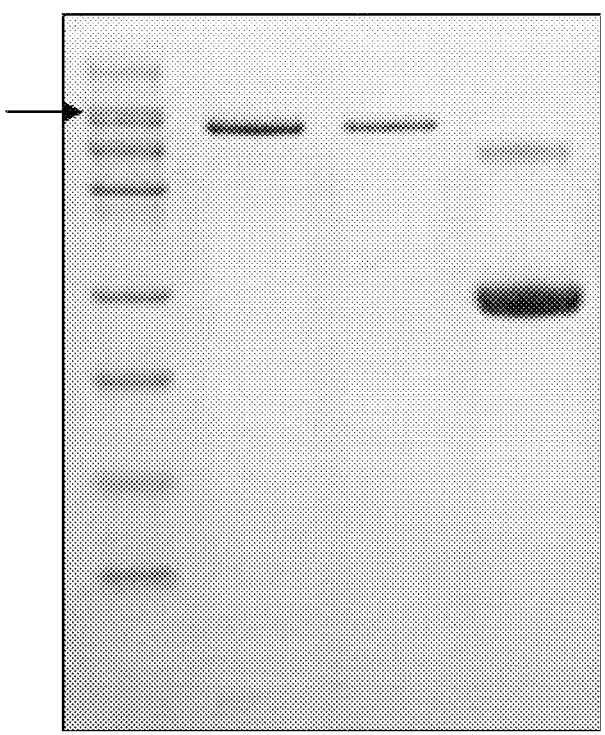
FIG. 3 shows a gel with four lanes. From left to right the lanes contain: MW markers; a I-II-III chimera; a I-II-III chimera; and a BSA standard. The arrow indicates a MW of 214 kDa.

Except for the I-III-II chimera (SEQ ID NO: 13) the expressed chimeras had a molecular weight of 205 kDa, could be expressed in E. coli in soluble form, and were purified from the soluble proteins. For example, FIG. 3 shows a gel of the I-II-III chimera at 1.6mg/ml with 90% purity.

Efficacy Testing

Various model systems of pneumococcal disease were used for testing efficacy of the chimeras.

In a mouse model of intraperitoneal infection, antigens were administered intraperitoneally and the challenge was intraperitoneal. Six-week-old, specific-pathogen-free female BALB/c or CD1 mice were immunized intraperitoneally on days 0, 14, and 28. Immunizations were done using single recombinant proteins (20 µg/mouse) or with a combination of them (10 µg each/mouse), along with aluminium hydroxide or Freund's adjuvant. Controls received identical courses of saline plus adjuvant. Mice were then challenged intraperitoneally with a lethal dose of TIGR4 (typical challenge dose ~1×10$^2$ CFU/mouse), Finland[6B]-12 (~2.×10$^4$ CFU/mouse) or 35B-SME15 (1×10$^4$ CFU/mouse). These three strains express RrgB clades I, II or III, respectively, and the TIGR4 strain is very virulent. Efficacy of immunisation is tested by evaluating the effect of vaccination on bacteremia (at 5 and/or 24 hours post infection) and mortality (monitored for at least 10 days following bacterial challenge).

In a model of intravenous infection, antigens were administered intraperitoneally and the challenge was intravenous. Five-week-old CD1 or BALB/c mice were immunized intraperitoneally on days 0, 14, and 28. Immunizations were done using recombinant proteins individually (20 µg/mouse) or with a combination of them (10 µg each/mouse), along with Freund's adjuvant. Controls received identical courses of saline plus adjuvant. Mice were then challenged intravenously with a lethal dose of TIGR4 (typical challenge dose ~5×10$^6$ CFU/mouse), Finland[6B]-12 (~2.×10$^7$ CFU/mouse) or 35B-SME15 (~5×10$^7$ CFU/mouse). Efficacy of vaccine candidates is tested by evaluating the effect of vaccination on bacteremia (at 48 hours post-infection) and mortality (monitored for 10 days following bacterial challenge or longer, depending on the infecting strain).

For example, CD 1 mice were immunised with the chimeras and then challenged with TIGR4. FIG. 1 shows bacteremia after the challenge. Geometric mean CFUs were as follows, together with a U-test comparison against the control group:

| Chimera | I-II-III | II-III-I | II-I-III | III-I-II | III-II-I | Control |
| --- | --- | --- | --- | --- | --- | --- |
| CFU/ml | 170 | 66 | 780 | 88 | 59 | 74000 |
| U-test | 0.014 | 0.004 | 0.056 | 0.007 | 0.004 | — |

Figure 2:
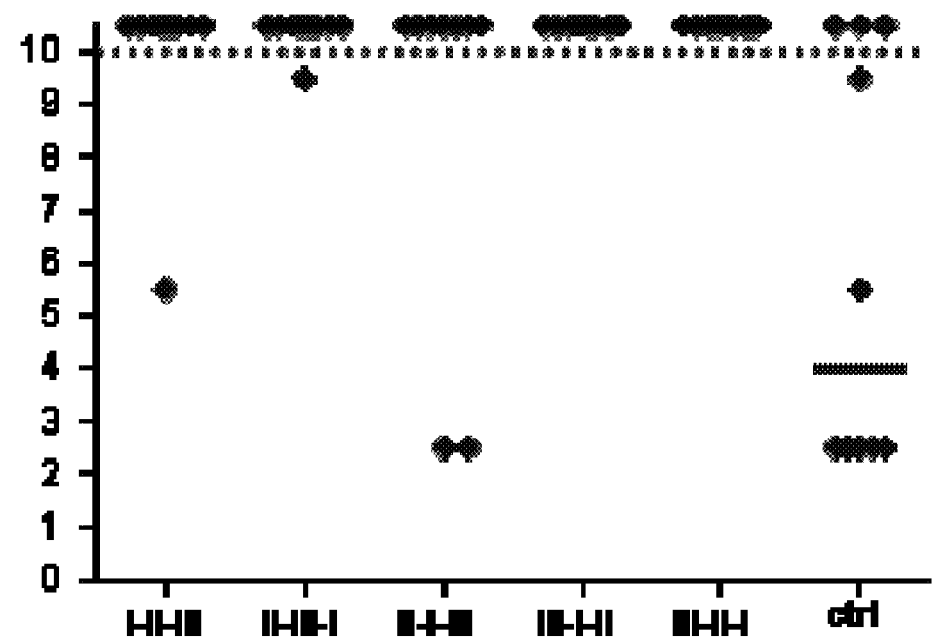
FIG. 2 shows results of a mortality study with five RrgB chimeras and a control. The figures are survival time in days. Each mark shows data for a single mouse.

FIG. 2 shows mortality after the challenge. Median survival times in days were as follows:

| Chimera | I-II-III | II-III-I | II-I-III | III-I-II | III-II-I | Control |
| --- | --- | --- | --- | --- | --- | --- |
| Survival | 10.5 | 10.5 | 10.5 | 10.5 | 10.5 | 4 |
| U-test | 0.007 | 0.006 | 0.048 | 0.003 | 0.003 | — |

FIGS. 30 to 33 show the results of bacteremia and mortality assays for mice immunised intraperitoneally with 20 µg of the III-II-I chimera. FIG. 30 shows data for i.v. challenge with TIGR4, FIG. 31 shows data for i.p. challenge with TIGR4, FIG. 32 shows data for i.v. challenge with 35B-SME15 and FIG. 33 shows data for i.v. challenge with 6B Finland 12.

The following table summarises results obtained in two different models of challenge with three different strains which express, respectively, RrgB in clade I, II or III:

| Challenge | | I-II-III | | III-I-II | | II-III-I | | III-II-I | | II-I-III | |
|---|---|---|---|---|---|---|---|---|---|---|---|
| Strain | Rt | B'emia | M'tality | B'emia | M'tality | B'emia | M'tality | B'emia | M'tality | B'emia | M'tality |
| TIGR4 | IP | +++ | +++ | +++ | +++ | +++ | ++ | +++ | +++ | +++ | +++ |
| Fin$^{6B}$12 | IP | − | − | − | − | ++ | − | − | − | + | − |
| 35B-S | IP | ++ | + | ++ | ++ | − | + | ++ | + | − | + |
| TIGR4 | IV | ++ | +++ | +++ | +++ | +++ | ++ | +++ | +++ | + | + |
| Fin$^{6B}$12 | IV | ++ | + | +++ | − | +++ | + | +++ | +++ | +++ | +++ |
| 35B-S | IV | +++ | +++ | +++ | +++ | +++ | ++ | +++ | +++ | + | ++ |

+++ = P < 0.01 against control;
++ = P < 0.05;
+ = P < 0.1

Therefore the combination of different clades of RrgB allows for broader coverage against pneumococcal strains than single RrgB antigens.

In further tests RrgB chimeras were adjuvanted with alum and tested for protection against TIGR4 intraperitoneal challenge. Chimeras I-II-III and III-II-I were highly protective against bacteremia, and the III-II-I chimera was also protective in terms of survival (FIG. 7).

Figure 13:
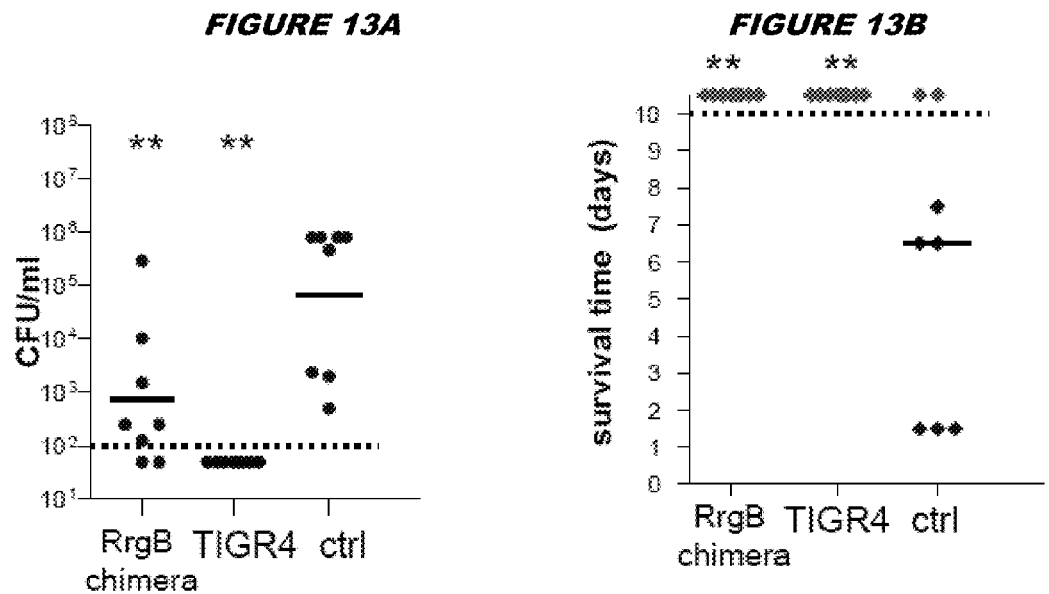
FIG. 13 shows (A) bacteremia and (B) mortality data after immunisation with 20 µg RrgB III-II-I chimera.

Further tests used intranasal challenge after intraperitoneal immunisation with one of four different chimeras (I-II-III, III-II-I, II-III-I, II-I-III). All chimeras showed efficacy or a trend to reduce bacteremia after intranasal TIGR4 challenge. The II-III-I chimera gave good decrease of bacteremia and a non-significant trend of survival increase upon T4 challenge. A PsaA control showed almost no efficacy, measured either by bacteremia or mortality, whereas the II-III-I chimera decreased bacteremia and increased survival. FIG. 13 shows results for an RrgB III-II-I Chimera in a 24 hour bacteremia assay (FIG. 13A) and a mortality assay (FIG. 13B) in BalB/c mice, immunized intraperitoneally with 20 μg chimera (0-14-28 days) and challenged intranasally with TIGR4.

Figure 8:
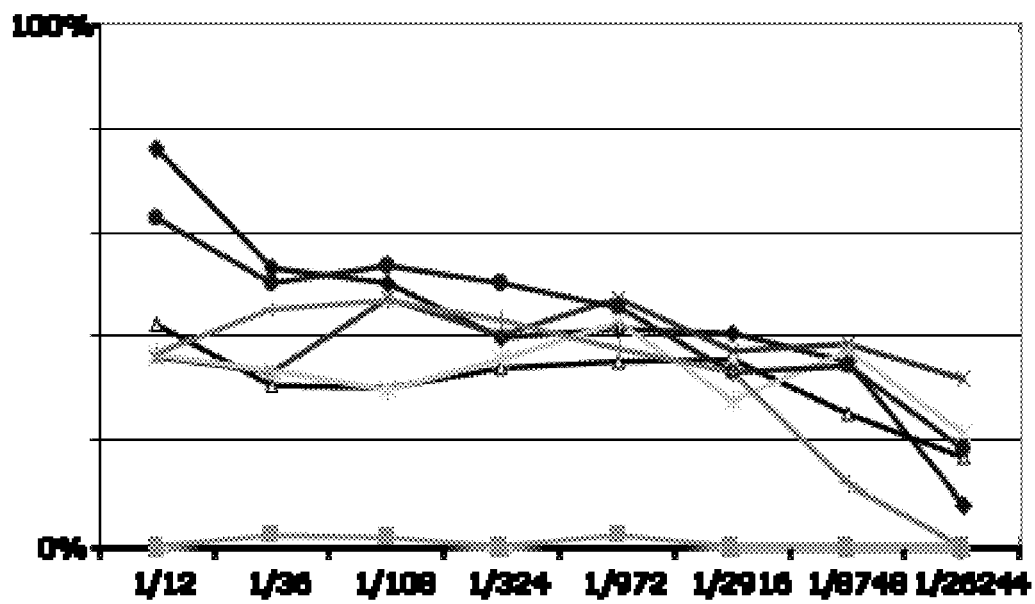
FIG. 8 shows OPKA results against TIGR4 strain, showing % OPKA killing against serum dilution. Diamonds show positive control sera; pre-immune sera are filled boxes, visible near the x-axis; the other five lines are for sera raised against the five chimeras.
Figure 10:
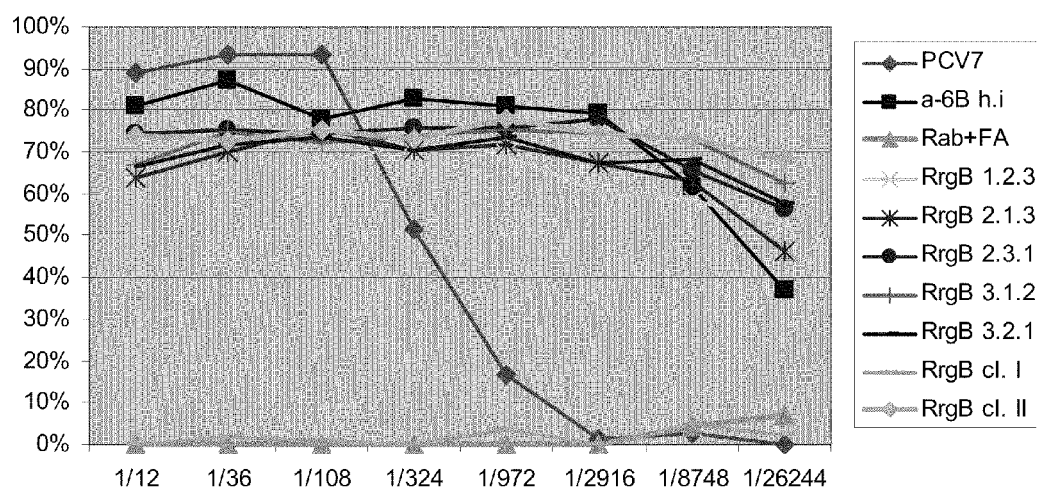
FIG. 10 shows OPKA results against *S. pneumoniae* serotype 6B, showing % killing against serum dilution.
Figure 11:
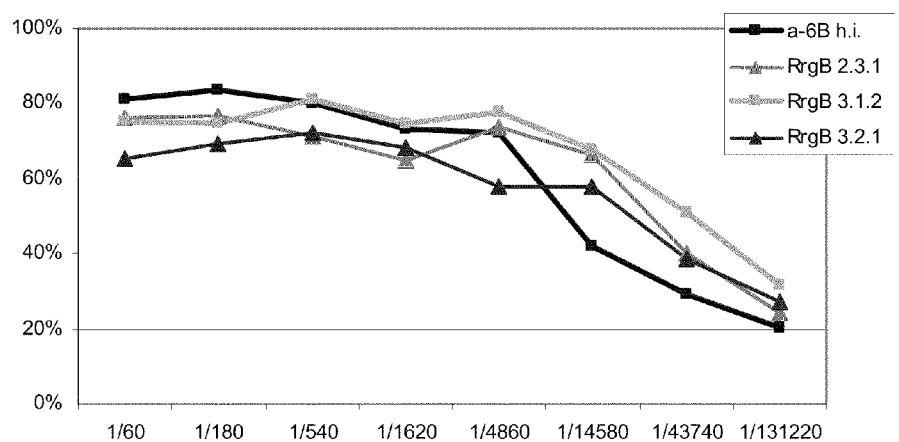
FIG. 11 shows OPKA results against *S. pneumoniae* serotype 6B, showing % killing against serum dilution up to a dilution of 1/131220.

Antibodies against all five RrgB chimeras were also found to mediate in vitro killing of pneumococci in OPKA. For instance, FIG. 8 shows results against the TIGR4 strain. FIG. 10 shows results against S. pneumoniae serotype 6B in an OPKA assay (rabbits subcutaneously immunized with 100 μg of each chimera at days 0, 21 and 35), which shows that no difference in killing percentage is observed between the five chimeras and that the chimeras show killing that is comparable to the conjugate vaccine PCV7. FIG. 11 shows that killing is specific and dependent on antibody concentration, showing that by increasing the dilution up to 1/131220, the percentage killing decreases in the tested chimera curves similarly to the positive control.

FIG. 12 shows a 48 hour bacteremia (FIG. 12A) and mortality (FIG. 12B) assay using a III-II-I chimera (immunised i.p. and challenged i.p. with 35B-SME15) is comparable when using different chimera doses (2 μg and 20 μg).

Figure 14:
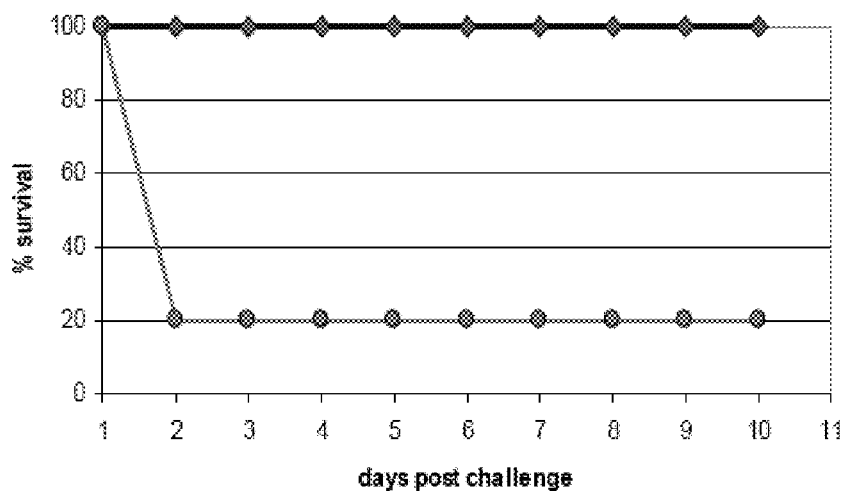
FIG. 14 demonstrates that the III-II-I RrgB chimera is protective using the MF59 adjuvant. Diamonds show adjuvanted RrgB chimera, circles show MF59 alone.

FIG. 14 shows that RrgB III-II-I chimera is protective using MF59 adjuvant in BalB/c mice, intraperitoneal immunisation with 20 μg chimera (0-14-28 days) and challenged intransally.

FIG. 15 shows that RrgB III-II-I chimera is protective upon subcutaneous immunization in BalB/c mice, immunized subcutaneously and challenged intraperitoneally with TIGR4 (130CFU/mouse). FIG. 15A shows a 24 hour bacteremia assay and FIG. 15B shows a mortality assay.

FIG. 16 shows that RrgB III-II-I chimera elicits production of functional antibodies in a passive protection study, compared to a Normal Rabbit Serum (NRS) control, in a 24 hour bacteremia assay.

Figure 18:
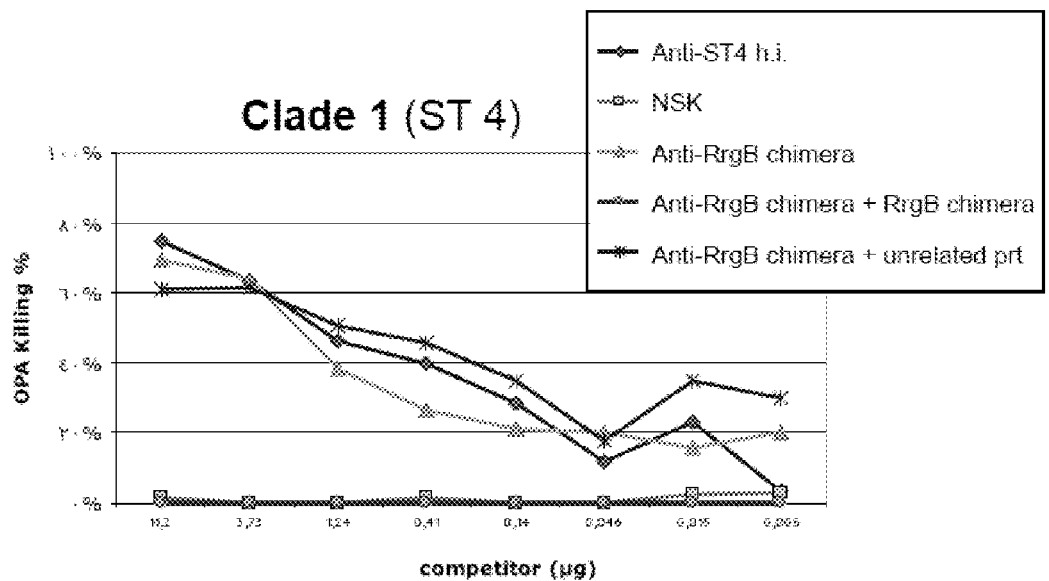
FIG. 18 shows OPKA results against TIGR4 strain, showing that the OPA activity is specifically due to antibodies against RrgB III-II-I chimeras.

FIG. 17 shows that antibodies are functional in OPA against strains of the three clades and FIG. 18 shows that the OPA activity is specifically due to the antibodies against RrgB III-II-I chimera.

Figure 19:
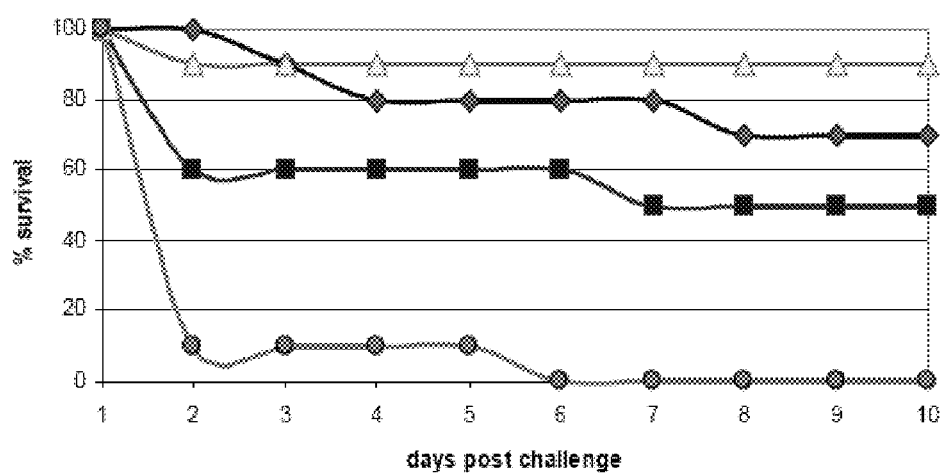
FIG. 19 shows that single RrgB domains confer protection in vivo. Triangles show RrgB chimera, diamonds show D1 domain, squares show D4 domain and circles show Alum.

FIG. 19 shows that sible RrgB domains confer protection in vivo. Specifically, the data show % survival of BalB/c mice immunised with the RrgB D1 domain or the RrgB D4 domain (i.p. immunization 20 μg, 0-14-28 days; i.p. challenge with TIGR4 100CFU).

FIG. 23 shows a 48 hour bacteremia (FIG. 23A) and mortality (FIG. 23B) assay using a III-II-I chimera when combined with different combinations of further polypeptide antigens (20 μg antigens with alum; immunised i.p. and challenged i.v. with 6B-Finland 1.2E+08 CFU/mouse). In both (A) and (B): column 1 shows a combination of spr0057, spr0096 and spr2021; column 2 shows a combination of SP2216-1, SP1732-3 and PsaA; column 3 shows RrgB III-II-I chimera; column 4 shows RrgB III-II-I chimera combined with spr0057, spr0096 and spr2021; column 5 shows RrgB III-II-I chimera combined with SP2216-1, SP1732-3 and PsaA; and column 6 shows an alum control. These data show that the efficacy of a combination of SP2216-1, SP1732-3 and PsaA is significantly increased when combined with the RrgB chimera.

FIG. 24 shows a 48 hour bacteremia (FIG. 24A) and mortality (FIG. 24B) assay using a III-II-I chimera when combined with different combinations of further polypeptide antigens (20 μg antigens with alum; immunised i.p. and challenged i.v. with 35B-SME15 5.2E+07 CFU/mouse). In both (A) and (B): column 1 shows a combination of spr0057, spr0096 and spr2021; column 2 shows a combination of SP2216-1, SP1732-3 and PsaA; column 3 shows RrgB III-II-I chimera; column 4 shows RrgB III-II-I chimera combined with spr0057, spr0096 and spr2021; column 5 shows RrgB III-II-I chimera combined with SP2216-1, SP1732-3 and PsaA; and column 6 shows an alum control. These data show that the RrgB III-II-I chimera, and the combinations of the RrgB III-II-I chimera with other antigens, are all protective.

Figure 26:
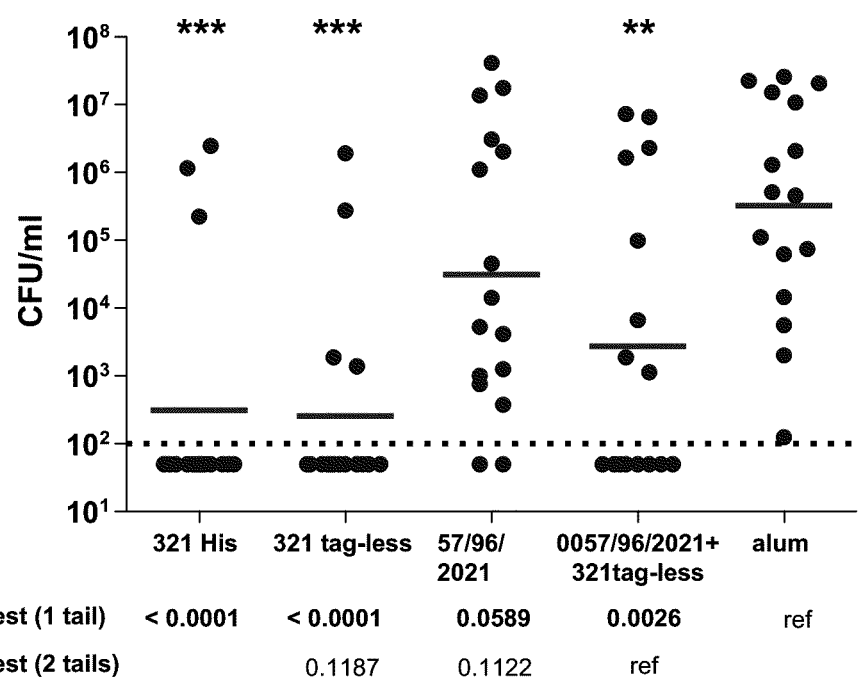
FIG. 26 shows a 24 hour bacteremia assay in BALB/c mice using a III-II-I chimera that contains a polyhistidine tag compared to (i) a tag-less III-II-I chimera, (ii) a combination of spr0057, spr0096 and spr2021, (iii) the combination of spr0057, spr0096 and spr2021 further combined with the tag-less III-II-I chimera, and (iv) an alum control (i.p. immunisation, i.p. challenge with TIGR4 1.6E+02 CFU/mouse).

FIG. 25 shows (A) a 24 hour bacteremia assay and (B) mortality data in BALB/c mice using a III-II-I chimera that contains a polyhistidine tag compared to a tag-less III-II-I chimera and an alum control (i.p. immunisation, i.p. challenge with TIGR4 2.1E+02 CFU/mouse). These data show that both the his-tagged and tag-less chimeras significantly protect against TIGR4 both in terms of bacteremia and survival, with the tag-less chimera showing the most significant protection. FIG. 26 shows similar data i.e. a 24 hour bacteremia assay in BALB/c mice using a III-II-I chimera that contains a polyhistidine tag compared to a tag-less III-II-I chimera and an alum control, further compared to a combination of spr0057, spr0096 and spr2021 antigens, and a combination of the spr0057, spr0096 and spr2021 antigens with the tag-less III-II-I chimera, (i.p. immunisation, i.p. challenge with TIGR4 1.6E+02 CFU/mouse). FIGS. 27 and 28 show data for i.v. challenge with 35B-SME15 (FIG. 27) and 6BFinland12 (FIG. 28), showing that tag-less III-II-I chimera showed the same protective efficacy as his-tagged III-II-I chimera against 35B-SME15 and 6BFinland12 i.v. challenge. Similarly, FIG. 29 shows that both tag-less and his-tagged III-II-I chimeras are protective against i.v. TIGR4 challenge.

FIG. 34 shows the results of 48 hour bacteremia and mortality assays for III-II-I chimera comparing a TIGR4 challenging strain over-expressing pilus to a challenging strain that only expresses very low amounts of pilus. These data show that protection is very good when the pilus is overexpressed and also when the pilus is only present at very low levels. FIG. 35 shows similar bacteremia data for both III-II-I and II-I-III chimeras comparing a 6BFin12 challenging strain over-expressing pilus (FIG. 35A) to a 6BFin12 challenging strain under-expressing pilus (FIG. 35B). The chimeras show significant protection against both the strain over-expressing and the strain underexpressing pilus.

Antimicrobial Resistance

Figure 36:
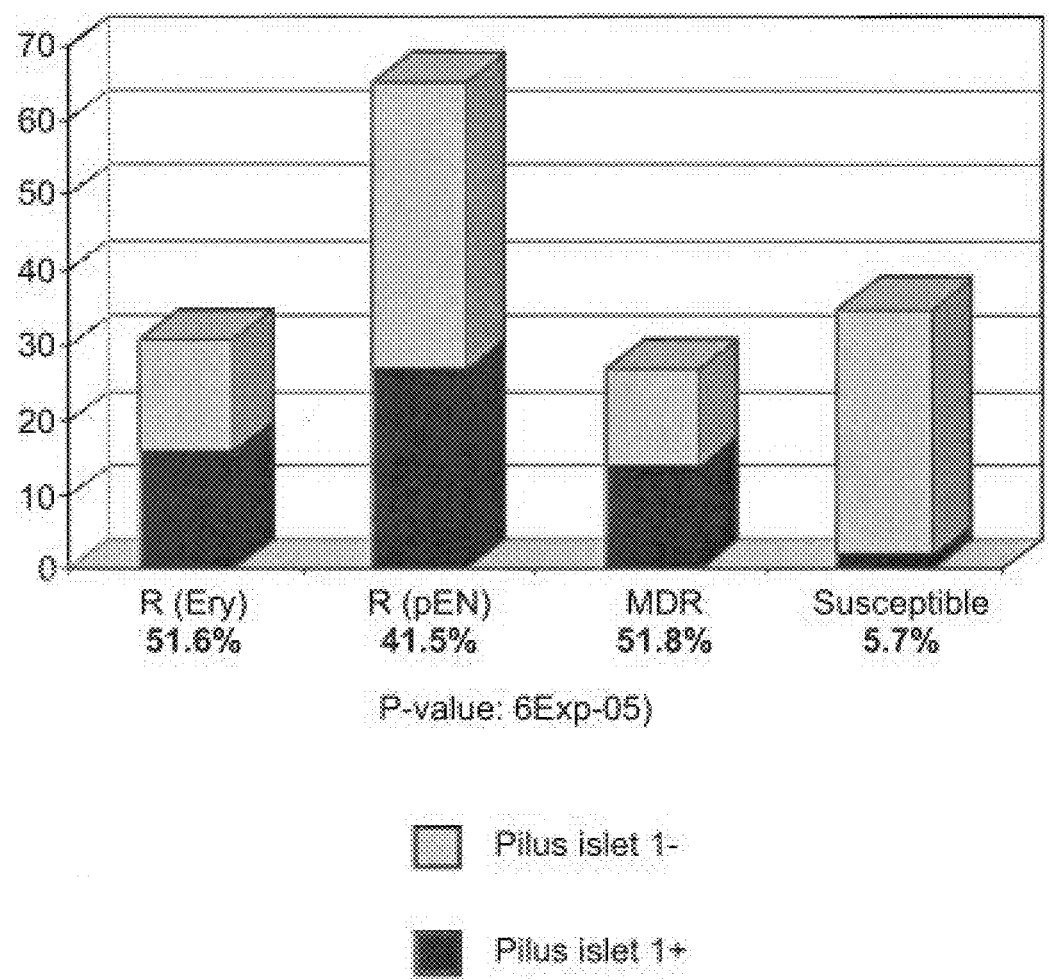
FIG. 36 is an in silico analysis of the MLST database showing that, for a collection of 113 Acute Otitis Media S. pneumoniae isolates, pilus-1 is more prevalent in strains that are resistant to antibiotics (erythromycin-resistance, penicillin-resistance and multiple-drug-resistance) compared to strains that are susceptible to antibiotics.

FIG. 36 shows that pilus-1 is more prevalent in pneumococcal strains that are resistant to antiobiotics (erythromycin-resistance, penicillin-resistance and multiple-drug-resistance) compared to strains that are susceptible to antibiotics. There is a significant association between pilus-1 presence and antibiotic resistance. An increase in the presence of pilus-1 in antibiotic-resistant strains has also been observed in the multi-resistant PMEN strain collection (data not shown). These data suggest that immunising against pilus-1 using an immunogenic composition including multiple RrgB clades will have the additional advantage of protecting against pneumococci that are resistant to antibiotic treatment, for example erythromycin-resistant strains, penicillin-resistant strains and multiply-resistant strains.

Monoclonal Antibodies

Figure 5:
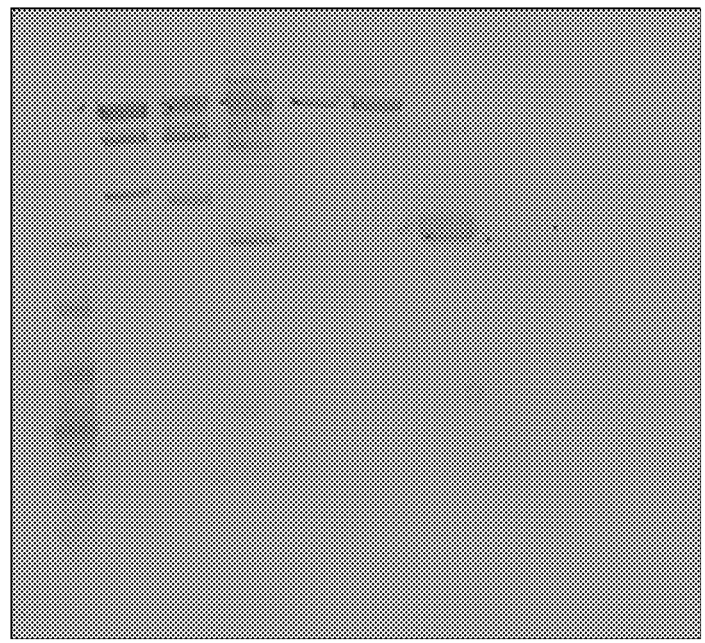
FIGS. 5 and 6 show western blots using mAbs raised against the TIGR4 sequence (FIG. 5) or the 6B sequence (FIG. 6). Lanes are, from left to right: marker; RrgB I-II-III; RrgB II-I-III; RrgB II-III-I; RrgB III-I-II; RrgB III-II-I; RrgB TIGR4; RrgB 6B; RrgB 23F; BSA control.

Monoclonal antibodies were raised against the RrgB from TIGR4. Four mAbs were studied in more detail (named 23B8/B6, 23F8/10, 23E1/A9 and 30A8/A8). 23B8/B6 and 23F8/10 bound to the full-length RrgB from TIGR4, to the D1 domain fragment, and also to a D1-D2-D3 fragment, but not to a D4 fragment. Conversely, 23E1/A9 bound to the full-length protein and so the D4 domain fragment but not to a D1-D2-D3 fragment, or a D4 fragment. 30A8/A8 bound to the full-length RrgB protein but not to any of the domain fragments. The mAbs did not bind to RrgB protein from Finland$^{6B}$-12 or 23F strains, but they did bind to all five chimeras which were expressed. The binding results are shown in FIG. 5 and confirm that the RrgB retains epitopes in its hybrid form.

Figure 4A:
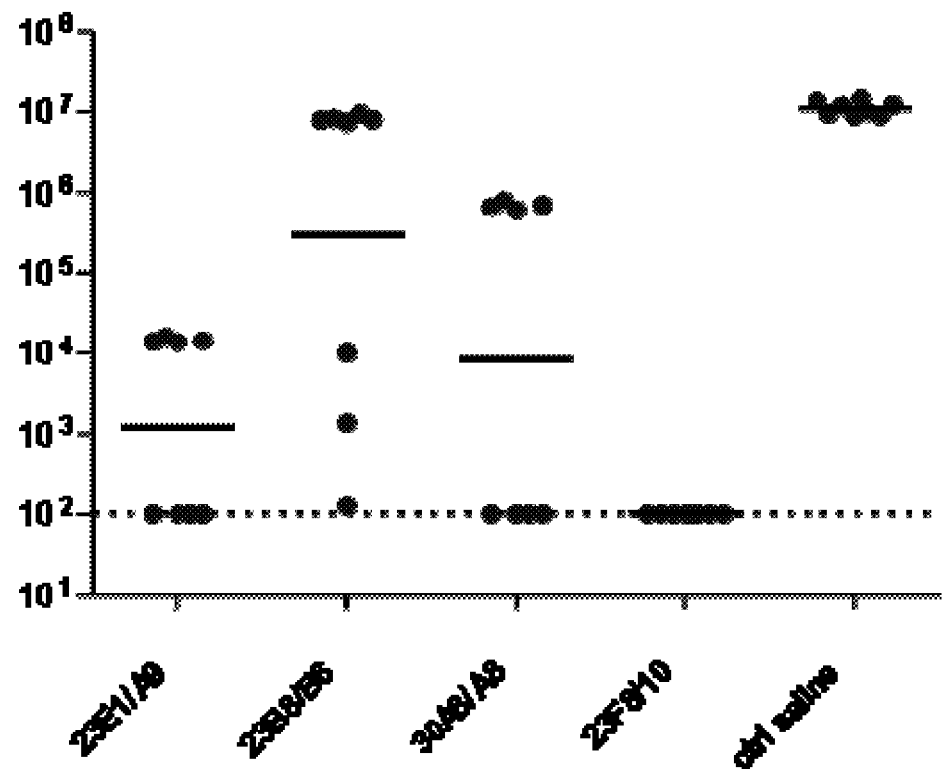
FIG. 4A shows passive protection data using four mAbs raised against the TIGR4 RrgB, or a saline control. The y-axis shows CFU/ml for 24 hour bacteremia.
Figure 4B:
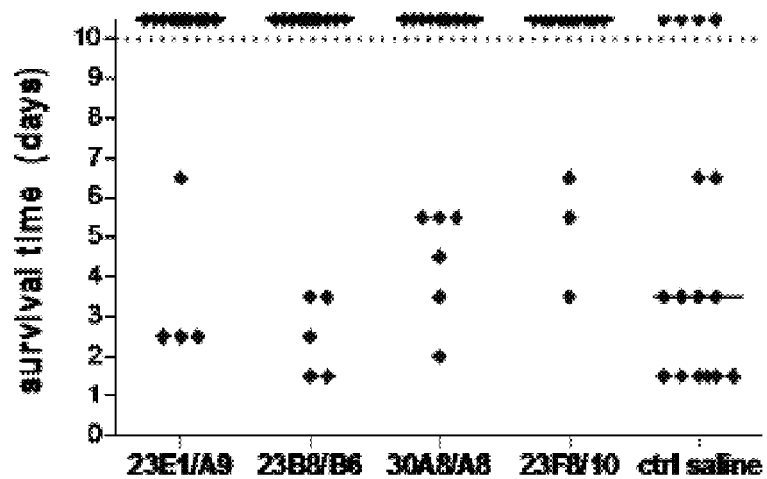
FIG. 4B shows results of a mortality study with the four mAbs raised against the TIGR4 RrgB

As shown in FIG. 4A, each of the four tested anti-TIGR4 mAbs was able to reduce bacteremia in a passive protection test, with the best results coming from 23F8/10. Each of the four tested anti-TIGR4 mAbs also guaranteed a significant ($p<0.01$ for all MAbs except 23B8/B6, $P=0.021$) survival increase in a mortality assay (FIG. 4B).

To determine the epitope recognized by each of the four protective MAbs, the different RrgB domains were cloned, as single domains (D1, D2, D3, D4) or as multi-domain fragments (D1-3, D2-4, D3-4), expressed in *E. Coli* as His-tagged polypeptides and successfully purified in a soluble form by affinity chromatography on His-trap high performance columns (GE Healthcare). The recombinant proteins were then probed in western blot analysis against the MAbs by using FL RrgB clade I and BSA as positive and negative controls respectively.

The results, as shown in FIG. 20, showed that monoclonal antibodies have a different and specific reactivity on the recombinant proteins. Both mAb 23F8/10 and mAb 23 B8/B6 were able to specifically recognize the N-terminal domain D1, the mAb 23 E1/A9 recognized the C-terminal D4, while 30A8/A8, was able to detect only D2-4, suggesting the recognition of a conformational epitope between D2 and D4. These data were then subsequently confirmed by ELISA (data not shown).

Figure 6:
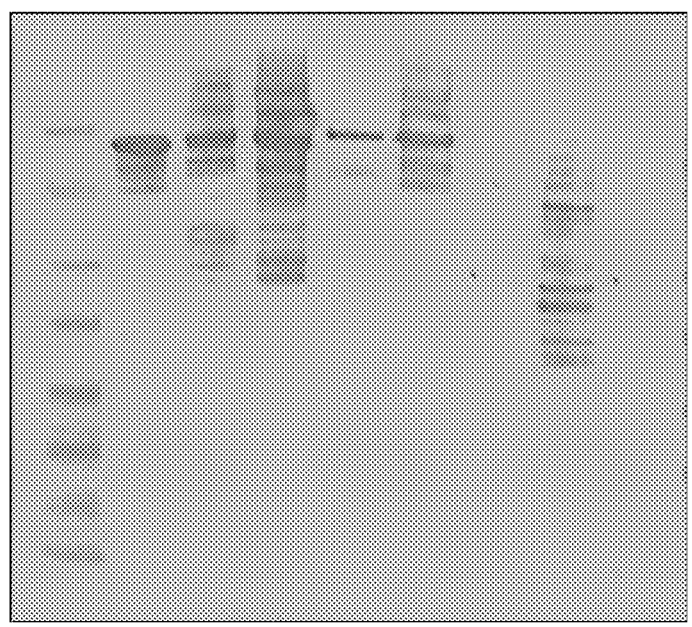

Monoclonal antibodies were also raised against the RrgB from Finland$^{6B}$-12. Two particular mAbs (2A5/29, 3A5/19) bound to the full-length RrgB from Finland$^{6B}$-12, but not to the RrgB protein from TIGR4 or 23F strains. The mAbs also bound to all five chimeras which were expressed. The binding results are shown in FIG. 6.

Epitope Mapping of Protective mAb 23F8/10

To map the region on the D1 domain containing the protective epitope recognized by mAb 23 F8/10 mass spectrometry analysis, Western Blot detection and limited proteolysis of the recombinant proteins were used in combination. This approach can be summarized in four main steps: (i) enzymatic or chemical partial cleavage of the protein, (ii) definition of sequence coverage of the generated fragments by MS analysis after their separation by SDS-PAGE, (iii) western blot analysis of the generated fragments, (iv) comparison of positive and negative bands in western blot in order to localize the epitope.

Figure 21:
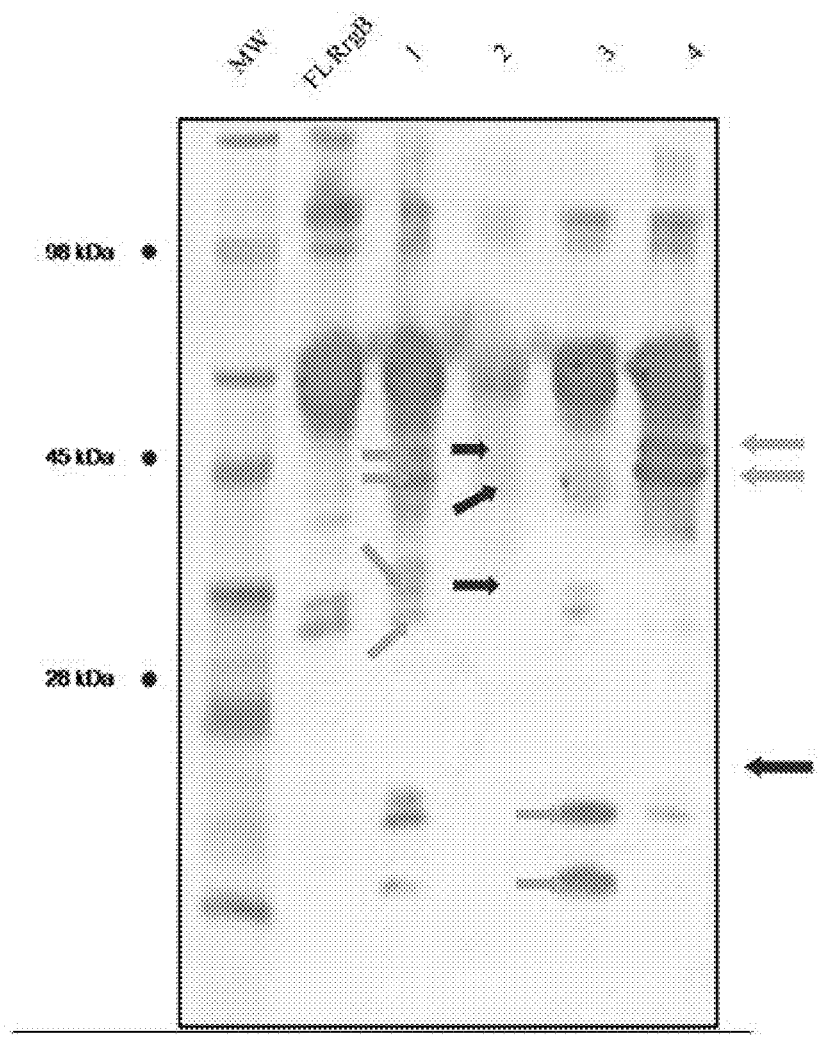
FIG. 21 shows a western blot analysis performed with monoclonal antibody 23F8/C10 binding to trypsin-digested RrgB.

The first step was to obtain from the full length RrgB a significant number of polypeptides showing a well resolved pattern after separation on SDS-PAGE. The protease selected for these experiments was trypsin, which cleaves proteins at the C-terminal side of arginine (R) and lysine (K) residues. 20 µg of full length RrgB was digested and the products of the digestion were separated with SDS-PAGE (5 µg of the full length protein, and 12 µg of the product of digestion). As noted above, and as shown in FIG. 20, the monoclonal antibody 23F8/10 recognized both the full length recombinant RrgB and the RrgB D1, as well as a high number of polypeptides derived from the cleavage of the full length protein with trypsin. The identification of both the positive and negative bands in the western blot analysis (with respect to the same Coomassie stained sample) was important for the epitope identification. The western blot with monoclonal antibody 23F8/C10 is shown as FIG. 21. About 20 Coomassie-stained proteolitic fragments, comprising both western blot (immunoblotted with MAb 23F8/C10) positive (green arrows) and negative (red arrows) bands, were excised from the gel and in situ digested with trypsin O/N and analyzed by MALDI-TOF/TOF mass spectrometry, in order to define the sequence coverage for each of them. The sequence coverage obtained for each analyzed fragment was defined between the most "N-terminal" and the most "C-terminal" tryptic peptides identified in the PMF spectra (peptide mass fingerprints). A schematic sequence coverage of the electrophoretic pattern of the trypsin products derived from full length RrgB, in association with western blot results, was prepared. This analysis suggested that the 23F8/10 epitope is between amino acid 32 and amino acid 141 of full length RrgB.

Figure 22:
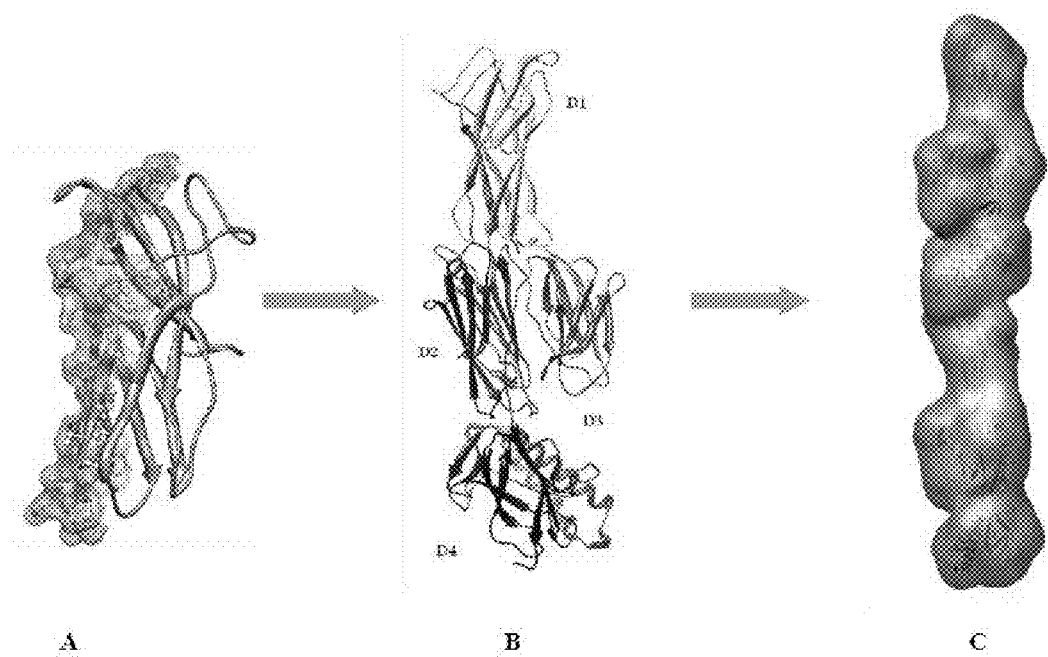
FIG. 22(A) is a model of RrgB domain D1 amino acid sequence onto the domain 1 crystal structure of *S. pyogenes* pilus backbone Spy0128. (B) is *S. pneumoniae* RrgB crystal structure (D2-D3) and modeled D1 domain. (C) is a 3D reconstruction electron density map of the *S. pneumoniae* pilus.

The same strategy was then used on the N-terminal domain D1, in order to narrow the region containing the epitope recognized by MAb 23F8/C10. 20 µg of D1 was digested and the products of the digestion were separated with SDS-PAGE (5 µg of the full length protein, and 12 µg of the product of digestion). Unlike full length digested RrgB, in this experiment the monoclonal antibody 23F8/10 recognized only full length D1 and some of the polypeptides derived from trypsin D1 digestion. Afterwards, both positive and negative bands were taken into consideration for further analysis. About 10 Coomassie-stained peptide fragments, comprising both positive and negative bands, were excised from the gel and in situ digested with trypsin O/N and analyzed by MALDI-TOF/TOF mass spectrometry, in order to define the sequence coverage for each of them. The sequence coverage obtained for each analyzed fragment was defined between the most "N-terminal" and the most "C-terminal" tryptic peptides identified in the PMF spectra (peptide mass fingerprints). The sequence coverage of the electrophoretic band of the trypsin products derived from RrgB D1 domain, as previously established in association with the results of the western blot, suggested that the region recognised by MAb 23F8/10 containing the protective epitope is from amino acid residue 55 to amino acid residue 89 of RrgB. The D1 amino acid sequence (for which no structural data are yet available) was modeled onto the domain 1 crystal structure of the S. pyogenes pilus backbone Spy0128 (overall homology about 27%). The residues that the data suggest are the epitope (aa 55-89) were mapped onto the model (FIG. 22A). In a 3D reconstruction of the electron density map of the pilus, obtained performing a rigid body fitting of the RrgB D1-4 structure, this epitope is shown to be surface exposed (FIGS. 22B & 22C).

RrgB Chimeras as Carrier Proteins

In addition to acting as vaccine components, the RrgB chimeras are suitable for use as carrier proteins in saccharide-carrier conjugates. The I-II-III and III-II-I chimeras were conjugated to a saccharide immunogen and IgG responses (GMT) against the saccharide were then measured by ELISA. Results were compared to a number of other pneumococcal proteins, and also to N19 and CRM197 as positive controls. Results from study VI/VII were as follows:

| CRM197 | N19 | I-II-III | III-II-I | 1287 | LRP | 1875 |
|---|---|---|---|---|---|---|
| 2688 | 1004 | 638 | 133 | 25 | 114 | 114 |

It will be understood that the invention has been described by way of example only and modifications may be made whilst remaining within the scope and spirit of the invention.

REFERENCES

[1] Barocchi et al. (2006) *PNAS USA* 103:2857-62.
[2] Bagnoli et al. (2008) *J Bacteriol.* 190(15):5480-92.
[3] WO2007/116322.
[4] LeMieux et al. (2006) *Infect Immun* 74:2453-6.
[5] Needleman & Wunsch (1970) *J. Mol. Biol.* 48, 443-453.
[6] Rice et al. (2000) *Trends Genet* 16:276-277.
[7] Bodanszky (1993) *Principles of Peptide Synthesis* (ISBN: 0387564314).
[8] Fields et al. (1997) *Meth Enzymol* 289: *Solid-Phase Peptide Synthesis.* ISBN: 0121821900.
[9] Chan & White (2000) *Fmoc Solid Phase Peptide Synthesis.* ISBN: 0199637245.
[10] Kullmann (1987) *Enzymatic Peptide Synthesis.* ISBN: 0849368413.
[11] Ibba (1996) *Biotechnol Genet Eng Rev* 13:197-216.
[12] U.S. Pat. No. 5,707,829
[13] *Vaccine Design* . . . (1995) eds. Powell & Newman. ISBN: 030644867X. Plenum.
[14] WO90/14837.
[15] WO90/14837.
[16] Podda & Del Giudice (2003) *Expert Rev Vaccines* 2:197-203.
[17] Podda (2001) *Vaccine* 19: 2673-2680.
[18] *Vaccine Design: The Subunit and Adjuvant Approach* (eds. Powell & Newman) Plenum Press 1995 (ISBN 0-306-44867-X).
[19] *Vaccine Adjuvants: Preparation Methods and Research Protocols* (Volume 42 of *Methods in Molecular Medicine* series). ISBN: 1-59259-083-7. Ed. O'Hagan.
[20] Allison & Byars (1992) *Res Immunol* 143:519-25.
[21] Hariharan et al. (1995) *Cancer Res* 55:3486-9.
[22] US-2007/014805.
[23] WO95/11700.
[24] U.S. Pat. No. 6,080,725.
[25] WO2006/113373.
[26] WO2005/097181.
[27] U.S. Pat. No. 5,057,540.
[28] WO96/33739.
[29] EP-A-0109942.
[30] WO96/11711.
[31] WO00/07621.
[32] Barr et al. (1998) *Advanced Drug Delivery Reviews* 32:247-271.
[33] Sjolanderet et al. (1998) *Advanced Drug Delivery Reviews* 32:321-338.
[34] Niikura et al. (2002) *Virology* 293:273-280.
[35] Lenz et al. (2001) *J Immunol* 166:5346-5355.
[36] Pinto et al. (2003) *J Infect Dis* 188:327-338.
[37] Gerber et al. (2001) *J Virol* 75:4752-4760.
[38] WO03/024480.
[39] WO03/024481.
[40] Gluck et al. (2002) *Vaccine* 20:B10-B16.
[41] EP-A-0689454.
[42] Johnson et al. (1999) *Bioorg Med Chem Lett* 9:2273-2278.
[43] Evans et al. (2003) *Expert Rev Vaccines* 2:219-229.
[44] Meraldi et al. (2003) *Vaccine* 21:2485-2491.
[45] Pajak et al. (2003) *Vaccine* 21:836-842.
[46] Kandimalla et al. (2003) *Nucleic Acids Research* 31:2393-2400.
[47] WO02/26757.
[48] WO99/62923.
[49] Krieg (2003) *Nature Medicine* 9:831-835.
[50] McCluskie et al. (2002) *FEMS Immunology and Medical Microbiology* 32:179-185.
[51] WO98/40100.
[52] U.S. Pat. No. 6,207,646.
[53] U.S. Pat. No. 6,239,116.
[54] U.S. Pat. No. 6,429,199.
[55] Kandimalla et al. (2003) *Biochemical Society Transactions* 31 (part 3):654-658.
[56] Blackwell et al. (2003) *J Immunol* 170:4061-4068.
[57] Krieg (2002) *Trends Immunol* 23:64-65.
[58] WO01/95935.
[59] Kandimalla et al. (2003) *BBRC* 306:948-953.
[60] Bhagat et al. (2003) *BBRC* 300:853-861.
[61] WO03/035836.
[62] Schellack et al. (2006) *Vaccine* 24:5461-72.
[63] WO95/17211.
[64] WO98/42375.
[65] Beignon et al. (2002) *Infect Immun* 70:3012-3019.
[66] Pizza et al. (2001) *Vaccine* 19:2534-2541.
[67] Pizza et al. (2000) *Int J Med Microbiol* 290:455-461.
[68] Scharton-Kersten et al. (2000) *Infect Immun* 68:5306-5313.
[69] Ryan et al. (1999) *Infect Immun* 67:6270-6280.
[70] Partidos et al. (1999) *Immunol Lett* 67:209-216.
[71] Peppoloni et al. (2003) *Expert Rev Vaccines* 2:285-293.
[72] Pine et al. (2002) *J Control Release* 85:263-270.

[73] Tebbey et al. (2000) *Vaccine* 18:2723-34.
[74] Domenighini et al. (1995) *Mol Microbiol* 15:1165-1167.
[75] WO99/40936.
[76] WO99/44636.
[77] Singh et all (2001) *J Cont Release* 70:267-276.
[78] WO99/27960.
[79] U.S. Pat. No. 6,090,406.
[80] U.S. Pat. No. 5,916,588.
[81] EP-A-0626169.
[82] WO99/52549.
[83] WO01/21207.
[84] WO01/21152.
[85] Andrianov et al. (1998) *Biomaterials* 19:109-115.
[86] Payne et al. (1998) *Adv Drug Delivery Review* 31:185-196.
[87] Stanley (2002) *Clin Exp Dermatol* 27:571-577.
[88] Jones (2003) *Curr Opin Investig Drugs* 4:214-218.
[89] WO99/11241.
[90] WO94/00153.
[91] WO98/57659.
[92] European patent applications 0835318, 0735898 and 0761231.
[93] Donnelly et al. (1997) *Annu Rev Immunol* 15:617-648.
[94] Strugnell et al. (1997) *Immunol Cell Biol* 75(4):364-369.
[95] Cui (2005) *Adv Genet* 54:257-89.
[96] Robinson & Torres (1997) *Seminars in Immunol* 9:271-283.
[97] Brunham et al. (2000) *J Infect Dis* 181 Suppl 3:S538-43.
[98] Svanholm et al. (2000) *Scand J Immunol* 51(4):345-53.
[99] *DNA Vaccination—Genetic Vaccination* (1998) eds. Koprowski et al. (ISBN 3540633928).
[100] *Gene Vaccination: Theory and Practice* (1998) ed. Raz (ISBN 3540644288).
[101] Findeis et al., *Trends Biotechnol.* (1993) 11:202
[102] Chiou et al. (1994) *Gene Therapeutics: Methods And Applications Of Direct Gene Transfer*. ed. Wolff
[103] Wu et al., *J. Biol. Chem.* (1988) 263:621
[104] Wu et al., *J. Biol. Chem.* (1994) 269:542
[105] Zenke et al., *Proc. Natl. Acad. Sci.* (USA) (1990) 87:3655
[106] Wu et al., *J. Biol. Chem.* (1991) 266:338
[107] Jolly, *Cancer Gene Therapy* (1994) 1:51
[108] Kimura, *Human Gene Therapy* (1994) 5:845
[109] Connelly, *Human Gene Therapy* (1995) 1:185
[110] Kaplitt, *Nature Genetics* (1994) 6:148
[111] WO 90/07936.
[112] WO 94/03622.
[113] WO 93/25698.
[114] WO 93/25234.
[115] U.S. Pat. No. 5,219,740.
[116] WO 93/11230.
[117] WO 93/10218.
[118] U.S. Pat. No. 4,777,127.
[119] GB Patent No. 2,200,651.
[120] EP-A-0345242.
[121] WO 91/02805.
[122] WO 94/12649.
[123] WO 93/03769.
[124] WO 93/19191.
[125] WO 94/28938.
[126] WO 95/11984.
[127] WO 95/00655.
[128] Curiel, *Hum. Gene Ther.* (1992) 3:147
[129] Wu, *J. Biol. Chem.* (1989) 264:16985
[130] U.S. Pat. No. 5,814,482.
[131] WO 95/07994.
[132] WO 96/17072.
[133] WO 95/30763.
[134] WO 97/42338.
[135] WO 90/11092.
[136] U.S. Pat. No. 5,580,859
[137] U.S. Pat. No. 5,422,120
[138] WO 95/13796.
[139] WO 94/23697.
[140] WO 91/14445.
[141] EP-0524968.
[142] Philip, *Mol. Cell Biol.* (1994) 14:2411
[143] Woffendin, *Proc. Natl. Acad. Sci.* (1994) 91:11581
[144] U.S. Pat. No. 5,206,152.
[145] WO 92/11033.
[146] U.S. Pat. No. 5,149,655.
[147] Zwijnenburg et al. (2001) *J Infect Dis* 183:1143-6.
[148] WO2009/016515.
[149] Hoskins et al. (2001) *J. Bacteriol.* 183:5709-5717.
[150] WO2004/092209.
[151] Kirkham et al. (2006) *Infect Immun.* 74(1):586-93.
[152] WO2005/108580.
[153] Berry et al. (1999) *Infect Immun* 67(2):981-5.
[154] U.S. Pat. No. 6,716,432.
[155] WO90/06951.
[156] WO99/03884.
[157] Baba et al. (2002) *Infect Immun* 70: 107-113.
[158] U.S. Pat. No. 7,217,791
[159] WO2008/061953.
[160] WO01/12219.
[161] Cao et al. (2007) *Vaccine* 25(27):4996-5005.
[162] WO2005/063283.
[163] WO2003/104272.
[164] WO00/37105.
[165] Adamou et al. (2001) *Infect Immun.* 69(2):949-58.
[166] Ogunniyi et al. (2007) *Infect Immun.* 75(1):350-7.
[167] WO98/18930.
[168] WO02/22168.
[169] Wizemann et al. (2001) *Infect Immun* 69:1593-8.
[170] WO99/53940.
[171] WO02/22167.
[172] WO02/08426.
[173] Briles et al. (2000) *J Infect Dis* 182:1694-1701.
[174] Talkington et al. (1996) *Microb Pathog.* 21(1):17-22.
[175] WO00/76540.
[176] Bethe et al. (2001) *FEMS Microbiol Lett.* 205(1):99-104.
[177] WO01/81380.
[178] Brown et al. (2001) *Infect Immun* 69:6702-6.
[179] Whalan et al. (2005) *FEMS Immunol Med Microbiol* 43:73-80.
[180] Jomaa et al. (2006) *Vaccine.* 24(24):5133-9.
[181] WO00/06738.
[182] Kuo et al. (1995) *Infect Immun* 63:2706-13.
[183] Michon et al. (1998) *Vaccine.* 16:1732-41.
[184] WO02/091998.
[185] *Research Disclosure,* 453077 (January 2002).
[186] EP-A-0372501.
[187] EP-A-0378881.
[188] EP-A-0427347.
[189] WO93/17712.
[190] WO94/03208.
[191] WO98/58668.
[192] EP-A-0471177.
[193] WO91/01146.

[194] Falugi et al. (2001) *Eur J Immunol* 31:3816-3824.
[195] Baraldo et al. (2004) *Infect Immun* 72(8):4884-7.
[196] EP-A-0594610.
[197] Ruan et al. (1990) *J Immunol* 145:3379-3384.
[198] WO00/56360.
[199] WO01/72337.
[200] WO00/61761.
[201] WO00/33882
[202] WO2007/071707
[203] WO99/42130.
[204] U.S. Pat. No. 4,761,283.
[205] U.S. Pat. No. 4,356,170.
[206] U.S. Pat. No. 4,882,317.
[207] U.S. Pat. No. 4,695,624.
[208] *Mol. Immunol.,* 1985, 22, 907-919
[209] EP-A-0208375.
[210] Bethell G. S. et al., *J. Biol. Chem.,* 1979, 254, 2572-4
[211] Hearn M. T. W., *J. Chromatogr.,* 1981, 218, 509-18
[212] WO00/10599.
[213] Gever et al., Med. Microbiol. Immunol, 165 : 171-288 (1979).
[214] U.S. Pat. No. 4,057,685.
[215] U.S. Pat. Nos. 4,673,574; 4,761,283; 4,808,700.
[216] U.S. Pat. No. 4,459,286.
[217] U.S. Pat. No. 4,965,338.
[218] U.S. Pat. No. 4,663,160.
[219] WO2007/000343.
[220] *Vaccines.* (eds. Plotkin & Orenstein). 4th edition, 2004, ISBN: 0-7216-9688-0.
[221] Rappuoli et al. (1991) *TIBTECH* 9:232-238.
[222] Giuliani et al. (2006) *Proc Natl Acad Sci USA* 103 (29):10834-9.
[223] Brandt et al. (2006) *J Antimicrob Chemother.* 58(6): 1291-4. Epub 2006 Oct 26
[224] Winter et al., (1991) *Nature* 349:293-99
[225] U.S. Pat. No. 4,816,567.
[226] Inbar et al., (1972) *Proc. Natl. Acad. Sci. U.S.A.* 69:2659-62.
[227] Ehrlich et al., (1980) *Biochem* 19:4091-96.
[228] Huston et al., (1988) Proc. Natl. Acad. Sci. U.S.A. 85:5897-83.
[229] Pack et al., (1992) *Biochem* 31, 1579-84.
[230] Cumber et al., (1992) *J. Immunology* 149B, 120-26.
[231] Riechmann et al., (1988) *Nature* 332, 323-27.
[232] Verhoeyan et al., (1988) *Science* 239, 1534-36.
[233] GB 2,276,169.
[234] Gennaro (2000) *Remington: The Science and Practice of Pharmacy.* 20th edition, ISBN: 0683306472.
[235] *Methods In Enzymology* (S. Colowick and N. Kaplan, eds., Academic Press, Inc.)
[236] *Handbook of Experimental Immunology,* Vols. I-IV (D. M. Weir and C. C. Blackwell, eds, 1986, Blackwell Scientific Publications)
[237] Sambrook et al. (2001) *Molecular Cloning: A Laboratory Manual,* 3rd edition (Cold Spring Harbor Laboratory Press).
[238] *Handbook of Surface and Colloidal Chemistry* (Birdi, K. S. ed., CRC Press, 1997)
[239] Ausubel et al. (eds) (2002) *Short protocols in molecular biology,* 5th edition (Current Protocols).
[240] *Molecular Biology Techniques: An Intensive Laboratory Course,* (Ream et al., eds., 1998, Academic Press)
[241] *PCR (Introduction to Biotechniques Series),* 2nd ed. (Newton & Graham eds., 1997, Springer Verlag)
[242] Geysen et al. (1984) *PNAS USA* 81:3998-4002.
[243] Carter (1994) *Methods Mol Biol* 36:207-23.
[244] Jameson, B A et al. 1988, *CABIOS* 4(1):181-186.
[245] Raddrizzani & Hammer (2000) *Brief Bioinform* 1(2): 179-89.
[246] Bublil et al. (2007) *Proteins* 68(1):294-304.
[247] De Lalla et al. (1999) *J. Immunol.* 163:1725-29.
[248] Kwok et al. (2001) *Trends Immunol* 22:583-88.
[249] Brusic et al. (1998) *Bioinformatics* 14(2):121-30
[250] Meister et al. (1995) *Vaccine* 13(6):581-91.
[251] Roberts et al. (1996) *AIDS Res Hum Retroviruses* 12(7):593-610.
[252] Maksyutov & Zagrebelnaya (1993) *Comput Appl Biosci* 9(3):291-7.
[253] Feller & de la Cruz (1991) *Nature* 349(6311):720-1.
[254] Hopp (1993) *Peptide Research* 6:183-190.
[255] Welling et al. (1985) *FEBS Lett.* 188:215-218.
[256] Davenport et al. (1995) *Immunogenetics* 42:392-297.
[257] Tsurui & Takahashi (2007) *J Pharmacol Sci.* 105(4): 299-316.
[258] Tong et al. (2007) *Brief Bioinform.* 8(2):96-108.
[259] Schirle et al. (2001) *J Immunol Methods.* 257(1-2): 1-16.
[260] Chen et al. (2007) *Amino Acids* 33(3):423-8.
[261] *Current Protocols in Molecular Biology* (F. M. Ausubel et al., eds., 1987) Supplement 30
[262] Smith & Waterman (1981) *Adv. Appl. Math.* 2: 482-489.

---

The invention claimed is:

1. An immunogenic composition comprising at least two of:
   (a) a first polypeptide comprising a first amino acid sequence, where the first amino acid sequence comprises an amino acid sequence (i) having at least 90% sequence identity to SEQ ID NO: 1 and/or (ii) consisting of a fragment of at least 7 contiguous amino acids from SEQ ID NO: 1;
   (b) a second polypeptide, comprising a second amino acid sequence, where the second amino acid sequence comprises an amino acid sequence (i) having at least 90% sequence identity to SEQ ID NO: 2 and/or (ii) consisting of a fragment of at least 50 contiguous amino acids from SEQ ID NO: 2; and/or
   (c) a third polypeptide, comprising a third amino acid sequence, where the third amino acid sequence comprises an amino acid sequence (i) having at least 90% sequence identity to SEQ ID NO: 3 and/or (ii) consisting of a fragment of at least 29 contiguous amino acids from SEQ ID NO: 3.

2. A polypeptide comprising at least two of:
   (a) a first amino acid sequence comprising an amino acid sequence (i) having at least 90% sequence identity to SEQ ID NO: 1 and/or (ii) consisting of a fragment of at least 7 contiguous amino acids from SEQ ID NO: 1;
   (b) a second amino acid sequence comprising an amino acid sequence (i) having at least 90% sequence identity to SEQ ID NO: 2 and/or (ii) consisting of a fragment of at least 50 contiguous amino acids from SEQ ID NO: 2; and/or
   (c) a third amino acid sequence comprising an amino acid sequence (i) having at least 90% sequence identity to SEQ ID NO: 3 and/or (ii) consisting of a fragment of at least 29 contiguous amino acids from SEQ ID NO: 3.

3. A polypeptide comprising amino acid sequence:

$$A-\{-X-L-\}_n-B$$

wherein: each X is an amino acid sequence of first polypeptide, second polypeptide or third polypeptide as defined in claim 1; L is an optional linker amino acid sequence; A is an optional N terminal amino acid sequence; B is an optional C terminal amino acid sequence; n is an integer of 2 or more.

4. The polypeptide of claim 2 or claim 3, comprising an amino acid sequence selected from the group consisting of: SEQ ID NOs: 11, 13, 15, 17, 19 and 21.

5. An immunogenic composition comprising at least two of:
   (a) a first polypeptide comprising a first amino acid sequence, where the first amino acid sequence comprises an amino acid sequence consisting of a fragment of at least 7 contiguous amino acids from SEQ ID NO: 1;
   (b) a second polypeptide, comprising a second amino acid sequence, where the second amino acid sequence comprises an amino acid sequence consisting of a fragment of at least 7 contiguous amino acids from SEQ ID NO: 2; and/or
   (c) a third polypeptide, comprising a third amino acid sequence, where the third amino acid sequence comprises an amino acid sequence consisting of a fragment of at least 7 contiguous amino acids from SEQ ID NO: 3;
   wherein, the fragment of at least 7 contiguous amino acids from SEQ ID NO: 1 is not present within SEQ ID NO: 2 or within SEQ ID NO: 3, the fragment of at least 7 contiguous amino acids from SEQ ID NO: 2 is not present within SEQ ID NO: 1 or within SEQ ID NO: 3, and the fragment of at least 7 contiguous amino acids from SEQ ID NO: 3 is not present within SEQ ID NO: 1 or within SEQ ID NO: 2.

6. The immunogenic composition of claim 1, where the first polypeptide comprises a first amino acid sequence having at least 90% sequence identity to SEQ ID NO: 1, where the second polypeptide comprises a second amino acid sequence having at least 90% sequence identity to SEQ ID NO: 2, and where the third polypeptide comprises a third amino acid sequence having at least 90% sequence identity to SEQ ID NO: 3.

7. The polypeptide of claim 2, where the first amino acid sequence comprises an amino acid sequence having at least 90% sequence identity to SEQ ID NO: 1, where the second amino acid sequences comprises an amino acid sequence having at least 90% sequence identity to SEQ ID NO: 2, and where the third amino acid sequence comprises an amino acid sequence having at least 90% sequence identity to SEQ ID NO: 3.

* * * * *

SEQUENCE LISTING

<160> NUMBER OF SEQ ID NOS: 99

<210> SEQ ID NO 1
<211> LENGTH: 665
<212> TYPE: PRT
<213> ORGANISM: Streptococcus pneumoniae

<400> SEQUENCE: 1

```
Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Gly Thr
            20                  25                  30

Thr Thr Thr Ser Val Thr Val His Lys Leu Leu Ala Thr Asp Gly Asp
        35                  40                  45
```

```
Met Asp Lys Ile Ala Asn Glu Leu Glu Thr Gly Asn Tyr Ala Gly Asn
 50                  55                  60
Lys Val Gly Val Leu Pro Ala Asn Ala Lys Glu Ile Ala Gly Val Met
 65                  70                  75                  80
Phe Val Trp Thr Asn Thr Asn Asn Glu Ile Ile Asp Glu Asn Gly Gln
                 85                  90                  95
Thr Leu Gly Val Asn Ile Asp Pro Gln Thr Phe Lys Leu Ser Gly Ala
                100                 105                 110
Met Pro Ala Thr Ala Met Lys Lys Leu Thr Glu Ala Glu Gly Ala Lys
                115                 120                 125
Phe Asn Thr Ala Asn Leu Pro Ala Ala Lys Tyr Lys Ile Tyr Glu Ile
130                 135                 140
His Ser Leu Ser Thr Tyr Val Gly Glu Asp Gly Ala Thr Leu Thr Gly
145                 150                 155                 160
Ser Lys Ala Val Pro Ile Glu Ile Glu Leu Pro Leu Asn Asp Val Val
                165                 170                 175
Asp Ala His Val Tyr Pro Lys Asn Thr Glu Ala Lys Pro Lys Ile Asp
                180                 185                 190
Lys Asp Phe Lys Gly Lys Ala Asn Pro Asp Thr Pro Arg Val Asp Lys
                195                 200                 205
Asp Thr Pro Val Asn His Gln Val Gly Asp Val Val Glu Tyr Glu Ile
210                 215                 220
Val Thr Lys Ile Pro Ala Leu Ala Asn Tyr Ala Thr Ala Asn Trp Ser
225                 230                 235                 240
Asp Arg Met Thr Glu Gly Leu Ala Phe Asn Lys Gly Thr Val Lys Val
                245                 250                 255
Thr Val Asp Asp Val Ala Leu Glu Ala Gly Asp Tyr Ala Leu Thr Glu
                260                 265                 270
Val Ala Thr Gly Phe Asp Leu Lys Leu Thr Asp Ala Gly Leu Ala Lys
                275                 280                 285
Val Asn Asp Gln Asn Ala Glu Lys Thr Val Lys Ile Thr Tyr Ser Ala
290                 295                 300
Thr Leu Asn Asp Lys Ala Ile Val Glu Val Pro Glu Ser Asn Asp Val
305                 310                 315                 320
Thr Phe Asn Tyr Gly Asn Asn Pro Asp His Gly Asn Thr Pro Lys Pro
                325                 330                 335
Asn Lys Pro Asn Glu Asn Gly Asp Leu Thr Leu Thr Lys Thr Trp Val
                340                 345                 350
Asp Ala Thr Gly Ala Pro Ile Pro Ala Gly Ala Glu Ala Thr Phe Asp
                355                 360                 365
Leu Val Asn Ala Gln Thr Gly Lys Val Val Gln Thr Val Thr Leu Thr
370                 375                 380
Thr Asp Lys Asn Thr Val Thr Val Asn Gly Leu Asp Lys Asn Thr Glu
385                 390                 395                 400
Tyr Lys Phe Val Glu Arg Ser Ile Lys Gly Tyr Ser Ala Asp Tyr Gln
                405                 410                 415
Glu Ile Thr Thr Ala Gly Glu Ile Ala Val Lys Asn Trp Lys Asp Glu
                420                 425                 430
Asn Pro Lys Pro Leu Asp Pro Thr Glu Pro Lys Val Val Thr Tyr Gly
                435                 440                 445
Lys Lys Phe Val Lys Val Asn Asp Lys Asp Asn Arg Leu Ala Gly Ala
                450                 455                 460
Glu Phe Val Ile Ala Asn Ala Asp Asn Ala Gly Gln Tyr Leu Ala Arg
465                 470                 475                 480
```

```
Lys Ala Asp Lys Val Ser Gln Glu Lys Gln Leu Val Val Thr Thr
                485                 490                 495
Lys Asp Ala Leu Asp Arg Ala Val Ala Ala Tyr Asn Ala Leu Thr Ala
            500                 505                 510
Gln Gln Gln Thr Gln Gln Glu Lys Glu Lys Val Asp Lys Ala Gln Ala
            515                 520                 525
Ala Tyr Asn Ala Ala Val Ile Ala Ala Asn Asn Ala Phe Glu Trp Val
        530                 535                 540
Ala Asp Lys Asp Asn Glu Asn Val Val Lys Leu Val Ser Asp Ala Gln
545                 550                 555                 560
Gly Arg Phe Glu Ile Thr Gly Leu Leu Ala Gly Thr Tyr Tyr Leu Glu
                565                 570                 575
Glu Thr Lys Gln Pro Ala Gly Tyr Ala Leu Leu Thr Ser Arg Gln Lys
            580                 585                 590
Phe Glu Val Thr Ala Thr Ser Tyr Ser Ala Thr Gly Gln Gly Ile Glu
        595                 600                 605
Tyr Thr Ala Gly Ser Gly Lys Asp Asp Ala Thr Lys Val Val Asn Lys
610                 615                 620
Lys Ile Thr Ile Pro Gln Thr Gly Gly Ile Gly Thr Ile Phe Ala
625                 630                 635                 640
Val Ala Gly Ala Ala Ile Met Gly Ile Ala Val Tyr Ala Tyr Val Lys
                645                 650                 655
Asn Asn Lys Asp Glu Asp Gln Leu Ala
                660                 665

<210> SEQ ID NO 2
<211> LENGTH: 644
<212> TYPE: PRT
<213> ORGANISM: Streptococcus pneumoniae

<400> SEQUENCE: 2

Met Lys Ser Ile Asn Lys Phe Leu Thr Met Leu Ala Ala Leu Leu Leu
1               5                   10                  15
Thr Ala Ser Ser Leu Phe Ser Ala Ala Thr Val Phe Ala Ala Asp Asn
            20                  25                  30
Val Ser Thr Ala Pro Asp Ala Val Thr Lys Thr Leu Thr Ile His Lys
        35                  40                  45
Leu Leu Leu Ser Glu Asp Asp Leu Lys Thr Trp Asp Thr Asn Gly Pro
    50                  55                  60
Lys Gly Tyr Asp Gly Thr Gln Ser Ser Leu Lys Asp Leu Thr Gly Val
65                  70                  75                  80
Val Ala Glu Glu Ile Pro Asn Val Tyr Phe Glu Leu Gln Lys Tyr Asn
                85                  90                  95
Leu Thr Asp Gly Lys Glu Lys Glu Asn Leu Lys Asp Ser Lys Trp
            100                 105                 110
Thr Thr Val His Gly Leu Thr Thr Lys Asp Gly Leu Lys Ile Glu
        115                 120                 125
Thr Ser Thr Leu Lys Gly Val Tyr Arg Ile Arg Glu Asp Arg Thr Lys
    130                 135                 140
Thr Thr Tyr Val Gly Pro Asn Gly Gln Val Leu Thr Gly Ser Lys Ala
145                 150                 155                 160
Val Pro Ala Leu Val Thr Leu Pro Leu Val Asn Asn Asn Gly Thr Val
                165                 170                 175
Ile Asp Ala His Val Phe Pro Lys Asn Ser Tyr Asn Lys Pro Val Val
            180                 185                 190
```

-continued

```
Asp Lys Arg Ile Ala Asp Thr Leu Asn Tyr Asn Asp Gln Asn Gly Leu
            195                 200                 205
Ser Ile Gly Thr Lys Ile Pro Tyr Val Val Asn Thr Thr Ile Pro Ser
        210                 215                 220
Asn Ala Thr Phe Ala Thr Ser Phe Trp Ser Asp Glu Met Thr Glu Gly
225                 230                 235                 240
Leu Thr Tyr Asn Glu Asp Val Thr Ile Thr Leu Asn Asn Val Ala Met
                245                 250                 255
Asp Gln Ala Asp Tyr Glu Val Thr Lys Gly Asn Asn Gly Phe Asn Leu
            260                 265                 270
Lys Leu Thr Glu Ala Gly Leu Ala Lys Ile Asn Gly Lys Asp Ala Asp
        275                 280                 285
Gln Lys Ile Gln Ile Thr Tyr Ser Ala Thr Leu Asn Ser Leu Ala Val
    290                 295                 300
Ala Asp Ile Pro Glu Ser Asn Asp Ile Thr Tyr His Tyr Gly Asn His
305                 310                 315                 320
Gln Asp His Gly Asn Thr Pro Lys Pro Thr Lys Pro Asn Asn Gly Gln
                325                 330                 335
Ile Thr Val Thr Lys Thr Trp Asp Ser Gln Pro Ala Pro Glu Gly Val
            340                 345                 350
Lys Ala Thr Val Gln Leu Val Asn Ala Lys Thr Gly Glu Lys Val Gly
        355                 360                 365
Ala Pro Val Glu Leu Ser Glu Asn Asn Trp Thr Tyr Thr Trp Ser Gly
    370                 375                 380
Leu Asp Asn Ser Ile Glu Tyr Lys Val Glu Glu Tyr Asn Gly Tyr
385                 390                 395                 400
Ser Ala Glu Tyr Thr Val Glu Ser Lys Gly Lys Leu Gly Val Lys Asn
                405                 410                 415
Trp Lys Asp Asn Asn Pro Ala Pro Ile Asn Pro Glu Glu Pro Arg Val
            420                 425                 430
Lys Thr Tyr Gly Lys Lys Phe Val Lys Val Asp Gln Lys Asp Thr Arg
        435                 440                 445
Leu Glu Asn Ala Gln Phe Val Val Lys Lys Ala Asp Ser Asn Lys Tyr
    450                 455                 460
Ile Ala Phe Lys Ser Thr Ala Gln Gln Ala Ala Asp Glu Lys Ala Ala
465                 470                 475                 480
Ala Thr Ala Lys Gln Lys Leu Asp Ala Ala Val Ala Ala Tyr Thr Asn
                485                 490                 495
Ala Ala Asp Lys Gln Ala Ala Gln Ala Leu Val Asp Gln Ala Gln Gln
            500                 505                 510
Glu Tyr Asn Val Ala Tyr Lys Glu Ala Lys Phe Gly Tyr Val Glu Val
        515                 520                 525
Ala Gly Lys Asp Glu Ala Met Val Leu Thr Ser Asn Thr Asp Gly Gln
    530                 535                 540
Phe Gln Ile Ser Gly Leu Ala Ala Gly Thr Tyr Lys Leu Glu Glu Ile
545                 550                 555                 560
Lys Ala Pro Glu Gly Phe Ala Lys Ile Asp Asp Val Glu Phe Val Val
                565                 570                 575
Gly Ala Gly Ser Trp Asn Gln Gly Glu Phe Asn Tyr Leu Lys Asp Val
            580                 585                 590
Gln Lys Asn Asp Ala Thr Lys Val Val Asn Lys Lys Ile Thr Ile Pro
        595                 600                 605
Gln Thr Gly Gly Ile Gly Thr Ile Ile Phe Ala Val Ala Gly Ala Ala
```

```
              610                 615                 620
Ile Met Gly Ile Ala Val Tyr Ala Tyr Val Lys Asn Asn Lys Asp Glu
625                 630                 635                 640

Asp Gln Leu Ala

<210> SEQ ID NO 3
<211> LENGTH: 654
<212> TYPE: PRT
<213> ORGANISM: Streptococcus pneumoniae

<400> SEQUENCE: 3

Met Lys Ser Ile Asn Lys Phe Leu Thr Ile Leu Ala Ala Leu Leu Leu
1               5                   10                  15

Thr Val Ser Ser Leu Phe Ser Ala Ala Thr Val Phe Ala Ala Glu Gln
                20                  25                  30

Lys Thr Lys Thr Leu Thr Val His Lys Leu Leu Met Thr Asp Gln Glu
            35                  40                  45

Leu Asp Ala Trp Asn Ser Asp Ala Ile Thr Thr Ala Gly Tyr Asp Gly
50                  55                  60

Ser Gln Asn Phe Glu Gln Phe Lys Gln Leu Gln Gly Val Pro Gln Gly
65                  70                  75                  80

Val Thr Glu Ile Ser Gly Val Ala Phe Glu Leu Gln Ser Tyr Thr Gly
                85                  90                  95

Pro Gln Gly Lys Glu Gln Glu Asn Leu Thr Asn Asp Ala Val Trp Thr
            100                 105                 110

Ala Val Asn Lys Gly Val Thr Thr Glu Thr Gly Val Lys Phe Asp Thr
        115                 120                 125

Glu Val Leu Gln Gly Thr Tyr Arg Leu Val Glu Val Arg Lys Glu Ser
130                 135                 140

Thr Tyr Val Gly Pro Asn Gly Lys Val Leu Thr Gly Met Lys Ala Val
145                 150                 155                 160

Pro Ala Leu Ile Thr Leu Pro Leu Val Asn Gln Asn Gly Val Val Glu
                165                 170                 175

Asn Ala His Val Tyr Pro Lys Asn Ser Glu Asp Lys Pro Thr Ala Thr
            180                 185                 190

Lys Thr Phe Asp Thr Ala Ala Gly Phe Val Asp Pro Gly Glu Lys Gly
        195                 200                 205

Leu Ala Ile Gly Thr Lys Val Pro Tyr Ile Val Thr Thr Thr Ile Pro
210                 215                 220

Lys Asn Ser Thr Leu Ala Thr Ala Phe Trp Ser Asp Glu Met Thr Glu
225                 230                 235                 240

Gly Leu Asp Tyr Asn Gly Asp Val Val Asn Tyr Asn Gly Gln Pro
                245                 250                 255

Leu Asp Asn Ser His Tyr Thr Leu Glu Ala Gly His Asn Gly Phe Ile
            260                 265                 270

Leu Lys Leu Asn Glu Lys Gly Leu Glu Ala Ile Asn Gly Lys Asp Ala
        275                 280                 285

Glu Ala Thr Ile Thr Leu Lys Tyr Thr Ala Thr Leu Asn Ala Leu Ala
290                 295                 300

Val Ala Asp Val Pro Glu Ala Asn Asp Val Thr Phe His Tyr Gly Asn
305                 310                 315                 320

Asn Pro Gly His Gly Asn Thr Pro Lys Pro Asn Lys Pro Lys Asn Gly
                325                 330                 335

Glu Leu Thr Ile Thr Lys Thr Trp Ala Asp Ala Lys Asp Ala Pro Ile
            340                 345                 350
```

Ala Gly Val Glu Val Thr Phe Asp Leu Val Asn Ala Gln Thr Gly Glu
        355                 360                 365

Val Val Lys Val Pro Gly His Glu Thr Gly Ile Val Leu Asn Gln Thr
370                 375                 380

Asn Asn Trp Thr Phe Thr Ala Thr Gly Leu Asp Asn Thr Glu Tyr
385                 390                 395                 400

Lys Phe Val Glu Arg Thr Ile Lys Gly Tyr Ser Ala Asp Tyr Gln Thr
                405                 410                 415

Ile Thr Glu Thr Gly Lys Ile Ala Val Lys Asn Trp Lys Asp Glu Asn
                420                 425                 430

Pro Glu Pro Ile Asn Pro Glu Pro Arg Val Lys Thr Tyr Gly Lys
        435                 440                 445

Lys Phe Val Lys Val Asp Gln Lys Asp Glu Arg Leu Lys Glu Ala Gln
        450                 455                 460

Phe Val Val Lys Asn Glu Gln Gly Lys Tyr Leu Ala Leu Lys Ser Ala
465                 470                 475                 480

Ala Gln Gln Ala Val Asn Glu Lys Ala Ala Glu Ala Lys Gln Ala
                485                 490                 495

Leu Asp Ala Ala Ile Ala Ala Tyr Thr Asn Ala Ala Asp Lys Asn Ala
                500                 505                 510

Ala Gln Ala Val Val Asp Ala Ala Gln Lys Thr Tyr Asn Asp Asn Tyr
                515                 520                 525

Arg Ala Ala Arg Phe Gly Tyr Val Glu Val Glu Arg Lys Glu Asp Ala
530                 535                 540

Leu Val Leu Thr Ser Asn Thr Asp Gly Gln Phe Gln Ile Ser Gly Leu
545                 550                 555                 560

Ala Ala Gly Ser Tyr Thr Leu Glu Glu Thr Lys Ala Pro Glu Gly Phe
                565                 570                 575

Ala Lys Leu Gly Asp Val Lys Phe Glu Val Gly Ala Gly Ser Trp Asn
                580                 585                 590

Gln Gly Asp Phe Asn Tyr Leu Lys Asp Val Gln Lys Asn Asp Ala Thr
                595                 600                 605

Lys Val Val Asn Lys Lys Ile Thr Ile Pro Gln Thr Gly Gly Ile Gly
        610                 615                 620

Thr Ile Ile Phe Ala Val Ala Gly Ala Val Ile Met Gly Ile Ala Val
625                 630                 635                 640

Tyr Ala Tyr Val Lys Asn Asn Lys Asp Glu Asp Gln Leu Ala
                645                 650

<210> SEQ ID NO 4
<211> LENGTH: 604
<212> TYPE: PRT
<213> ORGANISM: Streptococcus pneumoniae
<220> FEATURE:
<223> OTHER INFORMATION: Fragment of SEQ ID NO: 1

<400> SEQUENCE: 4

Ala Ala Thr Val Phe Ala Ala Gly Thr Thr Thr Thr Ser Val Thr Val
1               5                   10                  15

His Lys Leu Leu Ala Thr Asp Gly Asp Met Asp Lys Ile Ala Asn Glu
                20                  25                  30

Leu Glu Thr Gly Asn Tyr Ala Gly Asn Lys Val Gly Val Leu Pro Ala
        35                  40                  45

Asn Ala Lys Glu Ile Ala Gly Val Met Phe Val Trp Thr Asn Thr Asn
        50                  55                  60

```
Asn Glu Ile Ile Asp Glu Asn Gly Gln Thr Leu Gly Val Asn Ile Asp
 65                  70                  75                  80

Pro Gln Thr Phe Lys Leu Ser Gly Ala Met Pro Ala Thr Ala Met Lys
                 85                  90                  95

Lys Leu Thr Glu Ala Glu Gly Ala Lys Phe Asn Thr Ala Asn Leu Pro
            100                 105                 110

Ala Ala Lys Tyr Lys Ile Tyr Glu Ile His Ser Leu Ser Thr Tyr Val
        115                 120                 125

Gly Glu Asp Gly Ala Thr Leu Thr Gly Ser Lys Ala Val Pro Ile Glu
    130                 135                 140

Ile Glu Leu Pro Leu Asn Asp Val Val Asp Ala His Val Tyr Pro Lys
145                 150                 155                 160

Asn Thr Glu Ala Lys Pro Lys Ile Asp Lys Asp Phe Lys Gly Lys Ala
                165                 170                 175

Asn Pro Asp Thr Pro Arg Val Asp Lys Asp Thr Pro Val Asn His Gln
            180                 185                 190

Val Gly Asp Val Val Glu Tyr Glu Ile Val Thr Lys Ile Pro Ala Leu
        195                 200                 205

Ala Asn Tyr Ala Thr Ala Asn Trp Ser Asp Arg Met Thr Glu Gly Leu
210                 215                 220

Ala Phe Asn Lys Gly Thr Val Lys Val Thr Val Asp Asp Val Ala Leu
225                 230                 235                 240

Glu Ala Gly Asp Tyr Ala Leu Thr Glu Val Ala Thr Gly Phe Asp Leu
                245                 250                 255

Lys Leu Thr Asp Ala Gly Leu Ala Lys Val Asn Asp Gln Asn Ala Glu
            260                 265                 270

Lys Thr Val Lys Ile Thr Tyr Ser Ala Thr Leu Asn Asp Lys Ala Ile
        275                 280                 285

Val Glu Val Pro Glu Ser Asn Asp Val Thr Phe Asn Tyr Gly Asn Asn
    290                 295                 300

Pro Asp His Gly Asn Thr Pro Lys Pro Asn Lys Pro Asn Glu Asn Gly
305                 310                 315                 320

Asp Leu Thr Leu Thr Lys Thr Trp Val Asp Ala Thr Gly Ala Pro Ile
                325                 330                 335

Pro Ala Gly Ala Glu Ala Thr Phe Asp Leu Val Asn Ala Gln Thr Gly
            340                 345                 350

Lys Val Val Gln Thr Val Thr Leu Thr Thr Asp Lys Asn Thr Val Thr
        355                 360                 365

Val Asn Gly Leu Asp Lys Asn Thr Glu Tyr Lys Phe Val Glu Arg Ser
    370                 375                 380

Ile Lys Gly Tyr Ser Ala Asp Tyr Gln Glu Ile Thr Thr Ala Gly Glu
385                 390                 395                 400

Ile Ala Val Lys Asn Trp Lys Asp Glu Asn Pro Lys Pro Leu Asp Pro
                405                 410                 415

Thr Glu Pro Lys Val Val Thr Tyr Gly Lys Lys Phe Val Lys Val Asn
            420                 425                 430

Asp Lys Asp Asn Arg Leu Ala Gly Ala Glu Phe Val Ile Ala Asn Ala
        435                 440                 445

Asp Asn Ala Gly Gln Tyr Leu Ala Arg Lys Ala Asp Lys Val Ser Gln
    450                 455                 460

Glu Glu Lys Gln Leu Val Val Thr Lys Asp Ala Leu Asp Arg Ala
465                 470                 475                 480

Val Ala Ala Tyr Asn Ala Leu Thr Ala Gln Gln Gln Thr Gln Gln Glu
                485                 490                 495
```

Lys Glu Lys Val Asp Lys Ala Gln Ala Ala Tyr Asn Ala Ala Val Ile
                500                 505                 510

Ala Ala Asn Asn Ala Phe Glu Trp Val Ala Asp Lys Asp Asn Glu Asn
            515                 520                 525

Val Val Lys Leu Val Ser Asp Ala Gln Gly Arg Phe Glu Ile Thr Gly
530                 535                 540

Leu Leu Ala Gly Thr Tyr Tyr Leu Glu Glu Thr Lys Gln Pro Ala Gly
545                 550                 555                 560

Tyr Ala Leu Leu Thr Ser Arg Gln Lys Phe Glu Val Thr Ala Thr Ser
                565                 570                 575

Tyr Ser Ala Thr Gly Gln Gly Ile Glu Tyr Thr Ala Gly Ser Gly Lys
            580                 585                 590

Asp Asp Ala Thr Lys Val Val Asn Lys Lys Ile Thr
            595                 600

<210> SEQ ID NO 5
<211> LENGTH: 583
<212> TYPE: PRT
<213> ORGANISM: Streptococcus pneumoniae
<220> FEATURE:
<223> OTHER INFORMATION: Fragment of SEQ ID NO: 2

<400> SEQUENCE: 5

Ala Ala Thr Val Phe Ala Ala Asp Asn Val Ser Thr Ala Pro Asp Ala
1               5                   10                  15

Val Thr Lys Thr Leu Thr Ile His Lys Leu Leu Leu Ser Glu Asp Asp
            20                  25                  30

Leu Lys Thr Trp Asp Thr Asn Gly Pro Lys Gly Tyr Asp Gly Thr Gln
        35                  40                  45

Ser Ser Leu Lys Asp Leu Thr Gly Val Val Ala Glu Glu Ile Pro Asn
50                  55                  60

Val Tyr Phe Glu Leu Gln Lys Tyr Asn Leu Thr Asp Gly Lys Glu Lys
65                  70                  75                  80

Glu Asn Leu Lys Asp Asp Ser Lys Trp Thr Thr Val His Gly Gly Leu
                85                  90                  95

Thr Thr Lys Asp Gly Leu Lys Ile Glu Thr Ser Thr Leu Lys Gly Val
            100                 105                 110

Tyr Arg Ile Arg Glu Asp Arg Thr Lys Thr Thr Tyr Val Gly Pro Asn
        115                 120                 125

Gly Gln Val Leu Thr Gly Ser Lys Ala Val Pro Ala Leu Val Thr Leu
130                 135                 140

Pro Leu Val Asn Asn Asn Gly Thr Val Ile Asp Ala His Val Phe Pro
145                 150                 155                 160

Lys Asn Ser Tyr Asn Lys Pro Val Val Asp Lys Arg Ile Ala Asp Thr
                165                 170                 175

Leu Asn Tyr Asn Asp Gln Asn Gly Leu Ser Ile Gly Thr Lys Ile Pro
            180                 185                 190

Tyr Val Val Asn Thr Thr Ile Pro Ser Asn Ala Thr Phe Ala Thr Ser
        195                 200                 205

Phe Trp Ser Asp Glu Met Thr Glu Gly Leu Tyr Asn Glu Asp Val
210                 215                 220

Thr Ile Thr Leu Asn Asn Val Ala Met Asp Gln Ala Asp Tyr Glu Val
225                 230                 235                 240

Thr Lys Gly Asn Asn Gly Phe Asn Leu Lys Leu Thr Glu Ala Gly Leu
                245                 250                 255

```
Ala Lys Ile Asn Gly Lys Asp Ala Asp Gln Lys Ile Gln Ile Thr Tyr
            260                 265                 270

Ser Ala Thr Leu Asn Ser Leu Ala Val Ala Asp Ile Pro Glu Ser Asn
            275                 280                 285

Asp Ile Thr Tyr His Tyr Gly Asn His Gln Asp His Gly Asn Thr Pro
            290                 295                 300

Lys Pro Thr Lys Pro Asn Asn Gly Gln Ile Thr Val Thr Lys Thr Trp
305                 310                 315                 320

Asp Ser Gln Pro Ala Pro Glu Gly Val Lys Ala Thr Val Gln Leu Val
            325                 330                 335

Asn Ala Lys Thr Gly Glu Lys Val Gly Ala Pro Val Glu Leu Ser Glu
            340                 345                 350

Asn Asn Trp Thr Tyr Thr Trp Ser Gly Leu Asp Asn Ser Ile Glu Tyr
            355                 360                 365

Lys Val Glu Glu Glu Tyr Asn Gly Tyr Ser Ala Glu Tyr Thr Val Glu
            370                 375                 380

Ser Lys Gly Lys Leu Gly Val Lys Asn Trp Lys Asp Asn Asn Pro Ala
385                 390                 395                 400

Pro Ile Asn Pro Glu Glu Pro Arg Val Lys Thr Tyr Gly Lys Lys Phe
            405                 410                 415

Val Lys Val Asp Gln Lys Asp Thr Arg Leu Glu Asn Ala Gln Phe Val
            420                 425                 430

Val Lys Lys Ala Asp Ser Asn Lys Tyr Ile Ala Phe Lys Ser Thr Ala
            435                 440                 445

Gln Gln Ala Ala Asp Glu Lys Ala Ala Thr Ala Lys Gln Lys Leu
            450                 455                 460

Asp Ala Ala Val Ala Ala Tyr Thr Asn Ala Ala Asp Lys Gln Ala Ala
465                 470                 475                 480

Gln Ala Leu Val Asp Gln Ala Gln Gln Glu Tyr Asn Val Ala Tyr Lys
            485                 490                 495

Glu Ala Lys Phe Gly Tyr Val Glu Val Ala Gly Lys Asp Glu Ala Met
            500                 505                 510

Val Leu Thr Ser Asn Thr Asp Gly Gln Phe Gln Ile Ser Gly Leu Ala
            515                 520                 525

Ala Gly Thr Tyr Lys Leu Glu Glu Ile Lys Ala Pro Glu Gly Phe Ala
            530                 535                 540

Lys Ile Asp Asp Val Glu Phe Val Val Gly Ala Gly Ser Trp Asn Gln
545                 550                 555                 560

Gly Glu Phe Asn Tyr Leu Lys Asp Val Gln Lys Asn Asp Ala Thr Lys
            565                 570                 575

Val Val Asn Lys Lys Ile Thr
            580

<210> SEQ ID NO 6
<211> LENGTH: 587
<212> TYPE: PRT
<213> ORGANISM: Streptococcus pneumoniae
<220> FEATURE:
<223> OTHER INFORMATION: Fragment of SEQ ID NO: 3

<400> SEQUENCE: 6

Ala Glu Gln Lys Thr Lys Thr Leu Thr Val His Lys Leu Leu Met Thr
1               5                   10                  15

Asp Gln Glu Leu Asp Ala Trp Asn Ser Asp Ala Ile Thr Thr Ala Gly
            20                  25                  30

Tyr Asp Gly Ser Gln Asn Phe Glu Gln Phe Lys Gln Leu Gln Gly Val
```

```
                35                  40                  45
Pro Gln Gly Val Thr Glu Ile Ser Gly Val Ala Phe Glu Leu Gln Ser
            50                  55                  60

Tyr Thr Gly Pro Gln Gly Lys Glu Gln Glu Asn Leu Thr Asn Asp Ala
65                  70                  75                  80

Val Trp Thr Ala Val Asn Lys Gly Val Thr Thr Glu Thr Gly Val Lys
                85                  90                  95

Phe Asp Thr Glu Val Leu Gln Gly Thr Tyr Arg Leu Val Glu Val Arg
            100                 105                 110

Lys Glu Ser Thr Tyr Val Gly Pro Asn Gly Lys Val Leu Thr Gly Met
            115                 120                 125

Lys Ala Val Pro Ala Leu Ile Thr Leu Pro Leu Val Asn Gln Asn Gly
            130                 135                 140

Val Val Glu Asn Ala His Val Tyr Pro Lys Asn Ser Glu Asp Lys Pro
145                 150                 155                 160

Thr Ala Thr Lys Thr Phe Asp Thr Ala Ala Gly Phe Val Asp Pro Gly
                165                 170                 175

Glu Lys Gly Leu Ala Ile Gly Thr Lys Val Pro Tyr Ile Val Thr Thr
            180                 185                 190

Thr Ile Pro Lys Asn Ser Thr Leu Ala Thr Ala Phe Trp Ser Asp Glu
            195                 200                 205

Met Thr Glu Gly Leu Asp Tyr Asn Gly Asp Val Val Asn Tyr Asn
            210                 215                 220

Gly Gln Pro Leu Asp Asn Ser His Tyr Thr Leu Glu Ala Gly His Asn
225                 230                 235                 240

Gly Phe Ile Leu Lys Leu Asn Glu Lys Gly Leu Glu Ala Ile Asn Gly
                245                 250                 255

Lys Asp Ala Glu Ala Thr Ile Thr Leu Lys Tyr Thr Ala Thr Leu Asn
            260                 265                 270

Ala Leu Ala Val Ala Asp Val Pro Glu Ala Asn Asp Val Thr Phe His
            275                 280                 285

Tyr Gly Asn Asn Pro Gly His Gly Asn Thr Pro Lys Pro Asn Lys Pro
290                 295                 300

Lys Asn Gly Glu Leu Thr Ile Thr Lys Thr Trp Ala Asp Ala Lys Asp
305                 310                 315                 320

Ala Pro Ile Ala Gly Val Glu Val Thr Phe Asp Leu Val Asn Ala Gln
                325                 330                 335

Thr Gly Glu Val Val Lys Val Pro Gly His Glu Thr Gly Ile Val Leu
            340                 345                 350

Asn Gln Thr Asn Asn Trp Thr Phe Thr Ala Thr Gly Leu Asp Asn Asn
            355                 360                 365

Thr Glu Tyr Lys Phe Val Glu Arg Thr Ile Lys Gly Tyr Ser Ala Asp
            370                 375                 380

Tyr Gln Thr Ile Thr Glu Thr Gly Lys Ile Ala Val Lys Asn Trp Lys
385                 390                 395                 400

Asp Glu Asn Pro Glu Pro Ile Asn Pro Glu Glu Pro Arg Val Lys Thr
                405                 410                 415

Tyr Gly Lys Lys Phe Val Lys Val Asp Gln Lys Asp Glu Arg Leu Lys
            420                 425                 430

Glu Ala Gln Phe Val Val Lys Asn Glu Gln Gly Lys Tyr Leu Ala Leu
            435                 440                 445

Lys Ser Ala Ala Gln Gln Ala Val Asn Glu Lys Ala Ala Ala Glu Ala
450                 455                 460
```

```
Lys Gln Ala Leu Asp Ala Ala Ile Ala Ala Tyr Thr Asn Ala Ala Asp
465                 470                 475                 480

Lys Asn Ala Ala Gln Ala Val Val Asp Ala Gln Lys Thr Tyr Asn
                485                 490                 495

Asp Asn Tyr Arg Ala Ala Arg Phe Gly Tyr Val Glu Val Glu Arg Lys
            500                 505                 510

Glu Asp Ala Leu Val Leu Thr Ser Asn Thr Asp Gly Gln Phe Gln Ile
            515                 520                 525

Ser Gly Leu Ala Ala Gly Ser Tyr Thr Leu Glu Glu Thr Lys Ala Pro
            530                 535                 540

Glu Gly Phe Ala Lys Leu Gly Asp Val Lys Phe Glu Val Gly Ala Gly
545                 550                 555                 560

Ser Trp Asn Gln Gly Asp Phe Asn Tyr Leu Lys Asp Val Gln Lys Asn
                565                 570                 575

Asp Ala Thr Lys Val Val Asn Lys Lys Ile Thr
            580                 585

<210> SEQ ID NO 7
<211> LENGTH: 6
<212> TYPE: PRT
<213> ORGANISM: Artificial
<220> FEATURE:
<223> OTHER INFORMATION: linker amino acid sequence

<400> SEQUENCE: 7

Gly Ser Gly Gly Gly Gly
1               5

<210> SEQ ID NO 8
<211> LENGTH: 8
<212> TYPE: PRT
<213> ORGANISM: Artificial
<220> FEATURE:
<223> OTHER INFORMATION: linker amino acid sequence

<400> SEQUENCE: 8

Gly Ser Gly Ser Gly Gly Gly Gly
1               5

<210> SEQ ID NO 9
<211> LENGTH: 6
<212> TYPE: PRT
<213> ORGANISM: Artificial
<220> FEATURE:
<223> OTHER INFORMATION: hexa-His tag

<400> SEQUENCE: 9

His His His His His His
1               5

<210> SEQ ID NO 10
<211> LENGTH: 8
<212> TYPE: PRT
<213> ORGANISM: Artificial
<220> FEATURE:
<223> OTHER INFORMATION: linker

<400> SEQUENCE: 10

Leu Gly Gly Ser Gly Gly Gly Gly
1               5

<210> SEQ ID NO 11
<211> LENGTH: 1801
<212> TYPE: PRT
```

<213> ORGANISM: Artificial Sequence
<220> FEATURE:
<223> OTHER INFORMATION: RrgB I-II-III

<400> SEQUENCE: 11

```
Met Ala Ser Ala Ala Thr Val Phe Ala Ala Gly Thr Thr Thr Ser
1               5                   10                  15

Val Thr Val His Lys Leu Leu Ala Thr Asp Gly Asp Met Asp Lys Ile
            20                  25                  30

Ala Asn Glu Leu Glu Thr Gly Asn Tyr Ala Gly Asn Lys Val Gly Val
        35                  40                  45

Leu Pro Ala Asn Ala Lys Glu Ile Ala Gly Val Met Phe Val Trp Thr
    50                  55                  60

Asn Thr Asn Asn Glu Ile Ile Asp Glu Asn Gly Gln Thr Leu Gly Val
65                  70                  75                  80

Asn Ile Asp Pro Gln Thr Phe Lys Leu Ser Gly Ala Met Pro Ala Thr
                85                  90                  95

Ala Met Lys Lys Leu Thr Glu Ala Glu Gly Ala Lys Phe Asn Thr Ala
            100                 105                 110

Asn Leu Pro Ala Ala Lys Tyr Lys Ile Tyr Glu Ile His Ser Leu Ser
        115                 120                 125

Thr Tyr Val Gly Glu Asp Gly Ala Thr Leu Thr Gly Ser Lys Ala Val
    130                 135                 140

Pro Ile Glu Ile Glu Leu Pro Leu Asn Asp Val Val Asp Ala His Val
145                 150                 155                 160

Tyr Pro Lys Asn Thr Glu Ala Lys Pro Lys Ile Asp Lys Asp Phe Lys
                165                 170                 175

Gly Lys Ala Asn Pro Asp Thr Pro Arg Val Asp Lys Asp Thr Pro Val
            180                 185                 190

Asn His Gln Val Gly Asp Val Val Glu Tyr Glu Ile Val Thr Lys Ile
        195                 200                 205

Pro Ala Leu Ala Asn Tyr Ala Thr Ala Asn Trp Ser Asp Arg Met Thr
    210                 215                 220

Glu Gly Leu Ala Phe Asn Lys Gly Thr Val Lys Val Thr Val Asp Asp
225                 230                 235                 240

Val Ala Leu Glu Ala Gly Asp Tyr Ala Leu Thr Glu Val Ala Thr Gly
                245                 250                 255

Phe Asp Leu Lys Leu Thr Asp Ala Gly Leu Ala Lys Val Asn Asp Gln
            260                 265                 270

Asn Ala Glu Lys Thr Val Lys Ile Thr Tyr Ser Ala Thr Leu Asn Asp
        275                 280                 285

Lys Ala Ile Val Glu Val Pro Glu Ser Asn Asp Val Thr Phe Asn Tyr
    290                 295                 300

Gly Asn Asn Pro Asp His Gly Asn Thr Pro Lys Pro Asn Lys Pro Asn
305                 310                 315                 320

Glu Asn Gly Asp Leu Thr Leu Thr Lys Thr Trp Val Asp Ala Thr Gly
                325                 330                 335

Ala Pro Ile Pro Ala Gly Ala Glu Ala Thr Phe Asp Leu Val Asn Ala
            340                 345                 350

Gln Thr Gly Lys Val Val Gln Thr Val Thr Leu Thr Thr Asp Lys Asn
        355                 360                 365

Thr Val Thr Val Asn Gly Leu Asp Lys Asn Thr Glu Tyr Lys Phe Val
    370                 375                 380

Glu Arg Ser Ile Lys Gly Tyr Ser Ala Asp Tyr Gln Glu Ile Thr Thr
385                 390                 395                 400
```

```
Ala Gly Glu Ile Ala Val Lys Asn Trp Lys Asp Glu Asn Pro Lys Pro
                405                 410                 415

Leu Asp Pro Thr Glu Pro Lys Val Val Thr Tyr Gly Lys Lys Phe Val
            420                 425                 430

Lys Val Asn Asp Lys Asp Asn Arg Leu Ala Gly Ala Glu Phe Val Ile
                435                 440                 445

Ala Asn Ala Asp Asn Ala Gly Gln Tyr Leu Ala Arg Lys Ala Asp Lys
        450                 455                 460

Val Ser Gln Glu Glu Lys Gln Leu Val Val Thr Thr Lys Asp Ala Leu
465                 470                 475                 480

Asp Arg Ala Val Ala Ala Tyr Asn Ala Leu Thr Ala Gln Gln Gln Thr
                485                 490                 495

Gln Gln Glu Lys Glu Lys Val Asp Lys Ala Gln Ala Ala Tyr Asn Ala
                500                 505                 510

Ala Val Ile Ala Ala Asn Asn Ala Phe Glu Trp Val Ala Asp Lys Asp
            515                 520                 525

Asn Glu Asn Val Val Lys Leu Val Ser Asp Ala Gln Gly Arg Phe Glu
        530                 535                 540

Ile Thr Gly Leu Leu Ala Gly Thr Tyr Tyr Leu Glu Gly Thr Lys Gln
545                 550                 555                 560

Pro Ala Gly Tyr Ala Leu Leu Thr Ser Arg Gln Lys Phe Glu Val Thr
                565                 570                 575

Ala Thr Ser Tyr Ser Ala Thr Gly Gln Gly Ile Glu Tyr Thr Ala Gly
            580                 585                 590

Ser Gly Lys Asp Asp Ala Thr Lys Val Val Asn Lys Lys Ile Thr Gly
        595                 600                 605

Ser Gly Ser Gly Gly Gly Ala Ala Thr Val Phe Ala Ala Asp Asn
        610                 615                 620

Val Ser Thr Ala Pro Asp Ala Val Thr Lys Thr Leu Thr Ile His Lys
625                 630                 635                 640

Leu Leu Leu Ser Glu Asp Asp Leu Lys Thr Trp Asp Thr Asn Gly Pro
                645                 650                 655

Lys Gly Tyr Asp Gly Thr Gln Ser Ser Leu Lys Asp Leu Thr Gly Val
                660                 665                 670

Val Ala Glu Glu Ile Pro Asn Val Tyr Phe Glu Leu Gln Lys Tyr Asn
            675                 680                 685

Leu Thr Asp Gly Lys Glu Lys Glu Asn Leu Lys Asp Ser Lys Trp
        690                 695                 700

Thr Thr Val His Gly Gly Leu Thr Thr Lys Asp Gly Leu Lys Ile Glu
705                 710                 715                 720

Thr Ser Thr Leu Lys Gly Val Tyr Arg Ile Arg Glu Asp Arg Thr Lys
                725                 730                 735

Thr Thr Tyr Val Gly Pro Asn Gly Gln Val Leu Thr Gly Ser Lys Ala
            740                 745                 750

Val Pro Ala Leu Val Thr Leu Pro Leu Val Asn Asn Gly Thr Val
        755                 760                 765

Ile Asp Ala His Val Phe Pro Lys Asn Ser Tyr Asn Lys Pro Val Val
        770                 775                 780

Asp Lys Arg Ile Ala Asp Thr Leu Asn Tyr Asn Asp Gln Asn Gly Leu
785                 790                 795                 800

Ser Ile Gly Thr Lys Ile Pro Tyr Val Val Asn Thr Thr Ile Pro Ser
            805                 810                 815

Asn Ala Thr Phe Ala Thr Ser Phe Trp Ser Asp Glu Met Thr Glu Gly
```

-continued

```
                820                 825                 830
Leu Thr Tyr Asn Glu Asp Val Thr Ile Thr Leu Asn Asn Val Ala Met
            835                 840                 845
Asp Gln Ala Asp Tyr Glu Val Thr Lys Gly Asn Asn Gly Phe Asn Leu
        850                 855                 860
Lys Leu Thr Glu Ala Gly Leu Ala Lys Ile Asn Gly Lys Asp Ala Asp
865                 870                 875                 880
Gln Lys Ile Gln Ile Thr Tyr Ser Ala Thr Leu Asn Ser Leu Ala Val
            885                 890                 895
Ala Asp Ile Pro Glu Ser Asn Asp Ile Thr Tyr His Tyr Gly Asn His
        900                 905                 910
Gln Asp His Gly Asn Thr Pro Lys Pro Thr Lys Pro Asn Asn Gly Gln
            915                 920                 925
Ile Thr Val Thr Lys Thr Trp Asp Ser Gln Pro Ala Pro Glu Gly Val
        930                 935                 940
Lys Ala Thr Val Gln Leu Val Asn Ala Lys Thr Gly Glu Lys Val Gly
945                 950                 955                 960
Ala Pro Val Glu Leu Ser Glu Asn Asn Trp Thr Tyr Thr Trp Ser Gly
            965                 970                 975
Leu Asp Asn Ser Ile Glu Tyr Lys Val Glu Glu Tyr Asn Gly Tyr
        980                 985                 990
Ser Ala Glu Tyr Thr Val Glu Ser Lys Gly Lys Leu Gly Val Lys Asn
            995                 1000                1005
Trp Lys Asp Asn Asn Pro Ala Pro Ile Asn Pro Glu Glu Pro Arg Val
        1010                1015                1020
Lys Thr Tyr Gly Lys Lys Phe Val Lys Val Asp Gln Lys Asp Thr Arg
1025                1030                1035                1040
Leu Glu Asn Ala Gln Phe Val Val Lys Ala Asp Ser Asn Lys Tyr
        1045                1050                1055
Ile Ala Phe Lys Ser Thr Ala Gln Gln Ala Ala Asp Glu Lys Ala Ala
            1060                1065                1070
Ala Thr Ala Lys Gln Lys Leu Asp Ala Ala Val Ala Ala Tyr Thr Asn
        1075                1080                1085
Ala Ala Asp Lys Gln Ala Ala Gln Ala Leu Val Asp Gln Ala Gln Gln
        1090                1095                1100
Glu Tyr Asn Val Ala Tyr Lys Glu Ala Lys Phe Gly Tyr Val Glu Val
1105                1110                1115                1120
Ala Gly Lys Asp Glu Ala Met Val Leu Thr Ser Asn Thr Asp Gly Gln
            1125                1130                1135
Phe Gln Ile Ser Gly Leu Ala Ala Gly Thr Tyr Lys Leu Glu Glu Ile
            1140                1145                1150
Lys Ala Pro Glu Gly Phe Ala Lys Ile Asp Asp Val Glu Phe Val Val
        1155                1160                1165
Gly Ala Gly Ser Trp Asn Gln Gly Glu Phe Asn Tyr Leu Lys Asp Val
        1170                1175                1180
Gln Lys Asn Asp Ala Thr Lys Val Val Asn Lys Lys Ile Thr Leu Gly
1185                1190                1195                1200
Gly Ser Gly Gly Gly Gly Ala Glu Gln Lys Thr Lys Thr Leu Thr Val
            1205                1210                1215
His Lys Leu Leu Met Thr Asp Gln Glu Leu Asp Ala Trp Asn Ser Asp
            1220                1225                1230
Ala Ile Thr Thr Ala Gly Tyr Asp Gly Ser Gln Asn Phe Glu Gln Phe
            1235                1240                1245
```

-continued

```
Lys Gln Leu Gln Gly Val Pro Gln Gly Val Thr Glu Ile Ser Gly Val
        1250                1255                1260

Ala Phe Glu Leu Gln Ser Tyr Thr Gly Pro Gln Gly Lys Glu Gln Glu
1265                1270                1275                1280

Asn Leu Thr Asn Asp Ala Val Trp Thr Ala Val Asn Lys Gly Val Thr
                1285                1290                1295

Thr Glu Thr Gly Val Lys Phe Asp Thr Glu Val Leu Gln Gly Thr Tyr
            1300                1305                1310

Arg Leu Val Glu Val Arg Lys Glu Ser Thr Tyr Val Gly Pro Asn Gly
        1315                1320                1325

Lys Val Leu Thr Gly Met Lys Ala Val Pro Ala Leu Ile Ile Leu Pro
1330                1335                1340

Leu Val Asn Gln Asn Gly Val Val Glu Asn Ala His Val Tyr Pro Lys
1345                1350                1355                1360

Asn Ser Glu Asp Lys Pro Thr Ala Thr Lys Thr Phe Asp Thr Ala Ala
                1365                1370                1375

Gly Phe Val Asp Pro Gly Glu Lys Gly Leu Ala Ile Gly Thr Lys Val
            1380                1385                1390

Pro Tyr Ile Val Thr Thr Thr Ile Pro Lys Asn Ser Thr Leu Ala Thr
        1395                1400                1405

Ala Phe Trp Ser Asp Glu Met Thr Glu Gly Leu Asp Tyr Asn Gly Asp
    1410                1415                1420

Val Val Val Asn Tyr Asn Gly Gln Pro Leu Asp Asn Ser His Tyr Thr
1425                1430                1435                1440

Leu Glu Ala Gly His Asn Gly Phe Ile Leu Lys Leu Asn Glu Lys Gly
                1445                1450                1455

Leu Glu Ala Ile Asn Gly Lys Asp Ala Glu Ala Thr Ile Thr Leu Lys
            1460                1465                1470

Tyr Thr Ala Thr Leu Asn Ala Leu Ala Val Ala Asp Val Pro Glu Ala
        1475                1480                1485

Asn Asp Val Thr Phe His Tyr Gly Asn Asn Pro Gly His Gly Asn Thr
    1490                1495                1500

Pro Lys Pro Asn Lys Pro Lys Asn Gly Glu Leu Thr Ile Thr Lys Thr
1505                1510                1515                1520

Trp Ala Asp Ala Lys Asp Ala Pro Ile Ala Gly Val Glu Val Thr Phe
                1525                1530                1535

Asp Leu Val Asn Ala Gln Thr Gly Glu Val Val Lys Val Pro Gly His
            1540                1545                1550

Glu Thr Gly Ile Val Leu Asn Gln Thr Asn Asn Trp Thr Phe Thr Ala
        1555                1560                1565

Thr Gly Leu Asp Asn Asn Thr Glu Tyr Lys Phe Val Glu Arg Thr Ile
    1570                1575                1580

Lys Gly Tyr Ser Ala Asp Tyr Gln Thr Ile Thr Glu Thr Gly Lys Ile
1585                1590                1595                1600

Ala Val Lys Asn Trp Lys Asp Glu Asn Pro Glu Pro Ile Asn Pro Glu
                1605                1610                1615

Glu Pro Arg Val Lys Thr Tyr Gly Lys Lys Phe Val Lys Val Asp Gln
            1620                1625                1630

Lys Asp Glu Arg Leu Lys Glu Ala Gln Phe Val Val Lys Asn Glu Gln
        1635                1640                1645

Gly Lys Tyr Leu Ala Leu Lys Ser Ala Ala Gln Gln Ala Val Asn Glu
    1650                1655                1660

Lys Ala Ala Ala Glu Ala Lys Gln Ala Leu Asp Ala Ala Ile Ala Ala
1665                1670                1675                1680
```

```
Tyr Thr Asn Ala Ala Asp Lys Asn Ala Ala Gln Ala Val Val Asp Ala
            1685                1690                1695

Ala Gln Lys Thr Tyr Asn Asp Asn Tyr Arg Ala Ala Arg Phe Gly Tyr
        1700                1705                1710

Val Glu Val Glu Arg Lys Glu Asp Ala Leu Val Leu Thr Ser Asn Thr
    1715                1720                1725

Asp Gly Gln Phe Gln Ile Ser Gly Leu Ala Ala Gly Ser Tyr Thr Leu
1730                1735                1740

Glu Glu Thr Lys Ala Pro Glu Gly Phe Ala Lys Leu Gly Asp Val Lys
1745                1750                1755                1760

Phe Glu Val Gly Ala Gly Ser Trp Asn Gln Gly Asp Phe Asn Tyr Leu
            1765                1770                1775

Lys Asp Val Gln Lys Asn Asp Ala Thr Lys Val Val Asn Lys Lys Ile
        1780                1785                1790

Thr Leu Gly His His His His His His
        1795                1800

<210> SEQ ID NO 12
<211> LENGTH: 5403
<212> TYPE: DNA
<213> ORGANISM: Artificial Sequence
<220> FEATURE:
<223> OTHER INFORMATION: Sequence encoding SEQ ID NO: 11

<400> SEQUENCE: 12
atggctagcg ctgcaacagt ttttgcggct gggacgacaa caacatctgt taccgttcat      60
aaactattgg caacagatgg ggatatggat aaaattgcaa atgagttaga aacaggtaac     120
tatgctggta taaagtgggt gttctacct gcaaatgcaa agaaattgc cggtgttatg      180 ttcgtttgga caaatactaa taatgaaatt attgatgaaa atggccaaac tctaggagtg     240
aatattgatc cacaaacatt taaactctca ggggcaatgc cggcaactgc aatgaaaaaa     300
ttaacagaag ctgaaggagc taaatttaac acggcaaatt taccagctgc taagtataaa     360
atttatgaaa ttcacagttt atcaacttat gtcggtgaag atggagcaac cttaacaggt     420
tctaaagcag ttccaattga aattgaatta ccattgaacg atgttgtgga tgcgcatgtg     480
tatccaaaaa atacagaagc aaagccaaaa attgataaag atttcaaagg taaagcaaat     540
ccagatacac cacgtgtaga taaagataca cctgtgaacc accaagttgg agatgttgta     600
gagtacgaaa ttgttacaaa aattccagca cttgctaatt atgcaacagc aaactggagc     660
gatagaatga ctgaaggttt ggcattcaac aaaggtacag tgaaagtaac tgttgatgat     720
gttgcacttg aagcaggtga ttatgctcta acagaagtag caactggttt tgatttgaaa     780
ttaacagatg ctggtttagc taaagtgaat gaccaaaacg ctgaaaaaac tgtgaaaatc     840
acttattcgg caacattgaa tgacaaagca attgtagaag taccagaatc taatgatgta     900
acatttaact atggtaataa tccagatcac gggaatactc caaagccgaa taagccaaat     960
gaaaacggcg atttgacatt gaccaagaca tgggttgatg ctacaggtgc accaattccg    1020
gctggagctg aagcaacgtt cgatttggtt aatgctcaga ctggtaaagt tgtacaaact    1080
gtaactttga acagacaa aaatacagtt actgttaacg gattggataa aaatacagaa    1140
tataaattcg ttgaacgtag tataaaaggg tattcagcag attatcaaga atcactaca    1200 gctggagaaa ttgctgtcaa gaactggaaa gacgaaaatc caaaaccact tgatccaaca    1260
gagccaaaag ttgttacata tggtaaaaag tttgtcaaag ttaatgataa agataatcgt    1320
ttagctgggg cagaatttgt aattgcaaat gctgataatg ctggtcaata tttagcacgt    1380
```

```
aaagcagata aagtgagtca agaagagaag cagttggttg ttacaacaaa ggatgcttta   1440
gatagagcag ttgctgctta taacgctctt actgcacaac aacaaactca gcaagaaaaa   1500
gagaaagttg acaaagctca agctgcttat aatgctgctg tgattgctgc caacaatgca   1560
tttgaatggg tggcagataa ggacaatgaa aatgttgtga aattagtttc tgatgcacaa   1620
ggtcgctttg aaattacagg ccttcttgca ggtacatatt acttagaaga aacaaaacag   1680
cctgctggtt atgcattact aactagccgt cagaaatttg aagtcactgc aacttcttat   1740
tcagcgactg gacaaggcat tgagtatact gctggttcag gtaaagatga cgctacaaaa   1800
gtagtcaaca aaaaaatcac tggatccggc agcggtggcg gtggcgctgc aacagttttt   1860
gcggcggaca atgttagtac agcaccagat gctgttacta aaactttaac aatcccataag  1920 ttactgctct cagaagatga tttaaagact tgggatacaa acggtcctaa aggatatgat   1980
ggaactcaat ctagtttaaa agatttaact ggagttgtag ctgaggaaat tccaaatgta   2040
tactttgaat tacaaaagta taatttgact gatggtaagg aaaagaaaaa tcttaaagat   2100
gatagtaaat ggacaacagt tcatggtggt ttgacaacta agatggact taaaattgaa   2160 accagtactc ttaaaggtgt gtatcgtatt cgtgaggata gaacaaagac tacctatgtt   2220
ggtcctaatg ggcaagtatt aacaggttca aaagccgtac ctgctcttgt aactcttcca   2280
cttgttaaca ataatggtac agtaattgat gcacatgttt tccctaaaaa ttcatataat   2340
aaaccagttg tagataaaag aattgctgat actttgaatt ataacgatca aaatggtctg   2400
tctatcggta ctaaaatccc atatgttgtt aatacaacaa ttccaagtaa tgcaacattt   2460
gcaacttcat tttggtcaga tgaaatgaca gaaggtctaa cttataatga agatgtaaca   2520
attactttga ataatgtagc tatggatcaa gctgattatg aagtcactaa aggaaataat   2580
ggctttaact taaaattaac agaagcaggt ttagctaaaa ttaatggtaa ggatgcagac   2640
caaaaaatcc aaaattactta ctcagctact ttgaactcac ttgctgttgc agacattcct   2700
gaaagtaacg atattacata tcattacgga aatcatcaag atcatgggaa tactccaaaa   2760
ccaactaaac ctaataatgg tcaaattaca gtaactaaga catgggacag tcaacctgct   2820 cctgagggg tgaaagcgac tgttcaactt gtaaatgcca agactggtga aaagtcggt    2880 gctcctgtag aactttcaga aaataattgg acatatactt ggagtggtct agataattct   2940
attgaataca agttgaaga agaatataat ggatactcag ctgaatacac agtagagagc   3000
aaagggaagt tggggtaaa aaactggaaa gataataacc cagctccaat caatcctgaa   3060
gaaccacgtg taaaaacata cggtaaaaag tttgtcaaag tagaccaaaa agatactcgt   3120
ctagaaaatg cgcagttcgt tgttaaaaaa gcagatagca ataaatatat tgcctttaag   3180
tcaactgcac aacaagctgc agatgaaaaa gcagcagcaa ctgcaaaaca aaaattggat   3240
gcagcggtag cagcttacac aaatgctgca gataagcaag ccgctcaagc tctagtagat   3300
caagcacagc aagaatacaa tgtagcttac aaagaagcca atttggttta tgttgaagta   3360
gctgaaaaag atgaagcaat ggttcttact tctaatacgg atggtcaatt ccaaattta   3420 ggtcttgctg ctggtactta taaattagaa gaaattaaag ctccagaagg ttttgcgaaa   3480
attgatgatg tagaatttgt tgttggagca ggttcttgga atcaaggtga gtttaattac   3540
ttaaaagatg ttcaaaagaa tgacgctaca aagtagtca acaaaaaaat cactctcgag   3600
ggcagcggtg gcggtggcgc ggaacaaaaa actaagacac ttacagttca taaattattg   3660
atgacagatc aagagcttga cgcttggaat tctgatgcga ttactactgc aggttatgac   3720
ggttcgcaaa attttgaaca gttcaaacaa cttcaaggtg ttccacaagg agtaaccgaa   3780
```

```
atctctggtg ttgcattcga gttacagagt tatacgggtc ctcaaggaaa agaacaagaa    3840
aatttaacga atgatgcggt ttggactgcg gttaataaag gtgtgacgac tgaaacgggt    3900
gttaaatttg atactgaagt tttacaaggg acatatcgtc ttgtcgaagt acgtaaagaa    3960
tcgacttatg tcggtccaaa tggtaaagtt ttaacaggta tgaaagctgt tcctgcttta    4020
attattctgc cgcttgtaaa ccaaaatggt gttgtagaaa atgcacatgt ctatccaaag    4080
aattctgaag acaaacctac agcaacgaaa acatttgata ctgcagcagg tttcgtagat    4140
ccaggtgaaa aaggtttagc aattggcact aaggtaccgt atattgttac aacaactatt    4200
ccgaaaaact caactcttgc aacagctttc tggtcagatg aaatgacaga aggtctagat    4260
tataatggtg atgtagttgt taattataat ggtcaaccgc ttgataattc tcattacaca    4320
ttagaagcag gtcataatgg ctttatcttg aagttaaatg aaaaaggtct ggaagcaatc    4380
aacggtaaag atgcagaagc aacaattacg ttgaagtata ctgcaacttt aaatgctctt    4440
gctgttgctg atgtgccaga agcgaatgat gtaacattcc attatggaaa caacccaggt    4500
catggtaaca ctccaaaacc aaacaaacct aaaaacggtg aacttacaat tactaaaaca    4560
tgggctgatg ctaaagatgc tcctatagca ggtgtagaag taacttttga tttggtaaat    4620
gctcagacag gtgaggtcgt taaagtacct ggacatgaaa caggtattgt attgaatcaa    4680
acaaataatt ggacatttac tgctacaggt cttgataata atacagaata taaatttgtt    4740
gaacggacaa ttaagggata ttctgcagat taccaaacaa ttactgaaac aggaaaaatt    4800
gctgttaaaa actggaaaga tgaaaatcca gaaccaataa atcctgaaga gccacgtgta    4860
aaaacatatg gtaaaaaatt cgttaaggtt gaccaaaaag acgaacgctt aaaagaagca    4920
caattcgttg tgaagaatga gcaagggaaa tatcttgcac tcaaatctgc agcacaacaa    4980
gctgtaaatg agaaagctgc cgcagaagcg aaacaagcgc tagatgcagc gatagcagcc    5040
tatacaaatg ctgcagataa aaatgcagca caagctgtag tagatgctgc gcaaaaaaca    5100
tataatgaca attacagagc agctagattt ggctatgtag aagtagagag aaaagaagat    5160
gcgttagttc ttacttctaa cactgatggt caattccaaa tttcaggtct tgctgctgga    5220
agctacacgt tggaagaaac aaaagctcca gaaggctttg caaaacttgg agatgtgaag    5280
tttgaggttg gagcaggttc ttggaatcaa ggtgatttca attatttaaa agatgttcag    5340
aagaacgacg ctacaaaagt agtcaacaaa aaaatcacgc tcgagcacca ccaccaccac    5400
cac                                                                  5403
```

<210> SEQ ID NO 13
<211> LENGTH: 1801
<212> TYPE: PRT
<213> ORGANISM: Artificial Sequence
<220> FEATURE:
<223> OTHER INFORMATION: RrgB I-III-II

<400> SEQUENCE: 13

```
Met Ala Ser Ala Ala Thr Val Phe Ala Ala Gly Thr Thr Thr Thr Ser
1               5                   10                  15

Val Thr Val His Lys Leu Leu Ala Thr Asp Gly Asp Met Asp Lys Ile
                20                  25                  30

Ala Asn Glu Leu Glu Thr Gly Asn Tyr Ala Gly Asn Lys Val Gly Val
            35                  40                  45

Leu Pro Ala Asn Ala Lys Glu Ile Ala Gly Val Met Phe Val Trp Thr
        50                  55                  60

Asn Thr Asn Asn Glu Ile Ile Asp Glu Asn Gly Gln Thr Leu Gly Val
```

```
                65                  70                  75                  80
        Asn Ile Asp Pro Gln Thr Phe Lys Leu Ser Gly Ala Met Pro Ala Thr
                                85                  90                  95

Ala Met Lys Lys Leu Thr Glu Ala Glu Gly Ala Lys Phe Asn Thr Ala
                        100                 105                 110

Asn Leu Pro Ala Ala Lys Tyr Lys Ile Tyr Glu Ile His Ser Leu Ser
                        115                 120                 125

Thr Tyr Val Gly Glu Asp Gly Ala Thr Leu Thr Gly Ser Lys Ala Val
                        130                 135                 140

Pro Ile Glu Ile Glu Leu Pro Leu Asn Asp Val Val Asp Ala His Val
        145                 150                 155                 160

Tyr Pro Lys Asn Thr Glu Ala Lys Pro Lys Ile Asp Lys Asp Phe Lys
                        165                 170                 175

Gly Lys Ala Asn Pro Asp Thr Pro Arg Val Asp Lys Asp Thr Pro Val
                        180                 185                 190

Asn His Gln Val Gly Asp Val Val Glu Tyr Glu Ile Val Thr Lys Ile
                        195                 200                 205

Pro Ala Leu Ala Asn Tyr Ala Thr Ala Asn Trp Ser Asp Arg Met Thr
        210                 215                 220

Glu Gly Leu Ala Phe Asn Lys Gly Thr Val Lys Val Thr Val Asp Asp
        225                 230                 235                 240

Val Ala Leu Glu Ala Gly Asp Tyr Ala Leu Thr Glu Val Ala Thr Gly
                        245                 250                 255

Phe Asp Leu Lys Leu Thr Asp Ala Gly Leu Ala Lys Val Asn Asp Gln
                        260                 265                 270

Asn Ala Glu Lys Thr Val Lys Ile Thr Tyr Ser Ala Thr Leu Asn Asp
                        275                 280                 285

Lys Ala Ile Val Glu Val Pro Glu Ser Asn Asp Val Thr Phe Asn Tyr
                        290                 295                 300

Gly Asn Asn Pro Asp His Gly Asn Thr Pro Lys Pro Asn Lys Pro Asn
        305                 310                 315                 320

Glu Asn Gly Asp Leu Thr Leu Thr Lys Thr Trp Val Asp Ala Thr Gly
                        325                 330                 335

Ala Pro Ile Pro Ala Gly Ala Glu Ala Thr Phe Asp Leu Val Asn Ala
                        340                 345                 350

Gln Thr Gly Lys Val Val Gln Thr Val Thr Leu Thr Thr Asp Lys Asn
                        355                 360                 365

Thr Val Thr Val Asn Gly Leu Asp Lys Asn Thr Glu Tyr Lys Phe Val
                        370                 375                 380

Glu Arg Ser Ile Lys Gly Tyr Ser Ala Asp Tyr Gln Glu Ile Thr Thr
        385                 390                 395                 400

Ala Gly Glu Ile Ala Val Lys Asn Trp Lys Asp Glu Asn Pro Lys Pro
                        405                 410                 415

Leu Asp Pro Thr Glu Pro Lys Val Val Thr Tyr Gly Lys Lys Phe Val
                        420                 425                 430

Lys Val Asn Asp Lys Asp Asn Arg Leu Ala Gly Ala Glu Phe Val Ile
                        435                 440                 445

Ala Asn Ala Asp Asn Ala Gly Gln Tyr Leu Ala Arg Lys Ala Asp Lys
                        450                 455                 460

Val Ser Gln Glu Glu Lys Gln Leu Val Val Thr Lys Asp Ala Leu
        465                 470                 475                 480

Asp Arg Ala Val Ala Ala Tyr Asn Ala Leu Thr Ala Gln Gln Gln Thr
                        485                 490                 495
```

-continued

```
Gln Gln Glu Lys Glu Lys Val Asp Lys Ala Gln Ala Ala Tyr Asn Ala
        500                 505                 510
Ala Val Ile Ala Ala Asn Asn Ala Phe Glu Trp Val Ala Asp Lys Asp
            515                 520                 525
Asn Glu Asn Val Val Lys Leu Val Ser Asp Ala Gln Gly Arg Phe Glu
530                 535                 540
Ile Thr Gly Leu Leu Ala Gly Thr Tyr Tyr Leu Glu Glu Thr Lys Gln
545                 550                 555                 560
Pro Ala Gly Tyr Ala Leu Leu Thr Ser Arg Gln Lys Phe Glu Val Thr
                565                 570                 575
Ala Thr Ser Tyr Ser Ala Thr Gly Gln Gly Ile Glu Tyr Thr Ala Gly
                580                 585                 590
Ser Gly Lys Asp Asp Ala Thr Lys Val Val Asn Lys Lys Ile Thr Gly
            595                 600                 605
Ser Gly Ser Gly Gly Gly Ala Glu Gln Lys Thr Lys Thr Leu Thr
        610                 615                 620
Val His Lys Leu Leu Met Thr Asp Gln Glu Leu Asp Ala Trp Asn Ser
625                 630                 635                 640
Asp Ala Ile Thr Thr Ala Gly Tyr Asp Gly Ser Gln Asn Phe Glu Gln
                645                 650                 655
Phe Lys Gln Leu Gln Gly Val Pro Gln Gly Val Thr Glu Ile Ser Gly
                660                 665                 670
Val Ala Phe Glu Leu Gln Ser Tyr Thr Gly Pro Gln Gly Lys Glu Gln
            675                 680                 685
Glu Asn Leu Thr Asn Asp Ala Val Trp Thr Ala Val Asn Lys Gly Val
        690                 695                 700
Thr Thr Glu Thr Gly Val Lys Phe Asp Thr Glu Val Leu Gln Gly Thr
705                 710                 715                 720
Tyr Arg Leu Val Glu Val Arg Lys Glu Ser Thr Tyr Val Gly Pro Asn
                725                 730                 735
Gly Lys Val Leu Thr Gly Met Lys Ala Val Pro Ala Leu Ile Ile Leu
            740                 745                 750
Pro Leu Val Asn Gln Asn Gly Val Val Glu Asn Ala His Val Tyr Pro
        755                 760                 765
Lys Asn Ser Glu Asp Lys Pro Thr Ala Thr Lys Thr Phe Asp Thr Ala
770                 775                 780
Ala Gly Phe Val Asp Pro Gly Glu Lys Gly Leu Ala Ile Gly Thr Lys
785                 790                 795                 800
Val Pro Tyr Ile Val Thr Thr Ile Pro Lys Asn Ser Thr Leu Ala
                805                 810                 815
Thr Ala Phe Trp Ser Asp Glu Met Thr Glu Gly Leu Asp Tyr Asn Gly
            820                 825                 830
Asp Val Val Asn Tyr Asn Gly Gln Pro Leu Asp Asn Ser His Tyr
                835                 840                 845
Thr Leu Glu Ala Gly His Asn Gly Phe Ile Leu Lys Leu Asn Glu Lys
        850                 855                 860
Gly Leu Glu Ala Ile Asn Gly Lys Asp Ala Glu Ala Thr Ile Thr Leu
865                 870                 875                 880
Lys Tyr Thr Ala Thr Leu Asn Ala Leu Ala Val Ala Asp Val Pro Glu
                885                 890                 895
Ala Asn Asp Val Thr Phe His Tyr Gly Asn Asn Pro Gly His Gly Asn
            900                 905                 910
Thr Pro Lys Pro Asn Lys Pro Lys Asn Gly Glu Leu Thr Ile Thr Lys
        915                 920                 925
```

Thr Trp Ala Asp Ala Lys Asp Ala Pro Ile Ala Gly Val Glu Val Thr
            930                 935                 940

Phe Asp Leu Val Asn Ala Gln Thr Gly Glu Val Val Lys Val Pro Gly
945                 950                 955                 960

His Glu Thr Gly Ile Val Leu Asn Gln Thr Asn Asn Trp Thr Phe Thr
            965                 970                 975

Ala Thr Gly Leu Asp Asn Asn Thr Glu Tyr Lys Phe Val Glu Arg Thr
            980                 985                 990

Ile Lys Gly Tyr Ser Ala Asp Tyr Gln Thr Ile Thr Glu Thr Gly Lys
            995                 1000                1005

Ile Ala Val Lys Asn Trp Lys Asp Glu Asn Pro Glu Pro Ile Asn Pro
        1010                1015                1020

Glu Glu Pro Arg Val Lys Thr Tyr Gly Lys Lys Phe Val Lys Val Asp
1025                1030                1035                1040

Gln Lys Asp Glu Arg Leu Lys Glu Ala Gln Phe Val Val Lys Asn Glu
            1045                1050                1055

Gln Gly Lys Tyr Leu Ala Leu Lys Ser Ala Ala Gln Ala Val Asn
        1060                1065                1070

Glu Lys Ala Ala Glu Ala Lys Gln Ala Leu Asp Ala Ala Ile Ala
        1075                1080                1085

Ala Tyr Thr Asn Ala Ala Asp Lys Asn Ala Ala Gln Ala Val Val Asp
        1090                1095                1100

Ala Ala Gln Lys Thr Tyr Asn Asp Asn Tyr Arg Ala Ala Arg Phe Gly
1105                1110                1115                1120

Tyr Val Glu Val Glu Arg Lys Glu Asp Ala Leu Val Leu Thr Ser Asn
            1125                1130                1135

Thr Asp Gly Gln Phe Gln Ile Ser Gly Leu Ala Ala Gly Ser Tyr Thr
            1140                1145                1150

Leu Glu Glu Thr Lys Ala Pro Glu Gly Phe Ala Lys Leu Gly Asp Val
            1155                1160                1165

Lys Phe Glu Val Gly Ala Gly Ser Trp Asn Gln Gly Asp Phe Asn Tyr
        1170                1175                1180

Leu Lys Asp Val Gln Lys Asn Asp Ala Thr Lys Val Val Asn Lys Lys
1185                1190                1195                1200

Ile Thr Leu Gly Gly Ser Gly Gly Gly Ala Ala Thr Val Phe Ala
        1205                1210                1215

Ala Asp Asn Val Ser Thr Ala Pro Asp Ala Val Thr Lys Thr Leu Thr
        1220                1225                1230

Ile His Lys Leu Leu Leu Ser Glu Asp Asp Leu Lys Thr Trp Asp Thr
        1235                1240                1245

Asn Gly Pro Lys Gly Tyr Asp Gly Thr Gln Ser Ser Leu Lys Asp Leu
        1250                1255                1260

Thr Gly Val Val Ala Glu Glu Ile Pro Asn Val Tyr Phe Glu Leu Gln
1265                1270                1275                1280

Lys Tyr Asn Leu Thr Asp Gly Lys Glu Lys Glu Asn Leu Lys Asp Asp
            1285                1290                1295

Ser Lys Trp Thr Thr Val His Gly Gly Leu Thr Thr Lys Asp Gly Leu
        1300                1305                1310

Lys Ile Glu Thr Ser Thr Leu Lys Gly Val Tyr Arg Ile Arg Glu Asp
        1315                1320                1325

Arg Thr Lys Thr Thr Tyr Val Gly Pro Asn Gly Gln Val Leu Thr Gly
        1330                1335                1340

Ser Lys Ala Val Pro Ala Leu Val Thr Leu Pro Leu Val Asn Asn Asn

```
            1345                1350                1355                1360
Gly Thr Val Ile Asp Ala His Val Phe Pro Lys Asn Ser Tyr Asn Lys
                1365                1370                1375
Pro Val Val Asp Lys Arg Ile Ala Asp Thr Leu Asn Tyr Asn Asp Gln
            1380                1385                1390
Asn Gly Leu Ser Ile Gly Thr Lys Ile Pro Tyr Val Asn Thr Thr
            1395                1400                1405
Ile Pro Ser Asn Ala Thr Phe Ala Thr Ser Phe Trp Ser Asp Glu Met
        1410                1415                1420
Thr Glu Gly Leu Thr Tyr Asn Glu Asp Val Thr Ile Thr Leu Asn Asn
1425                1430                1435                1440
Val Ala Met Asp Gln Ala Asp Tyr Glu Val Thr Lys Gly Asn Gly
                1445                1450                1455
Phe Asn Leu Lys Leu Thr Glu Ala Gly Leu Ala Lys Ile Asn Gly Lys
            1460                1465                1470
Asp Ala Asp Gln Lys Ile Gln Ile Thr Tyr Ser Ala Thr Leu Asn Ser
            1475                1480                1485
Leu Ala Val Ala Asp Ile Pro Glu Ser Asn Asp Ile Thr Tyr His Tyr
        1490                1495                1500
Gly Asn His Gln Asp His Gly Asn Thr Pro Lys Pro Thr Lys Pro Asn
1505                1510                1515                1520
Asn Gly Gln Ile Thr Val Thr Lys Thr Trp Asp Ser Gln Pro Ala Pro
                1525                1530                1535
Glu Gly Val Lys Ala Thr Val Gln Leu Val Asn Ala Lys Thr Gly Glu
            1540                1545                1550
Lys Val Gly Ala Pro Val Glu Leu Ser Glu Asn Asn Trp Thr Tyr Thr
        1555                1560                1565
Trp Ser Gly Leu Asp Asn Ser Ile Glu Tyr Lys Val Glu Glu Tyr
        1570                1575                1580
Asn Gly Tyr Ser Ala Glu Tyr Thr Val Glu Ser Lys Gly Lys Leu Gly
1585                1590                1595                1600
Val Lys Asn Trp Lys Asp Asn Asn Pro Ala Pro Ile Asn Pro Glu Glu
                1605                1610                1615
Pro Arg Val Lys Thr Tyr Gly Lys Lys Phe Val Lys Val Asp Gln Lys
            1620                1625                1630
Asp Thr Arg Leu Glu Asn Ala Gln Phe Val Val Lys Lys Ala Asp Ser
            1635                1640                1645
Asn Lys Tyr Ile Ala Phe Lys Ser Thr Ala Gln Gln Ala Ala Asp Glu
        1650                1655                1660
Lys Ala Ala Ala Thr Ala Lys Gln Lys Leu Asp Ala Ala Val Ala Ala
1665                1670                1675                1680
Tyr Thr Asn Ala Ala Asp Lys Gln Ala Ala Gln Ala Leu Val Asp Gln
                1685                1690                1695
Ala Gln Gln Glu Tyr Asn Val Ala Tyr Lys Ala Lys Phe Gly Tyr
                1700                1705                1710
Val Glu Val Ala Gly Lys Asp Glu Ala Met Val Leu Thr Ser Asn Thr
            1715                1720                1725
Asp Gly Gln Phe Gln Ile Ser Gly Leu Ala Ala Gly Thr Tyr Lys Leu
        1730                1735                1740
Glu Glu Ile Lys Ala Pro Glu Gly Phe Ala Lys Ile Asp Asp Val Glu
1745                1750                1755                1760
Phe Val Val Gly Ala Gly Ser Trp Asn Gln Gly Glu Phe Asn Tyr Leu
                1765                1770                1775
```

Lys Asp Val Gln Lys Asn Asp Ala Thr Lys Val Val Asn Lys Lys Ile
        1780                1785                1790

Thr Leu Gly His His His His His His
        1795                1800

<210> SEQ ID NO 14
<211> LENGTH: 5403
<212> TYPE: DNA
<213> ORGANISM: Artificial Sequence
<220> FEATURE:
<223> OTHER INFORMATION: Sequence encoding SEQ ID NO: 13

<400> SEQUENCE: 14

| | | | | | | |
|---|---|---|---|---|---|---|
| atggctagcg | ctgcaacagt | ttttgcggct | gggacgacaa | caacatctgt | taccgttcat | 60 |
| aaactattgg | caacagatgg | ggatatggat | aaaattgcaa | atgagttaga | aacaggtaac | 120 |
| tatgctggta | ataaagtggg | tgttctacct | gcaaatgcaa | agaaattgc | cggtgttatg | 180 |
| ttcgtttgga | caaatactaa | taatgaaatt | attgatgaaa | atggccaaac | tctaggagtg | 240 |
| aatattgatc | cacaaacatt | taaactctca | ggggcaatgc | cggcaactgc | aatgaaaaaa | 300 |
| ttaacagaag | ctgaaggagc | taaatttaac | acggcaaatt | taccagctgc | taagtataaa | 360 |
| atttatgaaa | ttcacagttt | atcaacttat | gtcggtgaag | atggagcaac | cttaacaggt | 420 |
| tctaaagcag | ttccaattga | aattgaatta | ccattgaacg | atgttgtgga | tgcgcatgtg | 480 |
| tatccaaaaa | atacagaagc | aaagccaaaa | attgataaag | atttcaaagg | taaagcaaat | 540 |
| ccagatacac | cacgtgtaga | taaagataca | cctgtgaacc | accaagttgg | agatgttgta | 600 |
| gagtacgaaa | ttgttacaaa | aattccagca | cttgctaatt | atgcaacagc | aaactggagc | 660 |
| gatagaatga | ctgaaggttt | ggcattcaac | aaaggtacag | tgaaagtaac | tgttgatgat | 720 |
| gttgcacttg | aagcaggtga | ttatgctcta | acagaagtag | caactggttt | tgatttgaaa | 780 |
| ttaacagatg | ctggtttagc | taaagtgaat | gaccaaaacg | ctgaaaaaac | tgtgaaaatc | 840 |
| acttattcgg | caacattgaa | tgacaaagca | attgtagaag | taccagaatc | taatgatgta | 900 |
| acatttaact | atggtaataa | tccagatcac | gggaatactc | caaagccgaa | taagccaaat | 960 |
| gaaaacggcg | atttgacatt | gaccaagaca | tgggttgatg | ctacaggtgc | accaattccg | 1020 |
| gctggagctg | aagcaacgtt | cgatttggtt | aatgctcaga | ctggtaaagt | tgtacaaact | 1080 |
| gtaactttga | caacagacaa | aaatacagtt | actgttaacg | gattggataa | aaatacagaa | 1140 |
| tataaattcg | ttgaacgtag | tataaaaggg | tattcagcag | attatcaaga | aatcactaca | 1200 |
| gctggagaaa | ttgctgtcaa | gaactggaaa | gacgaaaatc | caaaaccact | tgatccaaca | 1260 |
| gagccaaaag | ttgttacata | tggtaaaaag | tttgtcaaag | ttaatgataa | agataatcgt | 1320 |
| ttagctgggg | cagaatttgt | aattgcaaat | gctgataatg | ctggtcaata | tttagcacgt | 1380 |
| aaagcagata | aagtgagtca | agaagagaag | cagttggttg | ttacaacaaa | ggatgcttta | 1440 |
| gatagagcag | ttgctgctta | taacgctctt | actgcacaac | aacaaactca | gcaagaaaaa | 1500 |
| gagaaagttg | acaaagctca | agctgcttat | aatgctgctg | tgattgctgc | caacaatgca | 1560 |
| tttgaatggg | tggcagataa | ggacaatgaa | atgttgtga | attagtttc | tgatgcacaa | 1620 |
| ggtcgctttg | aaattacagg | ccttcttgca | ggtacatatt | acttagaaga | aacaaaacag | 1680 |
| cctgctggtt | atgcattact | aactagccgt | cagaaatttg | aagtcactgc | aacttcttat | 1740 |
| tcagcgactg | gacaaggcat | tgagtatact | gctggttcag | gtaaagatga | cgctacaaaa | 1800 |
| gtagtcaaca | aaaaaatcac | tggatccggc | agcggtggcg | gtggcgcgga | acaaaaaact | 1860 |
| aagacactta | cagttcataa | attattgatg | acagatcaag | agcttgacgc | ttggaattct | 1920 |

```
gatgcgatta ctactgcagg ttatgacggt tcgcaaaatt ttgaacagtt caaacaactt      1980
caaggtgttc cacaaggagt aaccgaaatc tctggtgttg cattcgagtt acagagttat      2040
acgggtcctc aaggaaaaga acaagaaaat ttaacgaatg atgcggtttg gactgcggtt      2100
aataaaggtg tgacgactga aacgggtgtt aaatttgata ctgaagtttt acaagggaca      2160
tatcgtcttg tcgaagtacg taaagaatcg acttatgtcg gtccaaatgg taaagtttta      2220
acaggtatga aagctgttcc tgctttaatt attctgccgc ttgtaaacca aaatggtgtt      2280
gtagaaaatg cacatgtcta tccaaagaat tctgaagaca aacctacagc aacgaaaaca      2340
tttgatactg cagcaggttt cgtagatcca ggtgaaaaag gtttagcaat tggcactaag      2400
gtaccgtata ttgttacaac aactattccg aaaaactcaa ctcttgcaac agctttctgg      2460
tcagatgaaa tgacagaagg tctagattat aatggtgatg tagttgttaa ttataatggt      2520
caaccgcttg ataattctca ttacacatta gaagcaggtc ataatggctt tatcttgaag      2580
ttaaatgaaa aaggtctgga agcaatcaac ggtaaagatg cagaagcaac aattacgttg      2640
aagtatactg caactttaaa tgctcttgct gttgctgatg tgccagaagc gaatgatgta      2700
acattccatt atggaaacaa cccaggtcat ggtaacactc caaaaccaaa caaacctaaa      2760
aacggtgaac ttacaattac taaaacatgg gctgatgcta agatgctccc tatagcaggt      2820
gtagaagtaa cttttgattt ggtaaatgct cagacaggtg aggtcgttaa agtacctgga      2880
catgaaacag gtattgtatt gaatcaaaca aataattgga catttactgc tacaggtctt      2940
gataataata cagaatataa atttgttgaa cggacaatta agggatattc tgcagattac      3000
caaacaatta ctgaaacagg aaaaattgct gttaaaaact ggaaagatga aaatccagaa      3060
ccaataaatc ctgaagagcc acgtgtaaaa acatatggta aaaaattcgt taaggttgac      3120
caaaaagacg aacgcttaaa agaagcacaa ttcgttgtga agaatgagca agggaaatat      3180
cttgcactca aatctgcagc acaacaagct gtaaatgaga aagctgccgc agaagcgaaa      3240
caagcgctag atgcagcgat agcagcctat acaaatgctg cagataaaaa tgcagcacaa      3300
gctgtagtag atgctgcgca aaaaacatat aatgacaatt acagagcagc tagatttggc      3360
tatgtagaag tagagagaaa agaagatgcg ttagttctta cttctaacac tgatggtcaa      3420
ttccaaattt caggtcttgc tgctggaagc tacacgttgg aagaaacaaa agctccagaa      3480
ggctttgcaa aacttggaga tgtgaagttt gaggttggag caggttcttg gaatcaaggt      3540
gatttcaatt atttaaaaga tgttcagaag aacgacgcta caaaagtagt caacaaaaaa      3600
atcacgctcg agggcagcgg tggcggtggc gctgcaacag tttttgcggc ggacaatgtt      3660
agtacagcac cagatgctgt tactaaaact ttaacaatcc ataagttact gctctcagaa      3720
gatgatttaa agacttggga tacaaacggt cctaaaggat atgatggaac tcaatctagt      3780
ttaaaagatt taactggagt tgtagctgag gaaattccaa atgtatactt tgaattacaa      3840
aagtataatt tgactgatgg taaggaaaaa gaaaatctta agatgatag taaatggaca      3900 acagttcatg gtggtttgac aactaaagat ggacttaaaa ttgaaaccag tactcttaaa      3960
ggtgtgtatc gtattcgtga ggatagaaca aagactacct atgttggtcc taatgggcaa      4020
gtattaacag gttcaaaagc cgtacctgct cttgtaactc ttccacttgt taacaataat      4080
ggtacagtaa ttgatgcaca tgttttccct aaaaattcat ataataaacc agttgtagat      4140
aaaagaattg ctgatacttt gaattataac gatcaaaatg gtctgtctat cggtactaaa      4200
atcccatatg ttgttaatac aacaattcca agtaatgcaa catttgcaac ttcattttgg      4260
tcagatgaaa tgacagaagg tctaacttat aatgaagatg taacaattac tttgaataat      4320
```

-continued

```
gtagctatgg atcaagctga ttatgaagtc actaaaggaa ataatggctt taacttaaaa    4380
ttaacagaag caggtttagc taaaattaat ggtaaggatg cagaccaaaa aatccaaatt    4440
acttactcag ctactttgaa ctcacttgct gttgcagaca ttcctgaaag taacgatatt    4500
acatatcatt acggaaatca tcaagatcat gggaatactc caaaaccaac taaacctaat    4560
aatggtcaaa ttacagtaac taagacatgg gacagtcaac ctgctcctga gggggtgaaa    4620
gcgactgttc aacttgtaaa tgccaagact ggtgagaaag tcggtgctcc tgtagaactt    4680
tcagaaaata attggacata tacttggagt ggtctagata attctattga atacaaagtt    4740
gaagaagaat ataatggata ctcagctgaa tacacagtag agagcaaagg gaagttgggg    4800
gtaaaaaact ggaaagataa taacccagct ccaatcaatc ctgaagaacc acgtgtaaaa    4860
acatacggta aaaagtttgt caagtagac caaaaagata ctcgtctaga aaatgcgcag    4920
ttcgttgtta aaaagcaga tagcaataaa tatattgcct ttaagtcaac tgcacaacaa    4980
gctgcagatg aaaagcagc agcaactgca aacaaaaat tggatgcagc ggtagcagct    5040
tacacaaatg ctgcagataa gcaagccgct caagctctag tagatcaagc acagcaagaa    5100
tacaatgtag cttacaaaga agccaaattt ggttatgttg aagtagctgg aaaagatgaa    5160
gcaatggttc ttacttctaa tacggatggt caattccaaa tttcaggtct tgctgctggt    5220
acttataaat tagaagaaat taaagctcca gaaggttttg cgaaaattga tgatgtagaa    5280
tttgttgttg gagcaggttc ttggaatcaa ggtgagttta attacttaaa agatgttcaa    5340
aagaatgacg ctacaaaagt agtcaacaaa aaaatcactc tcgagcacca ccaccaccac    5400
cac                                                                 5403
```

<210> SEQ ID NO 15
<211> LENGTH: 1801
<212> TYPE: PRT
<213> ORGANISM: Artificial Sequence
<220> FEATURE:
<223> OTHER INFORMATION: RrgB III-II-I

<400> SEQUENCE: 15

```
Met Ala Ser Ala Glu Gln Lys Thr Lys Thr Leu Thr Val His Lys Leu
1               5                  10                  15

Leu Met Thr Asp Gln Glu Leu Asp Ala Trp Asn Ser Asp Ala Ile Thr
            20                  25                  30

Thr Ala Gly Tyr Asp Gly Ser Gln Asn Phe Glu Gln Phe Lys Gln Leu
        35                  40                  45

Gln Gly Val Pro Gln Gly Val Thr Glu Ile Ser Gly Val Ala Phe Glu
    50                  55                  60

Leu Gln Ser Tyr Thr Gly Pro Gln Gly Lys Glu Gln Glu Asn Leu Thr
65                  70                  75                  80

Asn Asp Ala Val Trp Thr Ala Val Asn Lys Gly Val Thr Thr Glu Thr
                85                  90                  95

Gly Val Lys Phe Asp Thr Glu Val Leu Gln Gly Thr Tyr Arg Leu Val
            100                 105                 110

Glu Val Arg Lys Glu Ser Thr Tyr Val Gly Pro Asn Gly Lys Val Leu
        115                 120                 125

Thr Gly Met Lys Ala Val Pro Ala Leu Ile Ile Leu Pro Leu Val Asn
    130                 135                 140

Gln Asn Gly Val Val Glu Asn Ala His Val Tyr Pro Lys Asn Ser Glu
145                 150                 155                 160

Asp Lys Pro Thr Ala Thr Lys Thr Phe Asp Thr Ala Ala Gly Phe Val
                165                 170                 175
```

```
Asp Pro Gly Glu Lys Gly Leu Ala Ile Gly Thr Lys Val Pro Tyr Ile
            180                 185                 190

Val Thr Thr Thr Ile Pro Lys Asn Ser Thr Leu Ala Thr Ala Phe Trp
        195                 200                 205

Ser Asp Glu Met Thr Glu Gly Leu Asp Tyr Asn Gly Asp Val Val
210                 215                 220

Asn Tyr Asn Gly Gln Pro Leu Asp Asn Ser His Tyr Thr Leu Glu Ala
225                 230                 235                 240

Gly His Asn Gly Phe Ile Leu Lys Leu Asn Glu Lys Gly Leu Glu Ala
                245                 250                 255

Ile Asn Gly Lys Asp Ala Glu Ala Thr Ile Thr Leu Lys Tyr Thr Ala
                260                 265                 270

Thr Leu Asn Ala Leu Ala Val Ala Asp Val Pro Glu Ala Asn Asp Val
            275                 280                 285

Thr Phe His Tyr Gly Asn Asn Pro Gly His Gly Asn Thr Pro Lys Pro
        290                 295                 300

Asn Lys Pro Lys Asn Gly Glu Leu Thr Ile Thr Lys Thr Trp Ala Asp
305                 310                 315                 320

Ala Lys Asp Ala Pro Ile Ala Gly Val Glu Val Thr Phe Asp Leu Val
                325                 330                 335

Asn Ala Gln Thr Gly Glu Val Val Lys Val Pro Gly His Glu Thr Gly
            340                 345                 350

Ile Val Leu Asn Gln Thr Asn Asn Trp Thr Phe Thr Ala Thr Gly Leu
        355                 360                 365

Asp Asn Asn Thr Glu Tyr Lys Phe Val Glu Arg Thr Ile Lys Gly Tyr
    370                 375                 380

Ser Ala Asp Tyr Gln Thr Ile Thr Glu Thr Gly Lys Ile Ala Val Lys
385                 390                 395                 400

Asn Trp Lys Asp Glu Asn Pro Glu Pro Ile Asn Pro Glu Glu Pro Arg
                405                 410                 415

Val Lys Thr Tyr Gly Lys Lys Phe Val Lys Val Asp Gln Lys Asp Glu
            420                 425                 430

Arg Leu Lys Glu Ala Gln Phe Val Val Lys Asn Glu Gln Gly Lys Tyr
        435                 440                 445

Leu Ala Leu Lys Ser Ala Ala Gln Gln Ala Val Asn Glu Lys Ala Ala
    450                 455                 460

Ala Glu Ala Lys Gln Ala Leu Asp Ala Ala Ile Ala Ala Tyr Thr Asn
465                 470                 475                 480

Ala Ala Asp Lys Asn Ala Ala Gln Ala Val Val Asp Ala Ala Gln Lys
                485                 490                 495

Thr Tyr Asn Asp Asn Tyr Arg Ala Ala Arg Phe Gly Tyr Val Glu Val
            500                 505                 510

Glu Arg Lys Glu Asp Ala Leu Val Leu Thr Ser Asn Thr Asp Gly Gln
        515                 520                 525

Phe Gln Ile Ser Gly Leu Ala Ala Gly Ser Tyr Thr Leu Glu Glu Thr
    530                 535                 540

Lys Ala Pro Glu Gly Phe Ala Lys Leu Gly Asp Val Lys Phe Glu Val
545                 550                 555                 560

Gly Ala Gly Ser Trp Asn Gln Gly Asp Phe Asn Tyr Leu Lys Asp Val
                565                 570                 575

Gln Lys Asn Asp Ala Thr Lys Val Val Asn Lys Lys Ile Thr Gly Ser
            580                 585                 590

Gly Ser Gly Gly Gly Gly Ala Ala Thr Val Phe Ala Ala Asp Asn Val
```

```
                595                 600                 605
Ser Thr Ala Pro Asp Ala Val Thr Lys Thr Leu Thr Ile His Lys Leu
610                 615                 620

Leu Leu Ser Glu Asp Asp Leu Lys Thr Trp Asp Thr Asn Gly Pro Lys
625                 630                 635                 640

Gly Tyr Asp Gly Thr Gln Ser Ser Leu Lys Asp Leu Thr Gly Val Val
                645                 650                 655

Ala Glu Glu Ile Pro Asn Val Tyr Phe Glu Leu Gln Lys Tyr Asn Leu
                660                 665                 670

Thr Asp Gly Lys Glu Lys Glu Asn Leu Lys Asp Ser Lys Trp Thr
    675                 680                 685

Thr Val His Gly Gly Leu Thr Thr Lys Asp Gly Leu Lys Ile Glu Thr
    690                 695                 700

Ser Thr Leu Lys Gly Val Tyr Arg Ile Arg Glu Asp Arg Thr Lys Thr
705                 710                 715                 720

Thr Tyr Val Gly Pro Asn Gly Gln Val Leu Thr Gly Ser Lys Ala Val
                725                 730                 735

Pro Ala Leu Val Thr Leu Pro Leu Val Asn Asn Gly Thr Val Ile
                740                 745                 750

Asp Ala His Val Phe Pro Lys Asn Ser Tyr Asn Lys Pro Val Val Asp
    755                 760                 765

Lys Arg Ile Ala Asp Thr Leu Asn Tyr Asn Asp Gln Asn Gly Leu Ser
770                 775                 780

Ile Gly Thr Lys Ile Pro Tyr Val Val Asn Thr Thr Ile Pro Ser Asn
785                 790                 795                 800

Ala Thr Phe Ala Thr Ser Phe Trp Ser Asp Glu Met Thr Glu Gly Leu
                805                 810                 815

Thr Tyr Asn Glu Asp Val Thr Ile Thr Leu Asn Asn Val Ala Met Asp
                820                 825                 830

Gln Ala Asp Tyr Glu Val Thr Lys Gly Asn Asn Gly Phe Asn Leu Lys
                835                 840                 845

Leu Thr Glu Ala Gly Leu Ala Lys Ile Asn Gly Lys Asp Ala Asp Gln
850                 855                 860

Lys Ile Gln Ile Thr Tyr Ser Ala Thr Leu Asn Ser Leu Ala Val Ala
865                 870                 875                 880

Asp Ile Pro Glu Ser Asn Asp Ile Thr Tyr His Tyr Gly Asn His Gln
                885                 890                 895

Asp His Gly Asn Thr Pro Lys Pro Thr Lys Pro Asn Asn Gly Gln Ile
                900                 905                 910

Thr Val Thr Lys Thr Trp Asp Ser Gln Pro Ala Pro Glu Gly Val Lys
    915                 920                 925

Ala Thr Val Gln Leu Val Asn Ala Lys Thr Gly Glu Lys Val Gly Ala
930                 935                 940

Pro Val Glu Leu Ser Glu Asn Asn Trp Thr Tyr Thr Trp Ser Gly Leu
945                 950                 955                 960

Asp Asn Ser Ile Glu Tyr Lys Val Glu Glu Tyr Asn Gly Tyr Ser
                965                 970                 975

Ala Glu Tyr Thr Val Glu Ser Lys Gly Lys Leu Gly Val Lys Asn Trp
                980                 985                 990

Lys Asp Asn Asn Pro Ala Pro Ile Asn Pro Glu Glu Pro Arg Val Lys
                995                 1000                1005

Thr Tyr Gly Lys Lys Phe Val Lys Val Asp Gln Lys Asp Thr Arg Leu
                1010                1015                1020
```

-continued

```
Glu Asn Ala Gln Phe Val Val Lys Lys Ala Asp Ser Asn Lys Tyr Ile
1025                1030                1035                1040

Ala Phe Lys Ser Thr Ala Gln Gln Ala Ala Asp Glu Lys Ala Ala Ala
            1045                1050                1055

Thr Ala Lys Gln Lys Leu Asp Ala Ala Val Ala Ala Tyr Thr Asn Ala
        1060                1065                1070

Ala Asp Lys Gln Ala Ala Gln Ala Leu Val Asp Gln Ala Gln Gln Glu
    1075                1080                1085

Tyr Asn Val Ala Tyr Lys Glu Ala Lys Phe Gly Tyr Val Glu Val Ala
1090                1095                1100

Gly Lys Asp Glu Ala Met Val Leu Thr Ser Asn Thr Asp Gly Gln Phe
1105                1110                1115                1120

Gln Ile Ser Gly Leu Ala Ala Gly Thr Tyr Lys Leu Glu Glu Ile Lys
            1125                1130                1135

Ala Pro Glu Gly Phe Ala Lys Ile Asp Asp Val Glu Phe Val Val Gly
        1140                1145                1150

Ala Gly Ser Trp Asn Gln Gly Glu Phe Asn Tyr Leu Lys Asp Val Gln
    1155                1160                1165

Lys Asn Asp Ala Thr Lys Val Val Asn Lys Lys Ile Thr Leu Gly Gly
1170                1175                1180

Ser Gly Gly Gly Gly Ala Ala Thr Val Phe Ala Ala Gly Thr Thr Thr
1185                1190                1195                1200

Thr Ser Val Thr Val His Lys Leu Leu Ala Thr Asp Gly Asp Met Asp
            1205                1210                1215

Lys Ile Ala Asn Glu Leu Glu Thr Gly Asn Tyr Ala Gly Asn Lys Val
        1220                1225                1230

Gly Val Leu Pro Ala Asn Ala Lys Glu Ile Ala Gly Val Met Phe Val
    1235                1240                1245

Trp Thr Asn Thr Asn Asn Glu Ile Ile Asp Glu Asn Gly Gln Thr Leu
1250                1255                1260

Gly Val Asn Ile Asp Pro Gln Thr Phe Lys Leu Ser Gly Ala Met Pro
1265                1270                1275                1280

Ala Thr Ala Met Lys Lys Leu Thr Glu Ala Glu Gly Ala Lys Phe Asn
            1285                1290                1295

Thr Ala Asn Leu Pro Ala Ala Lys Tyr Lys Ile Tyr Glu Ile His Ser
        1300                1305                1310

Leu Ser Thr Tyr Val Gly Glu Asp Gly Ala Thr Leu Thr Gly Ser Lys
    1315                1320                1325

Ala Val Pro Ile Glu Ile Glu Leu Pro Leu Asn Asp Val Val Asp Ala
    1330                1335                1340

His Val Tyr Pro Lys Asn Thr Glu Ala Lys Pro Lys Ile Asp Lys Asp
1345                1350                1355                1360

Phe Lys Gly Lys Ala Asn Pro Asp Thr Pro Arg Val Asp Lys Asp Thr
            1365                1370                1375

Pro Val Asn His Gln Val Gly Asp Val Val Glu Tyr Glu Ile Val Thr
        1380                1385                1390

Lys Ile Pro Ala Leu Ala Asn Tyr Ala Thr Ala Asn Trp Ser Asp Arg
    1395                1400                1405

Met Thr Glu Gly Leu Ala Phe Asn Lys Gly Thr Val Lys Val Thr Val
    1410                1415                1420

Asp Asp Val Ala Leu Glu Ala Gly Asp Tyr Ala Leu Thr Glu Val Ala
1425                1430                1435                1440

Thr Gly Phe Asp Leu Lys Leu Thr Asp Ala Gly Leu Ala Lys Val Asn
            1445                1450                1455
```

```
Asp Gln Asn Ala Glu Lys Thr Val Lys Ile Thr Tyr Ser Ala Thr Leu
            1460                1465                1470

Asn Asp Lys Ala Ile Val Glu Val Pro Glu Ser Asn Asp Val Thr Phe
        1475                1480                1485

Asn Tyr Gly Asn Asn Pro Asp His Gly Asn Thr Pro Lys Pro Asn Lys
    1490                1495                1500

Pro Asn Glu Asn Gly Asp Leu Thr Leu Thr Lys Thr Trp Val Asp Ala
1505                1510                1515                1520

Thr Gly Ala Pro Ile Pro Ala Gly Ala Glu Ala Thr Phe Asp Leu Val
                1525                1530                1535

Asn Ala Gln Thr Gly Lys Val Val Gln Thr Val Thr Leu Thr Thr Asp
            1540                1545                1550

Lys Asn Thr Val Thr Val Asn Gly Leu Asp Lys Asn Thr Glu Tyr Lys
        1555                1560                1565

Phe Val Glu Arg Ser Ile Lys Gly Tyr Ser Ala Asp Tyr Gln Glu Ile
    1570                1575                1580

Thr Thr Ala Gly Glu Ile Ala Val Lys Asn Trp Lys Asp Glu Asn Pro
1585                1590                1595                1600

Lys Pro Leu Asp Pro Thr Glu Pro Lys Val Thr Tyr Gly Lys Lys
                1605                1610                1615

Phe Val Lys Val Asn Asp Lys Asp Asn Arg Leu Ala Gly Ala Glu Phe
        1620                1625                1630

Val Ile Ala Asn Ala Asp Asn Ala Gly Gln Tyr Leu Ala Arg Lys Ala
            1635                1640                1645

Asp Lys Val Ser Gln Glu Glu Lys Gln Leu Val Val Thr Lys Asp
    1650                1655                1660

Ala Leu Asp Arg Ala Val Ala Ala Tyr Asn Ala Leu Thr Ala Gln Gln
1665                1670                1675                1680

Gln Thr Gln Gln Glu Lys Glu Lys Val Asp Lys Ala Gln Ala Ala Tyr
                1685                1690                1695

Asn Ala Ala Val Ile Ala Ala Asn Asn Ala Phe Glu Trp Val Ala Asp
            1700                1705                1710

Lys Asp Asn Glu Asn Val Val Lys Leu Val Ser Asp Ala Gln Gly Arg
        1715                1720                1725

Phe Glu Ile Thr Gly Leu Leu Ala Gly Thr Tyr Tyr Leu Glu Glu Thr
    1730                1735                1740

Lys Gln Pro Ala Gly Tyr Ala Leu Leu Thr Ser Arg Gln Lys Phe Glu
1745                1750                1755                1760

Val Thr Ala Thr Ser Tyr Ser Ala Thr Gly Gln Gly Ile Glu Tyr Thr
                1765                1770                1775

Ala Gly Ser Gly Lys Asp Asp Ala Thr Lys Val Val Asn Lys Lys Ile
            1780                1785                1790

Thr Leu Gly His His His His His His
        1795                1800

<210> SEQ ID NO 16
<211> LENGTH: 5403
<212> TYPE: DNA
<213> ORGANISM: Artificial Sequence
<220> FEATURE:
<223> OTHER INFORMATION: Sequence encoding SEQ ID NO: 15

<400> SEQUENCE: 16
atggctagcg cggaacaaaa aactaagaca cttacagttc ataaattatt gatgacagat      60
caagagcttg acgcttggaa ttctgatgcg attactactg caggttatga cggttcgcaa     120
```

```
aattttgaac agttcaaaca acttcaaggt gttccacaag gagtaaccga aatctctggt      180
gttgcattcg agttacagag ttatacgggt cctcaaggaa aagaacaaga aaatttaacg      240
aatgatgcgg tttggactgc ggttaataaa ggtgtgacga ctgaaacggg tgttaaattt      300
gatactgaag ttttacaagg gacatatcgt cttgtcgaag tacgtaaaga atcgacttat      360
gtcggtccaa atggtaaagt tttaacaggt atgaaagctg ttcctgctttt aattattctg     420 ccgcttgtaa accaaaatgg tgttgtagaa aatgcacatg tctatccaaa gaattctgaa      480
gacaaaccta cagcaacgaa aacatttgat actgcagcag gtttcgtaga tccaggtgaa      540
aaaggtttag caattggcac taaggtaccg tatattgtta caacaactat tccgaaaaac      600
tcaactcttg caacagcttt ctggtcagat gaaatgacag aaggtctaga ttataatggt      660
gatgtagttg ttaattataa tggtcaaccg cttgataatt ctcattacac attagaagca      720
ggtcataatg ctttatctt gaagttaaat gaaaaaggtc tggaagcaat caacggtaaa       780
gatgcagaag caacaattac gttgaagtat actgcaactt taaatgctct tgctgttgct     840
gatgtgccag aagcgaatga tgtaacattc cattatggaa acaacccagg tcatggtaac      900
actccaaaac caaacaaacc taaaaacggt gaacttacaa ttactaaaac atgggctgat      960 gctaagatg ctcctatagc aggtgtagaa gtaactttg atttggtaaa tgctcagaca       1020
ggtgaggtcg ttaaagtacc tggacatgaa acaggtattg tattgaatca acaaataat      1080 tggacattta ctgctacagg tcttgataat aatacagaat ataaatttgt tgaacggaca     1140
attaagggat attctgcaga ttaccaaaca attactgaaa caggaaaaat tgctgttaaa     1200
aactggaaag atgaaaatcc agaaccaata aatcctgaag agccacgtgt aaaaacatat     1260
ggtaaaaaat tcgttaaggt tgaccaaaaa gacgaacgct taaagaagc acaattcgtt      1320 gtgaagaatg agcaagggaa atatcttgca ctcaaatctg cagcacaaca agctgtaaat     1380
gagaaagctg ccgcagaagc gaaacaagcg ctagatgcag cgatagcagc ctatacaaat     1440
gctgcagata aaaatgcagc acaagctgta gtagatgctg cgcaaaaaac atataatgac    1500
aattacagag cagctagatt tggctatgta gaagtagaga gaaagaaga tgcgttagtt     1560 cttacttcta acactgatgg tcaattccaa atttcaggtc ttgctgctgg aagctacacg    1620
ttggaagaaa caaaagctcc agaaggcttt gcaaaacttg gagatgtgaa gtttgaggtt    1680
ggagcaggtt cttggaatca aggtgatttc aattatttaa aagatgttca gaagaacgac   1740
gctacaaaag tagtcaacaa aaaaatcacg ggatccggca gcggtggcgg tggcgctgca    1800 acagttttg cggcggacaa tgttagtaca gcaccagatg ctgttactaa aactttaaca      1860
atccataagt tactgctctc agaagatgat ttaaagactt gggatacaaa cggtcctaaa    1920
ggatatgatg gaactcaatc tagtttaaaa gatttaactg gagttgtagc tgaggaaatt   1980
ccaaatgtat actttgaatt acaaaagtat aatttgactg atggtaagga aaagagaaat   2040 cttaagatg atagtaaatg gacaacagtt catggtggtt tgacaactaa agatggactt    2100
aaaattgaaa ccagtactct taaaggtgtg tatcgtattc gtgaggatag aacaaagact   2160
acctatgttg gtcctaatgg gcaagtatta acaggttcaa aagccgtacc tgctcttgta   2220
actcttccac ttgttaacaa taatggtaca gtaattgatg cacatgtttt ccctaaaaat    2280
tcatataata aaccagttgt agataaaaga attgctgata ctttgaatta taacgatcaa    2340
aatggtctgt ctatcggtac taaaatccca tatgttgtta atacaacaat tccaagtaat   2400
gcaacatttg caacttcatt ttggtcagat gaaatgacag aaggtctaac ttataatgaa   2460
gatgtaacaa ttactttgaa taatgtagct atggatcaag ctgattatga agtcactaaa   2520
```

-continued

```
ggaaataatg gctttaactt aaaattaaca gaagcaggtt tagctaaaat taatggtaag   2580
gatgcagacc aaaaaatcca aattacttac tcagctactt tgaactcact tgctgttgca   2640
gacattcctg aaagtaacga tattacatat cattacggaa atcatcaaga tcatgggaat   2700
actccaaaac caactaaacc taataatggt caaattacag taactaagac atgggacagt   2760
caacctgctc ctgagggggt gaaagcgact gttcaacttg taaatgccaa gactggtgag   2820
aaagtcggtg ctcctgtaga actttcagaa ataattgga catatacttg gagtggtcta   2880
gataattcta ttgaatacaa agttgaagaa gaatataatg gatactcagc tgaatacaca   2940
gtagagagca aagggaagtt gggggtaaaa aactggaaag ataataaccc agctccaatc   3000
aatcctgaag aaccacgtgt aaaaacatac ggtaaaaagt ttgtcaaagt agaccaaaaa   3060
gatactcgtc tagaaaatgc gcagttcgtt gttaaaaaag cagatagcaa taaatatatt   3120
gcctttaagt caactgcaca acaagctgca gatgaaaaag cagcagcaac tgcaaaacaa   3180
aaattggatg cagcggtagc agcttacaca atgctgcag ataagcaagc cgctcaagct   3240
ctagtagatc aagcacagca agaatacaat gtagcttaca agaagccaa atttggttat   3300 gttgaagtag ctggaaaaga tgaagcaatg gttcttactt ctaatacgga tggtcaattc   3360
caaatttcag gtcttgctgc tggtacttat aaattagaag aaattaaagc tccagaaggt   3420
tttgcgaaaa ttgatgatgt agaatttgtt gttggagcag gttcttggaa tcaaggtgag   3480
tttaattact aaaagatgt tcaaaagaat gacgctacaa agtagtcaa caaaaaaatc   3540 actctcgagg gcagcggtgg cggtggcgct gcaacagttt ttgcggctgg gacgacaaca   3600
acatctgtta ccgttcataa actattggca acagatgggg atatggataa aattgcaaat   3660
gagttagaaa caggtaacta tgctggtaat aaagtgggtg ttctacctgc aaatgcaaaa   3720
gaaattgccg gtgttatgtt cgtttggaca aatactaata tgaaattat tgatgaaaat   3780 ggccaaactc taggagtgaa tattgatcca caaacattta aactctcagg ggcaatgccg   3840
gcaactgcaa tgaaaaaatt aacagaagct gaaggagcta aatttaacac ggcaaattta   3900
ccagctgcta agtataaaat ttatgaaatt cacagtttat caacttatgt cggtgaagat   3960
ggagcaacct taacaggttc taaagcagtt ccaattgaaa ttgaattacc attgaacgat   4020
gttgtggatg cgcatgtgta tccaaaaaat acagaagcaa agccaaaaat tgataaagat   4080
ttcaaaggta aagcaaatcc agatacacca cgtgtagata agatacacc tgtgaaccac   4140 caagttggag atgttgtaga gtacgaaatt gttacaaaaa ttccagcact tgctaattat   4200
gcaacagcaa actggagcga tagaatgact gaaggtttgg cattcaacaa aggtacagtg   4260
aaagtaactg ttgatgatgt tgcacttgaa gcaggtgatt atgctctaac agaagtagca   4320
actggttttg atttgaaatt aacagatgct ggtttagcta aagtgaatga ccaaaacgct   4380
gaaaaaactg tgaaaatcac ttattcggca acattgaatg acaaagcaat tgtagaagta   4440
ccagaatcta atgatgtaac atttaactat ggtaataatc cagatcacgg gaatactcca   4500
aagccgaata agccaaatga aaacggcgat ttgacattga ccaagacatg ggttgatgct   4560
acaggtgcac caattccggc tggagctgaa gcaacgttcg atttggttaa tgctcagact   4620
ggtaaagttg tacaaactgt aactttgaca acagacaaaa atacagttac tgttaacgga   4680
ttggataaaa atacagaata taaattcgtt gaacgtagta taaagggta ttcagcgat   4740 tatcaagaaa tcactacagc tggagaaatt gctgtcaaga actggaaaga cgaaaatcca   4800
aaaccacttg atccaacaga gccaaaagtt gttacatatg gtaaaagtt tgtcaaagtt   4860 aatgataaag ataatcgttt agctggggca gaatttgtaa ttgcaaatgc tgataatgct   4920
```

```
ggtcaatatt tagcacgtaa agcagataaa gtgagtcaag aagagaagca gttggttgtt    4980
acaacaaagg atgctttaga tagagcagtt gctgcttata acgctcttac tgcacaacaa    5040
caaactcagc aagaaaaaga gaaagttgac aaagctcaag ctgcttataa tgctgctgtg    5100
attgctgcca acaatgcatt tgaatgggtg gcagataagg acaatgaaaa tgttgtgaaa    5160
ttagtttctg atgcacaagg tcgctttgaa attacaggcc ttcttgcagg tacatattac    5220
ttagaagaaa caaaacagcc tgctggttat gcattactaa ctagccgtca gaaatttgaa    5280
gtcactgcaa cttcttattc agcgactgga caaggcattg agtatactgc tggttcaggt    5340
aaagatgacg ctacaaaagt agtcaacaaa aaaatcactc tcgagcacca ccaccaccac    5400
cac                                                                  5403
```

<210> SEQ ID NO 17
<211> LENGTH: 1801
<212> TYPE: PRT
<213> ORGANISM: Artificial Sequence
<220> FEATURE:
<223> OTHER INFORMATION: RrgB III-I-II

<400> SEQUENCE: 17

```
Met Ala Ser Ala Glu Gln Lys Thr Lys Thr Leu Thr Val His Lys Leu
1               5                   10                  15

Leu Met Thr Asp Gln Glu Leu Asp Ala Trp Asn Ser Asp Ala Ile Thr
            20                  25                  30

Thr Ala Gly Tyr Asp Gly Ser Gln Asn Phe Glu Gln Phe Lys Gln Leu
        35                  40                  45

Gln Gly Val Pro Gln Gly Val Thr Glu Ile Ser Gly Val Ala Phe Glu
    50                  55                  60

Leu Gln Ser Tyr Thr Gly Pro Gln Gly Lys Glu Gln Glu Asn Leu Thr
65                  70                  75                  80

Asn Asp Ala Val Trp Thr Ala Val Asn Lys Gly Val Thr Thr Glu Thr
                85                  90                  95

Gly Val Lys Phe Asp Thr Glu Val Leu Gln Gly Thr Tyr Arg Leu Val
            100                 105                 110

Glu Val Arg Lys Glu Ser Thr Tyr Val Gly Pro Asn Gly Lys Val Leu
        115                 120                 125

Thr Gly Met Lys Ala Val Pro Ala Leu Ile Ile Leu Pro Leu Val Asn
    130                 135                 140

Gln Asn Gly Val Val Glu Asn Ala His Val Tyr Pro Lys Asn Ser Glu
145                 150                 155                 160

Asp Lys Pro Thr Ala Thr Lys Thr Phe Asp Thr Ala Ala Gly Phe Val
                165                 170                 175

Asp Pro Gly Glu Lys Gly Leu Ala Ile Gly Thr Lys Val Pro Tyr Ile
            180                 185                 190

Val Thr Thr Thr Ile Pro Lys Asn Ser Thr Leu Ala Thr Ala Phe Trp
        195                 200                 205

Ser Asp Glu Met Thr Glu Gly Leu Asp Tyr Asn Gly Asp Val Val Val
    210                 215                 220

Asn Tyr Asn Gly Gln Pro Leu Asp Asn Ser His Tyr Thr Leu Glu Ala
225                 230                 235                 240

Gly His Asn Gly Phe Ile Leu Lys Leu Asn Glu Lys Gly Leu Glu Ala
                245                 250                 255

Ile Asn Gly Lys Asp Ala Glu Ala Thr Ile Thr Leu Lys Tyr Thr Ala
            260                 265                 270
```

```
Thr Leu Asn Ala Leu Ala Val Ala Asp Val Pro Glu Ala Asn Asp Val
        275                 280                 285

Thr Phe His Tyr Gly Asn Asn Pro Gly His Gly Asn Thr Pro Lys Pro
        290                 295                 300

Asn Lys Pro Lys Asn Gly Glu Leu Thr Ile Thr Lys Thr Trp Ala Asp
305                 310                 315                 320

Ala Lys Asp Ala Pro Ile Ala Gly Val Glu Val Thr Phe Asp Leu Val
                325                 330                 335

Asn Ala Gln Thr Gly Glu Val Val Lys Val Pro Gly His Glu Thr Gly
                340                 345                 350

Ile Val Leu Asn Gln Thr Asn Asn Trp Thr Phe Thr Ala Thr Gly Leu
                355                 360                 365

Asp Asn Asn Thr Glu Tyr Lys Phe Val Glu Arg Thr Ile Lys Gly Tyr
        370                 375                 380

Ser Ala Asp Tyr Gln Thr Ile Thr Glu Thr Gly Lys Ile Ala Val Lys
385                 390                 395                 400

Asn Trp Lys Asp Glu Asn Pro Glu Pro Ile Asn Pro Glu Glu Pro Arg
                    405                 410                 415

Val Lys Thr Tyr Gly Lys Lys Phe Val Lys Val Asp Gln Lys Asp Glu
                420                 425                 430

Arg Leu Lys Glu Ala Gln Phe Val Lys Asn Glu Gln Gly Lys Tyr
        435                 440                 445

Leu Ala Leu Lys Ser Ala Ala Gln Ala Val Asn Glu Lys Ala Ala
        450                 455                 460

Ala Glu Ala Lys Gln Ala Leu Asp Ala Ala Ile Ala Ala Tyr Thr Asn
465                 470                 475                 480

Ala Ala Asp Lys Asn Ala Gln Ala Val Val Asp Ala Ala Gln Lys
                485                 490                 495

Thr Tyr Asn Asp Asn Tyr Arg Ala Ala Arg Phe Gly Tyr Val Glu Val
                500                 505                 510

Glu Arg Lys Glu Asp Ala Leu Val Leu Thr Ser Asn Thr Asp Gly Gln
        515                 520                 525

Phe Gln Ile Ser Gly Leu Ala Ala Gly Ser Tyr Thr Leu Glu Glu Thr
        530                 535                 540

Lys Ala Pro Glu Gly Phe Ala Lys Leu Gly Asp Val Lys Phe Glu Val
545                 550                 555                 560

Gly Ala Gly Ser Trp Asn Gln Gly Asp Phe Asn Tyr Leu Lys Asp Val
                565                 570                 575

Gln Lys Asn Asp Ala Thr Lys Val Val Asn Lys Lys Ile Thr Gly Ser
                580                 585                 590

Gly Ser Gly Gly Gly Ala Ala Thr Val Phe Ala Ala Gly Thr Thr
        595                 600                 605

Thr Thr Ser Val Thr Val His Lys Leu Leu Ala Thr Asp Gly Asp Met
        610                 615                 620

Asp Lys Ile Ala Asn Glu Leu Glu Thr Gly Asn Tyr Ala Gly Asn Lys
625                 630                 635                 640

Val Gly Val Leu Pro Ala Asn Ala Lys Glu Ile Ala Gly Val Met Phe
                645                 650                 655

Val Trp Thr Asn Thr Asn Asn Glu Ile Ile Asp Glu Asn Gly Gln Thr
                660                 665                 670

Leu Gly Val Asn Ile Asp Pro Gln Thr Phe Lys Leu Ser Gly Ala Met
        675                 680                 685

Pro Ala Thr Ala Met Lys Lys Leu Thr Glu Ala Glu Gly Ala Lys Phe
690                 695                 700
```

```
Asn Thr Ala Asn Leu Pro Ala Ala Lys Tyr Lys Ile Tyr Glu Ile His
705                 710                 715                 720

Ser Leu Ser Thr Tyr Val Gly Glu Asp Gly Ala Thr Leu Thr Gly Ser
            725                 730                 735

Lys Ala Val Pro Ile Glu Ile Glu Leu Pro Leu Asn Asp Val Val Asp
                740                 745                 750

Ala His Val Tyr Pro Lys Asn Thr Glu Ala Lys Pro Lys Ile Asp Lys
            755                 760                 765

Asp Phe Lys Gly Lys Ala Asn Pro Asp Thr Pro Arg Val Asp Lys Asp
        770                 775                 780

Thr Pro Val Asn His Gln Val Gly Asp Val Val Glu Tyr Glu Ile Val
785                 790                 795                 800

Thr Lys Ile Pro Ala Leu Ala Asn Tyr Ala Thr Ala Asn Trp Ser Asp
                805                 810                 815

Arg Met Thr Glu Gly Leu Ala Phe Asn Lys Gly Thr Val Lys Val Thr
            820                 825                 830

Val Asp Asp Val Ala Leu Glu Ala Gly Asp Tyr Ala Leu Thr Glu Val
        835                 840                 845

Ala Thr Gly Phe Asp Leu Lys Leu Thr Asp Ala Gly Leu Ala Lys Val
        850                 855                 860

Asn Asp Gln Asn Ala Glu Lys Thr Val Lys Ile Thr Tyr Ser Ala Thr
865                 870                 875                 880

Leu Asn Asp Lys Ala Ile Val Glu Val Pro Glu Ser Asn Asp Val Thr
            885                 890                 895

Phe Asn Tyr Gly Asn Asn Pro Asp His Gly Asn Thr Pro Lys Pro Asn
        900                 905                 910

Lys Pro Asn Glu Asn Gly Asp Leu Thr Leu Thr Lys Thr Trp Val Asp
        915                 920                 925

Ala Thr Gly Ala Pro Ile Pro Ala Gly Ala Glu Ala Thr Phe Asp Leu
        930                 935                 940

Val Asn Ala Gln Thr Gly Lys Val Val Gln Thr Val Thr Leu Thr Thr
945                 950                 955                 960

Asp Lys Asn Thr Val Thr Val Asn Gly Leu Asp Lys Asn Thr Glu Tyr
            965                 970                 975

Lys Phe Val Glu Arg Ser Ile Lys Gly Tyr Ser Ala Asp Tyr Gln Glu
        980                 985                 990

Ile Thr Thr Ala Gly Glu Ile Ala Val Lys Asn Trp Lys Asp Glu Asn
        995                 1000                1005

Pro Lys Pro Leu Asp Pro Thr Glu Pro Lys Val Val Thr Tyr Gly Lys
    1010                1015                1020

Lys Phe Val Lys Val Asn Asp Lys Asp Asn Arg Leu Ala Gly Ala Glu
1025                1030                1035                1040

Phe Val Ile Ala Asn Ala Asp Asn Ala Gly Gln Tyr Leu Ala Arg Lys
                1045                1050                1055

Ala Asp Lys Val Ser Gln Glu Glu Lys Gln Leu Val Val Thr Thr Lys
                1060                1065                1070

Asp Ala Leu Asp Arg Ala Val Ala Ala Tyr Asn Ala Leu Thr Ala Gln
            1075                1080                1085

Gln Gln Thr Gln Gln Glu Lys Glu Lys Val Asp Lys Ala Gln Ala Ala
        1090                1095                1100

Tyr Asn Ala Ala Val Ile Ala Ala Asn Ala Phe Glu Trp Val Ala
1105                1110                1115                1120

Asp Lys Asp Asn Glu Asn Val Val Lys Leu Val Ser Asp Ala Gln Gly
```

```
                    1125                1130                1135
Arg Phe Glu Ile Thr Gly Leu Leu Ala Gly Thr Tyr Tyr Leu Glu Glu
                1140                1145                1150

Thr Lys Gln Pro Ala Gly Tyr Ala Leu Leu Thr Ser Arg Gln Lys Phe
            1155                1160                1165

Glu Val Thr Ala Thr Ser Tyr Ser Ala Thr Gly Gln Gly Ile Glu Tyr
        1170                1175                1180

Thr Ala Gly Ser Gly Lys Asp Asp Ala Thr Lys Val Val Asn Lys Lys
1185                1190                1195                1200

Ile Thr Leu Gly Gly Ser Gly Gly Gly Ala Ala Thr Val Phe Ala
                1205                1210                1215

Ala Asp Asn Val Ser Thr Ala Pro Asp Ala Val Thr Lys Thr Leu Thr
                1220                1225                1230

Ile His Lys Leu Leu Leu Ser Glu Asp Asp Leu Lys Thr Trp Asp Thr
            1235                1240                1245

Asn Gly Pro Lys Gly Tyr Asp Gly Thr Gln Ser Ser Leu Lys Asp Leu
        1250                1255                1260

Thr Gly Val Val Ala Glu Glu Ile Pro Asn Val Tyr Phe Glu Leu Gln
1265                1270                1275                1280

Lys Tyr Asn Leu Thr Asp Gly Lys Glu Lys Glu Asn Leu Lys Asp Asp
                1285                1290                1295

Ser Lys Trp Thr Thr Val His Gly Gly Leu Thr Thr Lys Asp Gly Leu
            1300                1305                1310

Lys Ile Glu Thr Ser Thr Leu Lys Gly Val Tyr Arg Ile Arg Glu Asp
        1315                1320                1325

Arg Thr Lys Thr Thr Tyr Val Gly Pro Asn Gly Gln Val Leu Thr Gly
        1330                1335                1340

Ser Lys Ala Val Pro Ala Leu Val Thr Leu Pro Leu Val Asn Asn Asn
1345                1350                1355                1360

Gly Thr Val Ile Asp Ala His Val Phe Pro Lys Asn Ser Tyr Asn Lys
                1365                1370                1375

Pro Val Val Asp Lys Arg Ile Ala Asp Thr Leu Asn Tyr Asn Asp Gln
            1380                1385                1390

Asn Gly Leu Ser Ile Gly Thr Lys Ile Pro Tyr Val Val Asn Thr Thr
        1395                1400                1405

Ile Pro Ser Asn Ala Thr Phe Ala Thr Ser Phe Trp Ser Asp Glu Met
        1410                1415                1420

Thr Glu Gly Leu Thr Tyr Asn Glu Asp Val Thr Ile Thr Leu Asn Asn
1425                1430                1435                1440

Val Ala Met Asp Gln Ala Asp Tyr Glu Val Thr Lys Gly Asn Asn Gly
                1445                1450                1455

Phe Asn Leu Lys Leu Thr Glu Ala Gly Leu Ala Lys Ile Asn Gly Lys
            1460                1465                1470

Asp Ala Asp Gln Lys Ile Gln Ile Thr Tyr Ser Ala Thr Leu Asn Ser
        1475                1480                1485

Leu Ala Val Ala Asp Ile Pro Glu Ser Asn Asp Ile Thr Tyr His Tyr
        1490                1495                1500

Gly Asn His Gln Asp His Gly Asn Thr Pro Lys Pro Thr Lys Pro Asn
1505                1510                1515                1520

Asn Gly Gln Ile Thr Val Thr Lys Thr Trp Asp Ser Gln Pro Ala Pro
                1525                1530                1535

Glu Gly Val Lys Ala Thr Val Gln Leu Val Asn Ala Lys Thr Gly Glu
            1540                1545                1550
```

Lys Val Gly Ala Pro Val Glu Leu Ser Glu Asn Asn Trp Thr Tyr Thr
    1555                1560                1565

Trp Ser Gly Leu Asp Asn Ser Ile Glu Tyr Lys Val Glu Glu Glu Tyr
    1570                1575                1580

Asn Gly Tyr Ser Ala Glu Tyr Thr Val Glu Ser Lys Gly Lys Leu Gly
1585                1590                1595                1600

Val Lys Asn Trp Lys Asp Asn Pro Ala Pro Ile Asn Pro Glu Glu
        1605                1610                1615

Pro Arg Val Lys Thr Tyr Gly Lys Lys Phe Val Lys Val Asp Gln Lys
        1620                1625                1630

Asp Thr Arg Leu Glu Asn Ala Gln Phe Val Val Lys Lys Ala Asp Ser
        1635                1640                1645

Asn Lys Tyr Ile Ala Phe Lys Ser Thr Ala Gln Gln Ala Ala Asp Glu
        1650                1655                1660

Lys Ala Ala Ala Thr Ala Lys Gln Lys Leu Asp Ala Ala Val Ala Ala
1665                1670                1675                1680

Tyr Thr Asn Ala Ala Asp Lys Gln Ala Ala Gln Ala Leu Val Asp Gln
                1685                1690                1695

Ala Gln Gln Glu Tyr Asn Val Ala Tyr Lys Glu Ala Lys Phe Gly Tyr
                1700                1705                1710

Val Glu Val Ala Gly Lys Asp Glu Ala Met Val Leu Thr Ser Asn Thr
        1715                1720                1725

Asp Gly Gln Phe Gln Ile Ser Gly Leu Ala Ala Gly Thr Tyr Lys Leu
        1730                1735                1740

Glu Glu Ile Lys Ala Pro Glu Gly Phe Ala Lys Ile Asp Asp Val Glu
1745                1750                1755                1760

Phe Val Val Gly Ala Gly Ser Trp Asn Gln Gly Glu Phe Asn Tyr Leu
                1765                1770                1775

Lys Asp Val Gln Lys Asn Asp Ala Thr Lys Val Val Asn Lys Lys Ile
                1780                1785                1790

Thr Leu Gly His His His His His His
        1795                1800

<210> SEQ ID NO 18
<211> LENGTH: 5403
<212> TYPE: DNA
<213> ORGANISM: Artificial Sequence
<220> FEATURE:
<223> OTHER INFORMATION: Sequence encoding SEQ ID NO: 17

<400> SEQUENCE: 18
atggctagcg cggaacaaaa aactaagaca cttacagttc ataaattatt gatgacagat      60
caagagcttg acgcttggaa ttctgatgcg attactactg caggttatga cggttcgcaa     120
aattttgaac agttcaaaca acttcaaggt gttccacaag gagtaaccga atctctggt     180 gttgcattcg agttacagag ttatacgggt cctcaaggaa agaacaaga aaatttaacg     240 aatgatgcgg tttggactgc ggttaataaa ggtgtgacga ctgaaacggg tgttaaattt     300
gatactgaag tttacaagg gacatatcgt cttgtcgaag tacgtaaaga atcgacttat     360
gtcggtccaa atggtaaagt tttaacaggt atgaaagctg ttcctgcttt aattattctg     420
ccgcttgtaa accaaaatgg tgttgtagaa aatgcacatg tctatccaaa gaattctgaa     480
gacaaaccta cagcaacgaa aacatttgat actgcagcag gtttcgtaga tccaggtgaa     540
aaaggtttag caattggcac taaggtaccg tatattgtta caacaactat tccgaaaaac     600
tcaactcttg caacagcttt ctggtcagat gaaatgacag aaggtctaga ttataatggt     660

```
gatgtagttg ttaattataa tggtcaaccg cttgataatt ctcattacac attagaagca    720
ggtcataatg gctttatctt gaagttaaat gaaaaaggtc tggaagcaat caacggtaaa    780
gatgcagaag caacaattac gttgaagtat actgcaactt taaatgctct tgctgttgct    840
gatgtgccag aagcgaatga tgtaacattc cattatggaa acaacccagg tcatggtaac    900
actccaaaac caaacaaacc taaaaacggt gaacttacaa ttactaaaac atgggctgat    960
gctaaagatg ctcctatagc aggtgtagaa gtaacttttg atttggtaaa tgctcagaca   1020
ggtgaggtcg ttaaagtacc tggacatgaa acaggtattg tattgaatca aacaaataat   1080
tggacattta ctgctacagg tcttgataat aatacagaat ataaatttgt tgaacggaca   1140
attaagggat attctgcaga ttaccaaaca attactgaaa caggaaaaat tgctgttaaa   1200
aactggaaaa atgaaaatcc agaaccaata aatcctgaag agccacgtgt aaaaacatat   1260
ggtaaaaaat tcgttaaggt tgaccaaaaa gacgaacgct taaaagaagc acaattcgtt   1320
gtgaagaatg agcaagggaa atatcttgca ctcaaatctg cagcacaaca agctgtaaat   1380
gagaaagctg ccgcagaagc gaaacaagcg ctagatgcag cgatagcagc ctatacaaat   1440
gctgcagata aaaatgcagc acaagctgta gtagatgctg cgcaaaaaac atataatgac   1500
aattacagag cagctagatt tggctatgta gaagtagaga gaaaagaaga tgcgttagtt   1560
cttacttcta acactgatgg tcaattccaa atttcaggtc ttgctgctgg aagctacacg   1620
ttggaagaaa caaaagctcc agaaggcttt gcaaaacttg gagatgtgaa gtttgaggtt   1680
ggagcaggtt cttggaatca aggtgatttc aattatttaa aagatgttca gaagaacgac   1740
gctacaaaag tagtcaacaa aaaaatcacg ggatccggca gcggtggcgg tggcgctgca   1800 acagttttg cggctgggac gacaacaaca tctgttaccg ttcataaact attggcaaca   1860
gatggggata tggataaaat tgcaaatgag ttagaaacag gtaactatgc tggtaataaa   1920
gtgggtgttc tacctgcaaa tgcaaaagaa attgccggtg ttatgttcgt ttggacaaat   1980
actaataatg aaattattga tgaaaatggc caaactctag gagtgaatat tgatccacaa   2040
acatttaaac tctcagggc aatgccggca actgcaatga aaaaattaac agaagctgaa   2100
ggagctaaat ttaacacggc aaatttacca gctgctaagt ataaaattta tgaaattcac   2160
agtttatcaa cttatgtcgg tgaagatgga gcaaccttaa caggttctaa agcagttcca   2220
attgaaattg aattaccatt gaacgatgtt gtggatgcgc atgtgtatcc aaaaaatca   2280 gaagcaaagc caaaaattga taaagatttc aaaggtaaag caaatccaga tacaccacgt   2340
gtagataaag atacacctgt gaaccaccaa gttggagatg ttgtagagta cgaaattgtt   2400
acaaaaattc cagcacttgc taattatgca acagcaaact ggagcgatag aatgactgaa   2460
ggtttggcat tcaacaaagg tacagtgaaa gtaactgttg atgatgttgc acttgaagca   2520
ggtgattatg ctctaacaga agtagcaact ggtttttgatt tgaaattaac agatgctggt   2580
ttagctaaag tgaatgacca aaacgctgaa aaaactgtga aaatcactta ttcggcaaca   2640
ttgaatgaca aagcaattgt agaagtacca gaatctaatg atgtaacatt taactatggt   2700
aataatccag atcacgggaa tactccaaag ccgaataagc caaatgaaaa cggcgatttg   2760
acattgacca agacatgggt tgatgctaca ggtgcaccaa ttccggctgg agctgaagca   2820
acgttcgatt tggttaatgc tcagactggt aaagttgtac aaactgtaac tttgacaaca   2880
gacaaaaata cagttactgt taacggattg gataaaaata cagaatataa attcgttgaa   2940
cgtagtataa aagggtattc agcagattat caagaaatca ctacagctgg agaaattgct   3000
gtcaagaact ggaaagacga aaatccaaaa ccacttgatc caacagagcc aaaagttgtt   3060
```

```
acatatggta aaaagtttgt caaagttaat gataaagata atcgtttagc tggggcagaa    3120
tttgtaattg caaatgctga taatgctggt caatatttag cacgtaaagc agataaagtg    3180
agtcaagaag agaagcagtt ggttgttaca acaaaggatg ctttagatag agcagttgct    3240
gcttataacg ctcttactgc acaacaacaa actcagcaag aaaagagaaa agttgacaaa    3300
gctcaagctg cttataatgc tgctgtgatt gctgccaaca atgcatttga atgggtggca    3360
gataaggaca atgaaaatgt tgtgaaatta gtttctgatg cacaaggtcg ctttgaaatt    3420
acaggccttc ttgcaggtac atattactta aagaaacaa  aacagcctgc tggttatgca    3480
ttactaacta gccgtcagaa atttgaagtc actgcaactt cttattcagc gactggacaa    3540
ggcattgagt atactgctgg ttcaggtaaa gatgacgcta caaaagtagt caacaaaaaa    3600
atcactctcg agggcagcgg tggcggtggc gctgcaacag tttttgcggc ggacaatgtt    3660
agtacagcac cagatgctgt tactaaaact ttaacaatcc ataagttact gctctcagaa    3720
gatgatttaa agacttggga tacaaacggt cctaaaggat atgatggaac tcaatctagt    3780
ttaaaagatt taactggagt tgtagctgag gaaattccaa atgtatactt tgaattacaa    3840
aagtataatt tgactgatgg taaggaaaaa gaaaatctta agatgatag  taaatggaca    3900
acagttcatg gtggtttgac aactaaagat ggacttaaaa ttgaaaccag tactcttaaa    3960
ggtgtgtatc gtattcgtga ggatagaaca aagactacct atgttggtcc taatgggcaa    4020
gtattaacag gttcaaaagc cgtacctgct cttgtaactc ttccacttgt taacaataat    4080
ggtacagtaa ttgatgcaca tgttttccct aaaaattcat ataataaacc agttgtagat    4140
aaaagaattg ctgatacttt gaattataac gatcaaaatg gtctgtctat cggtactaaa    4200
atcccatatg ttgttaatac aacaattcca agtaatgcaa catttgcaac ttcatttttgg   4260
tcagatgaaa tgacagaagg tctaacttat aatgaagatg taacaattac tttgaataat    4320
gtagctatgg atcaagctga ttatgaagtc actaaaggaa ataatggctt taacttaaaa    4380
ttaacagaag caggtttagc taaaattaat ggtaaggatg cagaccaaaa aatccaaatt    4440
acttactcag ctactttgaa ctcacttgct gttgcagaca ttcctgaaag taacgatatt    4500
acatatcatt acggaaatca tcaagatcat gggaatactc caaaaccaac taaacctaat    4560
aatggtcaaa ttacagtaac taagacatgg gacagtcaac ctgctcctga gggggtgaaa    4620
gcgactgttc aacttgtaaa tgccaagact ggtgagaaag tcggtgctcc tgtagaactt    4680
tcagaaaata attggacata tcttggagt  ggtctagata attctattga atacaaagtt    4740
gaagaagaat ataatggata ctcagctgaa tacacagtag agagcaaagg gaagttgggg    4800
gtaaaaaact ggaaagataa taacccagct ccaatcaatc ctgaagaacc acgtgtaaaa    4860
acatacggta aaaagtttgt caaagtagac caaaagata  ctcgtctaga aaatgcgcag    4920
ttcgttgtta aaaagcaga  tagcaataaa tatattgcct ttaagtcaac tgcacaacaa    4980
gctgcagatg aaaaagcagc agcaactgca aacaaaaat  tggatgcagc ggtagcagct    5040
tacacaaatg ctgcagataa gcaagccgct caagctctag tagatcaagc acagcaagaa    5100
tacaatgtag cttacaaaga agccaaattt ggttatgttg aagtagctgg aaaagatgaa    5160
gcaatggttc ttacttctaa tacggatggt caattccaaa tttcaggtct tgctgctggt    5220
acttataaat tagaagaaat taaagctcca gaaggttttg cgaaaattga tgatgtagaa    5280
tttgttgttg gagcaggttc ttggaatcaa ggtgagttta attacttaaa agatgttcaa    5340
aagaatgacg ctacaaaagt agtcaacaaa aaaatcactc tcgagcacca ccaccaccac    5400
cac                                                                   5403
```

<210> SEQ ID NO 19
<211> LENGTH: 1801
<212> TYPE: PRT
<213> ORGANISM: Artificial Sequence
<220> FEATURE:
<223> OTHER INFORMATION: RrgB II-III-I

<400> SEQUENCE: 19

```
Met Ala Ser Ala Ala Thr Val Phe Ala Ala Asp Asn Val Ser Thr Ala
1               5                   10                  15

Pro Asp Ala Val Thr Lys Thr Leu Thr Ile His Lys Leu Leu Leu Ser
            20                  25                  30

Glu Asp Leu Lys Thr Trp Asp Thr Asn Gly Pro Lys Gly Tyr Asp
        35                  40                  45

Gly Thr Gln Ser Ser Leu Lys Asp Leu Thr Gly Val Val Ala Glu Glu
    50                  55                  60

Ile Pro Asn Val Tyr Phe Glu Leu Gln Lys Tyr Asn Leu Thr Asp Gly
65                  70                  75                  80

Lys Glu Lys Glu Asn Leu Lys Asp Asp Ser Lys Trp Thr Thr Val His
                85                  90                  95

Gly Gly Leu Thr Thr Lys Asp Gly Leu Lys Ile Glu Thr Ser Thr Leu
            100                 105                 110

Lys Gly Val Tyr Arg Ile Arg Glu Asp Arg Thr Lys Thr Thr Tyr Val
        115                 120                 125

Gly Pro Asn Gly Gln Val Leu Thr Gly Ser Lys Ala Val Pro Ala Leu
    130                 135                 140

Val Thr Leu Pro Leu Val Asn Asn Gly Thr Val Ile Asp Ala His
145                 150                 155                 160

Val Phe Pro Lys Asn Ser Tyr Asn Lys Pro Val Val Asp Lys Arg Ile
                165                 170                 175

Ala Asp Thr Leu Asn Tyr Asn Asp Gln Asn Gly Leu Ser Ile Gly Thr
            180                 185                 190

Lys Ile Pro Tyr Val Val Asn Thr Thr Ile Pro Ser Asn Ala Thr Phe
        195                 200                 205

Ala Thr Ser Phe Trp Ser Asp Glu Met Thr Glu Gly Leu Thr Tyr Asn
    210                 215                 220

Glu Asp Val Thr Ile Thr Leu Asn Asn Val Ala Met Asp Gln Ala Asp
225                 230                 235                 240

Tyr Glu Val Thr Lys Gly Asn Asn Gly Phe Asn Leu Lys Leu Thr Glu
                245                 250                 255

Ala Gly Leu Ala Lys Ile Asn Gly Lys Asp Ala Asp Gln Lys Ile Gln
            260                 265                 270

Ile Thr Tyr Ser Ala Thr Leu Asn Ser Leu Ala Val Ala Asp Ile Pro
        275                 280                 285

Glu Ser Asn Asp Ile Thr Tyr His Tyr Gly Asn His Gln Asp His Gly
    290                 295                 300

Asn Thr Pro Lys Pro Thr Lys Pro Asn Asn Gly Gln Ile Thr Val Thr
305                 310                 315                 320

Lys Thr Trp Asp Ser Gln Pro Ala Pro Glu Gly Val Lys Ala Thr Val
                325                 330                 335

Gln Leu Val Asn Ala Lys Thr Gly Glu Lys Val Gly Ala Pro Val Glu
            340                 345                 350

Leu Ser Glu Asn Asn Trp Thr Tyr Thr Trp Ser Gly Leu Asp Asn Ser
        355                 360                 365

Ile Glu Tyr Lys Val Glu Glu Glu Tyr Asn Gly Tyr Ser Ala Glu Tyr
```

370                 375                 380
Thr Val Glu Ser Lys Gly Lys Leu Gly Val Lys Asn Trp Lys Asp Asn
385                 390                 395                 400

Asn Pro Ala Pro Ile Asn Pro Glu Glu Pro Arg Val Lys Thr Tyr Gly
                405                 410                 415

Lys Lys Phe Val Lys Val Asp Gln Lys Asp Thr Arg Leu Glu Asn Ala
            420                 425                 430

Gln Phe Val Val Lys Lys Ala Asp Ser Asn Lys Tyr Ile Ala Phe Lys
        435                 440                 445

Ser Thr Ala Gln Gln Ala Ala Asp Glu Lys Ala Ala Thr Ala Lys
    450                 455                 460

Gln Lys Leu Asp Ala Ala Val Ala Ala Tyr Thr Asn Ala Ala Asp Lys
465                 470                 475                 480

Gln Ala Ala Gln Ala Leu Val Asp Gln Ala Gln Glu Tyr Asn Val
                485                 490                 495

Ala Tyr Lys Glu Ala Lys Phe Gly Tyr Val Glu Val Ala Gly Lys Asp
            500                 505                 510

Glu Ala Met Val Leu Thr Ser Asn Thr Asp Gly Gln Phe Gln Ile Ser
        515                 520                 525

Gly Leu Ala Ala Gly Thr Tyr Lys Leu Glu Glu Ile Lys Ala Pro Glu
    530                 535                 540

Gly Phe Ala Lys Ile Asp Asp Val Glu Phe Val Val Gly Ala Gly Ser
545                 550                 555                 560

Trp Asn Gln Gly Glu Phe Asn Tyr Leu Lys Asp Val Gln Lys Asn Asp
                565                 570                 575

Ala Thr Lys Val Val Asn Lys Lys Ile Thr Gly Ser Gly Ser Gly Gly
            580                 585                 590

Gly Gly Ala Glu Gln Lys Thr Lys Thr Leu Thr Val His Lys Leu Leu
        595                 600                 605

Met Thr Asp Gln Glu Leu Asp Ala Trp Asn Ser Asp Ala Ile Thr Thr
    610                 615                 620

Ala Gly Tyr Asp Gly Ser Gln Asn Phe Glu Gln Phe Lys Gln Leu Gln
625                 630                 635                 640

Gly Val Pro Gln Gly Val Thr Glu Ile Ser Gly Val Ala Phe Glu Leu
                645                 650                 655

Gln Ser Tyr Thr Gly Pro Gln Gly Lys Glu Gln Glu Asn Leu Thr Asn
            660                 665                 670

Asp Ala Val Trp Thr Ala Val Asn Lys Gly Val Thr Thr Glu Thr Gly
        675                 680                 685

Val Lys Phe Asp Thr Glu Val Leu Gln Gly Thr Tyr Arg Leu Val Glu
    690                 695                 700

Val Arg Lys Glu Ser Thr Tyr Val Gly Pro Asn Gly Lys Val Leu Thr
705                 710                 715                 720

Gly Met Lys Ala Val Pro Ala Leu Ile Ile Leu Pro Leu Val Asn Gln
                725                 730                 735

Asn Gly Val Val Glu Asn Ala His Val Tyr Pro Lys Asn Ser Glu Asp
            740                 745                 750

Lys Pro Thr Ala Thr Lys Thr Phe Asp Thr Ala Gly Phe Val Asp
        755                 760                 765

Pro Gly Glu Lys Gly Leu Ala Ile Gly Thr Lys Val Pro Tyr Ile Val
    770                 775                 780

Thr Thr Thr Ile Pro Lys Asn Ser Thr Leu Ala Thr Ala Phe Trp Ser
785                 790                 795                 800

```
Asp Glu Met Thr Glu Gly Leu Asp Tyr Asn Gly Asp Val Val Asn
            805                 810                 815

Tyr Asn Gly Gln Pro Leu Asp Asn Ser His Tyr Thr Leu Glu Ala Gly
            820                 825                 830

His Asn Gly Phe Ile Leu Lys Leu Asn Glu Lys Gly Leu Glu Ala Ile
            835                 840                 845

Asn Gly Lys Asp Ala Glu Ala Thr Ile Thr Leu Lys Tyr Thr Ala Thr
850                 855                 860

Leu Asn Ala Leu Ala Val Ala Asp Val Pro Glu Ala Asn Asp Val Thr
865                 870                 875                 880

Phe His Tyr Gly Asn Asn Pro Gly His Gly Asn Thr Pro Lys Pro Asn
                885                 890                 895

Lys Pro Lys Asn Gly Glu Leu Thr Ile Thr Lys Thr Trp Ala Asp Ala
            900                 905                 910

Lys Asp Ala Pro Ile Ala Gly Val Glu Val Thr Phe Asp Leu Val Asn
            915                 920                 925

Ala Gln Thr Gly Glu Val Val Lys Val Pro Gly His Glu Thr Gly Ile
            930                 935                 940

Val Leu Asn Gln Thr Asn Asn Trp Thr Phe Thr Ala Thr Gly Leu Asp
945                 950                 955                 960

Asn Asn Thr Glu Tyr Lys Phe Val Glu Arg Thr Ile Lys Gly Tyr Ser
                965                 970                 975

Ala Asp Tyr Gln Thr Ile Thr Glu Thr Gly Lys Ile Ala Val Lys Asn
            980                 985                 990

Trp Lys Asp Glu Asn Pro Glu Pro Ile Asn Pro Glu Glu Pro Arg Val
            995                 1000                1005

Lys Thr Tyr Gly Lys Lys Phe Val Lys Val Asp Gln Lys Asp Glu Arg
    1010                1015                1020

Leu Lys Glu Ala Gln Phe Val Val Lys Asn Glu Gln Gly Lys Tyr Leu
1025                1030                1035                1040

Ala Leu Lys Ser Ala Ala Gln Gln Ala Val Asn Glu Lys Ala Ala Ala
                1045                1050                1055

Glu Ala Lys Gln Ala Leu Asp Ala Ala Ile Ala Ala Tyr Thr Asn Ala
            1060                1065                1070

Ala Asp Lys Asn Ala Ala Gln Ala Val Val Asp Ala Ala Gln Lys Thr
            1075                1080                1085

Tyr Asn Asp Asn Tyr Arg Ala Ala Arg Phe Gly Tyr Val Glu Val Glu
            1090                1095                1100

Arg Lys Glu Asp Ala Leu Val Leu Thr Ser Asn Thr Asp Gly Gln Phe
1105                1110                1115                1120

Gln Ile Ser Gly Leu Ala Ala Gly Ser Tyr Thr Leu Glu Glu Thr Lys
                1125                1130                1135

Ala Pro Glu Gly Phe Ala Lys Leu Gly Asp Val Lys Phe Glu Val Gly
            1140                1145                1150

Ala Gly Ser Trp Asn Gln Gly Asp Phe Asn Tyr Leu Lys Asp Val Gln
            1155                1160                1165

Lys Asn Asp Ala Thr Lys Val Val Asn Lys Lys Ile Thr Leu Gly Gly
            1170                1175                1180

Ser Gly Gly Gly Ala Ala Thr Val Phe Ala Ala Gly Thr Thr Thr
1185                1190                1195                1200

Thr Ser Val Thr Val His Lys Leu Leu Ala Thr Asp Gly Asp Met Asp
            1205                1210                1215

Lys Ile Ala Asn Glu Leu Glu Thr Gly Asn Tyr Ala Gly Asn Lys Val
            1220                1225                1230
```

```
Gly Val Leu Pro Ala Asn Ala Lys Glu Ile Ala Gly Val Met Phe Val
        1235                1240                1245

Trp Thr Asn Thr Asn Asn Glu Ile Ile Asp Glu Asn Gly Gln Thr Leu
        1250                1255                1260

Gly Val Asn Ile Asp Pro Gln Thr Phe Lys Leu Ser Gly Ala Met Pro
1265                1270                1275                1280

Ala Thr Ala Met Lys Lys Leu Thr Glu Ala Glu Gly Ala Lys Phe Asn
        1285                1290                1295

Thr Ala Asn Leu Pro Ala Ala Lys Tyr Lys Ile Tyr Glu Ile His Ser
        1300                1305                1310

Leu Ser Thr Tyr Val Gly Glu Asp Gly Ala Thr Leu Thr Gly Ser Lys
        1315                1320                1325

Ala Val Pro Ile Glu Ile Glu Leu Pro Leu Asn Asp Val Val Asp Ala
        1330                1335                1340

His Val Tyr Pro Lys Asn Thr Glu Ala Lys Pro Lys Ile Asp Lys Asp
1345                1350                1355                1360

Phe Lys Gly Lys Ala Asn Pro Asp Thr Pro Arg Val Asp Lys Asp Thr
        1365                1370                1375

Pro Val Asn His Gln Val Gly Asp Val Val Glu Tyr Glu Ile Val Thr
        1380                1385                1390

Lys Ile Pro Ala Leu Ala Asn Tyr Ala Thr Ala Asn Trp Ser Asp Arg
        1395                1400                1405

Met Thr Glu Gly Leu Ala Phe Asn Lys Gly Thr Val Lys Val Thr Val
        1410                1415                1420

Asp Asp Val Ala Leu Glu Ala Gly Asp Tyr Ala Leu Thr Glu Val Ala
1425                1430                1435                1440

Thr Gly Phe Asp Leu Lys Leu Thr Asp Ala Gly Leu Ala Lys Val Asn
        1445                1450                1455

Asp Gln Asn Ala Glu Lys Thr Val Lys Ile Thr Tyr Ser Ala Thr Leu
        1460                1465                1470

Asn Asp Lys Ala Ile Val Glu Val Pro Glu Ser Asn Asp Val Thr Phe
        1475                1480                1485

Asn Tyr Gly Asn Asn Pro Asp His Gly Asn Thr Pro Lys Pro Asn Lys
        1490                1495                1500

Pro Asn Glu Asn Gly Asp Leu Thr Leu Thr Lys Thr Trp Val Asp Ala
1505                1510                1515                1520

Thr Gly Ala Pro Ile Pro Ala Gly Ala Glu Ala Thr Phe Asp Leu Val
        1525                1530                1535

Asn Ala Gln Thr Gly Lys Val Val Gln Thr Val Thr Leu Thr Thr Asp
        1540                1545                1550

Lys Asn Thr Val Thr Val Asn Gly Leu Asp Lys Asn Thr Glu Tyr Lys
        1555                1560                1565

Phe Val Glu Arg Ser Ile Lys Gly Tyr Ser Ala Asp Tyr Gln Glu Ile
        1570                1575                1580

Thr Thr Ala Gly Glu Ile Ala Val Lys Asn Trp Lys Asp Glu Asn Pro
1585                1590                1595                1600

Lys Pro Leu Asp Pro Thr Glu Pro Lys Val Val Thr Tyr Gly Lys Lys
        1605                1610                1615

Phe Val Lys Val Asn Asp Lys Asp Asn Arg Leu Ala Gly Ala Glu Phe
        1620                1625                1630

Val Ile Ala Asn Ala Asp Asn Ala Gly Gln Tyr Leu Ala Arg Lys Ala
        1635                1640                1645

Asp Lys Val Ser Gln Glu Glu Lys Gln Leu Val Val Thr Thr Lys Asp
```

1650              1655              1660

Ala Leu Asp Arg Ala Val Ala Ala Tyr Asn Ala Leu Thr Ala Gln Gln
1665                1670              1675              1680

Gln Thr Gln Gln Glu Lys Glu Lys Val Asp Lys Ala Gln Ala Ala Tyr
                 1685              1690              1695

Asn Ala Ala Val Ile Ala Ala Asn Asn Ala Phe Glu Trp Val Ala Asp
            1700              1705              1710

Lys Asp Asn Glu Asn Val Val Lys Leu Val Ser Asp Ala Gln Gly Arg
        1715              1720              1725

Phe Glu Ile Thr Gly Leu Leu Ala Gly Thr Tyr Tyr Leu Glu Glu Thr
    1730              1735              1740

Lys Gln Pro Ala Gly Tyr Ala Leu Leu Thr Ser Arg Gln Lys Phe Glu
1745                1750              1755              1760

Val Thr Ala Thr Ser Tyr Ser Ala Thr Gly Gln Gly Ile Glu Tyr Thr
                1765              1770              1775

Ala Gly Ser Gly Lys Asp Asp Ala Thr Lys Val Val Asn Lys Lys Ile
            1780              1785              1790

Thr Leu Gly His His His His His His
        1795              1800

<210> SEQ ID NO 20
<211> LENGTH: 5403
<212> TYPE: DNA
<213> ORGANISM: Artificial Sequence
<220> FEATURE:
<223> OTHER INFORMATION: Sequence encoding SEQ ID NO: 19

<400> SEQUENCE: 20
atggctagcg ctgcaacagt ttttgcggcg gacaatgtta gtacagcacc agatgctgtt      60
actaaaactt taacaatcca taagttactg ctctcagaag atgatttaaa gacttgggat     120
acaaacggtc ctaaaggata tgatggaact caatctagtt taaagatttt aactggagtt     180
gtagctgagg aaattccaaa tgtatacttt gaattacaaa agtataattt gactgatggt     240
aaggaaaaag aaaatcttaa agatgatagt aaatggacaa cagttcatgg tggttttgaca     300 actaaagatg gacttaaaat tgaaaccagt actcttaaag gtgtgtatcg tattcgtgag     360
gatagaacaa agactaccta tgttggtcct aatgggcaag tattaacagg ttcaaaagcc     420
gtacctgctc ttgtaactct tccacttgtt aacaataatg gtacagtaat tgatgcacat     480
gttttcccta aaaattcata taataaacca gttgtagata aaagaattgc tgatactttg     540
aattataacg atcaaaatgg tctgtctatc ggtactaaaa tcccatatgt tgttaataca     600
acaattccaa gtaatgcaac atttgcaact tcattttggt cagatgaaat gacagaaggt     660
ctaacttata tgaagatgt aacaattact ttgaataatg tagctatgga tcaagctgat     720
tatgaagtca ctaaaggaaa taatggcttt aacttaaaat taacagaagc aggttttagct     780 aaaattaatg gtaaggatgc agaccaaaaa atccaaatta cttactcagc tactttgaac     840
tcacttgctg ttgcagacat tcctgaaagt aacgatatta catatcatta cggaaatcat     900
caagatcatg ggaatactcc aaaaccaact aaacctaata atggtcaaat tacagtaact     960
aagacatggg acagtcaacc tgctcctgag ggggtgaaag cgactgttca acttgtaaat    1020
gccaagactg tgagaaagt cggtgctcct gtagaacttt cagaaaataa ttggacatat    1080
acttggagtg gtctagataa ttctattgaa tacaaagttg aagaagaata taatggatac    1140
tcagctgaat acacagtaga gagcaaaggg aagttggggg taaaaaactg gaaagataat    1200
aacccagctc caatcaatcc tgaagaacca cgtgtaaaaa catacggtaa aaagtttgtc    1260

```
aaagtagacc aaaaagatac tcgtctagaa aatgcgcagt tcgttgttaa aaaagcagat   1320
agcaataaat atattgcctt taagtcaact gcacaacaag ctgcagatga aaaagcagca   1380
gcaactgcaa aacaaaaatt ggatgcagcg gtagcagctt acacaaatgc tgcagataag   1440
caagccgctc aagctctagt agatcaagca cagcaagaat acaatgtagc ttacaaagaa   1500
gccaaatttg gttatgttga agtagctgga aaagatgaag caatggttct tacttctaat   1560
acggatggtc aattccaaat ttcaggtctt gctgctggta cttataaatt agaagaaatt   1620
aaagctccag aaggttttgc gaaaattgat gatgtagaat tgttgttgg agcaggttct    1680 tggaatcaag gtgagtttaa ttacttaaaa gatgttcaaa agaatgacgc tacaaaagta   1740
gtcaacaaaa aaatcactgg atccggcagc ggtggcggtg gcgcggaaca aaaaactaag   1800
acacttacag ttcataaatt attgatgaca gatcaagagc ttgacgcttg gaattctgat   1860
gcgattacta ctgcaggtta tgacggttcg caaaattttg aacagttcaa acaacttcaa   1920
ggtgttccac aaggagtaac cgaaatctct ggtgttgcat tcgagttaca gagttatacg   1980
ggtcctcaag gaaagaaaca agaaaattta acgaatgatg cggtttggac tgcggttaat   2040
aaaggtgtga cgactgaaac gggtgttaaa tttgatactg aagttttaca agggacatat   2100
cgtcttgtcg aagtacgtaa agaatcgact tatgtcggtc caaatggtaa agttttaaca   2160
ggtatgaaag ctgttcctgc tttaattatt ctgccgcttg taaaccaaaa tggtgttgta   2220
gaaaatgcac atgtctatcc aaagaattct gaagacaaac ctacagcaac gaaaacattt   2280
gatactgcag caggtttcgt agatccaggt gaaaaaggtt tagcaattgg cactaaggta   2340
ccgtatattg ttacaacaac tattccgaaa aactcaactc ttgcaacagc tttctggtca   2400
gatgaaatga cagaaggtct agattataat ggtgatgtag ttgttaatta taatggtcaa   2460
ccgcttgata ttctcatta cacattagaa gcaggtcata atggctttat cttgaagtta   2520
aatgaaaaag gtctggaagc aatcaacggt aaagatgcag aagcaacaat tacgttgaag   2580
tatactgcaa ctttaaatgc tcttgctgtt gctgatgtgc cagaagcgaa tgatgtaaca   2640
ttccattatg gaaacaaccc aggtcatggt aacactccaa aaccaaacaa acctaaaaac   2700
ggtgaactta caattactaa acatgggct gatgctaaag atgctcctat agcaggtgta   2760
gaagtaactt tgatttggt aaatgctcag acaggtgagg tcgttaaagt acctggacat   2820
gaaacaggta ttgtattgaa tcaaacaaat aattggacat ttactgctac aggtcttgat   2880
aataatacag aatataaatt tgttgaacgg acaattaagg atattctgc agattaccaa    2940 acaattactg aaacaggaaa aattgctgtt aaaaactgga aagatgaaaa tccagaacca   3000
ataaatcctg aagagccacg tgtaaaaaca tatggtaaaa aattcgttaa ggttgaccaa   3060
aaagacgaac gcttaaaaga agcacaattc gttgtgaaga atgagcaagg gaaatatctt   3120
gcactcaaat ctgcagcaca acaagctgta aatgagaaag ctgccgcaga agcgaaacaa   3180
gcgctagatg cagcgatagc agcctataca aatgctgcag ataaaaatgc agcacaagct   3240
gtagtagatg ctgcgcaaaa aacatataat gacaattaca gagcagctag atttggctat   3300
gtagaagtag agagaaaaga agatgcgtta gttcttactt ctaacactga tggtcaattc   3360
caaatttcag gtcttgctgc tggaagctac acgttggaag aaacaaaagc tccagaaggc   3420
tttgcaaaac ttggagatgt gaagtttgag gttggagcag gttcttggaa tcaaggtgat   3480
ttcaattatt taaagatgt tcagaagaac gacgctacaa agtagtcaa caaaaaaatc    3540 acgctcgagg gcagcggtgg cggtggcgct gcaacagttt ttgcggctgg gacgacaaca   3600
acatctgtta ccgttcataa actattggca acagatgggg atatggataa aattgcaaat   3660
```

```
gagttagaaa caggtaacta tgctggtaat aaagtgggtg ttctacctgc aaatgcaaaa    3720
gaaattgccg gtgttatgtt cgtttggaca atactaata atgaaattat tgatgaaaat    3780
ggccaaactc taggagtgaa tattgatcca caaacattta aactctcagg ggcaatgccg    3840
gcaactgcaa tgaaaaaatt aacagaagct gaaggagcta atttaacac ggcaaattta    3900 ccagctgcta agtataaaat ttatgaaatt cacagtttat caacttatgt cggtgaagat    3960
ggagcaacct taacaggttc taaagcagtt ccaattgaaa ttgaattacc attgaacgat    4020
gttgtggatg cgcatgtgta tccaaaaaat acagaagcaa agccaaaaat tgataaagat    4080
ttcaaaggta aagcaaatcc agatacacca cgtgtagata aagatacacc tgtgaaccac    4140
caagttggag atgttgtaga gtacgaaatt gttacaaaaa ttccagcact tgctaattat    4200
gcaacagcaa actggagcga tagaatgact gaaggtttgg cattcaacaa aggtacagtg    4260
aaagtaactg ttgatgatgt tgcacttgaa gcaggtgatt atgctctaac agaagtagca    4320
actggttttg atttgaaatt aacagatgct ggtttagcta aagtgaatga ccaaaacgct    4380
gaaaaaactg tgaaaatcac ttattcggca acattgaatg acaaagcaat tgtagaagta    4440
ccagaatcta atgatgtaac atttaactat ggtaataatc cagatcacgg gaatactcca    4500
aagccgaata agccaaatga aaacggcgat ttgacattga ccaagacatg ggttgatgct    4560
acaggtgcac caattccggc tggagctgaa gcaacgttcg atttggttaa tgctcagact    4620
ggtaaagttg tacaaactgt aactttgaca acagacaaaa atacagttac tgttaacgga    4680
ttggataaaa atacagaata taaattcgtt gaacgtagta taaagggta ttcagcagat    4740 tatcaagaaa tcactacagc tggagaaatt gctgtcaaga actggaaaga cgaaaatcca    4800
aaaccacttg atccaacaga gccaaaagtt gttacatatg gtaaaaagtt tgtcaaagtt    4860
aatgataaag ataatcgttt agctggggca gaatttgtaa ttgcaaatgc tgataatgct    4920
ggtcaatatt tagcacgtaa agcagataaa gtgagtcaag aagagaagca gttggttgtt    4980
acaacaaagg atgctttaga tagagcagtt gctgcttata acgctcttac tgcacaacaa    5040
caaactcagc aagaaaaaga gaaagttgac aaagctcaag ctgcttataa tgctgctgtg    5100
attgctgcca acaatgcatt tgaatgggtg gcagataagg acaatgaaaa tgttgtgaaa    5160
ttagtttctg atgcacaagg tcgctttgaa attacaggcc ttcttgcagg tacatattac    5220
ttagaagaaa caaaacagcc tgctggttat gcattactaa ctagccgtca gaaatttgaa    5280
gtcactgcaa cttcttattc agcgactgga caaggcattg agtatactgc tggttcaggt    5340
aaagatgacg ctacaaaagt agtcaacaaa aaaatcactc tcgagcacca ccaccaccac    5400
cac                                                                 5403
```

<210> SEQ ID NO 21
<211> LENGTH: 1801
<212> TYPE: PRT
<213> ORGANISM: Artificial Sequence
<220> FEATURE:
<223> OTHER INFORMATION: RrgB II-I-III

<400> SEQUENCE: 21

Met Ala Ser Ala Ala Thr Val Phe Ala Ala Asp Asn Val Ser Thr Ala
1               5                   10                  15

Pro Asp Ala Val Thr Lys Thr Leu Thr Ile His Lys Leu Leu Leu Ser
            20                  25                  30

Glu Asp Asp Leu Lys Thr Trp Asp Thr Asn Gly Pro Lys Gly Tyr Asp
        35                  40                  45

```
Gly Thr Gln Ser Ser Leu Lys Asp Leu Thr Gly Val Val Ala Glu
         50                  55                  60

Ile Pro Asn Val Tyr Phe Glu Leu Gln Lys Tyr Asn Leu Thr Asp Gly
65                  70                  75                  80

Lys Glu Lys Glu Asn Leu Lys Asp Asp Ser Lys Trp Thr Thr Val His
                    85                  90                  95

Gly Gly Leu Thr Thr Lys Asp Gly Leu Lys Ile Glu Thr Ser Thr Leu
                100                 105                 110

Lys Gly Val Tyr Arg Ile Arg Glu Asp Arg Thr Lys Thr Thr Tyr Val
            115                 120                 125

Gly Pro Asn Gly Gln Val Leu Thr Gly Ser Lys Ala Val Pro Ala Leu
        130                 135                 140

Val Thr Leu Pro Leu Val Asn Asn Gly Thr Val Ile Asp Ala His
145                 150                 155                 160

Val Phe Pro Lys Asn Ser Tyr Asn Lys Pro Val Val Asp Lys Arg Ile
                165                 170                 175

Ala Asp Thr Leu Asn Tyr Asn Asp Gln Asn Gly Leu Ser Ile Gly Thr
            180                 185                 190

Lys Ile Pro Tyr Val Val Asn Thr Thr Ile Pro Ser Asn Ala Thr Phe
        195                 200                 205

Ala Thr Ser Phe Trp Ser Asp Glu Met Thr Glu Gly Leu Thr Tyr Asn
    210                 215                 220

Glu Asp Val Thr Ile Thr Leu Asn Asn Val Ala Met Asp Gln Ala Asp
225                 230                 235                 240

Tyr Glu Val Thr Lys Gly Asn Asn Gly Phe Asn Leu Lys Leu Thr Glu
                245                 250                 255

Ala Gly Leu Ala Lys Ile Asn Gly Lys Asp Ala Asp Gln Lys Ile Gln
            260                 265                 270

Ile Thr Tyr Ser Ala Thr Leu Asn Ser Leu Ala Val Ala Asp Ile Pro
        275                 280                 285

Glu Ser Asn Asp Ile Thr Tyr His Tyr Gly Asn His Gln Asp His Gly
    290                 295                 300

Asn Thr Pro Lys Pro Thr Lys Pro Asn Asn Gly Gln Ile Thr Val Thr
305                 310                 315                 320

Lys Thr Trp Asp Ser Gln Pro Ala Pro Glu Gly Val Lys Ala Thr Val
                325                 330                 335

Gln Leu Val Asn Ala Lys Thr Gly Glu Lys Val Gly Ala Pro Val Glu
            340                 345                 350

Leu Ser Glu Asn Asn Trp Thr Tyr Thr Trp Ser Gly Leu Asp Asn Ser
        355                 360                 365

Ile Glu Tyr Lys Val Glu Glu Tyr Asn Gly Tyr Ser Ala Glu Tyr
    370                 375                 380

Thr Val Glu Ser Lys Gly Lys Leu Gly Val Lys Asn Trp Lys Asp Asn
385                 390                 395                 400

Asn Pro Ala Pro Ile Asn Pro Glu Glu Pro Arg Val Lys Thr Tyr Gly
                405                 410                 415

Lys Lys Phe Val Lys Val Asp Gln Lys Asp Thr Arg Leu Glu Asn Ala
            420                 425                 430

Gln Phe Val Val Lys Lys Ala Asp Ser Asn Lys Tyr Ile Ala Phe Lys
        435                 440                 445

Ser Thr Ala Gln Gln Ala Ala Asp Glu Lys Ala Ala Thr Ala Lys
    450                 455                 460

Gln Lys Leu Asp Ala Ala Val Ala Ala Tyr Thr Asn Ala Ala Asp Lys
465                 470                 475                 480
```

```
Gln Ala Ala Gln Ala Leu Val Asp Gln Ala Gln Gln Glu Tyr Asn Val
                485                 490                 495

Ala Tyr Lys Glu Ala Lys Phe Gly Tyr Val Glu Val Ala Gly Lys Asp
            500                 505                 510

Glu Ala Met Val Leu Thr Ser Asn Thr Asp Gly Gln Phe Gln Ile Ser
            515                 520                 525

Gly Leu Ala Ala Gly Thr Tyr Lys Leu Glu Glu Ile Lys Ala Pro Glu
            530                 535                 540

Gly Phe Ala Lys Ile Asp Asp Val Glu Phe Val Val Gly Ala Gly Ser
545                 550                 555                 560

Trp Asn Gln Gly Glu Phe Asn Tyr Leu Lys Asp Val Gln Lys Asn Asp
                565                 570                 575

Ala Thr Lys Val Val Asn Lys Lys Ile Thr Gly Ser Gly Ser Gly Gly
            580                 585                 590

Gly Gly Ala Ala Thr Val Phe Ala Ala Gly Thr Thr Thr Ser Val
            595                 600                 605

Thr Val His Lys Leu Leu Ala Thr Asp Gly Asp Met Asp Lys Ile Ala
            610                 615                 620

Asn Glu Leu Glu Thr Gly Asn Tyr Ala Gly Asn Lys Val Gly Val Leu
625                 630                 635                 640

Pro Ala Asn Ala Lys Glu Ile Ala Gly Val Met Phe Val Trp Thr Asn
                645                 650                 655

Thr Asn Asn Glu Ile Ile Asp Glu Asn Gly Gln Thr Leu Gly Val Asn
            660                 665                 670

Ile Asp Pro Gln Thr Phe Lys Leu Ser Gly Ala Met Pro Ala Thr Ala
            675                 680                 685

Met Lys Lys Leu Thr Glu Ala Glu Gly Ala Lys Phe Asn Thr Ala Asn
            690                 695                 700

Leu Pro Ala Ala Lys Tyr Lys Ile Tyr Glu Ile His Ser Leu Ser Thr
705                 710                 715                 720

Tyr Val Gly Glu Asp Gly Ala Thr Leu Thr Gly Ser Lys Ala Val Pro
                725                 730                 735

Ile Glu Ile Glu Leu Pro Leu Asn Asp Val Val Asp Ala His Val Tyr
            740                 745                 750

Pro Lys Asn Thr Glu Ala Lys Pro Lys Ile Asp Lys Asp Phe Lys Gly
            755                 760                 765

Lys Ala Asn Pro Asp Thr Pro Arg Val Asp Lys Asp Thr Pro Val Asn
770                 775                 780

His Gln Val Gly Asp Val Val Glu Tyr Glu Ile Val Thr Lys Ile Pro
785                 790                 795                 800

Ala Leu Ala Asn Tyr Ala Thr Ala Asn Trp Ser Asp Arg Met Thr Glu
                805                 810                 815

Gly Leu Ala Phe Asn Lys Gly Thr Val Lys Val Thr Asp Asp Val
            820                 825                 830

Ala Leu Glu Ala Gly Asp Tyr Ala Leu Thr Glu Val Ala Thr Gly Phe
            835                 840                 845

Asp Leu Lys Leu Thr Asp Ala Gly Leu Ala Lys Val Asn Asp Gln Asn
            850                 855                 860

Ala Glu Lys Thr Val Lys Ile Thr Tyr Ser Ala Thr Leu Asn Asp Lys
865                 870                 875                 880

Ala Ile Val Glu Val Pro Glu Ser Asn Asp Val Thr Phe Asn Tyr Gly
                885                 890                 895

Asn Asn Pro Asp His Gly Asn Thr Pro Lys Pro Asn Lys Pro Asn Glu
```

```
                900             905             910
Asn Gly Asp Leu Thr Leu Thr Lys Thr Trp Val Asp Ala Thr Gly Ala
            915                 920                 925

Pro Ile Pro Ala Gly Ala Glu Ala Thr Phe Asp Leu Val Asn Ala Gln
            930                 935                 940

Thr Gly Lys Val Val Gln Thr Val Thr Leu Thr Thr Asp Lys Asn Thr
945                 950                 955                 960

Val Thr Val Asn Gly Leu Asp Lys Asn Thr Glu Tyr Lys Phe Val Glu
            965                 970                 975

Arg Ser Ile Lys Gly Tyr Ser Ala Asp Tyr Gln Glu Ile Thr Thr Ala
            980                 985                 990

Gly Glu Ile Ala Val Lys Asn Trp Lys Asp Glu Asn Pro Lys Pro Leu
            995                 1000                1005

Asp Pro Thr Glu Pro Lys Val Val Thr Tyr Gly Lys Lys Phe Val Lys
            1010                1015                1020

Val Asn Asp Lys Asp Asn Arg Leu Ala Gly Ala Glu Phe Val Ile Ala
1025                1030                1035                1040

Asn Ala Asp Asn Ala Gly Gln Tyr Leu Ala Arg Lys Ala Asp Lys Val
            1045                1050                1055

Ser Gln Glu Glu Lys Gln Leu Val Val Thr Thr Lys Asp Ala Leu Asp
            1060                1065                1070

Arg Ala Val Ala Ala Tyr Asn Ala Leu Thr Ala Gln Gln Thr Gln
            1075                1080                1085

Gln Glu Lys Glu Lys Val Asp Lys Ala Gln Ala Tyr Asn Ala Ala
            1090                1095                1100

Val Ile Ala Ala Asn Asn Ala Phe Glu Trp Val Ala Asp Lys Asp Asn
1105                1110                1115                1120

Glu Asn Val Val Lys Leu Val Ser Asp Ala Gln Gly Arg Phe Glu Ile
            1125                1130                1135

Thr Gly Leu Leu Ala Gly Thr Tyr Tyr Leu Glu Glu Lys Gln Pro
            1140                1145                1150

Ala Gly Tyr Ala Leu Leu Thr Ser Arg Gln Lys Phe Glu Val Thr Ala
            1155                1160                1165

Thr Ser Tyr Ser Ala Thr Gly Gln Gly Ile Glu Tyr Thr Ala Gly Ser
    1170                1175                1180

Gly Lys Asp Asp Ala Thr Lys Val Val Asn Lys Lys Ile Thr Leu Gly
1185                1190                1195                1200

Gly Ser Gly Gly Gly Gly Ala Glu Gln Lys Thr Lys Thr Leu Thr Val
            1205                1210                1215

His Lys Leu Leu Met Thr Asp Gln Glu Leu Asp Ala Trp Asn Ser Asp
            1220                1225                1230

Ala Ile Thr Thr Ala Gly Tyr Asp Gly Ser Gln Asn Phe Glu Gln Phe
            1235                1240                1245

Lys Gln Leu Gln Gly Val Pro Gln Gly Val Thr Glu Ile Ser Gly Val
            1250                1255                1260

Ala Phe Glu Leu Gln Ser Tyr Thr Gly Pro Gln Gly Lys Glu Gln Glu
1265                1270                1275                1280

Asn Leu Thr Asn Asp Ala Val Trp Thr Ala Val Asn Lys Gly Val Thr
            1285                1290                1295

Thr Glu Thr Gly Val Lys Phe Asp Thr Glu Val Leu Gln Gly Thr Tyr
            1300                1305                1310

Arg Leu Val Glu Val Arg Lys Glu Ser Thr Tyr Val Gly Pro Asn Gly
            1315                1320                1325
```

-continued

```
Lys Val Leu Thr Gly Met Lys Ala Val Pro Ala Leu Ile Ile Leu Pro
1330                1335                1340

Leu Val Asn Gln Asn Gly Val Val Glu Asn Ala His Val Tyr Pro Lys
1345                1350                1355                1360

Asn Ser Glu Asp Lys Pro Thr Ala Thr Lys Thr Phe Asp Thr Ala Ala
                1365                1370                1375

Gly Phe Val Asp Pro Gly Glu Lys Gly Leu Ala Ile Gly Thr Lys Val
                1380                1385                1390

Pro Tyr Ile Val Thr Thr Thr Ile Pro Lys Asn Ser Thr Leu Ala Thr
                1395                1400                1405

Ala Phe Trp Ser Asp Glu Met Thr Glu Gly Leu Asp Tyr Asn Gly Asp
    1410                1415                1420

Val Val Val Asn Tyr Asn Gly Gln Pro Leu Asp Asn Ser His Tyr Thr
1425                1430                1435                1440

Leu Glu Ala Gly His Asn Gly Phe Ile Leu Lys Leu Asn Glu Lys Gly
                1445                1450                1455

Leu Glu Ala Ile Asn Gly Lys Asp Ala Glu Ala Thr Ile Thr Leu Lys
                1460                1465                1470

Tyr Thr Ala Thr Leu Asn Ala Leu Ala Val Ala Asp Val Pro Glu Ala
                1475                1480                1485

Asn Asp Val Thr Phe His Tyr Gly Asn Asn Pro Gly His Gly Asn Thr
    1490                1495                1500

Pro Lys Pro Asn Lys Pro Lys Asn Gly Glu Leu Thr Ile Thr Lys Thr
1505                1510                1515                1520

Trp Ala Asp Ala Lys Asp Ala Pro Ile Ala Gly Val Glu Val Thr Phe
                1525                1530                1535

Asp Leu Val Asn Ala Gln Thr Gly Glu Val Val Lys Val Pro Gly His
                1540                1545                1550

Glu Thr Gly Ile Val Leu Asn Gln Thr Asn Asn Trp Thr Phe Thr Ala
    1555                1560                1565

Thr Gly Leu Asp Asn Asn Thr Glu Tyr Lys Phe Val Glu Arg Thr Ile
    1570                1575                1580

Lys Gly Tyr Ser Ala Asp Tyr Gln Thr Ile Thr Glu Thr Gly Lys Ile
1585                1590                1595                1600

Ala Val Lys Asn Trp Lys Asp Glu Asn Pro Glu Pro Ile Asn Pro Glu
                1605                1610                1615

Glu Pro Arg Val Lys Thr Tyr Gly Lys Lys Phe Val Lys Val Asp Gln
                1620                1625                1630

Lys Asp Glu Arg Leu Lys Glu Ala Gln Phe Val Val Lys Asn Glu Gln
                1635                1640                1645

Gly Lys Tyr Leu Ala Leu Lys Ser Ala Ala Gln Gln Ala Val Asn Glu
    1650                1655                1660

Lys Ala Ala Ala Glu Ala Lys Gln Ala Leu Asp Ala Ala Ile Ala Ala
1665                1670                1675                1680

Tyr Thr Asn Ala Ala Asp Lys Asn Ala Ala Gln Ala Val Val Asp Ala
                1685                1690                1695

Ala Gln Lys Thr Tyr Asn Asp Asn Tyr Arg Ala Ala Arg Phe Gly Tyr
                1700                1705                1710

Val Glu Val Glu Arg Lys Glu Asp Ala Leu Val Leu Thr Ser Asn Thr
                1715                1720                1725

Asp Gly Gln Phe Gln Ile Ser Gly Leu Ala Ala Gly Ser Tyr Thr Leu
    1730                1735                1740

Glu Glu Thr Lys Ala Pro Glu Gly Phe Ala Lys Leu Gly Asp Val Lys
1745                1750                1755                1760
```

Phe Glu Val Gly Ala Gly Ser Trp Asn Gln Gly Asp Phe Asn Tyr Leu
              1765                1770                1775

Lys Asp Val Gln Lys Asn Asp Ala Thr Lys Val Val Asn Lys Lys Ile
          1780                1785                1790

Thr Leu Gly His His His His His His
         1795                1800

<210> SEQ ID NO 22
<211> LENGTH: 5403
<212> TYPE: DNA
<213> ORGANISM: Artificial Sequence
<220> FEATURE:
<223> OTHER INFORMATION: Sequence encoding SEQ ID NO: 21

<400> SEQUENCE: 22

```
atggctagcg ctgcaacagt ttttgcggcg gacaatgtta gtacagcacc agatgctgtt      60
actaaaactt taacaatcca taagttactg ctctcagaag atgatttaaa gacttgggat     120
acaaacggtc ctaaaggata tgatggaact caatctagtt taaaagattt aactggagtt     180
gtagctgagg aaattccaaa tgtatacttt gaattacaaa agtataattt gactgatggt     240
aaggaaaaag aaaatcttaa agatgatagt aaatggacaa cagttcatgg tggtttgaca     300
actaaagatg gacttaaaat tgaaaccagt actcttaaag gtgtgtatcg tattcgtgag     360
gatagaacaa agactaccta tgttggtcct aatgggcaag tattaacagg ttcaaaagcc     420
gtacctgctc ttgtaactct tccacttgtt aacaataatg gtacagtaat tgatgcacat     480
gttttcccta aaaattcata taataaacca gttgtagata aagaattgc tgatactttg      540
aattataacg atcaaaatgg tctgtctatc ggtactaaaa tcccatatgt tgttaataca     600
acaattccaa gtaatgcaac atttgcaact tcattttggt cagatgaaat gacagaaggt     660
ctaacttata tgaagatgt aacaattact ttgaataatg tagctatgga tcaagctgat     720
tatgaagtca ctaaaggaaa taatggcttt aacttaaaat taacagaagc aggtttagct     780
aaaattaatg gtaaggatgc agaccaaaaa atccaaatta cttactcagc tactttgaac     840
tcacttgctg ttgcagacat tcctgaaagt aacgatatta catatcatta cggaaatcat     900
caagatcatg ggaatactcc aaaaccaact aaacctaata tggtcaaat tacagtaact     960
aagacatggg acagtcaacc tgctcctgag ggggtgaaag cgactgttca acttgtaaat    1020
gccaagactg gtgagaaagt cggtgctcct gtagaacttt cagaaaataa ttggacatat    1080
acttggagtg gtctagataa ttctattgaa tacaaagttg aagaagaata taatggatac    1140
tcagctgaat acacagtaga gagcaaaggg aagttggggg taaaaaactg aaagataat     1200
aacccagctc caatcaatcc tgaagaacca cgtgtaaaaa catacggtaa aaagtttgtc    1260
aaagtagacc aaaaagatac tcgtctagaa aatgcgcagt tcgttgttaa aaaagcagat    1320
agcaataaat atattgcctt taagtcaact gcacaacaag ctgcagatga aaagcagca     1380
gcaactgcaa acaaaaaatt ggatgcagcg gtagcagctt acacaaatgc tgcagataag    1440
caagccgctc aagctctagt agatcaagca cagcaagaat acaatgtagc ttacaaagaa    1500
gccaaatttg ttatgttga agtagctgga aaagatgaag caatggttct tacttctaat    1560
acggatggtc aattccaaat ttcaggtctt gctgctggta cttataaatt agaagaaatt    1620
aaagctccag aaggttttgc gaaaattgat gatgtagaat ttgttgttgg agcaggttct    1680
tggaatcaag gtgagtttaa ttacttaaaa gatgttcaaa agaatgacgc tacaaaagta    1740
gtcaacaaaa aaatcactgg atccggcagc ggtggcggtg gcgctgcaac agtttttgcg    1800
```

```
gctgggacga caacaacatc tgttaccgtt cataaactat tggcaacaga tggggatatg   1860
gataaaattg caaatgagtt agaaacaggt aactatgctg gtaataaagt gggtgttcta   1920
cctgcaaatg caaagaaat tgccggtgtt atgttcgttt ggacaaatac taataatgaa    1980
attattgatg aaaatggcca aactctagga gtgaatattg atccacaaac atttaaactc   2040 tcagggcaa tgccggcaac tgcaatgaaa aaattaacag aagctgaagg agctaaattt    2100
aacacggcaa atttaccagc tgctaagtat aaaatttatg aaattcacag tttatcaact   2160
tatgtcggtg aagatggagc aaccttaaca ggttctaaag cagttccaat tgaaattgaa   2220
ttaccattga acgatgttgt ggatgcgcat gtgtatccaa aaaatacaga agcaaagcca   2280
aaaattgata agatttcaa aggtaaagca atccagata caccacgtgt agataaagat     2340
acacctgtga accaccaagt tggagatgtt gtagagtacg aaattgttac aaaaattcca   2400
gcacttgcta attatgcaac agcaaactgg agcgatagaa tgactgaagg tttggcattc   2460
aacaaaggta cagtgaaagt aactgttgat gatgttgcac ttgaagcagg tgattatgct   2520
ctaacagaag tagcaactgg ttttgatttg aaattaacag atgctggttt agctaaagtg   2580
aatgaccaaa acgctgaaaa aactgtgaaa atcacttatt cggcaacatt gaatgacaaa   2640
gcaattgtag aagtaccaga atctaatgat gtaacattta actatggtaa taatccagat   2700
cacgggaata ctccaaagcc gaataagcca atgaaaaacg gcgatttgac attgaccaag   2760 acatggttg atgctacagg tgcaccaatt ccggctggag ctgaagcaac gttcgatttg    2820
gttaatgctc agactggtaa agttgtacaa actgtaactt tgacaacaga caaaaataca   2880
gttactgtta acggattgga taaaaataca gaatataaat tcgttgaacg tagtataaaa   2940
gggtattcag cagattatca agaaatcact acagctggag aaattgctgt caagaactgg   3000
aaagacgaaa atccaaaacc acttgatcca acagagccaa agtgttac atatggtaaa     3060 aagtttgtca agttaatga taaagataat cgtttagctg gggcagaatt tgtaattgca    3120
aatgctgata atgctggtca atatttagca cgtaaagcag ataaagtgag tcaagaagag   3180
aagcagttgg ttgttacaac aaaggatgct ttagatagag cagttgctgc ttataacgct   3240
cttactgcac aacaacaaac tcagcaagaa aaagagaaag ttgacaaagc tcaagctgct   3300
tataatgctg ctgtgattgc tgccaacaat gcatttgaat gggtggcaga taaggacaat   3360
gaaaatgttg tgaaattagt ttctgatgca caaggtcgct ttgaaattac aggccttctt   3420
gcaggtacat attacttaga agaaacaaaa cagcctgctg gttatgcatt actaactagc   3480
cgtcagaaat ttgaagtcac tgcaacttct tattcagcga ctggacaagg cattgagtat   3540
actgctggtt caggtaaaga tgacgctaca aaagtagtca acaaaaaaat cactctcgag   3600
ggcagcggtg gcggtggcgc ggaacaaaaa actaagacac ttacagttca taaattattg   3660
atgacagatc aagagcttga cgcttggaat tctgatgcga ttactactgc aggttatgac   3720
ggttcgcaaa attttgaaca gttcaaacaa cttcaaggtg ttccacaagg agtaaccgaa   3780
atctctggtg ttgcattcga gttacagagt tatacgggtc ctcaaggaaa agaacaagaa   3840
aatttaacga atgatgcggt ttggactgcg gttaataaag gtgtgacgac tgaaacgggt   3900
gttaaatttg atactgaagt tttacaaggg acatatcgtc ttgtcgaagt acgtaaagaa   3960
tcgacttatg tcggtccaaa tggtaaagtt ttaacaggta tgaaagctgt tcctgcttta   4020
attattctgc cgcttgtaaa ccaaaatggt gttgtagaaa atgcacatgt ctatccaaag   4080
aattctgaag acaaacctac agcaacgaaa acatttgata ctgcagcagg tttcgtagat   4140
ccaggtgaaa aaggtttagc aattggcact aaggtaccgt atattgttac aacaactatt   4200
```

```
ccgaaaaact caactcttgc aacagctttc tggtcagatg aaatgacaga aggtctagat    4260
tataatggtg atgtagttgt taattataat ggtcaaccgc ttgataattc tcattacaca    4320
ttagaagcag gtcataatgg ctttatcttg aagttaaatg aaaaaggtct ggaagcaatc    4380
aacggtaaag atgcagaagc aacaattacg ttgaagtata ctgcaacttt aaatgctctt    4440
gctgttgctg atgtgccaga agcgaatgat gtaacattcc attatggaaa caacccaggt    4500
catggtaaca ctccaaaacc aaacaaacct aaaaacggtg aacttacaat tactaaaaca    4560
tgggctgatg ctaaagatgc tcctatagca ggtgtagaag taacttttga tttggtaaat    4620
gctcagacag gtgaggtcgt taaagtacct ggacatgaaa caggtattgt attgaatcaa    4680
acaaataatt ggacatttac tgctacaggt cttgataata atacagaata taaatttgtt    4740
gaacggacaa ttaagggata ttctgcagat taccaaacaa ttactgaaac aggaaaaatt    4800
gctgttaaaa actggaaaga tgaaaatcca gaaccaataa atcctgaaga gccacgtgta    4860
aaaacatatg gtaaaaaatt cgttaaggtt gaccaaaaag acgaacgctt aaaagaagca    4920
caattcgttg tgaagaatga gcaagggaaa tatcttgcac tcaaatctgc agcacaacaa    4980
gctgtaaatg agaagctgc cgcagaagcg aaacaagcgc tagatgcagc gatagcagcc    5040
tatacaaatg ctgcagataa aaatgcagca caagctgtag tagatgctgc gcaaaaaaca    5100
tataatgaca attacagagc agctagattt ggctatgtag aagtagagag aaaagaagat    5160
gcgttagttc ttacttctaa cactgatggt caattccaaa tttcaggtct tgctgctgga    5220
agctacacgt tggaagaaac aaaagctcca gaaggctttg caaaacttgg agatgtgaag    5280
tttgaggttg gagcaggttc ttggaatcaa ggtgatttca attatttaaa agatgttcag    5340
aagaacgacg ctacaaaagt agtcaacaaa aaaatcacgc tcgagcacca ccaccaccac    5400
cac                                                                 5403

<210> SEQ ID NO 23
<211> LENGTH: 1312
<212> TYPE: PRT
<213> ORGANISM: Streptococcus pneumoniae
<220> FEATURE:
<223> OTHER INFORMATION: full length spr0057 as found in the R6 strain

<400> SEQUENCE: 23

Met Lys His Glu Lys Gln Gln Arg Phe Ser Ile Arg Lys Tyr Ala Val
1               5                   10                  15

Gly Ala Ala Ser Val Leu Ile Gly Phe Ala Phe Gln Ala Gln Thr Val
            20                  25                  30

Ala Ala Asp Gly Val Thr Pro Thr Thr Thr Glu Asn Gln Pro Thr Ile
        35                  40                  45

His Thr Val Ser Asp Ser Pro Gln Ser Ser Glu Asn Arg Thr Glu Glu
    50                  55                  60

Thr Pro Lys Ala Glu Leu Gln Pro Glu Ala Pro Lys Thr Val Glu Thr
65                  70                  75                  80

Glu Thr Pro Ala Thr Asp Lys Val Ala Ser Leu Pro Lys Thr Glu Glu
                85                  90                  95

Lys Pro Gln Glu Glu Val Ser Ser Thr Pro Ser Asp Lys Ala Glu Val
            100                 105                 110

Val Thr Pro Thr Ser Ala Glu Lys Glu Thr Ala Asn Lys Lys Glu Glu
        115                 120                 125

Glu Ala Ser Pro Lys Lys Glu Glu Ala Lys Glu Val Asp Ser Lys Glu
    130                 135                 140

Ser Asn Thr Asp Lys Thr Asp Lys Asp Lys Pro Ala Lys Lys Asp Glu
```

```
           145                 150                 155                 160
Ala Lys Ala Glu Ala Asp Lys Pro Glu Thr Glu Thr Gly Lys Glu Arg
                    165                 170                 175
Ala Ala Thr Val Asn Glu Lys Leu Ala Lys Lys Ile Val Ser Ile
                180                 185                 190
Asp Ala Gly Arg Lys Tyr Phe Ser Pro Glu Gln Leu Lys Glu Ile Ile
            195                 200                 205
Asp Lys Ala Lys His Tyr Gly Tyr Thr Asp Leu His Leu Leu Val Gly
    210                 215                 220
Asn Asp Gly Leu Arg Phe Met Leu Asp Asp Met Ser Ile Thr Ala Asn
225                 230                 235                 240
Gly Lys Thr Tyr Ala Ser Asp Asp Val Lys Arg Ala Ile Glu Lys Gly
                245                 250                 255
Thr Asn Asp Tyr Tyr Asn Asp Pro Asn Gly Asn His Leu Thr Glu Ser
            260                 265                 270
Gln Met Thr Asp Leu Ile Asn Tyr Ala Lys Asp Lys Gly Ile Gly Leu
        275                 280                 285
Ile Pro Thr Val Asn Ser Pro Gly His Met Asp Ala Ile Leu Asn Ala
    290                 295                 300
Met Lys Glu Leu Gly Ile Gln Asn Pro Asn Phe Ser Tyr Phe Gly Lys
305                 310                 315                 320
Lys Ser Ala Arg Thr Val Asp Leu Asp Asn Glu Gln Ala Val Ala Phe
                325                 330                 335
Thr Lys Ala Leu Ile Asp Lys Tyr Ala Ala Tyr Phe Ala Lys Lys Thr
            340                 345                 350
Glu Ile Phe Asn Ile Gly Leu Asp Glu Tyr Ala Asn Asp Ala Thr Asp
        355                 360                 365
Ala Lys Gly Trp Ser Val Leu Gln Ala Asp Lys Tyr Tyr Pro Asn Glu
    370                 375                 380
Gly Tyr Pro Val Lys Gly Tyr Glu Lys Phe Ile Ala Tyr Ala Asn Asp
385                 390                 395                 400
Leu Ala Arg Ile Val Lys Ser His Gly Leu Lys Pro Met Ala Phe Asn
                405                 410                 415
Asp Gly Ile Tyr Tyr Asn Ser Asp Thr Ser Phe Gly Ser Phe Asp Lys
            420                 425                 430
Asp Ile Ile Val Ser Met Trp Thr Gly Gly Trp Gly Gly Tyr Asp Val
        435                 440                 445
Ala Ser Ser Lys Leu Leu Ala Glu Lys Gly His Gln Ile Leu Asn Thr
    450                 455                 460
Asn Asp Ala Trp Cys Tyr Val Leu Gly Arg Asn Ala Asp Gly Gln Gly
465                 470                 475                 480
Trp Tyr Asn Leu Asp Gln Gly Leu Asn Gly Ile Lys Asn Thr Pro Ile
                485                 490                 495
Thr Ser Val Pro Lys Thr Glu Gly Ala Asp Ile Pro Ile Ile Gly Gly
            500                 505                 510
Met Val Ala Ala Trp Ala Asp Thr Pro Ser Ala Arg Tyr Ser Pro Ser
        515                 520                 525
His Leu Phe Lys Leu Met Arg His Phe Ala Asn Ala Asn Ala Glu Tyr
    530                 535                 540
Phe Ala Ala Asp Tyr Glu Ser Ala Glu Gln Ala Leu Asn Glu Val Pro
545                 550                 555                 560
Lys Asp Leu Asn Arg Tyr Thr Ala Glu Ser Val Ala Ala Val Lys Glu
                565                 570                 575
```

```
Ala Glu Lys Ala Ile Arg Ser Leu Asp Ser Asn Leu Ser Arg Ala Gln
            580                 585                 590

Gln Asp Thr Ile Asp Gln Ala Ile Ala Lys Leu Gln Glu Thr Val Asn
        595                 600                 605

Asn Leu Thr Leu Thr Pro Glu Ala Gln Lys Glu Glu Ala Lys Arg
    610                 615                 620

Glu Val Glu Lys Leu Ala Lys Asn Lys Val Ile Ser Ile Asp Ala Gly
625                 630                 635                 640

Arg Lys Tyr Phe Thr Leu Asp Gln Leu Lys Arg Ile Val Asp Lys Ala
                645                 650                 655

Ser Glu Leu Gly Tyr Ser Asp Val His Leu Leu Leu Gly Asn Asp Gly
            660                 665                 670

Leu Arg Phe Leu Leu Asn Asp Met Thr Ile Thr Ala Asn Gly Lys Thr
                675                 680                 685

Tyr Ala Ser Asp Asp Val Lys Lys Ala Ile Ile Glu Gly Thr Lys Ala
        690                 695                 700

Tyr Tyr Asp Asp Pro Asn Gly Thr Ala Leu Thr Gln Ala Glu Val Thr
705                 710                 715                 720

Glu Leu Ile Glu Tyr Ala Lys Ser Lys Asp Ile Gly Leu Ile Pro Ala
                725                 730                 735

Ile Asn Ser Pro Gly His Met Asp Ala Met Leu Val Ala Met Glu Lys
            740                 745                 750

Leu Gly Ile Lys Asn Pro Gln Ala His Phe Asp Lys Val Ser Lys Thr
                755                 760                 765

Thr Met Asp Leu Lys Asn Glu Glu Ala Met Asn Phe Val Lys Ala Leu
770                 775                 780

Ile Gly Lys Tyr Met Asp Phe Phe Ala Gly Lys Thr Lys Ile Phe Asn
785                 790                 795                 800

Phe Gly Thr Asp Glu Tyr Ala Asn Asp Ala Thr Ser Ala Gln Gly Trp
                805                 810                 815

Tyr Tyr Leu Lys Trp Tyr Gln Leu Tyr Gly Lys Phe Ala Glu Tyr Ala
                820                 825                 830

Asn Thr Leu Ala Ala Met Ala Lys Glu Arg Gly Leu Gln Pro Met Ala
        835                 840                 845

Phe Asn Asp Gly Phe Tyr Tyr Glu Asp Lys Asp Val Gln Phe Asp
    850                 855                 860

Lys Asp Val Leu Ile Ser Tyr Trp Ser Lys Gly Trp Trp Gly Tyr Asn
865                 870                 875                 880

Leu Ala Ser Pro Gln Tyr Leu Ala Ser Lys Gly Tyr Lys Phe Leu Asn
                885                 890                 895

Thr Asn Gly Asp Trp Tyr Tyr Val Ile Gly Asn His Lys Gln Asp Glu
            900                 905                 910

Ala Tyr Pro Leu Ser Lys Ala Val Glu Asn Ser Gly Lys Val Pro Phe
        915                 920                 925

Asn Gln Leu Ala Ser Thr Lys Tyr Pro Glu Val Asp Leu Pro Thr Val
    930                 935                 940

Gly Ser Met Leu Ser Ile Trp Ala Asp Arg Pro Ser Ala Glu Tyr Lys
945                 950                 955                 960

Glu Glu Glu Ile Phe Glu Leu Met Thr Ala Phe Ala Asp His Asn Lys
                965                 970                 975

Asp Tyr Phe Arg Ala Asn Tyr Asn Ala Leu Arg Glu Glu Leu Ala Lys
                980                 985                 990

Ile Pro Thr Asn Leu Glu Gly Tyr Ser Lys Glu Ser Leu Glu Ala Leu
            995                 1000                1005
```

```
Asp Ala Ala Lys Thr Ala Leu Asn Tyr Asn Leu Asn Arg Asn Lys Gln
            1010                1015                1020

Ala Glu Leu Asp Thr Leu Val Ala Asn Leu Lys Ala Ala Leu Gln Gly
1025                1030                1035                1040

Leu Lys Pro Ala Ala Thr His Ser Gly Ser Leu Asp Glu Asn Glu Val
            1045                1050                1055

Ala Ala Asn Val Glu Thr Arg Pro Glu Leu Ile Thr Arg Thr Glu Glu
1060                1065                1070

Ile Pro Phe Glu Val Ile Lys Lys Glu Asn Pro Asn Leu Pro Ala Gly
            1075                1080                1085

Gln Glu Asn Ile Ile Thr Ala Gly Val Lys Gly Glu Arg Thr His Tyr
1090                1095                1100

Ile Ser Val Leu Thr Glu Asn Gly Lys Thr Thr Glu Thr Val Leu Asp
1105                1110                1115                1120

Ser Gln Val Thr Lys Glu Val Ile Asn Gln Val Val Glu Val Gly Ser
            1125                1130                1135

Pro Val Thr His Lys Gly Asp Glu Ser Gly Leu Ala Pro Thr Thr Glu
            1140                1145                1150

Val Lys Pro Arg Leu Asp Ile Gln Glu Glu Ile Pro Phe Thr Thr
            1155                1160                1165

Val Thr Arg Glu Asn Pro Leu Leu Leu Lys Gly Lys Thr Gln Val Ile
            1170                1175                1180

Thr Lys Gly Val Asn Gly His Arg Ser Asn Phe Tyr Ser Val Ser Thr
1185                1190                1195                1200

Ser Ala Asp Gly Lys Glu Val Lys Thr Leu Val Asn Ser Val Val Ala
            1205                1210                1215

Gln Glu Ala Val Thr Gln Ile Val Glu Val Gly Thr Met Val Thr His
            1220                1225                1230

Val Gly Asp Glu Asn Gly Gln Ala Ala Ile Ala Glu Glu Lys Pro Lys
            1235                1240                1245

Leu Glu Ile Pro Ser Gln Pro Ala Pro Ser Thr Ala Pro Ala Glu Glu
            1250                1255                1260

Ser Lys Ala Leu Pro Gln Asp Pro Ala Pro Val Val Thr Glu Lys Lys
1265                1270                1275                1280

Leu Pro Glu Thr Gly Thr His Asp Ser Ala Glu Leu Val Ala Gly
            1285                1290                1295

Leu Met Ser Thr Leu Ala Ala Tyr Gly Leu Thr Lys Arg Lys Glu Asp
            1300                1305                1310

<210> SEQ ID NO 24
<211> LENGTH: 1062
<212> TYPE: PRT
<213> ORGANISM: Streptococcus pneumoniae
<220> FEATURE:
<223> OTHER INFORMATION: spr0057 with N-terminal and C-terminal
      truncations

<400> SEQUENCE: 24

Leu His Leu Leu Val Gly Asn Asp Gly Leu Arg Phe Met Leu Asp Asp
1               5                   10                  15

Met Ser Ile Thr Ala Asn Gly Lys Thr Tyr Ala Ser Asp Asp Val Lys
            20                  25                  30

Arg Ala Ile Glu Lys Gly Thr Asn Asp Tyr Tyr Asn Asp Pro Asn Gly
        35                  40                  45

Asn His Leu Thr Glu Ser Gln Met Thr Asp Leu Ile Asn Tyr Ala Lys
    50                  55                  60
```

-continued

```
Asp Lys Gly Ile Gly Leu Ile Pro Thr Val Asn Ser Pro Gly His Met
65                  70                  75                  80

Asp Ala Ile Leu Asn Ala Met Lys Glu Leu Gly Ile Gln Asn Pro Asn
                85                  90                  95

Phe Ser Tyr Phe Gly Lys Lys Ser Ala Arg Thr Val Asp Leu Asp Asn
            100                 105                 110

Glu Gln Ala Val Ala Phe Thr Lys Ala Leu Ile Asp Lys Tyr Ala Ala
        115                 120                 125

Tyr Phe Ala Lys Lys Thr Glu Ile Phe Asn Ile Gly Leu Asp Glu Tyr
130                 135                 140

Ala Asn Asp Ala Thr Asp Ala Lys Gly Trp Ser Val Leu Gln Ala Asp
145                 150                 155                 160

Lys Tyr Tyr Pro Asn Glu Gly Tyr Pro Val Lys Gly Tyr Glu Lys Phe
                165                 170                 175

Ile Ala Tyr Ala Asn Asp Leu Ala Arg Ile Val Lys Ser His Gly Leu
            180                 185                 190

Lys Pro Met Ala Phe Asn Asp Gly Ile Tyr Tyr Asn Ser Asp Thr Ser
        195                 200                 205

Phe Gly Ser Phe Asp Lys Asp Ile Ile Val Ser Met Trp Thr Gly Gly
210                 215                 220

Trp Gly Gly Tyr Asp Val Ala Ser Ser Lys Leu Leu Ala Glu Lys Gly
225                 230                 235                 240

His Gln Ile Leu Asn Thr Asn Asp Ala Trp Cys Tyr Val Leu Gly Arg
                245                 250                 255

Asn Ala Asp Gly Gln Gly Trp Tyr Asn Leu Asp Gln Gly Leu Asn Gly
            260                 265                 270

Ile Lys Asn Thr Pro Ile Thr Ser Val Pro Lys Thr Glu Gly Ala Asp
        275                 280                 285

Ile Pro Ile Ile Gly Gly Met Val Ala Ala Trp Ala Asp Thr Pro Ser
290                 295                 300

Ala Arg Tyr Ser Pro Ser His Leu Phe Lys Leu Met Arg His Phe Ala
305                 310                 315                 320

Asn Ala Asn Ala Glu Tyr Phe Ala Ala Asp Tyr Glu Ser Ala Glu Gln
                325                 330                 335

Ala Leu Asn Glu Val Pro Lys Asp Leu Asn Arg Tyr Thr Ala Glu Ser
            340                 345                 350

Val Ala Ala Val Lys Glu Ala Glu Lys Ala Ile Arg Ser Leu Asp Ser
        355                 360                 365

Asn Leu Ser Arg Ala Gln Gln Asp Thr Ile Asp Gln Ala Ile Ala Lys
370                 375                 380

Leu Gln Glu Thr Val Asn Asn Leu Thr Leu Thr Pro Glu Ala Gln Lys
385                 390                 395                 400

Glu Glu Glu Ala Lys Arg Glu Val Glu Lys Leu Ala Lys Asn Lys Val
                405                 410                 415

Ile Ser Ile Asp Ala Gly Arg Lys Tyr Phe Thr Leu Asp Gln Leu Lys
            420                 425                 430

Arg Ile Val Asp Lys Ala Ser Glu Leu Gly Tyr Ser Asp Val His Leu
        435                 440                 445

Leu Leu Gly Asn Asp Gly Leu Arg Phe Leu Leu Asn Asp Met Thr Ile
450                 455                 460

Thr Ala Asn Gly Lys Thr Tyr Ala Ser Asp Asp Val Lys Lys Ala Ile
465                 470                 475                 480

Ile Glu Gly Thr Lys Ala Tyr Tyr Asp Asp Pro Asn Gly Thr Ala Leu
```

-continued

```
                485                 490                 495
Thr Gln Ala Glu Val Thr Glu Leu Ile Glu Tyr Ala Lys Ser Lys Asp
            500                 505                 510
Ile Gly Leu Ile Pro Ala Ile Asn Ser Pro Gly His Met Asp Ala Met
        515                 520                 525
Leu Val Ala Met Glu Lys Leu Gly Ile Lys Asn Pro Gln Ala His Phe
    530                 535                 540
Asp Lys Val Ser Lys Thr Thr Met Asp Leu Lys Asn Glu Glu Ala Met
545                 550                 555                 560
Asn Phe Val Lys Ala Leu Ile Gly Lys Tyr Met Asp Phe Phe Ala Gly
            565                 570                 575
Lys Thr Lys Ile Phe Asn Phe Gly Thr Asp Glu Tyr Ala Asn Asp Ala
        580                 585                 590
Thr Ser Ala Gln Gly Trp Tyr Tyr Leu Lys Trp Tyr Gln Leu Tyr Gly
    595                 600                 605
Lys Phe Ala Glu Tyr Ala Asn Thr Leu Ala Ala Met Ala Lys Glu Arg
    610                 615                 620
Gly Leu Gln Pro Met Ala Phe Asn Asp Gly Phe Tyr Tyr Glu Asp Lys
625                 630                 635                 640
Asp Asp Val Gln Phe Asp Lys Asp Val Leu Ile Ser Tyr Trp Ser Lys
            645                 650                 655
Gly Trp Trp Gly Tyr Asn Leu Ala Ser Pro Gln Tyr Leu Ala Ser Lys
        660                 665                 670
Gly Tyr Lys Phe Leu Asn Thr Asn Gly Asp Trp Tyr Tyr Val Ile Gly
    675                 680                 685
Asn His Lys Gln Asp Glu Ala Tyr Pro Leu Ser Lys Ala Val Glu Asn
    690                 695                 700
Ser Gly Lys Val Pro Phe Asn Gln Leu Ala Ser Thr Lys Tyr Pro Glu
705                 710                 715                 720
Val Asp Leu Pro Thr Val Gly Ser Met Leu Ser Ile Trp Ala Asp Arg
            725                 730                 735
Pro Ser Ala Glu Tyr Lys Glu Glu Ile Phe Glu Leu Met Thr Ala
        740                 745                 750
Phe Ala Asp His Asn Lys Asp Tyr Phe Arg Ala Asn Tyr Asn Ala Leu
    755                 760                 765
Arg Glu Glu Leu Ala Lys Ile Pro Thr Asn Leu Glu Gly Tyr Ser Lys
    770                 775                 780
Glu Ser Leu Glu Ala Leu Asp Ala Ala Lys Thr Ala Leu Asn Tyr Asn
785                 790                 795                 800
Leu Asn Arg Asn Lys Gln Ala Glu Leu Asp Thr Leu Val Ala Asn Leu
            805                 810                 815
Lys Ala Ala Leu Gln Gly Leu Lys Pro Ala Ala Thr His Ser Gly Ser
        820                 825                 830
Leu Asp Glu Asn Glu Val Ala Ala Asn Val Gly Thr Arg Pro Glu Leu
    835                 840                 845
Ile Thr Arg Thr Glu Glu Ile Pro Phe Glu Val Ile Lys Lys Glu Asn
    850                 855                 860
Pro Asn Leu Pro Ala Gly Gln Glu Asn Ile Ile Thr Ala Gly Val Lys
865                 870                 875                 880
Gly Glu Arg Thr His Tyr Ile Ser Val Leu Thr Glu Asn Gly Lys Thr
            885                 890                 895
Thr Glu Thr Val Leu Asp Ser Gln Val Thr Lys Glu Val Ile Asn Gln
        900                 905                 910
```

```
Val Val Glu Val Gly Ser Pro Val Thr His Lys Gly Asp Glu Ser Gly
        915                 920                 925

Leu Ala Pro Thr Thr Glu Val Lys Pro Arg Leu Asp Ile Gln Glu Glu
        930                 935                 940

Glu Ile Pro Phe Thr Thr Val Thr Arg Glu Asn Pro Leu Leu Leu Lys
945                 950                 955                 960

Gly Lys Thr Gln Val Ile Thr Lys Gly Val Asn Gly His Arg Ser Asn
                965                 970                 975

Phe Tyr Ser Val Ser Thr Ser Ala Asp Gly Lys Glu Val Lys Thr Leu
                980                 985                 990

Val Asn Ser Val Val Ala Gln Glu Ala Val Thr Gln Ile Val Glu Val
            995                 1000                1005

Gly Thr Met Val Thr His Val Gly Asp Glu Asn Gly Gln Ala Ala Ile
        1010                1015                1020

Ala Glu Glu Lys Pro Lys Leu Glu Ile Pro Ser Gln Pro Ala Pro Ser
1025                1030                1035                1040

Thr Ala Pro Ala Glu Glu Ser Lys Ala Leu Pro Gln Asp Pro Ala Pro
                1045                1050                1055

Val Val Thr Glu Lys Lys
            1060

<210> SEQ ID NO 25
<211> LENGTH: 2228
<212> TYPE: PRT
<213> ORGANISM: Streptococcus pneumoniae
<220> FEATURE:
<223> OTHER INFORMATION: full length spr0565 as found in the R6 strain

<400> SEQUENCE: 25

Met Gly Lys Gly His Trp Asn Arg Lys Arg Val Tyr Ser Ile Arg Lys
1               5                   10                  15

Phe Ala Val Gly Ala Cys Ser Val Met Ile Gly Thr Cys Ala Val Leu
            20                  25                  30

Leu Gly Gly Asn Ile Ala Gly Glu Ser Val Val Tyr Ala Asp Glu Thr
        35                  40                  45

Leu Ile Thr His Thr Ala Glu Lys Pro Lys Glu Glu Lys Met Ile Val
    50                  55                  60

Glu Glu Lys Ala Asp Lys Ala Leu Glu Thr Lys Asn Val Val Glu Arg
65                  70                  75                  80

Thr Glu Gln Ser Glu Pro Ser Ser Thr Glu Ala Ile Ala Ser Glu Lys
                85                  90                  95

Lys Glu Asp Glu Ala Val Thr Pro Lys Glu Glu Lys Val Ser Ala Lys
            100                 105                 110

Pro Glu Glu Lys Ala Pro Arg Ile Glu Ser Gln Ala Ser Ser Gln Glu
        115                 120                 125

Lys Pro Leu Lys Glu Asp Ala Lys Ala Val Thr Asn Glu Glu Val Asn
    130                 135                 140

Gln Met Ile Glu Asn Arg Lys Val Asp Phe Asn Gln Asn Trp Tyr Phe
145                 150                 155                 160

Lys Leu Asn Ala Asn Ser Lys Glu Ala Ile Lys Pro Asp Ala Asp Val
                165                 170                 175

Ser Thr Trp Lys Lys Leu Asp Leu Pro Tyr Asp Trp Ser Ile Phe Asn
            180                 185                 190

Asp Phe Asp His Glu Ser Pro Ala Gln Asn Glu Gly Gln Leu Asn
        195                 200                 205

Gly Gly Glu Ala Trp Tyr Arg Lys Thr Phe Lys Leu Asp Glu Lys Asp
```

```
            210                 215                 220
Leu Lys Lys Asn Val Arg Leu Thr Phe Asp Gly Val Tyr Met Asp Ser
225                 230                 235                 240

Gln Val Tyr Val Asn Gly Gln Leu Val Gly His Tyr Pro Asn Gly Tyr
                245                 250                 255

Asn Gln Phe Ser Tyr Asp Ile Thr Lys Tyr Leu Tyr Lys Asp Gly Arg
                260                 265                 270

Glu Asn Val Ile Ala Val His Ala Val Asn Lys Gln Pro Ser Ser Arg
                275                 280                 285

Trp Tyr Ser Gly Ser Gly Ile Tyr Arg Asp Val Thr Leu Gln Val Thr
        290                 295                 300

Asp Lys Val His Val Glu Lys Asn Gly Thr Thr Ile Leu Thr Pro Lys
305                 310                 315                 320

Leu Glu Glu Gln Gln His Gly Lys Val Glu Thr His Val Thr Ser Lys
                325                 330                 335

Ile Val Asn Thr Asp Asp Lys Asp His Glu Leu Val Ala Glu Tyr Gln
                340                 345                 350

Ile Val Glu Arg Gly Gly His Ala Val Thr Gly Leu Val Arg Thr Ala
                355                 360                 365

Ser Arg Thr Leu Lys Ala His Glu Ser Thr Ser Leu Asp Ala Ile Leu
        370                 375                 380

Glu Val Glu Arg Pro Lys Leu Trp Thr Val Leu Asn Asp Lys Pro Ala
385                 390                 395                 400

Leu Tyr Glu Leu Ile Thr Arg Val Tyr Arg Asp Gly Gln Leu Val Asp
                405                 410                 415

Ala Lys Lys Asp Leu Phe Gly Tyr Arg Tyr Tyr His Trp Thr Pro Asn
                420                 425                 430

Glu Gly Phe Ser Leu Asn Gly Glu Arg Ile Lys Phe His Gly Val Ser
        435                 440                 445

Leu His His Asp His Gly Ala Leu Gly Ala Glu Glu Asn Tyr Lys Ala
        450                 455                 460

Glu Tyr Arg Arg Leu Lys Gln Met Lys Glu Met Gly Val Asn Ser Ile
465                 470                 475                 480

Arg Thr Thr His Asn Pro Ala Ser Glu Gln Thr Leu Gln Ile Ala Ala
                485                 490                 495

Glu Leu Gly Leu Leu Val Gln Glu Glu Ala Phe Asp Thr Trp Tyr Gly
                500                 505                 510

Gly Lys Lys Pro Tyr Asp Tyr Gly Arg Phe Phe Glu Lys Asp Ala Thr
        515                 520                 525

His Pro Glu Ala Arg Lys Gly Glu Lys Trp Ser Asp Phe Asp Leu Arg
        530                 535                 540

Thr Met Val Glu Arg Gly Lys Asn Asn Pro Ala Ile Phe Met Trp Ser
545                 550                 555                 560

Ile Gly Asn Glu Ile Gly Glu Ala Asn Gly Asp Ala His Ser Leu Ala
                565                 570                 575

Thr Val Lys Arg Leu Val Lys Val Ile Lys Asp Val Asp Lys Thr Arg
                580                 585                 590

Tyr Val Thr Met Gly Ala Asp Lys Phe Arg Phe Gly Asn Gly Ser Gly
        595                 600                 605

Gly His Glu Lys Ile Ala Asp Glu Leu Asp Ala Val Gly Phe Asn Tyr
        610                 615                 620

Ser Glu Asp Asn Tyr Lys Ala Leu Arg Ala Lys His Pro Lys Trp Leu
625                 630                 635                 640
```

-continued

```
Ile Tyr Gly Ser Glu Thr Ser Ser Ala Thr Arg Thr Arg Gly Ser Tyr
            645                 650                 655

Tyr Arg Pro Glu Arg Glu Leu Lys His Ser Asn Gly Pro Glu Arg Asn
        660                 665                 670

Tyr Glu Gln Ser Asp Tyr Gly Asn Asp Arg Val Gly Trp Gly Lys Thr
        675                 680                 685

Ala Thr Ala Ser Trp Thr Phe Asp Arg Asp Asn Ala Gly Tyr Ala Gly
        690                 695                 700

Gln Phe Ile Trp Thr Gly Thr Asp Tyr Ile Gly Glu Pro Thr Pro Trp
705                 710                 715                 720

His Asn Gln Asn Gln Thr Pro Val Lys Ser Ser Tyr Phe Gly Ile Val
                725                 730                 735

Asp Thr Ala Gly Ile Pro Lys His Asp Phe Tyr Leu Tyr Gln Ser Gln
            740                 745                 750

Trp Val Ser Val Lys Lys Pro Met Val His Leu Leu Pro His Trp
            755                 760                 765

Asn Trp Glu Asn Lys Glu Leu Ala Ser Lys Val Ala Asp Ser Glu Gly
        770                 775                 780

Lys Ile Pro Val Arg Ala Tyr Ser Asn Ala Ser Ser Val Glu Leu Phe
785                 790                 795                 800

Leu Asn Gly Lys Ser Leu Gly Leu Lys Thr Phe Asn Lys Lys Gln Thr
                805                 810                 815

Ser Asp Gly Arg Thr Tyr Gln Glu Gly Ala Asn Ala Asn Glu Leu Tyr
            820                 825                 830

Leu Glu Trp Lys Val Ala Tyr Gln Pro Gly Thr Leu Glu Ala Ile Ala
                835                 840                 845

Arg Asp Glu Ser Gly Lys Glu Ile Ala Arg Asp Lys Ile Thr Thr Ala
850                 855                 860

Gly Lys Pro Ala Ala Val Arg Leu Ile Lys Glu Asp His Ala Ile Ala
865                 870                 875                 880

Ala Asp Gly Lys Asp Leu Thr Tyr Ile Tyr Tyr Glu Ile Val Asp Ser
                885                 890                 895

Gln Gly Asn Val Val Pro Thr Ala Asn Asn Leu Val Arg Phe Gln Leu
            900                 905                 910

His Gly Gln Gly Gln Leu Val Gly Val Asp Asn Gly Glu Gln Ala Ser
        915                 920                 925

Arg Glu Arg Tyr Lys Ala Gln Ala Asp Gly Ser Trp Ile Arg Lys Ala
        930                 935                 940

Phe Asn Gly Lys Gly Val Ala Ile Val Lys Ser Thr Glu Gln Ala Gly
945                 950                 955                 960

Lys Phe Thr Leu Thr Ala His Ser Asp Leu Leu Lys Ser Asn Gln Val
                965                 970                 975

Thr Val Phe Thr Gly Lys Lys Glu Gly Gln Glu Lys Thr Val Leu Gly
            980                 985                 990

Thr Glu Val Pro Lys Val Gln Thr Ile Ile Gly Glu Ala Pro Glu Met
        995                 1000                1005

Pro Thr Thr Val Pro Phe Val Tyr Ser Asp Gly Ser Arg Ala Glu Arg
        1010                1015                1020

Pro Val Thr Trp Ser Leu Val Asp Val Ser Lys Pro Gly Ile Val Thr
1025                1030                1035                1040

Val Lys Gly Met Ala Asp Gly Arg Glu Val Glu Ala Arg Val Glu Val
                1045                1050                1055

Ile Ala Leu Lys Ser Glu Leu Pro Val Val Lys Arg Ile Ala Pro Asn
            1060                1065                1070
```

```
Thr Asn Leu Asn Ser Val Asp Lys Ser Val Ser Tyr Val Leu Thr Asp
        1075                1080                1085

Gly Ser Val Gln Glu Tyr Glu Val Asp Lys Trp Glu Ile Ala Glu Glu
        1090                1095                1100

Asp Lys Ala Lys Leu Ala Ile Pro Gly Ser Arg Ile Gln Ala Thr Gly
1105                1110                1115                1120

Tyr Leu Glu Gly Gln Pro Ile His Ala Thr Leu Val Val Glu Glu Gly
        1125                1130                1135

Asn Pro Ala Ala Pro Val Val Pro Thr Val Thr Val Gly Gly Glu Ala
        1140                1145                1150

Val Thr Gly Leu Thr Ser Arg Gln Pro Met Gln Tyr Arg Thr Leu Ser
        1155                1160                1165

Tyr Gly Ala Gln Leu Pro Glu Val Thr Ala Ser Ala Glu Asn Ala Asp
        1170                1175                1180

Val Thr Val Leu Gln Ala Ser Ala Ala Asn Gly Met Arg Ala Ser Ile
1185                1190                1195                1200

Phe Ile Gln Pro Lys Asp Gly Gly Pro Leu Gln Thr Tyr Ala Ile Gln
        1205                1210                1215

Phe Leu Glu Glu Ala Pro Lys Ile Ala His Leu Ser Leu Gln Val Glu
        1220                1225                1230

Lys Ala Asp Ser Leu Lys Glu Asp Gln Thr Val Lys Leu Ser Val Arg
        1235                1240                1245

Ala His Tyr Gln Asp Gly Thr Gln Ala Val Leu Pro Ala Asp Lys Val
        1250                1255                1260

Thr Phe Ser Thr Ser Gly Glu Gly Glu Val Ala Ile Arg Lys Gly Met
1265                1270                1275                1280

Leu Glu Leu His Lys Pro Gly Ala Val Thr Leu Asn Ala Glu Tyr Glu
        1285                1290                1295

Gly Ala Lys Gly Gln Val Glu Leu Thr Ile Gln Ala Asn Thr Glu Lys
        1300                1305                1310

Lys Ile Ala Gln Ser Ile Arg Pro Val Asn Val Val Thr Asp Leu His
        1315                1320                1325

Gln Glu Pro Ser Leu Pro Ala Thr Val Thr Val Glu Tyr Asp Lys Gly
        1330                1335                1340

Phe Pro Lys Thr His Lys Val Thr Trp Gln Ala Ile Pro Lys Glu Lys
1345                1350                1355                1360

Leu Asp Ser Tyr Gln Ile Phe Glu Val Leu Gly Lys Val Glu Gly Ile
        1365                1370                1375

Asp Leu Glu Ala Arg Ala Lys Val Ser Val Glu Gly Ile Val Ser Val
        1380                1385                1390

Glu Glu Val Ser Val Thr Thr Pro Ile Ala Glu Ala Pro Gln Leu Pro
        1395                1400                1405

Glu Ser Val Arg Thr Tyr Asp Ser Asn Gly His Val Ser Ser Ala Lys
        1410                1415                1420

Val Ala Trp Asp Ala Ile Arg Pro Glu Gln Tyr Ala Lys Glu Gly Val
1425                1430                1435                1440

Phe Thr Val Asn Gly Arg Leu Glu Gly Thr Gln Leu Thr Thr Lys Leu
        1445                1450                1455

His Val Arg Val Ser Ala Gln Thr Glu Gln Gly Ala Asn Ile Ser Asp
        1460                1465                1470

Gln Trp Thr Gly Ser Glu Leu Pro Leu Ala Phe Ala Ser Asp Ser Asn
        1475                1480                1485

Pro Ser Asp Pro Val Ser Asn Val Asn Asp Lys Leu Ile Ser Tyr Asn
```

```
             1490           1495           1500

Asn Gln Pro Ala Asn Arg Trp Thr Asn Trp Asn Arg Ser Asn Pro Glu
1505                1510                1515                1520

Ala Ser Val Gly Val Leu Phe Gly Asp Ser Gly Ile Leu Ser Lys Arg
                1525                1530                1535

Ser Val Asp Asn Leu Ser Val Gly Phe His Glu Asp His Gly Val Gly
            1540                1545                1550

Ala Pro Lys Ser Tyr Val Ile Glu Tyr Tyr Val Gly Lys Thr Val Pro
        1555                1560                1565

Thr Ala Pro Lys Asn Pro Ser Phe Val Gly Asn Glu Asp His Val Phe
    1570                1575                1580

Asn Asp Ser Ala Asn Trp Lys Pro Val Thr Asn Leu Lys Ala Pro Ala
1585                1590                1595                1600

Gln Leu Lys Ala Gly Glu Met Asn His Phe Ser Phe Asp Lys Val Glu
                1605                1610                1615

Thr Tyr Ala Ile Arg Ile Arg Met Val Lys Ala Asp Asn Lys Arg Gly
            1620                1625                1630

Thr Ser Ile Thr Glu Val Gln Ile Phe Ala Lys Gln Val Ala Ala Ala
        1635                1640                1645

Lys Gln Gly Gln Thr Arg Ile Gln Val Asp Gly Lys Asp Leu Ala Asn
    1650                1655                1660

Phe Asn Pro Asp Leu Thr Asp Tyr Tyr Leu Glu Ser Val Asp Gly Lys
1665                1670                1675                1680

Val Pro Ala Val Thr Ala Asn Val Ser Asn Asn Gly Leu Ala Thr Val
                1685                1690                1695

Val Pro Ser Val Arg Glu Gly Glu Pro Val Arg Val Ile Ala Lys Ala
            1700                1705                1710

Glu Asn Gly Asp Ile Leu Gly Glu Tyr Arg Leu His Phe Thr Lys Asp
        1715                1720                1725

Lys Asn Leu Leu Ser His Lys Pro Val Ala Ala Val Lys Gln Ala Arg
    1730                1735                1740

Leu Leu Gln Val Gly Gln Ala Leu Glu Leu Pro Thr Lys Val Pro Val
1745                1750                1755                1760

Tyr Phe Thr Gly Lys Asp Gly Tyr Glu Thr Lys Asp Leu Thr Val Glu
                1765                1770                1775

Trp Glu Glu Val Pro Ala Glu Asn Leu Thr Lys Ala Gly Gln Phe Thr
            1780                1785                1790

Val Arg Gly Arg Val Leu Gly Ser Asn Leu Val Ala Glu Val Thr Val
        1795                1800                1805

Arg Val Thr Asp Lys Leu Gly Glu Thr Leu Ser Asp Asn Pro Asn Tyr
    1810                1815                1820

Asp Glu Asn Ser Asn Gln Ala Phe Ala Ser Ala Thr Asn Asp Ile Asp
1825                1830                1835                1840

Lys Asn Ser His Asp Arg Val Asp Tyr Leu Asn Asp Gly Asp His Ser
                1845                1850                1855

Glu Asn Arg Arg Trp Thr Asn Trp Ser Pro Thr Pro Ser Ser Asn Pro
            1860                1865                1870

Glu Val Ser Ala Gly Val Ile Phe Arg Glu Asn Gly Lys Ile Val Glu
        1875                1880                1885

Arg Thr Val Ala Gln Ala Lys Leu His Phe Phe Ala Asp Ser Gly Thr
    1890                1895                1900

Asp Ala Pro Ser Lys Leu Val Leu Glu Arg Tyr Val Gly Pro Gly Phe
1905                1910                1915                1920
```

-continued

Glu Val Pro Thr Tyr Tyr Ser Asn Tyr Gln Ala Tyr Glu Ser Gly His
            1925                1930                1935

Pro Phe Asn Asn Pro Glu Asn Trp Glu Ala Val Pro Tyr Arg Ala Asp
        1940                1945                1950

Lys Asp Ile Ala Ala Gly Asp Glu Ile Asn Val Thr Phe Lys Ala Val
    1955                1960                1965

Lys Ala Lys Val Met Arg Trp Arg Met Glu Arg Lys Ala Asp Lys Ser
1970                1975                1980

Gly Val Ala Met Ile Glu Met Thr Phe Leu Ala Pro Ser Glu Leu Pro
1985                1990                1995                2000

Gln Glu Ser Thr Gln Ser Lys Ile Leu Val Asp Gly Lys Glu Leu Ala
            2005                2010                2015

Asp Phe Ala Glu Asn Arg Gln Asp Tyr Gln Ile Thr Tyr Lys Gly Gln
        2020                2025                2030

Arg Pro Lys Val Ser Val Glu Glu Asn Asn Gln Val Ala Ser Thr Val
    2035                2040                2045

Val Asp Ser Gly Glu Asp Ser Leu Pro Val Leu Val Arg Leu Val Ser
2050                2055                2060

Glu Ser Gly Lys Gln Val Lys Glu Tyr Arg Ile Gln Leu Thr Lys Glu
2065                2070                2075                2080

Lys Pro Val Ser Ala Val Gln Glu Asp Leu Pro Lys Leu Glu Phe Val
            2085                2090                2095

Glu Lys Asp Leu Ala Tyr Lys Thr Val Glu Lys Asp Ser Thr Leu
        2100                2105                2110

Tyr Leu Gly Glu Thr Arg Val Glu Gln Glu Gly Lys Val Gly Lys Glu
    2115                2120                2125

Arg Ile Phe Thr Val Ile Asn Pro Asp Gly Ser Lys Glu Glu Lys Leu
        2130                2135                2140

Arg Glu Val Val Glu Val Pro Thr Asp Arg Ile Val Leu Val Gly Thr
2145                2150                2155                2160

Lys Pro Val Ala Gln Glu Ala Lys Lys Pro Gln Val Ser Glu Lys Ala
            2165                2170                2175

Asp Thr Lys Pro Ile Asp Ser Ser Glu Ala Asp Gln Thr Asn Lys Ala
        2180                2185                2190

Gln Leu Pro Asn Thr Gly Ser Ala Ala Ser Gln Ala Ala Val Ala Ala
    2195                2200                2205

Gly Leu Ala Leu Leu Gly Leu Ser Ala Gly Leu Val Val Thr Lys Gly
    2210                2215                2220

Lys Lys Glu Asp
2225

<210> SEQ ID NO 26
<211> LENGTH: 247
<212> TYPE: PRT
<213> ORGANISM: Streptococcus pneumoniae
<220> FEATURE:
<223> OTHER INFORMATION: full length spr1098 as found in the R6 strain

<400> SEQUENCE: 26

Met Ser Gln Lys Asn Asn Lys Lys Asn Lys Arg Lys Asn Leu Leu
1               5                   10                  15

Thr Asn Ile Leu Ala Gly Phe Leu Ile Leu Ser Leu Ala Leu Ile
            20                  25                  30

Phe Asn Thr Gln Ile Arg Asn Ile Phe Ile Val Trp Asn Thr Asn Lys
        35                  40                  45

Tyr Gln Val Ser Gln Val Ser Lys Glu Lys Leu Glu Glu Asn Gln Asp

```
                50                  55                  60
Thr Glu Gly Asn Phe Asp Phe Asp Ser Val Lys Ala Ile Ser Ser Glu
 65                  70                  75                  80

Ala Val Leu Thr Ser Gln Trp Asp Ala Gln Lys Leu Pro Val Ile Gly
                 85                  90                  95

Gly Ile Ala Ile Pro Glu Leu Glu Met Asn Leu Pro Ile Phe Lys Gly
                100                 105                 110

Leu Asp Asn Val Asn Leu Phe Tyr Gly Ala Gly Thr Met Lys Arg Glu
                115                 120                 125

Gln Val Met Gly Glu Gly Asn Tyr Ser Leu Ala Ser His His Ile Phe
            130                 135                 140

Gly Val Asp Asn Ala Asn Lys Met Leu Phe Ser Pro Leu Asp Asn Ala
145                 150                 155                 160

Lys Asn Gly Met Lys Ile Tyr Leu Thr Asp Lys Asn Lys Val Tyr Thr
                165                 170                 175

Tyr Glu Ile Arg Glu Val Lys Arg Val Thr Pro Asp Arg Val Asp Glu
                180                 185                 190

Val Asp Asp Arg Asp Gly Val Asn Glu Ile Thr Leu Val Thr Cys Glu
                195                 200                 205

Asp Leu Ala Ala Thr Glu Arg Ile Ile Val Lys Gly Asp Leu Lys Glu
            210                 215                 220

Thr Lys Asp Tyr Ser Gln Thr Ser Asp Glu Ile Leu Thr Ala Phe Asn
225                 230                 235                 240

Gln Pro Tyr Lys Gln Phe Tyr
                245

<210> SEQ ID NO 27
<211> LENGTH: 1062
<212> TYPE: PRT
<213> ORGANISM: Streptococcus pneumoniae
<220> FEATURE:
<223> OTHER INFORMATION: a variant of SEQ ID NO: 24 based on a different
      wild-type strain

<400> SEQUENCE: 27

Leu His Leu Leu Val Gly Asn Asp Gly Leu Arg Phe Met Leu Asp Asp
 1               5                  10                  15

Met Ser Ile Thr Ala Asn Gly Lys Thr Tyr Ala Ser Asp Asp Val Lys
                20                  25                  30

Arg Ala Ile Glu Lys Gly Thr Asn Asp Tyr Tyr Asn Asp Pro Asn Gly
             35                  40                  45

Asn His Leu Thr Glu Ser Gln Met Thr Asp Leu Ile Asn Tyr Ala Lys
 50                  55                  60

Asp Lys Gly Ile Gly Leu Ile Pro Thr Val Asn Ser Pro Gly His Met
 65                  70                  75                  80

Asp Ala Ile Leu Asn Ala Met Lys Glu Leu Gly Ile Gln Asn Pro Asn
                 85                  90                  95

Phe Ser Tyr Phe Gly Lys Lys Ser Ala Arg Thr Val Asp Leu Asp Asn
                100                 105                 110

Glu Gln Ala Val Ala Phe Thr Lys Ala Leu Ile Asp Lys Tyr Ala Ala
             115                 120                 125

Tyr Phe Ala Lys Lys Thr Glu Ile Phe Asn Ile Gly Leu Asp Glu Tyr
            130                 135                 140

Ala Asn Asp Ala Thr Asp Ala Lys Gly Trp Ser Val Leu Gln Ala Asp
145                 150                 155                 160

Lys Tyr Tyr Pro Asn Glu Gly Tyr Pro Val Lys Gly Tyr Glu Lys Phe
```

-continued

```
                165                 170                 175
Ile Ala Tyr Ala Asn Asp Leu Ala Arg Ile Val Lys Ser His Gly Leu
            180                 185                 190

Lys Pro Met Ala Phe Asn Asp Gly Ile Tyr Tyr Asn Ser Asp Thr Ser
        195                 200                 205

Phe Gly Ser Phe Asp Lys Asp Ile Ile Val Ser Met Trp Thr Gly Gly
    210                 215                 220

Trp Gly Gly Tyr Asp Val Ala Ser Ser Lys Leu Leu Ala Glu Lys Gly
225                 230                 235                 240

His Gln Ile Leu Asn Thr Asn Asp Ala Trp Tyr Tyr Val Leu Gly Arg
                245                 250                 255

Asn Ala Asp Gly Gln Gly Trp Tyr Asn Leu Asp Gln Gly Leu Asn Gly
            260                 265                 270

Ile Lys Asn Thr Pro Ile Thr Ser Val Pro Lys Thr Glu Gly Ala Asp
        275                 280                 285

Ile Pro Ile Ile Gly Gly Met Val Ala Ala Trp Ala Asp Thr Pro Ser
    290                 295                 300

Ala Arg Tyr Ser Pro Ser Arg Leu Phe Lys Leu Met Arg His Phe Ala
305                 310                 315                 320

Asn Ala Asn Ala Glu Tyr Phe Ala Ala Asp Tyr Glu Ser Ala Glu Gln
                325                 330                 335

Ala Leu Asn Glu Val Pro Lys Asp Leu Asn Arg Tyr Thr Ala Glu Ser
            340                 345                 350

Val Thr Ala Val Lys Glu Ala Glu Lys Ala Ile Arg Ser Leu Asp Ser
        355                 360                 365

Asn Leu Ser Arg Ala Gln Gln Asp Thr Ile Asp Gln Ala Ile Ala Lys
    370                 375                 380

Leu Gln Glu Thr Val Asn Asn Leu Thr Leu Thr Pro Glu Ala Gln Lys
385                 390                 395                 400

Glu Glu Glu Ala Lys Arg Glu Val Glu Lys Leu Ala Lys Asn Lys Val
                405                 410                 415

Ile Ser Ile Asp Ala Gly Arg Lys Tyr Phe Thr Leu Asn Gln Leu Lys
            420                 425                 430

Arg Ile Val Asp Lys Ala Ser Glu Leu Gly Tyr Ser Asp Val His Leu
        435                 440                 445

Leu Leu Gly Asn Asp Gly Leu Arg Phe Leu Leu Asp Asp Met Thr Ile
    450                 455                 460

Thr Ala Asn Gly Lys Thr Tyr Ala Ser Asp Asp Val Lys Lys Ala Ile
465                 470                 475                 480

Ile Glu Gly Thr Lys Ala Tyr Tyr Asp Asp Pro Asn Gly Thr Ala Leu
                485                 490                 495

Thr Gln Ala Glu Val Thr Glu Leu Ile Glu Tyr Ala Lys Ser Lys Asp
            500                 505                 510

Ile Gly Leu Ile Pro Ala Ile Asn Ser Pro Gly His Met Asp Ala Met
        515                 520                 525

Leu Val Ala Met Glu Lys Leu Gly Ile Lys Asn Pro Gln Ala His Phe
    530                 535                 540

Asp Lys Val Ser Lys Thr Thr Met Asp Leu Lys Asn Glu Glu Ala Met
545                 550                 555                 560

Asn Phe Val Lys Ala Leu Ile Gly Lys Tyr Met Asp Phe Phe Ala Gly
                565                 570                 575

Lys Thr Lys Ile Phe Asn Phe Gly Thr Asp Glu Tyr Ala Asn Asp Ala
            580                 585                 590
```

```
Thr Ser Ala Gln Gly Trp Tyr Tyr Leu Lys Trp Tyr Gln Leu Tyr Gly
            595                 600                 605

Lys Phe Ala Glu Tyr Ala Asn Thr Leu Ala Ala Met Ala Lys Glu Arg
            610                 615                 620

Gly Leu Gln Pro Met Ala Phe Asn Asp Gly Phe Tyr Tyr Glu Asp Lys
625                 630                 635                 640

Asp Asp Val Gln Phe Asp Lys Asp Val Leu Ile Ser Tyr Trp Ser Lys
                645                 650                 655

Gly Trp Trp Gly Tyr Asn Leu Ala Ser Pro Gln Tyr Leu Ala Ser Lys
            660                 665                 670

Gly Tyr Lys Phe Leu Asn Thr Asn Gly Asp Trp Tyr Tyr Ile Leu Gly
            675                 680                 685

Gln Lys Pro Glu Asp Gly Gly Phe Leu Lys Lys Ala Ile Glu Asn
            690                 695                 700

Thr Gly Lys Thr Pro Phe Asn Gln Leu Ala Ser Thr Lys Tyr Pro Glu
705                 710                 715                 720

Val Asp Leu Pro Thr Val Gly Ser Met Leu Ser Ile Trp Ala Asp Arg
                725                 730                 735

Pro Ser Ala Glu Tyr Lys Glu Glu Ile Phe Glu Leu Met Thr Ala
            740                 745                 750

Phe Ala Asp His Asn Lys Asp Tyr Phe Arg Ala Asn Tyr Asn Ala Leu
            755                 760                 765

Arg Glu Glu Leu Ala Lys Ile Pro Thr Asn Leu Glu Gly Tyr Ser Lys
            770                 775                 780

Glu Ser Leu Glu Ala Leu Asp Ala Ala Lys Thr Ala Leu Asn Tyr Asn
785                 790                 795                 800

Leu Asn Arg Asn Lys Gln Ala Glu Leu Asp Thr Leu Val Ala Asn Leu
                805                 810                 815

Lys Ala Ala Leu Gln Gly Leu Lys Pro Ala Val Thr His Ser Gly Ser
            820                 825                 830

Leu Asp Glu Asn Glu Val Ala Ala Asn Val Glu Thr Arg Pro Glu Leu
            835                 840                 845

Ile Thr Arg Thr Glu Glu Ile Pro Phe Glu Val Ile Lys Lys Glu Asn
850                 855                 860

Pro Asn Leu Pro Ala Gly Gln Glu Asn Ile Ile Thr Ala Gly Val Lys
865                 870                 875                 880

Gly Glu Arg Thr His Tyr Ile Ser Val Leu Thr Glu Asn Gly Lys Thr
                885                 890                 895

Thr Glu Thr Val Leu Asp Ser Gln Val Thr Lys Glu Val Ile Asn Gln
            900                 905                 910

Val Val Glu Val Gly Ala Pro Thr His Lys Gly Asp Glu Ser Gly
            915                 920                 925

Leu Ala Pro Thr Thr Glu Val Lys Pro Arg Leu Asp Ile Gln Glu Glu
930                 935                 940

Glu Ile Pro Phe Thr Thr Val Thr Cys Glu Asn Pro Leu Leu Leu Lys
945                 950                 955                 960

Gly Lys Thr Gln Val Ile Thr Lys Gly Val Asn Gly His Arg Ser Asn
                965                 970                 975

Phe Tyr Ser Val Ser Thr Ser Ala Asp Gly Lys Glu Val Lys Thr Leu
            980                 985                 990

Val Asn Ser Val Val Ala Gln Glu Ala Val Thr Gln Ile Val Glu Val
            995                 1000                1005

Gly Thr Met Val Thr His Val Gly Asp Glu Asn Gly Gln Ala Ala Ile
            1010                1015                1020
```

```
Ala Glu Glu Lys Pro Lys Leu Glu Ile Pro Ser Gln Pro Ala Pro Ser
1025                1030                1035                1040

Thr Ala Pro Ala Glu Glu Ser Lys Val Leu Pro Gln Asp Pro Ala Pro
            1045                1050                1055

Val Val Thr Glu Lys Lys
            1060

<210> SEQ ID NO 28
<211> LENGTH: 128
<212> TYPE: PRT
<213> ORGANISM: Streptococcus pneumoniae
<220> FEATURE:
<223> OTHER INFORMATION: full length spr1416 as found in the R6 strain

<400> SEQUENCE: 28

Met Glu Lys Asp Met Asn Leu Lys Arg Glu Gln Glu Phe Val Ser Gln
1               5                   10                  15

Tyr His Phe Asp Ala Arg Asn Phe Glu Trp Glu Asn Glu Asn Gly Ala
            20                  25                  30

Pro Glu Thr Lys Val Asp Val Asn Phe Gln Leu Leu Gln His Asp Gln
        35                  40                  45

Glu Asn Gln Val Thr Ser Leu Ile Val Ile Leu Ser Phe Met Ile Val
    50                  55                  60

Phe Asp Lys Phe Val Ile Ser Gly Thr Ile Ser Gln Val Asn His Ile
65                  70                  75                  80

Asp Gly Arg Ile Val Asn Glu Pro Asn Glu Leu Asn Gln Glu Glu Val
                85                  90                  95

Glu Thr Leu Ala Arg Pro Cys Leu Asn Met Leu Asn Arg Leu Thr Tyr
            100                 105                 110

Glu Val Thr Glu Ile Ala Leu Asp Leu Pro Gly Ile Asn Leu Glu Phe
        115                 120                 125

<210> SEQ ID NO 29
<211> LENGTH: 259
<212> TYPE: PRT
<213> ORGANISM: Streptococcus pneumoniae
<220> FEATURE:
<223> OTHER INFORMATION: full length spr1418 as found in the R6 strain

<400> SEQUENCE: 29

Met Lys Lys Asn Ser Leu Tyr Ile Ile Ser Ser Leu Phe Phe Ala Cys
1               5                   10                  15

Val Leu Phe Val Tyr Ala Thr Ala Thr Asn Phe Gln Asn Ser Thr Ser
            20                  25                  30

Ala Arg Gln Val Lys Thr Glu Thr Tyr Thr Asn Thr Val Thr Asn Val
        35                  40                  45

Pro Ile Asp Ile Arg Tyr Asn Ser Asp Lys Tyr Phe Ile Ser Gly Phe
    50                  55                  60

Ala Ser Glu Val Ser Val Val Leu Thr Gly Ala Asn Arg Leu Ser Leu
65                  70                  75                  80

Ala Ser Glu Met Gln Glu Ser Thr Arg Lys Phe Lys Val Thr Ala Asp
                85                  90                  95

Leu Thr Asp Ala Gly Val Gly Thr Ile Glu Val Pro Leu Ser Ile Glu
            100                 105                 110

Asp Leu Pro Asn Gly Leu Thr Ala Val Ala Thr Pro Gln Lys Ile Thr
        115                 120                 125

Val Lys Ile Gly Lys Lys Ala Gln Lys Asp Lys Val Lys Ile Val Pro
    130                 135                 140
```

-continued

```
Glu Ile Asp Pro Ser Gln Ile Asp Ser Arg Val Gln Ile Glu Asn Val
145                 150                 155                 160

Met Val Ser Asp Lys Glu Val Ser Ile Thr Ser Asp Gln Glu Thr Leu
                165                 170                 175

Asp Arg Ile Asp Lys Ile Ile Ala Val Leu Pro Thr Ser Glu Arg Ile
            180                 185                 190

Thr Gly Asn Tyr Ser Gly Ser Val Pro Leu Gln Ala Ile Asp Arg Asn
        195                 200                 205

Gly Val Val Leu Pro Ala Val Ile Thr Pro Phe Asp Thr Ile Met Lys
    210                 215                 220

Val Thr Thr Lys Pro Val Ala Pro Ser Ser Ser Thr Ser Asn Ser Ser
225                 230                 235                 240

Thr Ser Ser Ser Ser Glu Thr Ser Ser Ser Thr Lys Ala Thr Ser Ser
                245                 250                 255

Lys Thr Asn

<210> SEQ ID NO 30
<211> LENGTH: 721
<212> TYPE: PRT
<213> ORGANISM: Streptococcus pneumoniae
<220> FEATURE:
<223> OTHER INFORMATION: full length spr0867 as found in the R6 strain

<400> SEQUENCE: 30

Met Asn Leu Gly Glu Phe Trp Tyr Asn Lys Ile Asn Lys Asn Arg Gly
1               5                   10                  15

Arg Arg Leu Met Lys Lys Val Arg Phe Ile Phe Leu Ala Leu Leu Phe
                20                  25                  30

Phe Leu Ala Ser Pro Glu Gly Ala Met Ala Ser Asp Gly Thr Trp Gln
            35                  40                  45

Gly Lys Gln Tyr Leu Lys Glu Asp Gly Ser Gln Ala Ala Asn Glu Trp
        50                  55                  60

Val Phe Asp Thr His Tyr Gln Ser Trp Phe Tyr Ile Lys Ala Asp Ala
65                  70                  75                  80

Asn Tyr Ala Glu Asn Glu Trp Leu Lys Gln Gly Asp Asp Tyr Phe Tyr
                85                  90                  95

Leu Lys Ser Gly Gly Tyr Met Ala Lys Ser Glu Trp Val Glu Asp Lys
            100                 105                 110

Gly Ala Phe Tyr Tyr Leu Asp Gln Asp Gly Lys Met Lys Arg Asn Ala
        115                 120                 125

Trp Val Gly Thr Ser Tyr Val Gly Ala Thr Gly Ala Lys Val Ile Glu
    130                 135                 140

Asp Trp Val Tyr Asp Ser Gln Tyr Asp Ala Trp Phe Tyr Ile Lys Ala
145                 150                 155                 160

Asp Gly Gln His Ala Glu Lys Glu Trp Leu Gln Ile Lys Gly Lys Asp
                165                 170                 175

Tyr Tyr Phe Lys Ser Gly Gly Tyr Leu Leu Thr Ser Gln Trp Ile Asn
            180                 185                 190

Gln Ala Tyr Val Asn Ala Ser Gly Ala Lys Val Gln Gln Gly Trp Leu
        195                 200                 205

Phe Asp Lys Gln Tyr Gln Ser Trp Phe Tyr Ile Lys Glu Asn Gly Asn
    210                 215                 220

Tyr Ala Asp Lys Glu Trp Ile Phe Glu Asn Gly His Tyr Tyr Tyr Leu
225                 230                 235                 240

Lys Ser Gly Gly Tyr Met Ala Ala Asn Glu Trp Ile Trp Asp Lys Glu
```

-continued

```
                245                 250                 255
Ser Trp Phe Tyr Leu Lys Phe Asp Gly Lys Ile Ala Glu Lys Glu Trp
                    260                 265                 270

Val Tyr Asp Ser His Ser Gln Ala Trp Tyr Tyr Phe Lys Ser Gly Gly
                275                 280                 285

Tyr Met Ala Ala Asn Glu Trp Ile Trp Asp Lys Glu Ser Trp Phe Tyr
                290                 295                 300

Leu Lys Phe Asp Gly Lys Met Ala Glu Lys Glu Trp Val Tyr Asp Ser
305                 310                 315                 320

His Ser Gln Ala Trp Tyr Tyr Phe Lys Ser Gly Gly Tyr Met Thr Ala
                    325                 330                 335

Asn Glu Trp Ile Trp Asp Lys Glu Ser Trp Phe Tyr Leu Lys Ser Asp
                    340                 345                 350

Gly Lys Ile Ala Glu Lys Glu Trp Val Tyr Asp Ser His Ser Gln Ala
                    355                 360                 365

Trp Tyr Tyr Phe Lys Ser Gly Gly Tyr Met Thr Ala Asn Glu Trp Ile
                    370                 375                 380

Trp Asp Lys Glu Ser Trp Phe Tyr Leu Lys Ser Asp Gly Lys Met Ala
385                 390                 395                 400

Glu Lys Glu Trp Val Tyr Asp Ser His Ser Gln Ala Trp Tyr Tyr Phe
                    405                 410                 415

Lys Ser Gly Gly Tyr Met Ala Lys Asn Glu Thr Val Asp Gly Tyr Gln
                    420                 425                 430

Leu Gly Ser Asp Gly Lys Trp Leu Gly Gly Lys Ala Thr Asn Lys Asn
                    435                 440                 445

Ala Ala Tyr Tyr Gln Val Val Pro Val Thr Ala Asn Val Tyr Asp Ser
                    450                 455                 460

Asp Gly Glu Lys Leu Ser Tyr Ile Ser Gln Gly Ser Val Val Trp Leu
465                 470                 475                 480

Asp Lys Asp Arg Lys Ser Asp Asp Lys Arg Leu Ala Ile Thr Ile Ser
                    485                 490                 495

Gly Leu Ser Gly Tyr Met Lys Thr Glu Asp Leu Gln Ala Leu Asp Ala
                    500                 505                 510

Ser Lys Asp Phe Ile Pro Tyr Tyr Glu Ser Asp Gly His Arg Phe Tyr
                    515                 520                 525

His Tyr Val Ala Gln Asn Ala Ser Ile Pro Val Ala Ser His Leu Ser
                    530                 535                 540

Asp Met Glu Val Gly Lys Lys Tyr Tyr Ser Ala Asp Gly Leu His Phe
545                 550                 555                 560

Asp Gly Phe Lys Leu Glu Asn Pro Phe Leu Phe Lys Asp Leu Thr Glu
                    565                 570                 575

Ala Thr Asn Tyr Ser Ala Glu Glu Leu Asp Lys Val Phe Ser Leu Leu
                    580                 585                 590

Asn Ile Asn Asn Ser Leu Leu Glu Asn Lys Gly Ala Thr Phe Lys Glu
                    595                 600                 605

Ala Glu Glu His Tyr His Ile Asn Ala Leu Tyr Leu Leu Ala His Ser
                    610                 615                 620

Ala Leu Glu Ser Asn Trp Gly Arg Ser Lys Ile Ala Lys Asp Lys Asn
625                 630                 635                 640

Asn Phe Phe Gly Ile Thr Ala Tyr Asp Thr Thr Pro Tyr Leu Ser Ala
                    645                 650                 655

Lys Thr Phe Asp Asp Val Asp Lys Gly Ile Leu Gly Ala Thr Lys Trp
                    660                 665                 670
```

```
Ile Lys Glu Asn Tyr Ile Asp Arg Gly Arg Thr Phe Leu Gly Asn Lys
            675                 680                 685

Ala Ser Gly Met Asn Val Glu Tyr Ala Ser Asp Pro Tyr Trp Gly Glu
            690                 695                 700

Lys Ile Ala Ser Met Met Lys Ile Asn Glu Lys Leu Gly Gly Lys
705                 710                 715                 720

Asp

<210> SEQ ID NO 31
<211> LENGTH: 501
<212> TYPE: PRT
<213> ORGANISM: Streptococcus pneumoniae
<220> FEATURE:
<223> OTHER INFORMATION: full length spr1431 as found in the R6 strain

<400> SEQUENCE: 31

Met Ser Val Thr Phe Phe Ile Gly Glu Glu Arg Leu Lys Ile Lys Ile
1               5                   10                  15

Gly Leu Ala Ser Ile Cys Leu Leu Gly Leu Ala Thr Ser His Val Ala
            20                  25                  30

Ala Asn Glu Thr Glu Val Ala Lys Thr Ser Gln Asp Thr Thr Thr Ala
        35                  40                  45

Ser Ser Ser Ser Glu Gln Asn Gln Ser Ser Asn Lys Thr Gln Thr Ser
50                  55                  60

Ala Glu Val Gln Thr Asn Ala Ala Tyr Trp Asp Gly Asp Tyr Tyr
65                  70                  75                  80

Val Lys Asp Asp Gly Ser Lys Ala Gln Ser Glu Trp Ile Phe Asp Asn
                85                  90                  95

Tyr Tyr Lys Ala Trp Phe Tyr Ile Asn Ser Asp Gly Arg Tyr Ser Gln
            100                 105                 110

Asn Glu Trp His Gly Asn Tyr Tyr Leu Lys Ser Gly Tyr Met Ala
        115                 120                 125

Gln Asn Glu Trp Ile Tyr Asp Ser Asn Tyr Lys Ser Trp Phe Tyr Leu
130                 135                 140

Lys Ser Asp Gly Ala Tyr Ala His Gln Glu Trp Gln Leu Ile Gly Asn
145                 150                 155                 160

Lys Trp Tyr Tyr Phe Lys Lys Trp Gly Tyr Met Ala Lys Ser Gln Trp
                165                 170                 175

Gln Gly Ser Tyr Phe Leu Asn Gly Gln Gly Ala Met Ile Gln Asn Glu
            180                 185                 190

Trp Leu Tyr Asp Pro Ala Tyr Ser Ala Tyr Phe Tyr Leu Lys Ser Asp
        195                 200                 205

Gly Thr Tyr Ala Asn Gln Glu Trp Gln Lys Val Gly Gly Lys Trp Tyr
210                 215                 220

Tyr Phe Lys Lys Trp Gly Tyr Met Ala Arg Asn Glu Trp Gln Gly Asn
225                 230                 235                 240

Tyr Tyr Leu Thr Gly Ser Gly Ala Met Ala Thr Asp Glu Val Ile Met
                245                 250                 255

Asp Gly Ala Arg Tyr Ile Phe Ala Ala Ser Gly Glu Leu Lys Glu Lys
            260                 265                 270

Lys Asp Leu Asn Val Gly Trp Val His Arg Asp Gly Lys Arg Tyr Phe
        275                 280                 285

Phe Asn Asn Arg Glu Glu Gln Val Gly Thr Glu His Ala Lys Lys Ile
    290                 295                 300

Ile Asp Ile Ser Glu His Asn Gly Arg Ile Asn Asp Trp Lys Lys Val
305                 310                 315                 320
```

-continued

```
Ile Asp Glu Asn Lys Val Asp Gly Val Ile Val Arg Leu Gly Tyr Ser
            325                 330                 335

Gly Lys Glu Asp Lys Glu Leu Ala His Asn Ile Lys Glu Leu Asn Arg
            340                 345                 350

Leu Gly Ile Pro Tyr Gly Val Tyr Leu Tyr Thr Tyr Ala Glu Asn Glu
            355                 360                 365

Thr Asp Ala Glu Asn Asp Ala Lys Gln Thr Ile Glu Leu Ile Lys Lys
370                 375                 380

Tyr Asn Met Asn Leu Ser Tyr Pro Ile Tyr Tyr Asp Val Glu Asn Trp
385                 390                 395                 400

Glu Tyr Val Asn Lys Ser Lys Arg Ala Pro Ser Asp Thr Asp Thr Trp
            405                 410                 415

Val Lys Ile Ile Asn Lys Tyr Met Asp Thr Met Lys Gln Ala Gly Tyr
            420                 425                 430

Gln Asn Val Tyr Val Tyr Ser Tyr Arg Ser Leu Leu Gln Thr Arg Leu
            435                 440                 445

Lys His Pro Asp Ile Leu Lys His Val Asn Trp Val Ala Ala Tyr Thr
            450                 455                 460

Asn Ala Leu Glu Trp Glu Asn Pro Tyr Tyr Ser Gly Glu Lys Gly Trp
465                 470                 475                 480

Gln Tyr Thr Ser Ser Glu Tyr Met Lys Gly Ile Gln Gly Arg Val Asp
            485                 490                 495

Val Ser Val Trp Tyr
            500

<210> SEQ ID NO 32
<211> LENGTH: 471
<212> TYPE: PRT
<213> ORGANISM: Streptococcus pneumoniae
<220> FEATURE:
<223> OTHER INFORMATION: full length spr1739 as found in the R6 strain

<400> SEQUENCE: 32

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
        50                  55                  60

Thr Asn Asp Ser Arg Leu Tyr Pro Gly Ala Leu Val Val Asp Glu
65                  70                  75              80

Thr Leu Leu Glu Asn Asn Pro Thr Leu Leu Ala Val Asp Arg Ala Pro
            85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
            130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
            165                 170                 175
```

```
Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Ser Lys Ser
                245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
            290                 295                 300

Gly Lys Val Asp Met Val Glu Asp Leu Ile Gln Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asp Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
            450                 455                 460

Glu Asp Lys Val Glu Asn Asp
465                 470

<210> SEQ ID NO 33
<211> LENGTH: 392
<212> TYPE: PRT
<213> ORGANISM: Streptococcus pneumoniae
<220> FEATURE:
<223> OTHER INFORMATION: spr2021 as found in the R6 strain

<400> SEQUENCE: 33

Met Lys Lys Lys Ile Leu Ala Ser Leu Leu Leu Ser Thr Val Met Val
1               5                   10                  15

Ser Gln Val Ala Val Leu Thr Thr Ala His Ala Glu Thr Thr Asp Asp
                20                  25                  30

Lys Ile Ala Ala Gln Asp Asn Lys Ile Ser Asn Leu Thr Ala Gln Gln
            35                  40                  45

Gln Glu Ala Gln Lys Gln Val Asp Gln Ile Gln Glu Gln Val Ser Ala
50                  55                  60

Ile Gln Ala Glu Gln Ser Asn Leu Gln Ala Glu Asn Asp Arg Leu Gln
```

```
                65                  70                  75                  80
Ala Glu Ser Lys Lys Leu Glu Gly Glu Ile Thr Glu Leu Ser Lys Asn
                        85                  90                  95

Ile Val Ser Arg Asn Gln Ser Leu Glu Lys Gln Ala Arg Ser Ala Gln
                100                 105                 110

Thr Asn Gly Ala Val Thr Ser Tyr Ile Asn Thr Ile Val Asn Ser Lys
                115                 120                 125

Ser Ile Thr Glu Ala Ile Ser Arg Val Ala Ala Met Ser Glu Ile Val
                130                 135                 140

Ser Ala Asn Asn Lys Met Leu Glu Gln Gln Lys Ala Asp Lys Lys Ala
145                 150                 155                 160

Ile Ser Glu Lys Gln Val Ala Asn Asn Asp Ala Ile Asn Thr Val Ile
                165                 170                 175

Ala Asn Gln Gln Lys Leu Ala Asp Asp Ala Gln Ala Leu Thr Thr Lys
                180                 185                 190

Gln Ala Glu Leu Lys Ala Ala Glu Leu Ser Leu Ala Ala Glu Lys Ala
                195                 200                 205

Thr Ala Glu Gly Glu Lys Ala Ser Leu Leu Glu Gln Lys Ala Ala Ala
210                 215                 220

Glu Ala Glu Ala Arg Ala Ala Val Ala Glu Ala Tyr Lys Glu
225                 230                 235                 240

Lys Arg Ala Ser Gln Gln Gln Ser Val Leu Ala Ser Ala Asn Thr Asn
                245                 250                 255

Leu Thr Ala Gln Val Gln Ala Val Ser Glu Ser Ala Ala Ala Pro Val
                260                 265                 270

Arg Ala Lys Val Arg Pro Thr Tyr Ser Thr Asn Ala Ser Ser Tyr Pro
                275                 280                 285

Ile Gly Glu Cys Thr Trp Gly Val Lys Thr Leu Ala Pro Trp Ala Gly
                290                 295                 300

Asp Tyr Trp Gly Asn Gly Ala Gln Trp Ala Thr Ser Ala Ala Ala Ala
305                 310                 315                 320

Gly Phe Arg Thr Gly Ser Thr Pro Gln Val Gly Ala Ile Ala Cys Trp
                325                 330                 335

Asn Asp Gly Gly Tyr Gly His Val Ala Val Val Thr Ala Val Glu Ser
                340                 345                 350

Thr Thr Arg Ile Gln Val Ser Glu Ser Asn Tyr Ala Gly Asn Arg Thr
                355                 360                 365

Ile Gly Asn His Arg Gly Trp Phe Asn Pro Thr Thr Ser Glu Gly
                370                 375                 380

Phe Val Thr Tyr Ile Tyr Ala Asp
385                 390

<210> SEQ ID NO 34
<211> LENGTH: 167
<212> TYPE: PRT
<213> ORGANISM: Streptococcus pneumoniae
<220> FEATURE:
<223> OTHER INFORMATION: full length spr0096 as found in the R6 strain

<400> SEQUENCE: 34

Met Lys Ser Ile Thr Lys Lys Ile Lys Ala Thr Leu Ala Gly Val Ala
1               5                   10                  15

Ala Leu Phe Ala Val Phe Ala Pro Ser Phe Val Ser Ala Gln Glu Ser
                20                  25                  30

Ser Thr Tyr Thr Val Lys Glu Gly Asp Thr Leu Ser Glu Ile Ala Glu
                35                  40                  45
```

```
Thr His Asn Thr Thr Val Glu Lys Leu Ala Glu Asn His Ile Asp
         50                  55                  60

Asn Ile His Leu Ile Tyr Val Asp Gln Glu Leu Val Ile Asp Gly Pro
65                  70                  75                  80

Val Ala Pro Val Ala Thr Pro Ala Pro Ala Thr Tyr Ala Ala Pro Ala
             85                  90                  95

Ala Gln Asp Glu Thr Val Ser Ala Pro Val Ala Glu Thr Pro Val Val
            100                 105                 110

Ser Glu Thr Val Val Ser Thr Val Ser Gly Ser Glu Ala Glu Ala Lys
            115                 120                 125

Glu Trp Ile Ala Gln Lys Glu Ser Gly Gly Ser Tyr Thr Ala Thr Asn
            130                 135                 140

Gly Arg Tyr Ile Gly Arg Tyr Gly Ser Trp Thr Ala Ala Lys Asn Phe
145                 150                 155                 160

Trp Leu Asn Asn Gly Trp Tyr
                165

<210> SEQ ID NO 35
<211> LENGTH: 380
<212> TYPE: PRT
<213> ORGANISM: Streptococcus pneumoniae
<220> FEATURE:
<223> OTHER INFORMATION: full length spr1875 as found in the R6 strain

<400> SEQUENCE: 35

Met Lys Lys Arg Met Leu Leu Ala Ser Thr Val Ala Leu Ser Phe Ala
1               5                   10                  15

Pro Val Leu Ala Thr Gln Ala Glu Glu Val Leu Trp Thr Ala Arg Ser
            20                  25                  30

Val Glu Gln Ile Gln Asn Asp Leu Thr Lys Thr Asp Asn Lys Thr Ser
        35                  40                  45

Tyr Thr Val Gln Tyr Gly Asp Thr Leu Ser Thr Ile Ala Glu Ala Leu
    50                  55                  60

Gly Val Asp Val Thr Val Leu Ala Asn Leu Asn Lys Ile Thr Asn Met
65                  70                  75                  80

Asp Leu Ile Phe Pro Glu Thr Val Leu Thr Thr Thr Val Asn Glu Ala
                85                  90                  95

Glu Glu Val Thr Glu Val Glu Ile Gln Thr Pro Gln Ala Asp Ser Ser
            100                 105                 110

Glu Glu Val Thr Thr Ala Thr Ala Asp Leu Thr Thr Asn Gln Val Thr
            115                 120                 125

Val Asp Asp Gln Thr Val Gln Val Ala Asp Leu Ser Gln Pro Ile Ala
            130                 135                 140

Glu Ala Pro Lys Glu Val Ala Ser Ser Ser Glu Val Thr Lys Thr Val
145                 150                 155                 160

Ile Ala Ser Glu Glu Val Ala Pro Ser Thr Gly Thr Ser Val Pro Glu
                165                 170                 175

Glu Gln Thr Ala Glu Thr Ser Ser Ala Val Ala Glu Glu Ala Pro Gln
            180                 185                 190

Glu Thr Thr Pro Ala Glu Lys Gln Glu Thr Gln Thr Ser Pro Gln Ala
            195                 200                 205

Ala Ser Ala Val Glu Ala Thr Thr Ser Ser Glu Ala Lys Glu Val
            210                 215                 220

Ala Ser Ser Asn Gly Ala Thr Ala Ala Val Ser Thr Tyr Gln Pro Glu
225                 230                 235                 240
```

-continued

Glu Thr Lys Ile Ile Ser Thr Thr Tyr Glu Ala Pro Ala Ala Pro Asp
                245                 250                 255

Tyr Ala Gly Leu Ala Val Ala Lys Ser Glu Asn Ala Gly Leu Gln Pro
            260                 265                 270

Gln Thr Ala Ala Phe Lys Glu Glu Ile Ala Asn Leu Phe Gly Ile Thr
        275                 280                 285

Ser Phe Ser Gly Tyr Arg Pro Gly Asp Ser Gly Asp His Gly Lys Gly
    290                 295                 300

Leu Ala Ile Asp Phe Met Val Pro Glu Arg Ser Glu Leu Gly Asp Lys
305                 310                 315                 320

Ile Ala Glu Tyr Ala Ile Gln Asn Met Ala Ser Arg Gly Ile Ser Tyr
                325                 330                 335

Ile Ile Trp Lys Gln Arg Phe Tyr Ala Pro Phe Asp Ser Lys Tyr Gly
            340                 345                 350

Pro Ala Asn Thr Trp Asn Pro Met Pro Asp Arg Gly Ser Val Thr Glu
        355                 360                 365

Asn His Tyr Asp His Val His Val Ser Met Asn Gly
    370                 375                 380

<210> SEQ ID NO 36
<211> LENGTH: 659
<212> TYPE: PRT
<213> ORGANISM: Streptococcus pneumoniae
<220> FEATURE:
<223> OTHER INFORMATION: full length spr1707 as found in the R6 strain

<400> SEQUENCE: 36

Met Lys Lys Asn Arg Val Phe Ala Thr Ala Gly Leu Val Leu Leu Ala
1               5                   10                  15

Ala Gly Val Leu Ala Ala Cys Ser Ser Ser Lys Ser Ser Asp Ser Ser
            20                  25                  30

Ala Pro Lys Ala Tyr Gly Tyr Val Tyr Thr Ala Asp Pro Glu Thr Leu
        35                  40                  45

Asp Tyr Leu Ile Ser Arg Lys Asn Ser Thr Thr Val Val Thr Ser Asn
    50                  55                  60

Gly Ile Asp Gly Leu Phe Thr Asn Asp Asn Tyr Gly Asn Leu Ala Pro
65                  70                  75                  80

Ala Val Ala Glu Asp Trp Glu Val Ser Lys Asp Gly Leu Thr Tyr Thr
                85                  90                  95

Tyr Lys Ile Arg Lys Gly Val Lys Trp Phe Thr Ser Asp Gly Glu Glu
            100                 105                 110

Tyr Ala Glu Val Thr Ala Lys Asp Phe Val Asn Gly Leu Lys His Ala
        115                 120                 125

Ala Asp Lys Lys Ser Glu Ala Met Tyr Leu Ala Glu Asn Ser Val Lys
    130                 135                 140

Gly Leu Ala Asp Tyr Leu Ser Gly Thr Ser Thr Asp Phe Ser Thr Val
145                 150                 155                 160

Gly Val Lys Ala Val Asp Asp Tyr Thr Leu Gln Tyr Thr Leu Asn Gln
                165                 170                 175

Pro Glu Pro Phe Trp Asn Ser Lys Leu Thr Tyr Ser Ile Phe Trp Pro
            180                 185                 190

Leu Asn Glu Glu Phe Glu Thr Ser Lys Gly Ser Asp Phe Ala Lys Pro
        195                 200                 205

Thr Asp Pro Thr Ser Leu Leu Tyr Asn Gly Pro Phe Leu Leu Lys Gly
    210                 215                 220

Leu Thr Ala Lys Ser Ser Val Glu Phe Val Lys Asn Glu Gln Tyr Trp

```
                225                 230                 235                 240
Asp Lys Glu Asn Val His Leu Asp Thr Ile Asn Leu Ala Tyr Tyr Asp
                    245                 250                 255
Gly Ser Asp Gln Glu Ser Leu Glu Arg Asn Phe Thr Ser Gly Ala Tyr
                260                 265                 270
Ser Tyr Ala Arg Leu Tyr Pro Thr Ser Ser Asn Tyr Ser Lys Val Ala
                275                 280                 285
Glu Glu Tyr Lys Asp Asn Ile Tyr Tyr Thr Gln Ser Gly Ser Gly Ile
            290                 295                 300
Ala Gly Leu Gly Val Asn Ile Asp Arg Gln Ser Tyr Asn Tyr Thr Ser
305                 310                 315                 320
Lys Thr Thr Asp Ser Glu Lys Val Ala Thr Lys Ala Leu Leu Asn
                325                 330                 335
Lys Asp Phe Arg Gln Ala Leu Asn Phe Ala Leu Asp Arg Ser Ala Tyr
                340                 345                 350
Ser Ala Gln Ile Asn Gly Lys Asp Gly Ala Ala Leu Ala Val Arg Asn
                355                 360                 365
Leu Phe Val Lys Pro Asp Phe Val Ser Ala Gly Glu Lys Thr Phe Gly
            370                 375                 380
Asp Leu Val Ala Ala Gln Leu Pro Ala Tyr Gly Asp Glu Trp Lys Gly
385                 390                 395                 400
Val Asn Leu Ala Asp Gly Gln Asp Gly Leu Phe Asn Ala Asp Lys Ala
                405                 410                 415
Lys Ala Glu Phe Ala Lys Ala Lys Ala Leu Glu Ala Asp Gly Val
                420                 425                 430
Gln Phe Pro Ile His Leu Asp Val Pro Val Asp Gln Ala Ser Lys Asn
                435                 440                 445
Tyr Ile Ser Arg Ile Gln Ser Phe Lys Gln Ser Val Glu Thr Val Leu
            450                 455                 460
Gly Val Glu Asn Val Val Val Asp Ile Gln Gln Met Thr Ser Asp Glu
465                 470                 475                 480
Phe Leu Asn Ile Thr Tyr Tyr Ala Ala Asn Ala Ser Ser Glu Asp Trp
                485                 490                 495
Asp Val Ser Gly Gly Val Ser Trp Gly Pro Asp Tyr Gln Asp Pro Ser
                500                 505                 510
Thr Tyr Leu Asp Ile Leu Lys Thr Thr Ser Glu Thr Thr Lys Thr
            515                 520                 525
Tyr Leu Gly Phe Asp Asn Pro Asn Ser Pro Ser Val Val Gln Val Gly
            530                 535                 540
Leu Lys Glu Tyr Asp Lys Leu Val Asp Glu Ala Ala Lys Glu Thr Ser
545                 550                 555                 560
Asp Leu Asn Val Arg Tyr Glu Lys Tyr Ala Ala Ala Gln Ala Trp Leu
                565                 570                 575
Thr Asp Ser Ser Leu Phe Ile Pro Ala Met Ala Ser Ser Gly Ala Ala
                580                 585                 590
Pro Val Leu Ser Arg Ile Val Pro Phe Thr Gly Ala Ser Ala Gln Thr
            595                 600                 605
Gly Ser Lys Gly Ser Asp Val Tyr Phe Lys Tyr Leu Lys Leu Gln Asp
            610                 615                 620
Lys Ala Val Thr Lys Glu Glu Tyr Glu Lys Ala Arg Glu Lys Trp Leu
625                 630                 635                 640
Lys Glu Lys Ala Glu Ser Asn Glu Lys Ala Gln Lys Glu Leu Ala Ser
                645                 650                 655
```

His Val Lys

<210> SEQ ID NO 37
<211> LENGTH: 313
<212> TYPE: PRT
<213> ORGANISM: Streptococcus pneumoniae
<220> FEATURE:
<223> OTHER INFORMATION: amino acid sequence of full length spr0884

<400> SEQUENCE: 37

Met Lys Lys Lys Leu Leu Ala Gly Ala Ile Thr Leu Leu Ser Val Ala
1               5                   10                  15

Thr Leu Ala Ala Cys Ser Lys Gly Ser Glu Gly Ala Asp Leu Ile Ser
            20                  25                  30

Met Lys Gly Asp Val Ile Thr Glu His Gln Phe Tyr Glu Gln Val Lys
        35                  40                  45

Asn Asn Pro Ser Ala Gln Gln Val Leu Leu Asn Met Thr Ile Gln Lys
    50                  55                  60

Val Phe Glu Lys Gln Tyr Gly Ser Glu Leu Asp Asp Lys Glu Val Asp
65                  70                  75                  80

Asp Thr Ile Ala Glu Glu Lys Lys Gln Tyr Gly Glu Asn Tyr Gln Arg
                85                  90                  95

Val Leu Ser Gln Ala Gly Met Thr Leu Glu Thr Arg Lys Ala Gln Ile
            100                 105                 110

Arg Thr Ser Lys Leu Val Glu Leu Ala Val Lys Lys Val Ala Glu Ala
        115                 120                 125

Glu Leu Thr Asp Glu Ala Tyr Lys Lys Ala Phe Asp Glu Tyr Thr Pro
    130                 135                 140

Asp Val Thr Ala Gln Ile Ile Arg Leu Asn Asn Glu Asp Lys Ala Lys
145                 150                 155                 160

Glu Val Leu Glu Lys Ala Lys Ala Glu Gly Ala Asp Phe Ala Gln Leu
                165                 170                 175

Ala Lys Asp Asn Ser Thr Asp Glu Lys Thr Lys Glu Asn Gly Gly Glu
            180                 185                 190

Ile Thr Phe Asp Ser Ala Ser Thr Glu Val Pro Glu Gln Val Lys Lys
        195                 200                 205

Ala Ala Phe Ala Leu Asp Val Asp Gly Val Ser Asp Val Ile Thr Ala
    210                 215                 220

Thr Gly Thr Gln Ala Tyr Ser Ser Gln Tyr Tyr Ile Val Lys Leu Thr
225                 230                 235                 240

Lys Lys Thr Glu Lys Ser Ser Asn Ile Asp Asp Tyr Lys Glu Lys Leu
                245                 250                 255

Lys Thr Val Ile Leu Thr Gln Lys Gln Asn Asp Ser Thr Phe Val Gln
            260                 265                 270

Ser Ile Ile Gly Lys Glu Leu Gln Ala Ala Asn Ile Lys Val Lys Asp
        275                 280                 285

Gln Ala Phe Gln Asn Ile Phe Thr Gln Tyr Ile Gly Gly Gly Asp Ser
    290                 295                 300

Ser Ser Ser Ser Ser Thr Ser Asn Glu
305                 310

<210> SEQ ID NO 38
<211> LENGTH: 1247
<212> TYPE: PRT
<213> ORGANISM: Streptococcus pneumoniae
<220> FEATURE:
<223> OTHER INFORMATION: spr0057 protein which omits the natural leader
      peptide and sortase recognition sequences

<400> SEQUENCE: 38

Ala Asp Gly Val Thr Pro Thr Thr Glu Asn Gln Pro Thr Ile His
1               5                   10                  15

Thr Val Ser Asp Ser Pro Gln Ser Ser Glu Asn Arg Thr Glu Glu Thr
            20                  25                  30

Pro Lys Ala Glu Leu Gln Pro Glu Ala Pro Lys Thr Val Glu Thr Glu
        35                  40                  45

Thr Pro Ala Thr Asp Lys Val Ala Ser Leu Pro Lys Thr Glu Glu Lys
    50                  55                  60

Pro Gln Glu Glu Val Ser Ser Thr Pro Ser Asp Lys Ala Glu Val Val
65                  70                  75                  80

Thr Pro Thr Ser Ala Glu Lys Glu Thr Ala Asn Lys Lys Glu Glu Glu
                85                  90                  95

Ala Ser Pro Lys Lys Glu Ala Lys Glu Val Asp Ser Lys Glu Ser
            100                 105                 110

Asn Thr Asp Lys Thr Asp Lys Asp Lys Pro Ala Lys Lys Asp Glu Ala
        115                 120                 125

Lys Ala Glu Ala Asp Lys Pro Glu Thr Glu Thr Gly Lys Glu Arg Ala
130                 135                 140

Ala Thr Val Asn Glu Lys Leu Ala Lys Lys Ile Val Ser Ile Asp
145                 150                 155                 160

Ala Gly Arg Lys Tyr Phe Ser Pro Glu Gln Leu Lys Glu Ile Ile Asp
            165                 170                 175

Lys Ala Lys His Tyr Gly Tyr Thr Asp Leu His Leu Leu Val Gly Asn
        180                 185                 190

Asp Gly Leu Arg Phe Met Leu Asp Asp Met Ser Ile Thr Ala Asn Gly
        195                 200                 205

Lys Thr Tyr Ala Ser Asp Asp Val Lys Arg Ala Ile Glu Lys Gly Thr
210                 215                 220

Asn Asp Tyr Tyr Asn Asp Pro Asn Gly Asn His Leu Thr Glu Ser Gln
225                 230                 235                 240

Met Thr Asp Leu Ile Asn Tyr Ala Lys Asp Lys Gly Ile Gly Leu Ile
            245                 250                 255

Pro Thr Val Asn Ser Pro Gly His Met Asp Ala Ile Leu Asn Ala Met
        260                 265                 270

Lys Glu Leu Gly Ile Gln Asn Pro Asn Phe Ser Tyr Phe Gly Lys Lys
        275                 280                 285

Ser Ala Arg Thr Val Asp Leu Asp Asn Glu Gln Ala Val Ala Phe Thr
290                 295                 300

Lys Ala Leu Ile Asp Lys Tyr Ala Ala Tyr Phe Ala Lys Lys Thr Glu
305                 310                 315                 320

Ile Phe Asn Ile Gly Leu Asp Glu Tyr Ala Asn Asp Ala Thr Asp Ala
            325                 330                 335

Lys Gly Trp Ser Val Leu Gln Ala Asp Lys Tyr Tyr Pro Asn Glu Gly
        340                 345                 350

Tyr Pro Val Lys Gly Tyr Glu Lys Phe Ile Ala Tyr Ala Asn Asp Leu
        355                 360                 365

Ala Arg Ile Val Lys Ser His Gly Leu Lys Pro Met Ala Phe Asn Asp
370                 375                 380

Gly Ile Tyr Tyr Asn Ser Asp Thr Ser Phe Gly Ser Phe Asp Lys Asp
385                 390                 395                 400

Ile Ile Val Ser Met Trp Thr Gly Gly Trp Gly Gly Tyr Asp Val Ala
            405                 410                 415

-continued

```
Ser Ser Lys Leu Leu Ala Glu Lys Gly His Gln Ile Leu Asn Thr Asn
        420                 425                 430
Asp Ala Trp Cys Tyr Val Leu Arg Asn Ala Asp Gly Gln Gly Trp
        435                 440                 445
Tyr Asn Leu Asp Gln Gly Leu Asn Gly Ile Lys Asn Thr Pro Ile Thr
450                     455                 460
Ser Val Pro Lys Thr Glu Gly Ala Asp Ile Pro Ile Ile Gly Gly Met
465                 470                 475                 480
Val Ala Ala Trp Ala Asp Thr Pro Ser Ala Arg Tyr Ser Pro Ser His
                485                 490                 495
Leu Phe Lys Leu Met Arg His Phe Ala Asn Ala Asn Ala Glu Tyr Phe
            500                 505                 510
Ala Ala Asp Tyr Glu Ser Ala Glu Gln Ala Leu Asn Glu Val Pro Lys
            515                 520                 525
Asp Leu Asn Arg Tyr Thr Ala Glu Ser Val Ala Val Lys Glu Ala
        530                 535                 540
Glu Lys Ala Ile Arg Ser Leu Asp Ser Asn Leu Ser Arg Ala Gln Gln
545                 550                 555                 560
Asp Thr Ile Asp Gln Ala Ile Ala Lys Leu Gln Glu Thr Val Asn Asn
                565                 570                 575
Leu Thr Leu Thr Pro Glu Ala Gln Lys Glu Glu Ala Lys Arg Glu
            580                 585                 590
Val Glu Lys Leu Ala Lys Asn Lys Val Ile Ser Ile Asp Ala Gly Arg
        595                 600                 605
Lys Tyr Phe Thr Leu Asp Gln Leu Lys Arg Ile Val Asp Lys Ala Ser
610                 615                 620
Glu Leu Gly Tyr Ser Asp Val His Leu Leu Gly Asn Asp Gly Leu
625                 630                 635                 640
Arg Phe Leu Leu Asn Asp Met Thr Ile Thr Ala Asn Gly Lys Thr Tyr
                645                 650                 655
Ala Ser Asp Asp Val Lys Lys Ala Ile Ile Glu Gly Thr Lys Ala Tyr
                660                 665                 670
Tyr Asp Asp Pro Asn Gly Thr Ala Leu Thr Gln Ala Glu Val Thr Glu
        675                 680                 685
Leu Ile Glu Tyr Ala Lys Ser Lys Asp Ile Gly Leu Ile Pro Ala Ile
        690                 695                 700
Asn Ser Pro Gly His Met Asp Ala Met Leu Val Ala Met Glu Lys Leu
705                 710                 715                 720
Gly Ile Lys Asn Pro Gln Ala His Phe Asp Lys Val Ser Lys Thr Thr
                725                 730                 735
Met Asp Leu Lys Asn Glu Glu Ala Met Asn Phe Val Lys Ala Leu Ile
            740                 745                 750
Gly Lys Tyr Met Asp Phe Phe Ala Gly Lys Thr Lys Ile Phe Asn Phe
        755                 760                 765
Gly Thr Asp Glu Tyr Ala Asn Asp Ala Thr Ser Ala Gln Gly Trp Tyr
    770                 775                 780
Tyr Leu Lys Trp Tyr Gln Leu Tyr Gly Lys Phe Ala Glu Tyr Ala Asn
785                 790                 795                 800
Thr Leu Ala Ala Met Ala Lys Glu Arg Gly Leu Gln Pro Met Ala Phe
                805                 810                 815
Asn Asp Gly Phe Tyr Tyr Glu Asp Lys Asp Val Gln Phe Asp Lys
            820                 825                 830
Asp Val Leu Ile Ser Tyr Trp Ser Lys Gly Trp Trp Gly Tyr Asn Leu
```

-continued

```
                 835                 840                 845
Ala Ser Pro Gln Tyr Leu Ala Ser Lys Gly Tyr Lys Phe Leu Asn Thr
850                 855                 860
Asn Gly Asp Trp Tyr Tyr Val Ile Gly Asn His Lys Gln Asp Glu Ala
865                 870                 875                 880
Tyr Pro Leu Ser Lys Ala Val Glu Asn Ser Gly Lys Val Pro Phe Asn
                885                 890                 895
Gln Leu Ala Ser Thr Lys Tyr Pro Glu Val Asp Leu Pro Thr Val Gly
                900                 905                 910
Ser Met Leu Ser Ile Trp Ala Asp Arg Pro Ser Ala Glu Tyr Lys Glu
                915                 920                 925
Glu Glu Ile Phe Glu Leu Met Thr Ala Phe Ala Asp His Asn Lys Asp
                930                 935                 940
Tyr Phe Arg Ala Asn Tyr Asn Ala Leu Arg Glu Glu Leu Ala Lys Ile
945                 950                 955                 960
Pro Thr Asn Leu Glu Gly Tyr Ser Lys Glu Ser Leu Glu Ala Leu Asp
                965                 970                 975
Ala Ala Lys Thr Ala Leu Asn Tyr Asn Leu Asn Arg Asn Lys Gln Ala
                980                 985                 990
Glu Leu Asp Thr Leu Val Ala Asn Leu Lys Ala Leu Gln Gly Leu
                995                 1000                1005
Lys Pro Ala Ala Thr His Ser Gly Ser Leu Asp Glu Asn Glu Val Ala
                1010                1015                1020
Ala Asn Val Glu Thr Arg Pro Glu Leu Ile Thr Arg Thr Glu Glu Ile
1025                1030                1035                1040
Pro Phe Glu Val Ile Lys Lys Glu Asn Pro Asn Leu Pro Ala Gly Gln
                1045                1050                1055
Glu Asn Ile Ile Thr Ala Gly Val Lys Gly Glu Arg Thr His Tyr Ile
                1060                1065                1070
Ser Val Leu Thr Glu Asn Gly Lys Thr Thr Glu Thr Val Leu Asp Ser
                1075                1080                1085
Gln Val Thr Lys Glu Val Ile Asn Gln Val Val Glu Val Gly Ser Pro
                1090                1095                1100
Val Thr His Lys Gly Asp Glu Ser Gly Leu Ala Pro Thr Thr Glu Val
1105                1110                1115                1120
Lys Pro Arg Leu Asp Ile Gln Glu Glu Ile Pro Phe Thr Thr Val
                1125                1130                1135
Thr Arg Glu Asn Pro Leu Leu Leu Lys Gly Lys Thr Gln Val Ile Thr
                1140                1145                1150
Lys Gly Val Asn Gly His Arg Ser Asn Phe Tyr Ser Val Ser Thr Ser
                1155                1160                1165
Ala Asp Gly Lys Glu Val Lys Thr Leu Val Asn Ser Val Val Ala Gln
                1170                1175                1180
Glu Ala Val Thr Gln Ile Val Glu Val Gly Thr Met Val Thr His Val
1185                1190                1195                1200
Gly Asp Glu Asn Gly Gln Ala Ala Ile Ala Glu Glu Lys Pro Lys Leu
                1205                1210                1215
Glu Ile Pro Ser Gln Pro Ala Pro Ser Thr Ala Pro Ala Glu Glu Ser
                1220                1225                1230
Lys Ala Leu Pro Gln Asp Pro Ala Pro Val Val Thr Glu Lys Lys
                1235                1240                1245

<210> SEQ ID NO 39
<211> LENGTH: 1008
```

```
<212> TYPE: PRT
<213> ORGANISM: Streptococcus pneumoniae
<220> FEATURE:
<223> OTHER INFORMATION: spr0286

<400> SEQUENCE: 39

Gly Ala Glu Glu Thr Thr Thr Asn Thr Ile Gln Gln Ser Gln Lys Glu
1               5                   10                  15

Val Gln Tyr Gln Gln Arg Asp Thr Lys Asn Leu Val Glu Asn Gly Asp
            20                  25                  30

Phe Gly Gln Thr Glu Asp Gly Ser Ser Pro Trp Thr Gly Ser Lys Ala
        35                  40                  45

Gln Gly Trp Ser Ala Trp Val Asp Gln Lys Asn Ser Ser Ala Asp Ala
    50                  55                  60

Ser Thr Arg Val Ile Glu Ala Lys Asp Gly Ala Ile Thr Ile Ser Ser
65                  70                  75                  80

Pro Glu Lys Leu Arg Ala Ala Val His Arg Met Val Pro Ile Glu Ala
                85                  90                  95

Lys Lys Lys Tyr Lys Leu Arg Phe Lys Ile Lys Thr Asp Asn Lys Val
            100                 105                 110

Gly Ile Ala Lys Val Arg Ile Glu Glu Ser Gly Lys Asp Lys Arg
        115                 120                 125

Leu Trp Asn Ser Ala Thr Thr Ser Gly Thr Lys Asp Trp Gln Thr Ile
130                 135                 140

Glu Ala Asp Tyr Ser Pro Thr Leu Asp Val Asp Lys Ile Lys Leu Glu
145                 150                 155                 160

Leu Phe Tyr Glu Thr Gly Thr Gly Thr Val Ser Phe Lys Asp Ile Glu
                165                 170                 175

Leu Val Glu Val Ala Asp Gln Pro Ser Glu Asp Ser Thr Asp Lys
            180                 185                 190

Gln Leu Glu Glu Lys Ile Asp Leu Pro Ile Gly Lys Lys His Val Phe
        195                 200                 205

Ser Leu Ala Asp Tyr Thr Tyr Lys Val Glu Asn Pro Asp Val Ala Ser
    210                 215                 220

Val Lys Asn Gly Ile Leu Glu Pro Leu Lys Glu Gly Thr Thr Asn Val
225                 230                 235                 240

Ile Val Ser Lys Asp Gly Lys Glu Val Lys Ile Pro Leu Lys Ile
                245                 250                 255

Leu Ala Ser Val Lys Asp Thr Tyr Thr Asp Arg Leu Asp Asp Trp Asn
            260                 265                 270

Gly Ile Ile Ala Gly Asn Gln Tyr Tyr Asp Ser Lys Asn Glu Gln Met
        275                 280                 285

Ala Lys Leu Asn Gln Glu Leu Glu Gly Lys Val Ala Asp Ser Leu Ser
    290                 295                 300

Ser Ile Ser Ser Gln Ala Asp Arg Ile Tyr Leu Trp Glu Lys Phe Ser
305                 310                 315                 320

Asn Tyr Lys Thr Ser Ala Asn Leu Thr Ala Thr Tyr Arg Lys Leu Glu
                325                 330                 335

Glu Met Ala Lys Gln Val Thr Asn Pro Ser Ser Arg Tyr Tyr Gln Asp
            340                 345                 350

Glu Thr Val Val Arg Thr Val Arg Asp Ser Met Glu Trp Met His Lys
        355                 360                 365

His Val Tyr Asn Ser Glu Lys Ser Ile Val Gly Asn Trp Trp Asp Tyr
    370                 375                 380

Glu Ile Gly Thr Pro Arg Ala Ile Asn Asn Thr Leu Ser Leu Met Lys
```

```
                385                 390                 395                 400
Glu Tyr Phe Ser Asp Glu Ile Lys Lys Tyr Thr Asp Val Ile Glu
                405                 410                 415
Lys Phe Val Pro Asp Pro Glu His Phe Arg Lys Thr Thr Asp Asn Pro
                420                 425                 430
Phe Lys Ala Leu Gly Gly Asn Leu Val Asp Met Gly Arg Val Lys Val
                435                 440                 445
Ile Ala Gly Leu Leu Arg Lys Asp Asp Gln Glu Ile Ser Ser Thr Ile
                450                 455                 460
Arg Ser Ile Glu Gln Val Phe Lys Leu Val Asp Gln Gly Gly Phe
465                 470                 475                 480
Tyr Gln Asp Gly Ser Tyr Ile Asp His Thr Asn Val Ala Tyr Thr Gly
                485                 490                 495
Ala Tyr Gly Asn Val Leu Ile Asp Gly Leu Ser Gln Leu Leu Pro Val
                500                 505                 510
Ile Gln Lys Thr Lys Asn Pro Ile Asp Lys Asp Lys Met Gln Thr Met
                515                 520                 525
Tyr His Trp Ile Asp Lys Ser Phe Ala Pro Leu Leu Val Asn Gly Glu
                530                 535                 540
Leu Met Asp Met Ser Arg Gly Arg Ser Ile Ser Arg Ala Asn Ser Glu
545                 550                 555                 560
Gly His Val Ala Ala Val Glu Val Leu Arg Gly Ile His Arg Ile Ala
                565                 570                 575
Asp Met Ser Glu Gly Glu Thr Lys Gln Arg Leu Gln Ser Leu Val Lys
                580                 585                 590
Thr Ile Val Gln Ser Asp Ser Tyr Tyr Asp Val Phe Lys Asn Leu Lys
                595                 600                 605
Thr Tyr Lys Asp Ile Ser Leu Met Gln Ser Leu Leu Ser Asp Ala Gly
                610                 615                 620
Val Ala Ser Val Pro Arg Thr Ser Tyr Leu Ser Ala Phe Asn Lys Met
625                 630                 635                 640
Asp Lys Thr Ala Met Tyr Asn Ala Glu Lys Gly Phe Gly Phe Gly Leu
                645                 650                 655
Ser Leu Phe Ser Ser Arg Thr Leu Asn Tyr Glu His Met Asn Lys Glu
                660                 665                 670
Asn Lys Arg Gly Trp Tyr Thr Ser Asp Gly Met Phe Tyr Leu Tyr Asn
                675                 680                 685
Gly Asp Leu Ser His Tyr Ser Asp Gly Tyr Trp Pro Thr Val Asn Pro
                690                 695                 700
Tyr Lys Met Pro Gly Thr Thr Glu Thr Asp Ala Lys Arg Ala Asp Ser
705                 710                 715                 720
Asp Thr Gly Lys Val Leu Pro Ser Ala Phe Val Gly Thr Ser Lys Leu
                725                 730                 735
Asp Asp Ala Asn Ala Thr Ala Thr Met Asp Phe Thr Asn Trp Asn Gln
                740                 745                 750
Thr Leu Thr Ala His Lys Ser Trp Phe Met Leu Lys Asp Lys Ile Ala
                755                 760                 765
Phe Leu Gly Ser Asn Ile Gln Asn Thr Ser Asp Thr Ala Ala Thr
                770                 775                 780
Thr Ile Asp Gln Arg Lys Leu Glu Ser Ser Asn Pro Tyr Lys Val Tyr
785                 790                 795                 800
Val Asn Asp Lys Glu Ala Ser Leu Thr Glu Gln Glu Lys Asp Tyr Pro
                805                 810                 815
```

-continued

```
Glu Thr Gln Ser Val Phe Leu Glu Ser Ser Asp Ser Lys Lys Asn Ile
            820                 825                 830

Gly Tyr Phe Phe Lys Lys Ser Ile Ser Met Ser Lys Ala Leu
        835                 840                 845

Gln Lys Gly Ala Trp Lys Asp Ile Asn Glu Gly Gln Ser Asp Lys Glu
    850                 855                 860

Val Glu Asn Glu Phe Leu Thr Ile Ser Gln Ala His Lys Gln Asn Gly
865                 870                 875                 880

Asp Ser Tyr Gly Tyr Met Leu Ile Pro Asn Val Asp Arg Ala Thr Phe
                885                 890                 895

Asn Gln Met Ile Lys Glu Leu Glu Ser Ser Leu Ile Glu Asn Asn Glu
            900                 905                 910

Thr Leu Gln Ser Val Tyr Asp Ala Lys Gln Gly Val Trp Gly Ile Val
        915                 920                 925

Lys Tyr Asp Asp Ser Val Ser Thr Ile Ser Asn Gln Phe Gln Val Leu
    930                 935                 940

Lys Arg Gly Val Tyr Thr Ile Arg Lys Glu Gly Asp Glu Tyr Lys Ile
945                 950                 955                 960

Ala Tyr Tyr Asn Pro Glu Thr Gln Glu Ser Ala Pro Asp Gln Glu Val
                965                 970                 975

Phe Lys Lys Leu Glu Gln Ala Ala Gln Pro Gln Val Gln Asn Ser Lys
            980                 985                 990

Glu Lys Glu Lys Ser Glu Glu Lys Asn His Ser Asp Gln Lys Asn
        995                1000                1005

<210> SEQ ID NO 40
<211> LENGTH: 628
<212> TYPE: PRT
<213> ORGANISM: Streptococcus pneumoniae
<220> FEATURE:
<223> OTHER INFORMATION: spr0286 fragment

<400> SEQUENCE: 40

Gly Ala Glu Glu Thr Thr Thr Asn Thr Ile Gln Gln Ser Gln Lys Glu
1               5                   10                  15

Val Gln Tyr Gln Gln Arg Asp Thr Lys Asn Leu Val Glu Asn Gly Asp
            20                  25                  30

Phe Gly Gln Thr Glu Asp Gly Ser Ser Pro Trp Thr Gly Ser Lys Ala
        35                  40                  45

Gln Gly Trp Ser Ala Trp Val Asp Gln Lys Asn Ser Ser Ala Asp Ala
    50                  55                  60

Ser Thr Arg Val Ile Glu Ala Lys Asp Gly Ala Ile Thr Ile Ser Ser
65                  70                  75                  80

Pro Glu Lys Leu Arg Ala Ala Val His Arg Met Val Pro Ile Glu Ala
                85                  90                  95

Lys Lys Lys Tyr Lys Leu Arg Phe Lys Ile Lys Thr Asp Asn Lys Val
            100                 105                 110

Gly Ile Ala Lys Val Arg Ile Ile Glu Glu Ser Gly Lys Asp Lys Arg
        115                 120                 125

Leu Trp Asn Ser Ala Thr Thr Ser Gly Thr Lys Asp Trp Gln Thr Ile
    130                 135                 140

Glu Ala Asp Tyr Ser Pro Thr Leu Asp Val Asp Lys Ile Lys Leu Glu
145                 150                 155                 160

Leu Phe Tyr Glu Thr Gly Thr Gly Thr Val Ser Phe Lys Asp Ile Glu
                165                 170                 175

Leu Val Glu Val Ala Asp Gln Pro Ser Glu Asp Ser Gln Thr Asp Lys
```

-continued

```
                180                 185                 190
Gln Leu Glu Glu Lys Ile Asp Leu Pro Ile Gly Lys Lys His Val Phe
            195                 200                 205
Ser Leu Ala Asp Tyr Thr Tyr Lys Val Glu Asn Pro Asp Val Ala Ser
            210                 215                 220
Val Lys Asn Gly Ile Leu Glu Pro Leu Lys Glu Gly Thr Thr Asn Val
225                 230                 235                 240
Ile Val Ser Lys Asp Gly Lys Glu Val Lys Lys Ile Pro Leu Lys Ile
            245                 250                 255
Leu Ala Ser Val Lys Asp Thr Tyr Thr Asp Arg Leu Ala Asp Trp Asn
            260                 265                 270
Gly Ile Ile Ala Gly Asn Gln Tyr Tyr Asp Ser Lys Asn Glu Gln Met
            275                 280                 285
Ala Lys Leu Asn Gln Glu Leu Glu Gly Lys Val Ala Asp Ser Leu Ser
            290                 295                 300
Ser Ile Ser Ser Gln Ala Asp Arg Ile Tyr Leu Trp Glu Lys Phe Ser
305                 310                 315                 320
Asn Tyr Lys Thr Ser Ala Asn Leu Thr Ala Thr Tyr Arg Lys Leu Glu
            325                 330                 335
Glu Met Ala Lys Gln Val Thr Asn Pro Ser Ser Arg Tyr Tyr Gln Asp
            340                 345                 350
Glu Thr Val Val Arg Thr Val Arg Asp Ser Met Glu Trp Met His Lys
            355                 360                 365
His Val Tyr Asn Ser Gly Lys Ser Ile Val Gly Asn Trp Trp Asp Tyr
            370                 375                 380
Glu Ile Gly Thr Pro Arg Ala Ile Asn Asn Thr Leu Ser Leu Met Lys
385                 390                 395                 400
Glu Tyr Phe Ser Asp Glu Ile Lys Lys Tyr Thr Asp Val Ile Glu
            405                 410                 415
Lys Phe Val Pro Asp Pro Glu His Phe Arg Lys Thr Thr Asp Asn Pro
            420                 425                 430
Phe Lys Ala Leu Gly Gly Asn Leu Val Asp Met Gly Arg Val Lys Val
            435                 440                 445
Ile Ala Gly Leu Leu Arg Lys Asp Asp Gln Glu Ile Ser Ser Thr Ile
450                 455                 460
Arg Ser Ile Glu Gln Val Phe Lys Leu Val Asp Gln Gly Glu Gly Phe
465                 470                 475                 480
Tyr Gln Asp Gly Ser Tyr Ile Asp His Thr Asn Val Ala Tyr Thr Gly
            485                 490                 495
Ala Tyr Gly Asn Val Leu Ile Asp Gly Leu Ser Gln Leu Leu Pro Val
            500                 505                 510
Ile Gln Lys Thr Lys Asn Pro Ile Asp Lys Asp Lys Met Gln Thr Met
            515                 520                 525
Tyr His Trp Ile Asp Lys Ser Phe Ala Pro Leu Leu Val Asn Gly Glu
            530                 535                 540
Leu Met Asp Met Ser Arg Gly Arg Ser Ile Ser Arg Ala Asn Ser Glu
545                 550                 555                 560
Gly His Val Ala Ala Val Glu Val Leu Arg Gly Ile His Arg Ile Ala
            565                 570                 575
Asp Met Ser Glu Gly Glu Thr Lys Gln Arg Leu Gln Ser Leu Val Lys
            580                 585                 590
Thr Ile Val Gln Ser Asp Ser Tyr Tyr Asp Val Phe Lys Asn Leu Lys
            595                 600                 605
```

```
Thr Tyr Lys Asp Ile Ser Leu Met Gln Ser Leu Leu Ser Asp Ala Gly
610                 615                 620

Val Ala Ser Val
625

<210> SEQ ID NO 41
<211> LENGTH: 452
<212> TYPE: PRT
<213> ORGANISM: Streptococcus pneumoniae
<220> FEATURE:
<223> OTHER INFORMATION: spr0286 fragment

<400> SEQUENCE: 41

Ala Asn Ser Glu Gly His Val Ala Val Glu Val Leu Arg Gly Ile
1               5                   10                  15

His Arg Ile Ala Asp Met Ser Glu Gly Thr Lys Gln Arg Leu Gln
            20                  25                  30

Ser Leu Val Lys Thr Ile Val Gln Ser Asp Ser Tyr Tyr Asp Val Phe
                35                  40                  45

Lys Asn Leu Lys Thr Tyr Lys Asp Ile Ser Leu Met Gln Ser Leu Leu
50                  55                  60

Ser Asp Ala Gly Val Ala Ser Val Pro Arg Thr Ser Tyr Leu Ser Ala
65                  70                  75                  80

Phe Asn Lys Met Asp Lys Thr Ala Met Tyr Asn Ala Glu Lys Gly Phe
                85                  90                  95

Gly Phe Gly Leu Ser Leu Phe Ser Ser Arg Thr Leu Asn Tyr Glu His
            100                 105                 110

Met Asn Lys Glu Asn Lys Arg Gly Trp Tyr Thr Ser Asp Gly Met Phe
        115                 120                 125

Tyr Leu Tyr Asn Gly Asp Leu Ser His Tyr Ser Asp Gly Tyr Trp Pro
130                 135                 140

Thr Val Asn Pro Tyr Lys Met Pro Gly Thr Thr Glu Thr Asp Ala Lys
145                 150                 155                 160

Arg Ala Asp Ser Asp Thr Gly Lys Val Leu Pro Ser Ala Phe Val Gly
                165                 170                 175

Thr Ser Lys Leu Asp Asp Ala Asn Ala Thr Ala Thr Met Asp Phe Thr
            180                 185                 190

Asn Trp Asn Gln Thr Leu Thr Ala His Lys Ser Trp Phe Met Leu Lys
        195                 200                 205

Asp Lys Ile Ala Phe Leu Gly Ser Asn Ile Gln Asn Thr Ser Thr Asp
210                 215                 220

Thr Ala Ala Thr Thr Ile Asp Gln Arg Lys Leu Glu Ser Ser Asn Pro
225                 230                 235                 240

Tyr Lys Val Tyr Val Asn Asp Lys Glu Ala Ser Leu Thr Glu Gln Glu
                245                 250                 255

Lys Asp Tyr Pro Glu Thr Gln Ser Val Phe Leu Glu Ser Ser Asp Ser
            260                 265                 270

Lys Lys Asn Ile Gly Tyr Phe Phe Lys Lys Ser Ser Ile Ser Met
        275                 280                 285

Ser Lys Ala Leu Gln Lys Gly Ala Trp Lys Asp Ile Asn Glu Gly Gln
290                 295                 300

Ser Asp Lys Glu Val Glu Asn Glu Phe Leu Thr Ile Ser Gln Ala His
305                 310                 315                 320

Lys Gln Asn Gly Asp Ser Tyr Gly Tyr Met Leu Ile Pro Asn Val Asp
                325                 330                 335

Arg Ala Thr Phe Asn Gln Met Ile Lys Glu Leu Glu Ser Ser Leu Ile
```

```
                    340                 345                 350
Glu Asn Asn Glu Thr Leu Gln Ser Val Tyr Asp Ala Lys Gln Gly Val
            355                 360                 365
Trp Gly Ile Val Lys Tyr Asp Asp Ser Val Ser Thr Ile Ser Asn Gln
        370                 375                 380
Phe Gln Val Leu Lys Arg Gly Val Tyr Thr Ile Arg Lys Glu Gly Asp
385                 390                 395                 400
Glu Tyr Lys Ile Ala Tyr Tyr Asn Pro Glu Thr Gln Glu Ser Ala Pro
                405                 410                 415
Asp Gln Glu Val Phe Lys Lys Leu Glu Gln Ala Ala Gln Pro Gln Val
            420                 425                 430
Gln Asn Ser Lys Glu Lys Glu Lys Ser Glu Glu Lys Asn His Ser
        435                 440                 445
Asp Gln Lys Asn
    450
```

<210> SEQ ID NO 42
<211> LENGTH: 2148
<212> TYPE: PRT
<213> ORGANISM: Streptococcus pneumoniae
<220> FEATURE:
<223> OTHER INFORMATION: spr0565 protein, which omits the natural leader peptide and sortase recognition sequences

<400> SEQUENCE: 42

```
Asp Glu Thr Leu Ile Thr His Thr Ala Glu Lys Pro Lys Glu Glu Lys
1               5                   10                  15
Met Ile Val Glu Glu Lys Ala Asp Lys Ala Leu Glu Thr Lys Asn Val
            20                  25                  30
Val Glu Arg Thr Glu Gln Ser Glu Pro Ser Ser Thr Glu Ala Ile Ala
        35                  40                  45
Ser Glu Lys Lys Glu Asp Glu Ala Val Thr Pro Lys Glu Glu Lys Val
    50                  55                  60
Ser Ala Lys Pro Glu Glu Lys Ala Pro Arg Ile Glu Ser Gln Ala Ser
65                  70                  75                  80
Ser Gln Glu Lys Pro Leu Lys Glu Asp Ala Lys Ala Val Thr Asn Glu
            85                  90                  95
Glu Val Asn Gln Met Ile Glu Asn Arg Lys Val Asp Phe Asn Gln Asn
        100                 105                 110
Trp Tyr Phe Lys Leu Asn Ala Asn Ser Lys Glu Ala Ile Lys Pro Asp
    115                 120                 125
Ala Asp Val Ser Thr Trp Lys Lys Leu Asp Leu Pro Tyr Asp Trp Ser
130                 135                 140
Ile Phe Asn Asp Phe Asp His Glu Ser Pro Ala Gln Asn Glu Gly Gly
145                 150                 155                 160
Gln Leu Asn Gly Gly Glu Ala Trp Tyr Arg Lys Thr Phe Lys Leu Asp
            165                 170                 175
Glu Lys Asp Leu Lys Lys Asn Val Arg Leu Thr Phe Asp Gly Val Tyr
        180                 185                 190
Met Asp Ser Gln Val Tyr Val Asn Gly Gln Leu Val Gly His Tyr Pro
    195                 200                 205
Asn Gly Tyr Asn Gln Phe Ser Tyr Asp Ile Thr Lys Tyr Leu Tyr Lys
210                 215                 220
Asp Gly Arg Glu Asn Val Ile Ala Val His Ala Val Asn Lys Gln Pro
225                 230                 235                 240
Ser Ser Arg Trp Tyr Ser Gly Ser Gly Ile Tyr Arg Asp Val Thr Leu
```

-continued

```
                245                 250                 255
Gln Val Thr Asp Lys Val His Val Glu Lys Asn Gly Thr Thr Ile Leu
                260                 265                 270

Thr Pro Lys Leu Glu Glu Gln Gln His Gly Lys Val Glu Thr His Val
            275                 280                 285

Thr Ser Lys Ile Val Asn Thr Asp Asp Lys Asp His Glu Leu Val Ala
        290                 295                 300

Glu Tyr Gln Ile Val Glu Arg Gly Gly His Ala Val Thr Gly Leu Val
305                 310                 315                 320

Arg Thr Ala Ser Arg Thr Leu Lys Ala His Glu Ser Thr Ser Leu Asp
                325                 330                 335

Ala Ile Leu Glu Val Glu Arg Pro Lys Leu Trp Thr Val Leu Asn Asp
            340                 345                 350

Lys Pro Ala Leu Tyr Glu Leu Ile Thr Arg Val Tyr Arg Asp Gly Gln
        355                 360                 365

Leu Val Asp Ala Lys Lys Asp Leu Phe Gly Tyr Arg Tyr Tyr His Trp
    370                 375                 380

Thr Pro Asn Glu Gly Phe Ser Leu Asn Gly Glu Arg Ile Lys Phe His
385                 390                 395                 400

Gly Val Ser Leu His His Asp His Gly Ala Leu Gly Ala Glu Glu Asn
                405                 410                 415

Tyr Lys Ala Glu Tyr Arg Arg Leu Lys Gln Met Lys Glu Met Gly Val
            420                 425                 430

Asn Ser Ile Arg Thr Thr His Asn Pro Ala Ser Glu Gln Thr Leu Gln
        435                 440                 445

Ile Ala Ala Glu Leu Gly Leu Leu Val Gln Glu Glu Ala Phe Asp Thr
    450                 455                 460

Trp Tyr Gly Gly Lys Lys Pro Tyr Asp Tyr Gly Arg Phe Phe Glu Lys
465                 470                 475                 480

Asp Ala Thr His Pro Glu Ala Arg Lys Gly Glu Lys Trp Ser Asp Phe
                485                 490                 495

Asp Leu Arg Thr Met Val Glu Arg Gly Lys Asn Asn Pro Ala Ile Phe
            500                 505                 510

Met Trp Ser Ile Gly Asn Glu Ile Gly Glu Ala Asn Gly Asp Ala His
        515                 520                 525

Ser Leu Ala Thr Val Lys Arg Leu Val Lys Val Ile Lys Asp Val Asp
    530                 535                 540

Lys Thr Arg Tyr Val Thr Met Gly Ala Asp Lys Phe Arg Phe Gly Asn
545                 550                 555                 560

Gly Ser Gly Gly His Glu Lys Ile Ala Asp Glu Leu Asp Ala Val Gly
                565                 570                 575

Phe Asn Tyr Ser Glu Asp Asn Tyr Lys Ala Leu Arg Ala Lys His Pro
            580                 585                 590

Lys Trp Leu Ile Tyr Gly Ser Glu Thr Ser Ser Ala Thr Arg Thr Arg
        595                 600                 605

Gly Ser Tyr Tyr Arg Pro Glu Arg Glu Leu Lys His Ser Asn Gly Pro
    610                 615                 620

Glu Arg Asn Tyr Glu Gln Ser Asp Tyr Gly Asn Asp Arg Val Gly Trp
625                 630                 635                 640

Gly Lys Thr Ala Thr Ala Ser Trp Thr Phe Asp Arg Asp Asn Ala Gly
                645                 650                 655

Tyr Ala Gly Gln Phe Ile Trp Thr Gly Thr Asp Tyr Ile Gly Glu Pro
            660                 665                 670
```

```
Thr Pro Trp His Asn Gln Asn Gln Thr Pro Val Lys Ser Ser Tyr Phe
        675                 680                 685

Gly Ile Val Asp Thr Ala Gly Ile Pro Lys His Asp Phe Tyr Leu Tyr
690                 695                 700

Gln Ser Gln Trp Val Ser Val Lys Lys Pro Met Val His Leu Leu
705                 710                 715                 720

Pro His Trp Asn Trp Glu Asn Lys Glu Leu Ala Ser Lys Val Ala Asp
                725                 730                 735

Ser Glu Gly Lys Ile Pro Val Arg Ala Tyr Ser Asn Ala Ser Ser Val
                740                 745                 750

Glu Leu Phe Leu Asn Gly Lys Ser Leu Gly Leu Lys Thr Phe Asn Lys
            755                 760                 765

Lys Gln Thr Ser Asp Gly Arg Thr Tyr Gln Glu Gly Ala Asn Ala Asn
770                 775                 780

Glu Leu Tyr Leu Glu Trp Lys Val Ala Tyr Gln Pro Gly Thr Leu Glu
785                 790                 795                 800

Ala Ile Ala Arg Asp Glu Ser Gly Lys Glu Ile Ala Arg Asp Lys Ile
                805                 810                 815

Thr Thr Ala Gly Lys Pro Ala Ala Val Arg Leu Ile Lys Glu Asp His
                820                 825                 830

Ala Ile Ala Ala Asp Gly Lys Asp Leu Thr Tyr Ile Tyr Tyr Glu Ile
                835                 840                 845

Val Asp Ser Gln Gly Asn Val Val Pro Thr Ala Asn Asn Leu Val Arg
850                 855                 860

Phe Gln Leu His Gly Gln Gly Gln Leu Val Gly Val Asp Asn Gly Glu
865                 870                 875                 880

Gln Ala Ser Arg Glu Arg Tyr Lys Ala Gln Ala Asp Gly Ser Trp Ile
                885                 890                 895

Arg Lys Ala Phe Asn Gly Lys Gly Val Ala Ile Val Lys Ser Thr Glu
                900                 905                 910

Gln Ala Gly Lys Phe Thr Leu Thr Ala His Ser Asp Leu Leu Lys Ser
            915                 920                 925

Asn Gln Val Thr Val Phe Thr Gly Lys Lys Glu Gly Gln Glu Lys Thr
930                 935                 940

Val Leu Gly Thr Glu Val Pro Lys Val Gln Thr Ile Ile Gly Glu Ala
945                 950                 955                 960

Pro Glu Met Pro Thr Thr Val Pro Phe Val Tyr Ser Asp Gly Ser Arg
                965                 970                 975

Ala Glu Arg Pro Val Thr Trp Ser Leu Val Asp Val Ser Lys Pro Gly
                980                 985                 990

Ile Val Thr Val Lys Gly Met Ala Asp Gly Arg Glu Val Glu Ala Arg
                995                 1000                1005

Val Glu Val Ile Ala Leu Lys Ser Glu Leu Pro Val Val Lys Arg Ile
    1010                1015                1020

Ala Pro Asn Thr Asn Leu Asn Ser Val Asp Lys Ser Val Ser Tyr Val
1025                1030                1035                1040

Leu Thr Asp Gly Ser Val Gln Glu Tyr Glu Val Asp Lys Trp Glu Ile
                1045                1050                1055

Ala Glu Glu Asp Lys Ala Lys Leu Ala Ile Pro Gly Ser Arg Ile Gln
                1060                1065                1070

Ala Thr Gly Tyr Leu Glu Gly Gln Pro Ile His Ala Thr Leu Val Val
            1075                1080                1085

Glu Glu Gly Asn Pro Ala Ala Pro Val Val Pro Thr Val Thr Val Gly
            1090                1095                1100
```

-continued

```
Gly Glu Ala Val Thr Gly Leu Thr Ser Arg Gln Pro Met Gln Tyr Arg
1105                1110                1115                1120

Thr Leu Ser Tyr Gly Ala Gln Leu Pro Glu Val Thr Ala Ser Ala Glu
            1125                1130                1135

Asn Ala Asp Val Thr Val Leu Gln Ala Ser Ala Ala Asn Gly Met Arg
        1140                1145                1150

Ala Ser Ile Phe Ile Gln Pro Lys Asp Gly Pro Leu Gln Thr Tyr
    1155                1160                1165

Ala Ile Gln Phe Leu Glu Glu Ala Pro Lys Ile Ala His Leu Ser Leu
    1170                1175                1180

Gln Val Glu Lys Ala Asp Ser Leu Lys Glu Asp Gln Thr Val Lys Leu
1185                1190                1195                1200

Ser Val Arg Ala His Tyr Gln Asp Gly Thr Gln Ala Val Leu Pro Ala
            1205                1210                1215

Asp Lys Val Thr Phe Ser Thr Ser Gly Glu Gly Glu Val Ala Ile Arg
        1220                1225                1230

Lys Gly Met Leu Glu Leu His Lys Pro Gly Ala Val Thr Leu Asn Ala
    1235                1240                1245

Glu Tyr Glu Gly Ala Lys Gly Gln Val Glu Leu Thr Ile Gln Ala Asn
    1250                1255                1260

Thr Glu Lys Lys Ile Ala Gln Ser Ile Arg Pro Val Asn Val Val Thr
1265                1270                1275                1280

Asp Leu His Gln Glu Pro Ser Leu Pro Ala Thr Val Thr Val Glu Tyr
            1285                1290                1295

Asp Lys Gly Phe Pro Lys Thr His Lys Val Thr Trp Gln Ala Ile Pro
        1300                1305                1310

Lys Glu Lys Leu Asp Ser Tyr Gln Ile Phe Glu Val Leu Gly Lys Val
    1315                1320                1325

Glu Gly Ile Asp Leu Glu Ala Arg Ala Lys Val Ser Val Glu Gly Ile
    1330                1335                1340

Val Ser Val Glu Glu Val Ser Val Thr Thr Pro Ile Ala Glu Ala Pro
1345                1350                1355                1360

Gln Leu Pro Glu Ser Val Arg Thr Tyr Asp Ser Asn Gly His Val Ser
            1365                1370                1375

Ser Ala Lys Val Ala Trp Asp Ala Ile Arg Pro Glu Gln Tyr Ala Lys
        1380                1385                1390

Glu Gly Val Phe Thr Val Asn Gly Arg Leu Glu Gly Thr Gln Leu Thr
    1395                1400                1405

Thr Lys Leu His Val Arg Val Ser Ala Gln Thr Glu Gln Gly Ala Asn
    1410                1415                1420

Ile Ser Asp Gln Trp Thr Gly Ser Glu Leu Pro Leu Ala Phe Ala Ser
1425                1430                1435                1440

Asp Ser Asn Pro Ser Asp Pro Val Ser Asn Val Asn Asp Lys Leu Ile
            1445                1450                1455

Ser Tyr Asn Asn Gln Pro Ala Asn Arg Trp Thr Asn Trp Asn Arg Ser
        1460                1465                1470

Asn Pro Glu Ala Ser Val Gly Val Leu Phe Gly Asp Ser Gly Ile Leu
    1475                1480                1485

Ser Lys Arg Ser Val Asp Asn Leu Ser Val Gly Phe His Glu Asp His
    1490                1495                1500

Gly Val Gly Ala Pro Lys Ser Tyr Val Ile Glu Tyr Tyr Val Gly Lys
1505                1510                1515                1520

Thr Val Pro Thr Ala Pro Lys Asn Pro Ser Phe Val Gly Asn Glu Asp
```

```
                    1525                1530                1535
His Val Phe Asn Asp Ser Ala Asn Trp Lys Pro Val Thr Asn Leu Lys
            1540                1545                1550

Ala Pro Ala Gln Leu Lys Ala Gly Glu Met Asn His Phe Ser Phe Asp
            1555                1560                1565

Lys Val Glu Thr Tyr Ala Ile Arg Ile Arg Met Val Lys Ala Asp Asn
            1570                1575                1580

Lys Arg Gly Thr Ser Ile Thr Glu Val Gln Ile Phe Ala Lys Gln Val
1585                1590                1595                1600

Ala Ala Ala Lys Gln Gly Gln Thr Arg Ile Gln Val Asp Gly Lys Asp
                1605                1610                1615

Leu Ala Asn Phe Asn Pro Asp Leu Thr Asp Tyr Tyr Leu Glu Ser Val
            1620                1625                1630

Asp Gly Lys Val Pro Ala Val Thr Ala Asn Val Ser Asn Asn Gly Leu
            1635                1640                1645

Ala Thr Val Val Pro Ser Val Arg Glu Gly Glu Pro Val Arg Val Ile
            1650                1655                1660

Ala Lys Ala Glu Asn Gly Asp Ile Leu Gly Glu Tyr Arg Leu His Phe
1665                1670                1675                1680

Thr Lys Asp Lys Asn Leu Leu Ser His Lys Pro Val Ala Ala Val Lys
                1685                1690                1695

Gln Ala Arg Leu Leu Gln Val Gly Gln Ala Leu Glu Leu Pro Thr Lys
            1700                1705                1710

Val Pro Val Tyr Phe Thr Gly Lys Asp Gly Tyr Glu Thr Lys Asp Leu
            1715                1720                1725

Thr Val Glu Trp Glu Glu Val Pro Ala Glu Asn Leu Thr Lys Ala Gly
            1730                1735                1740

Gln Phe Thr Val Arg Gly Arg Val Leu Gly Ser Asn Leu Val Ala Glu
1745                1750                1755                1760

Val Thr Val Arg Val Thr Asp Lys Leu Gly Glu Thr Leu Ser Asp Asn
                1765                1770                1775

Pro Asn Tyr Asp Glu Asn Ser Asn Gln Ala Phe Ala Ser Ala Thr Asn
            1780                1785                1790

Asp Ile Asp Lys Asn Ser His Asp Arg Val Asp Tyr Leu Asn Asp Gly
            1795                1800                1805

Asp His Ser Glu Asn Arg Arg Trp Thr Asn Trp Ser Pro Thr Pro Ser
            1810                1815                1820

Ser Asn Pro Glu Val Ser Ala Gly Val Ile Phe Arg Glu Asn Gly Lys
1825                1830                1835                1840

Ile Val Glu Arg Thr Val Ala Gln Ala Lys Leu His Phe Phe Ala Asp
                1845                1850                1855

Ser Gly Thr Asp Ala Pro Ser Lys Leu Val Leu Glu Arg Tyr Val Gly
            1860                1865                1870

Pro Gly Phe Glu Val Pro Thr Tyr Tyr Ser Asn Tyr Gln Ala Tyr Glu
            1875                1880                1885

Ser Gly His Pro Phe Asn Asn Pro Glu Asn Trp Glu Ala Val Pro Tyr
            1890                1895                1900

Arg Ala Asp Lys Asp Ile Ala Ala Gly Asp Glu Ile Asn Val Thr Phe
1905                1910                1915                1920

Lys Ala Val Lys Ala Lys Val Met Arg Trp Arg Met Glu Arg Lys Ala
                1925                1930                1935

Asp Lys Ser Gly Val Ala Met Ile Glu Met Thr Phe Leu Ala Pro Ser
            1940                1945                1950
```

Glu Leu Pro Gln Glu Ser Thr Gln Ser Lys Ile Leu Val Asp Gly Lys
        1955                1960                1965

Glu Leu Ala Asp Phe Ala Glu Asn Arg Gln Asp Tyr Gln Ile Thr Tyr
        1970                1975                1980

Lys Gly Gln Arg Pro Lys Val Ser Val Glu Glu Asn Asn Gln Val Ala
1985                1990                1995                2000

Ser Thr Val Val Asp Ser Gly Glu Asp Ser Leu Pro Val Leu Val Arg
        2005                2010                2015

Leu Val Ser Glu Ser Gly Lys Gln Val Lys Glu Tyr Arg Ile Gln Leu
        2020                2025                2030

Thr Lys Glu Lys Pro Val Ser Ala Val Gln Glu Asp Leu Pro Lys Leu
        2035                2040                2045

Glu Phe Val Glu Lys Asp Leu Ala Tyr Lys Thr Val Glu Lys Lys Asp
        2050                2055                2060

Ser Thr Leu Tyr Leu Gly Glu Thr Arg Val Glu Gln Glu Gly Lys Val
2065                2070                2075                2080

Gly Lys Glu Arg Ile Phe Thr Val Ile Asn Pro Asp Gly Ser Lys Glu
        2085                2090                2095

Glu Lys Leu Arg Glu Val Val Glu Val Pro Thr Asp Arg Ile Val Leu
        2100                2105                2110

Val Gly Thr Lys Pro Val Ala Gln Glu Ala Lys Lys Pro Gln Val Ser
        2115                2120                2125

Glu Lys Ala Asp Thr Lys Pro Ile Asp Ser Ser Glu Ala Asp Gln Thr
        2130                2135                2140

Asn Lys Ala Gln
2145

<210> SEQ ID NO 43
<211> LENGTH: 1063
<212> TYPE: PRT
<213> ORGANISM: Streptococcus pneumoniae
<220> FEATURE:
<223> OTHER INFORMATION: shortened version of spr0565

<400> SEQUENCE: 43

Asp Glu Thr Leu Ile Thr His Thr Ala Glu Lys Pro Lys Glu Glu Lys
1               5                   10                  15

Met Ile Val Glu Glu Lys Ala Asp Lys Ala Leu Glu Thr Lys Asn Val
            20                  25                  30

Val Glu Arg Thr Glu Gln Ser Glu Pro Ser Ser Thr Glu Ala Ile Ala
        35                  40                  45

Ser Glu Lys Lys Glu Asp Glu Ala Val Thr Pro Lys Glu Glu Lys Val
    50                  55                  60

Ser Ala Lys Pro Glu Glu Lys Ala Pro Arg Ile Glu Ser Gln Ala Ser
65                  70                  75                  80

Ser Gln Glu Lys Pro Leu Lys Gly Asp Ala Lys Ala Val Thr Asn Glu
            85                  90                  95

Glu Val Asn Gln Met Ile Glu Asn Arg Lys Val Asp Phe Asn Gln Asn
        100                 105                 110

Trp Tyr Phe Lys Leu Asn Ala Asn Ser Lys Glu Ala Ile Lys Pro Asp
    115                 120                 125

Ala Asp Val Ser Thr Trp Lys Lys Leu Asp Leu Pro Tyr Asp Trp Ser
        130                 135                 140

Ile Phe Asn Asp Phe Asp His Glu Ser Pro Ala Gln Asn Glu Gly Gly
145                 150                 155                 160

Gln Leu Asn Gly Gly Glu Ala Trp Tyr Arg Lys Thr Phe Lys Leu Asp

```
                        165                 170                 175
Glu Lys Asp Leu Lys Lys Asn Val Arg Leu Thr Phe Asp Gly Val Tyr
                180                 185                 190

Met Asp Ser Gln Val Tyr Val Asn Gly Gln Leu Val Gly His Tyr Pro
            195                 200                 205

Asn Gly Tyr Asn Gln Phe Ser Tyr Asp Ile Thr Lys Tyr Leu Tyr Lys
        210                 215                 220

Asp Gly Arg Glu Asn Val Ile Ala Val His Ala Val Asn Lys Gln Pro
225                 230                 235                 240

Ser Ser Arg Trp Tyr Ser Gly Ser Gly Ile Tyr Arg Asp Val Thr Leu
                245                 250                 255

Gln Val Thr Asp Lys Val His Val Glu Lys Asn Gly Thr Thr Ile Leu
            260                 265                 270

Thr Pro Lys Leu Glu Glu Gln His Gly Lys Val Glu Thr His Val
        275                 280                 285

Thr Ser Lys Ile Val Asn Thr Asp Asp Lys Asp His Glu Leu Val Ala
        290                 295                 300

Glu Tyr Gln Ile Val Glu Arg Gly Gly His Ala Val Thr Gly Leu Val
305                 310                 315                 320

Arg Thr Ala Ser Arg Thr Leu Lys Ala His Glu Ser Thr Ser Leu Asp
                325                 330                 335

Ala Ile Leu Glu Val Glu Arg Pro Lys Leu Trp Thr Val Leu Asn Asp
            340                 345                 350

Lys Pro Ala Leu Tyr Glu Leu Ile Thr Arg Val Tyr Arg Asp Gly Gln
        355                 360                 365

Leu Val Asp Ala Lys Lys Asp Leu Phe Gly Tyr Arg Tyr His Trp
        370                 375                 380

Thr Pro Asn Glu Gly Phe Ser Leu Asn Gly Glu Arg Ile Lys Phe His
385                 390                 395                 400

Gly Val Ser Leu His His Asp His Gly Ala Leu Gly Ala Glu Glu Asn
                405                 410                 415

Tyr Lys Ala Glu Tyr Arg Arg Leu Lys Gln Met Lys Glu Met Gly Val
            420                 425                 430

Asn Ser Ile Arg Thr Thr His Asn Pro Ala Ser Glu Gln Thr Leu Gln
        435                 440                 445

Ile Ala Ala Glu Leu Gly Leu Leu Val Gln Glu Glu Ala Phe Asp Thr
        450                 455                 460

Trp Tyr Gly Gly Lys Lys Pro Tyr Asp Tyr Gly Arg Phe Phe Glu Lys
465                 470                 475                 480

Asp Ala Thr His Pro Glu Ala Arg Lys Gly Glu Lys Trp Ser Asp Phe
                485                 490                 495

Asp Leu Arg Thr Met Val Glu Arg Gly Lys Asn Asn Pro Ala Ile Phe
            500                 505                 510

Met Trp Ser Ile Gly Asn Glu Ile Gly Glu Ala Asn Gly Asp Ala His
        515                 520                 525

Ser Leu Ala Thr Val Lys Arg Leu Val Lys Val Ile Lys Asp Val Asp
        530                 535                 540

Lys Thr Arg Tyr Val Thr Met Gly Ala Asp Lys Phe Arg Phe Gly Asn
545                 550                 555                 560

Gly Ser Gly Gly His Glu Lys Ile Ala Asp Glu Leu Asp Ala Val Gly
                565                 570                 575

Phe Asn Tyr Ser Glu Asp Asn Tyr Lys Ala Leu Arg Ala Lys His Pro
            580                 585                 590
```

-continued

```
Lys Trp Leu Ile Tyr Gly Ser Glu Thr Ser Ala Thr Arg Thr Arg
            595                 600                 605
Gly Ser Tyr Tyr Arg Pro Glu Arg Glu Leu Lys His Ser Asn Gly Pro
        610                 615                 620
Glu Arg Asn Tyr Glu Gln Ser Asp Tyr Gly Asn Asp Arg Val Gly Trp
625                 630                 635                 640
Gly Lys Thr Ala Thr Ala Ser Trp Thr Phe Asp Arg Asp Asn Ala Gly
                645                 650                 655
Tyr Ala Gly Gln Phe Ile Trp Thr Gly Thr Asp Tyr Ile Gly Glu Pro
            660                 665                 670
Thr Pro Trp His Asn Gln Asn Gln Thr Pro Val Lys Ser Ser Tyr Phe
        675                 680                 685
Gly Ile Val Asp Thr Ala Gly Ile Pro Lys His Asp Phe Tyr Leu Tyr
    690                 695                 700
Gln Ser Gln Trp Val Ser Val Lys Lys Pro Met Val His Leu Leu
705                 710                 715                 720
Pro His Trp Asn Trp Glu Asn Lys Glu Leu Ala Ser Lys Val Ala Asp
                725                 730                 735
Ser Glu Gly Lys Ile Pro Val Arg Ala Tyr Ser Asn Ala Ser Ser Val
            740                 745                 750
Glu Leu Phe Leu Asn Gly Lys Ser Leu Gly Leu Lys Thr Phe Asn Lys
        755                 760                 765
Lys Gln Thr Ser Asp Gly Arg Thr Tyr Gln Glu Gly Ala Asn Ala Asn
770                 775                 780
Glu Leu Tyr Leu Glu Trp Lys Val Ala Tyr Gln Pro Gly Thr Leu Glu
785                 790                 795                 800
Ala Ile Ala Arg Asp Glu Ser Gly Lys Glu Ile Ala Arg Asp Lys Ile
                805                 810                 815
Thr Thr Ala Gly Lys Pro Ala Ala Val Arg Leu Ile Lys Glu Asp His
            820                 825                 830
Ala Ile Ala Ala Asp Gly Lys Asp Leu Thr Tyr Ile Tyr Tyr Glu Ile
        835                 840                 845
Val Asp Ser Gln Gly Asn Val Val Pro Thr Ala Asn Asn Leu Val Arg
    850                 855                 860
Phe Gln Leu His Gly Gln Gly Gln Leu Val Gly Val Asp Asn Gly Glu
865                 870                 875                 880
Gln Ala Ser Arg Glu Arg Tyr Lys Ala Gln Ala Asp Gly Ser Trp Ile
                885                 890                 895
Arg Lys Ala Phe Asn Gly Lys Gly Val Ala Ile Val Lys Ser Thr Glu
            900                 905                 910
Gln Ala Gly Lys Phe Thr Leu Thr Ala His Ser Asp Leu Leu Lys Ser
        915                 920                 925
Asn Gln Val Thr Val Phe Thr Gly Lys Lys Glu Gly Gln Glu Lys Thr
    930                 935                 940
Val Leu Gly Thr Glu Val Pro Lys Val Gln Thr Ile Ile Gly Glu Ala
945                 950                 955                 960
Pro Glu Met Pro Thr Thr Val Pro Phe Val Tyr Ser Asp Gly Ser Arg
                965                 970                 975
Ala Glu Arg Pro Val Thr Trp Ser Leu Val Asp Val Ser Lys Pro Gly
            980                 985                 990
Ile Val Thr Val Lys Gly Met Ala Asp Gly Arg Glu Val Glu Ala Arg
        995                 1000                1005
Val Glu Val Ile Ala Leu Lys Ser Glu Leu Pro Val Val Lys Arg Ile
    1010                1015                1020
```

```
Ala Pro Asn Thr Asn Leu Asn Ser Val Asp Lys Ser Val Ser Tyr Val
1025                1030                1035                1040

Leu Thr Asp Gly Ser Val Gln Glu Tyr Glu Val Asp Lys Trp Glu Ile
            1045                1050                1055

Ala Glu Glu Asp Lys Ala Lys
            1060

<210> SEQ ID NO 44
<211> LENGTH: 1093
<212> TYPE: PRT
<213> ORGANISM: Streptococcus pneumoniae
<220> FEATURE:
<223> OTHER INFORMATION: shortened version of spr0565

<400> SEQUENCE: 44

Ile Ala Glu Glu Asp Lys Ala Lys Leu Ala Ile Pro Gly Ser Arg Ile
1               5                   10                  15

Gln Ala Thr Gly Tyr Leu Glu Gly Gln Pro Ile His Ala Thr Leu Val
            20                  25                  30

Val Glu Glu Gly Asn Pro Ala Ala Pro Val Val Pro Thr Val Thr Val
        35                  40                  45

Gly Gly Glu Ala Val Thr Gly Leu Thr Ser Arg Gln Pro Met Gln Tyr
    50                  55                  60

Arg Thr Leu Ser Tyr Gly Ala Gln Leu Pro Glu Val Thr Ala Ser Ala
65                  70                  75                  80

Glu Asn Ala Asp Val Thr Val Leu Gln Ala Ser Ala Ala Asn Gly Met
                85                  90                  95

Arg Ala Ser Ile Phe Ile Gln Pro Lys Asp Gly Gly Pro Leu Gln Thr
            100                 105                 110

Tyr Ala Ile Gln Phe Leu Glu Glu Ala Pro Lys Ile Ala His Leu Ser
        115                 120                 125

Leu Gln Val Glu Lys Ala Asp Ser Leu Lys Glu Asp Gln Thr Val Lys
    130                 135                 140

Leu Ser Val Arg Ala His Tyr Gln Asp Gly Thr Gln Ala Val Leu Pro
145                 150                 155                 160

Ala Asp Lys Val Thr Phe Ser Thr Ser Gly Glu Gly Glu Val Ala Ile
                165                 170                 175

Arg Lys Gly Met Leu Glu Leu His Lys Pro Gly Ala Val Thr Leu Asn
            180                 185                 190

Ala Glu Tyr Glu Gly Ala Lys Gly Gln Val Glu Leu Thr Ile Gln Ala
        195                 200                 205

Asn Thr Glu Lys Lys Ile Ala Gln Ser Ile Arg Pro Val Asn Val Val
    210                 215                 220

Thr Asp Leu His Gln Glu Pro Ser Leu Pro Ala Thr Val Thr Val Glu
225                 230                 235                 240

Tyr Asp Lys Gly Phe Pro Lys Thr His Lys Val Thr Trp Gln Ala Ile
                245                 250                 255

Pro Lys Glu Lys Leu Asp Ser Tyr Gln Ile Phe Glu Val Leu Gly Lys
            260                 265                 270

Val Glu Gly Ile Asp Leu Glu Ala Arg Ala Lys Val Ser Val Glu Gly
        275                 280                 285

Ile Val Ser Val Glu Val Ser Val Thr Thr Pro Ile Ala Glu Ala
    290                 295                 300

Pro Gln Leu Pro Glu Ser Val Arg Thr Tyr Asp Ser Asn Gly His Val
305                 310                 315                 320
```

-continued

Ser Ser Ala Lys Val Ala Trp Asp Ala Ile Arg Pro Glu Gln Tyr Ala
         325                 330                 335

Lys Glu Gly Val Phe Thr Val Asn Gly Arg Leu Glu Gly Thr Gln Leu
             340                 345                 350

Thr Thr Lys Leu His Val Arg Val Ser Ala Gln Thr Glu Gln Gly Ala
             355                 360                 365

Asn Ile Ser Asp Gln Trp Thr Gly Ser Glu Leu Pro Leu Ala Phe Ala
         370                 375                 380

Ser Asp Ser Asn Pro Ser Asp Pro Val Ser Asn Val Asn Asp Lys Leu
385                 390                 395                 400

Ile Ser Tyr Asn Asn Gln Pro Ala Asn Arg Trp Thr Asn Trp Asn Arg
             405                 410                 415

Ser Asn Pro Glu Ala Ser Val Gly Val Leu Phe Gly Asp Ser Gly Ile
             420                 425                 430

Leu Ser Lys Arg Ser Val Asp Asn Leu Ser Val Gly Phe His Glu Asp
         435                 440                 445

His Gly Val Gly Ala Pro Lys Ser Tyr Val Ile Glu Tyr Tyr Val Gly
         450                 455                 460

Lys Thr Val Pro Thr Ala Pro Lys Asn Pro Ser Phe Val Gly Asn Glu
465                 470                 475                 480

Asp His Val Phe Asn Asp Ser Ala Asn Trp Lys Pro Val Thr Asn Leu
             485                 490                 495

Lys Ala Pro Ala Gln Leu Lys Ala Gly Glu Met Asn His Phe Ser Phe
         500                 505                 510

Asp Lys Val Glu Thr Tyr Ala Ile Arg Ile Arg Met Val Lys Ala Asp
         515                 520                 525

Asn Lys Arg Gly Thr Ser Ile Thr Glu Val Gln Ile Phe Ala Lys Gln
         530                 535                 540

Val Ala Ala Lys Gln Gly Gln Thr Arg Ile Gln Val Asp Gly Lys
545                 550                 555                 560

Asp Leu Ala Asn Phe Asn Pro Asp Leu Thr Asp Tyr Tyr Leu Glu Ser
             565                 570                 575

Val Asp Gly Lys Val Pro Ala Val Thr Ala Asn Val Ser Asn Asn Gly
             580                 585                 590

Leu Ala Thr Val Val Pro Ser Val Arg Glu Gly Glu Pro Val Arg Val
         595                 600                 605

Ile Ala Lys Ala Glu Asn Gly Asp Ile Leu Gly Glu Tyr Arg Leu His
         610                 615                 620

Phe Thr Lys Asp Lys Asn Leu Leu Ser His Lys Pro Val Ala Ala Val
625                 630                 635                 640

Lys Gln Ala Arg Leu Leu Gln Val Gly Gln Ala Leu Glu Leu Pro Thr
             645                 650                 655

Lys Val Pro Val Tyr Phe Thr Gly Lys Asp Gly Tyr Glu Thr Lys Asp
             660                 665                 670

Leu Thr Val Glu Trp Glu Val Pro Ala Glu Asn Leu Thr Lys Ala
         675                 680                 685

Gly Gln Phe Thr Val Arg Gly Arg Val Leu Gly Ser Asn Leu Val Ala
         690                 695                 700

Glu Val Thr Val Arg Val Thr Asp Lys Leu Gly Glu Thr Leu Ser Asp
705                 710                 715                 720

Asn Pro Asn Tyr Asp Glu Asn Ser Asn Gln Ala Phe Ala Ser Ala Thr
             725                 730                 735

Asn Asp Ile Asp Lys Asn Ser His Asp Arg Val Asp Tyr Leu Asn Asp
         740                 745                 750

Gly Asp His Ser Glu Asn Arg Arg Trp Thr Asn Trp Ser Pro Thr Pro
            755                 760                 765

Ser Ser Asn Pro Glu Val Ser Ala Gly Val Ile Phe Arg Glu Asn Gly
        770                 775                 780

Lys Ile Val Glu Arg Thr Val Ala Gln Ala Lys Leu His Phe Phe Ala
785                 790                 795                 800

Asp Ser Gly Thr Asp Ala Pro Ser Lys Leu Val Leu Glu Arg Tyr Val
            805                 810                 815

Gly Pro Gly Phe Glu Val Pro Thr Tyr Tyr Ser Asn Tyr Gln Ala Tyr
            820                 825                 830

Glu Ser Gly His Pro Phe Asn Asn Pro Glu Asn Trp Glu Ala Val Pro
            835                 840                 845

Tyr Arg Ala Asp Lys Asp Ile Ala Ala Gly Asp Glu Ile Asn Val Thr
850                 855                 860

Phe Lys Ala Val Lys Ala Lys Val Met Arg Trp Arg Met Glu Arg Lys
865                 870                 875                 880

Ala Asp Lys Ser Gly Val Ala Met Ile Glu Met Thr Phe Leu Ala Pro
            885                 890                 895

Ser Glu Leu Pro Gln Glu Ser Thr Gln Ser Lys Ile Leu Val Asp Gly
            900                 905                 910

Lys Glu Leu Ala Asp Phe Ala Glu Asn Arg Gln Asp Tyr Gln Ile Thr
            915                 920                 925

Tyr Lys Gly Gln Arg Pro Lys Val Ser Val Glu Glu Asn Asn Gln Val
            930                 935                 940

Ala Ser Thr Val Val Asp Ser Gly Glu Asp Ser Leu Pro Val Leu Val
945                 950                 955                 960

Arg Leu Val Ser Glu Ser Gly Lys Gln Val Lys Glu Tyr Arg Ile Gln
            965                 970                 975

Leu Thr Lys Glu Lys Pro Val Ser Ala Val Gln Glu Asp Leu Pro Lys
            980                 985                 990

Leu Glu Phe Val Glu Lys Asp Leu Ala Tyr Lys Thr Val Lys Lys
            995                 1000                1005

Asp Ser Thr Leu Tyr Leu Gly Glu Thr Arg Val Glu Gln Glu Gly Lys
    1010                1015                1020

Val Gly Lys Glu Arg Ile Phe Thr Val Ile Asn Pro Asp Gly Ser Lys
1025                1030                1035                1040

Glu Glu Lys Leu Arg Glu Val Val Glu Val Pro Thr Asp Arg Ile Val
            1045                1050                1055

Leu Val Gly Thr Lys Pro Val Ala Gln Glu Ala Lys Lys Pro Gln Val
            1060                1065                1070

Ser Glu Lys Ala Asp Thr Lys Pro Ile Asp Ser Glu Ala Asp Gln
    1075                1080                1085

Thr Asn Lys Ala Gln
    1090

<210> SEQ ID NO 45
<211> LENGTH: 2233
<212> TYPE: PRT
<213> ORGANISM: Streptococcus pneumoniae
<220> FEATURE:
<223> OTHER INFORMATION: variant form of spr0565

<400> SEQUENCE: 45

Met Gly Lys Gly His Trp Asn Arg Lys Arg Val Tyr Ser Ile Arg Lys
1               5                   10                  15

-continued

```
Phe Ala Val Gly Ala Cys Ser Val Met Ile Gly Thr Cys Ala Val Leu
                 20                  25                  30

Leu Gly Gly Asn Ile Ala Gly Glu Ser Val Val Tyr Ala Asp Glu Thr
             35                  40                  45

Leu Ile Thr His Thr Ala Glu Lys Pro Lys Glu Glu Lys Met Ile Val
 50                  55                  60

Glu Glu Lys Ala Asp Lys Ala Leu Glu Thr Lys Asn Ile Val Glu Arg
 65                  70                  75                  80

Thr Glu Gln Ser Glu Pro Ser Ser Thr Glu Ala Ile Ala Ser Glu Lys
                 85                  90                  95

Lys Glu Asp Glu Ala Val Thr Pro Lys Glu Glu Lys Val Ser Ala Lys
            100                 105                 110

Pro Glu Glu Lys Ala Pro Arg Ile Glu Ser Gln Ala Ser Asn Gln Glu
            115                 120                 125

Lys Pro Leu Lys Glu Asp Ala Lys Ala Val Thr Asn Glu Glu Val Asn
        130                 135                 140

Gln Met Ile Glu Asp Arg Lys Val Asp Phe Asn Gln Asn Trp Tyr Phe
145                 150                 155                 160

Lys Leu Asn Ala Asn Ser Lys Glu Ala Ile Lys Pro Asp Ala Asp Val
                165                 170                 175

Ser Thr Trp Lys Lys Leu Asp Leu Pro Tyr Asp Trp Ser Ile Phe Asn
            180                 185                 190

Asp Phe Asp His Glu Ser Pro Ala Gln Asn Glu Gly Gly Gln Leu Asn
        195                 200                 205

Gly Gly Glu Ala Trp Tyr Arg Lys Thr Phe Lys Leu Asp Glu Lys Asp
210                 215                 220

Leu Lys Lys Asn Val Arg Leu Thr Phe Asp Gly Val Tyr Met Asp Ser
225                 230                 235                 240

Gln Val Tyr Val Asn Gly Gln Leu Val Gly His Tyr Pro Asn Gly Tyr
                245                 250                 255

Asn Gln Phe Ser Tyr Asp Ile Thr Lys Tyr Leu Gln Lys Asp Gly Arg
            260                 265                 270

Glu Asn Val Ile Ala Val His Ala Val Asn Lys Gln Pro Ser Ser Arg
        275                 280                 285

Trp Tyr Ser Gly Ser Gly Ile Tyr Arg Asp Val Thr Leu Gln Val Thr
290                 295                 300

Asp Lys Val His Val Glu Lys Asn Gly Thr Thr Ile Leu Thr Pro Lys
305                 310                 315                 320

Leu Glu Glu Gln Gln His Gly Lys Val Glu Thr His Val Thr Ser Lys
                325                 330                 335

Ile Val Asn Thr Asp Asp Lys Asp His Glu Leu Val Ala Glu Tyr Gln
            340                 345                 350

Ile Val Glu Arg Gly Gly His Ala Val Thr Gly Leu Val Arg Thr Ala
        355                 360                 365

Ser Arg Thr Leu Lys Ala His Glu Ser Thr Ser Leu Asp Ala Ile Leu
370                 375                 380

Glu Val Glu Arg Pro Lys Leu Trp Thr Val Leu Asn Asp Lys Pro Ala
385                 390                 395                 400

Leu Tyr Glu Leu Ile Thr Arg Val Tyr Arg Asp Gly Gln Leu Val Asp
                405                 410                 415

Ala Lys Lys Asp Leu Phe Gly Tyr Arg Tyr Tyr His Trp Thr Pro Asn
            420                 425                 430

Glu Gly Phe Ser Leu Asn Gly Glu Arg Ile Lys Phe His Gly Val Ser
        435                 440                 445
```

```
Leu His His Asp His Gly Ala Leu Gly Ala Glu Glu Asn Tyr Lys Ala
    450                 455                 460

Glu Tyr Arg Arg Leu Lys Gln Met Lys Glu Met Gly Val Asn Ser Ile
465                 470                 475                 480

Arg Thr Thr His Asn Pro Ala Ser Glu Gln Thr Leu Gln Ile Ala Ala
                485                 490                 495

Glu Leu Gly Leu Leu Val Gln Glu Ala Phe Asp Thr Trp Tyr Gly
                500                 505                 510

Gly Lys Lys Pro Tyr Asp Tyr Gly Arg Phe Phe Glu Lys Asp Ala Thr
                515                 520                 525

His Pro Glu Ala Arg Lys Gly Glu Lys Trp Ser Asp Phe Asp Leu Arg
                530                 535                 540

Thr Met Val Glu Arg Gly Lys Asn Asn Pro Ala Ile Phe Met Trp Ser
545                 550                 555                 560

Ile Gly Asn Glu Ile Gly Glu Ala Asn Gly Asp Ala His Ser Leu Ala
                565                 570                 575

Thr Val Lys Arg Leu Val Lys Val Ile Lys Asp Val Asp Lys Thr Arg
                580                 585                 590

Tyr Val Thr Met Gly Ala Asp Lys Phe Arg Phe Gly Asn Gly Ser Gly
                595                 600                 605

Gly His Glu Lys Ile Ala Asp Glu Leu Asp Ala Val Gly Phe Asn Tyr
                610                 615                 620

Ser Glu Asp Asn Tyr Lys Ala Leu Arg Ala Lys His Pro Lys Trp Leu
625                 630                 635                 640

Ile Tyr Gly Ser Glu Thr Ser Ser Ala Thr Arg Thr Arg Gly Ser Tyr
                645                 650                 655

Tyr Arg Pro Glu Arg Glu Leu Lys His Ser Asn Gly Pro Glu Arg Asn
                660                 665                 670

Tyr Glu Gln Ser Asp Tyr Gly Asn Asp Arg Val Gly Trp Gly Lys Thr
                675                 680                 685

Ala Thr Ala Ser Trp Thr Phe Asp Arg Asp Asn Ala Gly Tyr Ala Gly
                690                 695                 700

Gln Phe Ile Trp Thr Gly Thr Asp Tyr Ile Gly Glu Pro Thr Pro Trp
705                 710                 715                 720

His Asn Gln Asn Gln Thr Pro Val Lys Ser Ser Tyr Phe Gly Ile Val
                725                 730                 735

Asp Thr Ala Gly Ile Pro Lys His Asp Phe Tyr Leu Tyr Gln Ser Gln
                740                 745                 750

Trp Val Ser Val Lys Lys Pro Met Val His Leu Pro His Trp
                755                 760                 765

Asn Trp Glu Asn Lys Glu Leu Ala Ser Lys Val Ala Asp Ser Glu Gly
                770                 775                 780

Lys Ile Pro Val Arg Ala Tyr Ser Asn Ala Ser Ser Val Glu Leu Phe
785                 790                 795                 800

Leu Asn Gly Lys Ser Leu Gly Leu Lys Thr Phe Asn Lys Lys Gln Thr
                805                 810                 815

Ser Asp Gly Arg Thr Tyr Gln Glu Gly Ala Asn Ala Asn Glu Leu Tyr
                820                 825                 830

Leu Glu Trp Lys Val Ala Tyr Gln Pro Gly Thr Leu Glu Ala Ile Ala
                835                 840                 845

Arg Asp Glu Ser Gly Lys Glu Ile Ala Arg Asp Lys Ile Thr Thr Ala
850                 855                 860

Gly Lys Pro Ala Ala Val Arg Leu Ile Lys Glu Asp His Ala Ile Ala
```

-continued

```
            865                 870                 875                 880
Ala Asp Gly Lys Asp Leu Thr Tyr Ile Tyr Glu Ile Val Asp Ser
                    885                 890                 895
Gln Gly Asn Val Val Pro Thr Ala Asn Asn Leu Val Arg Phe Gln Leu
            900                 905                 910
His Gly Gln Gly Gln Leu Val Gly Val Asp Asn Gly Glu Gln Ala Ser
            915                 920                 925
Arg Glu Arg Tyr Lys Ala Gln Ala Asp Gly Ser Trp Ile Arg Lys Ala
            930                 935                 940
Phe Asn Gly Lys Gly Val Ala Ile Val Lys Ser Thr Glu Gln Ala Gly
945                 950                 955                 960
Lys Phe Thr Leu Thr Ala His Ser Asp Leu Leu Lys Ser Asn Gln Val
                    965                 970                 975
Thr Val Phe Thr Gly Lys Lys Glu Gly Gln Glu Lys Thr Val Leu Gly
                    980                 985                 990
Thr Glu Val Pro Lys Val Gln Thr Ile Ile Gly Glu Ala Pro Glu Met
                    995                 1000                1005
Pro Thr Thr Val Pro Phe Val Tyr Ser Asp Gly Ser Arg Ala Glu Arg
            1010                1015                1020
Pro Val Thr Trp Ser Ser Val Asp Val Ser Lys Pro Gly Ile Val Thr
1025                1030                1035                1040
Val Lys Gly Met Ala Asp Gly Arg Glu Val Glu Ala Arg Val Glu Val
                    1045                1050                1055
Ile Ala Leu Lys Ser Glu Leu Pro Val Val Lys Arg Ile Ala Pro Asn
                    1060                1065                1070
Thr Asp Leu Asn Ser Val Asp Lys Ser Val Ser Tyr Val Leu Ile Asp
                    1075                1080                1085
Gly Ser Val Glu Glu Tyr Glu Val Asp Lys Trp Glu Ile Ala Glu Glu
                    1090                1095                1100
Asp Lys Ala Lys Leu Ala Ile Pro Gly Ser Arg Ile Gln Ala Thr Gly
1105                1110                1115                1120
Tyr Leu Glu Gly Gln Pro Ile His Ala Thr Leu Val Val Glu Glu Gly
                    1125                1130                1135
Asn Pro Ala Ala Pro Ala Val Pro Thr Val Thr Val Gly Gly Glu Ala
                    1140                1145                1150
Val Thr Gly Leu Thr Ser Gln Lys Pro Met Gln Tyr Arg Thr Leu Ala
                    1155                1160                1165
Tyr Gly Ala Lys Leu Pro Glu Val Thr Ala Ser Ala Lys Asn Ala Ala
                    1170                1175                1180
Val Thr Val Leu Gln Ala Ser Ala Ala Asn Gly Met Arg Ala Ser Ile
1185                1190                1195                1200
Phe Ile Gln Pro Lys Asp Gly Gly Pro Leu Gln Thr Tyr Ala Ile Gln
                    1205                1210                1215
Phe Leu Glu Glu Ala Pro Lys Ile Ala His Leu Ser Leu Gln Val Glu
                    1220                1225                1230
Lys Ala Asp Ser Leu Lys Glu Asp Gln Thr Val Lys Leu Ser Val Arg
                    1235                1240                1245
Ala His Tyr Gln Asp Gly Thr Gln Ala Val Leu Pro Ala Asp Lys Val
            1250                1255                1260
Thr Phe Ser Thr Ser Gly Glu Gly Glu Val Ala Ile Arg Lys Gly Met
1265                1270                1275                1280
Leu Glu Leu His Lys Pro Gly Ala Val Thr Leu Asn Ala Glu Tyr Glu
                    1285                1290                1295
```

```
Gly Ala Lys Asp Gln Val Glu Leu Thr Ile Gln Ala Asn Thr Glu Lys
        1300                1305                1310

Lys Ile Ala Gln Ser Ile Arg Pro Val Asn Val Val Thr Asp Leu His
    1315                1320                1325

Gln Glu Pro Ser Leu Pro Ala Thr Val Thr Val Glu Tyr Asp Lys Gly
        1330                1335                1340

Phe Pro Lys Thr His Lys Val Thr Trp Gln Ala Ile Pro Lys Glu Lys
1345                1350                1355                1360

Leu Asp Ser Tyr Gln Thr Phe Glu Val Leu Gly Lys Val Glu Gly Ile
            1365                1370                1375

Asp Leu Glu Ala Arg Ala Lys Val Ser Val Glu Gly Ile Val Ser Val
        1380                1385                1390

Glu Glu Val Ser Val Thr Thr Pro Ile Ala Glu Ala Pro Gln Leu Pro
    1395                1400                1405

Glu Ser Val Arg Thr Tyr Asp Ser Asn Gly His Val Ser Ser Ala Lys
        1410                1415                1420

Val Ala Trp Asp Ala Ile Arg Pro Glu Gln Tyr Ala Lys Glu Gly Val
1425                1430                1435                1440

Phe Thr Val Asn Gly Arg Leu Glu Gly Thr Gln Leu Thr Thr Lys Leu
            1445                1450                1455

His Val Arg Val Ser Ala Gln Thr Glu Gln Gly Ala Asn Ile Ser Asp
        1460                1465                1470

Gln Trp Thr Gly Ser Glu Leu Pro Leu Ala Phe Ala Ser Asp Ser Asn
    1475                1480                1485

Pro Ser Asp Pro Val Ser Asn Val Asn Asp Lys Leu Ile Ser Tyr Asn
        1490                1495                1500

Asn Gln Pro Ala Asn Arg Trp Thr Asn Trp Asn Arg Thr Asn Pro Glu
1505                1510                1515                1520

Ala Ser Val Gly Val Leu Phe Gly Asp Ser Gly Ile Leu Ser Lys Arg
            1525                1530                1535

Ser Val Asp Asn Leu Ser Val Gly Phe His Glu Asp His Gly Val Gly
        1540                1545                1550

Val Pro Lys Ser Tyr Val Ile Glu Tyr Tyr Val Gly Lys Thr Val Pro
    1555                1560                1565

Thr Ala Pro Lys Asn Pro Ser Phe Val Gly Asn Glu Asp His Val Phe
        1570                1575                1580

Asn Asp Ser Ala Asn Trp Lys Pro Val Thr Asn Leu Lys Ala Pro Ala
1585                1590                1595                1600

Gln Leu Lys Ala Gly Glu Met Asn His Phe Ser Phe Asp Lys Val Glu
            1605                1610                1615

Thr Tyr Ala Val Arg Ile Arg Met Val Lys Ala Asp Asn Lys Arg Gly
        1620                1625                1630

Thr Ser Ile Thr Glu Val Gln Ile Phe Ala Lys Gln Val Ala Ala Ala
    1635                1640                1645

Lys Gln Gly Gln Thr Arg Ile Gln Val Asp Gly Lys Asp Leu Ala Asn
        1650                1655                1660

Phe Asn Pro Asp Leu Thr Asp Tyr Tyr Leu Glu Ser Val Asp Gly Lys
1665                1670                1675                1680

Val Pro Ala Val Thr Ala Ser Val Ser Asn Asn Gly Leu Ala Thr Val
            1685                1690                1695

Val Pro Ser Val Arg Glu Gly Glu Pro Val Arg Val Ile Ala Lys Ala
        1700                1705                1710

Glu Asn Gly Asp Ile Leu Gly Glu Tyr Arg Leu His Phe Thr Lys Asp
    1715                1720                1725
```

```
Lys Ser Leu Leu Ser His Lys Pro Val Ala Ala Val Lys Gln Ala Arg
        1730                1735                1740

Leu Leu Gln Val Gly Gln Ala Leu Glu Leu Pro Thr Lys Val Pro Val
1745                1750                1755                1760

Tyr Phe Thr Gly Lys Asp Gly Tyr Glu Thr Lys Asp Leu Thr Val Glu
                1765                1770                1775

Trp Glu Glu Val Pro Ala Glu Asn Leu Thr Lys Ala Gly Gln Phe Thr
            1780                1785                1790

Val Arg Gly Arg Val Leu Gly Ser Asn Leu Val Ala Glu Ile Thr Val
        1795                1800                1805

Arg Val Thr Asp Lys Leu Gly Glu Thr Leu Ser Asp Asn Pro Asn Tyr
    1810                1815                1820

Asp Glu Asn Ser Asn Gln Ala Phe Ala Ser Ala Thr Asn Asp Ile Asp
1825                1830                1835                1840

Lys Asn Ser His Asp Arg Val Asp Tyr Leu Asn Asp Gly Asp His Ser
                1845                1850                1855

Glu Asn Arg Arg Trp Thr Asn Trp Ser Pro Thr Pro Ser Ser Asn Pro
            1860                1865                1870

Glu Val Ser Ala Gly Val Ile Phe Arg Glu Asn Gly Lys Ile Val Glu
        1875                1880                1885

Arg Thr Val Thr Gln Gly Lys Val Gln Phe Phe Ala Asp Ser Gly Thr
    1890                1895                1900

Asp Ala Pro Ser Lys Leu Val Leu Glu Arg Tyr Val Gly Pro Glu Phe
1905                1910                1915                1920

Glu Val Pro Thr Tyr Tyr Ser Asn Tyr Gln Ala Tyr Ala Asp His
                1925                1930                1935

Pro Phe Asn Asn Pro Glu Asn Trp Glu Ala Val Pro Tyr Arg Ala Asp
            1940                1945                1950

Lys Asp Ile Ala Ala Gly Asp Glu Ile Asn Val Thr Phe Lys Ala Ile
        1955                1960                1965

Lys Ala Lys Ala Met Arg Trp Arg Met Glu Arg Lys Ala Asp Lys Ser
    1970                1975                1980

Gly Val Ala Met Ile Glu Met Thr Phe Leu Ala Pro Ser Glu Leu Pro
1985                1990                1995                2000

Gln Glu Ser Thr Gln Ser Lys Ile Leu Val Asp Gly Lys Glu Leu Ala
                2005                2010                2015

Asp Phe Ala Glu Asn Arg Gln Asp Tyr Gln Ile Thr Tyr Lys Gly Gln
            2020                2025                2030

Arg Pro Lys Val Ser Val Glu Glu Asn Asn Gln Val Ala Ser Thr Val
        2035                2040                2045

Val Asp Ser Gly Glu Asp Ser Phe Pro Val Leu Val Arg Leu Val Ser
    2050                2055                2060

Glu Ser Gly Lys Gln Val Lys Glu Tyr Arg Ile His Leu Thr Lys Glu
2065                2070                2075                2080

Lys Pro Val Ser Glu Lys Thr Val Ala Ala Val Gln Glu Asp Leu Pro
                2085                2090                2095

Lys Ile Glu Phe Val Glu Lys Asp Leu Ala Tyr Lys Thr Val Glu Lys
            2100                2105                2110

Lys Asp Ser Thr Leu Tyr Leu Gly Glu Thr Arg Val Glu Gln Glu Gly
        2115                2120                2125

Lys Val Gly Lys Glu Arg Ile Phe Thr Ala Ile Asn Pro Asp Gly Ser
        2130                2135                2140

Lys Glu Glu Lys Leu Arg Glu Val Val Glu Val Pro Thr Asp Arg Ile
```

```
            2145                2150                2155                2160
Val Leu Val Gly Thr Lys Pro Val Ala Gln Glu Ala Lys Lys Pro Gln
                    2165                2170                2175

Val Ser Glu Lys Ala Asp Thr Lys Pro Ile Asp Ser Ser Glu Ala Ser
            2180                2185                2190

Gln Thr Asn Lys Ala Gln Leu Pro Ser Thr Gly Ser Ala Ala Ser Gln
        2195                2200                2205

Ala Ala Val Ala Ala Gly Leu Thr Leu Leu Gly Leu Ser Ala Gly Leu
        2210                2215                2220

Val Val Thr Lys Gly Lys Lys Glu Asp
2225                2230

<210> SEQ ID NO 46
<211> LENGTH: 218
<212> TYPE: PRT
<213> ORGANISM: Streptococcus pneumoniae
<220> FEATURE:
<223> OTHER INFORMATION: fragment of SEQ ID NO: 26 which omits the
      natural leader peptide sequence

<400> SEQUENCE: 46

Ala Leu Ile Phe Asn Thr Gln Ile Arg Asn Ile Phe Ile Val Trp Asn
1               5                   10                  15

Thr Asn Lys Tyr Gln Val Ser Gln Val Ser Lys Glu Lys Leu Glu Glu
            20                  25                  30

Asn Gln Asp Thr Glu Gly Asn Phe Asp Phe Asp Ser Val Lys Ala Ile
        35                  40                  45

Ser Ser Glu Ala Val Leu Thr Ser Gln Trp Asp Ala Gln Lys Leu Pro
    50                  55                  60

Val Ile Gly Gly Ile Ala Ile Pro Glu Leu Glu Met Asn Leu Pro Ile
65                  70                  75                  80

Phe Lys Gly Leu Asp Asn Val Asn Leu Phe Tyr Gly Ala Gly Thr Met
                85                  90                  95

Lys Arg Glu Gln Val Met Gly Glu Gly Asn Tyr Ser Leu Ala Ser His
            100                 105                 110

His Ile Phe Gly Val Asp Asn Ala Asn Lys Met Leu Phe Ser Pro Leu
        115                 120                 125

Asp Asn Ala Lys Asn Gly Met Lys Ile Tyr Leu Thr Asp Lys Asn Lys
    130                 135                 140

Val Tyr Thr Tyr Glu Ile Arg Glu Val Lys Arg Val Thr Pro Asp Arg
145                 150                 155                 160

Val Asp Glu Val Asp Asp Arg Asp Gly Val Asn Glu Ile Thr Leu Val
                165                 170                 175

Thr Cys Glu Asp Leu Ala Ala Thr Glu Arg Ile Ile Val Lys Gly Asp
            180                 185                 190

Leu Lys Glu Thr Lys Asp Tyr Ser Gln Thr Ser Asp Glu Ile Leu Thr
        195                 200                 205

Ala Phe Asn Gln Pro Tyr Lys Gln Phe Tyr
    210                 215

<210> SEQ ID NO 47
<211> LENGTH: 165
<212> TYPE: PRT
<213> ORGANISM: Streptococcus pneumoniae
<220> FEATURE:
<223> OTHER INFORMATION: spr1345

<400> SEQUENCE: 47
```

```
Val Pro Lys Thr Ala Thr Ser Thr Glu Thr Lys Thr Ile Thr Arg Ile
1               5                   10                  15

Ile His Tyr Val Asp Lys Val Thr Asn Gln Asn Val Lys Glu Asp Val
                20                  25                  30

Val Gln Pro Val Thr Leu Ser Arg Thr Lys Thr Glu Asn Lys Val Thr
            35                  40                  45

Gly Val Val Thr Tyr Gly Glu Trp Thr Thr Gly Asn Trp Asp Glu Val
        50                  55                  60

Ile Ser Gly Lys Ile Asp Lys Tyr Lys Asp Pro Asp Ile Pro Thr Val
65              70                  75                  80

Glu Ser Gln Glu Val Thr Ser Asp Ser Ser Asp Lys Glu Ile Thr Val
                85                  90                  95

Arg Tyr Asp Arg Leu Ser Thr Pro Glu Lys Pro Ile Pro Gln Pro Asn
            100                 105                 110

Pro Glu His Pro Ser Val Pro Thr Pro Asn Pro Glu Leu Pro Asn Gln
        115                 120                 125

Glu Thr Pro Thr Pro Asp Lys Pro Thr Pro Glu Pro Gly Thr Pro Lys
    130                 135                 140

Thr Glu Thr Pro Val Asn Pro Asp Pro Glu Val Pro Thr Tyr Glu Thr
145                 150                 155                 160

Gly Lys Arg Glu Glu
                165

<210> SEQ ID NO 48
<211> LENGTH: 680
<212> TYPE: PRT
<213> ORGANISM: Streptococcus pneumoniae
<220> FEATURE:
<223> OTHER INFORMATION: Fragment of SEQ ID NO: 30 which omits the
      natural leader peptide sequence

<400> SEQUENCE: 48

Ala Ser Asp Gly Thr Trp Gln Gly Lys Gln Tyr Leu Lys Glu Asp Gly
1               5                   10                  15

Ser Gln Ala Ala Asn Glu Trp Val Phe Asp Thr His Tyr Gln Ser Trp
                20                  25                  30

Phe Tyr Ile Lys Ala Asp Ala Asn Tyr Ala Glu Asn Glu Trp Leu Lys
            35                  40                  45

Gln Gly Asp Asp Tyr Phe Tyr Leu Lys Ser Gly Tyr Met Ala Lys
        50                  55                  60

Ser Glu Trp Val Glu Asp Lys Gly Ala Phe Tyr Tyr Leu Asp Gln Asp
65              70                  75                  80

Gly Lys Met Lys Arg Asn Ala Trp Val Gly Thr Ser Tyr Val Gly Ala
                85                  90                  95

Thr Gly Ala Lys Val Ile Glu Asp Trp Val Tyr Asp Ser Gln Tyr Asp
            100                 105                 110

Ala Trp Phe Tyr Ile Lys Ala Asp Gly Gln His Ala Glu Lys Glu Trp
        115                 120                 125

Leu Gln Ile Lys Gly Lys Asp Tyr Tyr Phe Lys Ser Gly Gly Tyr Leu
    130                 135                 140

Leu Thr Ser Gln Trp Ile Asn Gln Ala Tyr Val Asn Ala Ser Gly Ala
145                 150                 155                 160

Lys Val Gln Gln Gly Trp Leu Phe Asp Lys Gln Tyr Lys Ser Trp Phe
                165                 170                 175

Tyr Ile Lys Glu Asn Gly Asn Tyr Ala Asp Lys Glu Trp Ile Phe Glu
                180                 185                 190
```

-continued

```
Asn Gly His Tyr Tyr Leu Lys Ser Gly Tyr Met Ala Ala Asn
        195                 200                 205

Glu Trp Ile Trp Asp Lys Glu Ser Trp Phe Tyr Leu Lys Phe Asp Gly
    210                 215                 220

Lys Ile Ala Glu Lys Glu Trp Val Tyr Asp Ser His Ser Gln Ala Trp
225                 230                 235                 240

Tyr Tyr Phe Lys Ser Gly Gly Tyr Met Ala Ala Asn Glu Trp Ile Trp
                245                 250                 255

Asp Lys Glu Ser Trp Phe Tyr Leu Lys Phe Asp Gly Lys Met Ala Glu
            260                 265                 270

Lys Glu Trp Val Tyr Asp Ser His Ser Gln Ala Trp Tyr Tyr Phe Lys
        275                 280                 285

Ser Gly Gly Tyr Met Thr Ala Asn Glu Trp Ile Trp Asp Lys Glu Ser
    290                 295                 300

Trp Phe Tyr Leu Lys Ser Asp Gly Lys Ile Ala Glu Lys Glu Trp Val
305                 310                 315                 320

Tyr Asp Ser His Ser Gln Ala Trp Tyr Tyr Phe Lys Ser Gly Gly Tyr
                325                 330                 335

Met Thr Ala Asn Glu Trp Ile Trp Asp Lys Glu Ser Trp Phe Tyr Leu
            340                 345                 350

Lys Ser Asp Gly Lys Met Ala Glu Lys Glu Trp Val Tyr Asp Ser His
        355                 360                 365

Ser Gln Ala Trp Tyr Tyr Phe Lys Ser Gly Gly Tyr Met Ala Lys Asn
    370                 375                 380

Glu Thr Val Asp Gly Tyr Gln Leu Gly Ser Asp Gly Lys Trp Leu Gly
385                 390                 395                 400

Gly Lys Ala Thr Asn Lys Asn Ala Ala Tyr Tyr Gln Val Val Pro Val
                405                 410                 415

Thr Ala Asn Val Tyr Asp Ser Asp Gly Glu Lys Leu Ser Tyr Ile Ser
            420                 425                 430

Gln Gly Ser Val Val Trp Leu Asp Lys Asp Arg Lys Ser Asp Asp Lys
        435                 440                 445

Arg Leu Ala Ile Thr Ile Ser Gly Leu Ser Gly Tyr Met Lys Thr Glu
450                 455                 460

Asp Leu Gln Ala Leu Asp Ala Ser Lys Asp Phe Ile Pro Tyr Glu
465                 470                 475                 480

Ser Asp Gly His Arg Phe Tyr His Tyr Val Ala Gln Asn Ala Ser Ile
                485                 490                 495

Pro Val Ala Ser His Leu Ser Asp Met Glu Val Gly Lys Lys Tyr Tyr
            500                 505                 510

Ser Ala Asp Gly Leu His Phe Asp Gly Phe Lys Leu Glu Asn Pro Phe
        515                 520                 525

Leu Phe Lys Asp Leu Thr Glu Ala Thr Asn Tyr Ser Ala Glu Glu Leu
530                 535                 540

Asp Lys Val Phe Ser Leu Leu Asn Ile Asn Asn Ser Leu Leu Glu Asn
545                 550                 555                 560

Lys Gly Ala Thr Phe Lys Glu Ala Glu Glu His Tyr His Ile Asn Ala
                565                 570                 575

Leu Tyr Leu Leu Ala His Ser Ala Leu Glu Ser Asn Trp Gly Arg Ser
            580                 585                 590

Lys Ile Ala Lys Asp Lys Asn Asn Phe Phe Gly Ile Thr Ala Tyr Asp
        595                 600                 605

Thr Thr Pro Tyr Leu Ser Ala Lys Thr Phe Asp Asp Val Asp Lys Gly
610                 615                 620
```

```
Ile Leu Gly Ala Thr Lys Trp Ile Lys Glu Asn Tyr Ile Asp Arg Gly
625                 630                 635                 640

Arg Thr Phe Leu Gly Asn Lys Ala Ser Gly Met Asn Val Glu Tyr Ala
            645                 650                 655

Ser Asp Pro Tyr Trp Gly Glu Lys Ile Ala Ser Val Met Met Lys Ile
            660                 665                 670

Asn Glu Lys Leu Gly Gly Lys Asp
        675                 680
```

<210> SEQ ID NO 49
<211> LENGTH: 469
<212> TYPE: PRT
<213> ORGANISM: Streptococcus pneumoniae
<220> FEATURE:
<223> OTHER INFORMATION: Fragment of SEQ ID NO: 31, which omits the
      natural leader peptide sequence

<400> SEQUENCE: 49

```
Ala Asn Glu Thr Glu Val Ala Lys Thr Ser Gln Asp Thr Thr Thr Ala
1               5                   10                  15

Ser Ser Ser Ser Glu Gln Asn Gln Ser Ser Asn Lys Thr Gln Thr Ser
            20                  25                  30

Ala Glu Val Gln Thr Asn Ala Ala Tyr Trp Asp Gly Asp Tyr Tyr
            35                  40                  45

Val Lys Asp Asp Gly Ser Lys Ala Gln Ser Glu Trp Ile Phe Asp Asn
    50                  55                  60

Tyr Tyr Lys Ala Trp Phe Tyr Ile Asn Ser Asp Gly Arg Tyr Ser Gln
65                  70                  75                  80

Asn Glu Trp His Gly Asn Tyr Tyr Leu Lys Ser Gly Gly Tyr Met Ala
                85                  90                  95

Gln Asn Glu Trp Ile Tyr Asp Ser Asn Tyr Lys Ser Trp Phe Tyr Leu
            100                 105                 110

Lys Ser Asp Gly Ala Tyr Ala His Gln Glu Trp Gln Leu Ile Gly Asn
        115                 120                 125

Lys Trp Tyr Tyr Phe Lys Lys Trp Gly Tyr Met Ala Lys Ser Gln Trp
    130                 135                 140

Gln Gly Ser Tyr Phe Leu Asn Gly Gln Gly Ala Met Ile Gln Asn Glu
145                 150                 155                 160

Trp Leu Tyr Asp Pro Ala Tyr Ser Ala Tyr Phe Tyr Leu Lys Ser Asp
                165                 170                 175

Gly Thr Tyr Ala Asn Gln Glu Trp Gln Lys Val Gly Gly Lys Trp Tyr
            180                 185                 190

Tyr Phe Lys Lys Trp Gly Tyr Met Ala Arg Asn Glu Trp Gln Gly Asn
        195                 200                 205

Tyr Tyr Leu Thr Gly Ser Gly Ala Met Ala Thr Asp Glu Val Ile Met
    210                 215                 220

Asp Gly Ala Arg Tyr Ile Phe Ala Ala Ser Gly Glu Leu Lys Glu Lys
225                 230                 235                 240

Lys Asp Leu Asn Val Gly Trp Val His Arg Asp Gly Lys Arg Tyr Phe
                245                 250                 255

Phe Asn Asn Arg Glu Glu Gln Val Gly Thr Glu His Ala Lys Lys Ile
            260                 265                 270

Ile Asp Ile Ser Glu His Asn Gly Arg Ile Asn Asp Trp Lys Lys Val
        275                 280                 285

Ile Asp Glu Asn Lys Val Asp Gly Val Ile Val Arg Leu Gly Tyr Ser
    290                 295                 300
```

```
Gly Lys Glu Asp Lys Glu Leu Ala His Asn Ile Lys Glu Leu Asn Arg
305                 310                 315                 320

Leu Gly Ile Pro Tyr Gly Val Tyr Leu Tyr Thr Tyr Ala Glu Asn Glu
                325                 330                 335

Thr Asp Ala Glu Asn Asp Ala Lys Gln Thr Ile Glu Leu Ile Lys Lys
            340                 345                 350

Tyr Asn Met Asn Leu Ser Tyr Pro Ile Tyr Tyr Asp Val Glu Asn Trp
        355                 360                 365

Glu Tyr Val Asn Lys Ser Lys Arg Ala Pro Ser Asp Thr Asp Thr Trp
    370                 375                 380

Val Lys Ile Ile Asn Lys Tyr Met Asp Thr Met Lys Gln Ala Gly Tyr
385                 390                 395                 400

Gln Asn Val Tyr Val Tyr Ser Tyr Arg Ser Leu Leu Gln Thr Arg Leu
                405                 410                 415

Lys His Pro Asp Ile Leu Lys His Val Asn Trp Val Ala Ala Tyr Thr
            420                 425                 430

Asn Ala Leu Glu Trp Glu Asn Pro Tyr Tyr Ser Gly Glu Lys Gly Trp
        435                 440                 445

Gln Tyr Thr Ser Ser Glu Tyr Met Lys Gly Ile Gln Gly Arg Val Asp
    450                 455                 460

Val Ser Val Trp Tyr
465

<210> SEQ ID NO 50
<211> LENGTH: 471
<212> TYPE: PRT
<213> ORGANISM: Streptococcus pneumoniae
<220> FEATURE:
<223> OTHER INFORMATION: SEQ ID NO: 32, including Pro325 to Leu mutation

<400> SEQUENCE: 50

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Val Arg Gly Ala Val Asn
        115                 120                 125

Asp Leu Leu Ala Lys Trp His Gln Asp Tyr Gly Gln Val Asn Asn Val
130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190
```

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
            245                 250                 255

Asp Glu Val Glu Ala Ala Phe Glu Ala Leu Ile Lys Gly Val Lys Val
        260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Leu Gly Leu Pro Ile Ser Tyr Thr Thr Ser Phe Leu
            325                 330                 335

Arg Asp Asn Val Val Ala Thr Phe Gln Asn Ser Thr Asp Tyr Val Glu
        340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
        420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 51
<211> LENGTH: 471
<212> TYPE: PRT
<213> ORGANISM: Streptococcus pneumoniae
<220> FEATURE:
<223> OTHER INFORMATION: SEQ ID NO: 32, which includes Pro325 to Leu and
      Trp433 to Phe mutations

<400> SEQUENCE: 51

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Asp Glu
65                  70                  75                  80

```
Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Leu Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Phe Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 52
<211> LENGTH: 464
<212> TYPE: PRT
<213> ORGANISM: Streptococcus pneumoniae
```

-continued

```
<220> FEATURE:
<223> OTHER INFORMATION: SEQ ID NO: 32 with Pro325 to Leu mutation with
      a 7-mer truncation

<400> SEQUENCE: 52
```

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
            85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
            130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
            165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
            210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
            245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Leu Gly Leu Pro Ile Ser Tyr Thr Thr Ser Phe Leu
            325                 330                 335

Arg Asp Asn Val Val Ala Thr Phe Gln Asn Ser Thr Tyr Val Glu
            340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
            370                 375                 380

Asp His Gln Gly Lys Glu Val Leu Thr Pro Lys Ala Trp Asp Arg Asn
385                 390                 395                 400

```
Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

<210> SEQ ID NO 53
<211> LENGTH: 366
<212> TYPE: PRT
<213> ORGANISM: Streptococcus pneumoniae
<220> FEATURE:
<223> OTHER INFORMATION: SEQ ID NO: 33 , which omits the natural leader
      peptide sequence

<400> SEQUENCE: 53

Ala Glu Thr Thr Asp Asp Lys Ile Ala Ala Gln Asp Asn Lys Ile Ser
1               5                   10                  15

Asn Leu Thr Ala Gln Gln Gln Glu Ala Gln Lys Gln Val Asp Gln Ile
            20                  25                  30

Gln Glu Gln Val Ser Ala Ile Gln Ala Glu Gln Ser Asn Leu Gln Ala
        35                  40                  45

Glu Asn Asp Arg Leu Gln Ala Glu Ser Lys Lys Leu Glu Gly Glu Ile
    50                  55                  60

Thr Glu Leu Ser Lys Asn Ile Val Ser Arg Asn Gln Ser Leu Glu Lys
65                  70                  75                  80

Gln Ala Arg Ser Ala Gln Thr Asn Gly Ala Val Thr Ser Tyr Ile Asn
                85                  90                  95

Thr Ile Val Asn Ser Lys Ser Ile Thr Glu Ala Ile Ser Arg Val Ala
            100                 105                 110

Ala Met Ser Glu Ile Val Ser Ala Asn Asn Lys Met Leu Glu Gln Gln
        115                 120                 125

Lys Ala Asp Lys Lys Ala Ile Ser Glu Lys Gln Val Ala Asn Asn Asp
    130                 135                 140

Ala Ile Asn Thr Val Ile Ala Asn Gln Gln Lys Leu Ala Asp Asp Ala
145                 150                 155                 160

Gln Ala Leu Thr Thr Lys Gln Ala Glu Leu Lys Ala Ala Glu Leu Ser
                165                 170                 175

Leu Ala Ala Glu Lys Ala Thr Ala Glu Gly Lys Ala Ser Leu Leu
            180                 185                 190

Glu Gln Lys Ala Ala Glu Ala Glu Ala Arg Ala Ala Ala Val Ala
    195                 200                 205

Glu Ala Ala Tyr Lys Glu Lys Arg Ala Ser Gln Gln Gln Ser Val Leu
    210                 215                 220

Ala Ser Ala Asn Thr Asn Leu Thr Ala Gln Val Gln Ala Val Ser Glu
225                 230                 235                 240

Ser Ala Ala Ala Pro Val Arg Ala Lys Val Arg Pro Thr Tyr Ser Thr
                245                 250                 255

Asn Ala Ser Ser Tyr Pro Ile Gly Glu Cys Thr Trp Gly Val Lys Thr
            260                 265                 270

Leu Ala Pro Trp Ala Gly Asp Tyr Trp Gly Asn Gly Ala Gln Trp Ala
        275                 280                 285

Thr Ser Ala Ala Ala Ala Gly Phe Arg Thr Gly Ser Thr Pro Gln Val
    290                 295                 300
```

-continued

Gly Ala Ile Ala Cys Trp Asn Asp Gly Gly Tyr Gly His Val Ala Val
305                 310                 315                 320

Val Thr Ala Val Glu Ser Thr Thr Arg Ile Gln Val Ser Glu Ser Asn
            325                 330                 335

Tyr Ala Gly Asn Arg Thr Ile Gly Asn His Arg Gly Trp Phe Asn Pro
        340                 345                 350

Thr Thr Thr Ser Glu Gly Phe Val Thr Tyr Ile Tyr Ala Asp
    355                 360                 365

<210> SEQ ID NO 54
<211> LENGTH: 195
<212> TYPE: PRT
<213> ORGANISM: Streptococcus pneumoniae
<220> FEATURE:
<223> OTHER INFORMATION: variant form of spr0096, with an insert near
      its C-terminus relative to SEQ ID NO: 34

<400> SEQUENCE: 54

Met Lys Ser Ile Thr Lys Lys Ile Lys Ala Thr Leu Ala Gly Val Ala
1               5                   10                  15

Ala Leu Phe Ala Val Phe Ala Pro Ser Phe Val Ser Ala Gln Glu Ser
            20                  25                  30

Ser Thr Tyr Thr Val Lys Glu Gly Asp Thr Leu Ser Glu Ile Ala Glu
        35                  40                  45

Thr His Asn Thr Thr Val Glu Lys Leu Ala Glu Asn His Ile Asp
    50                  55                  60

Asn Ile His Leu Ile Tyr Val Asp Gln Glu Leu Val Ile Asp Gly Pro
65                  70                  75                  80

Val Ala Pro Val Ala Thr Pro Ala Pro Ala Thr Tyr Ala Ala Pro Ala
                85                  90                  95

Ala Gln Asp Glu Thr Val Ser Ala Pro Val Ala Glu Thr Pro Val Val
            100                 105                 110

Ser Glu Thr Val Val Ser Thr Val Ser Gly Ser Glu Ala Glu Ala Lys
        115                 120                 125

Glu Trp Ile Ala Gln Lys Glu Ser Gly Gly Ser Tyr Thr Ala Thr Asn
    130                 135                 140

Gly Arg Tyr Ile Gly Arg Tyr Gln Leu Thr Asp Ser Tyr Leu Asn Gly
145                 150                 155                 160

Asp Tyr Ser Ala Glu Asn Gln Glu Arg Val Ala Asp Ala Tyr Val Ala
                165                 170                 175

Gly Arg Tyr Gly Ser Trp Thr Ala Ala Lys Asn Phe Trp Leu Asn Asn
            180                 185                 190

Gly Trp Tyr
        195

<210> SEQ ID NO 55
<211> LENGTH: 659
<212> TYPE: PRT
<213> ORGANISM: Streptococcus pneumoniae
<220> FEATURE:
<223> OTHER INFORMATION: variant form of spr1707

<400> SEQUENCE: 55

Met Lys Lys Asn Arg Val Phe Thr Ala Gly Leu Val Leu Leu Ala
1               5                   10                  15

Ala Gly Val Leu Ala Ala Cys Ser Ser Ser Lys Ser Ser Asp Ser Ser
            20                  25                  30

Ala Pro Lys Ala Tyr Gly Tyr Val Tyr Thr Ala Asp Pro Glu Thr Leu

-continued

```
            35                  40                  45
Asp Tyr Leu Ile Ser Ser Lys Asn Ser Thr Val Val Thr Ser Asn
 50                  55                  60
Gly Ile Asp Gly Leu Phe Thr Asn Asp Asn Tyr Gly Asn Leu Ala Pro
 65                  70                  75                  80
Ala Val Ala Glu Asp Trp Glu Val Ser Lys Asp Gly Leu Thr Tyr Thr
                     85                  90                  95
Tyr Lys Ile Arg Lys Gly Val Lys Trp Phe Thr Ser Asp Gly Glu Glu
                    100                 105                 110
Tyr Ala Glu Val Thr Ala Lys Asp Phe Val Asn Gly Leu Lys His Ala
                    115                 120                 125
Ala Asp Lys Lys Ser Glu Ala Met Tyr Leu Ala Glu Asn Ser Val Lys
 130                 135                 140
Gly Leu Ala Asp Tyr Leu Ser Gly Thr Ser Thr Asp Phe Ser Thr Val
 145                 150                 155                 160
Gly Val Lys Ala Val Asp Asp Tyr Thr Leu Gln Tyr Thr Leu Asn Gln
                    165                 170                 175
Pro Glu Pro Phe Trp Asn Ser Lys Leu Thr Tyr Ser Ile Phe Trp Pro
                    180                 185                 190
Leu Asn Glu Glu Phe Glu Thr Ser Lys Gly Ser Asp Phe Ala Lys Pro
                    195                 200                 205
Thr Asp Pro Thr Ser Leu Leu Tyr Asn Gly Pro Phe Leu Leu Lys Gly
 210                 215                 220
Leu Thr Ala Lys Ser Ser Val Glu Phe Val Lys Asn Glu Gln Tyr Trp
 225                 230                 235                 240
Asp Lys Glu Asn Val His Leu Asp Thr Ile Asn Leu Ala Tyr Tyr Asp
                    245                 250                 255
Gly Ser Asp Gln Glu Ser Leu Glu Arg Asn Phe Thr Ser Gly Ala Tyr
                    260                 265                 270
Ser Tyr Ala Arg Leu Tyr Pro Thr Ser Ser Asn Tyr Ser Lys Val Ala
                    275                 280                 285
Glu Glu Tyr Lys Asp Asn Ile Tyr Tyr Thr Gln Ser Gly Ser Gly Ile
 290                 295                 300
Ala Gly Leu Gly Val Asn Ile Asp Arg Gln Ser Tyr Asn Tyr Thr Ser
 305                 310                 315                 320
Lys Thr Thr Asp Ser Glu Lys Val Ala Thr Lys Lys Ala Leu Leu Asn
                    325                 330                 335
Lys Asp Phe Arg Gln Ala Leu Asn Phe Ala Leu Asp Arg Ser Ala Tyr
                    340                 345                 350
Ser Ala Gln Ile Asn Gly Lys Asp Gly Ala Ala Leu Ala Val Arg Asn
                    355                 360                 365
Leu Phe Val Lys Pro Asp Phe Val Ser Ala Gly Glu Lys Thr Phe Gly
 370                 375                 380
Asp Leu Val Ala Ala Gln Leu Pro Ala Tyr Gly Asp Glu Trp Lys Gly
 385                 390                 395                 400
Val Asn Leu Ala Asp Gly Gln Asp Gly Leu Phe Asn Ala Asp Lys Ala
                    405                 410                 415
Lys Ala Glu Phe Ala Lys Ala Lys Lys Ala Leu Glu Ala Asp Gly Val
                    420                 425                 430
Gln Phe Pro Ile His Leu Asp Val Pro Val Asp Gln Ala Ser Lys Asn
                    435                 440                 445
Tyr Ile Ser Arg Ile Gln Ser Phe Lys Gln Ser Val Glu Thr Val Leu
 450                 455                 460
```

```
Gly Val Glu Asn Val Val Asp Ile Gln Gln Met Thr Ser Asp Glu
465                 470                 475                 480

Phe Leu Asn Ile Thr Tyr Tyr Ala Ala Asn Ala Ser Ser Glu Asp Trp
                    485                 490                 495

Asp Val Ser Gly Gly Val Ser Trp Gly Pro Asp Tyr Gln Asp Pro Ser
                500                 505                 510

Thr Tyr Leu Asp Ile Leu Lys Thr Thr Ser Ser Glu Thr Thr Lys Thr
                515                 520                 525

Tyr Leu Gly Phe Asp Asn Pro Asn Ser Pro Ser Val Val Gln Val Gly
                530                 535                 540

Leu Lys Glu Tyr Asp Lys Leu Val Asp Glu Ala Ala Arg Glu Thr Ser
545                 550                 555                 560

Asp Leu Asn Val Arg Tyr Glu Lys Tyr Ala Ala Ala Gln Ala Trp Leu
                565                 570                 575

Thr Asp Ser Ser Leu Phe Ile Pro Ala Met Ala Ser Ser Gly Ala Ala
                580                 585                 590

Pro Val Leu Ser Arg Ile Val Pro Phe Thr Gly Ala Ser Ala Gln Thr
                595                 600                 605

Gly Ser Lys Gly Ser Asp Val Tyr Phe Lys Tyr Leu Lys Ser Gln Asp
                610                 615                 620

Lys Val Val Thr Lys Glu Glu Tyr Glu Lys Ala Arg Glu Lys Trp Leu
625                 630                 635                 640

Lys Glu Lys Ala Glu Ser Asn Glu Lys Ala Gln Lys Glu Leu Ala Ser
                645                 650                 655

His Val Lys

<210> SEQ ID NO 56
<211> LENGTH: 294
<212> TYPE: PRT
<213> ORGANISM: Streptococcus pneumoniae
<220> FEATURE:
<223> OTHER INFORMATION: Fragment of SEQ ID NO: 37, which omits the
      natural leader peptide sequence

<400> SEQUENCE: 56

Ala Cys Ser Lys Gly Ser Glu Gly Ala Asp Leu Ile Ser Met Lys Gly
1               5                   10                  15

Asp Val Ile Thr Glu His Gln Phe Tyr Glu Gln Val Lys Asn Asn Pro
                20                  25                  30

Ser Ala Gln Gln Val Leu Leu Asn Met Thr Ile Gln Lys Val Phe Glu
            35                  40                  45

Lys Gln Tyr Gly Ser Glu Leu Asp Asp Lys Glu Val Asp Asp Thr Ile
        50                  55                  60

Ala Glu Glu Lys Lys Gln Tyr Gly Glu Asn Tyr Gln Arg Val Leu Ser
65                  70                  75                  80

Gln Ala Gly Met Thr Leu Glu Thr Arg Lys Ala Gln Ile Arg Thr Ser
                85                  90                  95

Lys Leu Val Glu Leu Ala Val Lys Lys Val Ala Glu Ala Glu Leu Thr
                100                 105                 110

Asp Glu Ala Tyr Lys Lys Ala Phe Asp Glu Tyr Thr Pro Asp Val Thr
            115                 120                 125

Ala Gln Ile Ile Arg Leu Asn Asn Glu Asp Lys Ala Lys Glu Val Leu
        130                 135                 140

Glu Lys Ala Lys Ala Glu Gly Ala Asp Phe Ala Gln Leu Ala Lys Asp
145                 150                 155                 160

Asn Ser Thr Asp Glu Lys Thr Lys Glu Asn Gly Gly Glu Ile Thr Phe
```

```
                165                 170                 175
Asp Ser Ala Ser Thr Glu Val Pro Glu Gln Val Lys Lys Ala Ala Phe
            180                 185                 190

Ala Leu Asp Val Asp Gly Val Ser Asp Val Ile Thr Ala Thr Gly Thr
            195                 200                 205

Gln Ala Tyr Ser Ser Gln Tyr Tyr Ile Val Lys Leu Thr Lys Lys Thr
            210                 215                 220

Glu Lys Ser Ser Asn Ile Asp Asp Tyr Lys Lys Leu Lys Thr Val
225                 230                 235                 240

Ile Leu Thr Gln Lys Gln Asn Asp Ser Thr Phe Val Gln Ser Ile Ile
                245                 250                 255

Gly Lys Glu Leu Gln Ala Ala Asn Ile Lys Val Lys Asp Gln Ala Phe
            260                 265                 270

Gln Asn Ile Phe Thr Gln Tyr Ile Gly Gly Gly Asp Ser Ser Ser
            275                 280                 285

Ser Ser Thr Ser Asn Glu
        290

<210> SEQ ID NO 57
<211> LENGTH: 701
<212> TYPE: PRT
<213> ORGANISM: Streptococcus pneumoniae
<220> FEATURE:
<223> OTHER INFORMATION: spr1995

<400> SEQUENCE: 57

Met Phe Ala Ser Lys Ser Glu Arg Lys Val His Tyr Ser Ile Arg Lys
1               5                   10                  15

Phe Ser Ile Gly Val Ala Ser Val Ala Val Ala Ser Leu Val Met Gly
            20                  25                  30

Ser Val Val His Ala Thr Glu Asn Glu Gly Ser Thr Gln Ala Ala Thr
        35                  40                  45

Ser Ser Asn Met Ala Lys Thr Glu His Arg Lys Ala Ala Lys Gln Val
    50                  55                  60

Val Asp Glu Tyr Ile Glu Lys Met Leu Arg Glu Ile Gln Leu Asp Arg
65                  70                  75                  80

Arg Lys His Thr Gln Asn Val Ala Leu Asn Ile Lys Leu Ser Ala Ile
                85                  90                  95

Lys Thr Lys Tyr Leu Arg Glu Leu Asn Val Leu Glu Glu Lys Ser Lys
            100                 105                 110

Asp Glu Leu Pro Ser Glu Ile Lys Ala Lys Leu Asp Ala Phe Glu
        115                 120                 125

Lys Phe Lys Lys Asp Thr Leu Lys Pro Gly Glu Lys Val Ala Glu Ala
    130                 135                 140

Lys Lys Lys Val Glu Glu Ala Lys Lys Ala Glu Asp Gln Lys Glu
145                 150                 155                 160

Glu Asp Arg Arg Asn Tyr Pro Thr Asn Thr Tyr Lys Thr Leu Glu Leu
                165                 170                 175

Glu Ile Ala Glu Phe Asp Val Lys Val Lys Glu Ala Glu Leu Glu Leu
            180                 185                 190

Val Lys Glu Glu Ala Lys Glu Ser Arg Asn Glu Gly Thr Ile Lys Gln
        195                 200                 205

Ala Lys Glu Lys Val Glu Ser Lys Ala Glu Ala Thr Arg Leu Glu
    210                 215                 220

Asn Ile Lys Thr Asp Arg Lys Lys Ala Glu Glu Glu Ala Lys Arg Lys
225                 230                 235                 240
```

```
Ala Asp Ala Lys Leu Lys Glu Ala Asn Val Ala Thr Ser Asp Gln Gly
                245                 250                 255
Lys Pro Lys Gly Arg Ala Lys Arg Gly Val Pro Gly Glu Leu Ala Thr
            260                 265                 270
Pro Asp Lys Glu Asn Asp Ala Lys Ser Ser Asp Ser Ser Val Gly
            275                 280                 285
Glu Glu Thr Leu Pro Ser Ser Ser Leu Lys Ser Gly Lys Lys Val Ala
        290                 295                 300
Glu Ala Glu Lys Lys Val Glu Ala Glu Lys Lys Ala Lys Asp Gln
305                 310                 315                 320
Lys Glu Glu Asp Arg Arg Asn Tyr Pro Thr Asn Thr Tyr Lys Thr Leu
                325                 330                 335
Asp Leu Glu Ile Ala Glu Ser Asp Val Lys Val Lys Glu Ala Glu Leu
            340                 345                 350
Glu Leu Val Lys Glu Glu Ala Lys Glu Pro Arg Asp Glu Glu Lys Ile
        355                 360                 365
Lys Gln Ala Lys Ala Lys Val Glu Ser Lys Lys Ala Glu Ala Thr Arg
    370                 375                 380
Leu Glu Asn Ile Lys Thr Asp Arg Lys Lys Ala Glu Glu Ala Lys
385                 390                 395                 400
Arg Lys Ala Ala Glu Glu Asp Lys Val Lys Glu Lys Pro Ala Glu Gln
                405                 410                 415
Pro Gln Pro Ala Pro Ala Thr Gln Pro Glu Lys Pro Ala Pro Lys Pro
            420                 425                 430
Glu Lys Pro Ala Glu Gln Pro Lys Ala Glu Lys Thr Asp Asp Gln Gln
        435                 440                 445
Ala Glu Glu Asp Tyr Ala Arg Arg Ser Glu Glu Tyr Asn Arg Leu
    450                 455                 460
Thr Gln Gln Gln Pro Pro Lys Thr Glu Lys Pro Ala Gln Pro Ser Thr
465                 470                 475                 480
Pro Lys Thr Gly Trp Lys Gln Glu Asn Gly Met Trp Tyr Phe Tyr Asn
                485                 490                 495
Thr Asp Gly Ser Met Ala Thr Gly Trp Leu Gln Asn Asn Gly Ser Trp
            500                 505                 510
Tyr Tyr Leu Asn Ala Asn Gly Ala Met Ala Thr Gly Trp Leu Gln Asn
        515                 520                 525
Asn Gly Ser Trp Tyr Tyr Leu Asn Ala Asn Gly Ser Met Ala Thr Gly
    530                 535                 540
Trp Leu Gln Asn Asn Gly Ser Trp Tyr Tyr Leu Asn Ala Asn Gly Ala
545                 550                 555                 560
Met Ala Thr Gly Trp Leu Gln Tyr Asn Gly Ser Trp Tyr Tyr Leu Asn
                565                 570                 575
Ser Asn Gly Ala Met Ala Thr Gly Trp Leu Gln Tyr Asn Gly Ser Trp
            580                 585                 590
Tyr Tyr Leu Asn Ala Asn Gly Asp Met Ala Thr Gly Trp Leu Gln Asn
        595                 600                 605
Asn Gly Ser Trp Tyr Tyr Leu Asn Ala Asn Gly Asp Met Ala Thr Gly
    610                 615                 620
Trp Leu Gln Tyr Asn Gly Ser Trp Tyr Tyr Leu Asn Ala Asn Gly Asp
625                 630                 635                 640
Met Ala Thr Gly Trp Val Lys Asp Gly Asp Thr Trp Tyr Tyr Leu Glu
                645                 650                 655
Ala Ser Gly Ala Met Lys Ala Ser Gln Trp Phe Lys Val Ser Asp Lys
```

```
                    660              665              670
Trp Tyr Tyr Val Asn Gly Ser Gly Ala Leu Ala Val Asn Thr Thr Val
        675              680              685

Asp Gly Tyr Gly Val Asn Ala Asn Gly Glu Trp Val Asn
        690              695              700

<210> SEQ ID NO 58
<211> LENGTH: 196
<212> TYPE: PRT
<213> ORGANISM: Streptococcus pneumoniae
<220> FEATURE:
<223> OTHER INFORMATION: full length ClpP

<400> SEQUENCE: 58

Met Ile Pro Val Val Ile Glu Gln Thr Ser Arg Gly Glu Arg Ser Tyr
1               5                   10                  15

Asp Ile Tyr Ser Arg Leu Leu Lys Asp Arg Ile Ile Met Leu Thr Gly
            20                  25                  30

Pro Val Glu Asp Asn Met Ala Asn Ser Val Ile Ala Gln Leu Leu Phe
        35                  40                  45

Leu Asp Ala Gln Asp Ser Thr Lys Asp Ile Tyr Leu Tyr Val Asn Thr
50                  55                  60

Pro Gly Gly Ser Val Ser Ala Gly Leu Ala Ile Val Asp Thr Met Asn
65                  70                  75                  80

Phe Ile Lys Ala Asp Val Gln Thr Ile Val Met Gly Met Ala Ala Ser
                85                  90                  95

Met Gly Thr Val Ile Ala Ser Ser Gly Ala Lys Gly Lys Arg Phe Met
            100                 105                 110

Leu Pro Asn Ala Glu Tyr Met Ile His Gln Pro Met Gly Gly Thr Gly
        115                 120                 125

Gly Gly Thr Gln Gln Thr Asp Met Ala Ile Ala Ala Glu His Leu Leu
    130                 135                 140

Lys Thr Arg Asn Thr Leu Glu Lys Ile Leu Ala Glu Asn Ser Gly Gln
145                 150                 155                 160

Ser Met Glu Lys Val His Ala Asp Ala Glu Arg Asp Asn Trp Met Ser
                165                 170                 175

Ala Gln Glu Thr Leu Glu Tyr Gly Phe Ile Asp Glu Ile Met Ala Asn
            180                 185                 190

Asn Ser Leu Asn
        195

<210> SEQ ID NO 59
<211> LENGTH: 318
<212> TYPE: PRT
<213> ORGANISM: Streptococcus pneumoniae
<220> FEATURE:
<223> OTHER INFORMATION: full length LytA

<400> SEQUENCE: 59

Met Glu Ile Asn Val Ser Lys Leu Arg Thr Asp Leu Pro Gln Val Gly
1               5                   10                  15

Val Gln Pro Tyr Arg Gln Val His Ala His Ser Thr Gly Asn Pro His
            20                  25                  30

Ser Thr Val Gln Asn Glu Ala Asp Tyr His Trp Arg Lys Asp Pro Glu
        35                  40                  45

Leu Gly Phe Phe Ser His Ile Val Gly Asn Gly Cys Ile Met Gln Val
    50                  55                  60

Gly Pro Val Asp Asn Gly Ala Trp Asp Val Gly Gly Gly Trp Asn Ala
```

```
                65                  70                  75                  80
Glu Thr Tyr Ala Ala Val Glu Leu Ile Glu Ser His Ser Thr Lys Glu
                    85                  90                  95

Glu Phe Met Thr Asp Tyr Arg Leu Tyr Ile Glu Leu Leu Arg Asn Leu
                100                 105                 110

Ala Asp Glu Ala Gly Leu Pro Lys Thr Leu Asp Thr Gly Ser Leu Ala
                115                 120                 125

Gly Ile Lys Thr His Glu Tyr Cys Thr Asn Asn Gln Pro Asn Asn His
            130                 135                 140

Ser Asp His Val Asp Pro Tyr Pro Tyr Leu Ala Lys Trp Gly Ile Ser
145                 150                 155                 160

Arg Glu Gln Phe Lys His Asp Ile Glu Asn Gly Leu Thr Ile Glu Thr
                165                 170                 175

Gly Trp Gln Lys Asn Asp Thr Gly Tyr Trp Tyr Val His Ser Asp Gly
                180                 185                 190

Ser Tyr Pro Lys Asp Lys Phe Glu Lys Ile Asn Gly Thr Trp Tyr Tyr
                195                 200                 205

Phe Asp Ser Ser Gly Tyr Met Leu Ala Asp Arg Trp Arg Lys His Thr
            210                 215                 220

Asp Gly Asn Trp Tyr Trp Phe Asp Asn Ser Gly Glu Met Ala Thr Gly
225                 230                 235                 240

Trp Lys Lys Ile Ala Asp Lys Trp Tyr Tyr Phe Asn Glu Glu Gly Ala
                245                 250                 255

Met Lys Thr Gly Trp Val Lys Tyr Lys Asp Thr Trp Tyr Tyr Leu Asp
                260                 265                 270

Ala Lys Glu Gly Ala Met Val Ser Asn Ala Phe Ile Gln Ser Ala Asp
            275                 280                 285

Gly Thr Gly Trp Tyr Tyr Leu Lys Pro Asp Gly Thr Leu Ala Asp Arg
            290                 295                 300

Pro Glu Phe Thr Val Glu Pro Asp Gly Leu Ile Thr Val Lys
305                 310                 315

<210> SEQ ID NO 60
<211> LENGTH: 828
<212> TYPE: PRT
<213> ORGANISM: Streptococcus pneumoniae
<220> FEATURE:
<223> OTHER INFORMATION: full length PhtA precursor

<400> SEQUENCE: 60

Met Gln Leu Glu Ile Ser Asn Arg Lys Arg Val Ser Met Lys Ile Asn
1               5                   10                  15

Lys Lys Tyr Leu Val Gly Ser Ala Ala Ala Leu Ile Leu Ser Val Cys
                20                  25                  30

Ser Tyr Glu Leu Gly Leu Tyr Gln Ala Arg Thr Val Lys Glu Asn Asn
            35                  40                  45

Arg Val Ser Tyr Ile Asp Gly Lys Gln Ala Thr Gln Lys Thr Glu Asn
        50                  55                  60

Leu Thr Pro Asp Glu Val Ser Arg Glu Gly Ile Asn Ala Glu Gln
65                  70                  75                  80

Ile Val Ile Lys Ile Thr Asp Gln Gly Tyr Val Thr Ser His Gly Asp
                85                  90                  95

His Tyr His Tyr Tyr Asn Gly Lys Val Pro Tyr Asp Ala Ile Phe Ser
                100                 105                 110

Glu Glu Leu Leu Met Lys Asp Pro Asn Tyr Lys Leu Lys Asp Glu Asp
                115                 120                 125
```

```
Ile Val Asn Glu Val Lys Gly Gly Tyr Val Ile Lys Val Asp Gly Lys
    130                 135                 140

Tyr Tyr Val Tyr Leu Lys Asp Ala Ala His Ala Asp Asn Val Arg Thr
145                 150                 155                 160

Lys Glu Glu Ile Asn Arg Gln Lys Gln Glu His Ser Gln His Arg Glu
                165                 170                 175

Gly Gly Thr Pro Arg Asn Asp Gly Ala Val Ala Leu Ala Arg Ser Gln
                180                 185                 190

Gly Arg Tyr Thr Thr Asp Asp Gly Tyr Ile Phe Asn Ala Ser Asp Ile
            195                 200                 205

Ile Glu Asp Thr Gly Asp Ala Tyr Ile Val Pro His Gly Asp His Tyr
    210                 215                 220

His Tyr Ile Pro Lys Asn Glu Leu Ser Ala Ser Glu Leu Ala Ala Ala
225                 230                 235                 240

Glu Ala Phe Leu Ser Gly Arg Gly Asn Leu Ser Asn Ser Arg Thr Tyr
                245                 250                 255

Arg Arg Gln Asn Ser Asp Asn Thr Ser Arg Thr Asn Trp Val Pro Ser
                260                 265                 270

Val Ser Asn Pro Gly Thr Thr Asn Thr Asn Thr Ser Asn Asn Ser Asn
            275                 280                 285

Thr Asn Ser Gln Ala Ser Gln Ser Asn Asp Ile Asp Ser Leu Leu Lys
    290                 295                 300

Gln Leu Tyr Lys Leu Pro Leu Ser Gln Arg His Val Glu Ser Asp Gly
305                 310                 315                 320

Leu Val Phe Asp Pro Ala Gln Ile Thr Ser Arg Thr Ala Arg Gly Val
                325                 330                 335

Ala Val Pro His Gly Asp His Tyr His Phe Ile Pro Tyr Ser Gln Met
                340                 345                 350

Ser Glu Leu Glu Glu Arg Ile Ala Arg Ile Ile Pro Leu Arg Tyr Arg
            355                 360                 365

Ser Asn His Trp Val Pro Asp Ser Arg Pro Glu Gln Pro Ser Pro Gln
    370                 375                 380

Pro Thr Pro Glu Pro Ser Pro Gly Pro Gln Pro Ala Pro Asn Leu Lys
385                 390                 395                 400

Ile Asp Ser Asn Ser Ser Leu Val Ser Gln Leu Val Arg Lys Val Gly
                405                 410                 415

Glu Gly Tyr Val Phe Glu Glu Lys Gly Ile Ser Arg Tyr Val Phe Ala
                420                 425                 430

Lys Asp Leu Pro Ser Glu Thr Val Lys Asn Leu Glu Ser Lys Leu Ser
            435                 440                 445

Lys Gln Glu Ser Val Ser His Thr Leu Thr Ala Lys Lys Glu Asn Val
    450                 455                 460

Ala Pro Arg Asp Gln Glu Phe Tyr Asp Lys Ala Tyr Asn Leu Leu Thr
465                 470                 475                 480

Glu Ala His Lys Ala Leu Phe Glu Asn Lys Gly Arg Asn Ser Asp Phe
                485                 490                 495

Gln Ala Leu Asp Lys Leu Leu Glu Arg Leu Asn Asp Glu Ser Thr Asn
                500                 505                 510

Lys Glu Lys Leu Val Asp Asp Leu Leu Ala Phe Leu Ala Pro Ile Thr
            515                 520                 525

His Pro Glu Arg Leu Gly Lys Pro Asn Ser Gln Ile Glu Tyr Thr Glu
    530                 535                 540

Asp Glu Val Arg Ile Ala Gln Leu Ala Asp Lys Tyr Thr Thr Ser Asp
```

```
                 545                 550                 555                 560
Gly Tyr Ile Phe Asp Glu His Asp Ile Ile Ser Asp Glu Gly Asp Ala
                565                 570                 575

Tyr Val Thr Pro His Met Gly His Ser His Trp Ile Gly Lys Asp Ser
            580                 585                 590

Leu Ser Asp Lys Glu Lys Val Ala Ala Gln Ala Tyr Thr Lys Glu Lys
                595                 600                 605

Gly Ile Leu Pro Pro Ser Asp Ala Asp Val Lys Ala Asn Pro Thr
            610                 615                 620

Gly Asp Ser Ala Ala Ile Tyr Asn Arg Val Lys Gly Glu Lys Arg
625                 630                 635                 640

Ile Pro Leu Val Arg Leu Pro Tyr Met Val Glu His Thr Val Glu Val
                645                 650                 655

Lys Asn Gly Asn Leu Ile Ile Pro His Lys Asp His Tyr His Asn Ile
            660                 665                 670

Lys Phe Ala Trp Phe Asp Asp His Thr Tyr Lys Ala Pro Asn Gly Tyr
            675                 680                 685

Thr Leu Glu Asp Leu Phe Ala Thr Ile Lys Tyr Tyr Val Glu His Pro
        690                 695                 700

Asp Glu Arg Pro His Ser Asn Asp Gly Trp Gly Asn Ala Ser Glu His
705                 710                 715                 720

Val Leu Gly Lys Lys Asp His Ser Glu Asp Pro Asn Lys Asn Phe Lys
                725                 730                 735

Ala Asp Glu Glu Pro Val Glu Glu Thr Pro Ala Glu Pro Glu Val Pro
            740                 745                 750

Gln Val Glu Thr Glu Lys Val Glu Ala Gln Leu Lys Glu Ala Glu Val
            755                 760                 765

Leu Leu Ala Lys Val Thr Asp Ser Ser Leu Lys Ala Asn Ala Thr Glu
        770                 775                 780

Thr Leu Ala Gly Leu Arg Asn Asn Leu Thr Leu Gln Ile Met Asp Asn
785                 790                 795                 800

Asn Ser Ile Met Ala Glu Ala Glu Lys Leu Leu Ala Leu Leu Lys Gly
                805                 810                 815

Ser Asn Pro Ser Ser Val Ser Lys Glu Lys Ile Asn
                820                 825

<210> SEQ ID NO 61
<211> LENGTH: 819
<212> TYPE: PRT
<213> ORGANISM: Streptococcus pneumoniae
<220> FEATURE:
<223> OTHER INFORMATION: full length PhtB precursor
<220> FEATURE:
<221> NAME/KEY: misc_feature
<222> LOCATION: (578)...(578)
<223> OTHER INFORMATION: any amino acid residue; optionally lysine

<400> SEQUENCE: 61

Met Lys Ile Asn Lys Lys Tyr Leu Ala Gly Ser Val Ala Val Leu Ala
1               5                   10                  15

Leu Ser Val Cys Ser Tyr Glu Leu Gly Arg Tyr Gln Ala Gly Gln Asp
                20                  25                  30

Lys Lys Glu Ser Asn Arg Val Ala Tyr Ile Asp Gly Asp Gln Ala Gly
            35                  40                  45

Gln Lys Ala Glu Asn Leu Thr Pro Asp Glu Val Ser Lys Arg Glu Gly
        50                  55                  60

Ile Asn Ala Glu Gln Ile Val Ile Lys Ile Thr Asp Gln Gly Tyr Val
```

```
            65                  70                  75                  80
Thr Ser His Gly Asp His Tyr His Tyr Tyr Asn Gly Lys Val Pro Tyr
                    85                  90                  95
Asp Ala Ile Ile Ser Glu Glu Leu Leu Met Lys Asp Pro Asn Tyr Gln
                100                 105                 110
Leu Lys Asp Ser Asp Ile Val Asn Glu Ile Lys Gly Tyr Val Ile
            115                 120                 125
Lys Val Asn Gly Lys Tyr Val Tyr Leu Lys Asp Ala Ala His Ala
130                 135                 140
Asp Asn Ile Arg Thr Lys Glu Glu Ile Lys Arg Gln Lys Gln Glu Arg
145                 150                 155                 160
Ser His Asn His Asn Ser Arg Ala Asp Asn Ala Val Ala Ala Arg
                165                 170                 175
Ala Gln Gly Arg Tyr Thr Thr Asp Asp Gly Tyr Ile Phe Asn Ala Ser
                180                 185                 190
Asp Ile Ile Glu Asp Thr Gly Asp Ala Tyr Ile Val Pro His Gly Asp
            195                 200                 205
His Tyr His Tyr Ile Pro Lys Asn Glu Leu Ser Ala Ser Glu Leu Ala
            210                 215                 220
Ala Ala Glu Ala Tyr Trp Asn Gly Lys Gln Gly Ser Arg Pro Ser Ser
225                 230                 235                 240
Ser Ser Ser Tyr Asn Ala Asn Pro Ala Gln Pro Arg Leu Ser Glu Asn
                245                 250                 255
His Asn Leu Thr Val Thr Pro Thr Tyr His Gln Asn Gln Gly Glu Asn
                260                 265                 270
Ile Ser Ser Leu Leu Arg Glu Leu Tyr Ala Lys Pro Leu Ser Glu Arg
            275                 280                 285
His Val Glu Ser Asp Gly Leu Ile Phe Asp Pro Ala Gln Ile Thr Ser
            290                 295                 300
Arg Thr Ala Arg Gly Val Ala Val Pro His Gly Asn His Tyr His Phe
305                 310                 315                 320
Ile Pro Tyr Glu Gln Met Ser Glu Leu Glu Lys Arg Ile Ala Arg Ile
                325                 330                 335
Ile Pro Leu Arg Tyr Arg Ser Asn His Trp Val Pro Asp Ser Arg Pro
                340                 345                 350
Glu Glu Pro Ser Pro Gln Pro Thr Pro Glu Pro Ser Pro Ser Pro Gln
                355                 360                 365
Pro Ala Pro Ser Asn Pro Ile Asp Gly Lys Leu Val Lys Glu Ala Val
            370                 375                 380
Arg Lys Val Gly Asp Gly Tyr Val Phe Glu Glu Asn Gly Val Ser Arg
385                 390                 395                 400
Tyr Ile Pro Ala Lys Asp Leu Ser Ala Glu Thr Ala Ala Gly Ile Asp
                405                 410                 415
Ser Lys Leu Ala Lys Gln Glu Ser Leu Ser His Lys Leu Gly Thr Lys
                420                 425                 430
Lys Thr Asp Leu Pro Ser Ser Asp Arg Glu Phe Tyr Asn Lys Ala Tyr
            435                 440                 445
Asp Leu Leu Ala Arg Ile His Gln Asp Leu Asp Asn Lys Gly Arg
            450                 455                 460
Gln Val Asp Phe Glu Ala Leu Asp Asn Leu Leu Glu Arg Leu Lys Asp
465                 470                 475                 480
Val Ser Ser Asp Lys Val Lys Leu Val Glu Asp Ile Leu Ala Phe Leu
                485                 490                 495
```

```
Ala Pro Ile Arg His Pro Glu Arg Leu Gly Lys Pro Asn Ala Gln Ile
            500                 505                 510

Thr Tyr Thr Asp Asp Glu Ile Gln Val Ala Lys Leu Ala Gly Lys Tyr
        515                 520                 525

Thr Ala Glu Asp Gly Tyr Ile Phe Asp Pro Arg Asp Ile Thr Ser Asp
530                 535                 540

Glu Gly Asp Ala Tyr Val Thr Pro His Met Thr His Ser His Trp Ile
545                 550                 555                 560

Lys Lys Asp Ser Leu Ser Glu Ala Glu Arg Ala Ala Gln Ala Tyr
                565                 570                 575

Ala Xaa Glu Lys Gly Leu Thr Pro Ser Thr Asp His Gln Asp Ser
            580                 585                 590

Gly Asn Thr Glu Ala Lys Gly Ala Glu Ala Ile Tyr Asn Arg Val Lys
        595                 600                 605

Ala Ala Lys Lys Val Pro Leu Asp Arg Met Pro Tyr Asn Leu Gln Tyr
        610                 615                 620

Thr Val Glu Val Lys Asn Gly Ser Leu Ile Ile Pro His Tyr Asp His
625                 630                 635                 640

Tyr His Asn Ile Lys Phe Glu Trp Phe Asp Glu Gly Leu Tyr Glu Ala
                645                 650                 655

Pro Lys Gly Tyr Thr Leu Glu Asp Leu Leu Ala Thr Val Lys Tyr Tyr
            660                 665                 670

Val Glu His Pro Asn Glu Arg Pro His Ser Asp Asn Gly Phe Gly Asn
        675                 680                 685

Ala Ser Asp His Val Gln Arg Asn Lys Asn Gly Gln Ala Asp Thr Asn
        690                 695                 700

Gln Thr Glu Lys Pro Ser Glu Glu Lys Pro Gln Thr Glu Lys Pro Glu
705                 710                 715                 720

Glu Glu Thr Pro Arg Glu Glu Lys Pro Gln Ser Glu Lys Pro Glu Ser
                725                 730                 735

Pro Lys Pro Thr Glu Glu Pro Glu Glu Ser Pro Glu Glu Ser Glu Glu
            740                 745                 750

Pro Gln Val Glu Thr Lys Val Glu Glu Lys Leu Arg Glu Ala Glu
        755                 760                 765

Asp Leu Leu Gly Lys Ile Gln Asp Pro Ile Ile Lys Ser Asn Ala Lys
770                 775                 780

Glu Thr Leu Thr Gly Leu Lys Asn Asn Leu Leu Phe Gly Thr Gln Asp
785                 790                 795                 800

Asn Asn Thr Ile Met Ala Glu Ala Glu Lys Leu Leu Ala Leu Leu Lys
            805                 810                 815

Glu Ser Lys

<210> SEQ ID NO 62
<211> LENGTH: 853
<212> TYPE: PRT
<213> ORGANISM: Streptococcus pneumoniae
<220> FEATURE:
<223> OTHER INFORMATION: full length PhtD precursor

<400> SEQUENCE: 62

Met Lys Ile Asn Lys Lys Tyr Leu Ala Gly Ser Val Ala Val Leu Ala
1               5                   10                  15

Leu Ser Val Cys Ser Tyr Glu Leu Gly Arg His Gln Ala Gly Gln Val
                20                  25                  30

Lys Lys Glu Ser Asn Arg Val Ser Tyr Ile Asp Gly Asp Gln Ala Gly
            35                  40                  45
```

```
Gln Lys Ala Glu Asn Leu Thr Pro Asp Glu Val Ser Lys Arg Glu Gly
     50                  55                  60

Ile Asn Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                 85                  90                  95

Asp Ala Ile Ile Ser Glu Glu Leu Leu Met Lys Asp Pro Asn Tyr Gln
                100                 105                 110

Leu Lys Asp Ser Asp Ile Val Asn Glu Ile Lys Gly Gly Tyr Val Ile
            115                 120                 125

Lys Val Asp Gly Lys Tyr Tyr Val Tyr Leu Lys Asp Ala Ala His Ala
            130                 135                 140

Asp Asn Ile Arg Thr Lys Glu Glu Ile Lys Arg Gln Lys Gln Glu Arg
145                 150                 155                 160

Ser His Asn His Asn Ser Arg Ala Asp Asn Ala Val Ala Ala Ala Arg
                165                 170                 175

Ala Gln Gly Arg Tyr Thr Thr Asp Asp Gly Tyr Ile Phe Asn Ala Ser
                180                 185                 190

Asp Ile Ile Glu Asp Thr Gly Asp Ala Tyr Ile Val Pro His Gly Asp
            195                 200                 205

His Tyr His Tyr Ile Pro Lys Ser Asp Leu Ser Ala Ser Glu Leu Ala
            210                 215                 220

Ala Ala Gln Ala Tyr Trp Asn Gly Lys Gln Gly Ser Arg Pro Ser Ser
225                 230                 235                 240

Ser Ser Ser His Asn Ala Asn Pro Ala Gln Pro Arg Leu Ser Glu Asn
                245                 250                 255

His Asn Leu Thr Val Thr Pro Thr Tyr His Gln Asn Gly Glu Asn
                260                 265                 270

Ile Ser Ser Leu Leu Arg Glu Leu Tyr Ala Lys Pro Leu Ser Glu Arg
            275                 280                 285

His Val Glu Ser Asp Gly Leu Ile Phe Asp Pro Ala Gln Ile Thr Ser
            290                 295                 300

Arg Thr Ala Asn Gly Val Ala Val Pro His Gly Asp His Tyr His Phe
305                 310                 315                 320

Ile Pro Tyr Ser Gln Leu Ser Pro Leu Glu Glu Lys Leu Ala Arg Ile
                325                 330                 335

Ile Pro Leu Arg Tyr Arg Ser Asn His Trp Val Pro Asp Ser Arg Pro
            340                 345                 350

Glu Gln Pro Ser Pro Gln Ser Thr Pro Glu Pro Ser Pro Ser Pro Gln
            355                 360                 365

Pro Ala Pro Asn Pro Gln Pro Ala Pro Ser Asn Pro Ile Asp Glu Lys
            370                 375                 380

Leu Val Lys Glu Ala Val Arg Lys Val Gly Asp Gly Tyr Val Phe Glu
385                 390                 395                 400

Glu Asn Gly Val Pro Arg Tyr Ile Pro Ala Lys Asp Leu Ser Ala Glu
                405                 410                 415

Thr Ala Ala Gly Ile Asp Ser Lys Leu Ala Lys Gln Glu Ser Leu Ser
                420                 425                 430

His Lys Leu Gly Ala Lys Lys Thr Asp Leu Pro Ser Ser Asp Arg Glu
            435                 440                 445

Phe Tyr Asn Lys Ala Tyr Asp Leu Leu Ala Arg Ile His Gln Asp Leu
    450                 455                 460

Leu Asp Asn Lys Gly Arg Gln Val Asp Phe Glu Ala Leu Asp Asn Leu
```

```
                    465                 470                 475                 480
Leu Glu Arg Leu Lys Asp Val Ser Ser Asp Lys Val Lys Leu Val Asp
                    485                 490                 495

Asp Ile Leu Ala Phe Leu Ala Pro Ile Arg His Pro Glu Arg Leu Gly
                500                 505                 510

Lys Pro Asn Ala Gln Ile Thr Tyr Thr Asp Glu Ile Gln Val Ala
            515                 520                 525

Lys Leu Ala Gly Lys Tyr Thr Thr Glu Asp Gly Tyr Ile Phe Asp Pro
530                 535                 540

Arg Asp Ile Thr Ser Asp Glu Gly Asp Ala Tyr Val Thr Pro His Met
545                 550                 555                 560

Thr His Ser His Trp Ile Lys Lys Asp Ser Leu Ser Glu Ala Glu Arg
                565                 570                 575

Ala Ala Ala Gln Ala Tyr Ala Lys Glu Lys Gly Leu Thr Pro Pro Ser
            580                 585                 590

Thr Asp His Gln Asp Ser Gly Asn Thr Glu Ala Lys Gly Ala Glu Ala
            595                 600                 605

Ile Tyr Asn Arg Val Lys Ala Ala Lys Lys Val Pro Leu Asp Arg Met
        610                 615                 620

Pro Tyr Asn Leu Gln Tyr Thr Val Glu Val Lys Asn Gly Ser Leu Ile
625                 630                 635                 640

Ile Pro His Tyr Asp His Tyr His Asn Ile Lys Phe Glu Trp Phe Asp
                645                 650                 655

Glu Gly Leu Tyr Glu Ala Pro Lys Gly Tyr Ser Leu Gly Asp Leu Leu
            660                 665                 670

Ala Thr Val Lys Tyr Tyr Val Glu His Pro Asn Glu Arg Pro His Ser
            675                 680                 685

Asp Asn Gly Phe Gly Asn Ala Ser Asp His Val Gln Arg Asn Lys Asn
        690                 695                 700

Gly Gln Ala Asp Thr Asn Gln Thr Glu Lys Pro Asn Glu Glu Lys Pro
705                 710                 715                 720

Gln Thr Glu Lys Pro Glu Glu Asp Lys Glu His Asp Glu Val Ser Glu
                725                 730                 735

Pro Thr His Pro Glu Ser Asp Glu Lys Glu Asn His Val Gly Leu Asn
            740                 745                 750

Pro Ser Ala Asp Asn Leu Tyr Lys Pro Ser Thr Asp Thr Glu Glu Thr
            755                 760                 765

Glu Glu Glu Ala Glu Asp Thr Thr Asp Glu Ala Glu Ile Pro Gln Val
        770                 775                 780

Glu His Ser Val Ile Asn Ala Lys Ile Ala Glu Ala Glu Ala Leu Leu
785                 790                 795                 800

Glu Lys Val Thr Asp Ser Ser Ile Arg Gln Asn Ala Val Glu Thr Leu
                805                 810                 815

Thr Gly Leu Lys Ser Ser Leu Leu Leu Gly Thr Lys Asp Asn Asn Thr
            820                 825                 830

Ile Ser Ala Glu Val Asp Ser Leu Leu Ala Leu Leu Lys Glu Ser Gln
            835                 840                 845

Pro Thr Pro Ile Gln
    850

<210> SEQ ID NO 63
<211> LENGTH: 1039
<212> TYPE: PRT
<213> ORGANISM: Streptococcus pneumoniae
<220> FEATURE:
```

<223> OTHER INFORMATION: full length PhtE precursor

<400> SEQUENCE: 63

```
Met Lys Phe Ser Lys Lys Tyr Ile Ala Ala Gly Ser Ala Val Ile Val
 1               5                  10                  15

Ser Leu Ser Leu Cys Ala Tyr Ala Leu Asn Gln His Arg Ser Gln Glu
            20                  25                  30

Asn Lys Asp Asn Asn Arg Val Ser Tyr Val Asp Gly Ser Gln Ser Ser
        35                  40                  45

Gln Lys Ser Glu Asn Leu Thr Pro Asp Gln Val Ser Gln Lys Glu Gly
    50                  55                  60

Ile Gln Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Leu Phe Ser Glu Glu Leu Leu Met Lys Asp Pro Asn Tyr Gln
            100                 105                 110

Leu Lys Asp Ala Asp Ile Val Asn Glu Val Lys Gly Gly Tyr Ile Ile
        115                 120                 125

Lys Val Asp Gly Lys Tyr Tyr Val Tyr Leu Lys Asp Ala Ala His Ala
    130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
            180                 185                 190

Ile Ile Glu Asp Thr Gly Asn Ala Tyr Ile Val Pro His Gly Gly His
        195                 200                 205

Tyr His Tyr Ile Pro Lys Ser Asp Leu Ser Ala Ser Glu Leu Ala Ala
    210                 215                 220

Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
                245                 250                 255

Ser Thr Ser Lys Pro Ala Asn Lys Ser Glu Asn Leu Gln Ser Leu Leu
            260                 265                 270

Lys Glu Leu Tyr Asp Ser Pro Ser Ala Gln Arg Tyr Ser Glu Ser Asp
        275                 280                 285

Gly Leu Val Phe Asp Pro Ala Lys Ile Ile Ser Arg Thr Pro Asn Gly
    290                 295                 300

Val Ala Ile Pro His Gly Asp His Tyr His Phe Ile Pro Tyr Ser Lys
305                 310                 315                 320

Leu Ser Ala Leu Glu Glu Lys Ile Ala Arg Arg Val Pro Ile Ser Gly
                325                 330                 335

Thr Gly Ser Thr Val Ser Thr Asn Ala Lys Pro Asn Glu Val Val Ser
            340                 345                 350

Ser Leu Gly Ser Leu Ser Ser Asn Pro Ser Ser Leu Thr Thr Ser Lys
        355                 360                 365

Glu Leu Ser Ser Ala Ser Asp Gly Tyr Ile Phe Asn Pro Lys Asp Ile
    370                 375                 380

Val Glu Glu Thr Ala Thr Ala Tyr Ile Val Arg His Gly Asp His Phe
385                 390                 395                 400

His Tyr Ile Pro Lys Ser Asn Gln Ile Gly Gln Pro Thr Leu Pro Asn
```

```
                    405                 410                 415
Asn Ser Leu Ala Thr Pro Ser Pro Ser Leu Pro Ile Asn Pro Gly Ile
            420                 425                 430

Ser His Glu Lys His Glu Glu Asp Gly Tyr Gly Phe Asp Ala Asn Arg
        435                 440                 445

Ile Ile Ala Glu Asp Glu Ser Gly Phe Ile Met Ser His Gly Asn His
    450                 455                 460

Asn His Tyr Phe Phe Lys Lys Asp Leu Thr Glu Glu Gln Ile Lys Ala
465                 470                 475                 480

Ala Gln Lys His Leu Glu Glu Val Lys Thr Ser His Asn Gly Leu Asp
                485                 490                 495

Ser Leu Ser Ser His Glu Gln Asp Tyr Pro Gly Asn Ala Lys Glu Met
            500                 505                 510

Lys Asp Leu Asp Lys Lys Ile Glu Glu Lys Ile Ala Gly Ile Met Lys
        515                 520                 525

Gln Tyr Gly Val Lys Arg Glu Ser Ile Val Val Asn Lys Glu Lys Asn
    530                 535                 540

Ala Ile Ile Tyr Pro His Gly Asp His His Ala Asp Pro Ile Asp
545                 550                 555                 560

Glu His Lys Pro Val Gly Ile Gly His Ser His Ser Asn Tyr Glu Leu
                565                 570                 575

Phe Lys Pro Glu Glu Gly Val Ala Lys Lys Gly Asn Lys Val Tyr
            580                 585                 590

Thr Gly Glu Glu Leu Thr Asn Val Val Asn Leu Leu Lys Asn Ser Thr
        595                 600                 605

Phe Asn Asn Gln Asn Phe Thr Leu Ala Asn Gly Gln Lys Arg Val Ser
    610                 615                 620

Phe Ser Phe Pro Pro Glu Leu Glu Lys Lys Leu Gly Ile Asn Met Leu
625                 630                 635                 640

Val Lys Leu Ile Thr Pro Asp Gly Lys Val Leu Glu Lys Val Ser Gly
                645                 650                 655

Lys Val Phe Gly Glu Gly Val Gly Asn Ile Ala Asn Phe Glu Leu Asp
            660                 665                 670

Gln Pro Tyr Leu Pro Gly Gln Thr Phe Lys Tyr Thr Ile Ala Ser Lys
        675                 680                 685

Asp Tyr Pro Glu Val Ser Tyr Asp Gly Thr Phe Thr Val Pro Thr Ser
    690                 695                 700

Leu Ala Tyr Lys Met Ala Ser Gln Thr Ile Phe Tyr Pro Phe His Ala
705                 710                 715                 720

Gly Asp Thr Tyr Leu Arg Val Asn Pro Gln Phe Ala Val Pro Lys Gly
                725                 730                 735

Thr Asp Ala Leu Val Arg Val Phe Asp Glu Phe His Gly Asn Ala Tyr
            740                 745                 750

Leu Glu Asn Asn Tyr Lys Val Gly Glu Ile Lys Leu Pro Ile Pro Lys
        755                 760                 765

Leu Asn Gln Gly Thr Thr Arg Thr Ala Gly Asn Lys Ile Pro Val Thr
    770                 775                 780

Phe Met Ala Asn Ala Tyr Leu Asp Asn Gln Ser Thr Tyr Ile Val Glu
785                 790                 795                 800

Val Pro Ile Leu Glu Lys Glu Asn Gln Thr Asp Lys Pro Ser Ile Leu
                805                 810                 815

Pro Gln Phe Lys Arg Asn Lys Ala Gln Glu Asn Ser Lys Leu Asp Glu
            820                 825                 830
```

-continued

```
Lys Val Glu Pro Lys Thr Ser Glu Lys Val Glu Lys Glu Lys Leu
            835                 840                 845

Ser Glu Thr Gly Asn Ser Ser Asn Ser Thr Leu Glu Glu Val Pro
    850                 855                 860

Thr Val Asp Pro Val Gln Glu Lys Val Ala Lys Phe Ala Glu Ser Tyr
865                 870                 875                 880

Gly Met Lys Leu Glu Asn Val Leu Phe Asn Met Asp Gly Thr Ile Glu
                885                 890                 895

Leu Tyr Leu Pro Ser Gly Glu Val Ile Lys Lys Asn Met Ala Asp Phe
                900                 905                 910

Thr Gly Glu Ala Pro Gln Gly Asn Gly Glu Asn Lys Pro Ser Glu Asn
            915                 920                 925

Gly Lys Val Ser Thr Gly Thr Val Glu Asn Gln Pro Thr Glu Asn Lys
    930                 935                 940

Pro Ala Asp Ser Leu Pro Glu Ala Pro Asn Glu Lys Pro Val Lys Pro
945                 950                 955                 960

Glu Asn Ser Thr Asp Asn Gly Met Leu Asn Pro Glu Gly Asn Val Gly
                965                 970                 975

Ser Asp Pro Met Leu Asp Pro Ala Leu Glu Glu Ala Pro Ala Val Asp
                980                 985                 990

Pro Val Gln Glu Lys Leu Glu Lys Phe Thr Ala Ser Tyr Gly Leu Gly
            995                 1000                1005

Leu Asp Ser Val Ile Phe Asn Met Asp Gly Thr Ile Glu Leu Arg Leu
    1010                1015                1020

Pro Ser Gly Glu Val Ile Lys Lys Asn Leu Ser Asp Leu Ile Ala
1025                1030                1035

<210> SEQ ID NO 64
<211> LENGTH: 1876
<212> TYPE: PRT
<213> ORGANISM: Streptococcus pneumoniae
<220> FEATURE:
<223> OTHER INFORMATION: full length ZmpB

<400> SEQUENCE: 64

Met Phe Lys Lys Asp Arg Phe Ser Ile Arg Lys Ile Lys Gly Val Val
1               5                   10                  15

Gly Ser Val Phe Leu Gly Ser Leu Met Ala Pro Ser Val Val Asp
            20                  25                  30

Ala Ala Thr Tyr His Tyr Val Asn Lys Glu Ile Ile Ser Gln Glu Ala
        35                  40                  45

Lys Asp Leu Ile Gln Thr Gly Lys Pro Asp Arg Asn Glu Val Val Tyr
    50                  55                  60

Gly Leu Val Tyr Gln Lys Asp Gln Leu Pro Gln Thr Gly Thr Glu Ala
65                  70                  75                  80

Ser Val Leu Thr Ala Phe Gly Leu Leu Thr Val Gly Ser Leu Leu Leu
                85                  90                  95

Ile Tyr Lys Arg Lys Lys Ile Ala Ser Val Phe Leu Val Gly Thr Met
            100                 105                 110

Gly Leu Val Val Leu Pro Ser Ala Gly Ala Val Asp Pro Val Ala Thr
        115                 120                 125

Leu Ala Leu Ala Ser Arg Glu Gly Val Val Glu Met Glu Gly Tyr Arg
    130                 135                 140

Tyr Val Gly Tyr Leu Ser Gly Asp Ile Leu Lys Thr Leu Gly Leu Asp
145                 150                 155                 160

Thr Val Leu Glu Glu Thr Ser Ala Lys Pro Gly Glu Val Thr Val Val
```

```
                165                 170                 175
Glu Val Glu Thr Pro Gln Ser Thr Thr Asn Gln Glu Gln Ala Arg Thr
            180                 185                 190
Glu Asn Gln Val Val Glu Thr Glu Ala Pro Lys Glu Glu Ala Pro
        195                 200                 205
Lys Thr Glu Glu Ser Pro Lys Glu Pro Lys Ser Glu Val Lys Pro
    210                 215                 220
Thr Asp Asp Thr Leu Pro Lys Val Glu Gly Lys Glu Asp Ser Ala
225                 230                 235                 240
Glu Pro Ala Pro Val Glu Glu Val Gly Glu Val Glu Ser Lys Pro
                245                 250                 255
Glu Glu Lys Val Ala Val Lys Pro Glu Ser Gln Pro Ser Asp Lys Pro
            260                 265                 270
Ala Glu Glu Ser Lys Val Glu Gln Ala Gly Glu Pro Val Ala Pro Arg
        275                 280                 285
Lys Asp Glu Gln Ala Pro Val Glu Pro Glu Asn Gln Pro Glu Ala Pro
    290                 295                 300
Glu Glu Glu Lys Ala Val Glu Glu Thr Pro Lys Gln Glu Glu Ser Thr
305                 310                 315                 320
Pro Asp Thr Lys Ala Glu Glu Thr Val Glu Pro Lys Glu Glu Thr Lys
                325                 330                 335
Thr Ala Lys Gly Thr Gln Glu Glu Gly Lys Glu Gly Gln Ala Pro Val
            340                 345                 350
Gln Glu Val Asn Pro Glu Tyr Lys Val Thr Thr Gly Thr Val Glu Lys
        355                 360                 365
Ser Thr Glu Ser Glu Leu Asp Phe Thr Thr Glu Val Val Pro Asp Asp
    370                 375                 380
Thr Lys Tyr Val Asp Glu Glu Val Val Glu Arg Gln Gly Ser Lys Gly
385                 390                 395                 400
Val Gln Val Thr Lys Thr Thr Tyr Glu Thr Val Glu Val Val Glu Thr
                405                 410                 415
Asp Lys Val Leu Ser Thr Thr Thr Glu Val Lys Thr Pro Val Val Pro
            420                 425                 430
Lys Val Val Lys Lys Gly Thr Lys Pro Val Glu Thr Arg Glu Glu Val
        435                 440                 445
Ile Pro Phe Ala Thr Lys Glu Gln Glu Asp Asp Thr Leu Lys Arg Gly
    450                 455                 460
Thr Arg Gln Val Ala Gln Glu Gly Val Asn Gly Lys Lys Gln Ile Thr
465                 470                 475                 480
Glu Thr Tyr Lys Thr Ile Arg Gly Glu Lys Thr Asn Glu Ala Pro Thr
                485                 490                 495
Val Glu Glu Thr Val Leu Gln Ala Pro Gln Asp Glu Ile Ile Lys Lys
            500                 505                 510
Gly Thr Lys Gly Leu Glu Lys Pro Thr Leu Gln Trp Ala Asn Thr Glu
        515                 520                 525
Lys Asp Val Leu Lys Lys Ser Ala Thr Ala Ser Tyr Thr Leu Thr Lys
    530                 535                 540
Pro Ala Gly Val Glu Ile Lys Ser Ile Lys Leu Ala Leu Lys Asp Lys
545                 550                 555                 560
Asp Gly Gln Leu Val Lys Glu Val Thr Val Ala Glu Asn Asn Leu Asn
                565                 570                 575
Ala Thr Leu Asp Lys Leu Lys Tyr Tyr Gln Gly Tyr Thr Leu Ser Thr
            580                 585                 590
```

-continued

```
Thr Met Val Tyr Asp Arg Gly Glu Gly Glu Thr Glu Lys Leu Glu
        595                 600                 605

Asp Lys Gln Ile Gln Leu Asp Leu Lys Lys Val Glu Ile Lys Asn Ile
    610                 615                 620

Lys Glu Thr Ser Leu Met Asn Val Asp Ala Glu Gly Asn Glu Thr Asp
625                 630                 635                 640

Lys Ser Leu Leu Ser Glu Lys Pro Thr Asp Val Ser Gln Leu Tyr Leu
                645                 650                 655

Arg Val Thr Thr His Asp Asn Lys Val Thr Arg Leu Ala Val Ser Ser
                660                 665                 670

Val Glu Glu Val Val Asp Gly Lys Thr Leu Tyr Lys Val Ala
            675                 680                 685

Lys Ala Pro Asp Leu Val Gln Arg Arg Ala Asp Asp Thr Leu Ser Glu
    690                 695                 700

Glu Tyr Val His Tyr Phe Glu Lys Gln Leu Pro Lys Val Asn Asn Val
705                 710                 715                 720

Tyr Tyr Asn Phe Asn Glu Leu Val Lys Asp Met Gln Ala Asn Pro Met
                725                 730                 735

Gly Glu Phe Lys Leu Gly Ala Asp Leu Asn Ala Val Asn Val Lys Pro
                740                 745                 750

Ala Gly Lys Ala Tyr Val Met Ala Lys Phe Arg Gly Thr Leu Ser Ser
            755                 760                 765

Val Glu Asn His Gln Tyr Thr Ile His Asn Leu Glu Arg Pro Leu Phe
770                 775                 780

Asn Glu Ala Glu Gly Ala Thr Leu Lys Asn Phe Asn Leu Gly Asn Val
785                 790                 795                 800

Asn Ile Asn Met Pro Trp Ala Asp Lys Val Ala Pro Ile Gly Asn Met
                805                 810                 815

Phe Lys Lys Ser Thr Leu Glu Asn Ile Lys Val Val Gly Ser Val Thr
                820                 825                 830

Gly Asn Asn Asp Val Thr Gly Ala Val Asn Lys Leu Asp Glu Ala Asn
            835                 840                 845

Met Arg Asn Val Ala Phe Ile Gly Lys Ile Asn Ser Leu Gly Asp Lys
    850                 855                 860

Gly Trp Trp Ser Gly Gly Leu Val Ser Glu Ser Trp Arg Ser Asn Thr
865                 870                 875                 880

Asp Ser Val Tyr Phe Asp Gly Asp Ile Val Gly Asn Asn Ser Lys Phe
                885                 890                 895

Gly Gly Leu Val Ala Lys Val Asn His Gly Ser Asn Gln Trp Asp Val
                900                 905                 910

Lys Gln Lys Gly Arg Leu Thr Asn Ser Val Val Lys Gly Thr Met Thr
            915                 920                 925

Leu Lys Asn His Gly Gln Ser Gly Gly Leu Val His Glu Asn Tyr Asp
    930                 935                 940

Trp Gly Trp Val Glu Asn Asn Ile Ser Met Met Lys Val Asn Asn Gly
945                 950                 955                 960

Glu Ile Met Tyr Gly Ser Gly Ser Ile Asp Gly Asp Pro Tyr Phe Gly
                965                 970                 975

Phe Asp Tyr Phe Lys Asn Asn Tyr Tyr Val Lys Asp Val Ala Thr Gly
                980                 985                 990

Glu Ser Thr Tyr Lys Arg Ser Lys Gln Ile Gln Ser Ile Ser Gln Ala
            995                 1000                1005

Glu Ala Asp Ala Lys Ile Ala Asn Met Gly Ile Thr Ala Asn Thr Phe
    1010                1015                1020
```

-continued

```
Ala Ile Gln Asp Pro Val Val Asn Lys Leu Asn Arg Ile Ile Asp Arg
1025                1030                1035                1040

Asp Ser Glu Tyr Lys Ala Ile Gln Asp Tyr Gln Glu Thr Arg Asn Leu
            1045                1050                1055

Ala Tyr Arg Asn Leu Glu Lys Leu Gln Pro Phe Tyr Asn Lys Glu Trp
        1060                1065                1070

Ile Val Asn Gln Gly Asn Lys Leu Thr Asp Glu Ser Asn Leu Val Lys
    1075                1080                1085

Lys Thr Val Leu Ser Val Thr Gly Met Lys Ser Gly Gln Phe Val Thr
1090                1095                1100

Asp Leu Ser Ser Val Asp Lys Ile Met Ile His Tyr Ala Asp Gly Thr
1105                1110                1115                1120

Lys Glu Glu Phe Gly Val Ser Ala Ile Ser Asp Ser Arg Val Lys Gln
            1125                1130                1135

Val Lys Glu Tyr Asn Val Asp Asp Leu Gly Val Val Tyr Thr Pro Asn
        1140                1145                1150

Met Val Asp Lys Asn Arg Asp Ser Leu Ile Thr Lys Val Lys Glu Lys
    1155                1160                1165

Leu Ser Ser Val Ala Leu Asp Ser Ala Glu Val Lys Ser Ile Thr Asn
1170                1175                1180

Asn Pro Ala Ser Leu Tyr Leu Glu Glu Ser Phe Ala Glu Val Arg Glu
1185                1190                1195                1200

Thr Leu Asp Lys Leu Val Lys Ser Leu Leu Glu Asn Glu Asp His Gln
            1205                1210                1215

Leu Asn Ser Asp Glu Val Ala Glu Lys Ala Leu Leu Lys Lys Val Glu
        1220                1225                1230

Asp Asn Lys Ala Lys Ile Ile Leu Ala Leu Thr Tyr Leu Asn Arg Tyr
    1235                1240                1245

Tyr Gly Ile Asp Tyr Asp Gly Leu Asn Phe Lys His Leu Met Met Phe
1250                1255                1260

Lys Pro Asp Phe Tyr Gly Lys Thr Pro Ser Ile Leu Asp Phe Leu Ile
1265                1270                1275                1280

Arg Ile Gly Ser Ala Glu Lys Asn Leu Lys Gly Asp Arg Ser Leu Glu
            1285                1290                1295

Ala Tyr Arg Glu Val Ile Gly Thr Ile Gly Lys Gly Glu Leu Asn
        1300                1305                1310

Gly Leu Leu Gly Tyr Asn Met Arg Leu Phe Thr Lys Tyr Thr Asp Leu
    1315                1320                1325

Asn Asp Trp Phe Ile His Ala Ala Lys Asn Val Tyr Val Ser Glu Pro
1330                1335                1340

Glu Thr Thr Thr Glu Asp Phe Lys Asp Lys Arg His Arg Ile Tyr Asp
1345                1350                1355                1360

Gly Leu Asn Asn Asp Val His Gly Arg Met Ile Leu Pro Leu Leu Asn
            1365                1370                1375

Leu Lys Lys Ala His Ile Phe Val Ile Ser Thr Tyr Asn Thr Ile Ala
        1380                1385                1390

Phe Ser Ser Phe Glu Lys Tyr Gly Lys Asn Thr Glu Glu Arg Asn
    1395                1400                1405

Ala Tyr Lys Ala Glu Ile Asp Arg Val Ala Lys Ala Gln Gln Arg Tyr
1410                1415                1420

Leu Asp Phe Trp Ser Arg Leu Ala Leu Pro Lys Val Arg Asn Gln Leu
1425                1430                1435                1440

Leu Lys Ser Gln Asn Ser Val Pro Thr Pro Val Trp Asp Asn Gln Val
```

Tyr Val Gly Leu Gly Gly Ala Asn Arg Met Gly Tyr Gly Asp Gly Gly
            1445                1450                1455
                        1460                1465                1470

Arg Val Val Thr Pro Val Arg Glu Leu Phe Gly Pro Thr Asp Arg Trp
            1475                1480                1485

His Gln Ile Asn Trp Asn Met Gly Ala Met Ala Lys Ile Tyr Glu Arg
            1490                1495                1500

Pro Trp Lys Asp Asp Gln Val Tyr Phe Met Val Thr Asn Met Met Glu
1505                1510                1515                1520

Pro Phe Gly Ile Ser Ala Phe Thr His Glu Thr Thr His Val Asn Asp
                1525                1530                1535

Arg Met Ala Tyr Tyr Gly Gly Asp Trp His Arg Glu Gly Thr Asp Leu
                1540                1545                1550

Glu Ala Phe Ala Gln Gly Met Leu Gln Thr Pro Asp Lys Ser Thr Thr
                1555                1560                1565

Asn Gly Glu Tyr Gly Ala Leu Gly Ile Asn Met Ala Tyr Glu Arg Lys
            1570                1575                1580

Asn Asp Gly Glu Gln Leu Tyr Asn Tyr Asp Pro Glu Lys Leu Asp Ser
1585                1590                1595                1600

Arg Glu Lys Ile Asp Ser Tyr Met Lys Asn Tyr Asn Glu Ser Met Met
                1605                1610                1615

Met Leu Asp Tyr Leu Glu Ala Ser Ala Val Ile Arg Gln Asn Leu Ser
            1620                1625                1630

Asp Asn Ser Lys Trp Phe Lys Lys Met Asp Lys Glu Trp Arg Thr Asn
            1635                1640                1645

Ala Asp Arg Asn Arg Leu Ile Gly Glu Pro His Gln Trp Asp Lys Leu
            1650                1655                1660

Arg Asp Leu Thr Glu Glu Lys Lys Leu Pro Ile Asp Ser Ile Asp
1665                1670                1675                1680

Lys Leu Val Glu Asn Asn Phe Val Thr Leu His Gly Met Pro Lys Asn
                1685                1690                1695

Gly Arg Tyr Arg Thr Glu Gly Phe Asp Ser Ser Tyr Gln Pro Val Asn
                1700                1705                1710

Met Met Ala Gly Val Phe Gly Gly Asn Thr Ser Lys Ser Thr Val Gly
            1715                1720                1725

Ser Ile Ser Phe Lys His Asn Ala Phe Arg Met Trp Gly Tyr Tyr Gly
            1730                1735                1740

Tyr Glu Asn Gly Phe Ile Pro Tyr Val Ser Asn Lys Leu Lys Gly Ala
1745                1750                1755                1760

Ala Asn Lys Glu Asn Lys Gly Leu Leu Gly Asp Asp Phe Ile Ile Lys
                1765                1770                1775

Lys Val Ser Lys Asn Gln Phe Gln Asn Leu Glu Glu Trp Lys Lys His
            1780                1785                1790

Trp Tyr His Glu Val Tyr Asp Lys Ala Gln Lys Gly Phe Val Glu Ile
            1795                1800                1805

Glu Val Asp Gly Val Lys Ile Ser Thr Tyr Ala Gln Leu Gln Ser Leu
            1810                1815                1820

Phe Glu Glu Ala Val Ser Lys Asp Leu Ala Gly Met Asp Asp Lys Asn
            1825                1830                1835                1840

Ile Lys Asn His Tyr Gln Tyr Thr Glu Asn Leu Lys Trp Lys Ile Tyr
                1845                1850                1855

Lys Gln Leu Leu Lys Asn Thr Asp Gly Phe Ser Ser Asp Leu Phe Thr
            1860                1865                1870

```
Ala Pro Gln Ala
        1875

<210> SEQ ID NO 65
<211> LENGTH: 448
<212> TYPE: PRT
<213> ORGANISM: Streptococcus pneumoniae
<220> FEATURE:
<223> OTHER INFORMATION: full length CbpD

<400> SEQUENCE: 65

Met Lys Ile Leu Pro Phe Ile Ala Arg Gly Thr Ser Tyr Tyr Leu Lys
1               5                   10                  15

Met Ser Val Lys Lys Leu Val Pro Phe Leu Val Val Gly Leu Met Leu
                20                  25                  30

Ala Ala Gly Asp Ser Val Tyr Ala Tyr Ser Arg Gly Asn Gly Ser Ile
            35                  40                  45

Ala Arg Gly Asp Asp Tyr Pro Ala Tyr Lys Asn Gly Ser Gln Glu
        50                  55                  60

Ile Asp Gln Trp Arg Met Tyr Ser Arg Gln Cys Thr Ser Phe Val Ala
65                  70                  75                  80

Phe Arg Leu Ser Asn Val Asn Gly Phe Glu Ile Pro Ala Ala Tyr Gly
                85                  90                  95

Asn Ala Asn Glu Trp Gly His Arg Ala Arg Arg Glu Gly Tyr Arg Val
            100                 105                 110

Asp Asn Thr Pro Thr Ile Gly Ser Ile Thr Trp Ser Thr Ala Gly Thr
        115                 120                 125

Tyr Gly His Val Ala Trp Val Ser Asn Val Met Gly Asp Gln Ile Glu
    130                 135                 140

Ile Glu Glu Tyr Asn Tyr Gly Tyr Thr Glu Ser Tyr Asn Lys Arg Val
145                 150                 155                 160

Ile Lys Ala Asn Thr Met Thr Gly Phe Ile His Phe Lys Asp Leu Asp
                165                 170                 175

Ser Gly Ser Val Gly Asn Ser Gln Ser Ser Ala Ser Thr Gly Gly Thr
            180                 185                 190

His Tyr Phe Lys Thr Lys Ser Ala Ile Lys Thr Glu Pro Leu Val Ser
        195                 200                 205

Ala Thr Val Ile Asp Tyr Tyr Pro Gly Lys Val His Tyr Asp
    210                 215                 220

Gln Ile Leu Glu Lys Asp Gly Tyr Lys Trp Leu Ser Tyr Thr Ala Tyr
225                 230                 235                 240

Asn Gly Ser Tyr Arg Tyr Val Gln Leu Glu Ala Val Asn Lys Asn Pro
                245                 250                 255

Leu Gly Asn Ser Val Leu Ser Ser Gly Gly Thr His Tyr Phe Lys
            260                 265                 270

Ile Lys Ser Ala Ile Lys Thr Glu Pro Leu Val Ser Ala Thr Val Ile
        275                 280                 285

Asp Tyr Tyr Tyr Pro Gly Glu Lys Val His Tyr Asp Gln Ile Leu Glu
    290                 295                 300

Lys Asp Gly Tyr Lys Trp Leu Ser Tyr Thr Ala Tyr Asn Gly Ser Arg
305                 310                 315                 320

Arg Tyr Ile Gln Leu Glu Gly Val Thr Ser Ser Gln Asn Tyr Gln Asn
                325                 330                 335

Gln Ser Gly Asn Ile Ser Ser Tyr Gly Ser Asn Asn Ser Ser Thr Val
            340                 345                 350

Gly Trp Lys Lys Ile Asn Gly Ser Trp Tyr His Phe Lys Ser Asn Gly
```

-continued

```
                355                 360                 365
Ser Lys Ser Thr Gly Trp Leu Lys Asp Gly Ser Ser Trp Tyr Tyr Leu
370                 375                 380

Lys Leu Ser Gly Glu Met Gln Thr Gly Trp Leu Lys Glu Asn Gly Ser
385                 390                 395                 400

Trp Tyr Tyr Leu Gly Ser Ser Ala Met Lys Thr Gly Trp Tyr Gln
            405                 410                 415

Val Ser Gly Glu Trp Tyr Tyr Ser Ser Gly Ala Leu Ala Ile
        420                 425                 430

Asn Thr Thr Val Asp Gly Tyr Arg Val Asn Ser Asp Gly Glu Arg Val
            435                 440                 445

<210> SEQ ID NO 66
<211> LENGTH: 448
<212> TYPE: PRT
<213> ORGANISM: Streptococcus pneumoniae
<220> FEATURE:
<223> OTHER INFORMATION: variant of SEQ ID NO: 65

<400> SEQUENCE: 66

Met Lys Ile Leu Pro Phe Ile Ala Arg Gly Thr Ser Tyr Tyr Leu Lys
1               5                   10                  15

Met Ser Val Lys Lys Leu Val Pro Phe Leu Val Val Gly Leu Met Leu
            20                  25                  30

Ala Ala Gly Asp Ser Val Tyr Ala Tyr Ser Arg Gly Asn Gly Ser Ile
        35                  40                  45

Ala Arg Gly Asp Asp Tyr Pro Ala Tyr Tyr Lys Asn Gly Ser Gln Glu
    50                  55                  60

Ile Asp Gln Trp Arg Met Tyr Ser Arg Gln Cys Thr Ser Phe Val Ala
65                  70                  75                  80

Phe Arg Leu Ser Asn Val Asn Gly Phe Glu Ile Pro Ala Ala Tyr Gly
                85                  90                  95

Asn Ala Asn Glu Trp Gly His Arg Ala Arg Arg Glu Gly Tyr Arg Val
            100                 105                 110

Asp Asn Thr Pro Thr Ile Gly Ser Ile Thr Trp Ser Thr Ala Gly Thr
        115                 120                 125

Tyr Gly His Val Ala Trp Val Ser Asn Val Met Gly Asp Gln Ile Glu
    130                 135                 140

Ile Glu Glu Tyr Asn Tyr Gly Tyr Thr Glu Ser Tyr Asn Lys Arg Val
145                 150                 155                 160

Ile Lys Ala Asn Thr Met Thr Gly Phe Ile His Phe Lys Asp Leu Asp
                165                 170                 175

Gly Gly Ser Val Gly Asn Ser Gln Ser Ser Thr Ser Thr Gly Gly Thr
            180                 185                 190

His Tyr Phe Lys Thr Lys Ser Ala Ile Lys Thr Glu Pro Leu Ala Ser
        195                 200                 205

Gly Thr Val Ile Asp Tyr Tyr Pro Gly Glu Lys Val His Tyr Asp
    210                 215                 220

Gln Ile Leu Glu Lys Asp Gly Tyr Lys Trp Leu Ser Tyr Thr Ala Tyr
225                 230                 235                 240

Asn Gly Ser Tyr Arg Tyr Val Gln Leu Glu Ala Val Asn Lys Asn Pro
                245                 250                 255

Leu Gly Asn Ser Val Leu Ser Ser Thr Gly Thr His Tyr Phe Lys
            260                 265                 270

Thr Lys Ser Ala Ile Lys Thr Glu Pro Leu Val Ser Ala Thr Val Ile
        275                 280                 285
```

```
Asp Tyr Tyr Tyr Pro Gly Glu Lys Val His Tyr Asp Gln Ile Leu Glu
    290                 295                 300

Lys Asp Gly Tyr Lys Trp Leu Ser Tyr Thr Ala Tyr Asn Gly Ser Arg
305                 310                 315                 320

Arg Tyr Ile Gln Leu Glu Gly Val Thr Ser Ser Gln Asn Tyr Gln Asn
                325                 330                 335

Gln Ser Gly Asn Ile Ser Ser Tyr Gly Ser His Ser Ser Ser Thr Val
            340                 345                 350

Gly Trp Lys Lys Ile Asn Gly Ser Trp Tyr His Phe Lys Ser Asn Gly
        355                 360                 365

Ser Lys Ser Thr Gly Trp Leu Lys Asp Gly Ser Ser Trp Tyr Tyr Leu
    370                 375                 380

Lys Leu Ser Gly Glu Met Gln Thr Gly Trp Leu Lys Glu Asn Gly Leu
385                 390                 395                 400

Trp Tyr Tyr Leu Gly Ser Ser Gly Ala Met Lys Thr Gly Trp Tyr Gln
                405                 410                 415

Val Ser Gly Lys Trp Tyr Tyr Ser Tyr Ser Ser Gly Ala Leu Ala Val
            420                 425                 430

Asn Thr Thr Val Asp Gly Tyr Arg Val Asn Ser Asp Gly Glu Arg Val
        435                 440                 445

<210> SEQ ID NO 67
<211> LENGTH: 42
<212> TYPE: PRT
<213> ORGANISM: Streptococcus pneumoniae
<220> FEATURE:
<223> OTHER INFORMATION: full length CbpG

<400> SEQUENCE: 67

Met Leu Thr Asp Trp Gln Lys Val Asn Gly Asn Trp Tyr Tyr Leu Asn
1               5                   10                  15

Ser Asn Gly Ala Met Val Thr Gly Ser Gln Thr Ile Asp Gly Lys Val
            20                  25                  30

Tyr Asn Phe Ala Ser Ser Gly Glu Trp Ile
        35                  40

<210> SEQ ID NO 68
<211> LENGTH: 204
<212> TYPE: PRT
<213> ORGANISM: Streptococcus pneumoniae
<220> FEATURE:
<223> OTHER INFORMATION: full length PvaA

<400> SEQUENCE: 68

Met Phe Lys Arg Ile Arg Arg Val Leu Val Leu Ala Val Phe Leu Phe
1               5                   10                  15

Ala Gly Tyr Lys Ala Tyr Arg Val His Gln Asp Val Lys Gln Val Met
            20                  25                  30

Thr Tyr Gln Pro Met Val Arg Glu Ile Leu Ser Glu Gln Asp Thr Pro
        35                  40                  45

Ala Asn Glu Glu Leu Val Leu Ala Met Ile Tyr Thr Glu Thr Lys Gly
    50                  55                  60

Lys Glu Gly Asp Val Met Gln Ser Ser Glu Ser Ala Ser Gly Ser Thr
65                  70                  75                  80

Asn Thr Ile Asn Asp Asn Ala Ser Ser Ile Arg Gln Gly Ile Gln Thr
                85                  90                  95

Leu Thr Gly Asn Leu Tyr Leu Ala Gln Lys Lys Gly Val Asp Ile Trp
            100                 105                 110
```

```
Thr Ala Val Gln Ala Tyr Asn Phe Gly Pro Ala Tyr Ile Asp Phe Ile
            115                 120                 125

Ala Gln Asn Gly Lys Glu Asn Thr Leu Ala Leu Ala Lys Gln Tyr Ser
        130                 135                 140

Arg Glu Thr Val Ala Pro Leu Leu Gly Asn Arg Thr Gly Lys Thr Tyr
145                 150                 155                 160

Ser Tyr Ile His Pro Ile Ser Ile Phe His Gly Ala Glu Leu Tyr Val
                165                 170                 175

Asn Gly Gly Asn Tyr Tyr Ser Arg Gln Val Arg Leu Asn Leu Tyr
            180                 185                 190

Ile Ile Lys Cys Phe Thr Leu Phe Ser Thr Ser Gly
            195                 200

<210> SEQ ID NO 69
<211> LENGTH: 339
<212> TYPE: PRT
<213> ORGANISM: Streptococcus pneumoniae phage CP1
<220> FEATURE:
<223> OTHER INFORMATION: full length CPL1

<400> SEQUENCE: 69

Met Val Lys Lys Asn Asp Leu Phe Val Asp Val Ser His Asn Gly
1               5                   10                  15

Tyr Asp Ile Thr Gly Ile Leu Glu Gln Met Gly Thr Thr Asn Thr Ile
            20                  25                  30

Ile Lys Ile Ser Glu Ser Thr Thr Tyr Leu Asn Pro Cys Leu Ser Ala
            35                  40                  45

Gln Val Glu Gln Ser Asn Pro Ile Gly Phe Tyr His Phe Ala Arg Phe
        50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
            100                 105                 110

Gln Met Ile Ala Asp Ala Gly Tyr Lys Pro Ile Tyr Tyr Ser Tyr Lys
            115                 120                 125

Pro Phe Thr His Asp Asn Val Asp Tyr Gln Gln Ile Leu Ala Gln Phe
        130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
            180                 185                 190

Asp Asp Lys Pro Lys Thr Ala Gly Thr Trp Lys Gln Asp Ser Lys Gly
            195                 200                 205

Trp Trp Phe Arg Arg Asn Asn Gly Ser Phe Pro Tyr Asn Lys Trp Glu
210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Glu Lys Trp Tyr Tyr Leu Lys Asp
                245                 250                 255

Asn Gly Ala Met Ala Thr Gly Trp Val Leu Val Gly Ser Glu Trp Tyr
            260                 265                 270
```

```
Tyr Met Asp Asp Ser Gly Ala Met Val Thr Gly Trp Val Lys Tyr Lys
            275                 280                 285

Asn Asn Trp Tyr Tyr Met Thr Asn Glu Arg Gly Asn Met Val Ser Asn
        290                 295                 300

Glu Phe Ile Lys Ser Gly Lys Gly Trp Tyr Phe Met Asn Thr Asn Gly
305                 310                 315                 320

Glu Leu Ala Asp Asn Pro Ser Phe Thr Lys Glu Pro Asp Gly Leu Ile
                325                 330                 335

Thr Val Ala

<210> SEQ ID NO 70
<211> LENGTH: 279
<212> TYPE: PRT
<213> ORGANISM: Streptococcus pneumoniae
<220> FEATURE:
<223> OTHER INFORMATION: IC23

<400> SEQUENCE: 70

Met Ala Val Met Ala Tyr Pro Leu Val Ser Arg Leu Tyr Tyr Arg Val
1               5                   10                  15

Glu Ser Asn Gln Gln Ile Ala Asp Phe Asp Lys Glu Lys Ala Thr Leu
            20                  25                  30

Asp Glu Ala Asp Ile Asp Glu Arg Met Lys Leu Ala Gln Ala Phe Asn
        35                  40                  45

Asp Ser Leu Asn Asn Val Val Ser Gly Asp Pro Trp Ser Glu Glu Met
    50                  55                  60

Lys Lys Lys Gly Arg Ala Glu Tyr Ala Arg Met Leu Glu Ile His Glu
65                  70                  75                  80

Arg Met Gly His Val Glu Ile Pro Val Ile Asp Val Asp Leu Pro Val
                85                  90                  95

Tyr Ala Gly Thr Ala Glu Glu Val Leu Gln Gln Gly Ala Gly His Leu
            100                 105                 110

Glu Gly Thr Ser Leu Pro Ile Gly Gly Asn Ser Thr His Ala Val Ile
        115                 120                 125

Thr Ala His Thr Gly Leu Pro Thr Ala Lys Met Phe Thr Asp Leu Thr
    130                 135                 140

Lys Leu Lys Val Gly Asp Lys Phe Tyr Val His Asn Ile Lys Glu Val
145                 150                 155                 160

Met Ala Tyr Gln Val Asp Gln Val Lys Val Ile Glu Pro Thr Asn Phe
                165                 170                 175

Asp Asp Leu Leu Ile Val Pro Gly His Asp Tyr Val Thr Leu Leu Thr
            180                 185                 190

Cys Thr Pro Tyr Met Ile Asn Thr His Arg Leu Leu Val Arg Gly His
        195                 200                 205

Arg Ile Pro Tyr Val Ala Glu Val Glu Glu Phe Ile Ala Ala Asn
    210                 215                 220

Lys Leu Ser His Leu Tyr Arg Tyr Leu Phe Tyr Val Ala Val Gly Leu
225                 230                 235                 240

Ile Val Ile Leu Leu Trp Ile Ile Arg Arg Leu Arg Lys Lys Lys
                245                 250                 255

Gln Pro Glu Lys Ala Leu Lys Ala Leu Lys Ala Ala Arg Lys Glu Val
            260                 265                 270

Lys Val Glu Asp Gly Gln Gln
        275

<210> SEQ ID NO 71
```

```
<211> LENGTH: 612
<212> TYPE: PRT
<213> ORGANISM: Streptococcus pneumoniae
<220> FEATURE:
<223> OTHER INFORMATION: full length Hic

<400> SEQUENCE: 71

Met Phe Ala Phe Lys Lys Arg Arg Lys Val His Tyr Ser Ile Arg Lys
1               5                   10                  15

Phe Ser Ile Gly Val Ala Ser Val Ala Val Ala Ser Leu Phe Met Gly
            20                  25                  30

Ser Val Val His Ala Thr Glu Lys Glu Val Thr Thr Gln Val Ala Thr
        35                  40                  45

Ser Ser Asn Lys Ala Asn Lys Ser Gln Thr Glu His Met Lys Ala Ala
50                  55                  60

Lys Gln Val Asp Glu Tyr Ile Glu Lys Met Leu Ser Glu Ile Gln Leu
65                  70                  75                  80

Asp Arg Arg Lys His Thr Gln Asn Val Gly Leu Leu Thr Lys Leu Gly
                85                  90                  95

Ala Ile Lys Thr Glu Tyr Leu Arg Gly Leu Ser Val Ser Lys Glu Lys
            100                 105                 110

Ser Thr Ala Glu Leu Pro Ser Glu Ile Lys Glu Lys Leu Thr Ala Ala
        115                 120                 125

Phe Glu Gln Phe Lys Lys Asp Thr Leu Lys Ser Gly Lys Lys Val Ala
130                 135                 140

Glu Ala Gln Lys Lys Ala Lys Asp Gln Lys Glu Ala Lys Gln Glu Ile
145                 150                 155                 160

Glu Ala Leu Ile Val Lys His Lys Gly Arg Glu Ile Asp Leu Asp Arg
                165                 170                 175

Lys Lys Ala Lys Ala Ala Val Thr Glu His Leu Lys Lys Leu Leu Asn
            180                 185                 190

Asp Ile Glu Lys Asn Leu Lys Lys Glu Gln His Thr His Thr Val Glu
        195                 200                 205

Leu Ile Lys Asn Leu Lys Asp Ile Glu Lys Thr Tyr Leu His Lys Leu
210                 215                 220

Asp Glu Ser Thr Gln Lys Ala Gln Leu Gln Lys Leu Ile Ala Glu Ser
225                 230                 235                 240

Gln Ser Lys Leu Asp Glu Ala Phe Ser Lys Phe Lys Asn Gly Leu Ser
                245                 250                 255

Ser Ser Ser Asn Ser Gly Ser Ser Thr Lys Pro Glu Thr Pro Gln Pro
            260                 265                 270

Glu Thr Pro Lys Pro Glu Val Lys Pro Glu Leu Glu Thr Pro Lys Pro
        275                 280                 285

Glu Val Lys Pro Glu Pro Glu Thr Pro Lys Pro Glu Val Lys Pro Glu
290                 295                 300

Pro Glu Thr Pro Lys Pro Glu Val Lys Pro Glu Leu Glu Thr Pro Lys
305                 310                 315                 320

Pro Glu Val Lys Pro Glu Pro Glu Thr Pro Lys Pro Glu Val Lys Pro
                325                 330                 335

Glu Pro Glu Thr Pro Lys Pro Glu Val Lys Pro Glu Pro Glu Thr Pro
            340                 345                 350

Lys Pro Glu Val Lys Pro Glu Leu Glu Thr Pro Lys Pro Glu Val Lys
        355                 360                 365

Pro Glu Leu Glu Thr Pro Lys Pro Glu Val Lys Pro Glu Pro Glu Thr
370                 375                 380
```

```
Pro Lys Pro Glu Val Lys Pro Glu Leu Glu Thr Pro Lys Pro Glu Val
385                 390                 395                 400

Lys Pro Glu Pro Glu Thr Pro Lys Pro Glu Val Lys Pro Glu Leu Glu
                405                 410                 415

Thr Pro Lys Pro Glu Val Lys Pro Glu Pro Glu Thr Pro Lys Pro Glu
            420                 425                 430

Val Lys Pro Glu Leu Glu Thr Pro Lys Pro Glu Val Lys Pro Glu Pro
        435                 440                 445

Glu Thr Pro Lys Pro Glu Val Lys Pro Glu Pro Glu Thr Pro Lys Pro
    450                 455                 460

Glu Val Lys Pro Glu Pro Glu Thr Pro Lys Pro Glu Val Lys Pro Glu
465                 470                 475                 480

Leu Glu Thr Pro Lys Gln Lys Val Lys Pro Glu Pro Glu Thr Pro Lys
                485                 490                 495

Pro Glu Val Lys Pro Glu Pro Glu Thr Pro Lys Pro Glu Val Lys Pro
                500                 505                 510

Glu Leu Glu Thr Pro Lys Pro Glu Val Lys Pro Glu Leu Glu Ile Pro
            515                 520                 525

Lys Pro Glu Val Lys Pro Asp Asn Ser Lys Pro Gln Ala Asp Asp Lys
        530                 535                 540

Lys Pro Ser Thr Pro Asn Asn Leu Ser Lys Asp Lys Gln Ser Ser Asn
545                 550                 555                 560

Gln Ala Ser Thr Asn Glu Asn Lys Lys Gln Gly Pro Ala Thr Asn Lys
                565                 570                 575

Pro Lys Lys Ser Leu Pro Ser Thr Gly Ser Ile Ser Asn Leu Ala Leu
            580                 585                 590

Glu Ile Ala Gly Leu Leu Thr Leu Ala Gly Ala Thr Ile Leu Ala Lys
        595                 600                 605

Lys Arg Met Lys
        610

<210> SEQ ID NO 72
<211> LENGTH: 619
<212> TYPE: PRT
<213> ORGANISM: Streptococcus pneumoniae
<220> FEATURE:
<223> OTHER INFORMATION: full length PspA

<400> SEQUENCE: 72

Met Asn Lys Lys Met Ile Leu Thr Ser Leu Ala Ser Val Ala Ile
1               5                   10                  15

Leu Gly Ala Gly Phe Val Ala Ser Gln Pro Thr Val Val Arg Ala Glu
            20                  25                  30

Glu Ser Pro Val Ala Ser Gln Ser Lys Ala Glu Lys Asp Tyr Asp Ala
        35                  40                  45

Ala Lys Lys Asp Ala Lys Asn Ala Lys Lys Ala Val Glu Asp Ala Gln
    50                  55                  60

Lys Ala Leu Asp Asp Ala Lys Ala Ala Gln Lys Lys Tyr Asp Glu Asp
65                  70                  75                  80

Gln Lys Lys Thr Glu Glu Lys Ala Ala Leu Glu Lys Ala Ala Ser Glu
                85                  90                  95

Glu Met Asp Lys Ala Val Ala Ala Val Gln Gln Ala Tyr Leu Ala Tyr
            100                 105                 110

Gln Gln Ala Thr Asp Lys Ala Ala Lys Asp Ala Ala Asp Lys Met Ile
        115                 120                 125

Asp Glu Ala Lys Lys Arg Glu Glu Glu Ala Lys Thr Lys Phe Asn Thr
```

```
            130                 135                 140
Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
                165                 170                 175

Leu Glu Glu Ala Lys Ala Lys Leu Glu Glu Ala Glu Lys Lys Ala Thr
                180                 185                 190

Glu Ala Lys Gln Lys Val Asp Ala Glu Val Ala Pro Gln Ala Lys
                195                 200                 205

Ile Ala Glu Leu Glu Asn Gln Val His Arg Leu Glu Gln Glu Leu Lys
210                 215                 220

Glu Ile Asp Glu Ser Glu Ser Glu Asp Tyr Ala Lys Glu Gly Phe Arg
225                 230                 235                 240

Ala Pro Leu Gln Ser Lys Leu Asp Ala Lys Lys Ala Lys Leu Ser Lys
                245                 250                 255

Leu Glu Glu Leu Ser Asp Lys Ile Asp Glu Leu Asp Ala Glu Ile Ala
                260                 265                 270

Lys Leu Glu Asp Gln Leu Lys Ala Ala Glu Glu Asn Asn Asn Val Glu
                275                 280                 285

Asp Tyr Phe Lys Glu Gly Leu Glu Lys Thr Ile Ala Ala Lys Lys Ala
                290                 295                 300

Glu Leu Glu Lys Thr Glu Ala Asp Leu Lys Lys Ala Val Asn Glu Pro
305                 310                 315                 320

Glu Lys Pro Ala Pro Ala Pro Glu Thr Pro Ala Pro Glu Ala Pro Ala
                325                 330                 335

Glu Gln Pro Lys Pro Ala Pro Ala Pro Gln Pro Ala Pro Ala Pro Lys
                340                 345                 350

Pro Glu Lys Pro Ala Glu Gln Pro Lys Pro Glu Lys Thr Asp Asp Gln
                355                 360                 365

Gln Ala Glu Glu Asp Tyr Ala Arg Arg Ser Glu Glu Tyr Asn Arg
                370                 375                 380

Leu Thr Gln Gln Gln Pro Pro Lys Ala Glu Lys Pro Ala Pro Ala Pro
385                 390                 395                 400

Lys Thr Gly Trp Lys Gln Glu Asn Gly Met Trp Tyr Phe Tyr Asn Thr
                405                 410                 415

Asp Gly Ser Met Ala Thr Gly Trp Leu Gln Asn Asn Gly Ser Trp Tyr
                420                 425                 430

Tyr Leu Asn Ser Asn Gly Ala Met Ala Thr Gly Trp Leu Gln Tyr Asn
                435                 440                 445

Gly Ser Trp Tyr Tyr Leu Asn Ala Asn Gly Ala Met Ala Thr Gly Trp
                450                 455                 460

Ala Lys Val Asn Gly Ser Trp Tyr Tyr Leu Asn Ala Asn Gly Ala Met
465                 470                 475                 480

Ala Thr Gly Trp Leu Gln Tyr Asn Gly Ser Trp Tyr Tyr Leu Asn Ala
                485                 490                 495

Asn Gly Ala Met Ala Thr Gly Trp Ala Lys Val Asn Gly Ser Trp Tyr
                500                 505                 510

Tyr Leu Asn Ala Asn Gly Ala Met Ala Thr Gly Trp Leu Gln Tyr Asn
                515                 520                 525

Gly Ser Trp Tyr Tyr Leu Asn Ala Asn Gly Ala Met Ala Thr Gly Trp
                530                 535                 540

Ala Lys Val Asn Gly Ser Trp Tyr Tyr Leu Asn Ala Asn Gly Ala Met
545                 550                 555                 560
```

Ala Thr Gly Trp Val Lys Asp Gly Asp Thr Trp Tyr Leu Glu Ala
                565                 570                 575

Ser Gly Ala Met Lys Ala Ser Gln Trp Phe Lys Val Ser Asp Lys Trp
            580                 585                 590

Tyr Tyr Val Asn Gly Leu Gly Ala Leu Ala Val Asn Thr Thr Val Asp
        595                 600                 605

Gly Tyr Lys Val Asn Ala Asn Gly Glu Trp Val
        610                 615

<210> SEQ ID NO 73
<211> LENGTH: 309
<212> TYPE: PRT
<213> ORGANISM: Streptococcus pneumoniae
<220> FEATURE:
<223> OTHER INFORMATION: full length PsaA

<400> SEQUENCE: 73

Met Lys Lys Leu Gly Thr Leu Leu Val Leu Phe Leu Ser Ala Ile Ile
1               5                   10                  15

Leu Val Ala Cys Ala Ser Gly Lys Lys Asp Thr Thr Ser Gly Gln Lys
            20                  25                  30

Leu Lys Val Val Ala Thr Asn Ser Ile Ile Ala Asp Ile Thr Lys Asn
        35                  40                  45

Ile Ala Gly Asp Lys Ile Asp Leu His Ser Ile Val Pro Ile Gly Gln
    50                  55                  60

Asp Pro His Glu Tyr Glu Pro Leu Pro Glu Asp Val Lys Lys Thr Ser
65                  70                  75                  80

Glu Ala Asp Leu Ile Phe Tyr Asn Gly Ile Asn Leu Glu Thr Gly Gly
                85                  90                  95

Asn Ala Trp Phe Thr Lys Leu Val Glu Asn Ala Lys Lys Thr Glu Asn
            100                 105                 110

Lys Asp Tyr Phe Ala Val Ser Asp Gly Val Asp Val Ile Tyr Leu Glu
        115                 120                 125

Gly Gln Asn Glu Lys Gly Lys Glu Asp Pro His Ala Trp Leu Asn Leu
    130                 135                 140

Glu Asn Gly Ile Ile Phe Ala Lys Asn Ile Ala Lys Gln Leu Ser Ala
145                 150                 155                 160

Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
            180                 185                 190

Lys Ile Pro Ala Glu Lys Lys Leu Ile Val Thr Ser Glu Gly Ala Phe
        195                 200                 205

Lys Tyr Phe Ser Lys Ala Tyr Gly Val Pro Ser Ala Tyr Ile Trp Glu
    210                 215                 220

Ile Asn Thr Glu Glu Glu Gly Thr Pro Glu Gln Ile Lys Thr Leu Val
225                 230                 235                 240

Glu Lys Leu Arg Gln Thr Lys Val Pro Ser Leu Phe Val Glu Ser Ser
                245                 250                 255

Val Asp Asp Arg Pro Met Lys Thr Val Ser Gln Asp Thr Asn Ile Pro
            260                 265                 270

Ile Tyr Ala Gln Ile Phe Thr Asp Ser Ile Ala Glu Gln Gly Lys Glu
        275                 280                 285

Gly Asp Ser Tyr Tyr Ser Met Met Lys Tyr Asn Leu Asp Lys Ile Ala
    290                 295                 300

Glu Gly Leu Ala Lys

-continued

<210> SEQ ID NO 74
<211> LENGTH: 2144
<212> TYPE: PRT
<213> ORGANISM: Streptococcus pneumoniae
<220> FEATURE:
<223> OTHER INFORMATION: full length PrtA

<400> SEQUENCE: 74

| | | | | | | | | | | | | | | | |
|---|---|---|---|---|---|---|---|---|---|---|---|---|---|---|---|
| Met | Lys | Lys | Ser | Thr | Val | Leu | Ser | Leu | Thr | Thr | Ala | Ala | Val | Ile | Leu |
| 1 | | | | 5 | | | | | 10 | | | | | 15 | |
| Ala | Ala | Tyr | Ala | Pro | Asn | Glu | Val | Val | Leu | Ala | Asp | Thr | Ser | Ser | Ser |
| | | | 20 | | | | | 25 | | | | | 30 | | |
| Glu | Asp | Ala | Leu | Ser | Ile | Ser | Asp | Lys | Glu | Lys | Val | Val | Asp | Lys | |
| | | 35 | | | | | 40 | | | | | 45 | | | |
| Glu | Thr | Glu | Asn | Lys | Glu | Lys | His | Lys | Asp | Ile | His | Asn | Ala | Ile | Glu |
| | 50 | | | | | 55 | | | | | 60 | | | | |
| Thr | Ser | Lys | Asp | Thr | Glu | Lys | Lys | Thr | Thr | Ile | Ile | Glu | Glu | Lys | |
| 65 | | | | | 70 | | | | | 75 | | | | | 80 |
| Glu | Val | Val | Ser | Lys | Asn | Pro | Val | Ile | Asp | Thr | Lys | Thr | Ser | Asn | Glu |
| | | | | 85 | | | | | 90 | | | | | 95 | |
| Glu | Ala | Lys | Ile | Lys | Glu | Glu | Asn | Ser | Asn | Gln | Ser | Gln | Gly | Asp | His |
| | | | 100 | | | | | 105 | | | | | 110 | | |
| Thr | Asp | Ser | Phe | Val | Asn | Lys | Asn | Thr | Glu | Asn | Pro | Lys | Lys | Glu | Asp |
| | | 115 | | | | | 120 | | | | | 125 | | | |
| Lys | Val | Val | Tyr | Ile | Ala | Glu | Phe | Lys | Asp | Lys | Glu | Ser | Gly | Glu | Lys |
| | 130 | | | | | 135 | | | | | 140 | | | | |
| Ala | Ile | Lys | Gly | Leu | Ser | Asn | Leu | Lys | Asn | Thr | Lys | Val | Leu | Tyr | Thr |
| 145 | | | | | 150 | | | | | 155 | | | | | 160 |
| Tyr | Asp | Arg | Ile | Phe | Asn | Gly | Ser | Ala | Ile | Glu | Thr | Thr | Pro | Asp | Asn |
| | | | | 165 | | | | | 170 | | | | | 175 | |
| Leu | Asp | Lys | Ile | Lys | Gln | Ile | Glu | Gly | Ile | Ser | Ser | Ile | Glu | Arg | Ala |
| | | | 180 | | | | | 185 | | | | | 190 | | |
| Gln | Lys | Val | Gln | Pro | Met | Met | Asn | His | Ala | Arg | Lys | Glu | Ile | Gly | Val |
| | | 195 | | | | | 200 | | | | | 205 | | | |
| Glu | Glu | Ala | Ile | Asp | Tyr | Leu | Lys | Ser | Ile | Asn | Ala | Pro | Phe | Gly | Lys |
| | 210 | | | | | 215 | | | | | 220 | | | | |
| Asn | Phe | Asp | Gly | Arg | Gly | Met | Val | Ile | Ser | Asn | Ile | Asp | Thr | Gly | Thr |
| 225 | | | | | 230 | | | | | 235 | | | | | 240 |
| Asp | Tyr | Arg | His | Lys | Ala | Met | Arg | Ile | Asp | Asp | Ala | Lys | Ala | Ser | |
| | | | | 245 | | | | | 250 | | | | | 255 | |
| Met | Arg | Phe | Lys | Lys | Glu | Asp | Leu | Lys | Gly | Thr | Asp | Lys | Asn | Tyr | Trp |
| | | | 260 | | | | | 265 | | | | | 270 | | |
| Leu | Ser | Asp | Lys | Ile | Pro | His | Ala | Phe | Asn | Tyr | Tyr | Asn | Gly | Gly | Lys |
| | | 275 | | | | | 280 | | | | | 285 | | | |
| Ile | Thr | Val | Glu | Lys | Tyr | Asp | Asp | Gly | Arg | Asp | Tyr | Phe | Asp | Pro | His |
| | 290 | | | | | 295 | | | | | 300 | | | | |
| Gly | Met | His | Ile | Ala | Gly | Ile | Leu | Ala | Gly | Asn | Asp | Thr | Glu | Gln | Asp |
| 305 | | | | | 310 | | | | | 315 | | | | | 320 |
| Ile | Lys | Asn | Phe | Asn | Gly | Ile | Asp | Gly | Ile | Ala | Pro | Asn | Ala | Gln | Ile |
| | | | | 325 | | | | | 330 | | | | | 335 | |
| Phe | Ser | Tyr | Lys | Met | Tyr | Ser | Asp | Ala | Gly | Ser | Gly | Phe | Ala | Gly | Asp |
| | | | 340 | | | | | 345 | | | | | 350 | | |
| Glu | Thr | Met | Phe | His | Ala | Ile | Glu | Asp | Ser | Ile | Lys | His | Asn | Val | Asp |
| | | 355 | | | | | 360 | | | | | 365 | | | |

```
Val Val Ser Val Ser Ser Gly Phe Thr Gly Thr Gly Leu Val Gly Glu
    370                 375                 380

Lys Tyr Trp Gln Ala Ile Arg Ala Leu Arg Lys Ala Gly Ile Pro Met
385                 390                 395                 400

Val Val Ala Thr Gly Asn Tyr Ala Thr Ser Ala Ser Ser Ser Ser Trp
                405                 410                 415

Asp Leu Val Ala Asn Asn His Leu Lys Met Thr Asp Thr Gly Asn Val
            420                 425                 430

Thr Arg Thr Ala Ala His Glu Asp Ala Ile Ala Val Ala Ser Ala Lys
        435                 440                 445

Asn Gln Thr Val Glu Phe Asp Lys Val Asn Ile Gly Gly Glu Ser Phe
    450                 455                 460

Lys Tyr Arg Asn Ile Gly Ala Phe Phe Asp Lys Asn Lys Ile Thr Thr
465                 470                 475                 480

Asn Glu Asp Gly Thr Lys Ala Pro Ser Lys Leu Lys Phe Val Tyr Ile
                485                 490                 495

Gly Lys Gly Gln Asp Gln Asp Leu Ile Gly Leu Asp Leu Arg Gly Lys
            500                 505                 510

Ile Ala Val Met Asp Arg Ile Tyr Thr Lys Asp Leu Lys Asn Ala Phe
        515                 520                 525

Lys Lys Ala Met Asp Lys Gly Ala Arg Ala Ile Met Val Val Asn Thr
    530                 535                 540

Val Asn Tyr Tyr Asn Arg Asp Asn Trp Thr Glu Leu Pro Ala Met Gly
545                 550                 555                 560

Tyr Glu Ala Asp Glu Gly Thr Lys Ser Gln Val Phe Ser Ile Ser Gly
                565                 570                 575

Asp Asp Gly Val Lys Leu Trp Asn Met Ile Asn Pro Asp Lys Lys Thr
            580                 585                 590

Glu Val Lys Arg Asn Asn Lys Glu Asp Phe Lys Asp Lys Leu Glu Gln
        595                 600                 605

Tyr Tyr Pro Ile Asp Met Glu Ser Phe Asn Ser Asn Lys Pro Asn Val
    610                 615                 620

Gly Asp Glu Lys Glu Ile Asp Phe Lys Phe Ala Pro Asp Thr Asp Lys
625                 630                 635                 640

Glu Leu Tyr Lys Glu Asp Ile Ile Val Pro Ala Gly Ser Thr Ser Trp
                645                 650                 655

Gly Pro Arg Ile Asp Leu Leu Leu Lys Pro Asp Val Ser Ala Pro Gly
            660                 665                 670

Lys Asn Ile Lys Ser Thr Leu Asn Val Ile Asn Gly Lys Ser Thr Tyr
        675                 680                 685

Gly Tyr Met Ser Gly Thr Ser Met Ala Thr Pro Ile Val Ala Ala Ser
    690                 695                 700

Thr Val Leu Ile Arg Pro Lys Leu Lys Glu Met Leu Glu Arg Pro Val
705                 710                 715                 720

Leu Lys Asn Leu Lys Gly Asp Asp Lys Ile Asp Leu Thr Ser Leu Thr
                725                 730                 735

Lys Ile Ala Leu Gln Asn Thr Ala Arg Pro Met Met Asp Ala Thr Ser
            740                 745                 750

Trp Lys Glu Lys Ser Gln Tyr Phe Ala Ser Pro Arg Gln Gln Gly Ala
        755                 760                 765

Gly Leu Ile Asn Val Ala Asn Ala Leu Arg Asn Glu Val Val Ala Thr
    770                 775                 780

Phe Lys Asn Thr Asp Ser Lys Gly Leu Val Asn Ser Tyr Gly Ser Ile
```

```
                785                 790                 795                 800
        Ser Leu Lys Glu Ile Lys Gly Asp Lys Tyr Phe Thr Ile Lys Leu
                        805                 810                 815

His Asn Thr Ser Asn Arg Pro Leu Thr Phe Lys Val Ser Ala Ser Ala
                            820                 825                 830

Ile Thr Thr Asp Ser Leu Thr Asp Arg Leu Lys Leu Asp Glu Thr Tyr
                        835                 840                 845

Lys Asp Glu Lys Ser Pro Asp Gly Lys Gln Ile Val Pro Glu Ile His
                    850                 855                 860

Pro Glu Lys Val Lys Gly Ala Asn Ile Thr Phe Glu His Gly Thr Phe
        865                 870                 875                 880

Thr Ile Gly Ala Asn Ser Ser Phe Asp Leu Asn Ala Val Ile Asn Val
                            885                 890                 895

Gly Glu Ala Lys Asn Lys Asn Lys Phe Val Glu Ser Phe Ile His Phe
                        900                 905                 910

Glu Ser Val Glu Glu Met Glu Ala Leu Asn Ser Asn Gly Lys Lys Ile
                    915                 920                 925

Asn Phe Gln Pro Ser Leu Ser Met Pro Leu Met Gly Phe Ala Gly Asn
            930                 935                 940

Trp Asn His Glu Pro Ile Leu Asp Lys Trp Ala Trp Glu Glu Gly Ser
        945                 950                 955                 960

Arg Ser Lys Thr Leu Gly Gly Tyr Asp Asp Gly Lys Pro Lys Ile
                        965                 970                 975

Pro Gly Thr Leu Asn Lys Gly Ile Gly Gly Glu His Gly Ile Asp Lys
                    980                 985                 990

Phe Asn Pro Ala Gly Val Ile Gln Asn Arg Lys Asp Lys Asn Thr Thr
            995                 1000                1005

Ser Leu Asp Gln Asn Pro Glu Leu Phe Ala Phe Asn Asn Gln Gly Ile
            1010                1015                1020

Asn Ala Pro Ser Ser Gly Ser Lys Ile Ala Asn Ile Tyr Pro Leu
        1025                1030                1035                1040

Asp Ser Asn Gly Asn Pro Gln Asp Ala Gln Leu Glu Arg Gly Leu Thr
                        1045                1050                1055

Pro Ser Pro Leu Val Leu Arg Ser Ala Glu Glu Gly Leu Ile Ser Ile
                    1060                1065                1070

Val Asn Thr Asn Lys Glu Gly Glu Asn Gln Arg Asp Leu Lys Val Ile
            1075                1080                1085

Ser Arg Glu His Phe Ile Arg Gly Ile Leu Asn Ser Lys Ser Asn Asp
            1090                1095                1100

Ala Lys Gly Ile Lys Ser Ser Lys Leu Lys Val Trp Gly Asp Leu Lys
        1105                1110                1115                1120

Trp Asp Gly Leu Ile Tyr Asn Pro Arg Gly Arg Glu Glu Asn Ala Pro
                        1125                1130                1135

Glu Ser Lys Asp Asn Gln Asp Pro Ala Thr Lys Ile Arg Gly Gln Phe
                    1140                1145                1150

Glu Pro Ile Ala Glu Gly Gln Tyr Phe Tyr Lys Phe Lys Tyr Arg Leu
                    1155                1160                1165

Thr Lys Asp Tyr Pro Trp Gln Val Ser Tyr Ile Pro Val Lys Ile Asp
                    1170                1175                1180

Asn Thr Ala Pro Lys Ile Val Ser Val Asp Phe Ser Asn Pro Glu Lys
        1185                1190                1195                1200

Ile Lys Leu Ile Thr Lys Asp Thr Tyr His Lys Val Lys Asp Gln Tyr
                    1205                1210                1215
```

-continued

Lys Asn Glu Thr Leu Phe Ala Arg Asp Gln Lys Glu His Pro Glu Lys
                1220                1225                1230

Phe Asp Glu Ile Ala Asn Glu Val Trp Tyr Ala Gly Ala Ala Leu Val
                1235                1240                1245

Asn Glu Asp Gly Glu Val Glu Lys Asn Leu Glu Val Thr Tyr Ala Gly
                1250                1255                1260

Glu Gly Gln Gly Arg Asn Arg Lys Leu Asp Lys Asp Gly Asn Thr Ile
1265                1270                1275                1280

Tyr Glu Ile Lys Gly Ala Gly Asp Leu Arg Gly Lys Ile Ile Glu Val
                1285                1290                1295

Ile Ala Leu Asp Gly Ser Ser Asn Phe Thr Lys Ile His Arg Ile Lys
                1300                1305                1310

Phe Ala Asp Gln Ala Asp Glu Lys Gly Met Ile Ser Tyr Tyr Leu Val
                1315                1320                1325

Asp Pro Asp Lys Asp Ala Ser Lys Tyr Glu Lys Leu Gly Glu Ile Ser
                1330                1335                1340

Glu Asp Lys Leu Lys Asn Ala Lys Ser Pro Glu Glu Asn Thr Asn Asn
1345                1350                1355                1360

Asn Gln Ala Lys Asp Glu Asp Ser Lys Pro Asp Glu Lys Ser Ser Val
                1365                1370                1375

Glu Gly Glu Ala Ser Leu Glu Ile Asn Lys Thr Ile Ser Thr Ile Arg
                1380                1385                1390

Glu Phe Glu Asn Lys Asp Leu Lys Lys Leu Ile Lys Lys Lys Phe Arg
                1395                1400                1405

Glu Val Asn Asp Phe Thr Ser Glu Thr Gly Lys Arg Ile Glu Glu Tyr
                1410                1415                1420

Asp Tyr Lys Tyr Asp Asp Lys Gly Asn Ile Ile Ala Tyr Asp Gly
1425                1430                1435                1440

Ser Ala Leu Gln Tyr Glu Thr Glu Lys Phe Asp Glu Ile Lys Ser Lys
                1445                1450                1455

Ile Tyr Gly Val Leu Ser Pro Ser Lys Asp Gly His Phe Glu Ile Leu
                1460                1465                1470

Gly Lys Ile Ser Asn Val Ser Lys Asn Ala Lys Val Tyr Tyr Gly Asn
                1475                1480                1485

Ser Tyr Lys Ser Ile Glu Ile Lys Ala Thr Lys Tyr Asp Ser His Ser
                1490                1495                1500

Lys Thr Met Ile Phe Asp Leu Tyr Ala Asn Ile Asn Asp Ile Val Asp
1505                1510                1515                1520

Gly Leu Ala Phe Ala Gly Asp Met Arg Leu Phe Val Lys Asp Asp Asn
                1525                1530                1535

Gln Ile Lys Ala Glu Thr Lys Ile Arg Met Pro Glu Lys Asn Lys Glu
                1540                1545                1550

Thr Lys Ala Glu Tyr Pro Tyr Val Ser Ser Tyr Gly Asn Val Ile Glu
                1555                1560                1565

Leu Gly Glu Gly Asp Leu Ser Lys Asn Lys Pro Asp Asn Leu Thr Lys
                1570                1575                1580

Met Glu Ser Gly Lys Ile Tyr Ser Asp Ser Lys Gln Gln Tyr Leu
1585                1590                1595                1600

Leu Lys Asp Asn Ile Ile Leu Arg Lys Gly Tyr Ala Leu Lys Val Thr
                1605                1610                1615

Thr Tyr Asn Pro Gly Lys Thr Asp Met Leu Glu Gly Asn Gly Val Tyr
                1620                1625                1630

Ser Lys Glu Asp Ile Ala Lys Ile Gln Lys Ala Asn Pro Asn Leu Arg
                1635                1640                1645

```
Val Leu Ser Glu Thr Thr Ile Tyr Ala Asp Ser Arg Asn Val Glu Asp
    1650                1655                1660

Gly Arg Ser Thr Gln Ala Val Leu Met Ser Ala Leu Asp Gly Phe Asn
1665                1670                1675                1680

Ile Ile Arg Tyr Gln Val Phe Thr Phe Lys Met Asn Asp Lys Gly Glu
                1685                1690                1695

Ala Ile Asp Lys Asp Gly Asn Leu Val Thr Asp Ser Ser Lys Leu Val
            1700                1705                1710

Leu Phe Gly Lys Asp Asp Lys Glu Tyr Thr Gly Glu Asp Lys Ser Asn
        1715                1720                1725

Val Glu Ala Ile Lys Glu Asp Gly Ser Met Leu Phe Ile Asp Thr Lys
    1730                1735                1740

Pro Val Asn Leu Ser Met Asp Lys Asn Tyr Phe Asn Pro Ser Lys Ser
1745                1750                1755                1760

Asn Lys Ile Tyr Val Arg Asn Pro Glu Phe Tyr Leu Arg Gly Lys Ile
                1765                1770                1775

Ser Asp Lys Gly Gly Phe Asn Trp Glu Leu Arg Val Asn Glu Ser Val
            1780                1785                1790

Val Asp Asn Tyr Leu Ile Tyr Gly Asp Leu His Ile Asp Asn Thr Arg
        1795                1800                1805

Asp Phe Asn Ile Lys Leu Asn Val Lys Asp Gly Asp Ile Met Asp Trp
    1810                1815                1820

Gly Met Lys Asp Tyr Lys Ala Asn Gly Phe Pro Asp Lys Val Thr Asp
1825                1830                1835                1840

Met Asp Gly Asn Val Tyr Leu Gln Thr Gly Tyr Ser Asp Leu Asn Ala
                1845                1850                1855

Lys Ala Val Gly Val His Tyr Gln Phe Leu Tyr Asp Asn Val Lys Pro
            1860                1865                1870

Glu Val Asn Ile Asp Pro Lys Gly Asn Thr Ser Ile Glu Tyr Ala Asp
        1875                1880                1885

Gly Lys Ser Val Val Phe Asn Ile Asn Asp Lys Arg Asn Asn Gly Phe
    1890                1895                1900

Asp Gly Glu Ile Gln Glu Gln His Ile Tyr Val Asn Gly Lys Glu Tyr
1905                1910                1915                1920

Thr Ser Phe Asp Asp Ile Lys Gln Ile Thr Asp Lys Thr Leu Asn Ile
                1925                1930                1935

Lys Ile Val Val Lys Asp Phe Ala Arg Asn Thr Thr Val Lys Glu Phe
            1940                1945                1950

Ile Leu Asn Lys Asp Thr Gly Glu Val Ser Glu Leu Lys Pro His Arg
        1955                1960                1965

Val Thr Val Thr Ile Gln Asn Gly Lys Glu Met Ser Ser Thr Ile Val
    1970                1975                1980

Ser Glu Glu Asp Phe Ile Leu Pro Val Tyr Lys Gly Glu Leu Glu Lys
1985                1990                1995                2000

Gly Tyr Gln Phe Asp Gly Trp Glu Ile Ser Gly Phe Glu Gly Lys Lys
                2005                2010                2015

Asp Ala Gly Tyr Val Ile Asn Leu Ser Lys Asp Thr Phe Ile Lys Pro
            2020                2025                2030

Val Phe Lys Lys Ile Glu Glu Lys Lys Glu Glu Asn Lys Pro Thr
        2035                2040                2045

Phe Asp Val Ser Lys Lys Lys Asp Asn Pro Gln Val Asn His Ser Gln
    2050                2055                2060

Leu Asn Glu Ser His Arg Lys Glu Asp Leu Gln Arg Glu Asp His Ser
```

Gln Lys Ser Asp Ser Thr Lys Asp Val Thr Ala Thr Val Leu Asp Lys
2065                2070                2075                2080

Asn Asn Ile Ser Ser Lys Ser Thr Thr Asn Asn Pro Asn Lys Leu Pro
            2085                2090                2095

Lys Thr Gly Thr Ala Ser Gly Ala Gln Thr Leu Leu Ala Ala Gly Ile
    2115                2120                2125

Met Phe Ile Val Gly Ile Phe Leu Gly Leu Lys Lys Lys Asn Gln Asp
    2130                2135                2140

<210> SEQ ID NO 75
<211> LENGTH: 324
<212> TYPE: PRT
<213> ORGANISM: Streptococcus pneumoniae
<220> FEATURE:
<223> OTHER INFORMATION: full length Sp133

<400> SEQUENCE: 75

Met Arg Lys Lys Leu Phe Leu Thr Ser Ala Ala Ile Leu Trp Ala Val
1               5                   10                  15

Thr Ala Met Asn Ser Val His Ala Ala Thr Asp Val Gln Lys Val Ile
            20                  25                  30

Asp Glu Thr Tyr Val Gln Pro Glu Tyr Val Leu Gly Ser Ser Leu Ser
        35                  40                  45

Glu Asp Gln Lys Asn Gln Thr Leu Lys Lys Leu Gly Tyr Asn Ala Ser
    50                  55                  60

Thr Asp Thr Lys Glu Leu Lys Thr Met Thr Pro Asp Val Tyr Ser Lys
65                  70                  75                  80

Ile Met Asn Val Ala Asn Asp Ser Ser Leu Gln Leu Tyr Ser Ser Ala
                85                  90                  95

Lys Ile Gln Lys Leu Gly Asp Lys Ser Pro Leu Glu Val Lys Ile Glu
            100                 105                 110

Thr Pro Glu Asn Ile Thr Lys Val Thr Gln Asp Met Tyr Arg Asn Ala
        115                 120                 125

Ala Val Thr Leu Gly Val Glu His Ala Lys Ile Thr Val Ala Ala Pro
    130                 135                 140

Ile Pro Val Thr Gly Glu Ser Ala Leu Ala Gly Ile Tyr Tyr Ser Leu
145                 150                 155                 160

Glu Ala Asn Gly Ala Lys Val Pro Gln Ala Asn Lys Asp Leu Ala Gln
                165                 170                 175

Glu Glu Leu Lys Ala Leu Ser Asp Ile Asn Ala Glu Asn Lys Asp Lys
            180                 185                 190

Ser Gly Tyr Asp Ala Asn Lys Leu Asn Val Ala Leu Ala Asp Ile Lys
        195                 200                 205

Ser Gly Leu Ala Lys Ala Lys Glu Ser Lys Gly Asn Leu Thr Glu Glu
    210                 215                 220

Asp Ile Arg Lys Ile Val Glu Asp Thr Leu Lys Asn Tyr Lys Leu Asp
225                 230                 235                 240

Gln Val Ile Thr Gly Asn Gln Ile Asn Ile Ile Asn Phe Ala Leu
                245                 250                 255

Asn Leu Ser Lys Ser Asp Ile Leu Ser Asn Ala Asp Phe Thr Lys Thr
            260                 265                 270

Leu Asn Asp Leu Lys Gln Ser Ile Val Ser Gln Ala Gly Asp Ser Phe
        275                 280                 285

Lys Asn Ile Asn Leu Asn Phe Asp Ser Asp Lys Ala Leu Glu Asp Gly
    290                 295                 300

```
Gly Asn Phe Leu Ser Ser Leu Trp Gln Ala Leu Val Asn Phe Phe Lys
305                 310                 315                 320

Ser Phe Gly Ser

<210> SEQ ID NO 76
<211> LENGTH: 339
<212> TYPE: PRT
<213> ORGANISM: Streptococcus pneumoniae
<220> FEATURE:
<223> OTHER INFORMATION: full length PiaA

<400> SEQUENCE: 76

Met His Ala Lys Met Arg Asn Lys Lys Gln Ile Asn Leu Gly Ile Ile
1               5                   10                  15

Phe Val Ile Cys Leu Gly Leu Leu Ile Thr Ile Phe Leu Ser Leu Lys
                20                  25                  30

Leu Gly Thr Lys Glu Ile Asn Ile Arg Asp Phe Leu Ala Ala Phe Gly
            35                  40                  45

Met Gly Asn Thr Asn Asp Asp Phe Ile Lys Ser Ile Ile Tyr Lys Arg
50                  55                  60

Ile Pro Arg Thr Ile Phe Ala Ile Leu Ala Gly Ser Ser Leu Ala Ile
65                  70                  75                  80

Ser Gly Val Leu Met Gln Ser Val Thr Arg Asn Pro Ile Ala Asp Pro
                85                  90                  95

Gly Ile Leu Gly Ile Asn Thr Gly Ala Ser Leu Ser Val Val Ile Gly
            100                 105                 110

Leu Ser Phe Leu Gly Ile Ser Ser Ile Ser His Ile Ser Phe Ala
        115                 120                 125

Ile Ile Gly Gly Leu Val Ser Ala Ile Phe Val Tyr Ala Ile Ala Val
130                 135                 140

Ser Gly Lys Ala Gly Leu Thr Pro Ile Lys Leu Ala Leu Ser Gly Thr
145                 150                 155                 160

Cys Val Ser Met Ala Leu Ser Ser Phe Val Ser Phe Leu Ile Leu Pro
                165                 170                 175

Asn Asn Asn Val Leu Asp Lys Phe Arg Phe Trp Gln Ile Gly Ser Leu
            180                 185                 190

Gly Ala Ala Thr Leu Ser Ser Ile Ser Thr Leu Leu Pro Phe Ile Ile
        195                 200                 205

Leu Gly His Leu Ile Ala Ile Phe Ile Ser Ser Asp Leu Asn Ala Leu
210                 215                 220

Ala Met Gly Asp Glu Met Ala Val Gly Leu Gly Val Asn Val Asn Arg
225                 230                 235                 240

Ile Arg Ser Leu Ala Ile Ala Ser Val Leu Leu Cys Ser Ser Ile
                245                 250                 255

Thr Ala Ile Gly Gly Pro Ile Gly Phe Val Gly Leu Ile Val Pro His
            260                 265                 270

Phe Cys Gly Leu Phe Ile Ser Lys Asp Ile Arg Thr Met Thr Ile Ser
        275                 280                 285

Ser Ala Phe Ile Gly Ala Glu Leu Leu Leu Ile Cys Asp Ile Ile Gly
290                 295                 300

Arg Met Leu Gly Lys Pro Gly Glu Ile Glu Val Gly Ile Ile Thr Ala
305                 310                 315                 320

Ile Ile Gly Gly Pro Val Leu Ile Tyr Val Thr Met Lys Asn Arg Gly
                325                 330                 335

Val Asn Thr
```

<210> SEQ ID NO 77
<211> LENGTH: 321
<212> TYPE: PRT
<213> ORGANISM: Streptococcus pneumoniae
<220> FEATURE:
<223> OTHER INFORMATION: full length PiuA

<400> SEQUENCE: 77

| Met | Lys | Thr | Ser | Leu | Lys | Leu | Tyr | Phe | Thr | Ala | Leu | Val | Ala | Ser | Phe |
|---|---|---|---|---|---|---|---|---|---|---|---|---|---|---|---|
| 1 | | | | 5 | | | | | 10 | | | | | 15 | |

Leu Leu Leu Leu Gly Ala Cys Ser Thr Asn Ser Ser Thr Ser Gln Thr
            20                  25                  30

Glu Thr Ser Ser Ser Ala Pro Thr Glu Ile Thr Ile Lys Ser Ser Leu
        35                  40                  45

Asp Glu Val Lys Leu Ser Lys Val Pro Glu Lys Ile Val Thr Phe Asp
    50                  55                  60

Leu Gly Ala Ala Asp Thr Ile Arg Ala Leu Gly Phe Glu Lys Asn Ile
65                  70                  75                  80

Val Gly Met Pro Thr Lys Thr Val Pro Thr Tyr Leu Lys Asp Leu Val
                85                  90                  95

Gly Thr Val Lys Asn Val Gly Ser Met Lys Glu Pro Asp Leu Glu Ala
            100                 105                 110

Ile Ala Ala Leu Glu Pro Asp Leu Ile Ile Ala Ser Pro Arg Thr Gln
        115                 120                 125

Lys Phe Val Asp Lys Phe Lys Glu Ile Ala Pro Thr Val Leu Phe Gln
    130                 135                 140

Ala Ser Lys Asp Asp Tyr Trp Thr Ser Thr Lys Ala Asn Ile Glu Ser
145                 150                 155                 160

Leu Ala Ser Ala Phe Gly Glu Thr Ser Thr Gln Lys Ala Lys Glu Glu
                165                 170                 175

Leu Ala Lys Leu Asp Lys Ser Ile Gln Glu Val Ala Thr Lys Asn Glu
            180                 185                 190

Ser Ser Asp Lys Lys Ala Leu Ala Ile Leu Asn Glu Gly Lys Met
        195                 200                 205

Ala Ala Phe Gly Ala Lys Ser Arg Phe Ser Phe Leu Tyr Gln Thr Leu
210                 215                 220

Lys Phe Lys Pro Thr Asp Thr Lys Phe Glu Asp Ser Arg His Gly Gln
225                 230                 235                 240

Glu Val Ser Phe Glu Ser Val Lys Glu Ile Asn Pro Asp Ile Leu Phe
                245                 250                 255

Val Ile Asn Arg Thr Leu Ala Ile Gly Gly Asp Asn Ser Ser Asn Asp
            260                 265                 270

Gly Val Leu Glu Asn Ala Leu Ile Ala Glu Thr Pro Ala Ala Lys Asn
        275                 280                 285

Gly Lys Ile Ile Gln Leu Thr Pro Asp Leu Trp Tyr Leu Ser Gly Gly
    290                 295                 300

Gly Leu Glu Ser Thr Lys Leu Met Ile Glu Asp Ile Gln Lys Ala Leu
305                 310                 315                 320

Lys

<210> SEQ ID NO 78
<211> LENGTH: 279
<212> TYPE: PRT
<213> ORGANISM: Streptococcus pneumoniae
<220> FEATURE:
<223> OTHER INFORMATION: full length CbiO

```
<400> SEQUENCE: 78

Met Gly Ile Ala Leu Glu Asn Val Asn Phe Ile Tyr Gln Glu Gly Thr
1               5                   10                  15

Pro Leu Ala Ser Ala Ala Leu Ser Asp Val Ser Leu Thr Ile Glu Asp
            20                  25                  30

Gly Ser Tyr Thr Ala Leu Ile Gly His Thr Gly Ser Gly Lys Ser Thr
        35                  40                  45

Ile Leu Gln Leu Leu Asn Gly Leu Leu Val Pro Ser Gln Gly Ser Val
50                  55                  60

Arg Val Phe Asp Thr Leu Ile Thr Ser Thr Ser Lys Asn Lys Asp Ile
65                  70                  75                  80

Arg Gln Ile Arg Lys Gln Val Gly Leu Val Phe Gln Phe Ala Glu Asn
                85                  90                  95

Gln Ile Phe Glu Glu Thr Val Leu Lys Asp Val Ala Phe Gly Pro Gln
            100                 105                 110

Asn Phe Gly Val Ser Glu Glu Asp Ala Val Lys Thr Ala Arg Glu Lys
        115                 120                 125

Leu Ala Leu Val Gly Ile Asp Glu Ser Leu Phe Asp Arg Ser Pro Phe
    130                 135                 140

Glu Leu Ser Gly Gly Gln Met Arg Arg Val Ala Ile Ala Gly Ile Leu
145                 150                 155                 160

Ala Met Glu Pro Ser Ile Leu Val Leu Asp Glu Pro Thr Ala Gly Leu
                165                 170                 175

Asp Pro Leu Gly Arg Lys Glu Leu Met Thr Leu Phe Lys Lys Leu His
            180                 185                 190

Gln Ser Gly Met Thr Ile Val Leu Val Thr His Leu Met Asp Asp Val
        195                 200                 205

Ala Glu Tyr Ala Asn Gln Val Tyr Val Met Glu Lys Gly Arg Leu Val
    210                 215                 220

Lys Gly Gly Lys Pro Ser Asp Val Phe Gln Asp Val Val Phe Met Glu
225                 230                 235                 240

Glu Val Gln Leu Gly Val Pro Lys Ile Thr Ala Phe Cys Lys Arg Leu
                245                 250                 255

Ala Asp Arg Gly Val Ser Phe Lys Arg Leu Pro Ile Lys Ile Glu Glu
            260                 265                 270

Phe Lys Glu Ser Leu Asn Gly
        275

<210> SEQ ID NO 79
<211> LENGTH: 132
<212> TYPE: PRT
<213> ORGANISM: Streptococcus pneumoniae
<220> FEATURE:
<223> OTHER INFORMATION: 30S ribosomal protein S8

<400> SEQUENCE: 79

Met Val Met Thr Asp Pro Ile Ala Asp Phe Leu Thr Arg Ile Arg Asn
1               5                   10                  15

Ala Asn Gln Ala Lys His Glu Val Leu Glu Val Pro Ala Ser Asn Ile
            20                  25                  30

Lys Lys Gly Ile Ala Glu Ile Leu Lys Arg Glu Gly Phe Val Lys Asn
        35                  40                  45

Val Glu Ile Ile Glu Asp Asp Lys Gln Gly Val Ile Arg Val Phe Leu
50                  55                  60

Lys Tyr Gly Pro Asn Gly Glu Lys Val Ile Thr Asn Leu Lys Arg Val
```

```
                65                  70                  75                  80
Ser Lys Pro Gly Leu Arg Val Tyr Lys Lys Arg Glu Asp Leu Pro Lys
                    85                  90                  95

Val Leu Asn Gly Leu Gly Ile Ala Ile Leu Ser Thr Ser Glu Gly Leu
                100                 105                 110

Leu Thr Asp Lys Glu Ala Arg Gln Lys Asn Val Gly Gly Glu Val Ile
            115                 120                 125

Ala Tyr Val Trp
        130

<210> SEQ ID NO 80
<211> LENGTH: 26
<212> TYPE: DNA
<213> ORGANISM: Artificial
<220> FEATURE:
<223> OTHER INFORMATION: deoxynucleotide comprising 26-mer sequence 5'-
      (IC)13-3'
<220> FEATURE:
<221> NAME/KEY: misc_feature
<222> LOCATION: (1), (3), (5), (7), (9), (11), (13), (15), (17), (19),
      (21), (23), (25)
<223> OTHER INFORMATION: n = inosine

<400> SEQUENCE: 80
ncncncncnc ncncncncnc ncncnc                                            26

<210> SEQ ID NO 81
<211> LENGTH: 11
<212> TYPE: PRT
<213> ORGANISM: Artificial
<220> FEATURE:
<223> OTHER INFORMATION: polycationic peptide comprising 11-mer amino
      acid sequence

<400> SEQUENCE: 81

Lys Leu Lys Leu Leu Leu Leu Leu Lys Leu Lys
1               5                   10

<210> SEQ ID NO 82
<211> LENGTH: 1427
<212> TYPE: PRT
<213> ORGANISM: Artificial
<220> FEATURE:
<223> OTHER INFORMATION: hybrid protein; spr0057 and spr0096

<400> SEQUENCE: 82

Met Ala Asp Gly Val Thr Pro Thr Thr Glu Asn Gln Pro Thr Ile
1               5                   10                  15

His Thr Val Ser Asp Ser Pro Gln Ser Ser Glu Asn Arg Thr Glu Glu
                20                  25                  30

Thr Pro Lys Ala Val Leu Gln Pro Glu Ala Pro Lys Thr Val Glu Thr
            35                  40                  45

Glu Thr Pro Ala Thr Asp Lys Val Ala Ser Leu Pro Lys Thr Glu Glu
        50                  55                  60

Lys Pro Gln Glu Glu Val Ser Ser Thr Pro Ser Asp Lys Ala Glu Val
65                  70                  75                  80

Val Thr Pro Thr Ser Ala Glu Lys Glu Thr Ala Asn Lys Lys Ala Glu
                85                  90                  95

Glu Ala Ser Pro Lys Lys Glu Ala Lys Glu Val Asp Ser Lys Glu
            100                 105                 110

Ser Asn Thr Asp Lys Thr Asp Lys Asp Lys Pro Ala Lys Lys Asp Glu
        115                 120                 125
```

-continued

```
Ala Lys Ala Glu Ala Asp Lys Pro Ala Thr Glu Ala Gly Lys Glu Arg
130                 135                 140
Ala Ala Thr Val Asn Glu Lys Leu Ala Lys Lys Ile Val Ser Ile
145                 150                 155                 160
Asp Ala Gly Arg Lys Tyr Phe Ser Pro Glu Gln Leu Lys Glu Ile Ile
                165                 170                 175
Asp Lys Ala Lys His Tyr Gly Tyr Thr Asp Leu His Leu Leu Val Gly
            180                 185                 190
Asn Asp Gly Leu Arg Phe Met Leu Asp Asp Met Ser Ile Thr Ala Asn
                195                 200                 205
Gly Lys Thr Tyr Ala Ser Asp Val Lys Arg Ala Ile Glu Lys Gly
    210                 215                 220
Thr Asn Asp Tyr Asn Asp Pro Asn Gly Asn His Leu Thr Glu Ser
225                 230                 235                 240
Gln Met Thr Asp Leu Ile Asn Tyr Ala Lys Asp Lys Gly Ile Gly Leu
                245                 250                 255
Ile Pro Thr Val Asn Ser Pro Gly His Met Asp Ala Ile Leu Asn Ala
                260                 265                 270
Met Lys Glu Leu Gly Ile Gln Asn Pro Asn Phe Ser Tyr Phe Gly Lys
    275                 280                 285
Lys Ser Ala Arg Thr Val Asp Leu Asp Asn Glu Gln Ala Val Ala Phe
290                 295                 300
Thr Lys Ala Leu Ile Asp Lys Tyr Ala Ala Tyr Phe Ala Lys Lys Thr
305                 310                 315                 320
Glu Ile Phe Asn Ile Gly Leu Asp Glu Tyr Ala Asn Asp Ala Thr Asp
                325                 330                 335
Ala Lys Gly Trp Ser Val Leu Gln Ala Asp Lys Tyr Tyr Pro Asn Glu
            340                 345                 350
Gly Tyr Pro Val Lys Gly Tyr Glu Lys Phe Ile Ala Tyr Ala Asn Asp
            355                 360                 365
Leu Ala Arg Ile Val Lys Ser His Gly Leu Lys Pro Met Ala Phe Asn
370                 375                 380
Asp Gly Ile Tyr Tyr Asn Ser Asp Thr Ser Phe Gly Ser Phe Asp Lys
385                 390                 395                 400
Asp Ile Ile Val Ser Met Trp Thr Gly Gly Trp Gly Gly Tyr Asp Val
                405                 410                 415
Ala Ser Ser Lys Leu Leu Ala Glu Lys Gly His Gln Ile Leu Asn Thr
            420                 425                 430
Asn Asp Ala Trp Tyr Tyr Val Leu Gly Arg Asn Ala Asp Gly Gln Gly
                435                 440                 445
Trp Tyr Asn Leu Asp Gln Gly Leu Asn Gly Ile Lys Asn Thr Pro Ile
    450                 455                 460
Thr Ser Val Pro Lys Thr Glu Gly Ala Asp Ile Pro Ile Gly Gly
465                 470                 475                 480
Met Val Ala Ala Trp Ala Asp Thr Pro Ser Ala Arg Tyr Ser Pro Ser
                485                 490                 495
Arg Leu Phe Lys Leu Met Arg His Phe Ala Asn Ala Asn Ala Glu Tyr
            500                 505                 510
Phe Ala Ala Asp Tyr Glu Ser Ala Glu Gln Ala Leu Asn Glu Val Pro
            515                 520                 525
Lys Asp Leu Asn Arg Tyr Thr Ala Glu Ser Val Thr Ala Val Lys Glu
530                 535                 540
Ala Glu Lys Ala Ile Arg Ser Leu Asp Ser Asn Leu Ser Arg Ala Gln
545                 550                 555                 560
```

-continued

Gln Asp Thr Ile Asp Gln Ala Ile Ala Lys Leu Gln Glu Thr Val Asn
            565                 570                 575

Asn Leu Thr Leu Thr Pro Glu Ala Gln Lys Glu Glu Ala Lys Arg
        580                 585                 590

Glu Val Glu Lys Leu Ala Lys Asn Lys Val Ile Ser Ile Asp Ala Gly
    595                 600                 605

Arg Lys Tyr Phe Thr Leu Asn Gln Leu Lys Arg Ile Val Asp Lys Ala
    610                 615                 620

Ser Glu Leu Gly Tyr Ser Asp Val His Leu Leu Gly Asn Asp Gly
625                 630                 635                 640

Leu Arg Phe Leu Leu Asp Asp Met Thr Ile Thr Ala Asn Gly Lys Thr
            645                 650                 655

Tyr Ala Ser Asp Asp Val Lys Lys Ala Ile Ile Glu Gly Thr Lys Ala
            660                 665                 670

Tyr Tyr Asp Asp Pro Asn Gly Thr Ala Leu Thr Gln Ala Glu Val Thr
            675                 680                 685

Glu Leu Ile Glu Tyr Ala Lys Ser Lys Asp Ile Gly Leu Ile Pro Ala
    690                 695                 700

Ile Asn Ser Pro Gly His Met Asp Ala Met Leu Val Ala Met Glu Lys
705                 710                 715                 720

Leu Gly Ile Lys Asn Pro Gln Ala His Phe Asp Lys Val Ser Lys Thr
            725                 730                 735

Thr Met Asp Leu Lys Asn Glu Glu Ala Met Asn Phe Val Lys Ala Leu
            740                 745                 750

Ile Gly Lys Tyr Met Asp Phe Phe Ala Gly Lys Thr Lys Ile Phe Asn
    755                 760                 765

Phe Gly Thr Asp Glu Tyr Ala Asn Asp Ala Thr Ser Ala Gln Gly Trp
    770                 775                 780

Tyr Tyr Leu Lys Trp Tyr Gln Leu Tyr Gly Lys Phe Ala Glu Tyr Ala
785                 790                 795                 800

Asn Thr Leu Ala Ala Met Ala Lys Glu Arg Gly Leu Gln Pro Met Ala
            805                 810                 815

Phe Asn Asp Gly Phe Tyr Tyr Glu Asp Lys Asp Val Gln Phe Asp
        820                 825                 830

Lys Asp Val Leu Ile Ser Tyr Trp Ser Lys Gly Trp Gly Tyr Asn
    835                 840                 845

Leu Ala Ser Pro Gln Tyr Leu Ala Ser Lys Gly Tyr Lys Phe Leu Asn
    850                 855                 860

Thr Asn Gly Asp Trp Tyr Tyr Ile Leu Gly Gln Lys Pro Glu Asp Gly
865                 870                 875                 880

Gly Gly Phe Leu Lys Lys Ala Ile Glu Asn Thr Gly Lys Thr Pro Phe
            885                 890                 895

Asn Gln Leu Ala Ser Thr Lys Tyr Pro Glu Val Asp Leu Pro Thr Val
        900                 905                 910

Gly Ser Met Leu Ser Ile Trp Ala Asp Arg Pro Ser Ala Glu Tyr Lys
    915                 920                 925

Glu Glu Glu Ile Phe Glu Leu Met Thr Ala Phe Ala Asp His Asn Lys
    930                 935                 940

Asp Tyr Phe Arg Ala Asn Tyr Asn Ala Leu Arg Glu Glu Leu Ala Lys
945                 950                 955                 960

Ile Pro Thr Asn Leu Glu Gly Tyr Ser Lys Glu Ser Leu Glu Ala Leu
            965                 970                 975

Asp Ala Ala Lys Thr Ala Leu Asn Tyr Asn Leu Asn Arg Asn Lys Gln

-continued

```
               980             985             990
Ala Glu Leu Asp Thr Leu Val Ala Asn Leu Lys Ala Ala Leu Gln Gly
        995                 1000                1005
Leu Lys Pro Ala Val Thr His Ser Gly Ser Leu Asp Glu Asn Glu Val
        1010                1015                1020
Ala Ala Asn Val Glu Thr Arg Pro Glu Leu Ile Thr Arg Thr Glu Glu
1025                1030                1035                1040
Ile Pro Phe Glu Val Ile Lys Lys Glu Asn Pro Asn Leu Pro Ala Gly
                1045                1050                1055
Gln Glu Asn Ile Ile Thr Ala Gly Val Lys Gly Glu Arg Thr His Tyr
                1060                1065                1070
Ile Ser Val Leu Thr Glu Asn Gly Lys Thr Thr Glu Thr Val Leu Asp
            1075                1080                1085
Ser Gln Val Thr Lys Glu Val Ile Asn Gln Val Val Glu Val Gly Ala
        1090                1095                1100
Pro Val Thr His Lys Gly Asp Glu Ser Gly Leu Ala Pro Thr Thr Glu
1105                1110                1115                1120
Val Lys Pro Arg Leu Asp Ile Gln Glu Glu Glu Ile Pro Phe Thr Thr
                1125                1130                1135
Val Thr Cys Glu Asn Pro Leu Leu Leu Lys Gly Lys Thr Gln Val Ile
                1140                1145                1150
Thr Lys Gly Val Asn Gly His Arg Ser Asn Phe Tyr Ser Val Ser Thr
                1155                1160                1165
Ser Ala Asp Gly Lys Glu Val Lys Thr Leu Val Asn Ser Val Val Ala
            1170                1175                1180
Gln Glu Ala Val Thr Gln Ile Val Glu Val Gly Thr Met Val Thr His
1185                1190                1195                1200
Val Gly Asp Glu Asn Gly Gln Ala Ala Ile Ala Glu Glu Lys Pro Lys
                1205                1210                1215
Leu Glu Ile Pro Ser Gln Pro Ala Pro Ser Thr Ala Pro Ala Glu Glu
                1220                1225                1230
Ser Lys Val Leu Pro Gln Asp Pro Ala Pro Val Val Thr Glu Lys Lys
        1235                1240                1245
Gly Ser Gly Ser Gly Gly Gly Val Ser Ala Gln Glu Ser Ser Thr
        1250                1255                1260
Tyr Thr Val Lys Glu Gly Asp Thr Leu Ser Glu Ile Ala Glu Thr His
1265                1270                1275                1280
Asn Thr Thr Val Glu Lys Leu Ala Glu Asn Asn His Ile Asp Asn Ile
                1285                1290                1295
His Leu Ile Tyr Val Asp Gln Glu Leu Val Ile Asp Gly Pro Val Ala
                1300                1305                1310
Pro Val Ala Thr Pro Ala Pro Ala Thr Tyr Ala Ala Pro Ala Ala Gln
            1315                1320                1325
Asp Glu Thr Val Ser Ala Pro Val Ala Glu Thr Pro Val Val Ser Glu
        1330                1335                1340
Thr Val Val Ser Thr Val Ser Gly Ser Glu Ala Glu Ala Lys Glu Trp
1345                1350                1355                1360
Ile Ala Gln Lys Glu Ser Gly Gly Ser Tyr Thr Ala Thr Asn Gly Arg
                1365                1370                1375
Tyr Ile Gly Arg Tyr Gln Leu Thr Asp Ser Tyr Leu Asn Gly Asp Tyr
                1380                1385                1390
Ser Ala Glu Asn Gln Glu Arg Val Ala Asp Ala Tyr Val Ala Gly Arg
            1395                1400                1405
```

-continued

Tyr Gly Ser Trp Thr Ala Ala Lys Asn Phe Trp Leu Asn Asn Gly Trp
            1410                1415                1420

Tyr Leu Glu
1425

<210> SEQ ID NO 83
<211> LENGTH: 1242
<212> TYPE: PRT
<213> ORGANISM: Artificial
<220> FEATURE:
<223> OTHER INFORMATION: hybrid protein; spr0057 and spr0096

<400> SEQUENCE: 83

Met Leu His Leu Leu Val Gly Asn Asp Gly Leu Arg Phe Met Leu Asp
1               5                   10                  15

Asp Met Ser Ile Thr Ala Asn Gly Lys Thr Tyr Ala Ser Asp Asp Val
            20                  25                  30

Lys Arg Ala Ile Glu Lys Gly Thr Asn Asp Tyr Tyr Asn Asp Pro Asn
        35                  40                  45

Gly Asn His Leu Thr Glu Ser Gln Met Thr Asp Leu Ile Asn Tyr Ala
    50                  55                  60

Lys Asp Lys Gly Ile Gly Leu Ile Pro Thr Val Asn Ser Pro Gly His
65                  70                  75                  80

Met Asp Ala Ile Leu Asn Ala Met Lys Glu Leu Gly Ile Gln Asn Pro
                85                  90                  95

Asn Phe Ser Tyr Phe Gly Lys Lys Ser Ala Arg Thr Val Asp Leu Asp
            100                 105                 110

Asn Glu Gln Ala Val Ala Phe Thr Lys Ala Leu Ile Asp Lys Tyr Ala
        115                 120                 125

Ala Tyr Phe Ala Lys Lys Thr Glu Ile Phe Asn Ile Gly Leu Asp Glu
    130                 135                 140

Tyr Ala Asn Asp Ala Thr Asp Ala Lys Gly Trp Ser Val Leu Gln Ala
145                 150                 155                 160

Asp Lys Tyr Tyr Pro Asn Glu Gly Tyr Pro Val Lys Gly Tyr Glu Lys
                165                 170                 175

Phe Ile Ala Tyr Ala Asn Asp Leu Ala Arg Ile Val Lys Ser His Gly
            180                 185                 190

Leu Lys Pro Met Ala Phe Asn Asp Gly Ile Tyr Tyr Asn Ser Asp Thr
        195                 200                 205

Ser Phe Gly Ser Phe Asp Lys Asp Ile Ile Val Ser Met Trp Thr Gly
    210                 215                 220

Gly Trp Gly Gly Tyr Asp Val Ala Ser Ser Lys Leu Leu Ala Glu Lys
225                 230                 235                 240

Gly His Gln Ile Leu Asn Thr Asn Asp Ala Trp Tyr Tyr Val Leu Gly
                245                 250                 255

Arg Asn Ala Asp Gly Gln Gly Trp Tyr Asn Leu Asp Gln Gly Leu Asn
            260                 265                 270

Gly Ile Lys Asn Thr Pro Ile Thr Ser Val Pro Lys Thr Glu Gly Ala
        275                 280                 285

Asp Ile Pro Ile Ile Gly Gly Met Val Ala Ala Trp Ala Asp Thr Pro
    290                 295                 300

Ser Ala Arg Tyr Ser Pro Ser Arg Leu Phe Lys Leu Met Arg His Phe
305                 310                 315                 320

Ala Asn Ala Asn Ala Glu Tyr Phe Ala Ala Asp Tyr Glu Ser Ala Glu
                325                 330                 335

Gln Ala Leu Asn Glu Val Pro Lys Asp Leu Asn Arg Tyr Thr Ala Glu

```
                    340                 345                 350
Ser Val Thr Ala Val Lys Glu Ala Glu Lys Ala Ile Arg Ser Leu Asp
            355                 360                 365

Ser Asn Leu Ser Arg Ala Gln Gln Asp Thr Ile Asp Gln Ala Ile Ala
    370                 375                 380

Lys Leu Gln Glu Thr Val Asn Asn Leu Thr Leu Thr Pro Glu Ala Gln
385                 390                 395                 400

Lys Glu Glu Ala Lys Arg Glu Val Glu Lys Leu Ala Lys Asn Lys
                405                 410                 415

Val Ile Ser Ile Asp Ala Gly Arg Lys Tyr Phe Thr Leu Asn Gln Leu
            420                 425                 430

Lys Arg Ile Val Asp Lys Ala Ser Glu Leu Gly Tyr Ser Asp Val His
            435                 440                 445

Leu Leu Leu Gly Asn Asp Gly Leu Arg Phe Leu Leu Asp Asp Met Thr
            450                 455                 460

Ile Thr Ala Asn Gly Lys Thr Tyr Ala Ser Asp Asp Val Lys Lys Ala
465                 470                 475                 480

Ile Ile Glu Gly Thr Lys Ala Tyr Tyr Asp Asp Pro Asn Gly Thr Ala
                485                 490                 495

Leu Thr Gln Ala Glu Val Thr Glu Leu Ile Glu Tyr Ala Lys Ser Lys
            500                 505                 510

Asp Ile Gly Leu Ile Pro Ala Ile Asn Ser Pro Gly His Met Asp Ala
            515                 520                 525

Met Leu Val Ala Met Glu Lys Leu Gly Ile Lys Asn Pro Gln Ala His
            530                 535                 540

Phe Asp Lys Val Ser Lys Thr Thr Met Asp Leu Lys Asn Glu Glu Ala
545                 550                 555                 560

Met Asn Phe Val Lys Ala Leu Ile Gly Lys Tyr Met Asp Phe Phe Ala
                565                 570                 575

Gly Lys Thr Lys Ile Phe Asn Phe Gly Thr Asp Glu Tyr Ala Asn Asp
            580                 585                 590

Ala Thr Ser Ala Gln Gly Trp Tyr Tyr Leu Lys Trp Tyr Gln Leu Tyr
            595                 600                 605

Gly Lys Phe Ala Glu Tyr Ala Asn Thr Leu Ala Ala Met Ala Lys Glu
            610                 615                 620

Arg Gly Leu Gln Pro Met Ala Phe Asn Asp Gly Phe Tyr Tyr Glu Asp
625                 630                 635                 640

Lys Asp Asp Val Gln Phe Asp Lys Asp Val Leu Ile Ser Tyr Trp Ser
                645                 650                 655

Lys Gly Trp Trp Gly Tyr Asn Leu Ala Ser Pro Gln Tyr Leu Ala Ser
            660                 665                 670

Lys Gly Tyr Lys Phe Leu Asn Thr Asn Gly Asp Trp Tyr Tyr Ile Leu
            675                 680                 685

Gly Gln Lys Pro Glu Asp Gly Gly Phe Leu Lys Lys Ala Ile Glu
            690                 695                 700

Asn Thr Gly Lys Thr Pro Phe Asn Gln Leu Ala Ser Thr Lys Tyr Pro
705                 710                 715                 720

Glu Val Asp Leu Pro Thr Val Gly Ser Met Leu Ser Ile Trp Ala Asp
                725                 730                 735

Arg Pro Ser Ala Glu Tyr Lys Glu Glu Ile Phe Glu Leu Met Thr
            740                 745                 750

Ala Phe Ala Asp His Asn Lys Asp Tyr Phe Arg Ala Asn Tyr Asn Ala
            755                 760                 765
```

```
Leu Arg Glu Leu Ala Lys Ile Pro Thr Asn Leu Glu Gly Tyr Ser
    770             775             780

Lys Glu Ser Leu Glu Ala Leu Asp Ala Ala Lys Thr Ala Leu Asn Tyr
785             790             795                 800

Asn Leu Asn Arg Asn Lys Gln Ala Glu Leu Asp Thr Leu Val Ala Asn
            805             810             815

Leu Lys Ala Ala Leu Gln Gly Leu Lys Pro Ala Val Thr His Ser Gly
        820             825             830

Ser Leu Asp Glu Asn Glu Val Ala Ala Asn Val Glu Thr Arg Pro Glu
            835             840             845

Leu Ile Thr Arg Thr Glu Glu Ile Pro Phe Glu Val Ile Lys Lys Glu
        850             855             860

Asn Pro Asn Leu Pro Ala Gly Gln Glu Asn Ile Ile Thr Ala Gly Val
865             870             875             880

Lys Gly Glu Arg Thr His Tyr Ile Ser Val Leu Thr Glu Asn Gly Lys
            885             890             895

Thr Thr Glu Thr Val Leu Asp Ser Gln Val Thr Lys Glu Val Ile Asn
        900             905             910

Gln Val Val Glu Val Gly Ala Pro Val Thr His Lys Gly Asp Glu Ser
        915             920             925

Gly Leu Ala Pro Thr Thr Glu Val Lys Pro Arg Leu Asp Ile Gln Glu
    930             935             940

Glu Glu Ile Pro Phe Thr Thr Val Thr Cys Glu Asn Pro Leu Leu Leu
945             950             955             960

Lys Gly Lys Thr Gln Val Ile Thr Lys Gly Val Asn Gly His Arg Ser
            965             970             975

Asn Phe Tyr Ser Val Ser Thr Ser Ala Asp Gly Lys Glu Val Lys Thr
        980             985             990

Leu Val Asn Ser Val Val Ala Gln Glu Ala Val Thr Gln Ile Val Glu
        995             1000            1005

Val Gly Thr Met Val Thr His Val Gly Asp Glu Asn Gly Gln Ala Ala
    1010            1015            1020

Ile Ala Glu Glu Lys Pro Lys Leu Glu Ile Pro Ser Gln Pro Ala Pro
1025            1030            1035            1040

Ser Thr Ala Pro Ala Glu Glu Ser Lys Val Leu Pro Gln Asp Pro Ala
            1045            1050            1055

Pro Val Val Thr Glu Lys Lys Gly Ser Gly Ser Gly Gly Gly Gly Val
        1060            1065            1070

Ser Ala Gln Glu Ser Ser Thr Tyr Thr Val Lys Glu Gly Asp Thr Leu
        1075            1080            1085

Ser Glu Ile Ala Glu Thr His Asn Thr Thr Val Glu Lys Leu Ala Glu
    1090            1095            1100

Asn Asn His Ile Asp Asn Ile His Leu Ile Tyr Val Asp Gln Glu Leu
1105            1110            1115            1120

Val Ile Asp Gly Pro Val Ala Pro Val Ala Thr Pro Ala Pro Ala Thr
        1125            1130            1135

Tyr Ala Ala Pro Ala Ala Gln Asp Glu Thr Val Ser Ala Pro Val Ala
            1140            1145            1150

Glu Thr Pro Val Val Ser Glu Thr Val Val Ser Thr Val Ser Gly Ser
        1155            1160            1165

Glu Ala Glu Ala Lys Glu Trp Ile Ala Gln Lys Glu Ser Gly Gly Ser
    1170            1175            1180

Tyr Thr Ala Thr Asn Gly Arg Tyr Ile Gly Arg Tyr Gln Leu Thr Asp
1185            1190            1195            1200
```

Ser Tyr Leu Asn Gly Asp Tyr Ser Ala Glu Asn Gln Glu Arg Val Ala
              1205                1210                1215

Asp Ala Tyr Val Ala Gly Arg Tyr Gly Ser Trp Thr Ala Ala Lys Asn
            1220                1225                1230

Phe Trp Leu Asn Asn Gly Trp Tyr Leu Glu
        1235                1240

<210> SEQ ID NO 84
<211> LENGTH: 549
<212> TYPE: PRT
<213> ORGANISM: Artificial
<220> FEATURE:
<223> OTHER INFORMATION: hybrid protein; spr0096 and spr2021

<400> SEQUENCE: 84

Met Val Ser Ala Gln Glu Ser Ser Thr Tyr Thr Val Lys Glu Gly Asp
1               5                   10                  15

Thr Leu Ser Glu Ile Ala Glu Thr His Asn Thr Thr Val Glu Lys Leu
            20                  25                  30

Ala Glu Asn Asn His Ile Asp Asn Ile His Leu Ile Tyr Val Asp Gln
        35                  40                  45

Glu Leu Val Ile Asp Gly Pro Val Ala Pro Val Ala Thr Pro Ala Pro
    50                  55                  60

Ala Thr Tyr Ala Ala Pro Ala Ala Gln Asp Glu Thr Val Ser Ala Pro
65                  70                  75                  80

Val Ala Glu Thr Pro Val Val Ser Glu Thr Val Val Ser Thr Val Ser
                85                  90                  95

Gly Ser Glu Ala Glu Ala Lys Glu Trp Ile Ala Gln Lys Glu Ser Gly
            100                 105                 110

Gly Ser Tyr Thr Ala Thr Asn Gly Arg Tyr Ile Gly Arg Tyr Gln Leu
        115                 120                 125

Thr Asp Ser Tyr Leu Asn Gly Asp Tyr Ser Ala Glu Asn Gln Glu Arg
    130                 135                 140

Val Ala Asp Ala Tyr Val Ala Gly Arg Tyr Gly Ser Trp Thr Ala Ala
145                 150                 155                 160

Lys Asn Phe Trp Leu Asn Asn Gly Trp Tyr Gly Ser Gly Ser Gly Gly
                165                 170                 175

Gly Gly Ala Glu Thr Thr Asp Asp Lys Ile Ala Ala Gln Asp Asn Lys
            180                 185                 190

Ile Ser Asn Leu Thr Ala Gln Gln Gln Glu Ala Gln Lys Gln Val Asp
        195                 200                 205

Gln Ile Gln Glu Gln Val Ser Ala Ile Gln Ala Glu Gln Ser Asn Leu
    210                 215                 220

Gln Ala Glu Asn Asp Arg Leu Gln Ala Glu Ser Lys Lys Leu Glu Gly
225                 230                 235                 240

Glu Ile Thr Glu Leu Ser Lys Asn Ile Val Ser Arg Asn Gln Ser Leu
                245                 250                 255

Glu Lys Gln Ala Arg Ser Ala Gln Thr Asn Gly Ala Val Thr Ser Tyr
            260                 265                 270

Ile Asn Thr Ile Val Asn Ser Lys Ser Ile Thr Glu Ala Ile Ser Arg
        275                 280                 285

Val Ala Ala Met Ser Glu Ile Val Ser Ala Asn Asn Lys Met Leu Glu
    290                 295                 300

Gln Gln Lys Ala Asp Lys Lys Ala Ile Ser Glu Lys Gln Val Ala Asn
305                 310                 315                 320

```
Asn Asp Ala Ile Asn Thr Val Ile Ala Asn Gln Gln Lys Leu Ala Asp
                325                 330                 335
Asp Ala Gln Ala Leu Thr Thr Lys Gln Ala Glu Leu Lys Ala Ala Glu
            340                 345                 350
Leu Ser Leu Ala Ala Glu Lys Ala Thr Ala Glu Gly Glu Lys Ala Ser
                355                 360                 365
Leu Leu Glu Gln Lys Ala Ala Glu Ala Glu Ala Arg Ala Ala
            370                 375                 380
Val Ala Glu Ala Ala Tyr Lys Glu Lys Arg Ala Ser Gln Gln Gln Ser
385                 390                 395                 400
Val Leu Ala Ser Ala Asn Thr Asn Leu Thr Ala Gln Val Gln Ala Val
                405                 410                 415
Ser Glu Ser Ala Ala Ala Pro Val Arg Ala Lys Val Arg Pro Thr Tyr
            420                 425                 430
Ser Thr Asn Ala Ser Ser Tyr Pro Ile Gly Glu Cys Thr Trp Gly Val
                435                 440                 445
Lys Thr Leu Ala Pro Trp Ala Gly Asp Tyr Trp Asn Gly Ala Gln
            450                 455                 460
Trp Ala Thr Ser Ala Ala Ala Gly Phe Arg Thr Gly Ser Thr Pro
465                 470                 475                 480
Gln Val Gly Ala Ile Ala Cys Trp Asn Asp Gly Gly Tyr Gly His Val
                485                 490                 495
Ala Val Val Thr Ala Val Glu Ser Thr Thr Arg Ile Gln Val Ser Glu
                500                 505                 510
Ser Asn Tyr Ala Gly Asn Arg Thr Ile Gly Asn His Arg Gly Trp Phe
            515                 520                 525
Asn Pro Thr Thr Thr Ser Glu Gly Phe Val Thr Tyr Ile Tyr Ala Asp
            530                 535                 540
Ala Ala Ala Leu Glu
545

<210> SEQ ID NO 85
<211> LENGTH: 665
<212> TYPE: PRT
<213> ORGANISM: Streptococcus pneumoniae
<220> FEATURE:
<223> OTHER INFORMATION: RrgB sequence

<400> SEQUENCE: 85

Met Lys Ser Ile Asn Lys Phe Leu Thr Met Leu Ala Ala Leu Leu Leu
1               5                   10                  15
Thr Ala Ser Ser Leu Phe Ser Ala Ala Thr Val Phe Ala Ala Gly Thr
                20                  25                  30
Thr Thr Thr Ser Val Thr Val His Lys Leu Leu Ala Thr Asp Gly Asp
            35                  40                  45
Met Asp Lys Ile Ala Asn Glu Leu Glu Thr Gly Asn Tyr Ala Gly Asn
        50                  55                  60
Lys Val Gly Val Leu Pro Ala Asn Ala Lys Glu Ile Ala Gly Val Met
65              70                  75                  80
Phe Val Trp Thr Asn Thr Asn Glu Ile Ile Asp Glu Asn Gly Gln
                85                  90                  95
Thr Leu Gly Val Asn Ile Asp Pro Gln Thr Phe Lys Leu Ser Gly Ala
            100                 105                 110
Met Pro Ala Thr Ala Met Lys Lys Leu Thr Glu Ala Glu Gly Ala Lys
        115                 120                 125
Phe Asn Thr Ala Asn Leu Pro Ala Ala Lys Tyr Lys Ile Tyr Glu Ile
```

-continued

```
            130                 135                 140
His Ser Leu Ser Thr Tyr Val Gly Glu Asp Gly Ala Thr Leu Thr Gly
145                 150                 155                 160

Ser Lys Ala Val Pro Ile Glu Ile Glu Leu Pro Leu Asn Asp Val Val
                165                 170                 175

Asp Ala His Val Tyr Pro Lys Asn Thr Glu Ala Lys Pro Lys Ile Asp
            180                 185                 190

Lys Asp Phe Lys Gly Lys Ala Asn Pro Asp Thr Pro Arg Val Asp Lys
        195                 200                 205

Asp Thr Pro Val Asn His Gln Val Gly Asp Val Val Glu Tyr Glu Ile
    210                 215                 220

Val Thr Lys Ile Pro Ala Leu Ala Asn Tyr Ala Thr Ala Asn Trp Ser
225                 230                 235                 240

Asp Arg Met Thr Glu Gly Leu Ala Phe Asn Lys Gly Thr Val Lys Val
                245                 250                 255

Thr Val Asp Asp Val Ala Leu Glu Ala Gly Asp Tyr Ala Leu Thr Glu
            260                 265                 270

Val Ala Thr Gly Phe Asp Leu Lys Leu Thr Asp Ala Gly Leu Ala Lys
        275                 280                 285

Val Asn Asp Gln Asn Ala Glu Lys Thr Val Lys Ile Thr Tyr Ser Ala
    290                 295                 300

Thr Leu Asn Asp Lys Ala Ile Val Glu Val Pro Glu Ser Asn Asp Val
305                 310                 315                 320

Thr Phe Asn Tyr Gly Asn Asn Pro Asp His Gly Asn Thr Pro Lys Pro
                325                 330                 335

Asn Lys Pro Asn Glu Asn Gly Asp Leu Thr Leu Thr Lys Thr Trp Val
            340                 345                 350

Asp Ala Thr Gly Ala Pro Ile Pro Gly Ala Glu Ala Thr Phe Asp
        355                 360                 365

Leu Val Asn Ala Gln Thr Gly Lys Val Val Gln Thr Val Thr Leu Thr
    370                 375                 380

Thr Asp Lys Asn Thr Val Thr Val Asn Gly Leu Asp Lys Asn Thr Glu
385                 390                 395                 400

Tyr Lys Phe Val Glu Arg Ser Ile Lys Gly Tyr Ser Ala Asp Tyr Gln
                405                 410                 415

Glu Ile Thr Thr Ala Gly Glu Ile Ala Val Lys Asn Trp Lys Asp Glu
            420                 425                 430

Asn Pro Lys Pro Leu Asp Pro Thr Glu Pro Lys Val Val Thr Tyr Gly
        435                 440                 445

Lys Lys Phe Val Lys Val Asn Asp Lys Asp Asn Arg Leu Ala Gly Ala
    450                 455                 460

Glu Phe Val Ile Ala Asn Ala Asp Asn Ala Gly Gln Tyr Leu Ala Arg
465                 470                 475                 480

Lys Ala Asp Lys Val Ser Gln Glu Glu Lys Gly Leu Val Val Thr Thr
                485                 490                 495

Lys Asp Ala Leu Asp Arg Ala Val Ala Ala Tyr Asn Ala Leu Thr Ala
            500                 505                 510

Gln Gln Gln Thr Gln Gln Glu Lys Glu Lys Val Asp Lys Ala Gln Ala
        515                 520                 525

Ala Tyr Asn Ala Ala Val Ile Ala Ala Asn Asn Ala Phe Glu Trp Val
    530                 535                 540

Ala Asp Lys Asp Asn Glu Asn Val Val Lys Leu Val Ser Asp Ala Gln
545                 550                 555                 560
```

-continued

```
Gly Arg Phe Glu Ile Thr Gly Leu Leu Ala Gly Thr Tyr Tyr Leu Glu
                565                 570                 575
Glu Thr Lys Gln Pro Ala Gly Tyr Ala Leu Leu Thr Ser Arg Gln Lys
            580                 585                 590
Phe Glu Val Thr Ala Thr Ser Tyr Ser Ala Thr Gly Gln Gly Ile Glu
        595                 600                 605
Tyr Thr Ala Gly Ser Gly Lys Asp Asp Ala Thr Lys Val Val Asn Lys
    610                 615                 620
Lys Ile Thr Ile Pro Gln Thr Gly Gly Ile Gly Thr Ile Ile Phe Ala
625                 630                 635                 640
Val Ala Gly Ala Val Ile Met Gly Ile Ala Val Tyr Ala Tyr Val Lys
                645                 650                 655
Asn Asn Lys Asp Glu Asp Gln Leu Ala
                660                 665

<210> SEQ ID NO 86
<211> LENGTH: 644
<212> TYPE: PRT
<213> ORGANISM: Streptococcus pneumoniae
<220> FEATURE:
<223> OTHER INFORMATION: RrgB sequence

<400> SEQUENCE: 86

Met Lys Ser Ile Asn Lys Phe Leu Thr Met Leu Ala Ala Leu Leu Leu
1               5                   10                  15
Thr Ala Ser Ser Leu Phe Ser Ala Ala Thr Val Phe Ala Ala Asp Asn
                20                  25                  30
Val Ser Thr Ala Pro Asp Ala Val Thr Lys Thr Leu Thr Ile His Lys
            35                  40                  45
Leu Leu Leu Ser Glu Asp Asp Leu Lys Thr Trp Asp Thr Asn Gly Pro
        50                  55                  60
Lys Gly Tyr Asp Gly Thr Gln Ser Ser Leu Lys Asp Leu Thr Gly Val
65                  70                  75                  80
Val Ala Glu Glu Ile Pro Asn Val Tyr Phe Glu Leu Gln Lys Tyr Asn
                85                  90                  95
Leu Thr Asp Gly Lys Glu Lys Glu Asn Leu Lys Asp Asp Ser Lys Trp
                100                 105                 110
Thr Thr Val His Gly Gly Leu Thr Lys Asp Gly Leu Lys Ile Glu
            115                 120                 125
Thr Ser Thr Leu Lys Gly Val Tyr Arg Ile Arg Glu Asp Arg Thr Lys
        130                 135                 140
Thr Thr Tyr Val Gly Pro Asn Gly Gln Val Leu Thr Gly Ser Lys Ala
145                 150                 155                 160
Val Pro Ala Leu Val Thr Leu Pro Leu Val Asn Asn Asn Gly Thr Val
                165                 170                 175
Ile Asp Ala His Val Phe Pro Lys Asn Ser Tyr Asn Lys Pro Val Val
            180                 185                 190
Asp Lys Arg Ile Ala Asp Thr Leu Asn Tyr Asn Asp Gln Asn Gly Leu
        195                 200                 205
Ser Ile Gly Thr Lys Ile Pro Tyr Val Val Asn Thr Thr Ile Pro Ser
    210                 215                 220
Asn Ala Thr Phe Ala Thr Ser Phe Trp Ser Asp Glu Met Thr Glu Gly
225                 230                 235                 240
Leu Thr Tyr Asn Glu Asp Val Thr Ile Thr Leu Asn Asn Val Ala Met
                245                 250                 255
Asp Gln Ala Asp Tyr Glu Val Thr Lys Gly Ile Asn Gly Phe Asn Leu
```

```
                260             265             270
Lys Leu Thr Glu Ala Gly Leu Ala Lys Ile Asn Gly Lys Asp Ala Asp
            275                 280                 285
Gln Lys Ile Gln Ile Thr Tyr Ser Ala Thr Leu Asn Ser Leu Ala Val
            290                 295                 300
Ala Asp Ile Pro Glu Ser Asn Asp Ile Thr Tyr His Tyr Gly Asn His
305                 310                 315                 320
Gln Asp His Gly Asn Thr Pro Lys Pro Thr Lys Pro Asn Asn Gly Gln
                325                 330                 335
Ile Thr Val Thr Lys Thr Trp Asp Ser Gln Pro Ala Pro Glu Gly Val
            340                 345                 350
Lys Ala Thr Val Gln Leu Val Asn Ala Lys Thr Gly Glu Lys Val Gly
            355                 360                 365
Ala Pro Val Glu Leu Ser Glu Asn Asn Trp Thr Tyr Thr Trp Ser Gly
            370                 375                 380
Leu Asp Asn Ser Ile Glu Tyr Lys Val Glu Glu Tyr Asn Gly Tyr
385                 390                 395                 400
Ser Ala Glu Tyr Thr Val Glu Ser Lys Gly Lys Leu Gly Val Lys Asn
                405                 410                 415
Trp Lys Asp Asn Asn Pro Ala Pro Ile Asn Pro Glu Glu Pro Arg Val
            420                 425                 430
Lys Thr Tyr Gly Lys Lys Phe Val Lys Val Asp Gln Lys Asp Thr Arg
            435                 440                 445
Leu Glu Asn Ala Gln Phe Val Val Lys Ala Asp Ser Asn Lys Tyr
450                 455                 460
Ile Ala Phe Lys Ser Thr Ala Gln Gln Ala Ala Asp Glu Lys Ala Ala
465                 470                 475                 480
Ala Thr Ala Lys Gln Lys Leu Asp Ala Ala Val Ala Ala Tyr Thr Asn
                485                 490                 495
Ala Ala Asp Lys Gln Ala Ala Gln Ala Leu Val Asp Gln Ala Gln Gln
            500                 505                 510
Glu Tyr Asn Val Ala Tyr Lys Glu Ala Lys Phe Gly Tyr Val Glu Val
            515                 520                 525
Ala Gly Lys Asp Glu Ala Met Val Leu Thr Ser Asn Thr Asp Gly Gln
            530                 535                 540
Phe Gln Ile Ser Gly Leu Ala Ala Gly Thr Tyr Lys Leu Glu Glu Ile
545                 550                 555                 560
Lys Ala Pro Glu Gly Phe Ala Lys Ile Asp Asp Val Glu Phe Val Val
                565                 570                 575
Gly Ala Gly Ser Trp Asn Gln Gly Glu Phe Asn Tyr Leu Lys Asp Val
            580                 585                 590
Gln Lys Asn Asp Ala Thr Lys Val Val Asn Lys Lys Ile Thr Ile Pro
            595                 600                 605
Gln Thr Gly Gly Ile Gly Thr Ile Ile Phe Ala Val Ala Gly Ala Ala
            610                 615                 620
Ile Met Gly Ile Ala Val Tyr Ala Tyr Val Lys Asn Asn Lys Asp Glu
625                 630                 635                 640
Asp Gln Leu Ala

<210> SEQ ID NO 87
<211> LENGTH: 654
<212> TYPE: PRT
<213> ORGANISM: Streptococcus pneumoniae
<220> FEATURE:
<223> OTHER INFORMATION: RrgB sequence
```

<400> SEQUENCE: 87

```
Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Glu Gln
            20                  25                  30

Lys Thr Lys Thr Leu Thr Val His Lys Leu Leu Met Thr Asp Gln Glu
        35                  40                  45

Leu Asp Ala Trp Asn Ser Asp Ala Ile Thr Thr Ala Gly Tyr Asp Gly
    50                  55                  60

Ser Gln Asn Phe Glu Gln Phe Lys Gln Leu Gly Val Pro Gln Gly
65                  70                  75                  80

Val Thr Glu Ile Ser Gly Val Ala Phe Glu Leu Gln Ser Tyr Thr Gly
                85                  90                  95

Pro Gln Gly Lys Glu Gln Glu Asn Leu Thr Asn Asp Ala Val Trp Thr
            100                 105                 110

Ala Val Asn Lys Gly Val Thr Thr Glu Thr Gly Val Lys Phe Asp Thr
        115                 120                 125

Glu Val Leu Gln Gly Thr Tyr Arg Leu Val Glu Val Arg Lys Glu Ser
    130                 135                 140

Thr Tyr Val Gly Pro Asn Gly Lys Val Leu Thr Gly Met Lys Ala Val
145                 150                 155                 160

Pro Ala Leu Ile Ile Leu Pro Leu Val Asn Gln Asn Gly Val Val Glu
                165                 170                 175

Asn Ala His Val Tyr Pro Lys Asn Ser Glu Asp Lys Pro Thr Ala Thr
            180                 185                 190

Lys Thr Phe Asp Thr Ala Ala Gly Phe Val Asp Pro Gly Glu Lys Gly
        195                 200                 205

Leu Ala Ile Gly Thr Lys Val Pro Tyr Ile Val Thr Thr Ile Pro
    210                 215                 220

Lys Asn Ser Thr Leu Ala Thr Ala Phe Trp Ser Asp Glu Met Thr Glu
225                 230                 235                 240

Gly Leu Asp Tyr Asn Gly Asp Val Val Asn Tyr Asn Gly Gln Pro
                245                 250                 255

Leu Asp Asn Ser His Tyr Thr Leu Glu Ala Gly His Asn Gly Phe Ile
            260                 265                 270

Leu Lys Leu Asn Glu Lys Gly Leu Glu Ala Ile Asn Gly Lys Asp Ala
        275                 280                 285

Glu Ala Thr Ile Thr Leu Lys Tyr Thr Ala Thr Leu Asn Ala Leu Ala
    290                 295                 300

Val Ala Asp Val Pro Glu Ala Asn Asp Val Thr Phe His Tyr Gly Asn
305                 310                 315                 320

Asn Pro Gly His Gly Asn Thr Pro Lys Pro Asn Lys Pro Lys Asn Gly
                325                 330                 335

Glu Leu Thr Ile Thr Lys Thr Trp Ala Asp Ala Lys Asp Ala Pro Ile
            340                 345                 350

Ala Gly Val Glu Val Thr Phe Asp Leu Val Asn Ala Gln Thr Gly Glu
        355                 360                 365

Val Val Lys Val Pro Gly His Glu Thr Gly Ile Val Leu Asn Gln Thr
    370                 375                 380

Asn Asn Trp Thr Phe Thr Ala Thr Gly Leu Asp Asn Asn Thr Glu Tyr
385                 390                 395                 400

Lys Phe Val Glu Arg Thr Ile Lys Gly Tyr Ser Ala Asp Tyr Gln Thr
                405                 410                 415
```

```
Ile Thr Glu Thr Gly Lys Ile Ala Val Lys Asn Trp Lys Asp Glu Asn
                420                 425                 430

Pro Glu Pro Ile Asn Pro Glu Pro Arg Val Lys Thr Tyr Gly Lys
        435                 440                 445

Lys Phe Val Lys Val Asp Gln Lys Asp Glu Arg Leu Lys Glu Ala Gln
450                 455                 460

Phe Val Val Lys Asn Glu Gln Gly Lys Tyr Leu Ala Leu Lys Ser Ala
465                 470                 475                 480

Ala Gln Gln Ala Val Asn Glu Lys Ala Ala Glu Ala Lys Gln Ala
            485                 490                 495

Leu Asp Ala Ala Ile Ala Ala Tyr Thr Asn Ala Ala Asp Lys Asn Ala
                500                 505                 510

Ala Gln Ala Val Val Asp Ala Ala Gln Lys Thr Tyr Asn Asp Asn Tyr
            515                 520                 525

Arg Ala Ala Arg Phe Gly Tyr Val Glu Val Glu Arg Lys Glu Asp Ala
530                 535                 540

Leu Val Leu Thr Ser Asn Thr Asp Gly Gln Phe Gln Ile Ser Gly Leu
545                 550                 555                 560

Ala Ala Gly Ser Tyr Thr Leu Glu Glu Thr Lys Ala Pro Glu Gly Phe
            565                 570                 575

Ala Lys Leu Gly Asp Val Lys Phe Glu Val Gly Ala Gly Ser Trp Asn
                580                 585                 590

Gln Gly Asp Phe Asn Tyr Leu Lys Asp Val Gln Lys Asn Asp Ala Thr
            595                 600                 605

Lys Val Val Asn Lys Lys Ile Thr Ile Pro Gln Thr Gly Gly Ile Gly
        610                 615                 620

Thr Ile Ile Phe Ala Val Ala Gly Ala Val Ile Met Gly Ile Ala Val
625                 630                 635                 640

Tyr Ala Tyr Val Lys Asn Asn Lys Asp Glu Asp Gln Leu Ala
                645                 650

<210> SEQ ID NO 88
<211> LENGTH: 665
<212> TYPE: PRT
<213> ORGANISM: Streptococcus pneumoniae
<220> FEATURE:
<223> OTHER INFORMATION: RrgB sequence

<400> SEQUENCE: 88

Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Gly Thr
                20                  25                  30

Thr Thr Thr Ser Val Thr Val His Lys Leu Leu Ala Thr Asp Gly Asp
            35                  40                  45

Met Asp Lys Ile Ala Asn Glu Leu Glu Thr Gly Asn Tyr Ala Gly Asn
        50                  55                  60

Lys Val Gly Val Leu Pro Ala Asn Ala Lys Glu Ile Ala Gly Val Met
65                  70                  75                  80

Phe Val Trp Thr Asn Thr Asn Asn Glu Ile Ile Asp Glu Asn Gly Gln
                85                  90                  95

Thr Leu Gly Val Asn Ile Asp Pro Gln Thr Phe Lys Leu Ser Gly Ala
            100                 105                 110

Met Pro Thr Ala Met Lys Lys Leu Thr Glu Ala Glu Gly Ala Lys
        115                 120                 125
```

-continued

Phe Asn Thr Ala Asn Leu Pro Ala Ala Lys Tyr Lys Ile Tyr Glu Ile
130                 135                 140

His Ser Leu Ser Thr Tyr Val Gly Glu Asp Gly Ala Thr Leu Thr Gly
145                 150                 155                 160

Ser Lys Ala Val Pro Ile Glu Ile Glu Leu Pro Leu Asn Asp Val Val
            165                 170                 175

Asp Ala His Val Tyr Pro Lys Asn Thr Glu Ala Lys Pro Lys Ile Asp
            180                 185                 190

Lys Asp Phe Lys Gly Lys Ala Asn Pro Asp Thr Pro Arg Val Asp Lys
        195                 200                 205

Asp Thr Pro Val Asn His Gln Val Gly Asp Val Val Glu Tyr Glu Ile
        210                 215                 220

Val Thr Lys Ile Pro Ala Leu Ala Asn Tyr Ala Thr Ala Asn Trp Ser
225                 230                 235                 240

Asp Arg Met Thr Glu Gly Leu Ala Phe Asn Lys Gly Thr Val Lys Val
                245                 250                 255

Thr Val Asp Asp Val Ala Leu Glu Ala Gly Asp Tyr Ala Leu Thr Glu
            260                 265                 270

Val Ala Thr Gly Phe Asp Leu Lys Leu Thr Asp Ala Gly Leu Ala Lys
            275                 280                 285

Val Asn Asp Gln Asn Ala Glu Lys Thr Val Lys Ile Thr Tyr Ser Ala
290                 295                 300

Thr Leu Asn Asp Lys Ala Ile Val Glu Val Pro Glu Ser Asn Asp Val
305                 310                 315                 320

Thr Phe Asn Tyr Gly Asn Asn Pro Asp His Gly Asn Thr Pro Lys Pro
                325                 330                 335

Asn Lys Pro Asn Glu Asn Gly Asp Leu Thr Leu Thr Lys Thr Trp Val
            340                 345                 350

Asp Ala Thr Gly Ala Pro Ile Pro Ala Gly Ala Glu Ala Thr Phe Asp
            355                 360                 365

Leu Val Asn Ala Gln Thr Gly Lys Val Val Gln Thr Val Thr Leu Thr
        370                 375                 380

Thr Asp Lys Asn Thr Val Thr Val Asn Gly Leu Asp Lys Asn Thr Glu
385                 390                 395                 400

Tyr Lys Phe Val Glu Arg Ser Ile Lys Gly Tyr Ser Ala Asp Tyr Gln
                405                 410                 415

Glu Ile Thr Thr Ala Gly Glu Ile Ala Val Lys Asn Trp Lys Asp Glu
            420                 425                 430

Asn Pro Lys Pro Leu Asp Pro Thr Glu Pro Lys Val Val Thr Tyr Gly
        435                 440                 445

Lys Lys Phe Val Lys Val Asn Asp Lys Asp Asn Arg Leu Ala Gly Ala
450                 455                 460

Glu Phe Val Ile Ala Asn Ala Asp Asn Ala Gly Gln Tyr Leu Ala Arg
465                 470                 475                 480

Lys Ala Asp Lys Val Ser Gln Glu Glu Lys Gln Leu Val Val Thr Thr
                485                 490                 495

Lys Asp Ala Leu Asp Arg Ala Val Ala Ala Tyr Asn Ala Leu Thr Ala
            500                 505                 510

Gln Gln Gln Thr Gln Glu Lys Glu Lys Val Asp Lys Ala Gln Ala
        515                 520                 525

Ala Tyr Asn Ala Ala Val Ile Ala Ala Asn Ala Phe Glu Trp Val
530                 535                 540

Ala Asp Lys Asp Asn Glu Asn Val Val Lys Leu Val Ser Asp Ala Gln
545                 550                 555                 560

```
Gly Arg Phe Glu Ile Thr Gly Leu Leu Ala Gly Thr Tyr Tyr Leu Glu
                565                 570                 575

Glu Thr Lys Gln Pro Ala Gly Tyr Ala Leu Leu Thr Ser Arg Gln Lys
                580                 585                 590

Phe Glu Val Thr Ala Thr Ser Tyr Ser Ala Thr Gly Gln Gly Ile Glu
                595                 600                 605

Tyr Thr Ala Gly Ser Gly Lys Asp Asp Ala Thr Lys Val Val Asn Lys
                610                 615                 620

Lys Ile Met Ile Pro Gln Pro Gly Gly Ile Gly Thr Ile Ile Phe Ala
625                 630                 635                 640

Val Ala Gly Ala Val Ile Met Gly Ile Ala Val Tyr Ala Tyr Val Lys
                645                 650                 655

Asn Asn Lys Asp Glu Asp Gln Leu Ala
                660                 665

<210> SEQ ID NO 89
<211> LENGTH: 665
<212> TYPE: PRT
<213> ORGANISM: Streptococcus pneumoniae
<220> FEATURE:
<223> OTHER INFORMATION: RrgB sequence

<400> SEQUENCE: 89

Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Gly Thr
                20                  25                  30

Thr Thr Thr Ser Val Thr Val His Lys Leu Leu Ala Thr Asp Gly Asp
                35                  40                  45

Met Asp Lys Ile Ala Asn Glu Leu Glu Thr Gly Asn Tyr Ala Gly Asn
                50                  55                  60

Lys Val Gly Val Leu Pro Ala Asn Ala Lys Glu Ile Ala Gly Val Met
65                  70                  75                  80

Phe Val Trp Thr Asn Thr Asn Asn Glu Ile Ile Asp Glu Asn Gly Gln
                85                  90                  95

Thr Leu Gly Val Asn Ile Asp Pro Gln Thr Phe Lys Leu Ser Gly Ala
                100                 105                 110

Met Pro Ala Thr Ala Met Lys Lys Leu Thr Glu Ala Glu Gly Ala Lys
                115                 120                 125

Phe Asn Thr Ala Asn Leu Pro Ala Ala Lys Tyr Lys Ile Tyr Glu Ile
                130                 135                 140

His Ser Leu Ser Thr Tyr Val Gly Glu Asp Gly Ala Thr Leu Thr Gly
145                 150                 155                 160

Ser Lys Ala Val Pro Ile Glu Ile Glu Leu Pro Leu Asn Asp Val Val
                165                 170                 175

Asp Ala His Val Tyr Pro Lys Asn Thr Glu Ala Lys Pro Lys Ile Asp
                180                 185                 190

Lys Asp Phe Lys Gly Lys Ala Asn Pro Asp Thr Pro Arg Val Asp Lys
                195                 200                 205

Asp Thr Pro Val Asn His Gln Val Gly Asp Val Val Glu Tyr Glu Ile
                210                 215                 220

Val Thr Lys Ile Pro Ala Leu Ala Asn Tyr Ala Thr Ala Asn Trp Ser
225                 230                 235                 240

Asp Arg Met Thr Glu Gly Leu Ala Phe Asn Lys Gly Thr Val Lys Val
                245                 250                 255
```

```
Thr Val Asp Asp Val Ala Leu Glu Ala Gly Asp Tyr Ala Leu Thr Glu
            260                 265                 270

Val Ala Thr Gly Phe Asp Leu Lys Leu Thr Asp Ala Gly Leu Ala Lys
        275                 280                 285

Val Asn Asp Gln Asn Ala Glu Lys Thr Val Lys Ile Thr Tyr Ser Ala
290                 295                 300

Thr Leu Asn Asp Lys Ala Ile Val Glu Val Pro Glu Ser Asn Asp Val
305                 310                 315                 320

Thr Phe Asn Tyr Gly Asn Pro Asp His Gly Asn Thr Pro Lys Pro
            325                 330                 335

Asn Lys Pro Asn Glu Asn Gly Asp Leu Thr Leu Thr Lys Thr Trp Val
            340                 345                 350

Asp Asp Thr Gly Ala Ala Ile Pro Ala Gly Asp Glu Ala Thr Phe Asp
            355                 360                 365

Leu Val Asn Ala Gln Thr Gly Lys Val Val Gln Leu Val Thr Ser Ser
        370                 375                 380

Thr Asp Lys Asn Thr Val Thr Val Thr Gly Leu Asp Lys Asn Thr Glu
385                 390                 395                 400

Tyr Lys Phe Val Glu Arg Ser Ile Lys Gly Tyr Ser Asp Tyr Gln
            405                 410                 415

Glu Ile Thr Thr Ala Gly Glu Ile Ala Val Lys Asn Trp Lys Asp Glu
            420                 425                 430

Asn Pro Lys Pro Leu Asp Pro Thr Glu Pro Lys Val Val Thr Tyr Gly
        435                 440                 445

Lys Lys Phe Val Lys Val Asn Asp Lys Asp Asn Arg Leu Ala Gly Ala
450                 455                 460

Glu Phe Val Ile Ala Asn Ala Asp Asn Ala Gly Gln Tyr Leu Ala Arg
465                 470                 475                 480

Lys Ala Asp Lys Val Ser Gln Glu Glu Lys Gln Leu Val Val Thr Thr
            485                 490                 495

Lys Asp Ala Leu Asp Arg Ala Val Ala Ala Tyr Asn Ala Leu Thr Ala
            500                 505                 510

Gln Gln Gln Thr Gln Gln Glu Lys Glu Lys Val Asp Lys Ala Gln Ala
        515                 520                 525

Ala Tyr Asn Ala Ala Val Ile Ala Ala Asn Ala Phe Glu Trp Val
        530                 535                 540

Ala Asp Lys Asp Asn Glu Asn Val Val Lys Leu Val Ser Asp Ala Gln
545                 550                 555                 560

Gly Arg Phe Glu Ile Thr Gly Leu Leu Ala Gly Thr Tyr Tyr Leu Glu
            565                 570                 575

Glu Thr Lys Gln Pro Ala Gly Tyr Ala Leu Leu Thr Ser Arg Gln Lys
            580                 585                 590

Phe Glu Val Thr Ala Thr Ser Tyr Ser Ala Thr Gly Gln Gly Ile Glu
        595                 600                 605

Tyr Thr Ala Gly Ser Gly Lys Asp Asp Ala Thr Lys Val Val Asn Lys
        610                 615                 620

Lys Ile Thr Ile Pro Gln Thr Gly Gly Ile Gly Thr Ile Ile Phe Ala
625                 630                 635                 640

Val Ala Gly Ala Val Ile Met Gly Ile Ala Val Tyr Ala Tyr Val Lys
            645                 650                 655

Asn Asn Lys Asp Glu Asp His Leu Ala
            660                 665

<210> SEQ ID NO 90
```

<211> LENGTH: 644
<212> TYPE: PRT
<213> ORGANISM: Streptococcus pneumoniae
<220> FEATURE:
<223> OTHER INFORMATION: RrgB sequence

<400> SEQUENCE: 90

Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Asp Asn
            20                  25                  30

Val Ser Thr Ala Pro Asp Ala Val Thr Lys Thr Leu Thr Ile His Lys
        35                  40                  45

Leu Leu Leu Ser Glu Asp Asp Leu Lys Thr Trp Asp Thr Asn Gly Pro
    50                  55                  60

Lys Gly Tyr Asp Gly Thr Gln Ser Ser Leu Lys Asp Leu Thr Gly Val
65                  70                  75                  80

Val Ala Glu Glu Ile Pro Asn Val Tyr Phe Glu Leu Gln Lys Tyr Asn
                85                  90                  95

Leu Thr Asp Gly Lys Glu Lys Glu Asn Leu Lys Asp Asp Ser Lys Trp
            100                 105                 110

Thr Thr Val His Gly Gly Leu Thr Thr Lys Asp Gly Leu Lys Ile Glu
        115                 120                 125

Thr Ser Thr Leu Lys Gly Val Tyr Arg Ile Arg Glu Asp Arg Thr Lys
    130                 135                 140

Thr Tyr Val Gly Pro Asn Gly Gln Val Leu Thr Gly Ser Lys Ala
145                 150                 155                 160

Val Pro Ala Leu Val Thr Leu Pro Leu Val Asn Asn Asn Gly Thr Val
                165                 170                 175

Ile Asp Ala His Val Phe Pro Lys Asn Ser Tyr Asn Lys Pro Val Val
            180                 185                 190

Asp Lys Arg Ile Ala Asp Thr Leu Asn Tyr Asn Asp Gln Asn Gly Leu
        195                 200                 205

Ser Ile Gly Thr Lys Ile Pro Tyr Val Val Asn Thr Thr Ile Pro Ser
    210                 215                 220

Asn Ala Thr Phe Ala Thr Ser Phe Trp Ser Asp Glu Met Thr Glu Gly
225                 230                 235                 240

Leu Thr Tyr Asn Glu Asp Val Thr Ile Thr Leu Asn Asn Val Ala Met
                245                 250                 255

Asp Gln Ala Asp Tyr Glu Val Thr Lys Gly Ile Asn Gly Phe Asn Leu
            260                 265                 270

Lys Leu Thr Glu Ala Gly Leu Ala Lys Ile Asn Gly Lys Asp Ala Asp
        275                 280                 285

Gln Lys Ile Gln Ile Thr Tyr Ser Ala Thr Leu Asn Ser Leu Ala Val
    290                 295                 300

Ala Asp Ile Pro Glu Ser Asn Asp Ile Thr Tyr His Tyr Gly Asn His
305                 310                 315                 320

Gln Asp His Gly Asn Thr Pro Lys Pro Thr Lys Pro Asn Asn Gly Gln
                325                 330                 335

Ile Thr Val Thr Lys Thr Trp Asp Ser Gln Pro Ala Pro Glu Gly Val
            340                 345                 350

Lys Ala Thr Val Gln Leu Val Asn Ala Lys Thr Gly Glu Lys Val Gly
        355                 360                 365

Ala Pro Val Glu Leu Ser Glu Asn Asn Trp Thr Tyr Thr Trp Ser Gly
    370                 375                 380

-continued

Leu Asp Asn Ser Ile Glu Tyr Lys Val Glu Glu Tyr Asn Gly Tyr
385                 390                 395                 400

Ser Ala Glu Tyr Thr Val Glu Ser Lys Gly Lys Leu Gly Val Lys Asn
                405                 410                 415

Trp Lys Asp Asn Asn Pro Ala Pro Ile Asn Leu Glu Glu Pro Arg Val
            420                 425                 430

Lys Thr Tyr Gly Lys Lys Phe Val Lys Val Asp Gln Lys Asp Thr Arg
        435                 440                 445

Leu Glu Asn Ala Gln Phe Val Val Lys Ala Asp Ser Asn Lys Tyr
    450                 455                 460

Ile Ala Phe Lys Ser Thr Ala Gln Gln Ala Ala Asp Glu Lys Ala Ala
465                 470                 475                 480

Ala Thr Ala Lys Gln Lys Leu Asp Ala Ala Val Ala Ala Tyr Thr Asn
                485                 490                 495

Ala Ala Asp Lys Gln Ala Ala Gln Ala Leu Val Asp Gln Ala Gln Gln
            500                 505                 510

Glu Tyr Asn Val Ala Tyr Lys Glu Ala Lys Phe Gly Tyr Val Glu Val
        515                 520                 525

Ala Gly Lys Asp Glu Ala Met Val Leu Thr Ser Asn Thr Asp Gly Gln
530                 535                 540

Phe Gln Ile Ser Gly Leu Ala Ala Gly Thr Tyr Lys Leu Glu Glu Ile
545                 550                 555                 560

Lys Ala Pro Glu Gly Phe Ala Lys Ile Asp Asp Val Glu Phe Val Val
                565                 570                 575

Gly Ala Gly Ser Trp Asn Gln Gly Glu Phe Asn Tyr Leu Lys Asp Val
            580                 585                 590

Gln Lys Asn Asp Ala Thr Lys Val Val Asn Lys Lys Ile Thr Ile Pro
        595                 600                 605

Gln Thr Gly Gly Ile Gly Thr Ile Ile Phe Ala Val Ala Gly Ala Val
    610                 615                 620

Ile Met Gly Ile Ala Val Tyr Ala Tyr Val Lys Asn Asn Lys Asp Glu
625                 630                 635                 640

Asp Gln Leu Ala

<210> SEQ ID NO 91
<211> LENGTH: 644
<212> TYPE: PRT
<213> ORGANISM: Streptococcus pneumoniae
<220> FEATURE:
<223> OTHER INFORMATION: RrgB sequence

<400> SEQUENCE: 91

Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Asp Asn
                20                  25                  30

Val Ser Thr Ala Pro Asp Ala Val Thr Lys Thr Leu Thr Ile His Lys
            35                  40                  45

Leu Leu Leu Ser Glu Asp Leu Lys Thr Trp Asp Thr Asn Gly Pro
    50                  55                  60

Lys Gly Tyr Asp Gly Thr Gln Ser Ser Leu Lys Asp Leu Thr Gly Val
65                  70                  75                  80

Val Ala Glu Glu Ile Pro Asn Val Tyr Phe Glu Leu Gln Lys Tyr Asn
                85                  90                  95

Leu Thr Asp Gly Lys Glu Lys Glu Asn Leu Lys Asp Asp Ser Lys Trp
            100                 105                 110

```
Thr Thr Val His Gly Gly Leu Thr Thr Lys Asp Gly Leu Lys Ile Glu
        115                 120                 125

Thr Ser Thr Leu Lys Gly Val Tyr Arg Ile Arg Glu Asp Arg Thr Lys
130                 135                 140

Thr Thr Tyr Val Gly Pro Asn Gly Gln Val Leu Thr Gly Ser Lys Ala
145                 150                 155                 160

Val Pro Ala Leu Val Thr Leu Pro Leu Val Asn Asn Asn Gly Thr Val
                165                 170                 175

Ile Asp Ala His Val Phe Pro Lys Asn Ser Tyr Asn Lys Pro Val Val
            180                 185                 190

Asp Lys Arg Ile Ala Asp Thr Leu Asn Tyr Asn Asp Gln Asn Gly Leu
        195                 200                 205

Ser Ile Gly Thr Lys Ile Pro Tyr Val Val Asn Thr Thr Ile Pro Ser
    210                 215                 220

Asn Ala Thr Phe Ala Thr Ser Phe Trp Ser Asp Glu Met Thr Glu Gly
225                 230                 235                 240

Leu Thr Tyr Asn Glu Asp Val Thr Ile Thr Leu Asn Asn Val Ala Met
                245                 250                 255

Asp Gln Ala Asp Tyr Glu Val Thr Lys Gly Asn Asn Gly Phe Asn Leu
            260                 265                 270

Lys Leu Thr Glu Ala Gly Leu Ala Lys Ile Asn Gly Lys Asp Ala Asp
        275                 280                 285

Gln Lys Ile Gln Ile Thr Tyr Ser Ala Thr Leu Asn Ser Leu Ala Val
    290                 295                 300

Ala Asp Ile Pro Glu Ser Asn Asp Ile Thr Tyr His Tyr Gly Asn His
305                 310                 315                 320

Gln Asp His Gly Asn Thr Pro Lys Pro Thr Lys Pro Asn Asn Gly Gln
                325                 330                 335

Ile Thr Val Thr Lys Thr Trp Asp Ser Gln Pro Ala Pro Glu Gly Val
            340                 345                 350

Lys Ala Thr Val Gln Leu Val Asn Ala Lys Thr Gly Glu Lys Val Gly
        355                 360                 365

Ala Pro Val Glu Leu Ser Glu Asn Asn Trp Thr Tyr Thr Trp Ser Gly
    370                 375                 380

Leu Asp Asn Ser Ile Glu Tyr Lys Val Glu Glu Glu Tyr Asn Gly Tyr
385                 390                 395                 400

Ser Ala Glu Tyr Thr Val Glu Ser Lys Gly Lys Leu Gly Val Lys Asn
                405                 410                 415

Trp Lys Asp Asn Asn Pro Ala Pro Ile Asn Pro Glu Glu Pro Arg Val
            420                 425                 430

Lys Thr Tyr Gly Lys Lys Phe Val Lys Val Asp Gln Lys Asp Thr Arg
        435                 440                 445

Leu Glu Asn Ala Gln Phe Val Val Lys Lys Ala Asp Ser Asn Lys Tyr
    450                 455                 460

Ile Ala Phe Lys Ser Thr Ala Gln Gln Ala Ala Asp Glu Lys Ala Ala
465                 470                 475                 480

Ala Thr Ala Lys Gln Lys Leu Asp Ala Val Ala Ala Tyr Thr Asn
                485                 490                 495

Ala Ala Asp Lys Gln Asp Ala Gln Ala Leu Val Asp Gln Ala Gln Gln
            500                 505                 510

Glu Tyr Asn Val Ala Tyr Lys Glu Ala Lys Phe Gly Tyr Val Glu Val
        515                 520                 525

Ala Gly Lys Asp Glu Ala Met Val Leu Thr Ser Asn Thr Asp Gly Gln
```

-continued

```
                530                 535                 540
Phe Gln Ile Ser Gly Leu Ala Ala Gly Thr Tyr Lys Leu Glu Glu Ile
545                 550                 555                 560

Lys Ala Pro Glu Gly Phe Ala Lys Ile Asp Asp Val Glu Phe Val Val
                565                 570                 575

Gly Ala Gly Ser Trp Asn Gln Gly Glu Phe Asn Tyr Leu Lys Asp Val
                580                 585                 590

Gln Lys Asn Asp Ala Thr Lys Val Val Asn Lys Ile Thr Ile Pro
            595                 600                 605

Gln Thr Gly Gly Ile Gly Thr Ile Ile Phe Ala Val Ala Gly Ala Ala
            610                 615                 620

Ile Met Gly Ile Ala Val Tyr Ala Tyr Val Lys Asn Asn Lys Asp Glu
625                 630                 635                 640

Asp Gln Leu Ala

<210> SEQ ID NO 92
<211> LENGTH: 654
<212> TYPE: PRT
<213> ORGANISM: Streptococcus pneumoniae
<220> FEATURE:
<223> OTHER INFORMATION: RrgB sequence

<400> SEQUENCE: 92

Met Lys Ser Ile Asn Lys Phe Leu Thr Ile Leu Ala Ala Leu Leu Leu
1               5                   10                  15

Thr Val Ser Ser Leu Phe Ser Ala Ala Thr Val Phe Ala Ala Glu Gln
                20                  25                  30

Lys Thr Lys Thr Leu Thr Val His Lys Leu Leu Met Thr Asp Gln Glu
            35                  40                  45

Leu Asp Ala Trp Asn Ser Asp Ala Ile Thr Thr Ala Gly Tyr Asp Gly
        50                  55                  60

Ser Gln Asn Phe Glu Gln Phe Lys Gln Leu Gln Gly Val Pro Gln Gly
65                  70                  75                  80

Val Thr Glu Ile Ser Gly Val Ala Phe Glu Leu Gln Ser Tyr Thr Gly
                85                  90                  95

Pro Gln Gly Lys Glu Gln Glu Asn Leu Thr Asn Asp Ala Val Trp Thr
                100                 105                 110

Ala Val Asn Lys Gly Val Thr Thr Glu Thr Gly Val Lys Phe Asp Thr
            115                 120                 125

Glu Val Leu Gln Gly Thr Tyr Arg Leu Val Glu Val Arg Lys Glu Ser
        130                 135                 140

Thr Tyr Val Gly Pro Asn Gly Lys Val Leu Thr Gly Met Lys Ala Val
145                 150                 155                 160

Pro Ala Leu Ile Ile Leu Pro Leu Val Asn Gln Asn Gly Val Val Glu
                165                 170                 175

Asn Ala His Val Tyr Pro Lys Asn Ser Glu Asp Lys Pro Thr Ala Thr
            180                 185                 190

Lys Thr Phe Asp Thr Ala Ala Gly Phe Val Asp Pro Gly Glu Lys Gly
        195                 200                 205

Leu Ala Ile Gly Thr Lys Val Pro Tyr Ile Val Thr Thr Thr Ile Pro
    210                 215                 220

Lys Asn Ser Thr Leu Ala Thr Ala Phe Trp Ser Asp Glu Met Thr Glu
225                 230                 235                 240

Gly Leu Asp Tyr Asn Gly Asp Val Val Val Asn Tyr Asn Gly Gln Pro
                245                 250                 255
```

-continued

Leu Asp Asn Ser His Tyr Thr Leu Glu Ala Gly His Asn Gly Phe Ile
            260                 265                 270

Leu Lys Leu Asn Glu Lys Gly Leu Glu Ala Ile Asn Gly Lys Asp Ala
        275                 280                 285

Glu Ala Thr Ile Ala Leu Lys Tyr Thr Ala Thr Leu Asn Ala Leu Ala
    290                 295                 300

Val Ala Asp Val Pro Glu Ala Asn Asp Val Thr Phe His Tyr Gly Asn
305                 310                 315                 320

Asn Pro Gly His Gly Asn Thr Pro Lys Pro Asn Lys Pro Lys Asn Gly
                325                 330                 335

Glu Leu Thr Ile Thr Lys Thr Trp Ala Asp Ala Lys Asp Ala Pro Ile
            340                 345                 350

Ala Gly Val Glu Val Thr Phe Asp Leu Val Asn Ala Gln Thr Gly Glu
        355                 360                 365

Val Val Lys Val Pro Gly His Glu Thr Gly Ile Val Leu Asn Gln Thr
    370                 375                 380

Asn Asn Trp Thr Phe Thr Ala Thr Gly Leu Asp Asn Asn Thr Glu Tyr
385                 390                 395                 400

Lys Phe Val Glu Arg Thr Ile Lys Gly Tyr Ser Ala Asp Tyr Gln Thr
                405                 410                 415

Ile Thr Glu Thr Gly Lys Ile Ala Val Lys Asn Trp Lys Asp Glu Asn
            420                 425                 430

Pro Glu Pro Ile Asn Pro Glu Glu Pro Arg Val Lys Thr Tyr Gly Lys
        435                 440                 445

Lys Phe Val Lys Val Asp Gln Lys Asp Glu Arg Leu Lys Glu Ala Gln
    450                 455                 460

Phe Val Val Lys Asn Glu Gln Gly Lys Tyr Leu Ala Leu Lys Ser Ala
465                 470                 475                 480

Ala Gln Gln Ala Val Asn Glu Lys Ala Ala Glu Ala Lys Gln Ala
                485                 490                 495

Leu Asp Ala Ala Ile Ala Ala Tyr Thr Asn Ala Ala Asp Lys Asn Ala
            500                 505                 510

Ala Gln Ala Val Val Asp Ala Ala Gln Lys Thr Tyr Asn Asp Asn Tyr
        515                 520                 525

Arg Ala Ala Arg Phe Gly Tyr Val Glu Val Glu Arg Lys Glu Asp Ala
    530                 535                 540

Leu Val Leu Thr Ser Asn Thr Asp Gly Gln Phe Gln Ile Ser Gly Leu
545                 550                 555                 560

Ala Ala Gly Ser Tyr Thr Leu Glu Glu Thr Lys Ala Pro Glu Gly Phe
                565                 570                 575

Ala Lys Leu Gly Asp Val Lys Phe Glu Val Gly Ala Gly Ser Trp Asn
            580                 585                 590

Gln Gly Asp Phe Asn Tyr Leu Lys Asp Val Gln Lys Asn Asp Ala Thr
        595                 600                 605

Lys Val Val Asn Lys Lys Ile Thr Ile Pro Gln Thr Gly Gly Ile Gly
    610                 615                 620

Thr Ile Ile Phe Ala Val Ala Gly Ala Val Ile Met Gly Ile Ala Val
625                 630                 635                 640

Tyr Ala Tyr Val Lys Asn Asn Lys Asp Glu Asp Gln Leu Ala
                645                 650

<210> SEQ ID NO 93
<211> LENGTH: 654
<212> TYPE: PRT
<213> ORGANISM: Streptococcus pneumoniae

```
<220> FEATURE:
<223> OTHER INFORMATION: RrgB sequence

<400> SEQUENCE: 93

Met Lys Ser Ile Asn Lys Phe Leu Thr Ile Leu Ala Ala Leu Leu Leu
1               5                   10                  15

Thr Val Ser Ser Leu Phe Ser Ala Ala Thr Val Phe Ala Ala Glu Gln
            20                  25                  30

Lys Thr Lys Thr Leu Thr Val His Lys Leu Leu Met Thr Asp Gln Glu
        35                  40                  45

Leu Asp Ala Trp Asn Ser Asp Ala Ile Thr Thr Ala Gly Tyr Asp Gly
    50                  55                  60

Ser Gln Asn Phe Glu Gln Phe Lys Gln Leu Gln Gly Val Pro Gln Gly
65                  70                  75                  80

Val Thr Glu Ile Ser Gly Val Ala Phe Glu Leu Gln Ser Tyr Thr Gly
                85                  90                  95

Pro Gln Gly Lys Glu Gln Glu Asn Leu Thr Asn Asp Ala Val Trp Thr
            100                 105                 110

Ala Val Asn Lys Gly Val Thr Thr Glu Thr Gly Val Lys Phe Asp Thr
        115                 120                 125

Glu Val Leu Gln Gly Thr Tyr Arg Leu Val Glu Val Arg Lys Glu Ser
130                 135                 140

Thr Tyr Val Gly Pro Asn Gly Lys Val Leu Thr Gly Met Lys Ala Val
145                 150                 155                 160

Pro Ala Leu Ile Ile Leu Pro Leu Val Asn Gln Asn Gly Val Val Glu
                165                 170                 175

Asn Ala His Val Tyr Pro Lys Asn Ser Glu Asp Lys Pro Thr Ala Thr
            180                 185                 190

Lys Thr Phe Asp Thr Ala Ala Gly Phe Val Asp Pro Gly Glu Lys Gly
        195                 200                 205

Leu Ala Ile Gly Thr Lys Val Pro Tyr Ile Val Thr Thr Thr Ile Pro
210                 215                 220

Lys Asn Ser Thr Leu Ala Thr Ala Phe Trp Ser Asp Glu Met Thr Glu
225                 230                 235                 240

Gly Leu Asp Tyr Asn Gly Asp Val Val Asn Tyr Asn Gly Gln Pro
                245                 250                 255

Leu Asp Asn Ser His Tyr Thr Leu Lys Ala Gly His Asn Gly Phe Ile
            260                 265                 270

Leu Lys Leu Asn Glu Lys Gly Leu Glu Ala Ile Asn Gly Lys Asp Ala
        275                 280                 285

Glu Ala Thr Ile Thr Leu Lys Tyr Thr Ala Thr Leu Asn Ala Leu Ala
290                 295                 300

Val Ala Asp Val Pro Lys Ala Asn Asp Val Thr Phe His Tyr Gly Asn
305                 310                 315                 320

Asn Pro Gly His Gly Asn Thr Pro Lys Pro Asn Lys Pro Lys Asn Gly
                325                 330                 335

Glu Leu Thr Ile Thr Lys Thr Trp Ala Asp Ala Lys Asp Ala Pro Ile
            340                 345                 350

Ala Gly Val Glu Val Thr Phe Asp Leu Val Asn Ala Gln Thr Gly Glu
        355                 360                 365

Val Val Lys Val Pro Gly His Glu Thr Gly Ile Val Leu Asn Gln Thr
370                 375                 380

Asn Asn Trp Thr Phe Thr Ala Thr Gly Leu Asp Asn Asn Thr Glu Tyr
385                 390                 395                 400
```

```
Lys Phe Val Glu Arg Thr Ile Lys Gly Tyr Ser Ala Asp Tyr Gln Thr
                405                 410                 415

Ile Thr Glu Thr Gly Lys Ile Ala Val Lys Asn Trp Lys Asp Glu Asn
            420                 425                 430

Pro Glu Pro Ile Asn Pro Glu Glu Pro Arg Val Lys Thr Tyr Gly Lys
        435                 440                 445

Lys Phe Val Lys Val Asp Gln Lys Asp Glu Arg Leu Lys Glu Ala Gln
450                 455                 460

Phe Val Val Lys Asn Glu Gln Gly Lys Tyr Leu Ala Leu Lys Ser Ala
465                 470                 475                 480

Ala Gln Gln Ala Val Asn Glu Lys Ala Ala Glu Ala Lys Gln Ala
                485                 490                 495

Leu Asp Ala Ala Ile Ala Ala Tyr Thr Asn Ala Asp Lys Asn Ala
            500                 505                 510

Ala Gln Ala Val Val Asp Ala Gln Lys Thr Tyr Asn Asp Asn Tyr
        515                 520                 525

Arg Ala Ala Arg Phe Gly Tyr Val Glu Val Glu Arg Lys Glu Asp Ala
    530                 535                 540

Leu Val Leu Thr Ser Asn Thr Asp Gly Gln Phe Gln Ile Ser Gly Leu
545                 550                 555                 560

Ala Ala Gly Ser Tyr Thr Leu Glu Glu Thr Lys Ala Pro Glu Gly Phe
                565                 570                 575

Ala Lys Leu Gly Asp Val Lys Phe Glu Val Gly Ala Gly Ser Trp Asn
            580                 585                 590

Gln Gly Asp Phe Asn Tyr Leu Lys Asp Val Gln Lys Asn Asp Ala Thr
        595                 600                 605

Lys Val Val Asn Lys Lys Ile Thr Ile Pro Gln Thr Gly Gly Ile Gly
610                 615                 620

Thr Ile Ile Phe Ala Val Ala Gly Ala Val Ile Met Gly Ile Ala Val
625                 630                 635                 640

Tyr Ala Tyr Val Lys Asn Asn Lys Asp Glu Asp Gln Leu Ala
                645                 650

<210> SEQ ID NO 94
<211> LENGTH: 644
<212> TYPE: PRT
<213> ORGANISM: Streptococcus pneumoniae
<220> FEATURE:
<223> OTHER INFORMATION: RrgB sequence

<400> SEQUENCE: 94

Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Asp Asn
                20                  25                  30

Val Ser Thr Ala Pro Asp Ala Val Thr Lys Thr Leu Thr Ile His Lys
            35                  40                  45

Leu Leu Leu Ser Glu Asp Asp Leu Glu Thr Trp Asp Thr Asn Gly Pro
        50                  55                  60

Lys Gly Tyr Asp Gly Thr Gln Ser Ser Leu Lys Asp Leu Thr Gly Val
65                  70                  75                  80

Val Ala Glu Glu Ile Pro Asn Val Tyr Phe Glu Leu Gln Lys Tyr Asn
                85                  90                  95

Leu Thr Asp Gly Lys Glu Lys Glu Asn Leu Lys Asp Asp Ser Lys Trp
            100                 105                 110

Thr Thr Val His Gly Gly Leu Thr Thr Lys Asp Gly Leu Lys Ile Glu
```

```
            115                 120                 125
Thr Ser Thr Leu Lys Gly Val Tyr Arg Ile Arg Glu Asp Arg Thr Lys
        130                 135                 140
Thr Thr Tyr Val Gly Pro Asn Gly Gln Val Leu Thr Gly Ser Lys Ala
145                 150                 155                 160
Val Pro Ala Leu Val Thr Leu Pro Leu Val Asn Asn Gly Thr Val
                165                 170                 175
Ile Asp Ala His Val Phe Pro Lys Asn Ser Tyr Asn Lys Pro Val Val
            180                 185                 190
Asp Lys Arg Ile Ala Asp Thr Leu Asn Tyr Asn Asp Gln Asn Gly Leu
        195                 200                 205
Ser Ile Gly Thr Lys Ile Pro Tyr Val Val Asn Thr Thr Ile Pro Ser
    210                 215                 220
Asn Ala Thr Phe Ala Thr Ser Phe Trp Ser Asp Glu Met Thr Glu Gly
225                 230                 235                 240
Leu Thr Tyr Asn Glu Asp Val Thr Ile Thr Leu Asn Asn Val Ala Met
                245                 250                 255
Asp Gln Ala Asp Tyr Glu Val Thr Lys Gly Ile Asn Gly Phe Asn Leu
            260                 265                 270
Lys Leu Thr Glu Ala Gly Leu Ala Lys Ile Asn Gly Lys Asp Ala Asp
        275                 280                 285
Gln Lys Ile Gln Ile Thr Tyr Ser Ala Thr Leu Asn Ser Leu Ala Val
    290                 295                 300
Ala Asp Ile Pro Glu Ser Asn Asp Ile Thr Tyr His Tyr Gly Asn His
305                 310                 315                 320
Gln Asp His Gly Asn Thr Pro Lys Pro Thr Lys Pro Asn Asn Gly Gln
                325                 330                 335
Ile Thr Val Thr Lys Thr Trp Asp Ser Gln Pro Ala Pro Glu Gly Val
            340                 345                 350
Lys Ala Thr Val Gln Leu Val Asn Ala Lys Thr Gly Glu Lys Val Cys
        355                 360                 365
Ala Pro Val Glu Leu Ser Glu Asn Asn Trp Thr Tyr Thr Trp Ser Gly
    370                 375                 380
Leu Asp Asn Ser Ile Glu Tyr Lys Val Glu Glu Tyr Asn Gly Tyr
385                 390                 395                 400
Ser Ala Glu Tyr Thr Val Glu Ser Lys Gly Lys Leu Gly Val Lys Asn
                405                 410                 415
Trp Lys Asp Asn Asn Pro Ala Pro Ile Asn Pro Glu Glu Pro Arg Val
            420                 425                 430
Lys Thr Tyr Gly Lys Lys Phe Val Lys Val Asp Gln Lys Asp Thr Arg
        435                 440                 445
Leu Glu Asn Ala Gln Phe Val Val Lys Lys Ala Asp Ser Asn Lys Tyr
    450                 455                 460
Ile Ala Phe Lys Ser Thr Ala Gln Gln Ala Ala Asp Glu Lys Ala Ala
465                 470                 475                 480
Ala Thr Ala Lys Gln Lys Leu Asp Ala Ala Val Ala Ala Tyr Thr Asn
                485                 490                 495
Ala Ala Asp Lys Gln Ala Ala Gln Ala Leu Val Asp Gln Ala Gln Gln
            500                 505                 510
Glu Tyr Asn Val Ala Tyr Lys Glu Ala Lys Phe Gly Tyr Val Glu Val
        515                 520                 525
Ala Gly Lys Asp Glu Ala Met Val Leu Thr Ser Asn Thr Asp Gly Gln
    530                 535                 540
```

```
Phe Gln Ile Ser Gly Leu Ala Ala Gly Thr Tyr Lys Leu Glu Glu Ile
545                 550                 555                 560

Lys Ala Pro Glu Gly Phe Ala Lys Ile Asp Asp Val Glu Phe Val Val
                565                 570                 575

Gly Ala Gly Ser Trp Asn Gln Gly Glu Phe Asn Tyr Leu Lys Asp Val
            580                 585                 590

Gln Lys Asn Asp Ala Thr Lys Val Val Asn Lys Lys Ile Thr Ile Pro
        595                 600                 605

Gln Thr Gly Gly Ile Gly Thr Ile Ile Phe Ala Val Ala Gly Ala Ala
    610                 615                 620

Ile Met Gly Ile Ala Val Tyr Ala Tyr Val Lys Asn Asn Lys Asp Glu
625                 630                 635                 640

Asp Gln Leu Ala

<210> SEQ ID NO 95
<211> LENGTH: 654
<212> TYPE: PRT
<213> ORGANISM: Streptococcus pneumoniae
<220> FEATURE:
<223> OTHER INFORMATION: RrgB sequence

<400> SEQUENCE: 95

Met Lys Ser Ile Asn Lys Phe Leu Thr Ile Leu Ala Ala Leu Leu Leu
1               5                   10                  15

Thr Val Ser Ser Leu Phe Ser Ala Ala Thr Val Phe Ala Ala Glu Gln
            20                  25                  30

Lys Thr Lys Thr Leu Thr Val His Lys Leu Leu Met Thr Asp Gln Glu
        35                  40                  45

Leu Asp Ala Trp Asn Ser Asp Ala Ile Thr Thr Ala Gly Tyr Asp Gly
    50                  55                  60

Ser Gln Asn Phe Glu Gln Phe Lys Gln Leu Gln Gly Val Pro Gln Gly
65                  70                  75                  80

Val Thr Glu Ile Ser Gly Val Ala Phe Glu Leu Gln Ser Tyr Thr Gly
                85                  90                  95

Pro Gln Gly Lys Glu Gln Glu Asn Leu Thr Asn Asp Ala Val Trp Thr
            100                 105                 110

Ala Val Asn Lys Gly Val Thr Thr Glu Thr Gly Val Lys Phe Asp Thr
        115                 120                 125

Glu Val Leu Gln Gly Thr Tyr Arg Leu Val Glu Val Arg Lys Glu Ser
    130                 135                 140

Thr Tyr Val Gly Pro Asn Gly Lys Val Leu Thr Gly Met Lys Ala Val
145                 150                 155                 160

Pro Ala Leu Ile Thr Leu Pro Leu Val Asn Gln Asn Gly Val Val Glu
                165                 170                 175

Asn Ala His Val Tyr Pro Lys Asn Ser Glu Asp Lys Pro Thr Ala Thr
            180                 185                 190

Lys Thr Phe Asp Thr Ala Ala Gly Phe Val Asp Pro Gly Glu Lys Gly
        195                 200                 205

Leu Ala Ile Gly Thr Lys Val Pro Tyr Ile Val Thr Thr Thr Ile Pro
    210                 215                 220

Lys Asn Ser Thr Leu Ala Thr Ala Phe Trp Ser Asp Glu Met Thr Glu
225                 230                 235                 240

Gly Leu Asp Tyr Asn Gly Asp Val Val Asn Tyr Asn Gly Gln Pro
                245                 250                 255

Leu Asp Asn Ser His Tyr Thr Leu Glu Ala Gly His Asn Gly Phe Ile
            260                 265                 270
```

```
Leu Lys Leu Asn Glu Lys Gly Leu Glu Ala Ile Asn Gly Lys Asp Ala
        275                 280                 285

Lys Ala Thr Ile Thr Leu Lys Tyr Thr Ala Thr Leu Asn Ala Leu Ala
        290                 295                 300

Val Ala Asp Val Pro Glu Ala Asn Asp Val Thr Phe His Tyr Gly Asn
305                 310                 315                 320

Asn Pro Gly His Gly Asn Thr Pro Lys Pro Asn Lys Pro Lys Asn Gly
                325                 330                 335

Glu Leu Thr Ile Thr Lys Thr Trp Ala Asp Ala Lys Asp Ala Pro Ile
        340                 345                 350

Ala Gly Val Glu Val Thr Phe Asp Leu Val Asn Ala Gln Thr Gly Glu
        355                 360                 365

Val Val Lys Val Pro Gly His Glu Thr Gly Ile Val Leu Asn Gln Thr
        370                 375                 380

Asn Asn Trp Thr Phe Thr Ala Thr Gly Leu Asp Asn Asn Thr Glu Tyr
385                 390                 395                 400

Lys Phe Val Glu Arg Thr Ile Lys Gly Tyr Ser Ala Asp Tyr Gln Thr
                405                 410                 415

Ile Thr Glu Thr Gly Lys Ile Ala Val Lys Asn Trp Lys Asp Glu Asn
        420                 425                 430

Pro Glu Pro Ile Asn Pro Glu Glu Pro Arg Val Lys Thr Tyr Gly Lys
        435                 440                 445

Lys Phe Val Lys Val Asp Gln Lys Asp Glu Arg Leu Lys Glu Ala Gln
450                 455                 460

Phe Val Val Lys Asn Glu Gln Gly Lys Tyr Leu Ala Leu Lys Ser Ala
465                 470                 475                 480

Ala Gln Gln Ala Val Asn Glu Lys Ala Ala Glu Ala Lys Gln Ala
        485                 490                 495

Leu Asp Ala Ala Ile Ala Ala Tyr Thr Asn Ala Asp Lys Asn Ala
        500                 505                 510

Ala Gln Ala Val Val Asp Ala Ala Gln Lys Thr Tyr Asn Asp Asn Tyr
        515                 520                 525

Arg Ala Ala Arg Phe Gly Tyr Val Glu Val Glu Arg Lys Glu Asp Ala
530                 535                 540

Leu Val Leu Thr Ser Asn Thr Asp Gly Gln Phe Gln Ile Ser Gly Leu
545                 550                 555                 560

Ala Ala Gly Ser Tyr Thr Leu Glu Glu Thr Lys Ala Pro Glu Gly Phe
                565                 570                 575

Ala Lys Leu Gly Asp Val Lys Phe Glu Val Gly Ala Gly Ser Trp Asn
                580                 585                 590

Gln Gly Asp Phe Asn Tyr Leu Lys Asp Val Gln Lys Asn Asp Ala Thr
                595                 600                 605

Lys Val Val Asn Lys Lys Ile Thr Ile Pro Gln Thr Gly Gly Ile Gly
        610                 615                 620

Thr Ile Ile Phe Ala Val Ala Gly Ala Val Ile Met Gly Ile Ala Val
625                 630                 635                 640

Tyr Ala Tyr Val Lys Asn Asn Lys Asp Glu Asp Gln Leu Ala
                645                 650

<210> SEQ ID NO 96
<211> LENGTH: 644
<212> TYPE: PRT
<213> ORGANISM: Streptococcus pneumoniae
<220> FEATURE:
<223> OTHER INFORMATION: RrgB sequence
```

<400> SEQUENCE: 96

```
Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Asp Asn
            20                  25                  30

Val Ser Thr Ala Pro Asp Ala Val Thr Lys Thr Leu Thr Ile His Lys
        35                  40                  45

Leu Leu Leu Ser Glu Asp Leu Lys Thr Trp Asp Thr Asn Gly Pro
    50                  55                  60

Lys Gly Tyr Asp Gly Thr Gln Ser Ser Leu Lys Asp Leu Thr Gly Val
65                  70                  75                  80

Val Ala Glu Glu Ile Pro Asn Val Tyr Phe Glu Leu Gln Lys Tyr Asn
                85                  90                  95

Leu Thr Asp Gly Lys Glu Lys Glu Asn Leu Lys Asp Asp Ser Lys Trp
            100                 105                 110

Thr Thr Val His Gly Gly Leu Thr Thr Lys Asp Gly Leu Lys Ile Glu
        115                 120                 125

Thr Ser Thr Leu Lys Gly Val Tyr Arg Ile Arg Glu Asp Arg Thr Lys
    130                 135                 140

Thr Thr Tyr Val Gly Pro Asn Gly Gln Val Leu Thr Gly Ser Lys Ala
145                 150                 155                 160

Val Pro Ala Leu Val Thr Leu Pro Leu Val Asn Asn Asn Gly Thr Val
                165                 170                 175

Ile Asp Ala His Val Phe Pro Lys Asn Ser Tyr Asn Lys Pro Val Val
            180                 185                 190

Asp Lys Arg Ile Ala Asp Thr Leu Asn Tyr Asn Asp Gln Asn Gly Leu
        195                 200                 205

Ser Ile Gly Thr Lys Ile Pro Tyr Val Val Asn Thr Thr Ile Pro Ser
    210                 215                 220

Asn Ala Thr Phe Ala Thr Ser Phe Trp Ser Asp Glu Met Thr Glu Gly
225                 230                 235                 240

Leu Thr Tyr Asn Glu Asp Val Thr Ile Thr Leu Asn Asn Val Ala Met
                245                 250                 255

Asp Gln Ala Asp Tyr Glu Val Thr Lys Gly Ile Asn Gly Phe Asn Leu
            260                 265                 270

Lys Leu Thr Glu Ala Gly Leu Ala Lys Ile Asn Gly Lys Asp Ala Asp
        275                 280                 285

Gln Lys Ile Gln Ile Thr Tyr Ser Ala Thr Leu Asn Ser Leu Ala Val
    290                 295                 300

Ala Asp Ile Pro Glu Ser Asn Asp Ile Thr Tyr His Tyr Gly Asn His
305                 310                 315                 320

Gln Asp His Gly Asn Thr Pro Lys Pro Thr Lys Pro Asn Asn Gly Gln
            325                 330                 335

Ile Thr Val Thr Lys Thr Trp Asp Ser Gln Pro Ala Pro Glu Gly Val
        340                 345                 350

Lys Ala Thr Val Gln Leu Val Asn Ala Lys Thr Gly Glu Lys Val Gly
    355                 360                 365

Ala Pro Val Glu Leu Ser Glu Asn Asn Trp Thr Tyr Thr Trp Ser Gly
370                 375                 380

Leu Asp Asn Ser Ile Glu Tyr Lys Val Glu Glu Tyr Asn Gly Tyr
385                 390                 395                 400

Ser Ala Glu Tyr Thr Val Glu Ser Lys Gly Lys Leu Gly Val Lys Asn
                405                 410                 415
```

```
Trp Lys Asp Asn Asn Pro Ala Pro Ile Asn Leu Glu Glu Pro Arg Val
            420                 425                 430

Lys Thr Tyr Gly Lys Lys Phe Val Lys Val Asp Gln Lys Asp Thr Arg
            435                 440                 445

Leu Glu Asn Ala Gln Phe Val Val Lys Ala Asp Ser Asn Lys Tyr
450                 455                 460

Ile Ala Phe Lys Ser Thr Ala Gln Gln Ala Ala Asp Glu Lys Ala Ala
465                 470                 475                 480

Ala Ser Ala Lys Gln Lys Leu Asp Ala Ala Val Ala Ala Tyr Thr Asn
            485                 490                 495

Ala Ala Asp Lys Gln Ala Ala Gln Ala Leu Val Asp Gln Ala Gln Gln
            500                 505                 510

Glu Tyr Asn Val Ala Tyr Lys Glu Ala Lys Phe Gly Tyr Val Glu Val
            515                 520                 525

Ala Gly Lys Asp Glu Ala Met Val Leu Thr Ser Asn Thr Asp Gly Gln
            530                 535                 540

Phe Gln Ile Ser Gly Leu Ala Ala Gly Thr Tyr Lys Leu Glu Glu Ile
545                 550                 555                 560

Lys Ala Pro Glu Gly Phe Ala Lys Ile Asp Asp Val Glu Phe Val Val
            565                 570                 575

Gly Ala Gly Ser Trp Asn Gln Gly Glu Phe Asn Tyr Leu Lys Asp Val
            580                 585                 590

Gln Lys Asn Asp Ala Thr Lys Val Val Asn Lys Lys Ile Thr Ile Pro
            595                 600                 605

Gln Thr Gly Gly Ile Gly Thr Ile Ile Phe Ala Val Ala Gly Ala Ala
            610                 615                 620

Ile Met Gly Ile Ala Val Tyr Ala Tyr Val Lys Asn Asn Lys Asp Glu
625                 630                 635                 640

Asp Gln Leu Ala

<210> SEQ ID NO 97
<211> LENGTH: 251
<212> TYPE: PRT
<213> ORGANISM: Streptococcus pneumoniae
<220> FEATURE:
<223> OTHER INFORMATION: fragment of spr2021 (SP2216-1)

<400> SEQUENCE: 97

Glu Thr Thr Asp Asp Lys Ile Ala Ala Gln Asp Asn Lys Ile Ser Asn
1               5                   10                  15

Leu Thr Ala Gln Gln Glu Ala Gln Lys Gln Val Asp Gln Ile Gln
            20                  25                  30

Glu Gln Val Ser Ala Ile Gln Ala Glu Gln Ser Asn Leu Gln Ala Glu
            35                  40                  45

Asn Asp Arg Leu Gln Ala Glu Ser Lys Lys Leu Glu Gly Glu Ile Thr
50                  55                  60

Glu Leu Ser Lys Asn Ile Val Ser Arg Asn Gln Ser Leu Glu Lys Gln
65                  70                  75                  80

Ala Arg Ser Ala Gln Thr Asn Gly Ala Val Thr Ser Tyr Ile Asn Thr
            85                  90                  95

Ile Val Asn Ser Lys Ser Ile Thr Glu Ala Ile Ser Arg Val Ala Ala
                100                 105                 110

Met Ser Glu Ile Val Ser Ala Asn Asn Lys Met Leu Glu Gln Gln Lys
            115                 120                 125

Ala Asp Lys Lys Ala Ile Ser Glu Lys Gln Val Ala Asn Asn Asp Ala
```

```
            130                 135                 140
Ile Asn Thr Val Ile Ala Asn Gln Gln Lys Leu Ala Asp Asp Ala Gln
145                 150                 155                 160

Ala Leu Thr Thr Lys Gln Ala Glu Leu Lys Ala Ala Glu Leu Ser Leu
                165                 170                 175

Ala Ala Glu Lys Ala Thr Ala Glu Gly Glu Lys Ala Ser Leu Leu Glu
                180                 185                 190

Gln Lys Ala Ala Ala Glu Ala Glu Arg Ala Ala Val Ala Glu
                195                 200                 205

Ala Ala Tyr Lys Glu Lys Arg Ala Ser Gln Gln Ser Val Leu Ala
        210                 215                 220

Ser Ala Asn Thr Asn Leu Thr Ala Gln Val Gln Ala Val Ser Glu Ser
225                 230                 235                 240

Ala Ala Ala Pro Val Arg Ala Lys Val Arg Pro
                245                 250
```

<210> SEQ ID NO 98
<211> LENGTH: 315
<212> TYPE: PRT
<213> ORGANISM: Streptococcus pneumoniae
<220> FEATURE:
<223> OTHER INFORMATION: SP 1732-3

<400> SEQUENCE: 98

```
Tyr Leu Ile Leu Leu Ala Ser Leu Val Leu Ala Ala Ser Leu Ile
1               5                   10                  15

Trp Ile Leu Ser Arg Thr Pro Ala Thr Ile Ala Ile Pro Asp Val Ala
                20                  25                  30

Gly Gln Thr Val Ala Glu Ala Lys Ala Thr Leu Lys Lys Ala Asn Phe
            35                  40                  45

Glu Ile Gly Glu Glu Lys Thr Glu Ala Ser Glu Lys Val Glu Glu Gly
        50                  55                  60

Arg Ile Ile Arg Thr Asp Pro Gly Ala Gly Thr Gly Arg Lys Glu Gly
65                  70                  75                  80

Thr Lys Ile Asn Leu Val Val Ser Ser Gly Lys Gln Ser Phe Gln Ile
                85                  90                  95

Ser Asn Tyr Val Gly Arg Lys Ser Ser Asp Val Ile Ala Glu Leu Lys
                100                 105                 110

Glu Lys Lys Val Pro Asp Asn Leu Ile Lys Ile Glu Glu Glu Glu Ser
            115                 120                 125

Asn Glu Ser Glu Ala Gly Thr Val Leu Lys Gln Ser Leu Pro Glu Gly
        130                 135                 140

Thr Thr Tyr Asp Leu Ser Lys Ala Thr Gln Ile Val Leu Thr Val Ala
145                 150                 155                 160

Lys Lys Ala Thr Thr Ile Gln Leu Gly Asn Tyr Ile Gly Arg Asn Ser
                165                 170                 175

Thr Glu Val Ile Ser Glu Leu Lys Gln Lys Val Pro Glu Asn Leu
                180                 185                 190

Ile Lys Ile Glu Glu Glu Glu Ser Ser Glu Ser Glu Pro Gly Thr Ile
            195                 200                 205

Met Lys Gln Ser Pro Gly Ala Gly Thr Thr Tyr Asp Val Ser Lys Pro
        210                 215                 220

Thr Gln Ile Val Leu Thr Val Ala Lys Lys Val Thr Ser Val Ala Met
225                 230                 235                 240

Pro Ser Tyr Ile Gly Ser Ser Leu Glu Phe Thr Lys Asn Asn Leu Ile
                245                 250                 255
```

```
Gln Ile Val Gly Ile Lys Glu Ala Asn Ile Glu Val Val Glu Val Thr
            260                 265                 270

Thr Ala Pro Ala Gly Ser Val Glu Gly Met Val Val Glu Gln Ser Pro
        275                 280                 285

Arg Ala Gly Glu Lys Val Asp Leu Asn Lys Thr Arg Val Lys Ile Ser
    290                 295                 300

Ile Tyr Lys Pro Lys Thr Thr Ser Ala Thr Pro
305                 310                 315

<210> SEQ ID NO 99
<211> LENGTH: 289
<212> TYPE: PRT
<213> ORGANISM: Streptococcus pneumoniae
<220> FEATURE:
<223> OTHER INFORMATION: PsaA fragment

<400> SEQUENCE: 99

Ala Ser Gly Lys Lys Asp Thr Thr Ser Gly Gln Lys Leu Lys Val Val
1               5                   10                  15

Ala Thr Asn Ser Ile Ile Ala Asp Ile Thr Lys Asn Ile Ala Gly Asp
            20                  25                  30

Lys Ile Asp Leu His Ser Ile Val Pro Ile Gly Gln Asp Pro His Glu
        35                  40                  45

Tyr Glu Pro Leu Pro Glu Asp Val Lys Lys Thr Ser Glu Ala Asp Leu
    50                  55                  60

Ile Phe Tyr Asn Gly Ile Asn Leu Glu Thr Gly Gly Asn Ala Trp Phe
65                  70                  75                  80

Thr Lys Leu Val Glu Asn Ala Lys Lys Thr Glu Asn Lys Asp Tyr Phe
                85                  90                  95

Ala Val Ser Asp Gly Val Asp Val Ile Tyr Leu Glu Gly Gln Asn Glu
            100                 105                 110

Lys Gly Lys Glu Asp Pro His Ala Trp Leu Asn Leu Glu Asn Gly Ile
        115                 120                 125

Ile Phe Ala Lys Asn Ile Ala Lys Gln Leu Ser Ala Lys Asp Pro Asn
130                 135                 140

Asn Lys Glu Phe Tyr Glu Lys Asn Leu Lys Glu Tyr Thr Asp Lys Leu
145                 150                 155                 160

Asp Lys Leu Asp Lys Glu Ser Lys Asp Lys Phe Asn Lys Ile Pro Ala
                165                 170                 175

Glu Lys Lys Leu Ile Val Thr Ser Glu Gly Ala Phe Lys Tyr Phe Ser
            180                 185                 190

Lys Ala Tyr Gly Val Pro Ser Ala Tyr Ile Trp Glu Ile Asn Thr Glu
        195                 200                 205

Glu Glu Gly Thr Pro Glu Gln Ile Lys Thr Leu Val Glu Lys Leu Arg
    210                 215                 220

Gln Thr Lys Val Pro Ser Leu Phe Val Glu Ser Ser Val Asp Asp Arg
225                 230                 235                 240

Pro Met Lys Thr Val Ser Gln Asp Thr Asn Ile Pro Ile Tyr Ala Gln
                245                 250                 255

Ile Phe Thr Asp Ser Ile Ala Glu Gln Gly Lys Glu Gly Asp Ser Tyr
            260                 265                 270

Tyr Ser Met Met Lys Tyr Asn Leu Asp Lys Ile Ala Glu Gly Leu Ala
        275                 280                 285

Lys
```